US012642568B2

(12) United States Patent
Sharma et al.

(10) Patent No.: US 12,642,568 B2
(45) Date of Patent: Jun. 2, 2026

(54) DUODENAL ABLATION WITH IMPROVED DEPTH AND CONSISTENCY OF ABLATION

(71) Applicant: Aqua Medical, Inc., Santa Ana, CA (US)

(72) Inventors: Virender K. Sharma, Paradise Valley, AZ (US); Lloyd Mencinger, Rancho Palos Verdes, CA (US); Scott McGill, San Ramon, CA (US)

(73) Assignee: Aqua Medical, Inc., Santa Ana, CA (US)

( * ) Notice: Subject to any disclaimer, the term of this patent is extended or adjusted under 35 U.S.C. 154(b) by 277 days.

(21) Appl. No.: 18/593,883

(22) Filed: Mar. 2, 2024

(65) Prior Publication Data

US 2024/0398462 A1 Dec. 5, 2024

Related U.S. Application Data

(63) Continuation-in-part of application No. 18/517,488, filed on Nov. 22, 2023, now Pat. No. 12,279,803, (Continued)

(51) Int. Cl.
*A61B 18/04* (2006.01)
*A61B 18/00* (2006.01)

(52) U.S. Cl.
CPC .... *A61B 18/04* (2013.01); *A61B 2018/00261* (2013.01); *A61B 2018/00345* (2013.01); *A61B 2018/00488* (2013.01); *A61B 2018/00494* (2013.01); *A61B 2018/00541* (2013.01); *A61B 2018/00577* (2013.01);
(Continued)

(58) Field of Classification Search
CPC .......... A61B 18/04; A61B 2018/00261; A61B 2018/00494; A61B 2018/00744
See application file for complete search history.

(56) References Cited

U.S. PATENT DOCUMENTS

| 408,899 | A | 8/1889 | Small |
| 697,181 | A | 4/1902 | Smith |

(Continued)

FOREIGN PATENT DOCUMENTS

| CN | 2757751 Y | 2/2006 |
| CN | 1803113 A | 7/2006 |

(Continued)

OTHER PUBLICATIONS

Microsulis America, Inc.; Instructions for Use, Microsulis Microwave Endometrial Ablation (MEA) System; Microsulis Americas, Inc.—MEA System Instructions for Use; Dec. 2002; 62795/09/038 Issue 1; pp. 16-35; Microsulis Americas.

(Continued)

*Primary Examiner* — Joseph A Stoklosa
*Assistant Examiner* — Annie L Shoulders
(74) *Attorney, Agent, or Firm* — Novel IP

(57) ABSTRACT

Ablation catheters and systems include flexible catheter tips with at least one positioning element and ports for delivery of an ablative agent to a target tissue. The positioning element is used to define a treatment zone and position the catheter proximate the target tissue for ablation. Ablative fluid is delivered to the target tissue at subtherapeutic, therapeutic, or supratherapeutic doses over different time periods, with rest periods between each dose, to cause effective ablation of the target tissue.

20 Claims, 170 Drawing Sheets

Related U.S. Application Data which is a continuation of application No. 17/575,950, filed on Jan. 14, 2022, now Pat. No. 11,864,809, which is a continuation of application No. 16/428,598, filed on May 31, 2019, now Pat. No. 11,806,066.

(60) Provisional application No. 63/618,313, filed on Jan. 6, 2024, provisional application No. 63/596,196, filed on Nov. 3, 2023, provisional application No. 63/488,106, filed on Mar. 2, 2023, provisional application No. 62/679,694, filed on Jun. 1, 2018.

(52) U.S. Cl.
CPC ................ *A61B 2018/0072* (2013.01); *A61B 2018/00744* (2013.01); *A61B 2018/00982* (2013.01); *A61B 2018/048* (2013.01)

(56) References Cited

U.S. PATENT DOCUMENTS

| | | |
|---|---|---|
| 1,719,750 A | 7/1929 | Bridge |
| 3,818,913 A | 6/1974 | Wallach |
| 3,880,168 A | 4/1975 | Berman |
| 3,924,628 A | 12/1975 | Droegemueller |
| 3,930,505 A | 1/1976 | Wallach |
| 3,938,502 A | 2/1976 | Bom |
| 4,024,866 A | 5/1977 | Wallach |
| 4,083,077 A | 4/1978 | Knight |
| 4,672,962 A | 6/1987 | Hershenson |
| 4,672,963 A | 6/1987 | Barken |
| 4,682,596 A | 7/1987 | Bales |
| 4,701,587 A | 10/1987 | Carter |
| 4,748,979 A | 6/1988 | Hershenson |
| 4,773,410 A | 9/1988 | Blackmer |
| 4,793,352 A | 12/1988 | Eichenlaub |
| 4,828,544 A | 5/1989 | Lane |
| 4,872,920 A | 10/1989 | Flynn |
| 4,898,574 A | 2/1990 | Uchiyama |
| 4,915,113 A | 4/1990 | Holman |
| 4,950,266 A | 8/1990 | Sinofsky |
| 4,950,267 A | 8/1990 | Ishihara |
| 4,976,711 A | 12/1990 | Parins |
| 4,985,027 A | 1/1991 | Dressel |
| 5,006,119 A | 4/1991 | Acker |
| 5,011,566 A | 4/1991 | Hoffman |
| 5,045,056 A | 9/1991 | Behl |
| 5,084,043 A | 1/1992 | Hertzmann |
| 5,084,044 A | 1/1992 | Quint |
| 5,102,410 A | 4/1992 | Dressel |
| 5,112,328 A | 5/1992 | Taboada |
| 5,122,138 A | 6/1992 | Manwaring |
| 5,158,536 A | 10/1992 | Sekins |
| 5,190,539 A | 3/1993 | Fletcher |
| 5,217,459 A | 6/1993 | Kamerling |
| 5,217,465 A | 6/1993 | Steppe |
| 5,222,938 A | 6/1993 | Behl |
| 5,263,951 A | 11/1993 | Spears |
| 5,277,696 A | 1/1994 | Hagen |
| 5,298,298 A | 3/1994 | Hoffman |
| 5,312,399 A | 5/1994 | Hakky |
| 5,318,014 A | 6/1994 | Carter |
| 5,330,518 A | 7/1994 | Neilson |
| 5,331,947 A | 7/1994 | Shturman |
| 5,334,190 A | 8/1994 | Seiler |
| 5,344,397 A | 9/1994 | Heaven |
| 5,348,551 A | 9/1994 | Spears |
| 5,352,512 A | 10/1994 | Hoffman |
| 5,366,490 A | 11/1994 | Edwards |
| 5,370,609 A | 12/1994 | Drasler |
| 5,370,675 A | 12/1994 | Edwards |
| 5,385,544 A | 1/1995 | Edwards |
| 5,405,376 A | 4/1995 | Mulier |
| 5,409,453 A | 4/1995 | Lundquist |
| 5,417,686 A | 5/1995 | Peterson |
| 5,421,819 A | 6/1995 | Edwards |
| 5,424,620 A | 6/1995 | Cheon |
| 5,425,731 A | 6/1995 | Daniel |
| 5,425,931 A | 6/1995 | Arai |
| 5,433,708 A | 7/1995 | Nichols |
| 5,433,739 A | 7/1995 | Sluijter |
| 5,435,805 A | 7/1995 | Edwards |
| 5,437,629 A | 8/1995 | Goldrath |
| 5,443,470 A | 8/1995 | Stern |
| 5,449,380 A | 9/1995 | Chin |
| 5,451,208 A | 9/1995 | Goldrath |
| 5,462,521 A | 10/1995 | Brucker |
| 5,470,308 A | 11/1995 | Edwards |
| 5,470,309 A | 11/1995 | Edwards |
| 5,484,400 A | 1/1996 | Edwards |
| 5,500,012 A | 3/1996 | Brucker |
| 5,503,638 A | 4/1996 | Cooper |
| 5,524,620 A | 6/1996 | Rosenschein |
| 5,529,076 A | 6/1996 | Schachar |
| 5,531,676 A | 7/1996 | Edwards |
| 5,540,658 A | 7/1996 | Evans |
| 5,542,915 A | 8/1996 | Edwards |
| 5,542,916 A | 8/1996 | Hirsch |
| 5,542,928 A | 8/1996 | Evans |
| 5,545,171 A | 8/1996 | Sharkey |
| 5,549,628 A | 8/1996 | Cooper |
| 5,549,644 A | 8/1996 | Lundquist |
| 5,554,110 A | 9/1996 | Edwards |
| 5,554,172 A | 9/1996 | Horner |
| 5,556,377 A | 9/1996 | Rosen |
| 5,558,673 A | 9/1996 | Edwards |
| 5,562,608 A | 10/1996 | Sekins |
| 5,575,803 A | 11/1996 | Cooper |
| 5,584,872 A | 12/1996 | Lafontaine |
| 5,588,960 A | 12/1996 | Edwards |
| 5,591,125 A | 1/1997 | Edwards |
| 5,591,157 A | 1/1997 | Hennings |
| 5,591,162 A | 1/1997 | Fletcher |
| 5,599,294 A | 2/1997 | Edwards |
| 5,601,591 A | 2/1997 | Edwards |
| 5,609,151 A | 3/1997 | Mulier |
| 5,616,120 A | 4/1997 | Andrew |
| 5,620,440 A | 4/1997 | Heckele |
| 5,624,392 A | 4/1997 | Saab |
| 5,630,794 A | 5/1997 | Lax |
| 5,667,488 A | 9/1997 | Lundquist |
| 5,669,907 A | 9/1997 | Platt, Jr. |
| 5,672,153 A | 9/1997 | Lax |
| 5,672,290 A | 9/1997 | Levy |
| 5,674,191 A | 10/1997 | Edwards |
| 5,681,282 A | 10/1997 | Eggers |
| 5,683,366 A | 11/1997 | Eggers |
| 5,695,507 A | 12/1997 | Auth |
| 5,697,281 A | 12/1997 | Eggers |
| 5,697,536 A | 12/1997 | Eggers |
| 5,697,882 A | 12/1997 | Eggers |
| 5,697,909 A | 12/1997 | Eggers |
| 5,700,262 A | 12/1997 | Acosta |
| 5,707,352 A | 1/1998 | Sekins |
| 5,720,718 A | 2/1998 | Rosen |
| 5,720,719 A | 2/1998 | Edwards |
| 5,730,719 A | 3/1998 | Edwards |
| 5,735,811 A | 4/1998 | Brisken |
| 5,741,247 A | 4/1998 | Rizoiu |
| 5,741,248 A | 4/1998 | Stern |
| 5,743,870 A | 4/1998 | Edwards |
| 5,752,965 A | 5/1998 | Francis |
| 5,755,753 A | 5/1998 | Knowlton |
| 5,769,880 A | 6/1998 | Truckai |
| 5,782,914 A | 7/1998 | Schankereli |
| 5,785,521 A | 7/1998 | Rizoiu |
| 5,797,903 A | 8/1998 | Swanson |
| 5,800,379 A | 9/1998 | Edwards |
| 5,800,482 A | 9/1998 | Pomeranz |
| 5,800,493 A | 9/1998 | Stevens |
| 5,810,764 A | 9/1998 | Eggers |
| 5,820,580 A | 10/1998 | Edwards |
| 5,824,703 A | 10/1998 | Clark, Jr. |
| 5,827,268 A | 10/1998 | Laufer |

(56)          References Cited

U.S. PATENT DOCUMENTS

| | | | |
|---|---|---|---|
| 5,830,179 A | 11/1998 | Mikus |
| 5,836,906 A | 11/1998 | Edwards |
| 5,843,019 A | 12/1998 | Eggers |
| 5,843,073 A | 12/1998 | Sinofsky |
| 5,849,011 A | 12/1998 | Jones |
| 5,861,005 A | 1/1999 | Kontos |
| 5,871,469 A | 2/1999 | Eggers |
| 5,871,481 A | 2/1999 | Kannenberg |
| 5,873,855 A | 2/1999 | Eggers |
| 5,873,877 A | 2/1999 | Mcgaffigan |
| 5,879,329 A | 3/1999 | Ginsburg |
| 5,885,243 A | 3/1999 | Capetan |
| 5,888,198 A | 3/1999 | Eggers |
| 5,891,095 A | 4/1999 | Eggers |
| 5,891,134 A | 4/1999 | Goble |
| 5,891,457 A | 4/1999 | Neuwirth |
| 5,897,553 A | 4/1999 | Mulier |
| 5,902,272 A | 5/1999 | Eggers |
| 5,913,856 A | 6/1999 | Chia |
| 5,938,660 A | 8/1999 | Swartz |
| 5,944,686 A | 8/1999 | Patterson |
| 5,944,715 A | 8/1999 | Goble |
| 5,954,714 A | 9/1999 | Saadat |
| 5,957,919 A | 9/1999 | Laufer |
| 5,957,922 A | 9/1999 | Imran |
| 5,964,752 A | 10/1999 | Stone |
| 5,964,756 A | 10/1999 | Mcgaffigan |
| 5,968,037 A | 10/1999 | Rizoiu |
| 5,976,123 A | 11/1999 | Baumgardner |
| 5,980,504 A | 11/1999 | Sharkey |
| 5,980,516 A | 11/1999 | Mulier |
| 5,986,662 A | 11/1999 | Argiro |
| 5,989,212 A | 11/1999 | Sussman |
| 5,989,238 A | 11/1999 | Ginsburg |
| 5,989,249 A | 11/1999 | Kirwanjr |
| 5,989,445 A | 11/1999 | Wise |
| 5,997,499 A | 12/1999 | Sussman |
| 6,015,406 A | 1/2000 | Goble |
| 6,016,809 A | 1/2000 | Mulier |
| 6,017,361 A | 1/2000 | Mikus |
| 6,024,733 A | 2/2000 | Eggers |
| 6,027,501 A | 2/2000 | Goble |
| 6,032,077 A | 2/2000 | Pomeranz |
| 6,032,674 A | 3/2000 | Eggers |
| 6,036,713 A | 3/2000 | Kieturakis |
| 6,045,532 A | 4/2000 | Eggers |
| 6,045,549 A | 4/2000 | Smethers |
| 6,047,700 A | 4/2000 | Eggers |
| 6,053,172 A | 4/2000 | Hovda |
| 6,053,909 A | 4/2000 | Shadduck |
| 6,056,746 A | 5/2000 | Goble |
| 6,059,011 A | 5/2000 | Giolo |
| 6,063,079 A | 5/2000 | Hovda |
| 6,063,081 A | 5/2000 | Mulier |
| 6,066,132 A | 5/2000 | Chen |
| 6,066,134 A | 5/2000 | Eggers |
| 6,071,278 A | 6/2000 | Panescu |
| 6,074,358 A | 6/2000 | Andrew |
| 6,077,257 A | 6/2000 | Edwards |
| 6,080,128 A | 6/2000 | Sussman |
| 6,080,151 A | 6/2000 | Swartz |
| 6,083,255 A | 7/2000 | Laufer |
| 6,086,585 A | 7/2000 | Hovda |
| 6,095,149 A | 8/2000 | Sharkey |
| 6,099,251 A | 8/2000 | Lafleur |
| 6,102,046 A | 8/2000 | Weinstein |
| 6,102,885 A | 8/2000 | Bass |
| 6,105,581 A | 8/2000 | Eggers |
| 6,106,516 A | 8/2000 | Massengill |
| 6,109,268 A | 8/2000 | Thapliyal |
| 6,110,162 A | 8/2000 | Sussman |
| 6,112,123 A | 8/2000 | Kelleher |
| 6,113,593 A | 9/2000 | Tu |
| 6,113,597 A | 9/2000 | Eggers |
| 6,113,722 A | 9/2000 | Hoffman |
| 6,117,109 A | 9/2000 | Eggers |
| 6,126,682 A | 10/2000 | Sharkey |
| 6,130,671 A | 10/2000 | Argiro |
| 6,139,538 A | 10/2000 | Houghton |
| 6,139,571 A | 10/2000 | Fuller |
| 6,149,620 A | 11/2000 | Baker |
| 6,156,036 A | 12/2000 | Sussman |
| 6,159,194 A | 12/2000 | Eggers |
| 6,159,208 A | 12/2000 | Hovda |
| 6,162,232 A | 12/2000 | Shadduck |
| 6,168,594 B1 | 1/2001 | Lafontaine |
| 6,174,308 B1 | 1/2001 | Goble |
| 6,176,842 B1 | 1/2001 | Tachibana |
| 6,179,805 B1 | 1/2001 | Sussman |
| 6,179,824 B1 | 1/2001 | Eggers |
| 6,179,836 B1 | 1/2001 | Eggers |
| 6,183,469 B1 | 2/2001 | Thapliyal |
| 6,190,381 B1 | 2/2001 | Olsen |
| 6,194,066 B1 | 2/2001 | Hoffman |
| 6,196,989 B1 | 3/2001 | Padget |
| 6,200,333 B1 | 3/2001 | Laufer |
| 6,203,542 B1 | 3/2001 | Ellsberry |
| 6,206,847 B1 | 3/2001 | Edwards |
| 6,206,848 B1 | 3/2001 | Sussman |
| 6,210,402 B1 | 4/2001 | Olsen |
| 6,210,404 B1 | 4/2001 | Shadduck |
| 6,210,405 B1 | 4/2001 | Goble |
| 6,219,059 B1 | 4/2001 | Argiro |
| 6,224,592 B1 | 5/2001 | Eggers |
| 6,228,078 B1 | 5/2001 | Eggers |
| 6,228,081 B1 | 5/2001 | Goble |
| 6,228,082 B1 | 5/2001 | Baker |
| 6,231,567 B1 | 5/2001 | Rizoiu |
| 6,234,178 B1 | 5/2001 | Goble |
| 6,235,020 B1 | 5/2001 | Cheng |
| 6,235,025 B1 | 5/2001 | Swartz |
| 6,238,389 B1 | 5/2001 | Paddock |
| 6,238,391 B1 | 5/2001 | Olsen |
| 6,241,702 B1 | 6/2001 | Lundquist |
| 6,254,597 B1 | 7/2001 | Rizoiu |
| 6,254,600 B1 | 7/2001 | Willink |
| 6,258,087 B1 | 7/2001 | Edwards |
| 6,261,286 B1 | 7/2001 | Goble |
| 6,261,311 B1 | 7/2001 | Sharkey |
| 6,264,650 B1 | 7/2001 | Hovda |
| 6,264,651 B1 | 7/2001 | Underwood |
| 6,264,652 B1 | 7/2001 | Eggers |
| 6,264,654 B1 | 7/2001 | Swartz |
| 6,277,112 B1 | 8/2001 | Underwood |
| 6,277,114 B1 | 8/2001 | Bullivant |
| 6,277,130 B1 | 8/2001 | Shadduck |
| 6,283,961 B1 | 9/2001 | Underwood |
| 6,283,989 B1 | 9/2001 | Laufer |
| 6,287,274 B1 | 9/2001 | Sussman |
| 6,287,320 B1 | 9/2001 | Slepian |
| 6,290,715 B1 | 9/2001 | Sharkey |
| 6,293,942 B1 | 9/2001 | Goble |
| 6,296,636 B1 | 10/2001 | Cheng |
| 6,296,638 B1 | 10/2001 | Davison |
| 6,299,620 B1 | 10/2001 | Shadduck |
| 6,299,633 B1 | 10/2001 | Laufer |
| 6,300,150 B1 | 10/2001 | Venkatasubramanian |
| 6,306,129 B1 | 10/2001 | Little |
| 6,306,134 B1 | 10/2001 | Goble |
| 6,309,387 B1 | 10/2001 | Eggers |
| 6,312,408 B1 | 11/2001 | Eggers |
| 6,312,474 B1 | 11/2001 | Francis |
| 6,315,755 B1 | 11/2001 | Sussman |
| 6,319,222 B1 | 11/2001 | Andrew |
| 6,322,549 B1 | 11/2001 | Eggers |
| 6,322,558 B1 | 11/2001 | Taylor |
| 6,327,505 B1 | 12/2001 | Medhkour |
| 6,331,171 B1 | 12/2001 | Cohen |
| 6,355,032 B1 | 3/2002 | Hovda |
| 6,358,248 B1 | 3/2002 | Mulier |
| 6,363,937 B1 | 4/2002 | Hovda |
| 6,364,877 B1 | 4/2002 | Goble |
| 6,375,635 B1 | 4/2002 | Moutafis |
| 6,379,350 B1 | 4/2002 | Sharkey |

(56)          References Cited

U.S. PATENT DOCUMENTS

| | | |
|---|---|---|
| 6,379,351 B1 | 4/2002 | Thapliyal |
| 6,391,025 B1 | 5/2002 | Weinstein |
| 6,394,949 B1 | 5/2002 | Crowley |
| 6,394,996 B1 | 5/2002 | Lawrence |
| 6,398,759 B1 | 6/2002 | Sussman |
| 6,398,775 B1 | 6/2002 | Perkins |
| 6,409,723 B1 | 6/2002 | Edwards |
| 6,416,507 B1 | 7/2002 | Eggers |
| 6,416,508 B1 | 7/2002 | Eggers |
| 6,416,509 B1 | 7/2002 | Goble |
| 6,419,673 B1 | 7/2002 | Edwards |
| 6,423,027 B1 | 7/2002 | Gonon |
| 6,432,103 B1 | 8/2002 | Ellsberry |
| 6,440,127 B2 | 8/2002 | Mcgovern |
| 6,458,231 B1 | 10/2002 | Wapner |
| 6,461,296 B1 | 10/2002 | Desai |
| 6,461,350 B1 | 10/2002 | Underwood |
| 6,461,354 B1 | 10/2002 | Olsen |
| 6,464,694 B1 | 10/2002 | Massengill |
| 6,464,695 B2 | 10/2002 | Hovda |
| 6,464,696 B1 | 10/2002 | Oyama |
| 6,468,270 B1 | 10/2002 | Hovda |
| 6,468,274 B1 | 10/2002 | Alleyne |
| 6,468,313 B1 | 10/2002 | Claeson |
| 6,482,201 B1 | 11/2002 | Olsen |
| 6,482,202 B1 | 11/2002 | Goble |
| 6,488,673 B1 | 12/2002 | Laufer |
| 6,488,680 B1 | 12/2002 | Francischelli |
| 6,491,710 B2 | 12/2002 | Satake |
| 6,493,589 B1 | 12/2002 | Medhkour |
| 6,500,173 B2 | 12/2002 | Underwood |
| 6,508,816 B2 | 1/2003 | Shadduck |
| 6,510,854 B2 | 1/2003 | Goble |
| 6,517,568 B1 | 2/2003 | Sharkey |
| 6,522,930 B1 | 2/2003 | Schaer |
| 6,527,761 B1 | 3/2003 | Soltesz |
| 6,527,766 B1 | 3/2003 | Bair |
| 6,528,771 B1 | 3/2003 | Matsen |
| 6,540,741 B1 | 4/2003 | Underwood |
| 6,544,211 B1 | 4/2003 | Andrew |
| 6,544,248 B1 | 4/2003 | Bass |
| 6,544,261 B2 | 4/2003 | Ellsberry |
| 6,547,810 B1 | 4/2003 | Sharkey |
| 6,551,271 B2 | 4/2003 | Nguyen |
| 6,551,274 B2 | 4/2003 | Heiner |
| 6,551,300 B1 | 4/2003 | Mcgaffigan |
| 6,551,309 B1 | 4/2003 | LePivert |
| 6,557,559 B1 | 5/2003 | Eggers |
| 6,558,314 B1 | 5/2003 | Adelman |
| 6,558,379 B1 | 5/2003 | Batchelor |
| 6,566,636 B1 | 5/2003 | Bentley |
| 6,569,146 B1 | 5/2003 | Werner |
| 6,575,929 B2 | 6/2003 | Sussman |
| 6,575,932 B1 | 6/2003 | Obrien |
| 6,575,968 B1 | 6/2003 | Eggers |
| 6,579,270 B2 | 6/2003 | Sussman |
| 6,582,423 B1 | 6/2003 | Thapliyal |
| 6,585,639 B1 | 7/2003 | Kotmel |
| 6,585,732 B2 | 7/2003 | Mulier |
| 6,588,613 B1 | 7/2003 | Pechenik |
| 6,589,201 B1 | 7/2003 | Sussman |
| 6,589,204 B1 | 7/2003 | Sussman |
| 6,589,237 B2 | 7/2003 | Woloszko |
| 6,592,594 B2 | 7/2003 | Rimbaugh |
| 6,595,989 B1 | 7/2003 | Schaer |
| 6,595,990 B1 | 7/2003 | Weinstein |
| 6,599,311 B1 | 7/2003 | Biggs |
| 6,602,248 B1 | 8/2003 | Sharps |
| 6,605,087 B2 | 8/2003 | Swartz |
| 6,607,529 B1 | 8/2003 | Jones |
| 6,610,043 B1 | 8/2003 | Ingenito |
| 6,620,130 B1 | 9/2003 | Ginsburg |
| 6,620,155 B2 | 9/2003 | Underwood |
| 6,623,444 B2 | 9/2003 | Babaev |
| 6,629,974 B2 | 10/2003 | Penny |
| 6,632,193 B1 | 10/2003 | Davison |
| 6,632,220 B1 | 10/2003 | Eggers |
| 6,634,363 B1 | 10/2003 | Danek |
| 6,647,300 B1 | 11/2003 | Balasubramanian |
| 6,648,847 B2 | 11/2003 | Sussman |
| 6,652,594 B2 | 11/2003 | Francis |
| 6,653,525 B2 | 11/2003 | Ingenito |
| 6,659,106 B1 | 12/2003 | Hovda |
| 6,669,685 B1 | 12/2003 | Rizoiu |
| 6,669,694 B2 | 12/2003 | Shadduck |
| 6,673,071 B2 | 1/2004 | Vandusseldorp |
| 6,676,628 B2 | 1/2004 | Sussman |
| 6,676,629 B2 | 1/2004 | Andrew |
| 6,679,264 B1 | 1/2004 | Deem |
| 6,679,879 B2 | 1/2004 | Shadduck |
| 6,682,520 B2 | 1/2004 | Ingenito |
| 6,692,494 B1 | 2/2004 | Cooper |
| 6,695,839 B2 | 2/2004 | Sharkey |
| 6,699,244 B2 | 3/2004 | Carranza |
| 6,708,056 B2 | 3/2004 | Duchon |
| 6,712,811 B2 | 3/2004 | Underwood |
| 6,712,812 B2 | 3/2004 | Roschak |
| 6,716,252 B2 | 4/2004 | Lazarovitz |
| 6,719,738 B2 | 4/2004 | Mehier |
| 6,719,754 B2 | 4/2004 | Underwood |
| 6,719,755 B2 | 4/2004 | Sliwajr |
| 6,723,064 B2 | 4/2004 | Babaev |
| 6,726,684 B1 | 4/2004 | Woloszko |
| 6,726,696 B1 | 4/2004 | Houser |
| 6,726,708 B2 | 4/2004 | Lasheras |
| 6,730,079 B2 | 5/2004 | Lovewell |
| 6,734,405 B2 | 5/2004 | Centanni |
| 6,740,082 B2 | 5/2004 | Shadduck |
| 6,746,447 B2 | 6/2004 | Davison |
| 6,749,604 B1 | 6/2004 | Eggers |
| 6,755,794 B2 | 6/2004 | Soukup |
| 6,758,846 B2 | 7/2004 | Goble |
| 6,760,616 B2 | 7/2004 | Hoey |
| 6,763,836 B2 | 7/2004 | Tasto |
| 6,764,487 B2 | 7/2004 | Mulier |
| 6,766,202 B2 | 7/2004 | Underwood |
| 6,770,070 B1 | 8/2004 | Balbierz |
| 6,770,071 B2 | 8/2004 | Woloszko |
| 6,772,012 B2 | 8/2004 | Ricart |
| 6,773,431 B2 | 8/2004 | Eggers |
| 6,776,765 B2 | 8/2004 | Soukup |
| 6,776,780 B2 | 8/2004 | Mulier |
| 6,780,178 B2 | 8/2004 | Palanker |
| 6,780,180 B1 | 8/2004 | Goble |
| 6,805,130 B2 | 10/2004 | Tasto |
| 6,813,520 B2 | 11/2004 | Truckai |
| 6,827,718 B2 | 12/2004 | Hutchins |
| 6,832,996 B2 | 12/2004 | Woloszko |
| 6,837,884 B2 | 1/2005 | Woloszko |
| 6,837,886 B2 | 1/2005 | Collins |
| 6,837,887 B2 | 1/2005 | Woloszko |
| 6,837,888 B2 | 1/2005 | Ciarrocca |
| 6,852,108 B2 | 2/2005 | Barry |
| 6,860,847 B2 | 3/2005 | Alferness |
| 6,860,868 B1 | 3/2005 | Sussman |
| 6,875,194 B2 | 4/2005 | Mackool |
| 6,893,438 B2 | 5/2005 | Hall |
| 6,896,672 B1 | 5/2005 | Eggers |
| 6,896,674 B1 | 5/2005 | Woloszko |
| 6,896,675 B2 | 5/2005 | Leung |
| 6,901,927 B2 | 6/2005 | Deem |
| 6,904,909 B2 | 6/2005 | Andreas |
| 6,905,475 B2 | 6/2005 | Hauschild |
| 6,905,496 B1 | 6/2005 | Ellman |
| 6,907,881 B2 | 6/2005 | Suki |
| 6,911,028 B2 | 6/2005 | Shadduck |
| 6,915,806 B2 | 7/2005 | Pacek |
| 6,916,318 B2 | 7/2005 | Francischelli |
| 6,918,903 B2 | 7/2005 | Bass |
| 6,921,385 B2 | 7/2005 | Clements |
| 6,929,640 B1 | 8/2005 | Underwood |
| 6,929,642 B2 | 8/2005 | Xiao |
| 6,949,096 B2 | 9/2005 | Davison |
| 6,949,098 B2 | 9/2005 | Mulier |

(56) References Cited

U.S. PATENT DOCUMENTS

| | | | |
|---|---|---|---|
| 6,952,615 B2 | 10/2005 | Satake |
| 6,955,674 B2 | 10/2005 | Eick |
| 6,955,675 B2 | 10/2005 | Jain |
| 6,960,182 B2 | 11/2005 | Moutafis |
| 6,960,203 B2 | 11/2005 | Xiao |
| 6,960,204 B2 | 11/2005 | Eggers |
| 6,969,376 B2 | 11/2005 | Takagi |
| 6,972,014 B2 | 12/2005 | Eum |
| 6,986,769 B2 | 1/2006 | Nelson |
| 6,991,028 B2 | 1/2006 | Comeaux |
| 6,991,631 B2 | 1/2006 | Woloszko |
| 7,004,940 B2 | 2/2006 | Ryan |
| 7,004,941 B2 | 2/2006 | Tvinnereim |
| 7,014,652 B2 | 3/2006 | Cioanta |
| 7,022,088 B2 | 4/2006 | Keast |
| 7,025,762 B2 | 4/2006 | Johnston |
| 7,031,504 B1 | 4/2006 | Argiro |
| 7,083,612 B2 | 8/2006 | Littrup |
| 7,087,040 B2 | 8/2006 | Mcguckinjr |
| 7,089,064 B2 | 8/2006 | Manker |
| 7,094,215 B2 | 8/2006 | Davison |
| 7,101,367 B2 | 9/2006 | Xiao |
| 7,104,986 B2 | 9/2006 | Hovda |
| 7,105,007 B2 | 9/2006 | Hibler |
| 7,112,198 B2 | 9/2006 | Satake |
| 7,113,838 B2 | 9/2006 | Funk |
| RE39,358 E | 10/2006 | Goble |
| 7,128,748 B2 | 10/2006 | Mooradian |
| 7,130,697 B2 | 10/2006 | Chornenky |
| 7,131,969 B1 | 11/2006 | Hovda |
| 7,136,064 B2 | 11/2006 | Zuiderveld |
| 7,144,402 B2 | 12/2006 | Kuester, III |
| 7,144,588 B2 | 12/2006 | Oray |
| 7,153,301 B2 | 12/2006 | Swartz |
| 7,166,105 B2 | 1/2007 | Mulier |
| 7,169,143 B2 | 1/2007 | Eggers |
| 7,179,255 B2 | 2/2007 | Lettice |
| 7,186,234 B2 | 3/2007 | Dahla |
| 7,192,400 B2 | 3/2007 | Campbell |
| 7,192,428 B2 | 3/2007 | Eggers |
| 7,201,750 B1 | 4/2007 | Eggers |
| 7,217,268 B2 | 5/2007 | Eggers |
| 7,225,040 B2 | 5/2007 | Eller |
| 7,233,820 B2 | 6/2007 | Gilboa |
| 7,235,070 B2 | 6/2007 | Vanney |
| 7,237,555 B2 | 7/2007 | Kochamba |
| 7,241,293 B2 | 7/2007 | Davison |
| 7,261,709 B2 | 8/2007 | Swoyer |
| 7,261,710 B2 | 8/2007 | Elmouelhi |
| 7,270,658 B2 | 9/2007 | Woloszko |
| 7,270,659 B2 | 9/2007 | Ricart |
| 7,270,661 B2 | 9/2007 | Dahla |
| 7,276,063 B2 | 10/2007 | Davison |
| 7,280,881 B2 | 10/2007 | Eller |
| 7,297,143 B2 | 11/2007 | Woloszko |
| 7,297,145 B2 | 11/2007 | Woloszko |
| 7,320,325 B2 | 1/2008 | Duchon |
| 7,335,195 B2 | 2/2008 | Mehier |
| 7,335,197 B2 | 2/2008 | Sage |
| 7,340,307 B2 | 3/2008 | Maguire |
| 7,347,859 B2 | 3/2008 | Garabedian |
| 7,364,579 B2 | 4/2008 | Mulier |
| 7,410,486 B2 | 8/2008 | Fuimaono |
| 7,419,500 B2 | 9/2008 | Marko |
| 7,422,588 B2 | 9/2008 | Mulier |
| 7,429,262 B2 | 9/2008 | Woloszko |
| 7,435,250 B2 | 10/2008 | Francischelli |
| 7,470,228 B2 | 12/2008 | Connors |
| 7,470,272 B2 | 12/2008 | Mulier |
| 7,503,904 B2 | 3/2009 | Choi |
| 7,512,445 B2 | 3/2009 | Truckai |
| 7,549,987 B2 | 6/2009 | Shadduck |
| 7,559,367 B2 | 7/2009 | Vinegar |
| 7,585,295 B2 | 9/2009 | Ben-Nun |
| 7,597,147 B2 | 10/2009 | Vitek |
| 7,674,259 B2 | 3/2010 | Shadduck |
| 7,678,111 B2 | 3/2010 | Mulier |
| 7,727,228 B2 | 6/2010 | Abboud |
| 7,753,871 B2 | 7/2010 | Mehier |
| 7,794,460 B2 | 9/2010 | Mulier |
| 7,831,133 B2 | 11/2010 | Vinegar |
| 7,892,229 B2 | 2/2011 | Shadduck |
| 7,896,871 B2 | 3/2011 | Bhushan |
| 7,913,698 B2 | 3/2011 | Barry |
| 7,993,323 B2 | 8/2011 | Barry |
| 8,014,711 B2 | 9/2011 | Ito |
| 8,016,823 B2 | 9/2011 | Shadduck |
| 8,145,113 B2 | 3/2012 | Murakami |
| 8,147,532 B2 | 4/2012 | Barry |
| 8,187,269 B2 | 5/2012 | Shadduck |
| 8,216,224 B2 | 7/2012 | Morris |
| 8,224,165 B2 | 7/2012 | Vinegar |
| 8,226,637 B2 | 7/2012 | Satake |
| 8,229,588 B2 | 7/2012 | Tsen |
| 8,231,617 B2 | 7/2012 | Satake |
| 8,251,985 B2 | 8/2012 | Hoey |
| 8,272,383 B2 | 9/2012 | Hoey |
| 8,273,079 B2 | 9/2012 | Hoey |
| 8,313,485 B2 | 11/2012 | Shadduck |
| 8,322,335 B2 | 12/2012 | Barry |
| 8,355,623 B2 | 1/2013 | Vinegar |
| 8,372,065 B2 | 2/2013 | Hoey |
| 8,388,611 B2 | 3/2013 | Shadduck |
| 8,419,723 B2 | 4/2013 | Shadduck |
| 8,437,870 B2 | 5/2013 | Tsai |
| 8,444,636 B2 | 5/2013 | Shadduck |
| 8,512,326 B2 | 8/2013 | Shadduck |
| 8,521,074 B2 | 8/2013 | Murakami |
| 8,574,226 B2 | 11/2013 | Shadduck |
| 8,579,888 B2 | 11/2013 | Hoey |
| 8,579,892 B2 | 11/2013 | Hoey |
| 8,579,893 B2 | 11/2013 | Hoey |
| 8,585,645 B2 | 11/2013 | Barry |
| 8,585,692 B2 | 11/2013 | Shadduck |
| 8,632,530 B2 | 1/2014 | Hoey |
| 8,641,711 B2 | 2/2014 | Kelly |
| 8,647,339 B2 | 2/2014 | Satake |
| 8,721,632 B2 | 5/2014 | Hoey |
| 8,734,380 B2 | 5/2014 | Barry |
| 8,758,341 B2 | 6/2014 | Shadduck |
| 8,761,626 B2 | 6/2014 | Seo |
| 8,801,702 B2 | 8/2014 | Hoey |
| 8,805,466 B2 | 8/2014 | Salahieh |
| 8,858,549 B2 | 10/2014 | Shadduck |
| 8,900,223 B2 | 12/2014 | Shadduck |
| 8,911,430 B2 | 12/2014 | Hoey |
| 9,113,858 B2 | 8/2015 | Barry |
| 9,113,944 B2 | 8/2015 | Shadduck |
| 9,125,667 B2 | 9/2015 | Stone |
| 9,161,801 B2 | 10/2015 | Hoey |
| 9,179,973 B2 | 11/2015 | Nabutovsky |
| 9,198,708 B2 | 12/2015 | Hoey |
| 9,204,889 B2 | 12/2015 | Shadduck |
| 9,345,507 B2 | 5/2016 | Hoey |
| 9,387,310 B2 | 7/2016 | Satake |
| 9,433,457 B2 | 9/2016 | Shadduck |
| 9,468,487 B2 | 10/2016 | Shadduck |
| 9,526,555 B2 | 12/2016 | Hoey |
| 9,615,875 B2 | 4/2017 | Shadduck |
| 9,757,535 B2 | 9/2017 | Rajagopalan |
| 9,844,641 B2 | 12/2017 | Rajagopalan |
| 9,907,599 B2 | 3/2018 | Hoey |
| 9,974,607 B2 | 5/2018 | Stone |
| 10,179,019 B2 | 1/2019 | Chee |
| 10,299,857 B2 | 5/2019 | Rajagopalan |
| 10,842,557 B2 | 11/2020 | Sharma |
| 10,864,352 B2 | 12/2020 | Rajagopalan |
| 11,806,066 B2 | 11/2023 | Sharma |
| 11,864,809 B2 | 1/2024 | Sharma |
| 12,303,185 B2 | 5/2025 | Caplan |
| 12,329,439 B1 | 6/2025 | Caplan |
| 2001/0020167 A1 | 9/2001 | Woloszko |
| 2001/0029370 A1 | 10/2001 | Hodva |
| 2001/0037106 A1 | 11/2001 | Shadduck |

(56)　　　　References Cited

U.S. PATENT DOCUMENTS

| | | |
|---|---|---|
| 2002/0013601 A1 | 1/2002 | Nobles |
| 2002/0019627 A1 | 2/2002 | Maguire |
| 2002/0049438 A1 | 4/2002 | Sharkey |
| 2002/0077516 A1 | 6/2002 | Flanigan |
| 2002/0078956 A1 | 6/2002 | Sharpe |
| 2002/0082667 A1 | 6/2002 | Shadduck |
| 2002/0095152 A1 | 7/2002 | Ciarrocca |
| 2002/0111386 A1 | 8/2002 | Sekins |
| 2002/0133147 A1 | 9/2002 | Marchitto |
| 2002/0143325 A1 | 10/2002 | Sampson |
| 2002/0156470 A1 | 10/2002 | Shadduck |
| 2002/0161326 A1 | 10/2002 | Sussman |
| 2002/0177846 A1 | 11/2002 | Mulier |
| 2002/0193789 A1 | 12/2002 | Underwood |
| 2003/0028189 A1 | 2/2003 | Woloszko |
| 2003/0040742 A1 | 2/2003 | Underwood |
| 2003/0069575 A1 | 4/2003 | Chin |
| 2003/0088145 A1 | 5/2003 | Scott |
| 2003/0088246 A1 | 5/2003 | Swartz |
| 2003/0097126 A1 | 5/2003 | Woloszko |
| 2003/0099279 A1 | 5/2003 | Venkatasubramanian |
| 2003/0109869 A1 | 6/2003 | Shadduck |
| 2003/0130655 A1 | 7/2003 | Woloszko |
| 2003/0130738 A1 | 7/2003 | Hovda |
| 2003/0144654 A1 | 7/2003 | Hilal |
| 2003/0158545 A1 | 8/2003 | Hovda |
| 2003/0163178 A1 | 8/2003 | Davison |
| 2003/0181922 A1 | 9/2003 | Alferness |
| 2003/0204138 A1 | 10/2003 | Choi |
| 2003/0212394 A1 | 11/2003 | Pearson |
| 2003/0212395 A1 | 11/2003 | Woloszko |
| 2003/0216729 A1 | 11/2003 | Marchitto |
| 2003/0225364 A1 | 12/2003 | Kraft |
| 2004/0006333 A1 | 1/2004 | Arnold |
| 2004/0024398 A1 | 2/2004 | Hovda |
| 2004/0024399 A1 | 2/2004 | Sharps |
| 2004/0031494 A1 | 2/2004 | Danek |
| 2004/0037986 A1 | 2/2004 | Houston |
| 2004/0038868 A1 | 2/2004 | Ingenito |
| 2004/0047855 A1 | 3/2004 | Ingenito |
| 2004/0049180 A1 | 3/2004 | Sharps |
| 2004/0054366 A1 | 3/2004 | Davison |
| 2004/0055606 A1 | 3/2004 | Hendricksen |
| 2004/0059313 A1 | 3/2004 | Tachibana |
| 2004/0068256 A1 | 4/2004 | Rizoiu |
| 2004/0068306 A1 | 4/2004 | Shadduck |
| 2004/0087937 A1 | 5/2004 | Eggers |
| 2004/0116922 A1 | 6/2004 | Hovda |
| 2004/0193150 A1 | 9/2004 | Sharkey |
| 2004/0199226 A1 | 10/2004 | Shadduck |
| 2004/0230188 A1 | 11/2004 | Cioanta |
| 2004/0230190 A1 | 11/2004 | Dahla |
| 2004/0230316 A1 | 11/2004 | Cioanta |
| 2004/0254532 A1 | 12/2004 | Mehier |
| 2005/0004634 A1 | 1/2005 | Ricart |
| 2005/0010205 A1 | 1/2005 | Hovda |
| 2005/0015047 A1 | 1/2005 | Shah |
| 2005/0095168 A1 | 5/2005 | Centanni |
| 2005/0119650 A1 | 6/2005 | Sanders |
| 2005/0149065 A1 | 7/2005 | Modesitt |
| 2005/0166925 A1 | 8/2005 | Wilson |
| 2005/0171582 A1 | 8/2005 | Matlock |
| 2005/0177147 A1 | 8/2005 | Vancelette |
| 2005/0187543 A1 | 8/2005 | Underwood |
| 2005/0215991 A1 | 9/2005 | Altman |
| 2005/0222485 A1 | 10/2005 | Shaw |
| 2005/0228423 A1 | 10/2005 | Khashayar |
| 2005/0228424 A1 | 10/2005 | Khashayar |
| 2005/0240171 A1 | 10/2005 | Forrest |
| 2005/0267468 A1 | 12/2005 | Truckai |
| 2005/0283143 A1 | 12/2005 | Rizoiu |
| 2006/0004400 A1 | 1/2006 | Mcgurk |
| 2006/0036237 A1 | 2/2006 | Davison |
| 2006/0041277 A1 | 2/2006 | Deem |
| 2006/0047291 A1 | 3/2006 | Barry |
| 2006/0085054 A1 | 4/2006 | Zikorus |
| 2006/0089636 A1 | 4/2006 | Christopherson |
| 2006/0095032 A1 | 5/2006 | Jackson |
| 2006/0100619 A1 | 5/2006 | Mcclurken |
| 2006/0130830 A1 | 6/2006 | Barry |
| 2006/0135955 A1 | 6/2006 | Shadduck |
| 2006/0161233 A1 | 7/2006 | Barry |
| 2006/0178670 A1 | 8/2006 | Woloszko |
| 2006/0200076 A1 | 9/2006 | Gonzalez |
| 2006/0200191 A1 | 9/2006 | Zadno-Azizi |
| 2006/0224154 A1 | 10/2006 | Shadduck |
| 2006/0264832 A1 | 11/2006 | Skwarek |
| 2006/0276871 A1 | 12/2006 | Lamson |
| 2007/0032785 A1 | 2/2007 | Diederich |
| 2007/0036417 A1 | 2/2007 | Argiro |
| 2007/0049920 A1 | 3/2007 | Mcclurken |
| 2007/0083085 A1 | 4/2007 | Birnkrant |
| 2007/0091087 A1 | 4/2007 | Zuiderveld |
| 2007/0142846 A1 | 6/2007 | Catanese |
| 2007/0179496 A1 | 8/2007 | Swoyer |
| 2007/0225744 A1 | 9/2007 | Nobles |
| 2007/0225750 A1 | 9/2007 | Ren |
| 2007/0239197 A1 | 10/2007 | Dubey |
| 2007/0250056 A1 | 10/2007 | Vanney |
| 2007/0265687 A1 | 11/2007 | Deem |
| 2008/0021484 A1 | 1/2008 | Catanese |
| 2008/0021485 A1 | 1/2008 | Catanese |
| 2008/0033232 A1 | 2/2008 | Catanese |
| 2008/0033458 A1 | 2/2008 | Mclean |
| 2008/0033488 A1 | 2/2008 | Catanese |
| 2008/0033493 A1 | 2/2008 | Deckman |
| 2008/0039833 A1 | 2/2008 | Catanese |
| 2008/0039872 A1 | 2/2008 | Catanese |
| 2008/0039874 A1 | 2/2008 | Catanese |
| 2008/0039875 A1 | 2/2008 | Catanese |
| 2008/0039876 A1 | 2/2008 | Catanese |
| 2008/0039893 A1 | 2/2008 | Mclean |
| 2008/0039894 A1 | 2/2008 | Catanese |
| 2008/0046045 A1 | 2/2008 | Yon |
| 2008/0103566 A1 | 5/2008 | Mehier |
| 2008/0110457 A1 | 5/2008 | Barry |
| 2008/0114297 A1 | 5/2008 | Barry |
| 2008/0132826 A1 | 6/2008 | Shadduck |
| 2008/0167649 A1 | 7/2008 | Edwards |
| 2008/0183036 A1 | 7/2008 | Saadat |
| 2008/0208187 A1 | 8/2008 | Bhushan |
| 2008/0208189 A1 | 8/2008 | Van Wyk |
| 2008/0249399 A1 | 10/2008 | Appling |
| 2008/0275440 A1 | 11/2008 | Kratoska |
| 2008/0281267 A1 | 11/2008 | Mehier |
| 2008/0300571 A1 | 12/2008 | Lepivert |
| 2009/0018553 A1 | 1/2009 | Mclean |
| 2009/0054868 A1 | 2/2009 | Sharkey |
| 2009/0054869 A1 | 2/2009 | Sharkey |
| 2009/0054870 A1 | 2/2009 | Sharkey |
| 2009/0054871 A1 | 2/2009 | Sharkey |
| 2009/0082837 A1 | 3/2009 | Gellman |
| 2009/0099544 A1 | 4/2009 | Munrow |
| 2009/0105702 A1 | 4/2009 | Shadduck |
| 2009/0105703 A1 | 4/2009 | Shadduck |
| 2009/0125009 A1 | 5/2009 | Zikorus |
| 2009/0125010 A1 | 5/2009 | Sharkey |
| 2009/0149846 A1 | 6/2009 | Hoey |
| 2009/0216220 A1 | 8/2009 | Hoey |
| 2009/0221998 A1 | 9/2009 | Epstein |
| 2009/0227998 A1 | 9/2009 | Aljuri |
| 2009/0240244 A1 | 9/2009 | Malis |
| 2009/0277457 A1 | 11/2009 | Hoey |
| 2009/0301483 A1 | 12/2009 | Barry |
| 2009/0306640 A1 | 12/2009 | Glaze |
| 2009/0312753 A1 | 12/2009 | Shadduck |
| 2010/0016757 A1 | 1/2010 | Greenburg |
| 2010/0049031 A1 | 2/2010 | Fruland |
| 2010/0076416 A1 | 3/2010 | Hoey |
| 2010/0094270 A1 | 4/2010 | Sharma |
| 2010/0114082 A1 | 5/2010 | Sharma |
| 2010/0114083 A1 | 5/2010 | Sharma |
| 2010/0145254 A1 | 6/2010 | Shadduck |
| 2010/0145325 A1 | 6/2010 | Hoey |

(56)                References Cited

U.S. PATENT DOCUMENTS

| | | |
|---|---|---|
| 2010/0145326 A1 | 6/2010 | Hoey |
| 2010/0160905 A1 | 6/2010 | Shadduck |
| 2010/0168624 A1 | 7/2010 | Sliwa |
| 2010/0168736 A1 | 7/2010 | Wang |
| 2010/0179416 A1 | 7/2010 | Hoey |
| 2010/0179528 A1 | 7/2010 | Shadduck |
| 2010/0204688 A1 | 8/2010 | Hoey |
| 2010/0211070 A1 | 8/2010 | Subramaniam |
| 2010/0262133 A1 | 10/2010 | Hoey |
| 2010/0274260 A1 | 10/2010 | Darpiany |
| 2010/0286679 A1 | 11/2010 | Hoey |
| 2010/0292767 A1 | 11/2010 | Hoey |
| 2010/0298948 A1 | 11/2010 | Hoey |
| 2011/0077628 A1 | 3/2011 | Hoey |
| 2011/0118717 A1 | 5/2011 | Shadduck |
| 2011/0160648 A1 | 6/2011 | Hoey |
| 2011/0172654 A1 | 7/2011 | Barry |
| 2011/0184400 A1 | 7/2011 | Pageard |
| 2011/0190751 A1 | 8/2011 | Ingle |
| 2011/0238144 A1 | 9/2011 | Hoey |
| 2011/0264090 A1 | 10/2011 | Shadduck |
| 2011/0264176 A1 | 10/2011 | Jackson |
| 2011/0276046 A1 | 11/2011 | Heimbecher |
| 2012/0065632 A1 | 3/2012 | Shadduck |
| 2012/0078078 A1 | 3/2012 | Macadam |
| 2012/0101413 A1 | 4/2012 | Beetel |
| 2012/0116376 A1 | 5/2012 | Hoey |
| 2012/0165812 A1 | 6/2012 | Christian |
| 2012/0197245 A1 | 8/2012 | Burnett |
| 2012/0197358 A1 | 8/2012 | Prescott |
| 2012/0232409 A1 | 9/2012 | Stahmann |
| 2012/0259271 A1 | 10/2012 | Shadduck |
| 2012/0323167 A1 | 12/2012 | Hoey |
| 2013/0006231 A1 | 1/2013 | Sharma |
| 2013/0030410 A1 | 1/2013 | Drasler |
| 2013/0074847 A1 | 3/2013 | Hoey |
| 2013/0079645 A1 | 3/2013 | Amirana |
| 2013/0079772 A1 | 3/2013 | Shadduck |
| 2013/0116683 A1 | 5/2013 | Shadduck |
| 2013/0165914 A1 | 6/2013 | Satake |
| 2013/0172867 A1 | 7/2013 | Shadduck |
| 2013/0197555 A1 | 8/2013 | Schaer |
| 2013/0237978 A1 | 9/2013 | Shadduck |
| 2013/0267939 A1 | 10/2013 | Barry |
| 2013/0267947 A1 | 10/2013 | Orszulak |
| 2013/0274730 A1 | 10/2013 | Anderson |
| 2013/0296837 A1 | 11/2013 | Burnett |
| 2013/0345670 A1 | 12/2013 | Rajagopalan |
| 2014/0025057 A1 | 1/2014 | Hoey |
| 2014/0031805 A1 | 1/2014 | Shadduck |
| 2014/0107637 A1 | 4/2014 | Hoey |
| 2014/0114306 A1 | 4/2014 | Harada |
| 2014/0200568 A1 | 7/2014 | Sharma |
| 2014/0200569 A1 | 7/2014 | Shadduck |
| 2014/0200570 A1 | 7/2014 | Hoey |
| 2014/0276713 A1 | 9/2014 | Hoey |
| 2014/0288543 A1 | 9/2014 | Hoey |
| 2014/0324037 A1 | 10/2014 | Hoey |
| 2014/0357956 A1 | 12/2014 | Salahieh |
| 2014/0358137 A1 | 12/2014 | Hu |
| 2014/0371736 A1 | 12/2014 | Levin |
| 2015/0025515 A1 | 1/2015 | Hoey |
| 2015/0025516 A1 | 1/2015 | Hoey |
| 2015/0080883 A1 | 3/2015 | Haverkost |
| 2015/0126990 A1 | 5/2015 | Sharma |
| 2015/0148738 A1 | 5/2015 | Caplan |
| 2015/0182740 A1 | 7/2015 | Mickelsen |
| 2015/0265329 A1 | 9/2015 | Lalonde |
| 2016/0220297 A1 | 8/2016 | Kroon |
| 2016/0270838 A1 | 9/2016 | Hastings |
| 2016/0310200 A1 | 10/2016 | Wang |
| 2016/0354140 A1 | 12/2016 | Sharma |
| 2016/0354144 A1 | 12/2016 | Caplan |
| 2017/0165002 A1 | 6/2017 | Sharma |
| 2017/0231678 A1 | 8/2017 | Sharma |
| 2017/0312007 A1 | 11/2017 | Harlev |
| 2017/0312024 A1 | 11/2017 | Harlev |
| 2017/0333122 A1 | 11/2017 | Rajagopalan |
| 2017/0367755 A1 | 12/2017 | Sharma |
| 2019/0110830 A1 | 4/2019 | Hastings |
| 2019/0133712 A1 | 5/2019 | Sharma |
| 2019/0269449 A1 | 9/2019 | Hastings |
| 2019/0343571 A1 | 11/2019 | Shadduck |
| 2019/0388133 A1 | 12/2019 | Sharma |
| 2020/0085496 A1 | 3/2020 | Sharma |
| 2021/0007796 A1 | 1/2021 | Panescu |
| 2021/0145534 A1 | 5/2021 | Kulstad |
| 2021/0212745 A1 | 7/2021 | Jackson |
| 2022/0151674 A1 | 5/2022 | Sharma |

FOREIGN PATENT DOCUMENTS

| | | |
|---|---|---|
| CN | 102238920 | 9/2011 |
| CN | 102238920 A | 11/2011 |
| CN | 103582463 A | 2/2014 |
| CN | 103619276 A | 3/2014 |
| CN | 104856757 A | 8/2015 |
| CN | 104884118 A | 9/2015 |
| CN | 105228547 A | 1/2016 |
| CN | 105726292 A | 7/2016 |
| CN | 105813591 A | 7/2016 |
| CN | 107242901 A | 10/2017 |
| CN | 107847259 A | 3/2018 |
| EP | 0508942 A2 | 10/1992 |
| EP | 1602338 B1 | 12/2005 |
| EP | 1039862 B1 | 5/2008 |
| EP | 2341859 | 7/2011 |
| EP | 2884928 A1 | 6/2015 |
| FR | 2655548 | 6/1991 |
| WO | 1992010142 | 6/1992 |
| WO | 1995028198 A1 | 10/1995 |
| WO | 9902096 A | 1/1999 |
| WO | 1999053853 | 10/1999 |
| WO | 2000029055 | 5/2000 |
| WO | 2001024715 | 4/2001 |
| WO | 02069821 | 9/2002 |
| WO | 2002069821 | 9/2002 |
| WO | 2003070302 | 8/2003 |
| WO | 2003086498 | 10/2003 |
| WO | 2005025635 | 3/2005 |
| WO | 2005102175 | 11/2005 |
| WO | 2006003665 | 1/2006 |
| WO | 2006004482 | 1/2006 |
| WO | 2006019728 A2 | 2/2006 |
| WO | 2006055695 | 5/2006 |
| WO | 2006108974 | 10/2006 |
| WO | 2009009398 | 1/2009 |
| WO | 2009074844 A1 | 6/2009 |
| WO | 2010042461 A1 | 4/2010 |
| WO | 2012167213 A2 | 12/2012 |
| WO | 2013044182 A1 | 3/2013 |
| WO | 2013086461 A1 | 6/2013 |
| WO | 2013152119 A1 | 10/2013 |
| WO | 2014113724 A2 | 7/2014 |
| WO | 2017201504 A1 | 11/2017 |
| WO | 2018089773 A1 | 5/2018 |
| WO | 2021041818 A1 | 3/2021 |

OTHER PUBLICATIONS

International Search Report for PCT/US2017/033693, Oct. 2, 2017.
Thibeau; AW-06995-001; Text, Manual, Novasure, V1, EN, US; Aug. 26, 2011; pp. 1-23; Hologic, Inc.
Sharma et al; Barrett's Oesophagus, A randomised controlled trial of ablation of Barrett's oesophagus with multipolar electrocoagulation versus argon plasma coagulation in combination with acid suppression: long term results; Gut; 2006; 55:1233-1239; doi: 10.1136/gut.2005.086777.
International Search Report for PCT/US2016/012840, Aug. 18, 2016.
Sharma et al; Balloon-based, cicrumferential, endoscopic radiofrequency ablation of Barrett's esophagus: 1-year follow-up of 100 patients

(56)        References Cited

OTHER PUBLICATIONS (with video); Gastrointestinal Endoscopy; 2007; vol. 65, No. 2; 0016-5/$32.00 doi:10.1016/j.gie.2006.09.033; pp. 185-195.

Sanfilippo et al; Update: Options in Endometrial Ablation; Supplement to OBG Management; Dec. 2009; pp. S1-S24; Dowden Health Media.

United States FDA; Summary of Safety and Effectiveness Data: Cryogen, Inc .: Her Option Uterine Cryoablation Therapy System; PMA P000032; Sep. 14, 2001; pp. 1-22.

American Medical Systems, Inc.; her option office cryoablation therapy Resource Guide; 2007; pp. 1-29; American Medical Systems, Inc.. 10700 Bren Road West, Minnetonka, MN 55343 USA.

Boston Scientific; HTA System Endometrial Ablation System; 2006; BVU 1090 Rev. A 10M Sep. 2006-Sep. 2008; Boston Scientific Corporation, One Boston Scientific Place, Natick, MA 01760-1537.

Ethicon Women's Health & Urology; Instructions for Use, Gynecare Thermachoice III Uterine Balloon Therapy System, Thermal Balloon Ablation Silicone Catheter and Syringe (Single-Use); Mar. 26, 2008; pp. 1-156; TCIII_389630.R06_Main.indd; Gynecare, a division of Ethicon, Inc. a Johnson & Johnson company, Sommerville, NJ, 08876-0151 USA.

Johnston et al.; Cryoablation of Barrett's esophagus: a pilot study; Gastrointestinal Endoscopy; 2005; pp. 842-848; vol. 62, No. 6, 0016-5107/$30.00 doi:10.1016/j.gie.2005.05.008; American Society for Gastrointestinal Endoscopy.

Carter; Endometrial Ablation: More Choices, More Options; The Female Patient; 2005; pp. 35-40; 30(12).

International Search Report for PCT/US2009/059609, Mar. 5, 2010.

International Search Report for PCT/US2012/040639, Dec. 18, 2012.

International Search Report for PCT/US2014/012131, Jul. 30, 2014.

International Search Report for PCT/US19/50662, Jan. 7, 2020.

Written Opinion of the International Searching Authority for PCT/US19/50662, Jan. 7, 2020.

International Search Report for PCT/US19/34991, Sep. 20, 2019.

Written Opinion of the International Searching Authority for PCT/US19/34991, Sep. 20, 2019.

International Search Report for PCT/US21/13582, May 13, 2021.

Written Opinion of the International Searching Authority for PCT/US21/13582, May 13, 2021.

International Search Report for PCT/US20/48419, Dec. 18, 2020.

Written Opinion of the International Searching Authority for PCT/US20/48419, Dec. 18, 2020.

Kim, J. W., Kim, D. H., Roh, Y. K., Ju, S. Y., Nam, H. Y., Nam, G. E., Kim, D. W., Lee, S. H., Lee, C. W., Han, K., & Park, Y. G. ( 2015). Serum Ferritin Levels Are Positively Associated With Metabolically Obese Normal Weight: A Nationwide Population-Based Study. Medicine, 94(52), e2335 (Year: 2015).

Läpädat, A. M., Gheonea, D. I., Florescu, L. M., & Gheonea, I. A. (2019). Before and After Treatment Quantitative Assessment of Hepatic Steatosis in a Romanian Population Using Magnetic Resonance Liver Spectroscopy. Current health sciences journal, 45(3) 258-262 (Year: 2019).

Stål P. (2015). Liver fibrosis in non-alcoholic fatty liver disease—diagnostic challenge with prognostic significance. World journal of gastroenterology, 21(39), 11077-11087 (Year: 2015).

Singh, S., Allen, A. M., Wang, Z., Prokop, L. J., Murad, M. H., & Loomba, R. (2015). Fibrosis progression [. . . ] and meta-analysis of paired-biopsy studies. Clinical gastroenterology and hepatology : the official clinical practice journal of the American Gastroenterological Association, 13(4), 643-e40 (Year: 2015).

El-Zefzafy, W., Eltokhy, H., Mohamed, N. A., & Abu-Zahab, Z. (2015). Significance of Serum Cytokeratin-18 in Prediction of U Hepatocellular Carcinoma in Chronic Hepatitis C Infected Egyptian Patients. Open access Macedonian journal of medical sciences, 3(1), 117-123 (Year: 2015).

Lee, D. H., Lee, J. M., Yoon, J. H., Kim, Y. J., Lee, J. H., Yu, S. J., & Han, J. K. (2018). Liver Stiffness Measured by Two-Dimensional Shear-Wave Elastography: Prognostic Value after Radiofrequency Ablation for Hepatocellular Carcinoma. Liver cancer, 7(1), 65-75 (Year: 2018).

International Search Report for PCT/US2021/071778, Feb. 14, 2022.

"Understanding Microprocessors, Advantages of 32-bit CPUs and DSPs." Stevens. Stevens Water Monitoring Systems, Inc., May 12, 2008. Web. Feb. 4, 2013. < http://web.archive.org/web/20080512144927/http://www.stevenswater.com/articles/cpu.aspx>.

Hai; Photoselective Vaporization Prostatectomy: A Palliative Treatment Option for Men with Urinary Obstruction Secondary to Prostate Cancer; PCRI Prost. Cancer Rsrch. Inst. Reprint. from PCRI Insights Nov. 2005, vol. 8(4); pp. 4.

Van De Velde; Vapo-cauterization of the uterus; Amer. J. Med. Sci .; vol. CXVII; 1899.

Blacker; Vaporization of the uterus; J. Obstet. & Gyn .; pp. 488-511; 1901.

Neuwirth et al.; The endometrial ablator: a new instrument; Obst. & Gyn.; vol. 83; No. 5; part 1; pp. 792-796; 1994.

Prior et al.; Treatment of mennorrhagia by radiofrequency heating; Int. J. Hyperthermia; vol. 7; No. 2; pp. 213-220; 1991.

International Search Report for PCT/US24/18261, Sep. 25, 2024.

International Search Report for PCT/US24/25351, Jul. 15, 2024.

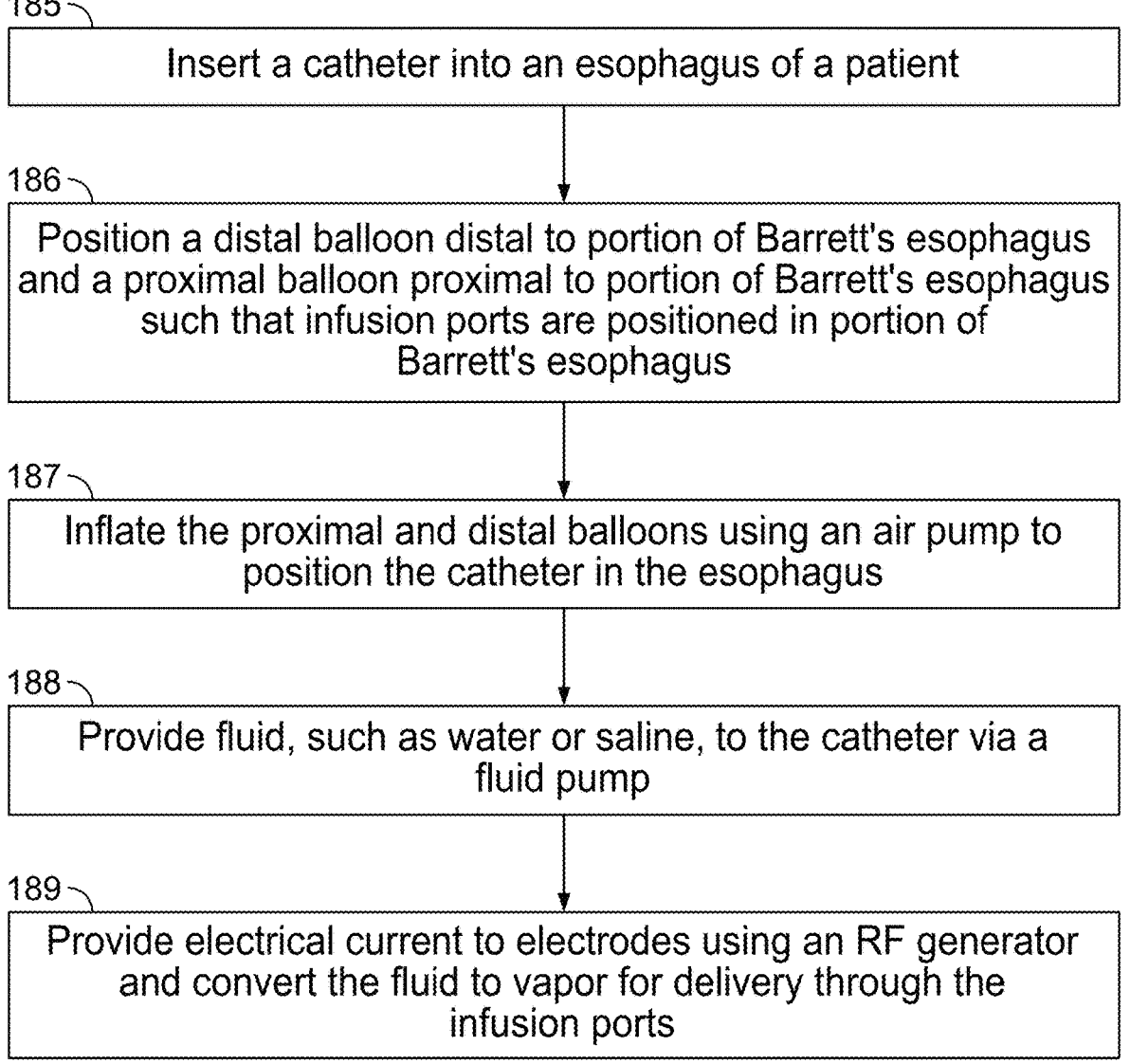

185 — Insert a catheter into an esophagus of a patient

186 — Position a distal balloon distal to portion of Barrett's esophagus and a proximal balloon proximal to portion of Barrett's esophagus such that infusion ports are positioned in portion of Barrett's esophagus 187 — Inflate the proximal and distal balloons using an air pump to position the catheter in the esophagus 188 — Provide fluid, such as water or saline, to the catheter via a fluid pump 189 — Provide electrical current to electrodes using an RF generator and convert the fluid to vapor for delivery through the infusion ports

FIG. 1J

112 Insert GI heat therapy device into GI tract

114 Initiate saline flow through heat therapy device

116 Heat saline to generate vapor

118 Condense vapor on tissue within GI tract

102 Insert ablation device into GI tract

104 Create seal

106 Deliver vapor into sealed portion

108 Condense vapor on tissue within GI tract

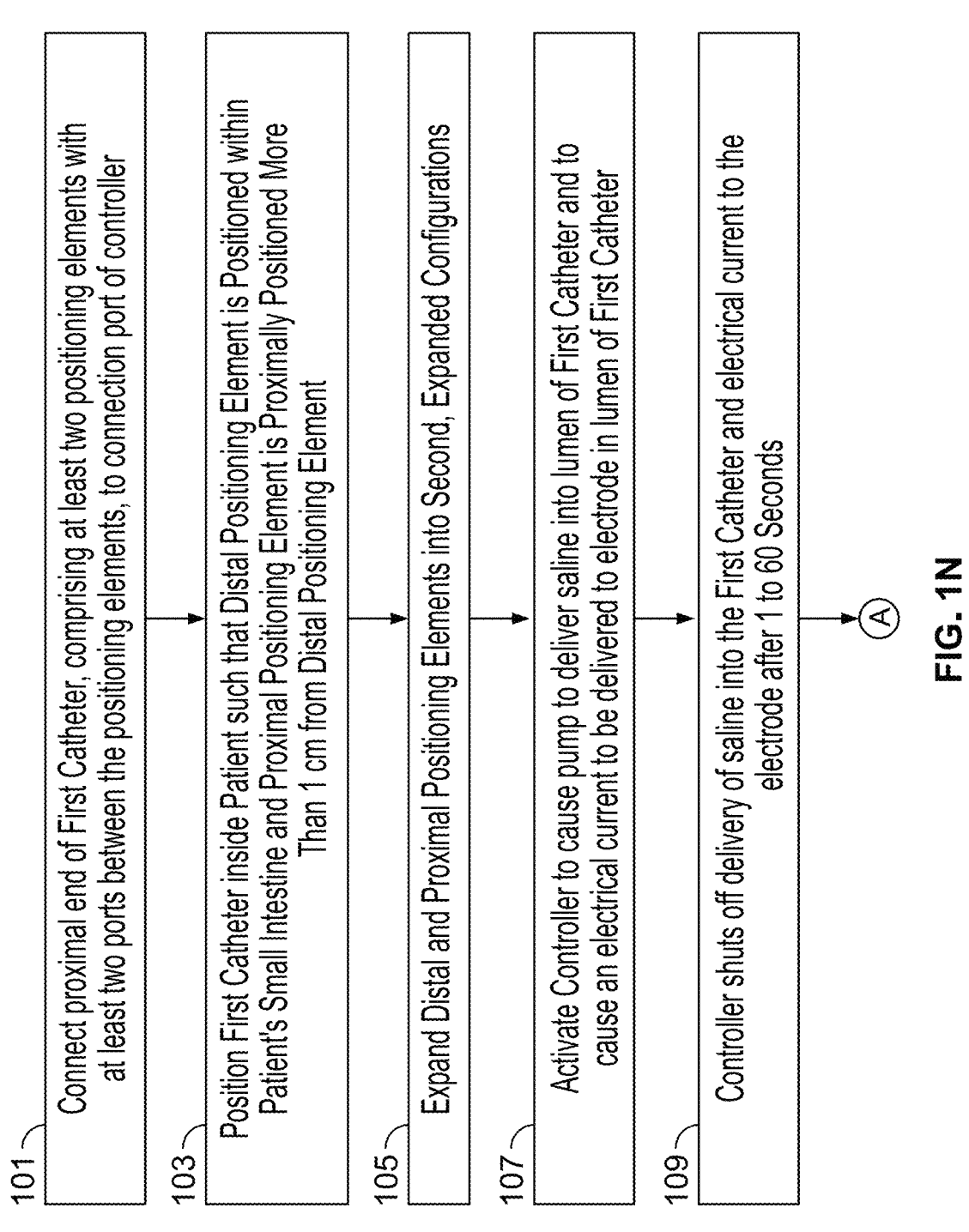

101 — Connect proximal end of First Catheter, comprising at least two positioning elements with at least two ports between the positioning elements, to connection port of controller 103 — Position First Catheter inside Patient such that Distal Positioning Element is Positioned within Patient's Small Intestine and Proximal Positioning Element is Proximally Positioned More Than 1 cm from Distal Positioning Element 105 — Expand Distal and Proximal Positioning Elements into Second, Expanded Configurations 107 — Activate Controller to cause pump to deliver saline into lumen of First Catheter and to cause an electrical current to be delivered to electrode in lumen of First Catheter 109 — Controller shuts off delivery of saline into the First Catheter and electrical current to the electrode after 1 to 60 Seconds

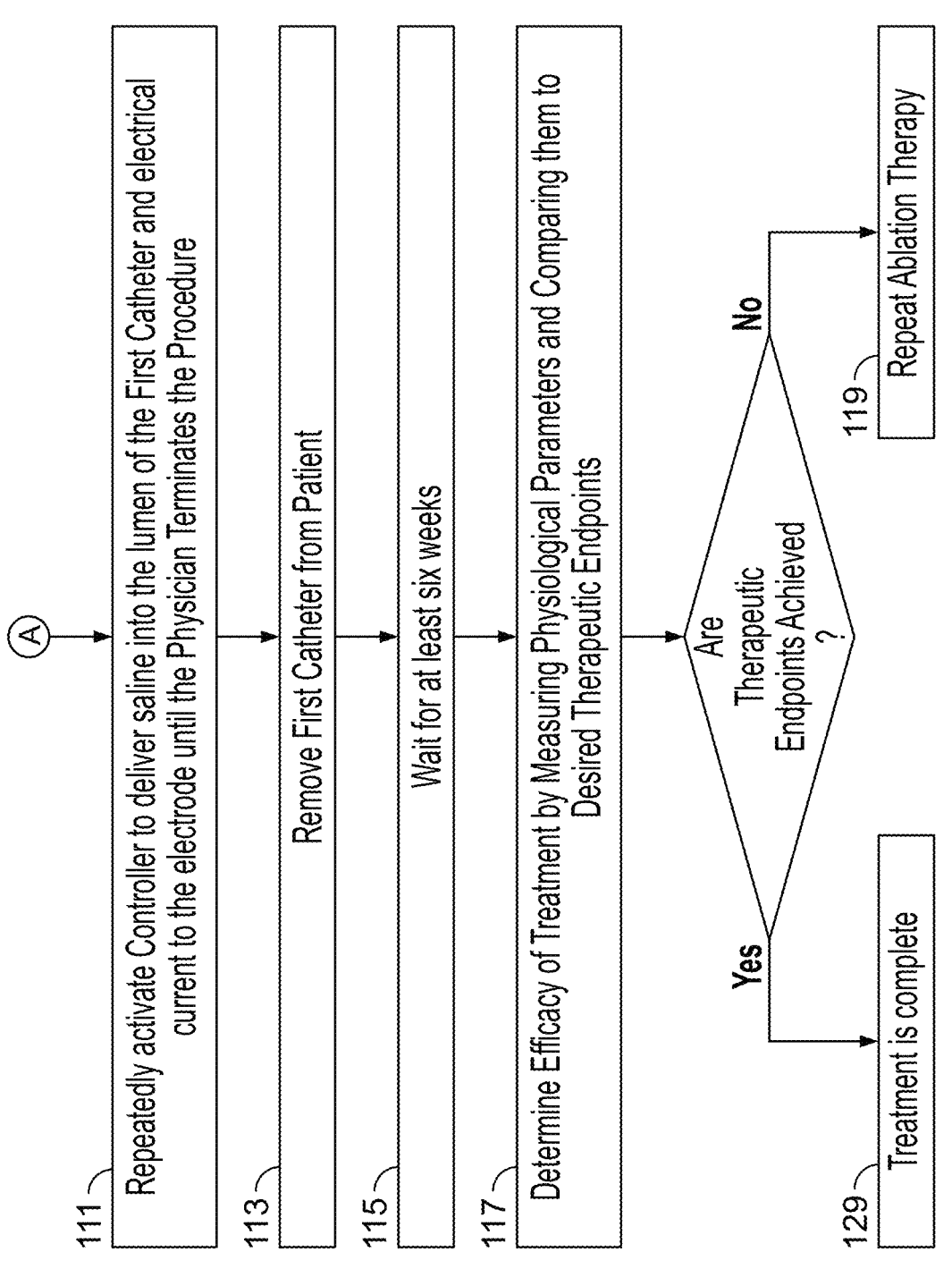

111 Repeatedly activate Controller to deliver saline into the lumen of the First Catheter and electrical current to the electrode until the Physician Terminates the Procedure 113 Remove First Catheter from Patient 115 Wait for at least six weeks 117 Determine Efficacy of Treatment by Measuring Physiological Parameters and Comparing them to Desired Therapeutic Endpoints Are Therapeutic Endpoints Achieved ?

No

Yes

119 Repeat Ablation Therapy

129 Treatment is complete

FIG. 1N (Cont.)

No silicone covering near edge. Silicone to stop 2-3mm from edge of stent/disk

104p

102p

100p

104p

104p

102p

100p

104p

BRAIDED TUBING - WITH CONDUCTIVE BRAID

- BRAIDED CATHETER BODY IS ONE "POLE".

- RF CURRENT PASSED BETWEEN CONDUCTIVE WIRE BRAID AND EXPOSED SECTIONS OF WIRE

- BRAID WIRE IS ONE POLE IN RF CIRCUIT, WIRE INSIDE OF TUBE IS SECOND POLE

FLEX-CIRCUIT DESIGN, FLEXIBLE CIRCUMFERENTIAL ELECTRODE

BI-POLAR TANDEM WIRE ELECTRODES

- SELECTIVELY REMOVE INSULATION TO EXPOSE WIRE ELECTRODE

- CAN REMOVE INSULATION FROM BOTH SIDES

| No | P/N | Description |
|---|---|---|
| 10 | | End Lure |
| 9 | | Reinforce Tube |
| 8 | | Back Handle |
| 7 | | Back Handle assy |
| 6 | | Front Handle |
| 5 | | Front Handle assy |
| 4 | | Distal Lock assy |
| 3 | | Outer Catheter |
| 2 | | Middle Catheter |
| 1 | | 19G EUS Needle |

1. Outer Catheter
2. Inner Catheter
3. Metal Needle Tip

1. Outer Catheter - 3.3 / 2.9: Braided Teflon
2. Middle Catheter -2.7 / 2.4: PTFE
3. Laser Cut Section
4. Needle-1.1/0.9:19G:SST
5. RF Electrode Array

| | Needle-19G | Inner Catheter | Outer Catheter |
|---|---|---|---|
| | SST 304 | PTFE | Braid-Braided |
| | Ø1.96/Ø1.76, Ø1.1/Ø0.9,Taper | Ø2.6/Ø2, Black | Ø3.3/Ø2.9, Bule, braided |
| | 3 | 2 | 1 |
| | 1 | 1 | 1 |

4101

4105

4102

Metal Needle

4201

4205

4301

4305

4202

4302

Insulated Coating

Insulating Material-PTFE, ePTFE or Silicone

Variable Stiffness allowing for bending at the middle portion yet allowing for pushability along the catheter body

Various Laser Cutting Designs

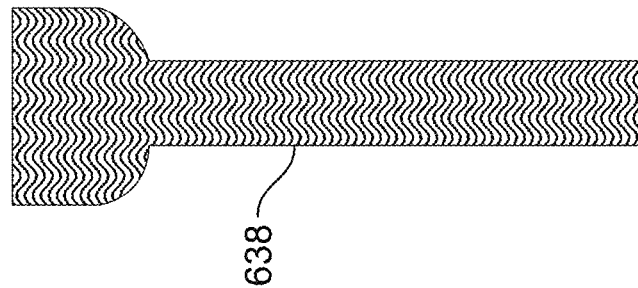
638
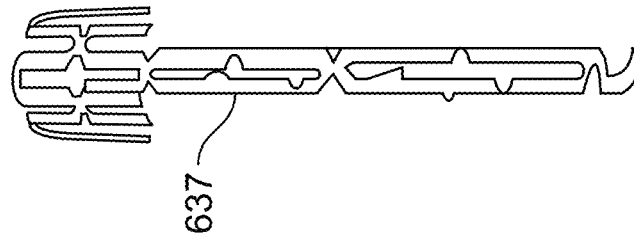
637
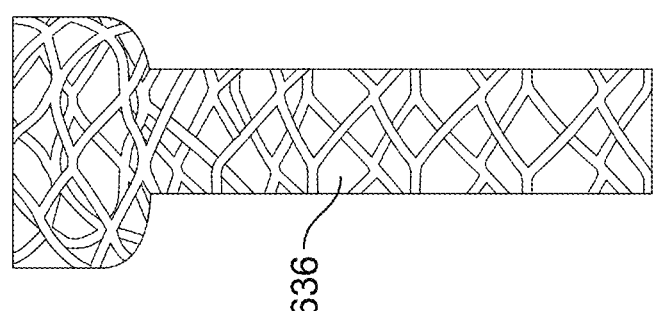
636
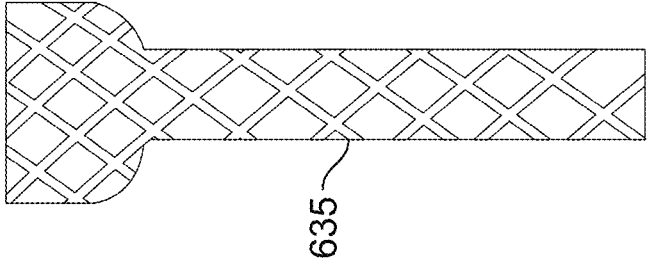
635
FIG. 6D

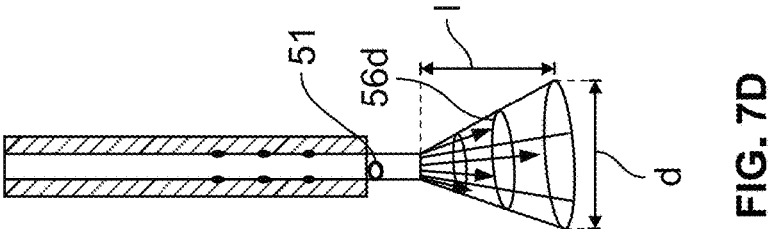
FIG. 7D
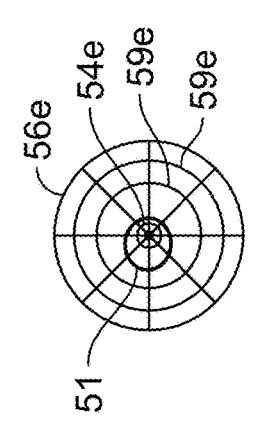
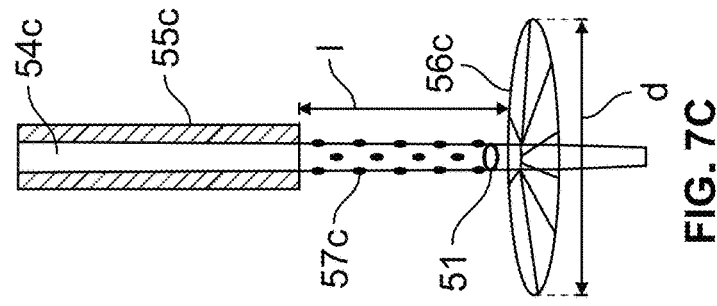
FIG. 7C
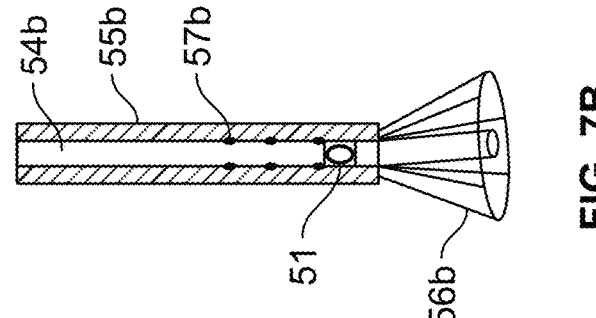
FIG. 7B
FIG. 7E
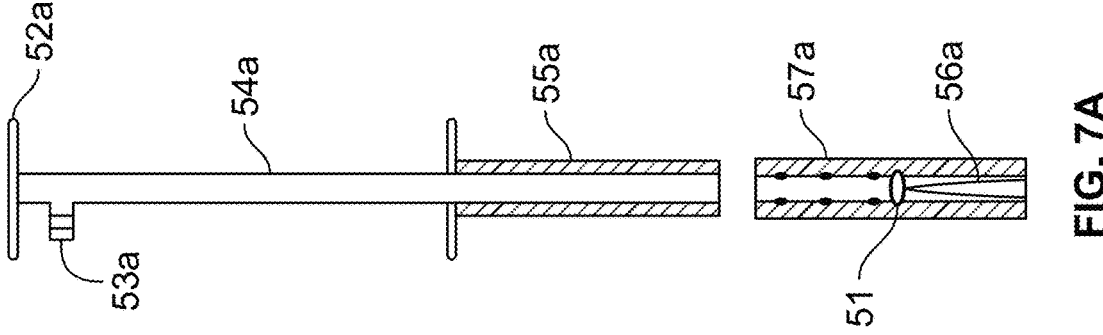
FIG. 7A Insulative Hood

805

806

807

Active RF electrode
808

815 Ball & Socket Joint

807 Catheter

806 Vapor Tip

Cone Attachment

805

810
812

837

815 Ball & Socket Joint

805

810
812

822

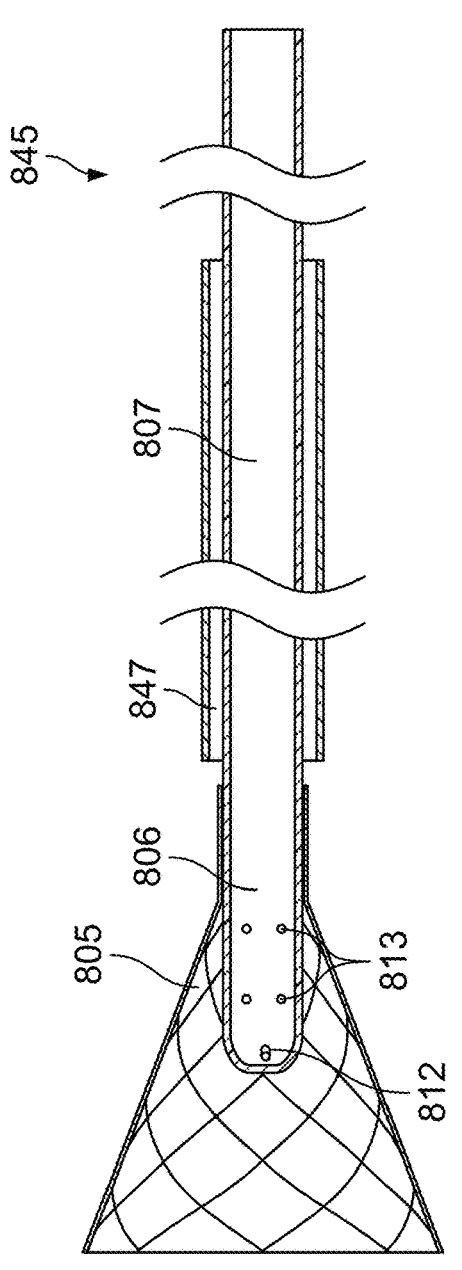
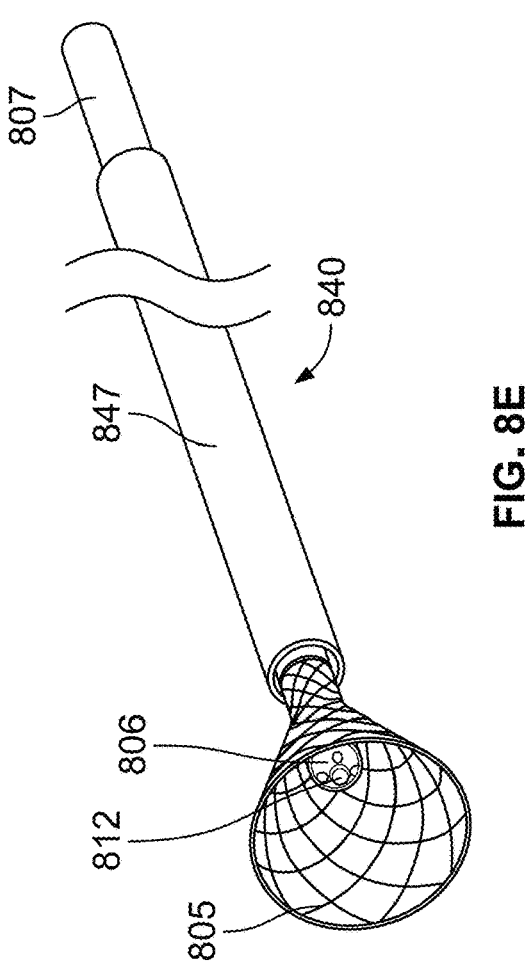
FIG. 8E
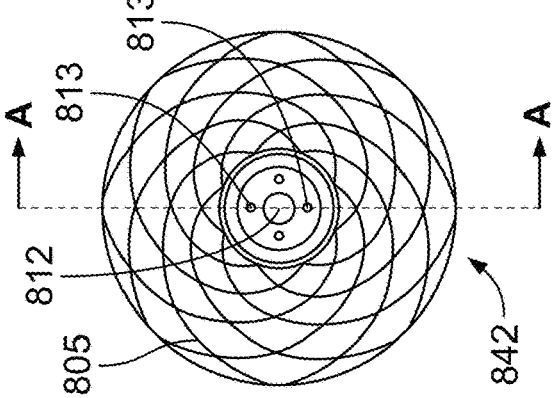

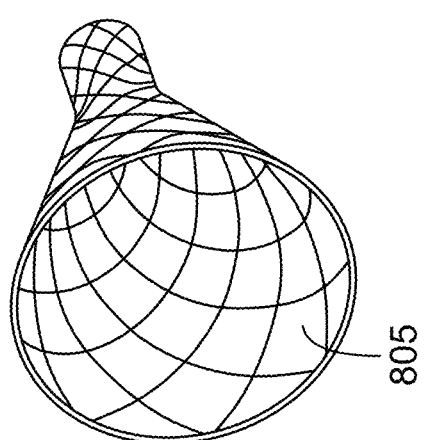
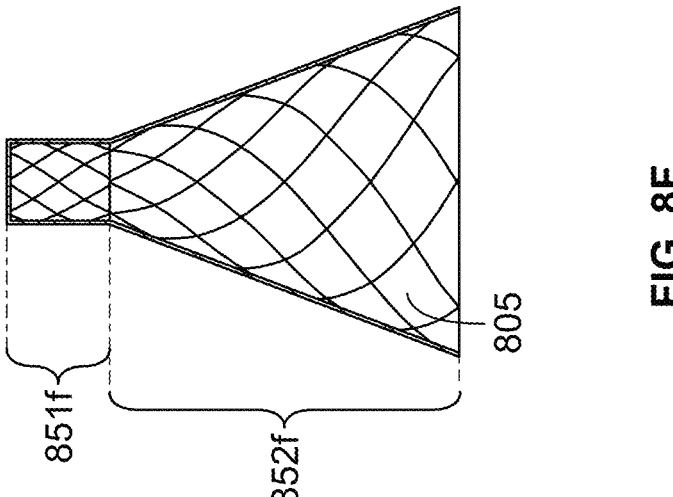
FIG. 8F
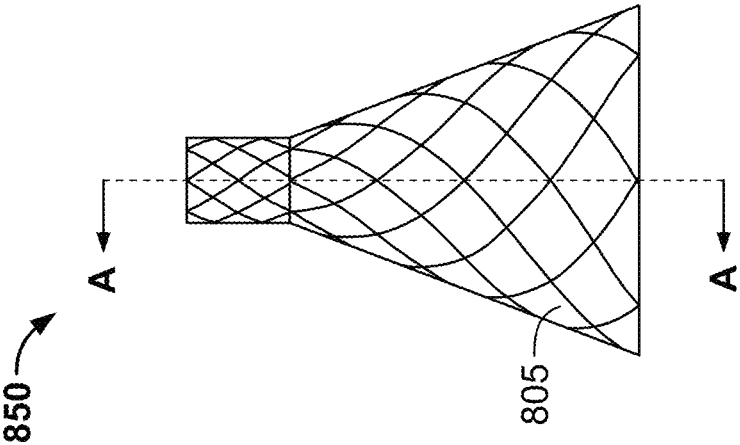

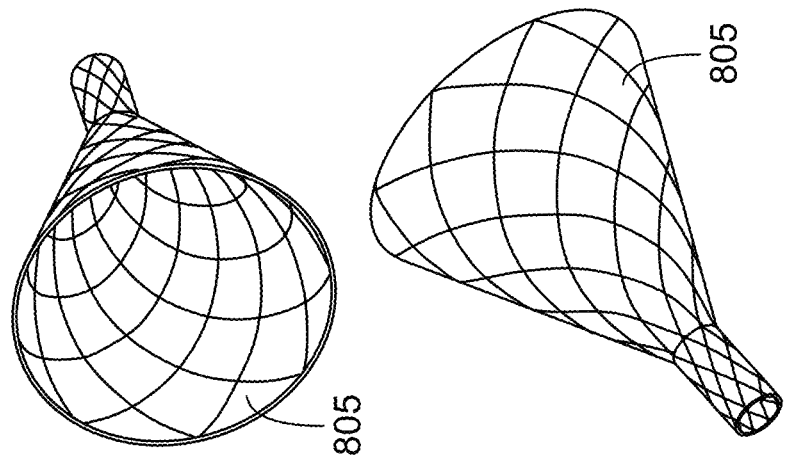
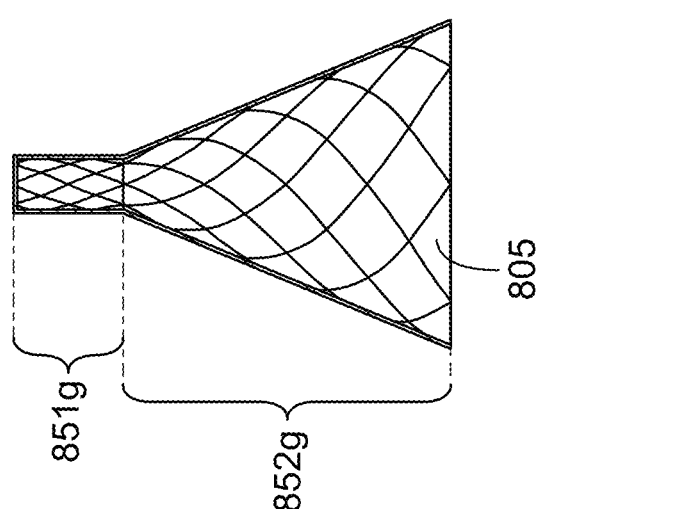
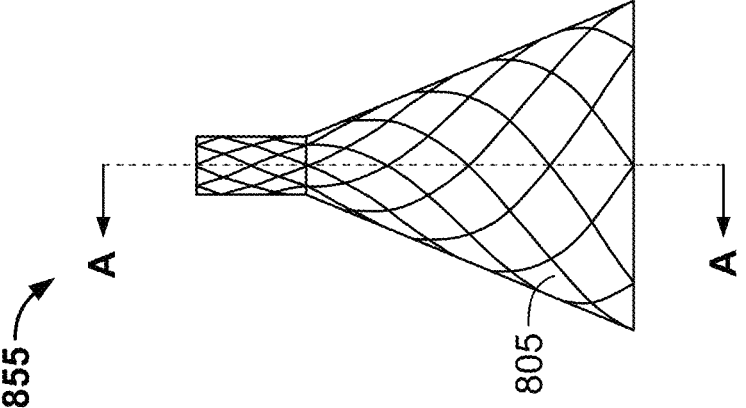
FIG. 8G

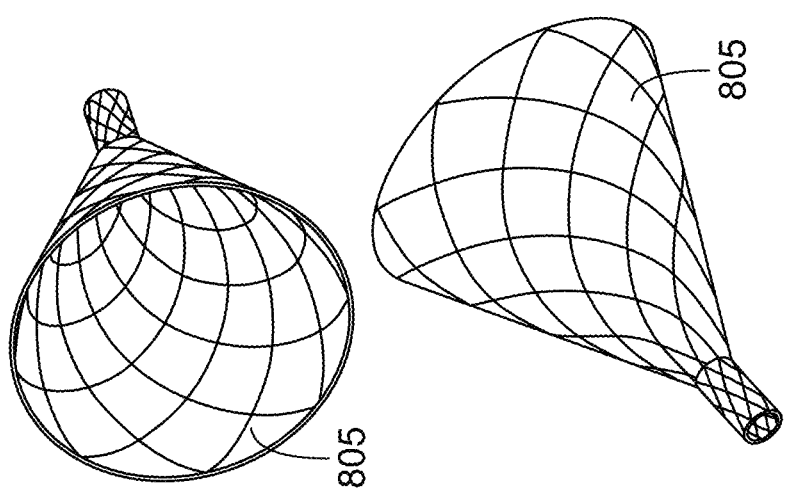
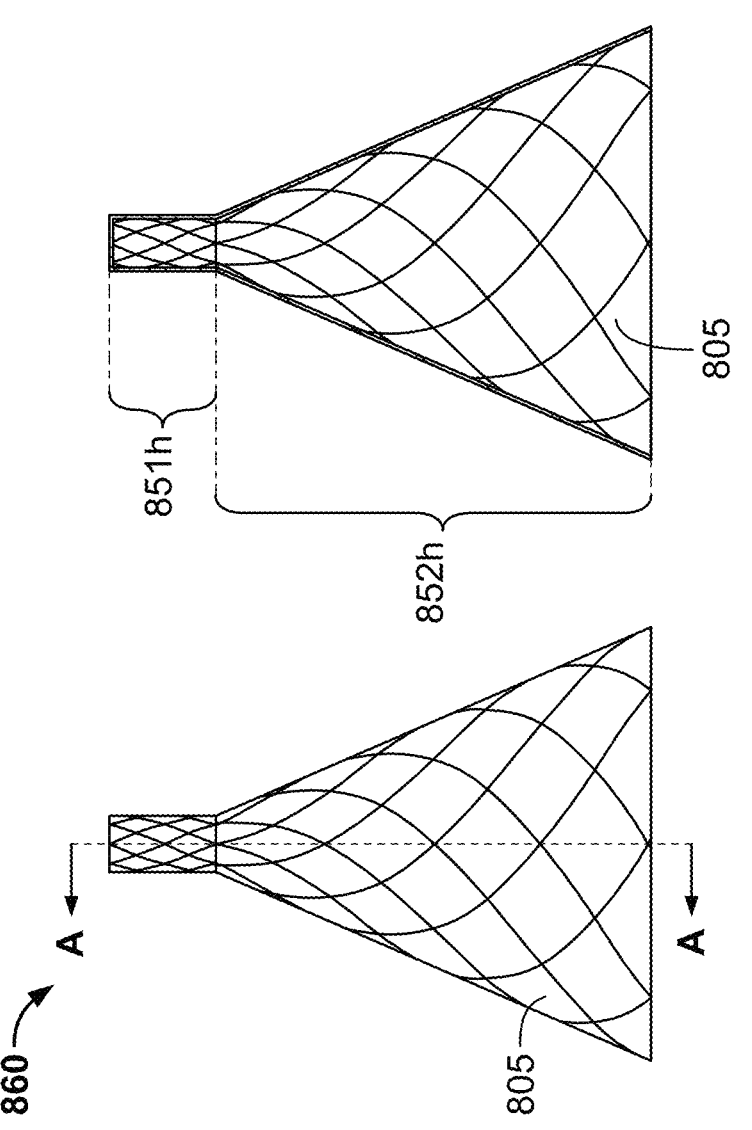
FIG. 8H

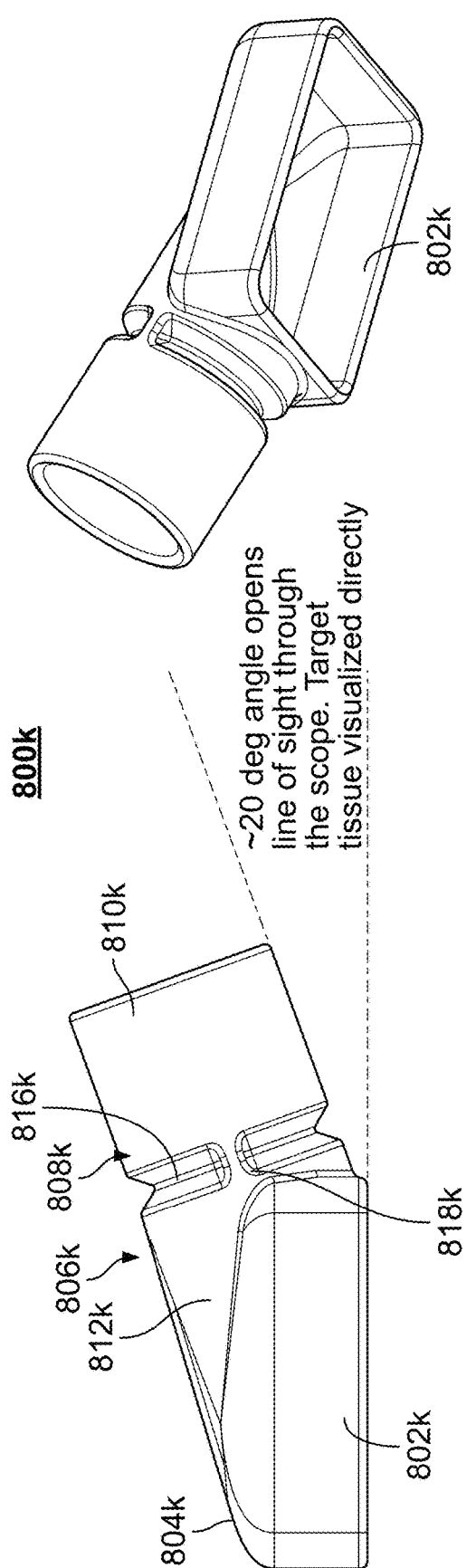
800k
~20 deg angle opens line of sight through the scope. Target tissue visualized directly
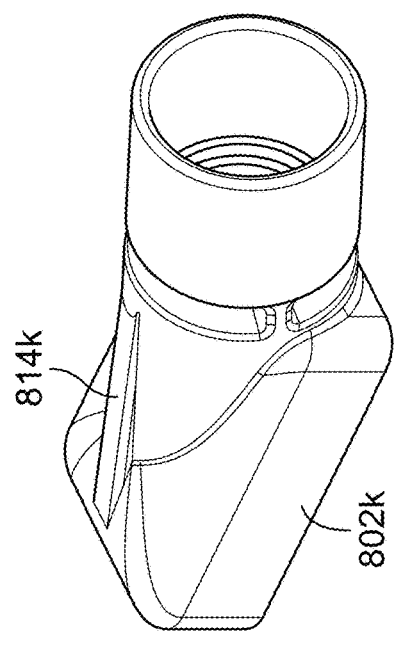
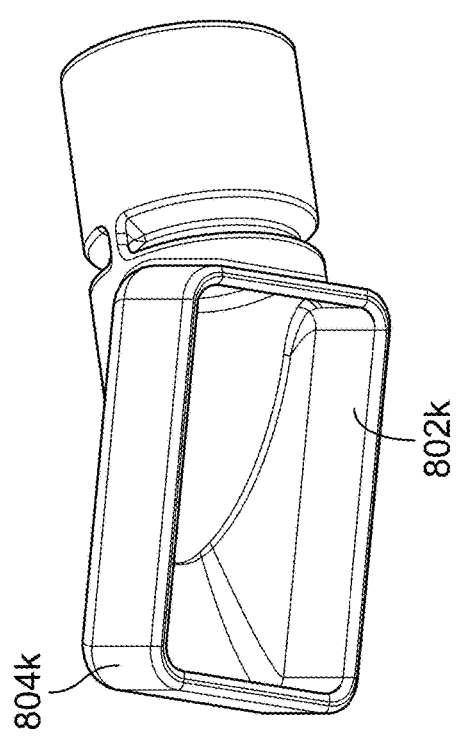
FIG. 8K 15×18mm distal cap
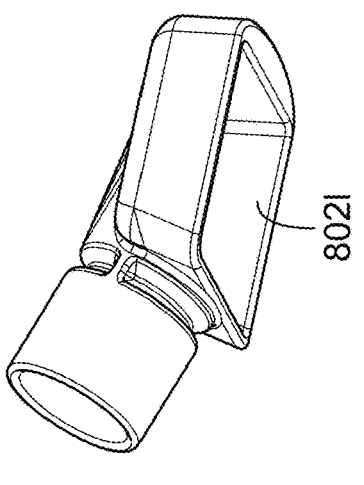
8021
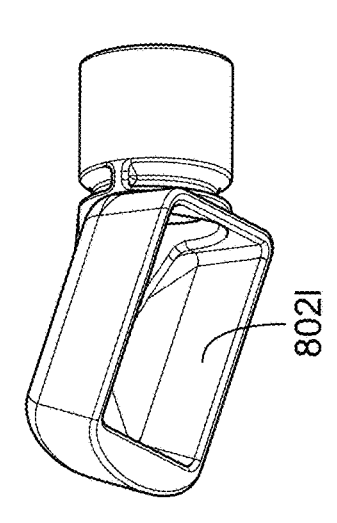
8021
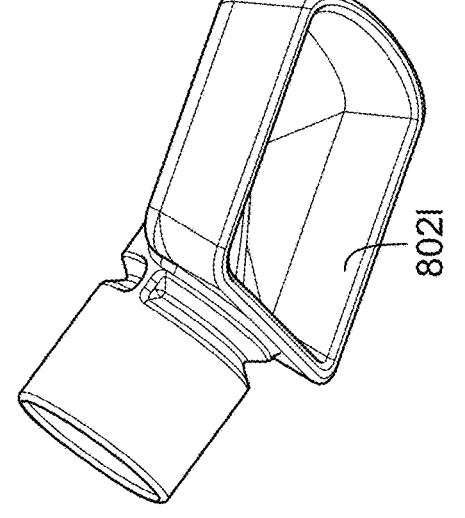
8021
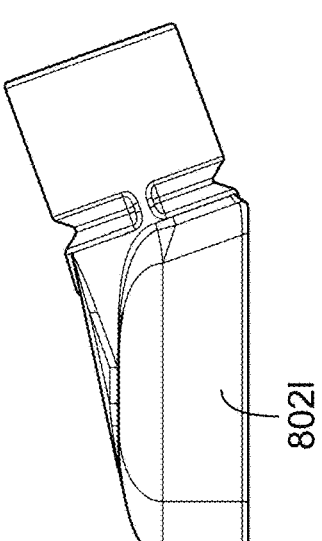
8021
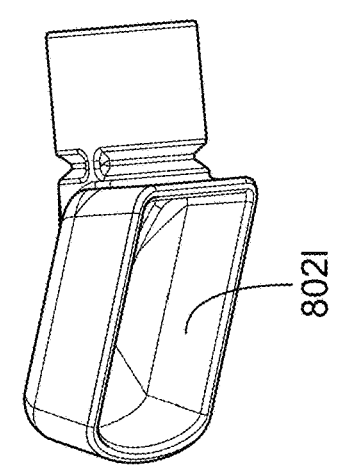
8021
FIG. 8L

Silicone covered

Soft connect by PTFE wire

836

A-A
3 : 1

Ø1.1

5

4

1

2

3

Opening:18*12

12

R1.8

31.4

24.5

18

6.9

17.25

7.25

(73°)

Ø2.33

A

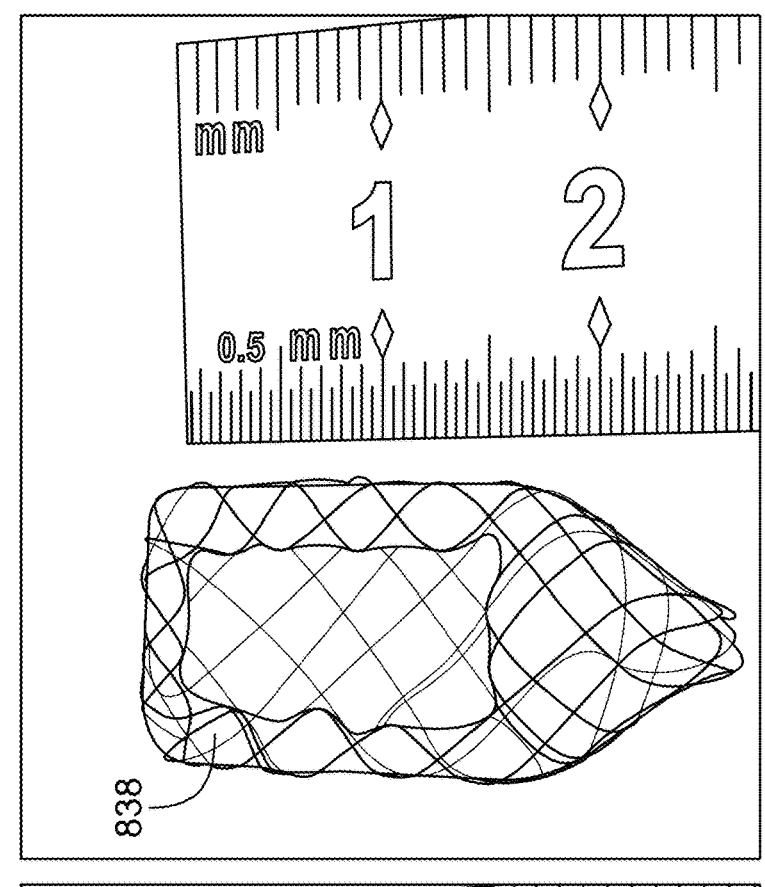
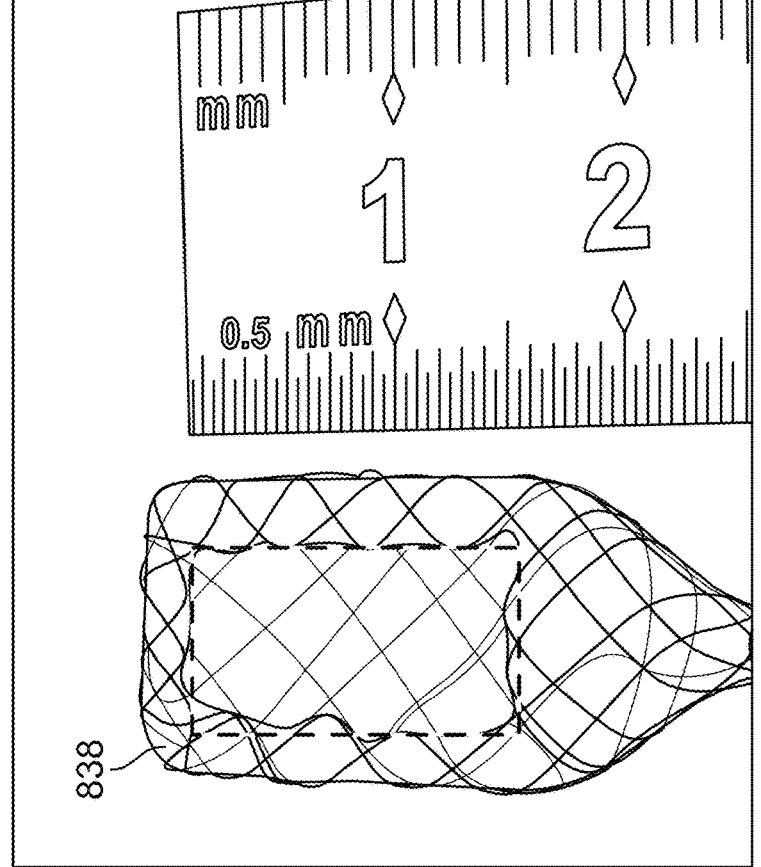
FIG. 8U

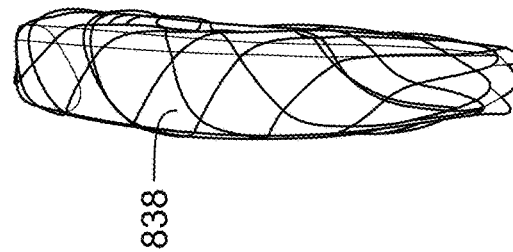
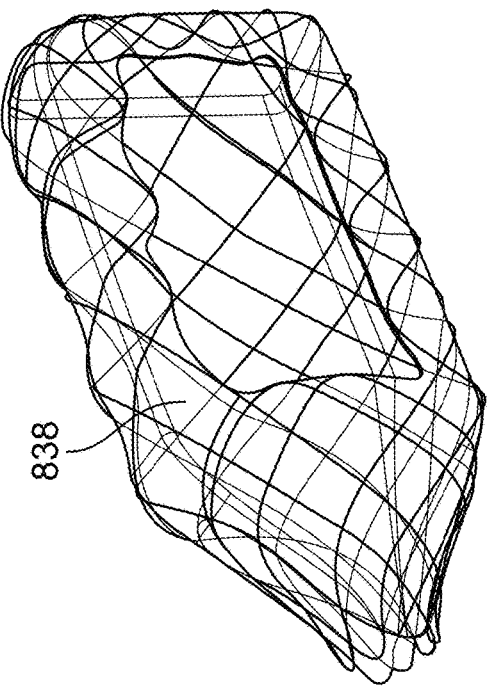
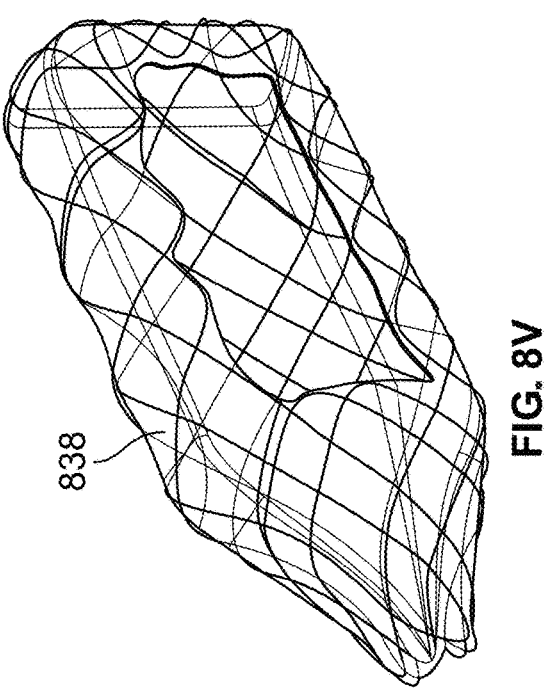
FIG. 8V

912 — Insert GI heat therapy device into GI tract

914 — Initiate saline flow through heat therapy device

916 — Heat saline to generate vapor

918 — Condense vapor on tissue within GI tract

902 — Insert ablation device into GI tract

904 — Create seal

906 — Deliver vapor into sealed portion

908 — Condense vapor on tissue within GI tract

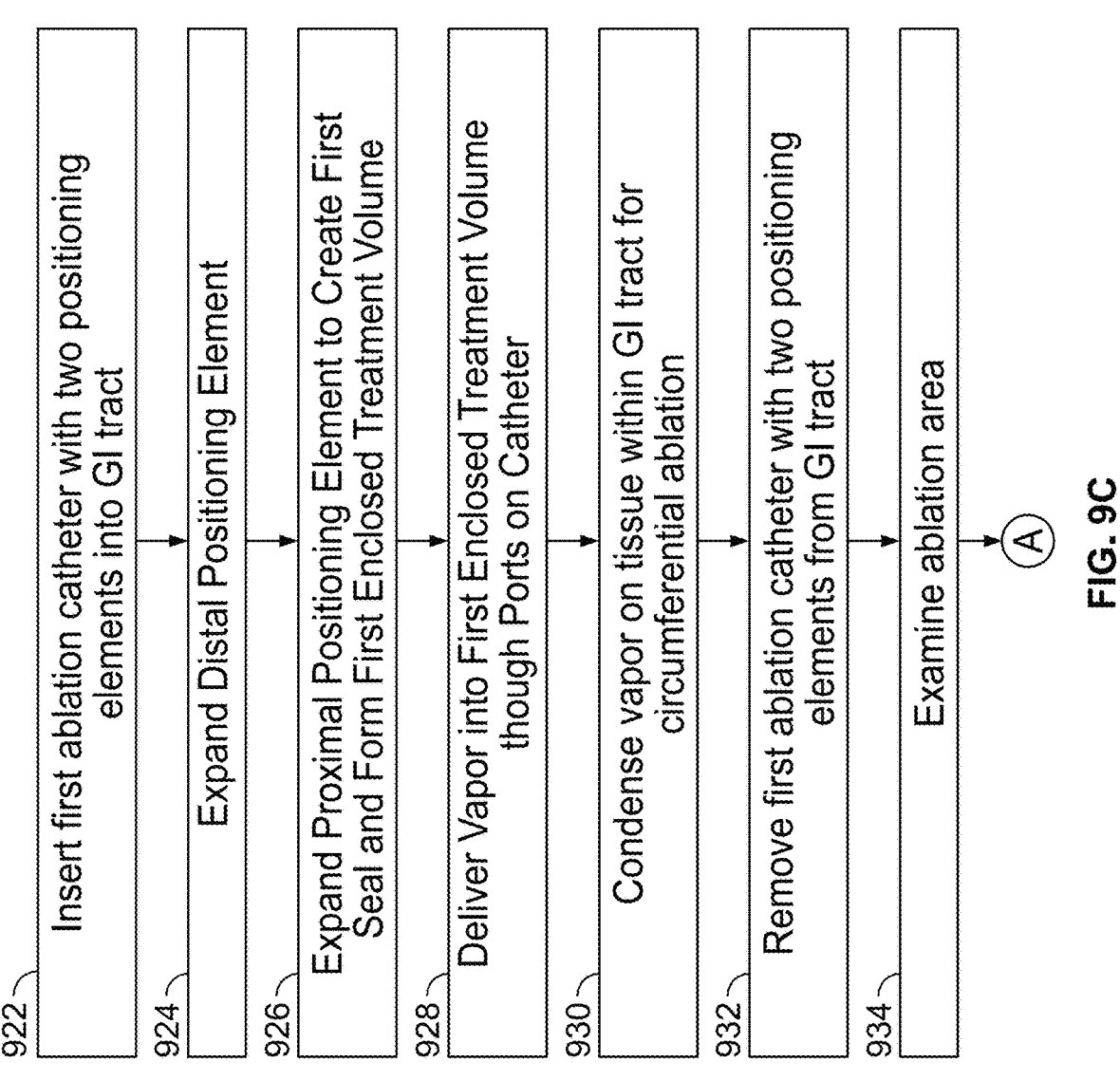

922 Insert first ablation catheter with two positioning elements into GI tract

924 Expand Distal Positioning Element

926 Expand Proximal Positioning Element to Create First Seal and Form First Enclosed Treatment Volume 928 Deliver Vapor into First Enclosed Treatment Volume though Ports on Catheter 930 Condense vapor on tissue within GI tract for circumferential ablation 932 Remove first ablation catheter with two positioning elements from GI tract 934 Examine ablation area

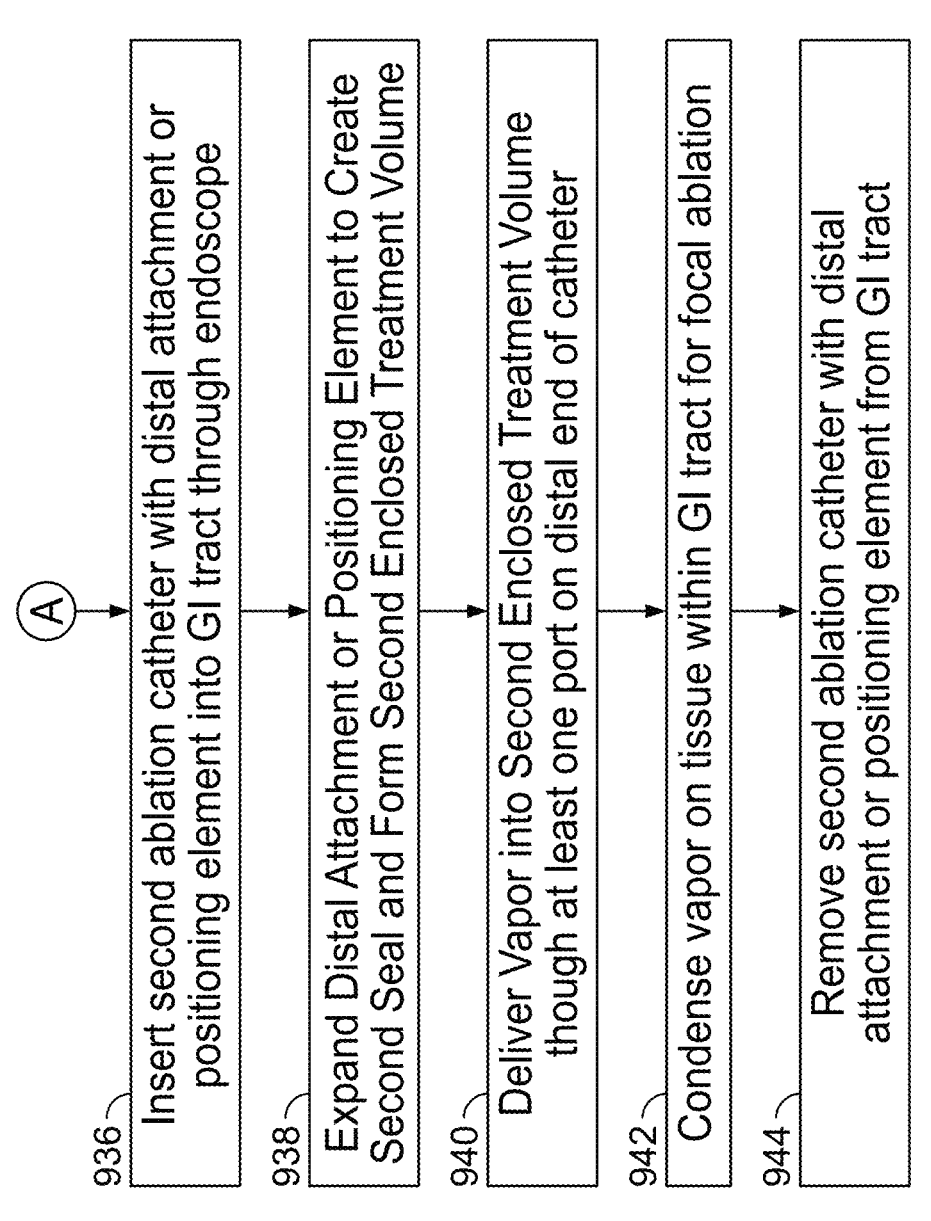

936 — Insert second ablation catheter with distal attachment or positioning element into GI tract through endoscope 938 — Expand Distal Attachment or Positioning Element to Create Second Seal and Form Second Enclosed Treatment Volume 940 — Deliver Vapor into Second Enclosed Treatment Volume though at least one port on distal end of catheter 942 — Condense vapor on tissue within GI tract for focal ablation 944 — Remove second ablation catheter with distal attachment or positioning element from GI tract

FIG. 9C (Cont.)

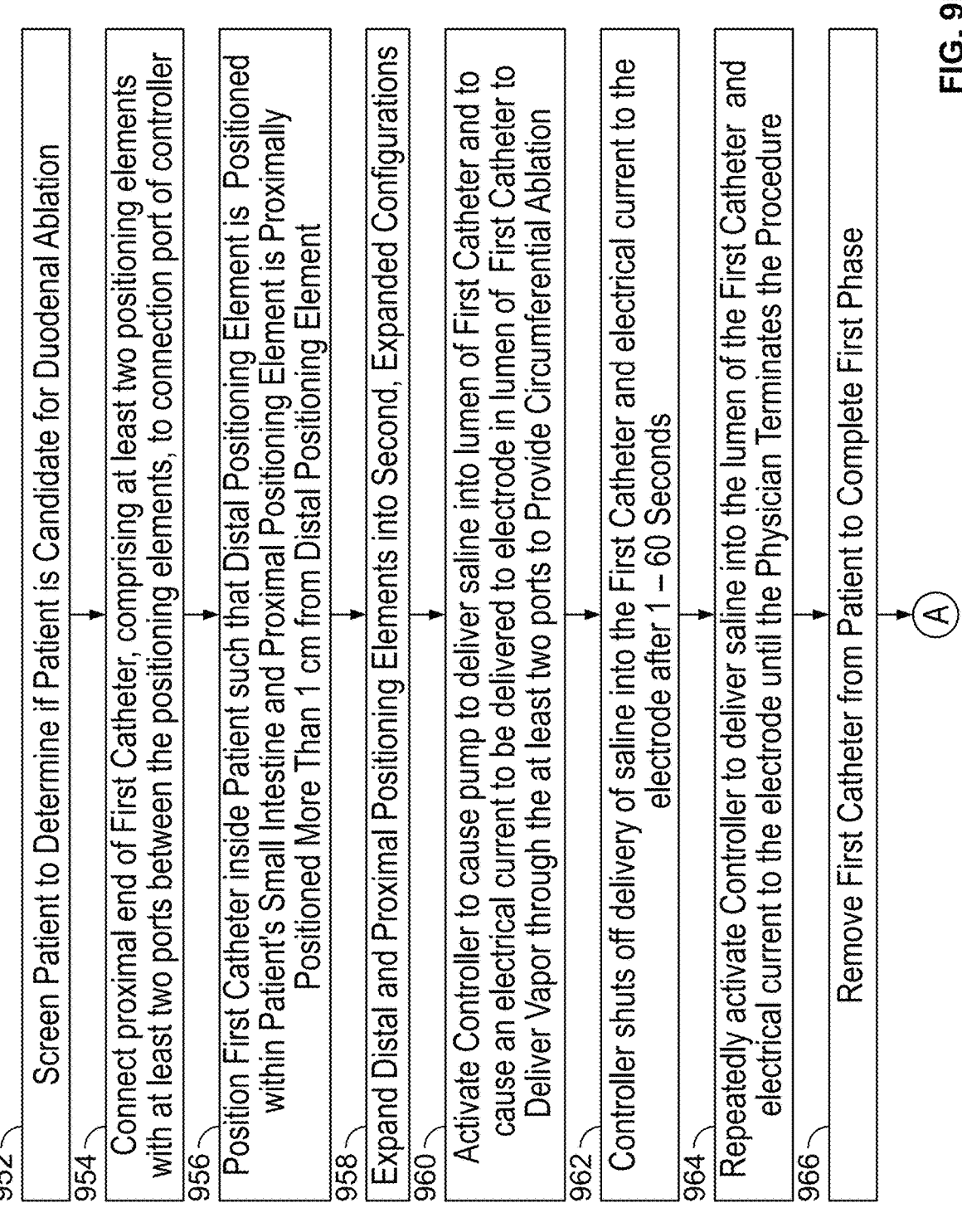

952 — Screen Patient to Determine if Patient is Candidate for Duodenal Ablation

954 — Connect proximal end of First Catheter, comprising at least two positioning elements with at least two ports between the positioning elements, to connection port of controller 956 — Position First Catheter inside Patient such that Distal Positioning Element is Positioned within Patient's Small Intestine and Proximal Positioning Element is Proximally Positioned More Than 1 cm from Distal Positioning Element 958 — Expand Distal and Proximal Positioning Elements into Second, Expanded Configurations 960 — Activate Controller to cause pump to deliver saline into lumen of First Catheter and to cause an electrical current to be delivered to electrode in lumen of First Catheter to Deliver Vapor through the at least two ports to Provide Circumferential Ablation 962 — Controller shuts off delivery of saline into the First Catheter and electrical current to the electrode after 1 – 60 Seconds 964 — Repeatedly activate Controller to deliver saline into the lumen of the First Catheter and electrical current to the electrode until the Physician Terminates the Procedure 966 — Remove First Catheter from Patient to Complete First Phase (A)

FIG. 9D

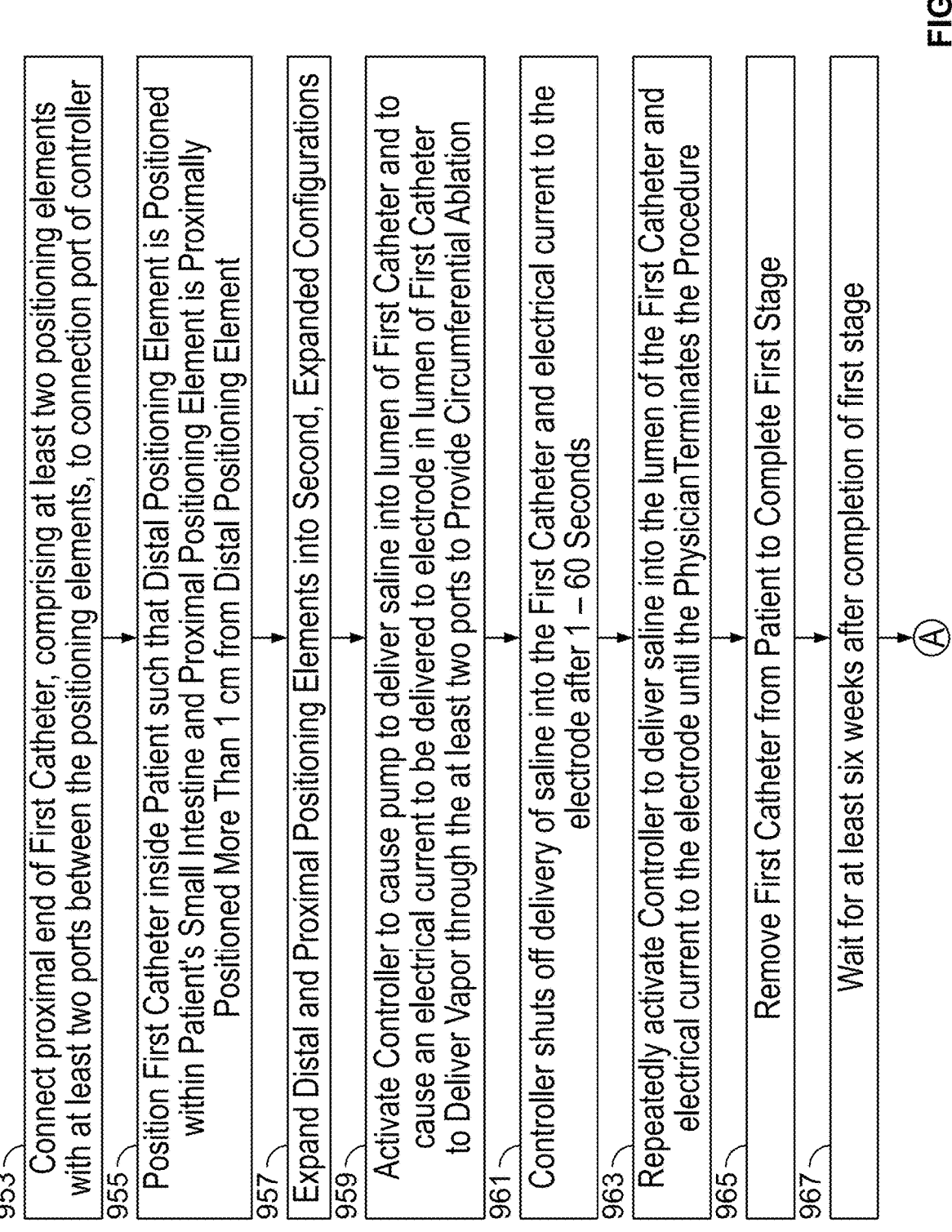

953 — Connect proximal end of First Catheter, comprising at least two positioning elements with at least two ports between the positioning elements, to connection port of controller 955 — Position First Catheter inside Patient such that Distal Positioning Element is Positioned within Patient's Small Intestine and Proximal Positioning Element is Proximally Positioned More Than 1 cm from Distal Positioning Element 957 — Expand Distal and Proximal Positioning Elements into Second, Expanded Configurations 959 — Activate Controller to cause pump to deliver saline into lumen of First Catheter and to cause an electrical current to be delivered to electrode in lumen of First Catheter to Deliver Vapor through the at least two ports to Provide Circumferential Ablation 961 — Controller shuts off delivery of saline into the First Catheter and electrical current to the electrode after 1 – 60 Seconds 963 — Repeatedly activate Controller to deliver saline into the lumen of the First Catheter and electrical current to the electrode until the Physician Terminates the Procedure 965 — Remove First Catheter from Patient to Complete First Stage 967 — Wait for at least six weeks after completion of first stage

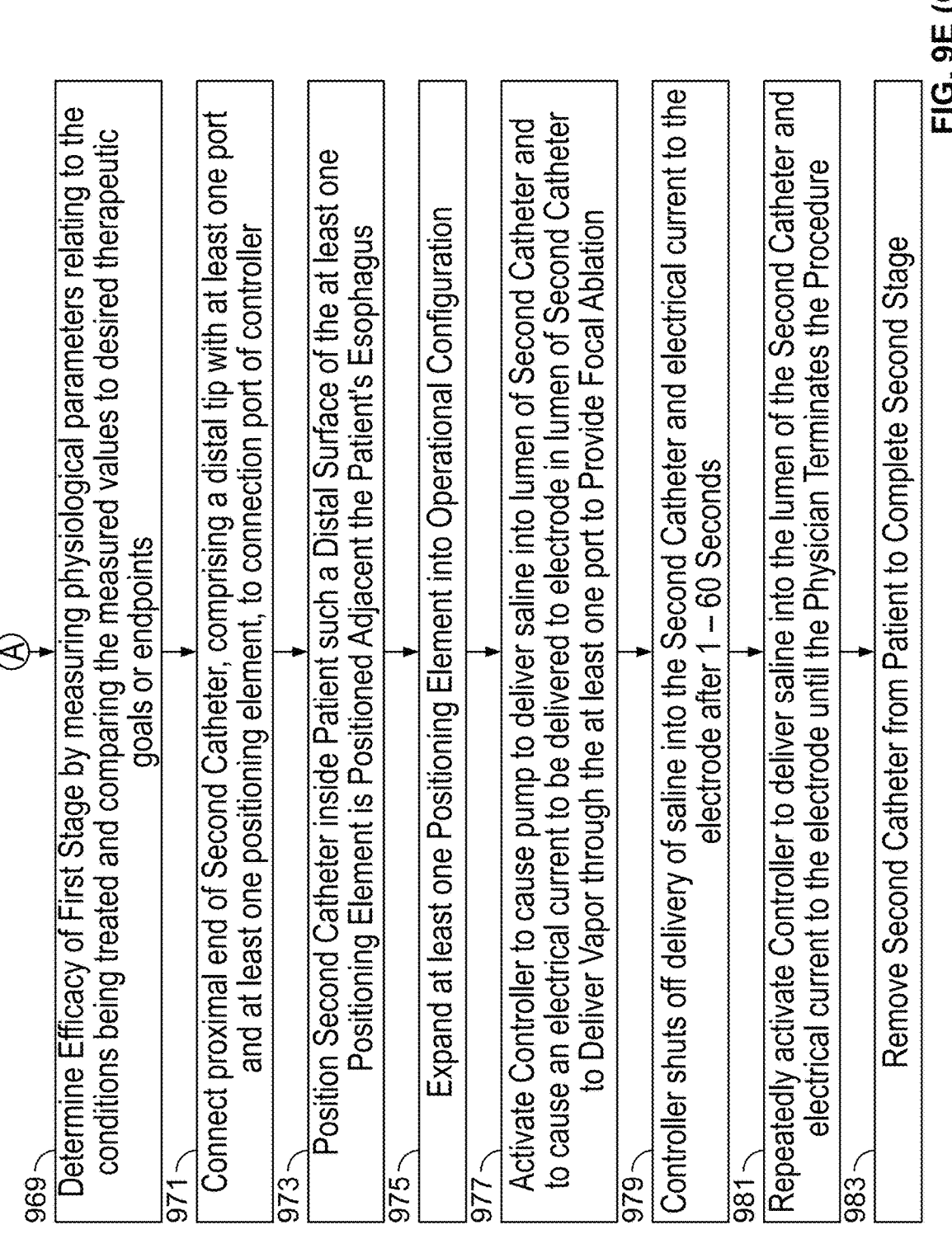

969 — Determine Efficacy of First Stage by measuring physiological parameters relating to the conditions being treated and comparing the measured values to desired therapeutic goals or endpoints 971 — Connect proximal end of Second Catheter, comprising a distal tip with at least one port and at least one positioning element, to connection port of controller 973 — Position Second Catheter inside Patient such a Distal Surface of the at least one Positioning Element is Positioned Adjacent the Patient's Esophagus 975 — Expand at least one Positioning Element into Operational Configuration 977 — Activate Controller to cause pump to deliver saline into lumen of Second Catheter and to cause an electrical current to be delivered to electrode in lumen of Second Catheter to Deliver Vapor through the at least one port to Provide Focal Ablation 979 — Controller shuts off delivery of saline into the Second Catheter and electrical current to the electrode after 1 – 60 Seconds 981 — Repeatedly activate Controller to deliver saline into the lumen of the Second Catheter and electrical current to the electrode until the Physician Terminates the Procedure 983 — Remove Second Catheter from Patient to Complete Second Stage

FIG. 9E (Cont.)

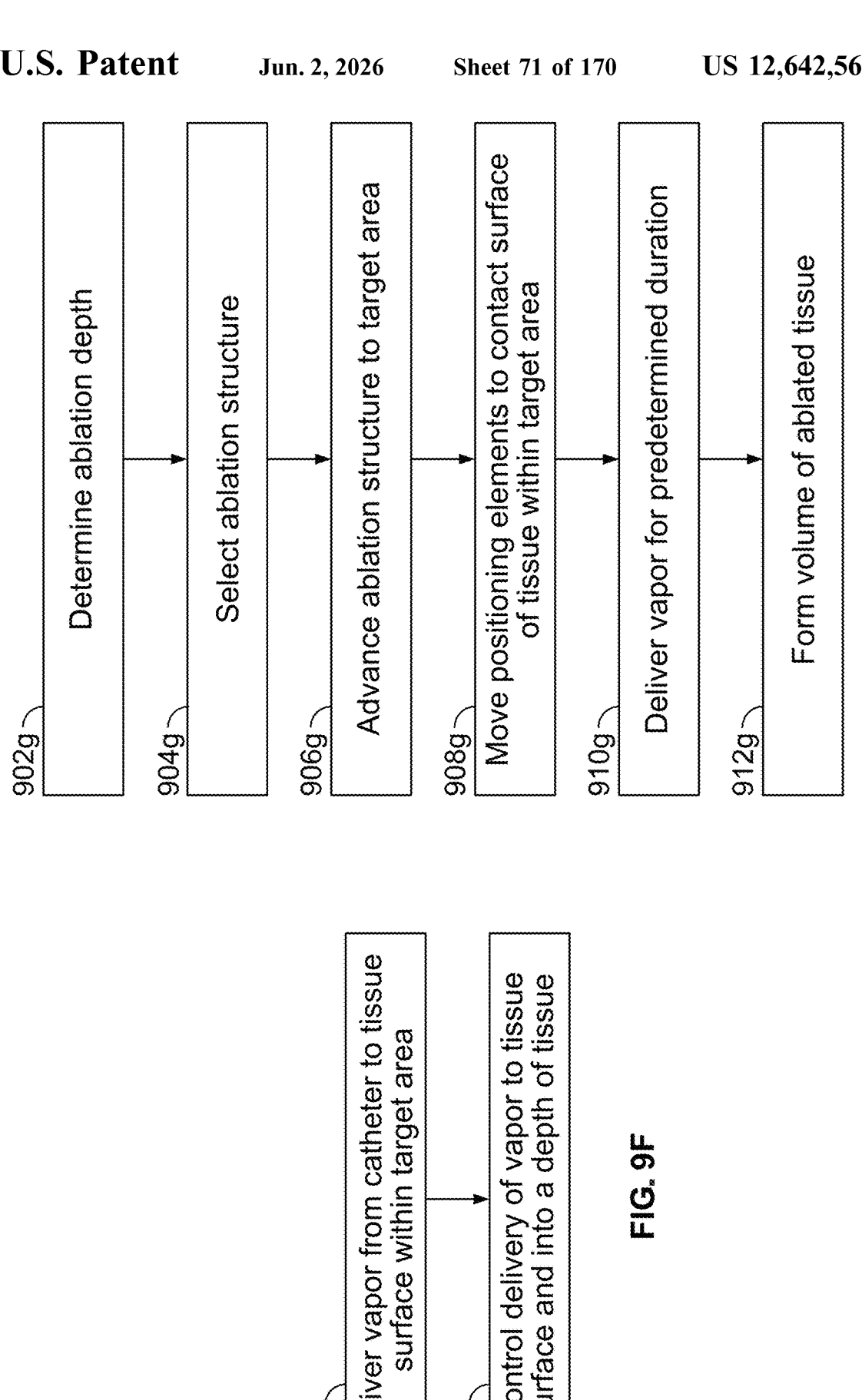

902g — Determine ablation depth

904g — Select ablation structure

906g — Advance ablation structure to target area

908g — Move positioning elements to contact surface of tissue within target area 910g — Deliver vapor for predetermined duration 912g — Form volume of ablated tissue

FIG. 9G

902f — Deliver vapor from catheter to tissue surface within target area

904f — Control delivery of vapor to tissue surface and into a depth of tissue

FIG. 9F

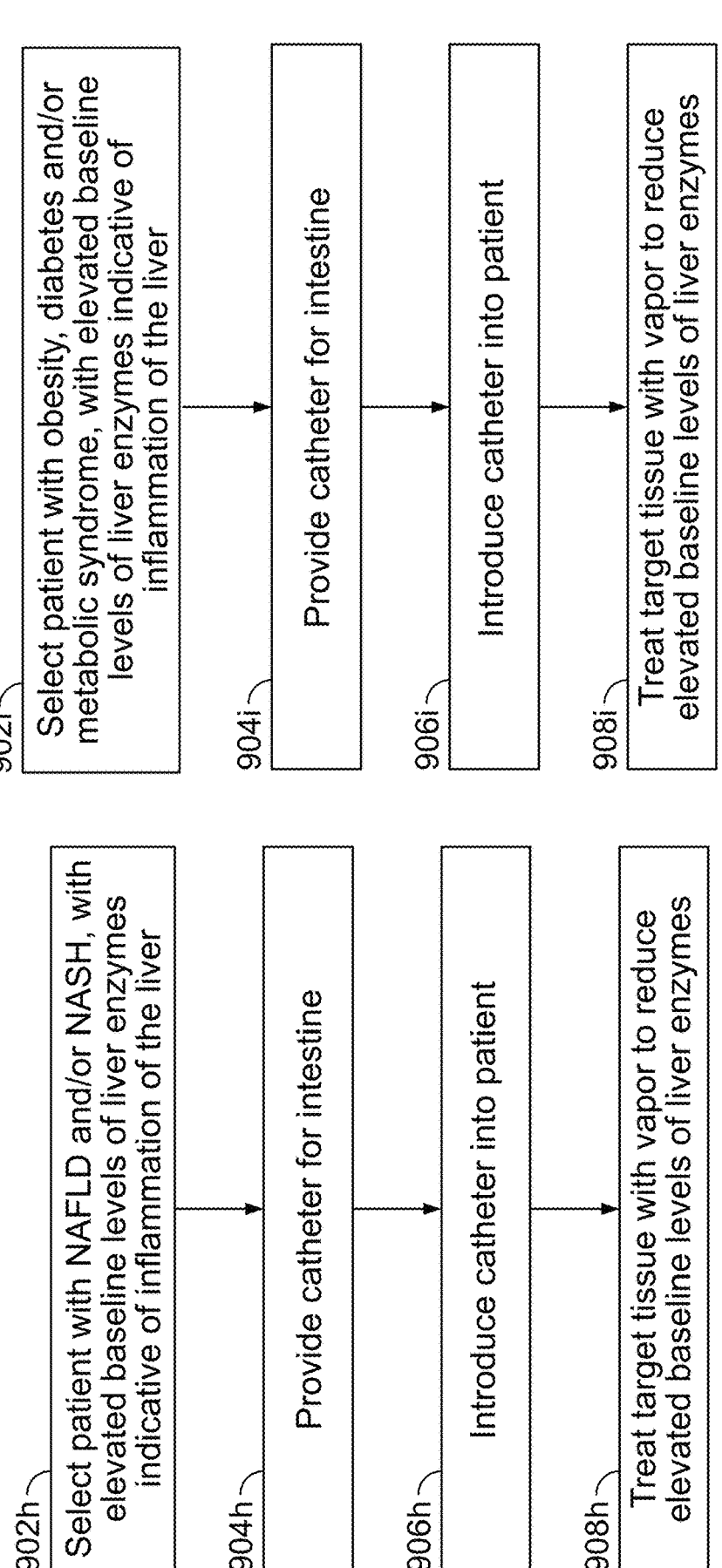

902i Select patient with obesity, diabetes and/or metabolic syndrome, with elevated baseline levels of liver enzymes indicative of inflammation of the liver 904i Provide catheter for intestine 906i Introduce catheter into patient 908i Treat target tissue with vapor to reduce elevated baseline levels of liver enzymes

FIG. 9I

902h Select patient with NAFLD and/or NASH, with elevated baseline levels of liver enzymes indicative of inflammation of the liver 904h Provide catheter for intestine 906h Introduce catheter into patient 908h Treat target tissue with vapor to reduce elevated baseline levels of liver enzymes

FIG. 9H

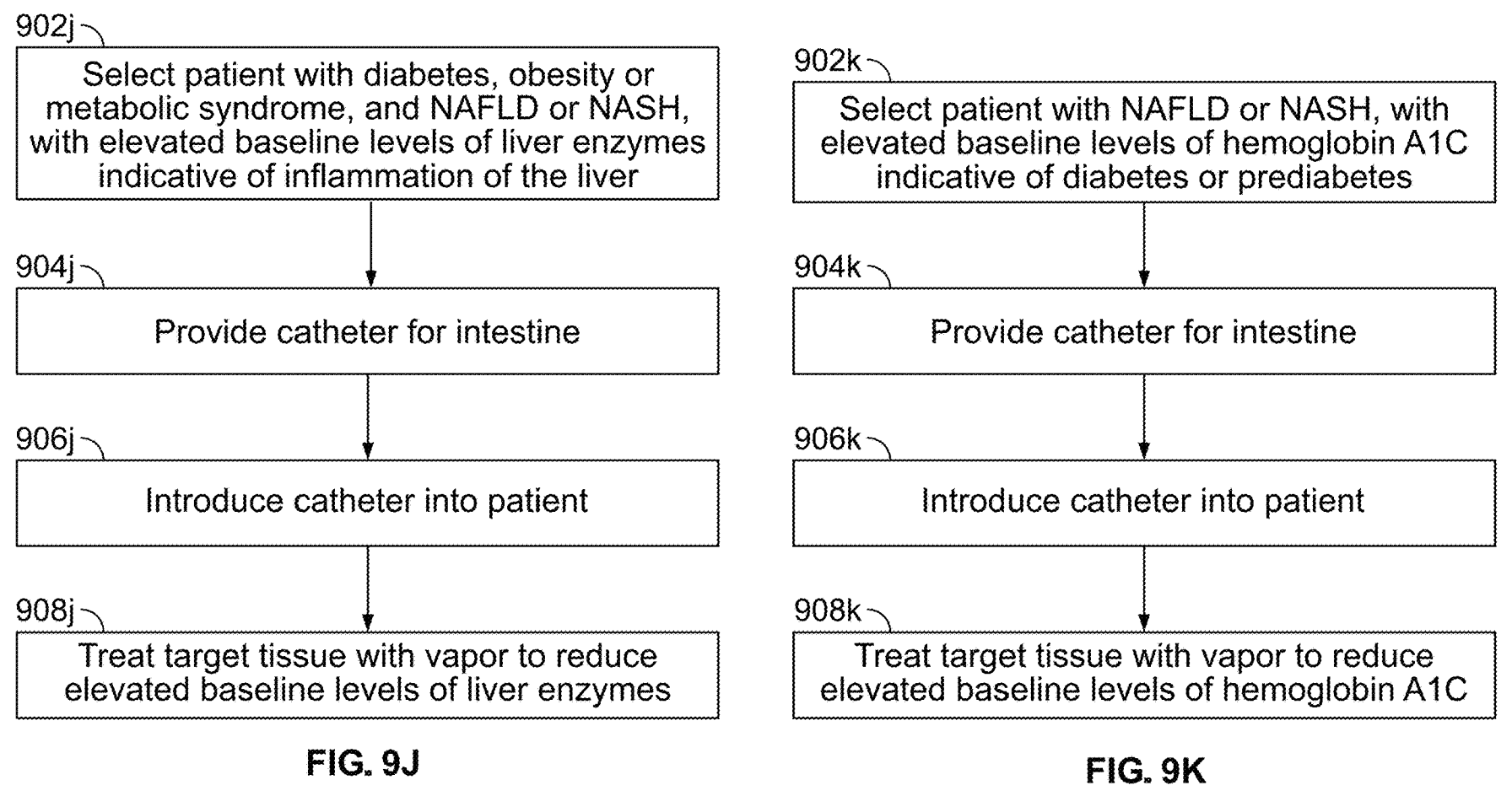

902k — Select patient with NAFLD or NASH, with elevated baseline levels of hemoglobin A1C indicative of diabetes or prediabetes 904k — Provide catheter for intestine 906k — Introduce catheter into patient 908k — Treat target tissue with vapor to reduce elevated baseline levels of hemoglobin A1C

FIG. 9K

902j — Select patient with diabetes, obesity or metabolic syndrome, and NAFLD or NASH, with elevated baseline levels of liver enzymes indicative of inflammation of the liver 904j — Provide catheter for intestine 906j — Introduce catheter into patient 908j — Treat target tissue with vapor to reduce elevated baseline levels of liver enzymes

FIG. 9J

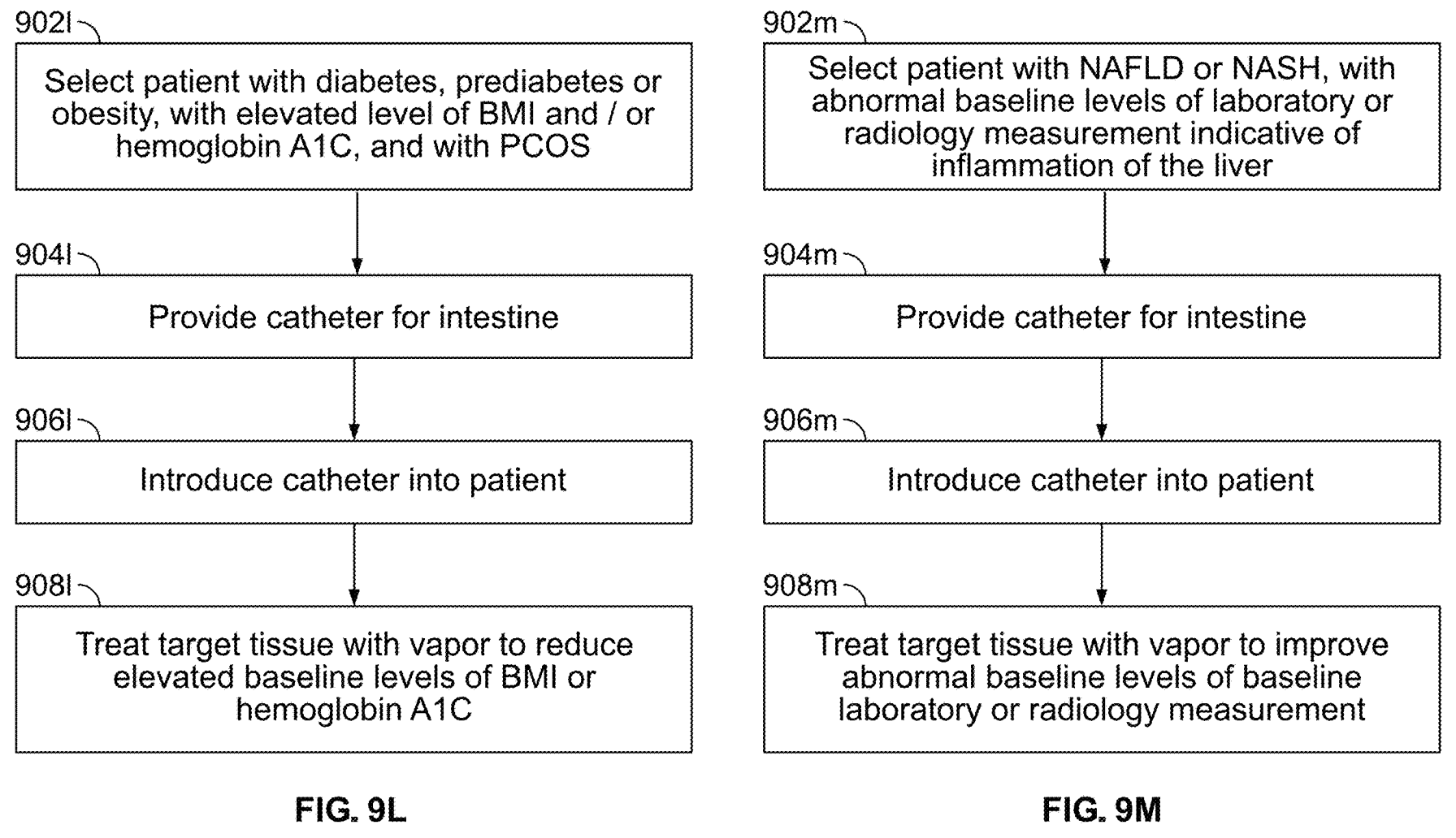

902m — Select patient with NAFLD or NASH, with abnormal baseline levels of laboratory or radiology measurement indicative of inflammation of the liver 904m — Provide catheter for intestine 906m — Introduce catheter into patient 908m — Treat target tissue with vapor to improve abnormal baseline levels of baseline laboratory or radiology measurement

FIG. 9M

902l — Select patient with diabetes, prediabetes or obesity, with elevated level of BMI and / or hemoglobin A1C, and with PCOS 904l — Provide catheter for intestine 906l — Introduce catheter into patient 908l — Treat target tissue with vapor to reduce elevated baseline levels of BMI or hemoglobin A1C

FIG. 9L

Aqua Catheter Design
_1145a_

Insulated Distal Surface with Outflow Ports

Electrode

FIG. 11A

Aqua Catheter Design
1145b

Insulated Distal Surface with Outflow Ports

Electrode

FIG. 11B

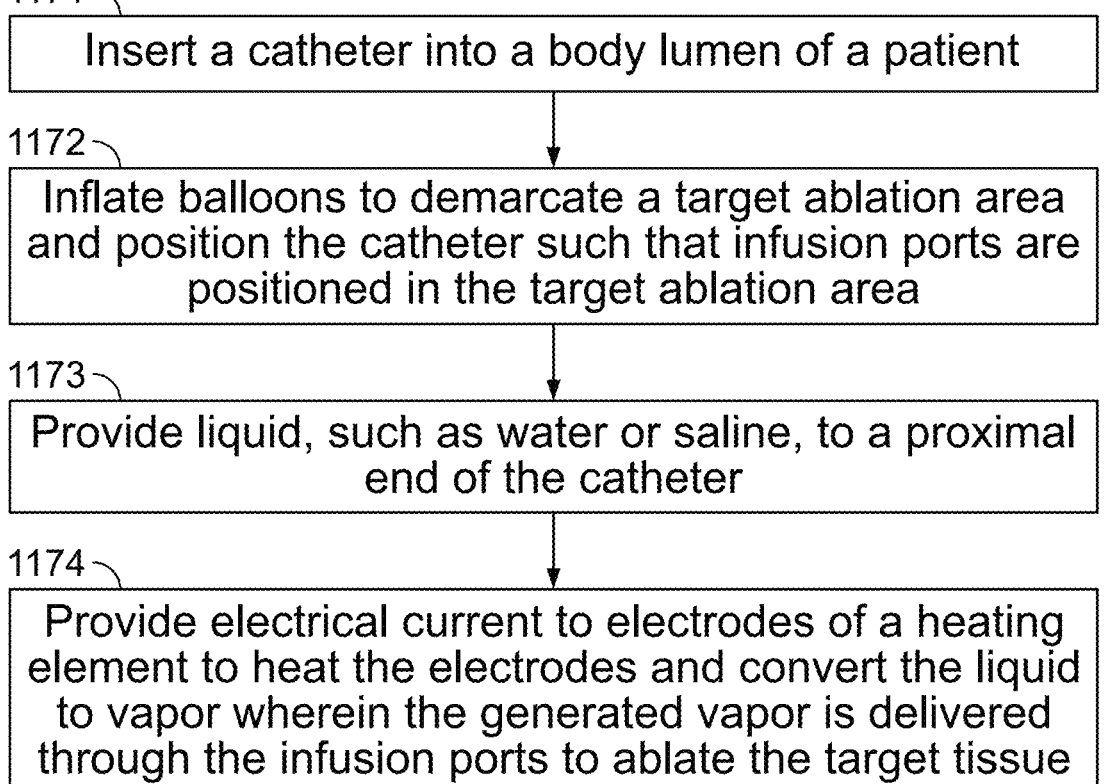

1171
Insert a catheter into a body lumen of a patient

1172
Inflate balloons to demarcate a target ablation area and position the catheter such that infusion ports are positioned in the target ablation area 1173
Provide liquid, such as water or saline, to a proximal end of the catheter 1174
Provide electrical current to electrodes of a heating element to heat the electrodes and convert the liquid to vapor wherein the generated vapor is delivered through the infusion ports to ablate the target tissue

MALE COUPLER
1230

COUPLER HOUSING
BODY
1236

WATER/SALINE
IN-FEED LINE
1225

THUMB LATCH
1237

1202

1205

Heat Chamber with
housed Metallic Core
inside
1215

INDUCTION COIL
1212
* Helically wrapped Litz wire
*TC Wires (x2) at input and output
side of HC

3-WAY
SOLENOID

1240

1250

COUPLER
HOUSING
BODY
1210

THUMB
LATCH

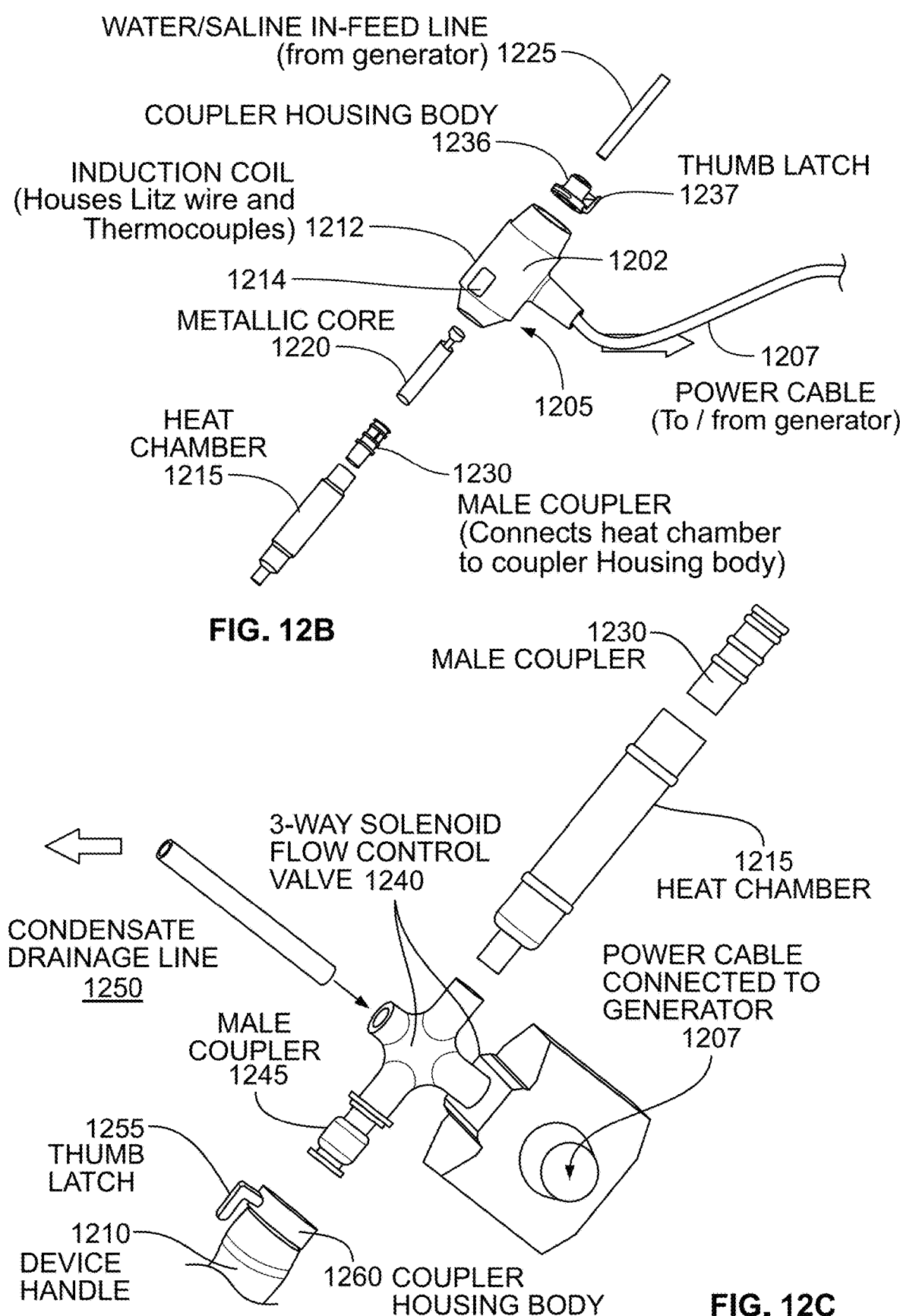

WATER/SALINE IN-FEED LINE
(from generator) 1225

COUPLER HOUSING BODY
1236

INDUCTION COIL
(Houses Litz wire and
Thermocouples) 1212

THUMB LATCH
1237

1214

1202

METALLIC CORE
1220

1205

HEAT
CHAMBER
1215

1230
MALE COUPLER
(Connects heat chamber
to coupler Housing body)

1207
POWER CABLE
(To / from generator)

FIG. 12B

1230
MALE COUPLER

3-WAY SOLENOID
FLOW CONTROL
VALVE 1240

1215
HEAT CHAMBER

CONDENSATE
DRAINAGE LINE
1250

POWER CABLE
CONNECTED TO
GENERATOR
1207

MALE
COUPLER
1245

1255
THUMB
LATCH

1210
DEVICE
HANDLE

1260 COUPLER
HOUSING BODY

PROXIMAL BALLOON
OD RANGE: 18-32mm

VAPOR COAGUALTION
ZONE: 4-6cm

1440

VAPOR JETS

1440

VAPOR JETS

1410

DISTAL BALLOON
OD RANGE: 18-32mm

1400

DUAL LUMEN
OUTER SHAFT
1407

PROXIMAL BALLOON
INFLATION LUMEN
1409

DUAL LUMEN
INNER SHAFT
1405

DISTAL BALLOON
INFLATION LUMEN
1417

1408
INNER SHAFT LUMEN

1415
VAPOR LUMEN

1500

COUPLER BODY
1502

PROXIMAL BALLOON
INFLATION PORT
1530

METALLIC LUER
1517

MULTI LUMEN
CATHETER SHAFT
1400

1515

1510

1535

1532

1505

1525      DISTAL BALLOON INFLATION PORT

1503

THUMB LATCH

1500

INDUCTION HEATER
(incorporates cable windings, delivering Alternating Current (AC) to heat metallic core)
1212

1205

1220

1202

1215
HEAT CHAMBER ASSEMBLY

1240

1502

1503

1500

DEVICE HANDLE

1517

1545

1207
POWER CABLE
(also houses thermocouple control cables)

1505

1502

1525

1555

1560

1559

1505

1525

1555

1405

STEAM SHAFT
LUMEN
1605

DISTAL BALLOON
INFLATION LUMEN
1610

1620
Steam shaft
auxiliary lumen

1600

1625
Steam shaft
auxiliary lumen

1615
PROXIMAL BALLOON
INFLATION LUMEN

THUMB LATCH 1670

COUPLER HOUSING HUB / BODY 1675

PROXIMAL BALLOON INFLATION PORT 1660

DISTAL BALLOON INFLATION PORT 1655

1652

25

EXTENSION BEYOND ENDOSCOPE THUMBSCREW ADJUSTMENT 1665

5 LUMEN CATHETER SHAFT 1600

1666

1650

1650

PROXIMAL BALLOON
INFLATION SIDELEG
1660

PROXIMAL BALLOON
INFLATION MANIFOLD
1662

1675

1655

DISTAL BALLOON
INFLATION SIDELEG

DISTAL BALLOON
INFLATION MANIFOLD

1656

1652

LENGTH BEYOND ENDSCOPE
ADJUSTMENT THUMBSCREW
1665

1666

1600
5 LUMEN SHAFT

THUMB LATCH & COUPLER HOUSING ASSEMBLY 1762

1760 VAPOR-IN LINE

MALE COUPLER (connected to vapor-in line)

1725 DISTAL BALLOON INFLATION PORT

1750 INDUCTION COIL MOUNTING BRACKET

1757 THUMB LATCH AND COUPLER HOUSING ASSEMBLY

INDUCTION COIL ASSEMBLY POWER CABLE (also houses to leads)

PROXIMAL BALLOON INFLATION PORT 1730

1710

1707

1715

1705

1720

1735 SOFT GRIP CLAMP

1756

1205

1755 WATER/SALINE IN LINE

1750

1735

1707

1705

1740

1745

1735

1750

1707

1705

1745

H/C + Core + End Caps = 1215
Pre-assemled

INSERT INTO 1770
REUSABLE COIL
CABLE HOUSING

1800

1803

1804

PRESSURE
SENSOR

1806
FLOW CONTROLS
(may / may not be included)

1802
SALINE BAG /
RESERVOIR

1805
COUPLER WITH
THUMB LATCH
(connects to proximal
end cap on heath
chamber assembly)

1803

1801
SALINE
SPIKE

1920
SALINE "IN" DELIVERY LINE
(attached to thumb latch
coupler and attached to heat chamber)

1915

1909

1912

1910

1906

1950

DISTAL BALLOON
INFLATION LINE
(attaches to balloon
inflation pump
in capital)
1908

1905
PROXIMAL BALLOON
INFLATION LINE
(attaches to balloon
inflation pump
in capital)

1917

2055

2058

2056

2060

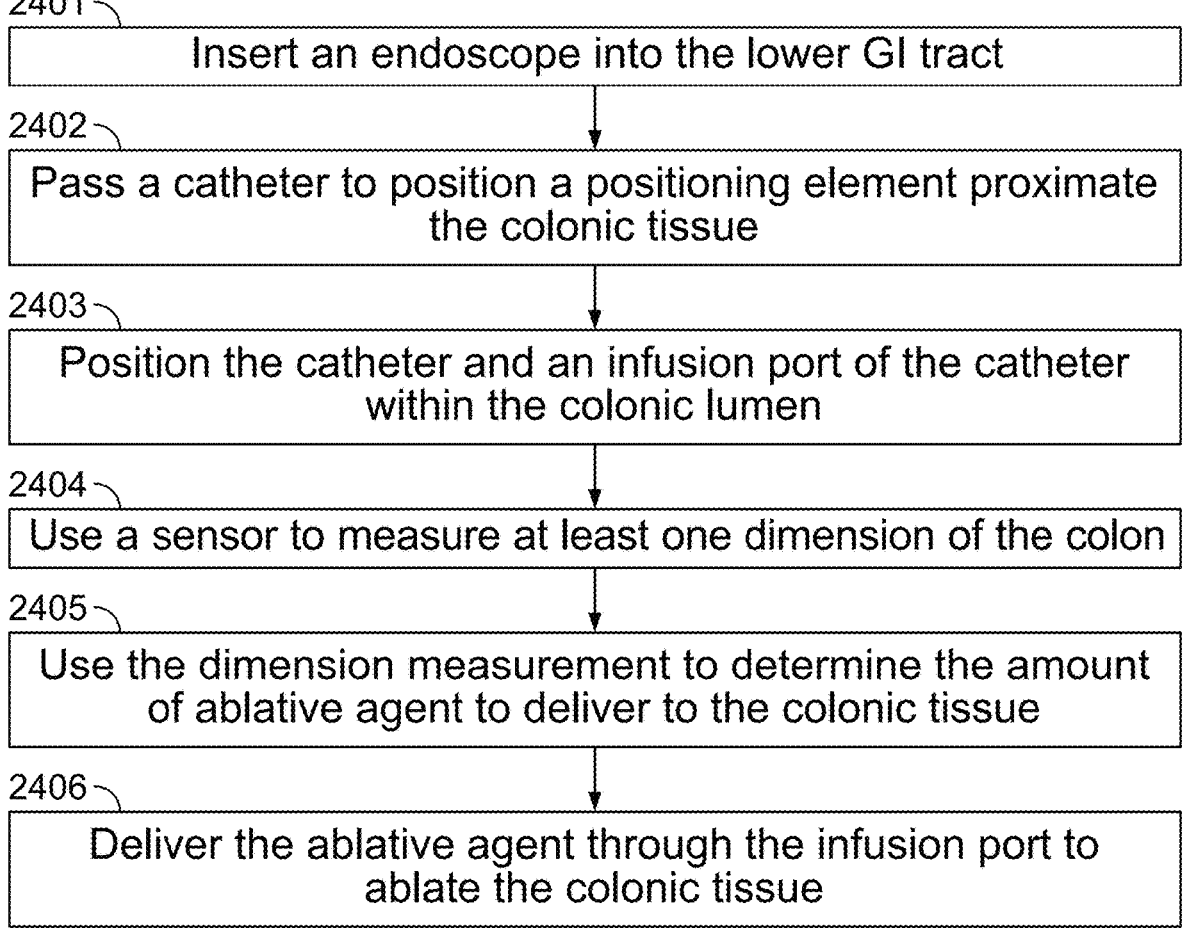

2401

Insert an endoscope into the lower GI tract

2402

Pass a catheter to position a positioning element proximate the colonic tissue

2403

Position the catheter and an infusion port of the catheter within the colonic lumen

2404

Use a sensor to measure at least one dimension of the colon

2405

Use the dimension measurement to determine the amount of ablative agent to deliver to the colonic tissue

2406

Deliver the ablative agent through the infusion port to ablate the colonic tissue

FIG. 24

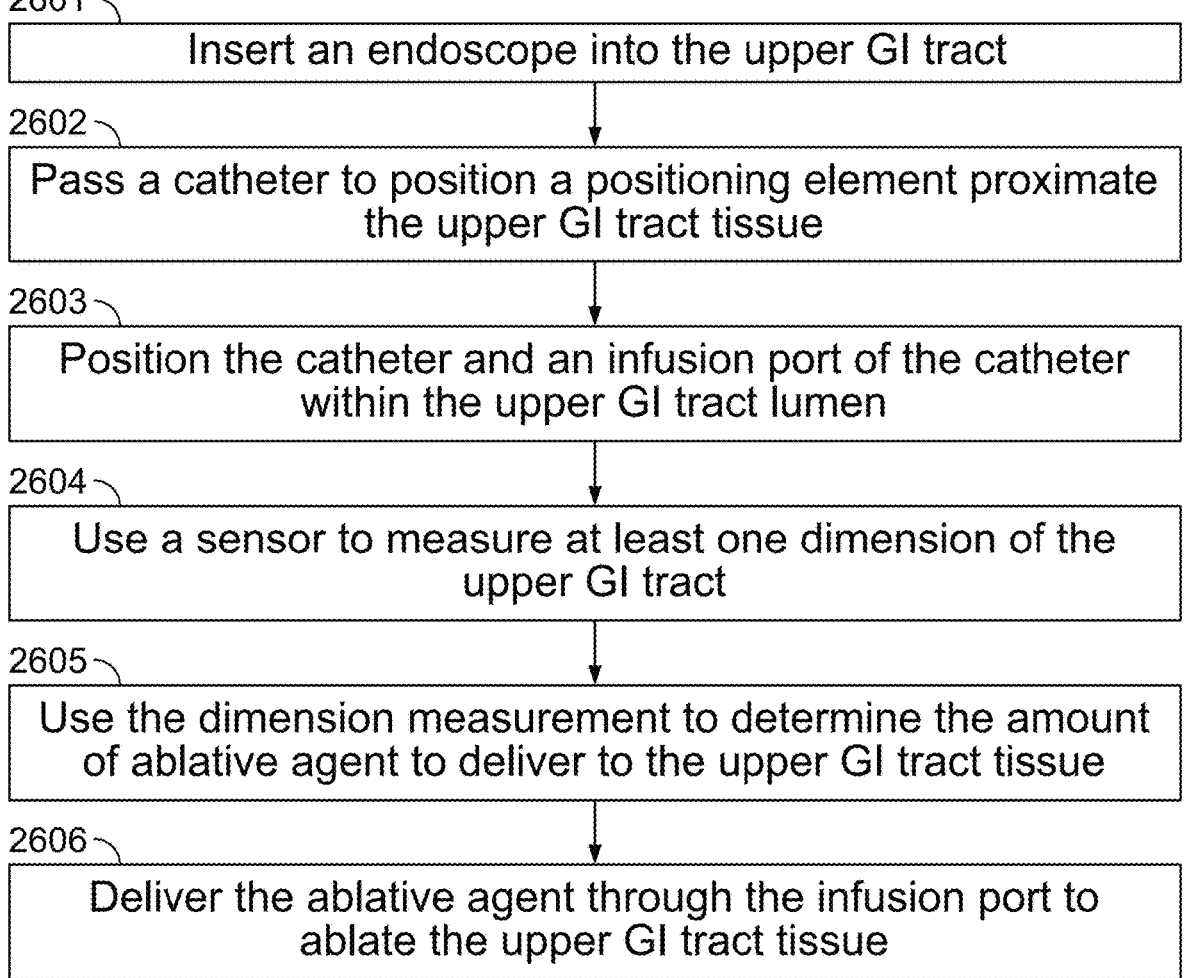

2601 — Insert an endoscope into the upper GI tract

2602 — Pass a catheter to position a positioning element proximate the upper GI tract tissue 2603 — Position the catheter and an infusion port of the catheter within the upper GI tract lumen 2604 — Use a sensor to measure at least one dimension of the upper GI tract 2605 — Use the dimension measurement to determine the amount of ablative agent to deliver to the upper GI tract tissue 2606 — Deliver the ablative agent through the infusion port to ablate the upper GI tract tissue

FIG. 26

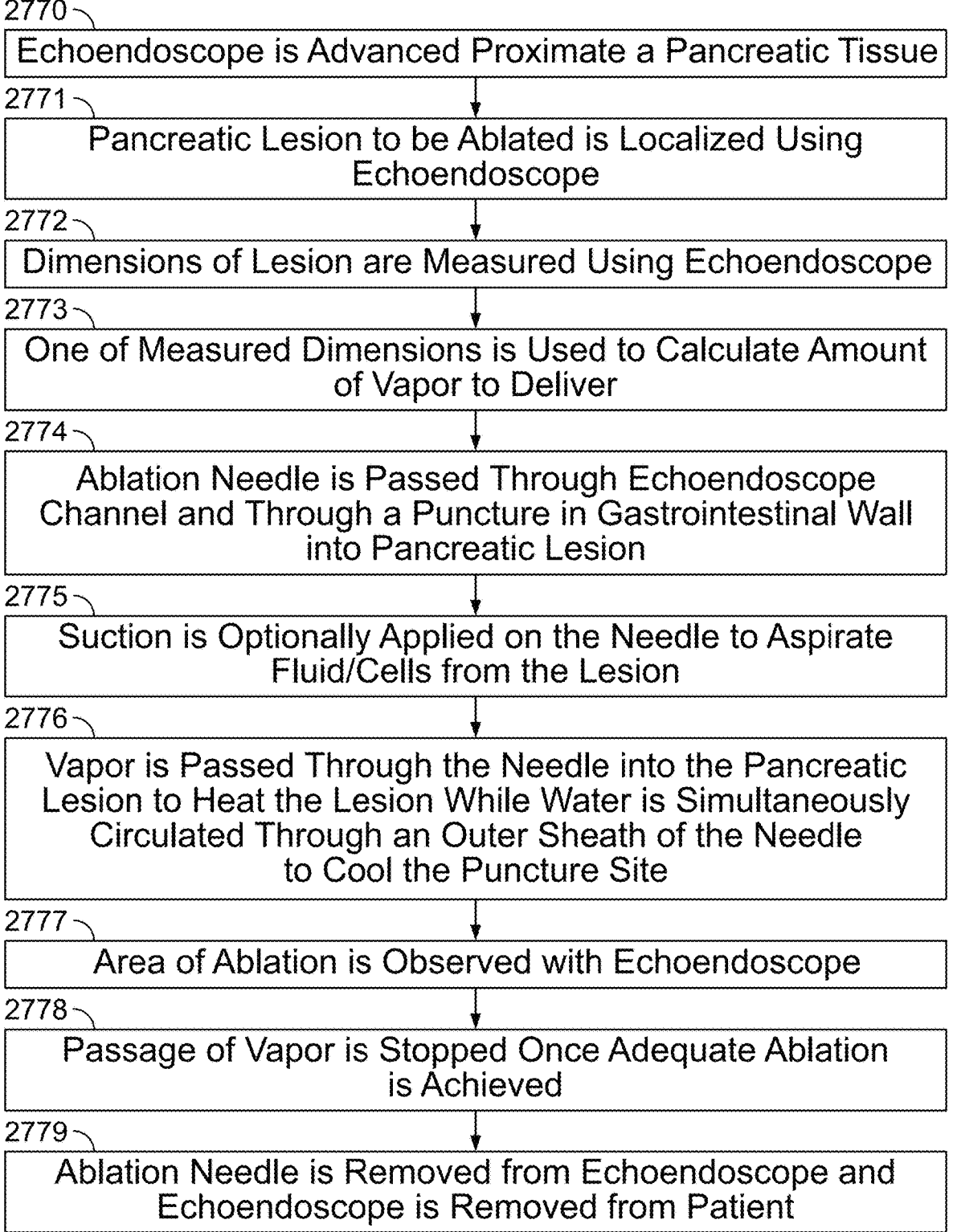

2770
Echoendoscope is Advanced Proximate a Pancreatic Tissue

2771
Pancreatic Lesion to be Ablated is Localized Using Echoendoscope

2772
Dimensions of Lesion are Measured Using Echoendoscope

2773
One of Measured Dimensions is Used to Calculate Amount of Vapor to Deliver

2774
Ablation Needle is Passed Through Echoendoscope Channel and Through a Puncture in Gastrointestinal Wall into Pancreatic Lesion 2775
Suction is Optionally Applied on the Needle to Aspirate Fluid/Cells from the Lesion 2776
Vapor is Passed Through the Needle into the Pancreatic Lesion to Heat the Lesion While Water is Simultaneously Circulated Through an Outer Sheath of the Needle to Cool the Puncture Site 2777
Area of Ablation is Observed with Echoendoscope 2778
Passage of Vapor is Stopped Once Adequate Ablation is Achieved 2779
Ablation Needle is Removed from Echoendoscope and Echoendoscope is Removed from Patient

FIG. 27B

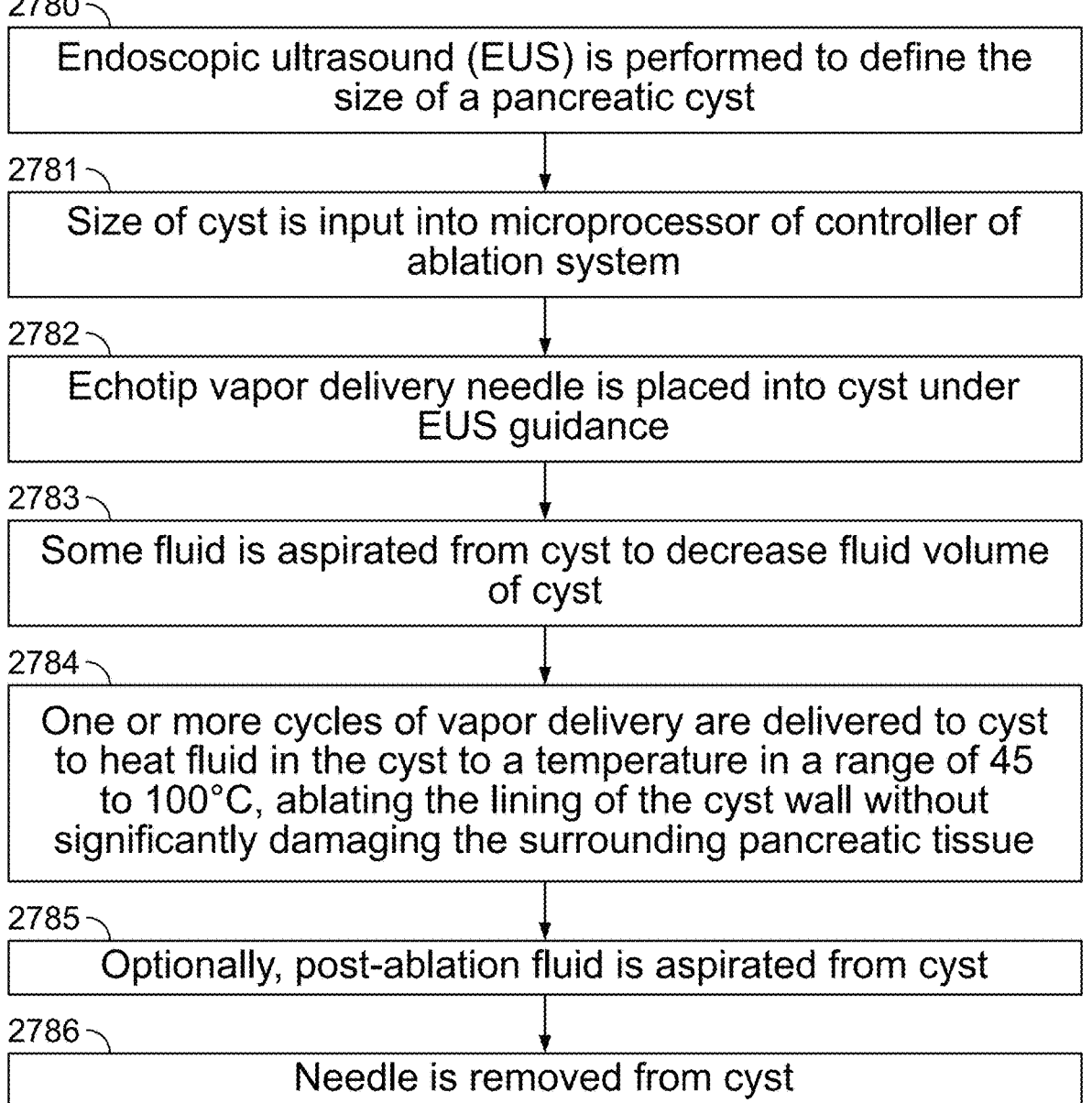

2780

Endoscopic ultrasound (EUS) is performed to define the size of a pancreatic cyst

2781

Size of cyst is input into microprocessor of controller of ablation system

2782

Echotip vapor delivery needle is placed into cyst under EUS guidance

2783

Some fluid is aspirated from cyst to decrease fluid volume of cyst

2784

One or more cycles of vapor delivery are delivered to cyst to heat fluid in the cyst to a temperature in a range of 45 to 100°C, ablating the lining of the cyst wall without significantly damaging the surrounding pancreatic tissue

2785

Optionally, post-ablation fluid is aspirated from cyst

2786

Needle is removed from cyst

FIG. 27C

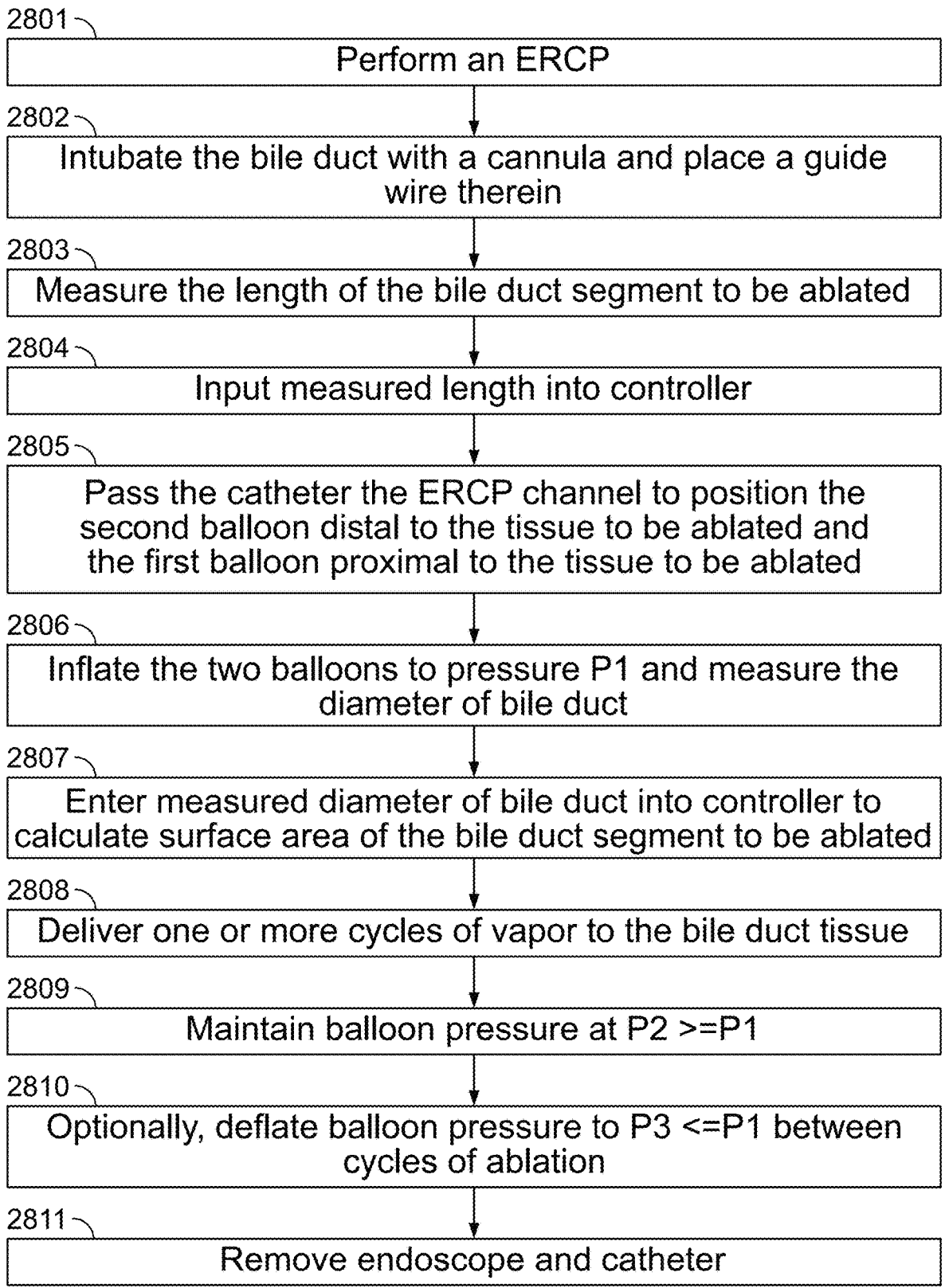

2801 — Perform an ERCP

2802 — Intubate the bile duct with a cannula and place a guide wire therein

2803 — Measure the length of the bile duct segment to be ablated

2804 — Input measured length into controller

2805 — Pass the catheter the ERCP channel to position the second balloon distal to the tissue to be ablated and the first balloon proximal to the tissue to be ablated 2806 — Inflate the two balloons to pressure P1 and measure the diameter of bile duct 2807 — Enter measured diameter of bile duct into controller to calculate surface area of the bile duct segment to be ablated 2808 — Deliver one or more cycles of vapor to the bile duct tissue 2809 — Maintain balloon pressure at P2 >=P1

2810 — Optionally, deflate balloon pressure to P3 <=P1 between cycles of ablation 2811 — Remove endoscope and catheter

FIG. 28

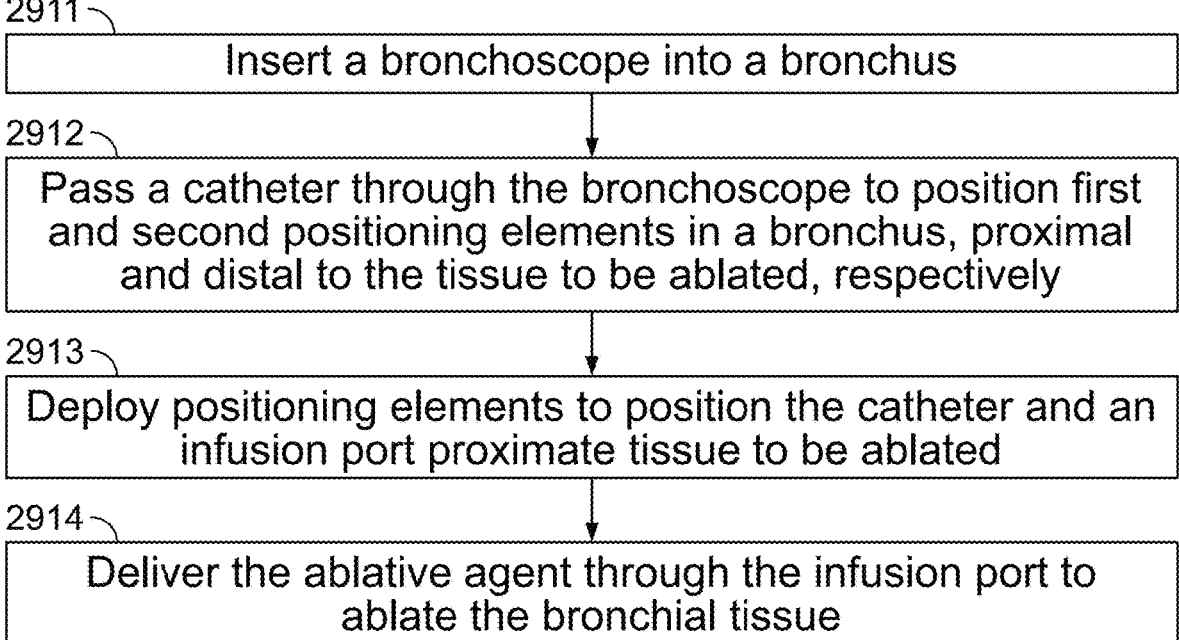

2911 ─

Insert a bronchoscope into a bronchus

2912 ─

Pass a catheter through the bronchoscope to position first and second positioning elements in a bronchus, proximal and distal to the tissue to be ablated, respectively

2913 ─

Deploy positioning elements to position the catheter and an infusion port proximate tissue to be ablated

2914 ─

Deliver the ablative agent through the infusion port to ablate the bronchial tissue

FIG. 29B

Saline In

3013

3014

Saline Out

3012 Air In

3010

3020 Electrode array

Vapor Channels 3022

Balloon 3015

3005

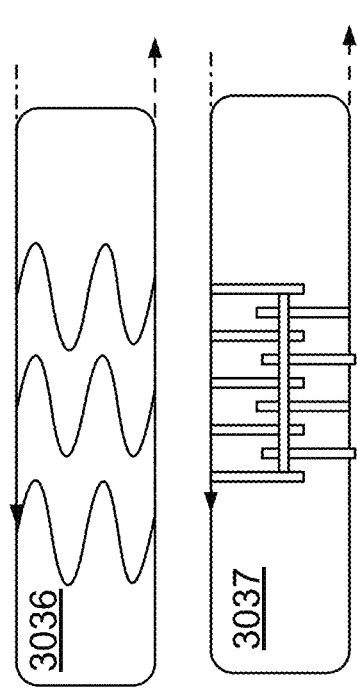
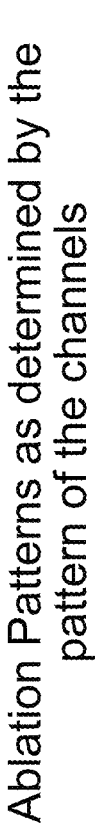
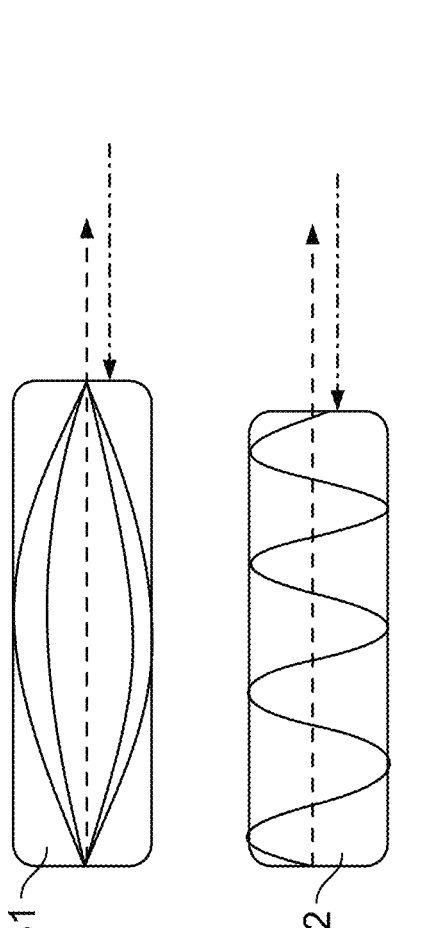
Ablation Patterns as determined by the pattern of the channels
3033
3034
3035
3036
3037
3031
3032
Vapor in
3040
Water out
3045
FIG. 30B

Lung Volume Reduction Catheter

First Segment: RB2 (Posterior)

3150

IP3 identifies disease region for treatment

3152

Vapour catheter placed via bronchoscope in airway

3154

Bronchoscope is positioned into airway of diseased region

3156

Vapour delivered for 3 to 10 seconds based on mass of region

Lung Volume Reduction

3220

3230

3235

130

130

130

+

-

3226

3225

3240

3245

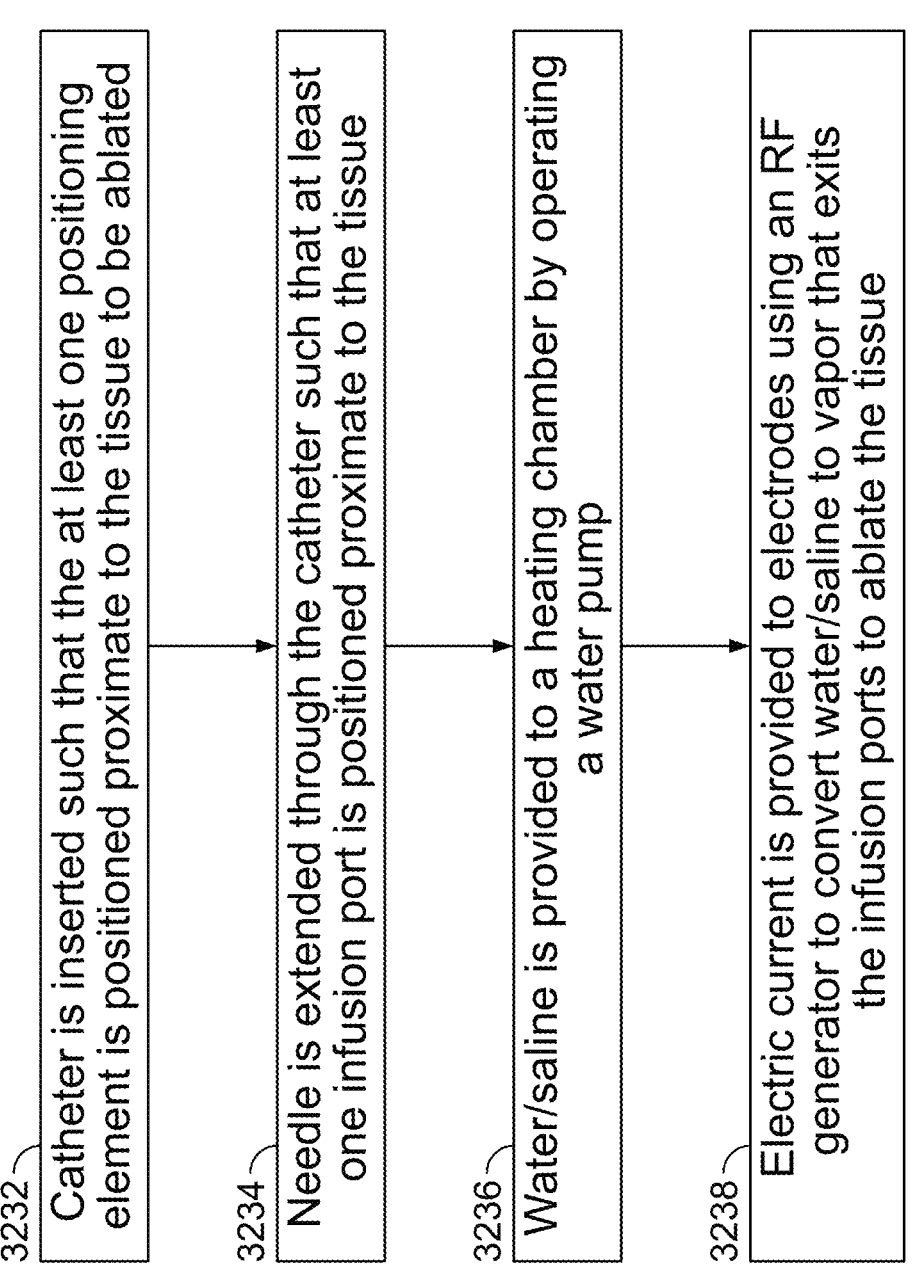

3232 Catheter is inserted such that the at least one positioning element is positioned proximate to the tissue to be ablated 3234 Needle is extended through the catheter such that at least one infusion port is positioned proximate to the tissue 3236 Water/saline is provided to a heating chamber by operating a water pump 3238 Electric current is provided to electrodes using an RF generator to convert water/saline to vapor that exits the infusion ports to ablate the tissue

FIG. 32C

3302 — Apply first portion of first dose of thermal energy

3304 — Apply second portion of first dose of thermal energy

3306 — Remove / reduce denatured mucus

3308 — Apply first portion of second dose of thermal energy

3310 — Apply second portion of first dose of thermal energy

3402 — Position the catheter proximate target surface within patient

3404 — Spray chemical to reduce or remove mucus

3406 — Scrape mechanically to reduce or remove mucus

3408 — Mucus coagulated ?

No

Yes

3410 — Aid edema formation

TEMPERATURE BENCH TESTING FIXTURE

Decline Position — 3604

Thermocouples — 3610

Incline Position — 3602

THERMOCOUPLE MAP

PRE-PUFF vs. COLD START ; STRAIGHT

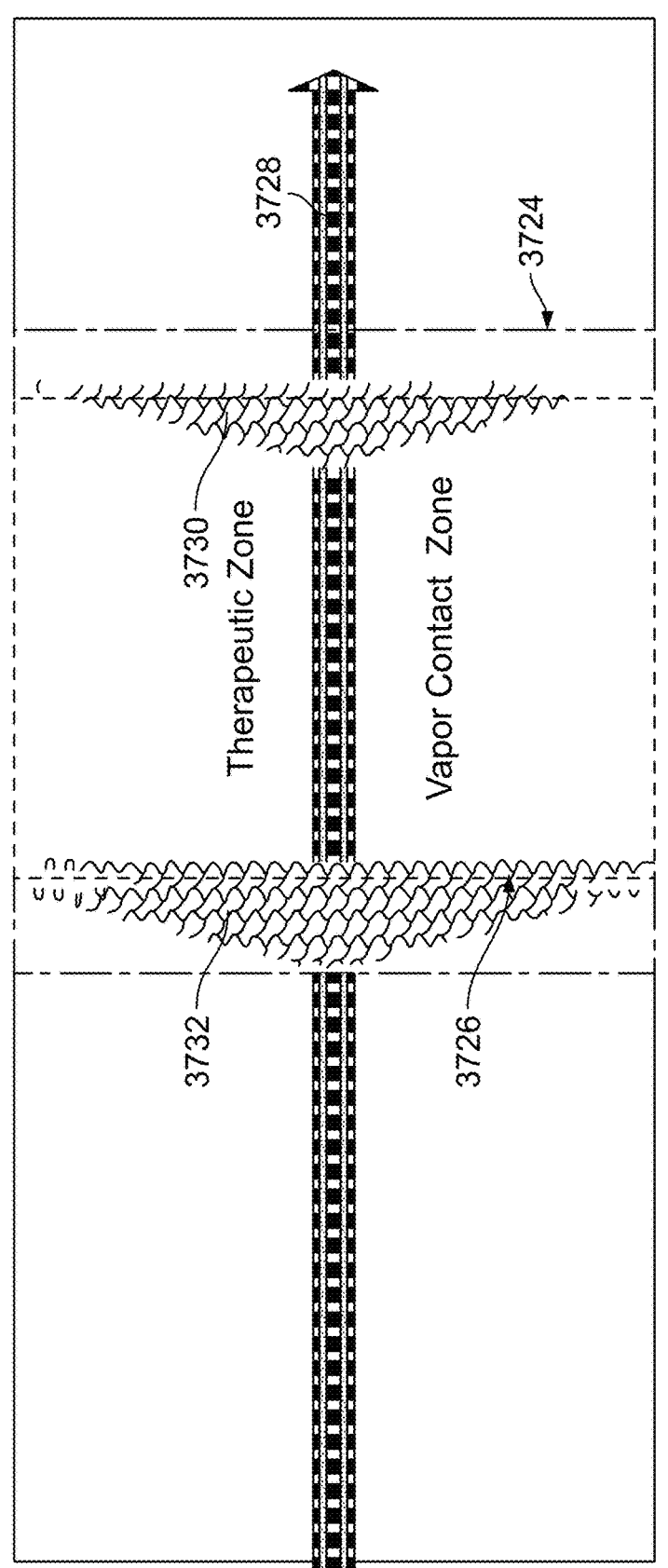

Device has one or more position elements, partially or completely covered by a membrane wherein the shape of the positioning element and the membrane coverage of the positioning element defines a vapor contact zone (VZ) and a therapeutic ablation zone (TZ).

- Wherein the TZ ≥ 75% of the VZ but < 100% of VZ
- Wherein the ratio of TZ to VZ is also controlled by a vapor delivery controller

FIG. 37B

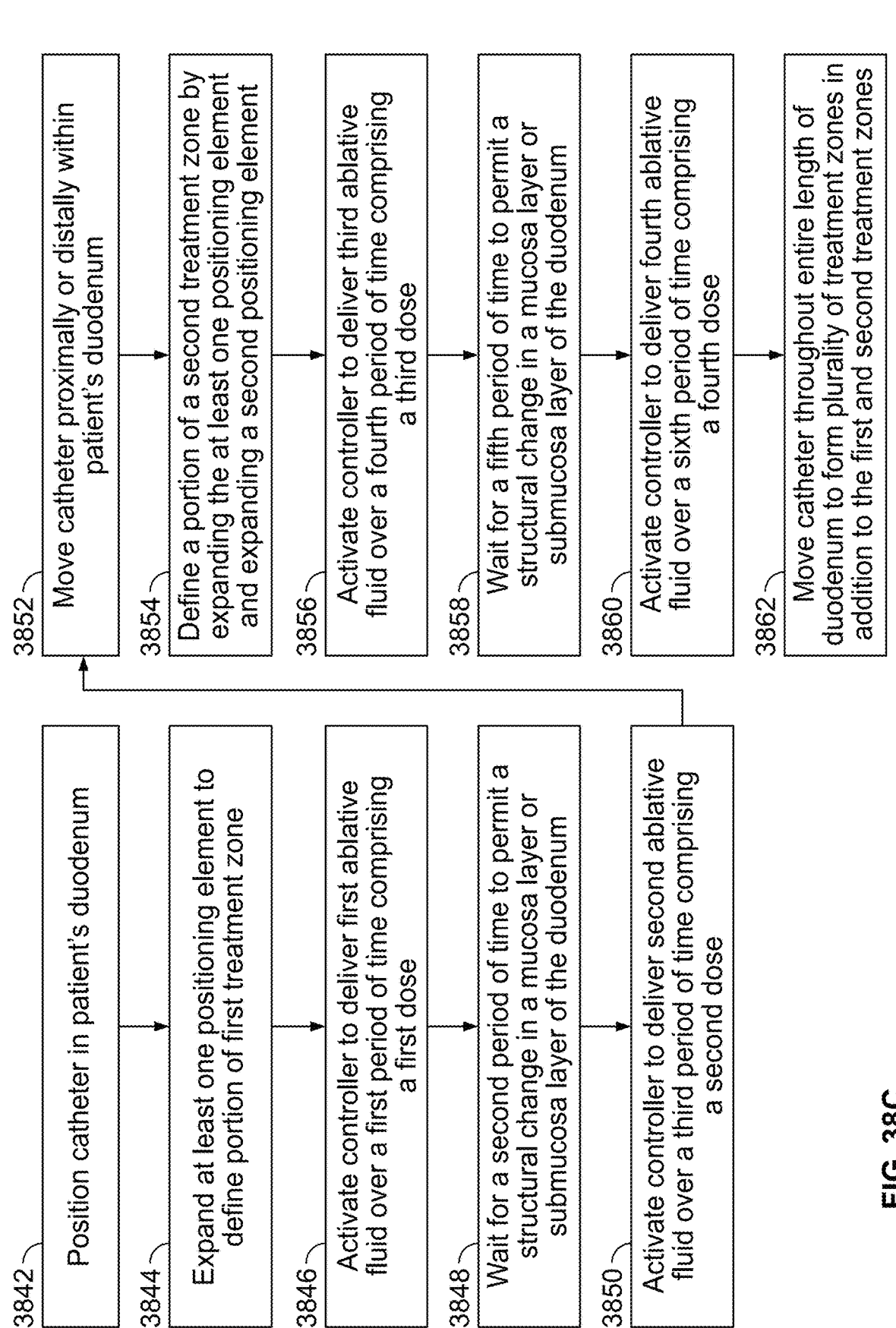

3842 — Position catheter in patient's duodenum

3844 — Expand at least one positioning element to define portion of first treatment zone 3846 — Activate controller to deliver first ablative fluid over a first period of time comprising a first dose 3848 — Wait for a second period of time to permit a structural change in a mucosa layer or submucosa layer of the duodenum 3850 — Activate controller to deliver second ablative fluid over a third period of time comprising a second dose 3852 — Move catheter proximally or distally within patient's duodenum 3854 — Define a portion of a second treatment zone by expanding the at least one positioning element and expanding a second positioning element 3856 — Activate controller to deliver third ablative fluid over a fourth period of time comprising a third dose 3858 — Wait for a fifth period of time to permit a structural change in a mucosa layer or submucosa layer of the duodenum 3860 — Activate controller to deliver fourth ablative fluid over a sixth period of time comprising a fourth dose 3862 — Move catheter throughout entire length of duodenum to form plurality of treatment zones in addition to the first and second treatment zones

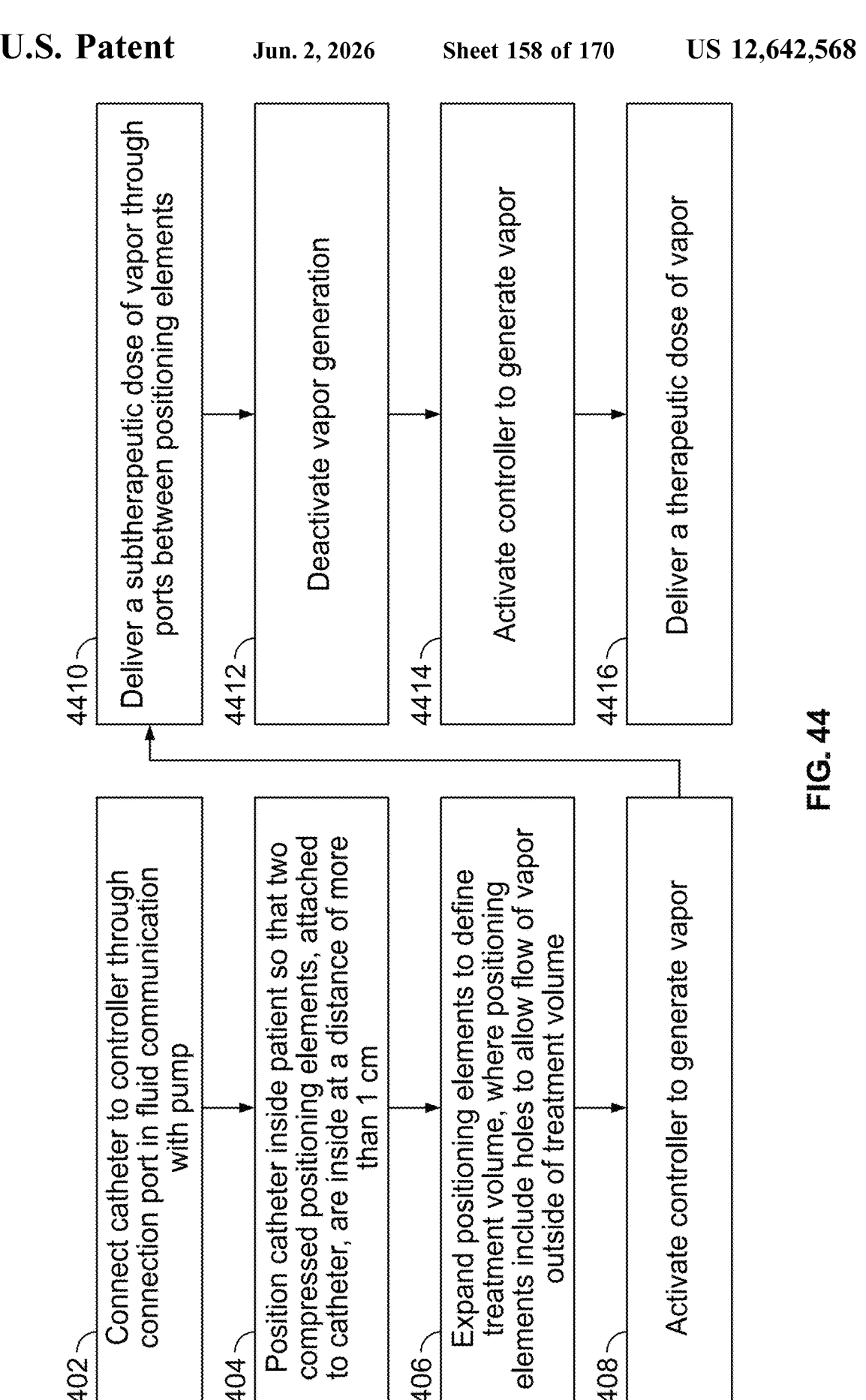

4402 — Connect catheter to controller through connection port in fluid communication with pump 4404 — Position catheter inside patient so that two compressed positioning elements, attached to catheter, are inside at a distance of more than 1 cm 4406 — Expand positioning elements to define treatment volume, where positioning elements include holes to allow flow of vapor outside of treatment volume 4408 — Activate controller to generate vapor 4410 — Deliver a subtherapeutic dose of vapor through ports between positioning elements 4412 — Deactivate vapor generation 4414 — Activate controller to generate vapor 4416 — Deliver a therapeutic dose of vapor

FIG. 44

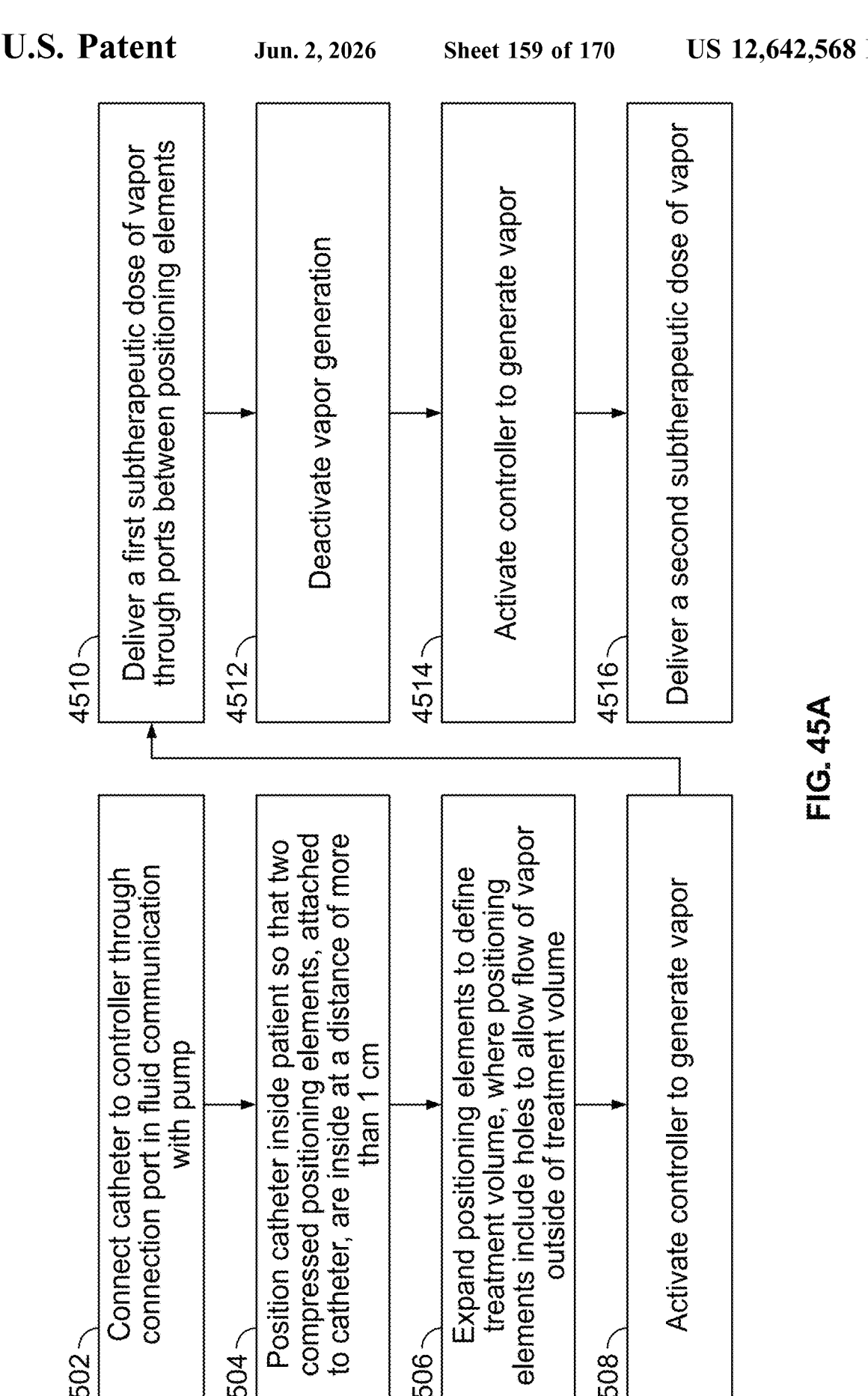

4502 Connect catheter to controller through connection port in fluid communication with pump 4504 Position catheter inside patient so that two compressed positioning elements, attached to catheter, are inside at a distance of more than 1 cm 4506 Expand positioning elements to define treatment volume, where positioning elements include holes to allow flow of vapor outside of treatment volume 4508 Activate controller to generate vapor 4510 Deliver a first subtherapeutic dose of vapor through ports between positioning elements 4512 Deactivate vapor generation 4514 Activate controller to generate vapor 4516 Deliver a second subtherapeutic dose of vapor

FIG. 45A

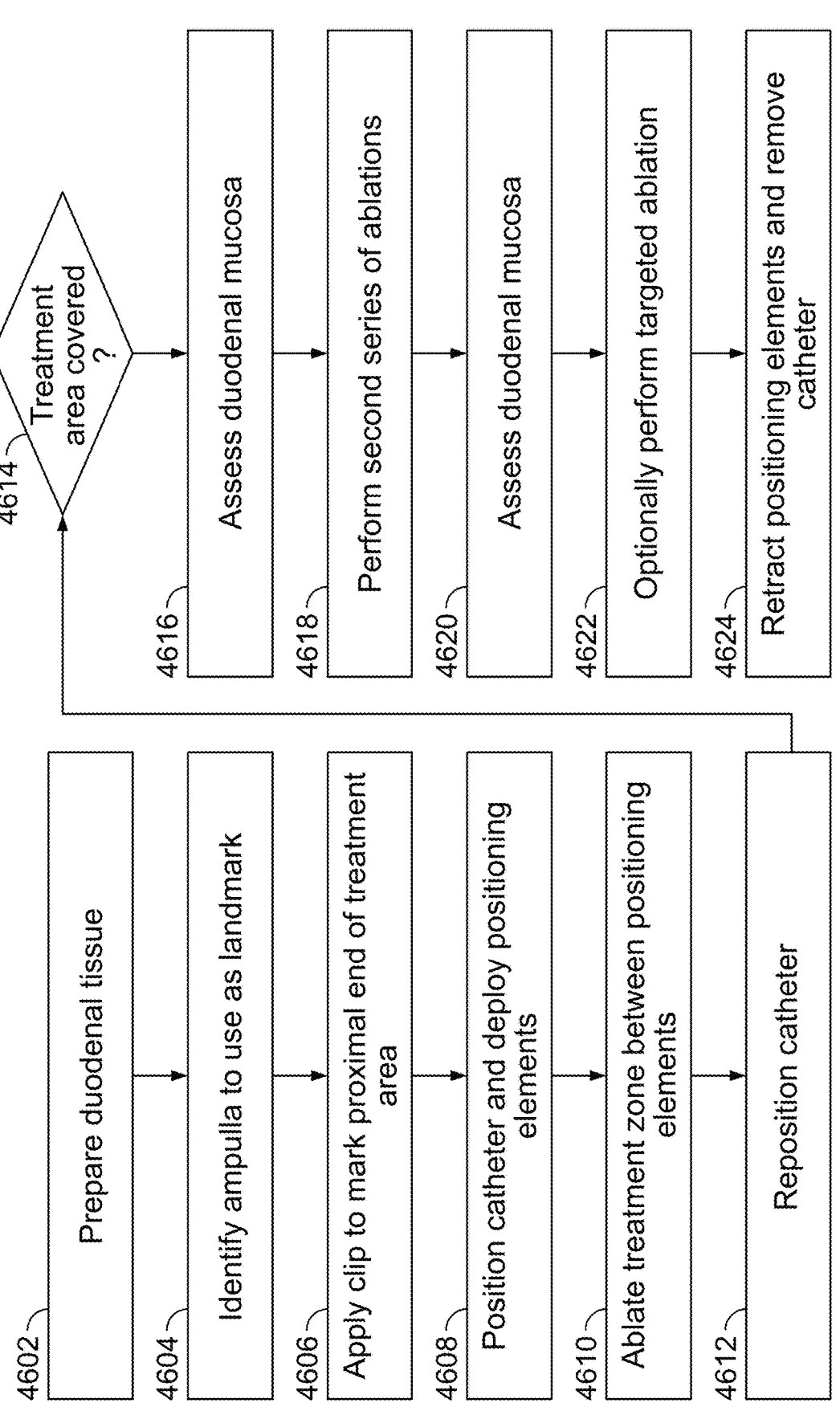

4602 — Prepare duodenal tissue

4604 — Identify ampulla to use as landmark

4606 — Apply clip to mark proximal end of treatment area

4608 — Position catheter and deploy positioning elements

4610 — Ablate treatment zone between positioning elements

4612 — Reposition catheter

4614 — Treatment area covered ?

4616 — Assess duodenal mucosa

4618 — Perform second series of ablations

4620 — Assess duodenal mucosa

4622 — Optionally perform targeted ablation

4624 — Retract positioning elements and remove catheter

FIG. 46A

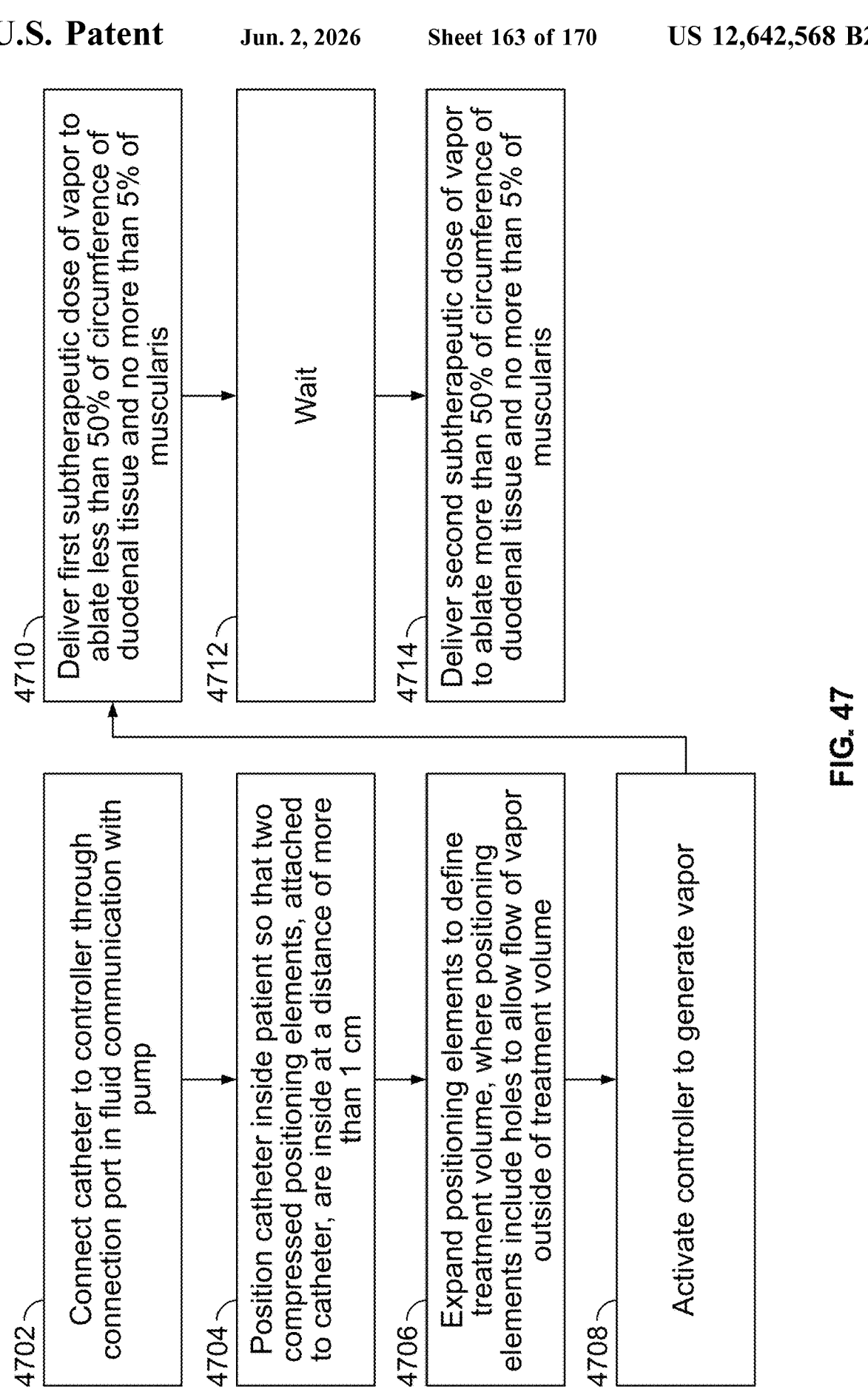

4710 Deliver first subtherapeutic dose of vapor to ablate less than 50% of circumference of duodenal tissue and no more than 5% of muscularis 4712 Wait 4714 Deliver second subtherapeutic dose of vapor to ablate more than 50% of circumference of duodenal tissue and no more than 5% of muscularis 4702 Connect catheter to controller through connection port in fluid communication with pump 4704 Position catheter inside patient so that two compressed positioning elements, attached to catheter, are inside at a distance of more than 1 cm 4706 Expand positioning elements to define treatment volume, where positioning elements include holes to allow flow of vapor outside of treatment volume 4708 Activate controller to generate vapor

FIG. 47

Glucose Levels: AM

| Period | Parameter | N | Mean | Std |
|---|---|---|---|---|
| Pre Ablation | Mean | 27 | 176.864 | 35.825 |
| Weeks 1-4 | Mean | 27 | 143.981 | 22.259 |
| Weeks 1-4 | Change | 27 | -32.883 | 33.981 |
| Weeks 5-8 | Mean | 27 | 146.839 | 18.959 |
| Weeks 5-8 | Change | 27 | -30.025 | 37.036 |
| Weeks 9-12 | Mean | 20 | 145.210 | 24.167 |
| Weeks 9-12 | Change | 20 | -30.677 | 36.169 |
| Weeks 13-16 | Mean | 10 | 156.214 | 34.099 |
| Weeks 13-16 | Change | 10 | -32.054 | 40.292 |

FIG. 49A

Glucose Levels: PM

| Period | Parameter | N | Mean | Std |
|---|---|---|---|---|
| Pre Ablation | Mean | 27 | 227.544 | 44.437 |
| Weeks 1-4 | Mean | 27 | 161.390 | 29.005 |
| Weeks 1-4 | Change | 27 | -66.154 | 46.382 |
| Weeks 5-8 | Mean | 27 | 164.290 | 28.556 |
| Weeks 5-8 | Change | 27 | -63.254 | 47.552 |
| Weeks 9-12 | Mean | 20 | 167.427 | 35.816 |
| Weeks 9-12 | Change | 20 | -61.714 | 47.514 |
| Weeks 13-16 | Mean | 10 | 185.392 | 52.908 |
| Weeks 13-16 | Change | 10 | -54.346 | 50.322 |

FIG. 49C

| Subgroup | N | Mean | Std | Median | Min | Max | 95% C.I | P-Value |
|---|---|---|---|---|---|---|---|---|
| Pre-Procedure | 27 | -0.067 | 0.598 | 0.0 | -1.6 | 1.0 | {-0.3, 0.17} | 0.5674 |
| Month 1 | 27 | -0.856 | 0.889 | -0.9 | -2.6 | 0.9 | {-1.21, -0.5} | <.0001 |
| Month 3 | 15 | -1.100 | 0.969 | -0.9 | -2.4 | 0.6 | {-1.64, -0.56} | 0.0006 |

DUODENAL ABLATION WITH IMPROVED DEPTH AND CONSISTENCY OF ABLATION

CROSS-REFERENCE

The present application relies on, for priority, U.S. Patent Provisional Application No. 63/618,313, titled "Vapor-Based Ablation Treatment Methods with Improved Treatment Volume Vapor Management" and filed on Jan. 6, 2024, U.S. Patent Provisional Application No. 63/596,196, of the same title and filed on Nov. 3, 2023, and U.S. Patent Provisional Application No. 63/488,106, of the same title and filed on Mar. 2, 2023.

The present application is also a continuation-in-part application of U.S. patent application Ser. No. 18/517,488, titled "Vapor-Based Ablation Treatment Methods with Improved Treatment Volume Vapor Management" and filed on Nov. 22, 2023, which is a continuation application of U.S. patent application Ser. No. 17/575,950, of the same title, filed on Jan. 14, 2022, and issued as U.S. Pat. No. 11,864,809 on Jan. 9, 2024, which is a continuation application of U.S. patent application Ser. No. 16/428,598, titled "Multi-Stage Vapor-Based Ablation Treatment Methods and Vapor Generation and Delivery Systems", filed on May 31, 2019, and issued as U.S. Pat. No. 11,806,066 on Nov. 7, 2023, which relies on, for priority, U.S. Patent Provisional Application No. 62/679,694, titled "Ablation Systems and Methods" and filed on Jun. 1, 2018, all of which are herein incorporated by reference in their entirety.

The present application relates to U.S. patent application Ser. No. 15/600,670, titled "Catheter With a Double Balloon Structure to Generate and Apply a Heated Ablative Zone to Tissue", filed on May 19, 2017, and issued as U.S. Pat. No. 10,695,126 on Jun. 30, 2020, which relies on U.S. Provisional Patent Application No. 62/425,144, entitled "Methods and Systems for Ablation" and filed on Nov. 22, 2016, and U.S. Provisional Patent Application No. 62/338,871, entitled "Cooled Coaxial Ablation Catheter" and filed on May 19, 2016, for priority.

The present application also relates to U.S. patent application Ser. No. 15/144,768, titled "Induction-Based Micro-Volume Heating System", filed on May 2, 2016, and issued as U.S. Pat. No. 10,064,697 on Sep. 4, 2018, which is a continuation-in-part application of U.S. patent application Ser. No. 14/594,444, titled "Method and Apparatus for Tissue Ablation", filed on Jan. 12, 2015, and issued as U.S. Pat. No. 9,561,068 on Feb. 7, 2017, which is a continuation-in-part application of U.S. patent application Ser. No. 14/158,687, of the same title, filed on Jan. 17, 2014, and issued as U.S. Pat. No. 9,561,067 on Feb. 7, 2017, which, in turn, relies on U.S. Provisional Patent Application No. 61/753,831, of the same title and filed on Jan. 17, 2013, for priority.

U.S. patent application Ser. No. 14/158,687 is also a continuation-in-part application of U.S. patent application Ser. No. 13/486,980, titled "Method and Apparatus for Tissue Ablation", filed on Jun. 1, 2012, and issued as U.S. Pat. No. 9,561,066 on Feb. 7, 2017, which, in turn, relies on U.S. Provisional Patent Application No. 61/493,344, of the same title and filed on Jun. 3, 2011, for priority.

U.S. patent application Ser. No. 13/486,980 is also a continuation-in-part application of U.S. patent application Ser. No. 12/573,939, titled "Method and Apparatus for Tissue Ablation" and filed on Oct. 6, 2009, which, in turn, relies on U.S. Provisional Patent Application No. 61/102, 885, of the same title and filed on Oct. 6, 2008, for priority.

All of the above referenced applications are herein incorporated by reference in their entirety.

FIELD

The present specification relates to systems and methods configured to generate and deliver vapor for ablation therapy. More particularly, the present specification relates to systems and methods comprising flexible catheter positioning elements and/or tips with needles or ports for delivering ablation therapy to specific organ systems.

BACKGROUND

Ablation, as it pertains to the present specification, relates to the removal or destruction of a body tissue, via the introduction of a destructive agent, such as radiofrequency energy, laser energy, ultrasonic energy, cyroagents, steam, or other forms or methods of generating heat. Ablation is commonly used to eliminate diseased or unwanted tissues, such as, but not limited to cysts, polyps, tumors, hemorrhoids, precancerous lesions and tissue, and other similar lesions.

Over the past decades several endoscopic therapies have been developed to treat Barrett's esophagus (BE) with early neoplasia. The current treatment strategy consists of endoscopic resection of visible abnormalities, followed by ablation therapy for residual flat BE. The most widely adopted ablation technique is radiofrequency ablation (RFA) which has proven to be effective, safe and durable. Nevertheless, RFA holds several disadvantages. RFA catheters lack a simple through-the-scope design and have to be mounted on or passed alongside the endoscope. This may not only be time-consuming, but also requires removal and reintroduction of the endoscope. Moreover, RFA may be technically difficult in an esophagus with altered anatomy or scarring as a consequence of a previous endoscopic resection. Lastly, RFA is associated with clinically relevant post-procedural pain.

To overcome these limitations, a novel vapor-based endoscopic ablation system was developed which may serve as an alternative. This radiofrequency vapor ablation (RFVA) system (Aqua Medical Inc., Santa Ana, California, USA) induces thermal ablation through high temperature water steam (100° C.) without making direct contact with the target tissue. Vapor ablation has already demonstrated to be safe and effective for the treatment of other medical conditions, such as lung emphysema, dysfunctional uterine bleeding, and benign prostatic hyperplasia.

Steam-based ablation systems, such as the ones disclosed in U.S. Pat. Nos. 9,615,875, 9,433,457, 9,376,497, 9,561, 068, 9,561,067, and 9,561,066, disclose ablation systems that controllably deliver steam through one or more lumens toward a tissue target. One problem that all such steam-based ablation systems have is the potential overheating or burning of healthy tissue. Steam passing through a channel within a body cavity heats surfaces of the channel and may cause exterior surfaces of the medical tool, other than the operational tool end itself, to become excessively hot. As a result, physicians may unintentionally burn healthy tissue when external portions of the device, other than the distal operational end of the tool, accidentally contacts healthy tissue. U.S. Pat. Nos. 9,561,068, 9,561,067, and 9,561,066 are hereby incorporated herein by reference.

Effective use of steam often requires controllably exposing a volume of tissue to steam. However, prior art approaches to steam ablation either fail to sufficiently enclose a volume being treated, thereby insufficiently exposing the tissue, or excessively enclose a volume being treated, thereby dangerously increasing pressure and/or temperature within the patient's organ. Pressure sensors located on the catheter may help regulate energy delivery, but they are not necessarily reliable and represent a critical point of potential failure in the system. Therefore, among the several disadvantages of the conventional approaches to performing vapor-based ablation, foremost is the difficulty of controlling energy deposition in order to achieve uniform ablation in the treatment zone. A lack of uniformity in ablation can cause certain portions of the treatment area to be insufficiently ablated, such as a small fraction of the depth of the mucosa layer of the patient's duodenum, while concurrently causing certain portions of the treatment area to be excessively ablated, such as a substantial fraction of the depth of the serosa layer of the patient's duodenum.

Conventional vapor ablation systems may selectively add cooling fluid to control temperature in the treatment area and/or use specialized application components, such as balloons or nozzles. However, these approaches add substantial complexity to the system and typically fail to provide the required uniformity.

It is therefore desirable to have steam-based ablation devices that integrate into the device itself safety mechanisms which prevent unwanted burning during use. It is further desirable to be able to provide a way to better control the amount of steam to which a target tissue is exposed. It is also desirable to be able to control a pressure level within an enclosed volume without relying on a pressure sensor in the catheter itself. It is further desirable to expose the target tissue to steam without increasing the pressure of the exposed tissue. Also, there is a need for a vapor-based ablation system that can achieve effective ablation uniformity within a defined treatment area. Finally, it is also desirable to provide steam-based ablation systems and methods used to treat various conditions including metabolic syndrome, pre-cancerous or cancerous tissue in the esophagus, duodenum, bile duct, stomach, colon, and pancreas.

SUMMARY

The present specification discloses a method for treating at least one of excess weight, obesity, eating disorders, metabolic syndrome, dyslipidemia, diabetes, polycystic ovarian disease, fatty liver disease, non-alcoholic fatty liver disease, or non-alcoholic steatohepatitis disease by ablating duodenal tissue using a vapor ablation system, wherein the vapor ablation system comprises a catheter having at least one positioning element configured to expand outward from the catheter, wherein, upon expansion, the at least one positioning element defines a portion of a first treatment zone, wherein ports are positioned on the catheter and are configured to direct ablative fluid from within the catheter out toward said first treatment zone, and wherein the vapor ablation system further comprises a controller having at least one processor in electrical communication with the catheter, the method comprising: positioning the catheter in a patient's duodenum; causing the at least one positioning element to expand and define the portion of the first treatment zone; activating the controller, wherein, upon activation, the controller delivers a first fluid to the catheter and causes the catheter to heat the first fluid to form a first ablative fluid such that the first ablative fluid leaves the catheter through the ports over a first period of time, wherein the first ablative fluid delivered over the first period constitutes a first dose and wherein the first dose comprises less energy than required to achieve effective ablation of tissue in the first treatment zone; after the first period of time, waiting a second period of time to permit a structural change in a mucosa layer or submucosa layer of the duodenum; and after said second period of time, activating the controller, wherein, upon activation, the controller is configured to deliver a second fluid to the catheter and cause the catheter to heat the second fluid to a second ablative fluid such that the second ablative fluid leaves the catheter through the ports over a third period of time, wherein the second ablative fluid delivered over the third period constitutes a second dose and wherein the second dose comprises at least one of a) less energy than required to achieve effective ablation of tissue in the first treatment zone, b) sufficient energy required to achieve effective ablation of tissue in the first treatment zone, or c) more energy than required to achieve effective ablation of tissue in the first treatment zone.

Optionally, the first dose is a subtherapeutic dose. Optionally, the second dose is a subtherapeutic dose. Optionally, the second dose is a therapeutic dose. Optionally, the second dose is a supratherapeutic dose.

Optionally, a volume of the first ablative fluid delivered over the first period of time and a volume of the second ablative fluid delivered over the third period of time are substantially equal. Optionally, a volume of the first ablative fluid delivered over the first period of time and a volume of the second ablative fluid delivered over the third period of time are different. Optionally, a volume of the first ablative fluid delivered over the first period of time is less than a volume of the second ablative fluid delivered over the third period of time.

Optionally, the method further comprises, after said third period of time, moving the catheter proximally or distally within the patient's duodenum. Optionally, the method further comprises, after moving said catheter, defining a portion of a second treatment zone. Optionally, defining the portion of the second treatment zone comprises expanding the at least one positioning element and expanding a second positioning element and wherein the second treatment zone is defined by the at least one positioning element being one on end of the second treatment zone and the second positioning element being on the other end of the second treatment zone.

Optionally, the second treatment zone at least partially overlaps with the first treatment zone. Optionally, the second treatment zone and the first treatment zone have between 5% and 95% of their respective tissue in common. Optionally, the second treatment zone and the first treatment zone have between 15% and 85% of their respective tissue in common.

Optionally, the method further comprises: after defining the portion of the second treatment zone, activating the controller, wherein, upon activation, the controller delivers a third fluid to the catheter and causes the catheter to heat the third fluid to form a third ablative fluid such that the third ablative fluid leaves the catheter through the ports over a fourth period of time, wherein the third ablative fluid delivered over the fourth period constitutes a third dose and wherein the third dose comprises less energy than required to achieve effective ablation of tissue in the second treatment zone; after the fourth period of time, waiting a fifth period of time to permit a structural change in a mucosa layer or submucosa layer of the duodenum; and after said fifth period of time, activating the controller, wherein, upon activation, the controller is configured to deliver a fourth fluid to the catheter and cause the catheter to heat the fourth fluid to a fourth ablative fluid such that the fourth ablative fluid leaves the catheter through the ports over a sixth period of time, wherein the fourth ablative fluid delivered over the sixth period of time constitutes a fourth dose and wherein the fourth dose comprises at least one of a) less energy than required to achieve effective ablation of tissue in the second treatment zone, b) sufficient energy required to achieve effective ablation of tissue in the second treatment zone, or c) more energy than required to achieve effective ablation of tissue in the second treatment zone. Optionally, the at least one positioning element and the second positioning element are configured to permit no more than 25% of the first ablative fluid and no more than 25% of the second ablative fluid to escape the first treatment zone. Optionally, the at least one positioning element and the second positioning element are configured to permit no more than 50% of the first ablative fluid and no more than 50% of the second ablative fluid to escape the first treatment zone.

Optionally, the method further comprises moving the catheter throughout an entire length the duodenum to form a plurality of treatment zones in addition to the first treatment zone and the second treatment zone. Optionally, each of the plurality of treatment zones overlaps with a neighboring treatment zone such that they share between 5% and 95% of their respective tissue in common. Optionally, each of the plurality of treatment zones overlaps with a neighboring treatment zone such that they share between 25% and 75% of their respective tissue in common. Optionally, each of the first treatment zone, second treatment zone, and the plurality of treatment zones does not encompass the patient's ampulla. Optionally, a treatment zone of the first treatment zone, second treatment zone, and the plurality of treatment zones that is nearest to the patient's ampulla begins less than 1 cm away from the patient's ampulla.

Optionally, the catheter is positioned in the patient's duodenum using an endoscope wherein, when the endoscope and catheter are positioned in the patient's duodenum, no other device is positioned in the patient's duodenum outside said endoscope.

Optionally, the first period of time is at least 20% less than the third period of time.

Optionally, the catheter further comprises a second positioning element, wherein the second positioning element together with the at least one positioning element define the first treatment zone and both the at least one positioning element and the second positioning element are configured to permit at least a portion of the first ablative fluid to escape from the first treatment zone. Optionally, the at least one positioning element and the second positioning element are configured to permit no more than 25% of the first ablative fluid and no more than 25% of the second ablative fluid to escape the first treatment zone. Optionally, the at least one positioning element and the second positioning element are configured to permit no more than 50% of the first ablative fluid and no more than 50% of the second ablative fluid to escape the first treatment zone.

Optionally, the method further comprises, after delivering the first dose and the second dose to the first treatment zone, at least partially collapsing the at least one positioning element and a second positioning element, moving the catheter proximally or distally from the first treatment zone, re-expanding the at least one positioning element and the second positioning element to define a second treatment zone, wherein the second treatment zone overlaps with, but is not the same as, the first treatment zone. Optionally, the method further comprises delivering two doses of ablative fluid to the second treatment zone and then repeating the steps of collapsing, moving, and re-expanding to form a plurality of treatment zones such that the first treatment zone, second treatment zone and plurality of treatment zones extend an entire length of the patient's duodenum. Optionally, the method further comprises applying at least two doses of ablative fluid to each of the plurality of treatment zones, wherein each of the plurality of treatment zones overlaps with a neighboring one of the plurality of treatment zones such that they share in a range of 5% to 95% of their tissue in common. Optionally, a first of the at least two doses is a subtherapeutic dose and a second of the at least two doses is at least one of a subtherapeutic dose, a therapeutic dose, or a supratherapeutic dose.

Optionally, the method further comprises delivering two doses of ablative fluid to the second treatment zone and then repeating the steps of collapsing, moving, and re-expanding to form a plurality of treatment zones such that the first treatment zone, second treatment zone and plurality of treatment zones extend a length of the patient's duodenum in a range of 9 cm to 23 cm. Optionally, the method further comprises applying at least two doses of ablative fluid to each of the plurality of treatment zones, wherein each of the plurality of treatment zones overlaps with a neighboring one of the plurality of treatment zones such that they share in a range of 5% to 95% of their tissue in common. Optionally, a first of the at least two doses is a subtherapeutic dose and a second of the at least two doses is at least one of a subtherapeutic dose, a therapeutic dose, or a supratherapeutic dose.

Optionally, the method further comprises measuring the patient's fasting glucose before performing the method and within 24 hours after performing the method, wherein the patient's fasting glucose within 24 hours after performing the method is at least 10% or 20 mg/dl less than the patient's fasting glucose before performing the method.

Optionally, the method further comprises measuring the patient's fasting glucose before performing the method and approximately 30 days after performing the method, wherein the patient's fasting glucose approximately 30 days after performing the method is at least 10% or 20 mg/dl less than the patient's fasting glucose before performing the method.

Optionally, the method further comprises measuring the patient's post-prandial glucose before performing the method and within 24 hours after performing the method, wherein the patient's post-prandial glucose within 24 hours after performing the method is at least 10% or 30 mg/dl less than the patient's post-prandial glucose before performing the method.

Optionally, the method further comprises measuring the patient's post-prandial glucose before performing the method and approximately 30 days after performing the method, wherein the patient's post-prandial glucose approximately 30 days after performing the method is at least 10% or 30 mg/dl less than the patient's post-prandial glucose before performing the method.

Optionally, the method further comprises measuring the patient's HbA1c level before performing the method and approximately four weeks after performing the method, wherein the patient's HbA1c level approximately four weeks after performing the method is at least 0.6% less than the patient's HbA1c level before performing the method.

Optionally, the method further comprises measuring the patient's HbA1c level before performing the method and approximately six months after performing the method, wherein the patient's HbA1c level approximately six months after performing the method is at least 0.6% less than the patient's HbA1c level before performing the method.

Optionally, the structural change is at least one of an edema, inflammation, cellular injury, or alternation of metabolic cellular processes.

Optionally, each of the first treatment zone, the second treatment zone and the plurality of treatment zones is defined by a plurality of consecutively positioned annular rings, wherein each of the plurality of consecutively positioned annual rings has an internal surface area, and wherein, after the method, at least 60% of the internal surface area of each of the plurality of consecutively positioned annual rings is effectively ablated.

Optionally, each of the first treatment zone, the second treatment zone and the plurality of treatment zones is defined by a plurality of consecutively positioned annular rings, wherein, after the method, each of the plurality of consecutively positioned annular rings has an effectively ablated region, and wherein the effectively ablated region's thickness along a length of each of the plurality of consecutively positioned annular rings varies no more than 50% from an average thickness of the effectively ablated region.

Optionally, the second period of time is in a range of 1 second to 50 minutes.

Optionally, each of the first dose and the second dose has an energy in a range of 50 Joules to 200 Joules.

The present specification also discloses a multi-stage method for treating at least one of excess weight, obesity, eating disorders, metabolic syndrome, dyslipidemia, diabetes, polycystic ovarian disease, fatty liver disease, non-alcoholic fatty liver disease, or non-alcoholic steatohepatitis disease by ablating duodenal tissue using a vapor ablation system, wherein the vapor ablation system comprises a catheter comprising a first positioning element, a second positioning elements, and ports positioned between the first positioning element and the second positioning element and comprises a controller having at least one processor in electrical communication with a catheter, the multi-stage method comprising: positioning the catheter in a patient's duodenum; causing the first positioning element and second positioning element to expand and define a first treatment zone; activating the controller, wherein, upon activation, the controller is configured to deliver to fluid to the catheter and cause the catheter to heat the fluid to a first vapor such that the first vapor leaves the catheter through the ports over a first period of time, wherein the first period of time is less than a period of time required to achieve effective ablation of tissue in the first treatment zone; after the first period of time, waiting a second period of time to permit a structural change in a mucosa layer or submucosa layer of the duodenum; and after said second period of time, activating the controller, wherein, upon activation, the controller is configured to deliver to fluid to the catheter and cause the catheter to heat the fluid to a second vapor such that the second vapor leaves the catheter through the ports over a third period of time, wherein the third period of time is a sufficient period of time required to achieve effective ablation of tissue in the first treatment zone.

Optionally, the method further comprises at least partially collapsing the first positioning element and second positioning element, moving the catheter proximally or distally from the first treatment zone, re-expanding the first positioning element and second positioning element to define a second treatment zone, wherein the second treatment zone overlaps with, but is not the same as, the first treatment zone. Optionally, the method further comprises repeating each of said collapsing, moving, and re-expanding steps to create a plurality of treatment zones, wherein each of the plurality of treatment zones at least partially overlaps with, but is not the same as, an adjacent one of the plurality of treatment zones. Optionally, at least one of the first treatment zone, second treatment zone, or plurality of treatment zones begins less than 1 cm away from the patient's ampulla.

Optionally, the catheter is positioned in the patient's duodenum using an endoscope, wherein, when the endoscope and catheter are positioned in the patient's duodenum, no other device is positioned in the patient's duodenum outside said endoscope.

Optionally, the first period of time is at least 20% less than the third period of time.

Optionally, the first positioning element and second positioning element are configured to permit at least a portion of the first vapor and a portion of the second vapor to escape from each of the first treatment zone, the second treatment zone, and the plurality of treatment zones.

Optionally, the first positioning element and second positioning element are configured to permit no more than 25% of the first vapor and 25% of the second vapor to escape from each of the first treatment zone, the second treatment zone, and the plurality of treatment zones.

Optionally, the method further comprises measuring the patient's fasting glucose before performing the multi-stage method and within 24 hours after performing the multi-stage method, wherein the patient's fasting glucose within 24 hours after performing the multi-stage method is at least 10% or 20 mg/dl less than the patient's fasting glucose before performing the multi-stage method.

Optionally, the method further comprises measuring the patient's fasting glucose before performing the multi-stage method and approximately 30 days after performing the multi-stage method, wherein the patient's fasting glucose approximately 30 days after performing the multi-stage method is at least 10% or 20 mg/dl less than the patient's fasting glucose before performing the multi-stage method.

Optionally, the method further comprises measuring the patient's post-prandial glucose before performing the multi-stage method and within 24 hours after performing the multi-stage method, wherein the patient's post-prandial glucose within 24 hours after performing the multi-stage method is at least 10% or 30 mg/dl less than the patient's post-prandial glucose before performing the multi-stage method.

Optionally, the method further comprises measuring the patient's post-prandial glucose before performing the multi-stage method and approximately 30 days after performing the multi-stage method, wherein the patient's post-prandial glucose approximately 30 days after performing the multi-stage method is at least 10% or 30 mg/dl less than the patient's post-prandial glucose before performing the multi-stage method.

Optionally, the method further comprises measuring the patient's HbA1c level before performing the multi-stage method and approximately four weeks after performing the multi-stage method, wherein the patient's HbA1c level approximately four weeks after performing the multi-stage method is at least 0.6% less than the patient's HbA1c level before performing the multi-stage method.

Optionally, the method further comprises measuring the patient's HbA1c level before performing the multi-stage method and approximately six months after performing the multi-stage method, wherein the patient's HbA1c level approximately six months after performing the multi-stage method is at least 0.6% less than the patient's HbA1c level before performing the multi-stage method.

Optionally, the structural change is at least one of an edema, inflammation, cellular injury, or alternation of metabolic cellular processes.

Optionally, each of the first treatment zone, second treatment zone and plurality of treatment zones is defined by a plurality of consecutively positioned annular rings, wherein each of the plurality of consecutively positioned annual rings has an internal surface area, and wherein, after the multi-stage method, at least 60% of the internal surface area of each of the plurality of consecutively positioned annual rings is effectively ablated.

Optionally, each of the first treatment zone, second treatment zone and plurality of treatment zones is defined by a plurality of consecutively positioned annular rings, wherein, after the multi-stage method, each of the plurality of consecutively positioned annular rings has an effectively ablated region, and wherein the effectively ablated region's thickness along a length of each of the plurality of consecutively positioned annular rings varies no more than 50% from an average thickness of the effectively ablated region.

The present specification also discloses a multi-stage method for treating at least one of excess weight, obesity, eating disorders, metabolic syndrome, dyslipidemia, diabetes, polycystic ovarian disease, fatty liver disease, non-alcoholic fatty liver disease, or non-alcoholic steatohepatitis disease by ablating duodenal tissue using a vapor ablation system, wherein the vapor ablation system comprises a catheter comprising a first positioning element, a second positioning elements, and ports positioned between the first positioning element and the second positioning element and comprises a controller having at least one processor in electrical communication with a catheter, the multi-stage method comprising: positioning the catheter in a patient's duodenum; causing the first positioning element and second positioning element to expand and define a first treatment zone; activating the controller, wherein, upon activation, the controller is configured to deliver to fluid to the catheter and cause the catheter to heat the fluid to a first vapor having a first energy dose such that the first vapor leaves the catheter through the ports, wherein the first energy dose is less than an energy dose required to achieve effective ablation of tissue in the first treatment zone; after the first period of time, waiting a second period of time to permit a structural change in a mucosa layer or submucosa layer of the duodenum; and after said second period of time, activating the controller, wherein, upon activation, the controller is configured to deliver to fluid to the catheter and cause the catheter to heat the fluid to a second vapor having a second energy dose such that the second vapor leaves the catheter through the ports, wherein the second energy dose is a sufficient energy dose required to achieve effective ablation of tissue in the first treatment zone.

Optionally, the method further comprises at least partially collapsing the first positioning element and second positioning element, moving the catheter proximally or distally from the first treatment zone, re-expanding the first positioning element and second positioning element to define a second treatment zone, wherein the second treatment zone overlaps with, but is not the same as, the first treatment zone.

Optionally, the method further comprises repeating each of said collapsing, moving, and re-expanding steps to create a plurality of treatment zones, wherein each of the plurality of treatment zones at least partially overlaps with, but is not the same as, an adjacent one of the plurality of treatment zones. Optionally, at least one of the first treatment zone, second treatment zone, or plurality of treatment zones begins less than 1 cm away from the patient's ampulla.

Optionally, the catheter is positioned in the patient's duodenum using an endoscope, wherein, when the endoscope and catheter are positioned in the patient's duodenum, no other device is positioned in the patient's duodenum outside said endoscope.

Optionally, the first period of time is at least 20% less than the third period of time.

Optionally, the first positioning element and second positioning element are configured to permit at least a portion of the first vapor and a portion of the second vapor to escape from each of the first treatment zone, the second treatment zone, and the plurality of treatment zones.

Optionally, the first positioning element and second positioning element are configured to permit no more than 25% of the first vapor and 25% of the second vapor to escape from each of the first treatment zone, the second treatment zone, and the plurality of treatment zones.

Optionally, the method further comprises measuring the patient's fasting glucose before performing the multi-stage method and within 24 hours after performing the multi-stage method, wherein the patient's fasting glucose within 24 hours after performing the multi-stage method is at least 10% or 20 mg/dl less than the patient's fasting glucose before performing the multi-stage method.

Optionally, the method further comprises measuring the patient's fasting glucose before performing the multi-stage method and approximately 30 days after performing the multi-stage method, wherein the patient's fasting glucose approximately 30 days after performing the multi-stage method is at least 10% or 20 mg/dl less than the patient's fasting glucose before performing the multi-stage method.

Optionally, the method further comprises measuring the patient's post-prandial glucose before performing the multi-stage method and within 24 hours after performing the multi-stage method, wherein the patient's post-prandial glucose within 24 hours after performing the multi-stage method is at least 10% or 30 mg/dl less than the patient's post-prandial glucose before performing the multi-stage method.

Optionally, the method further comprises measuring the patient's post-prandial glucose before performing the multi-stage method and approximately 30 days after performing the multi-stage method, wherein the patient's post-prandial glucose approximately 30 days after performing the multi-stage method is at least 10% or 30 mg/dl less than the patient's post-prandial glucose before performing the multi-stage method.

Optionally, the method further comprises measuring the patient's HbA1c level before performing the multi-stage method and approximately four weeks after performing the multi-stage method, wherein the patient's HbA1c level approximately four weeks after performing the multi-stage method is at least 0.6% less than the patient's HbA1c level before performing the multi-stage method.

Optionally, the method further comprises measuring the patient's HbA1c level before performing the multi-stage method and approximately six months after performing the multi-stage method, wherein the patient's HbA1c level approximately six months after performing the multi-stage method is at least 0.6% less than the patient's HbA1c level before performing the multi-stage method.

Optionally, the structural change is at least one of an edema, inflammation, cellular injury, or alternation of metabolic cellular processes.

Optionally, each of the first treatment zone, second treatment zone and plurality of treatment zones is defined by a plurality of consecutively positioned annular rings, wherein each of the plurality of consecutively positioned annual rings has an internal surface area, and wherein, after the multi-stage method, at least 60% of the internal surface area of each of the plurality of consecutively positioned annual rings is effectively ablated.

Optionally, of the first treatment zone, second treatment zone and plurality of treatment zones is defined by a plurality of consecutively positioned annular rings, wherein, after the multi-stage method, each of the plurality of consecutively positioned annular rings has an effectively ablated region, and wherein the effectively ablated region's thickness along a length of each of the plurality of consecutively positioned annular rings varies no more than 50% from an average thickness of the effectively ablated region.

The present specification discloses a method for treating at least one of excess weight, obesity, eating disorders, metabolic syndrome, dyslipidemia, diabetes, hyperglycemia, polycystic ovarian disease, fatty liver disease, cysts, non-alcoholic fatty liver disease, or non-alcoholic steatohepatitis disease by ablating duodenal tissue using a vapor ablation system, wherein the vapor ablation system comprises a controller having at least one processor in data communication with at least one pump and a catheter connection port in fluid communication with the at least one pump, the method comprising: connecting a proximal end of a first catheter to the catheter connection port to place the first catheter in fluid communication with the at least one pump, wherein the first catheter comprises at least two positioning elements separated along a length of the catheter and one or more ports positioned between the at least two positioning elements, wherein each of the at least two positioning elements has a first configuration and a second configuration, and wherein, in the first configuration, each of the at least two positioning elements is compressed within the catheter and in the second configuration, each of the at least two positioning elements is expanded to be at least partially outside the catheter; positioning the first catheter inside a patient, wherein the patient is in a first position, such that, upon being expanded into the second configuration, a distal one of the at least two positioning elements is positioned within in the patient's small intestine and a proximal one of the at least two positioning elements is proximally positioned more than 1 cm from the distal one of the at least two positioning elements; expanding each of the at least two positioning elements into their second configurations to define a treatment volume, wherein each of the at least two positioning elements are defined by a surface area and wherein each of the at least two positioning elements comprise a plurality of spaces within each of their respective surface areas sufficient to permit a flow of vapor out of the treatment volume in a range of 1 to 80% of a vapor input flow rate; activating the controller for a first treatment, wherein, upon activation, the controller is configured to cause the at least one pump to deliver saline into at least one lumen in the first catheter and, wherein, upon activation, the controller is configured to cause an electrical current to be delivered to at least one electrode positioned within the at least one lumen of the first catheter to thereby generate said vapor from the saline at said vapor input flow rate; delivering the vapor for the first treatment through ports positioned in the first catheter between the at least two positioning elements and into the treatment volume; deactivating the controller; changing the first position of the patient to a second position different from the first position; activating the controller for a second treatment, wherein, upon activation, the controller is configured to cause the at least one pump to deliver saline into at least one lumen in the first catheter and, wherein, upon activation, the controller is configured to cause an electrical current to be delivered to at least one electrode positioned within the at least one lumen of the first catheter to thereby generate said vapor from the saline at said vapor input flow rate; and delivering the vapor for the second treatment through ports positioned in the first catheter between the at least two positioning elements and into the treatment volume.

Optionally, the first catheter comprises at least one cylindrical positioning element with a length and a diameter wherein the at least one cylindrical positioning element is fixed to the catheter at a first end of the cylindrical positioning element and is configured to slide along a length of the catheter to the a second end of the cylindrical positioning element, opposite the first end, and one or more ports positioned between the first and second ends of the cylindrical positioning element, wherein the cylindrical positioning element has a first configuration and a second configuration, and wherein, in the first configuration, the positioning element is compressed within the catheter and in the second configuration, the positioning element is expanded to be at least partially outside the catheter. A method of using the first catheter comprises: positioning the first catheter inside a patient, wherein the patient is in a first position, such that, upon being expanded into the second configuration, the positioning element is positioned within in the patient's small intestine and is configured to cover more than 1 cm of the small intestine to define a treatment volume, wherein the positioning element is defined by a surface area and wherein the first and second ends of the positioning element comprise a plurality of spaces within each of their respective surface areas sufficient to permit a flow of vapor out of the treatment volume in a range of 1 to 80% of a vapor input flow rate; activating the controller for a first treatment, wherein, upon activation, the controller is configured to cause the at least one pump to deliver saline into at least one lumen in the first catheter and, wherein, upon activation, the controller is configured to cause an electrical current to be delivered to at least one electrode positioned within the at least one lumen of the first catheter to thereby generate said vapor from the saline at said vapor input flow rate; delivering the vapor for the first treatment through ports positioned in the first catheter within the positioning elements and into the treatment volume; deactivating the controller; changing the first position of the patient to a second position different from the first position; activating the controller for a second treatment, wherein, upon activation, the controller is configured to cause the at least one pump to deliver saline into at least one lumen in the first catheter and, wherein, upon activation, the controller is configured to cause an electrical current to be delivered to at least one electrode positioned within the at least one lumen of the first catheter to thereby generate said vapor from the saline at said vapor input flow rate; and delivering the vapor for the second treatment through ports positioned in the first catheter within the positioning element and into the treatment volume.

Optionally, the method further comprises inducing an acute inflammatory response with predominant neutrophils, prior to activating the controller for the first treatment.

Optionally, the method comprises ablating cumulatively 25% to 90% of the treatment volume. Optionally, the treatment volume has a cumulative length in a range from 2 cm to 25 cm.

Optionally, the method comprises limiting contiguous submucosa ablation to less than 50%.

Optionally, the method comprises limiting contiguous muscularis propria ablation to less than 5%.

Optionally, the method comprises delivering the vapor to the duodenal tissue of a length ranging from 2 cm to 25 cm.

Optionally, the method comprises delivering the vapor for a continuous duration in a range of 1 second to 10 seconds.

Optionally the method comprises of delivering an energy dose between 100 J and 500 J per application and cumulative energy dose between 1,000 J and 10,000 J per treatment session.

Optionally, each of the at least two positioning elements comprises a scalloped petal shaped surface.

Optionally, the one positioning element comprises a cylindrical shape with the length of the cylinder having an open structure allowing of passage of vapor through onto the intestinal wall while the two ends have a closed structure blocking the passage of some but not all the vapor into the intestinal lumen.

Optionally, the method comprises, prior to activating the controller for the first energy treatment, using a chemical pretreatment to remove a portion of a mucus layer covering the duodenal tissue. Optionally, the chemical is N acetyl cysteine. Optionally, using the chemical comprises spraying the chemical.

Optionally, the method comprises, prior to activating the controller for the first treatment, mechanically pretreating the intestine by scraping a surface of the intestinal tissue to remove a portion of a mucus layer covering the intestinal tissue. Optionally, the method further comprises suctioning the mucus layer.

Optionally, one or both of chemical pretreatment or mechanical pretreatment can be combined with energy based treatment of the intestinal mucosa to treat a human condition.

Optionally, the method compromises using one or more of the positioning elements to scrape a surface of the intestinal tissue to remove a portion of a mucus layer or debris covering the intestinal tissue.

Optionally, the method compromises of using one or more of an antispasmodic or an antiperistalsis agents to decrease or eliminate intestinal spasm or peristalsis. The agent can be administered prior to starting the procedure or during the procedure. The agent can be one of, but not limited to, a glucagon, Hyoscine butylbromide, Glycopyrrolate, Atropine, Pinaverium, Dicyclomine.

Optionally, the method comprises, prior to activating the controller for the first treatment: applying a first dose of the vapor at a first energy level, comprising: applying a first portion of the first dose to denature a mucus layer covering the duodenal tissue; and applying a second portion of the first dose of the vapor at the first energy level; removing denatured mucus layer using at least one of a spraying of a chemical or a scraping; and applying a second dose of the vapor, comprising: applying a first portion of the second dose to denature a mucus layer covering the duodenal tissue; and applying a second portion of the second dose of the vapor at a second energy level that is greater than the first energy level. Optionally, the chemical is N acetyl cysteine. Optionally, the first and second dose or first or second portion of each dose have same energy level. Optionally, the first and second dose or first or second portion of each dose have a different energy level.

The present specification also discloses a multi-stage method for treating at least one of excess weight, obesity, eating disorders, metabolic syndrome, dyslipidemia, diabetes, polycystic ovarian disease, fatty liver disease, non-alcoholic fatty liver disease, or non-alcoholic steatohepatitis disease by ablating duodenal tissue using a vapor ablation system, wherein the vapor ablation system comprises a controller having at least one processor in data communication with at least one pump and a catheter connection port in fluid communication with the at least pump, the multi-stage method comprising: connecting a proximal end of a first catheter to the catheter connection port to place the first catheter in fluid communication with the at least one pump, wherein the first catheter comprises at least two positioning elements separated along a length of the catheter and one or more ports positioned between the at least two positioning elements, wherein each of the at least two positioning elements has a first configuration and a second configuration, and wherein, in the first configuration, each of the at least two positioning elements is compressed within the catheter and in the second configuration, each of the at least two positioning elements is expanded to be at least partially outside the catheter; positioning the first catheter inside a patient such that, upon being expanded into the second configuration, a distal one of the at least two positioning elements is positioned within in the patient's small intestine and a proximal one of the at least two positioning elements is proximally positioned more than 1 cm from the distal one of the at least two positioning elements; expanding each of the at least two positioning elements into their second configurations; activating the controller, wherein, upon activation, the controller is configured to cause the at least one pump to deliver saline into at least one lumen in the first catheter and, wherein, upon activation, the controller is configured to cause an electrical current to be delivered to at least one electrode positioned within the at least one lumen of the first catheter; delivering vapor through ports positioned in the first catheter between the at least two positioning elements; using the controller, shutting off the delivery of saline and electrical current; removing the first catheter from the patient to complete a first stage of treating; waiting for at least six weeks; determining an efficacy of the first phase of treatment; depending on the determined efficacy, connecting a proximal end of a second catheter to the catheter connection port to place the second catheter in fluid communication with the at least one pump, wherein the second catheter comprises at least two positioning elements separated along a length of the catheter and one or more ports positioned between the at least two positioning elements, wherein each of the at least two positioning elements has a first configuration and a second configuration, and wherein, in the first configuration, each of the at least two positioning elements is compressed within the catheter and in the second configuration, each of the at least two positioning elements is expanded to be at least partially outside the catheter; positioning the second catheter inside a patient such that, upon being expanded into the second configuration, a distal one of the at least two positioning elements is positioned within in the patient's small intestine and a proximal one of the at least two positioning elements is proximally positioned more than 1 cm from the distal one of the at least two positioning elements; expanding each of the at least two positioning elements into their second configurations; activating the controller, wherein, upon activation, the controller is configured to cause the at least one pump to deliver saline into at least one lumen in the first catheter and, wherein, upon activation, the controller is configured to cause an electrical current to be delivered to at least one electrode positioned within the at least one lumen of the first catheter; delivering vapor through ports positioned in the second catheter between the at least two positioning elements; using the controller, shutting off the delivery of saline and electrical current; and removing the second catheter from the patient to complete a second stage of treatment.

Optionally, in both the first stage of treatment and second stage of treatment, the delivery of saline and electrical current is automatically shut off after no more than 60 seconds.

Optionally, the method further comprises, in both the first stage of treatment and second stage of treatment, repeatedly activating the controller to deliver saline into the lumen and electrical current to the at least one electrode using at least one of a foot pedal in data communication with the controller, a switch on the catheter, or a switch on the controller.

Optionally, in both the first stage of treatment and second stage of treatment, vapor is delivered such that an amount of energy in a range of 5 calories per second to 2500 calories per second is delivered.

Optionally, in both the first stage of treatment and second stage of treatment, vapor is delivered such that an amount of energy in a range of 5 calories to 40 calories per gram of tissue to be ablated is delivered.

Optionally, in both the first stage of treatment and second stage of treatment, vapor is delivered such that at least twenty-five percent of a circumference of the small intestine is ablated.

Optionally, in both the first stage of treatment and second stage of treatment, vapor is delivered such that at least a 5 cm of a cumulative length of the small intestine is ablated.

Optionally, in both the first stage of treatment and second stage of treatment, vapor is delivered such that at least a 5 cm of a continuous length of the small intestine is ablated.

Optionally, in the first stage of treatment, the at least two positioning elements, together with the small intestine, define an enclosed volume and wherein at least one of the at least two positioning elements is positioned relative the small intestine to permit a flow of air or energy out of the enclosed volume when the vapor is delivered.

Optionally, in the second stage of treatment, the at least two positioning elements, together with the small intestine, define an enclosed volume and wherein at least one of the at least two positioning elements is positioned relative the small intestine to permit a flow of air or energy out of the enclosed volume when the vapor is delivered.

Optionally, in the first stage of treatment, the at least one positioning element, together with the small intestine, define an enclosed volume wherein the at least one positioning element is positioned relative the small intestine to permit a flow of air or energy out of the enclosed volume when the vapor is delivered.

Optionally, in the second stage of treatment, the at least one positioning element, together with the small intestine, define an enclosed volume wherein the at least one positioning element is positioned relative the small intestine to permit a flow of air or energy out of the enclosed volume when the vapor is delivered.

Optionally, in both the first state of treatment and second stage of treatment, the efficacy is determined by at least one of an improvement of TIR by at least 10% and a TBR and TAR not clinically significantly worse than a pretreatment level.

Optionally, in both the first state of treatment and second stage of treatment, the efficacy is determined by at least one of an improvement of GMI by 10% and a CV not clinically significantly worse than a pretreatment level or improved by 5%.

Optionally, in both the first state of treatment and second stage of treatment, the efficacy is determined by at least one of time of hypoglycemia or time in hyperglycemia not clinically significantly worse than a pretreatment level or improved by 5%.

Optionally, in both the first state of treatment and second stage of treatment, the efficacy is determined by at least one of TBR or TAR clinically better by at least 5% than a pretreatment level.

Optionally, in both the first state of treatment and second stage of treatment, the efficacy is determined by at least one of time of hypoglycemia or time in hyperglycemia clinically better than a pretreatment level by at least 5%.

Optionally, in both the first state of treatment and second stage of treatment, the efficacy is determined by at least one of a relative improvement of Hb A1C level by at least 10% or absolute improvement of 0.5% compared to a pretreatment level and number of hypoglycemia or hyperglycemia episodes not clinically significantly worse than a pretreatment level.

Optionally, in both the first state of treatment and second stage of treatment, the efficacy is determined by at least one of an improvement of Hb A1C level or a TIR by at least 5% better than a pretreatment level and a reduction in the dose of an oral or an injectable antidiabetic medication by at least 25%.

Optionally, in both the first state of treatment and second stage of treatment, the efficacy is determined by at least one of an improvement of Hb A1C level or a TIR at least 5% better than a pretreatment level and a prevention of escalating a dose of an oral or an injectable antidiabetic medication.

Optionally, in both the first state of treatment and second stage of treatment, the efficacy is determined by at least one of an improvement of Hb A1C level or a TIR at least 5% better than a pretreatment level and a prevention of escalating a dose of an oral or an injectable antidiabetic medication.

Optionally, in both the first state of treatment and second stage of treatment, the efficacy is determined by at least one of an improvement of Hb A1C level or a TIR at least 5% better than a pretreatment level and escalating a cumulative dose or frequency of a combination of an oral or an injectable antidiabetic medication.

Optionally, in both the first state of treatment and second stage of treatment, the efficacy is determined by an improvement in any of the above parameter as defined above while reducing the dose of an antidiabetic medication from daily injectable to an injectable with less frequent administration. In most embodiments the daily injectable is a formulation of insulin and the alternate injectable is a GLP-1 analogue (Exenatide, Liraglutide, Semaglutide, Dulaglutide, Lixisenatide, Albiglutide, Liraglutide).

Optionally, in both the first state of treatment and second stage of treatment, the efficacy is determined by an improvement in any of the above parameter as defined above while improving the compliance with an antidiabetic medication regimen.

Optionally, in both the first state of treatment and second stage of treatment, the efficacy is determined by an improvement in any of the above parameter as defined above while improving the compliance with an antidiabetic diet and or lifestyle regimen.

Optionally, in both the first state of treatment and second stage of treatment, the efficacy is determined by at least one of: a total body weight of the patient decreases by at least 1% relative to a total body weight of the patient before ablation; an excess body weight of the patient decreases by at least 1% relative to an excess body weight of the patient before ablation; a total body weight of the patient decreases by at least 1% relative to a total body weight of the patient before ablation and a well-being level of the patient does not decrease more than 5% relative to a well-being level of the patient before ablation; an excess body weight of the patient decreases by at least 1% relative to an excess body weight of the patient before ablation and a well-being level of the patient does not decrease more than 5% relative to a well-being level of the patient before ablation; a pre-prandial ghrelin level of the patient decreases by at least 1% relative to a pre-prandial ghrelin level of the patient before ablation; a post-prandial ghrelin level of the patient decreases by at least 1% relative to a post-prandial ghrelin level of the patient before ablation; an exercise output of the patient increases by at least 1% relative to an exercise output of the patient before ablation; a glucagon-like peptide-1 level of the patient increases by at least 1% relative to a glucagon-like peptide-1 level of the patient before ablation; a leptin level of the patient increases by at least 1% relative to a leptin level of the patient before ablation; the patient's appetite decreases, over a predefined period of time, relative to the patient's appetite before ablation; a peptide YY level of the patient increases by at least 1% relative to a peptide YY level of the patient before ablation; a lipopolysaccharide level of the patient decreases by at least 1% relative to a lipopolysaccharide level of the patient before ablation; a motilin-related peptide level of the patient decreases by at least 1% relative to a motilin-related peptide level of the patient before ablation; a cholecystokinin level of the patient increases by at least 1% relative to a cholecystokinin level of the patient before ablation; a resting metabolic rate of the patient increases by at least 1% relative to a resting metabolic rate of the patient before ablation; a plasma-beta endorphin level of the patient increases by at least 1% relative to a plasma-beta endorphin level of the patient before ablation; an HbA1c level of the patient decreases by at least 0.3% relative to an HbA1c level of the patient before ablation; a triglyceride level of the patient decreases by at least 1% relative to a triglyceride level of the patient before ablation; a total blood cholesterol level of the patient decreases by at least 1% relative to a total blood cholesterol level of the patient before ablation; a glycemia level of the patient decreases by at least 1% relative to a glycemia level of the patient before ablation; a composition of the person's gut microbiota modulates from a first state before ablation to a second state after ablation, wherein the first state has a first level of bacteroidetes and a first level of firmicutes, wherein the second state has a second level of bacteroidetes and a second level of firmicutes, wherein the second level of bacteroidetes is greater than the first level of bacteroidetes by at least 3%, and wherein the second level of firmicutes is less than the first level of firmicutes by at least 3%; or, a cumulative daily dose of the patient's antidiabetic medications decreases by at least 10% relative to a cumulative daily dose of the patient's antidiabetic medications before ablation.

Optionally, in both the first state of treatment and second stage of treatment, the efficacy is determined by at least one of: a lipid profile of the patient improves by at least 10% relative a lipid profile of the patient before ablation, wherein lipid profile is defined at least by a ratio of LDL cholesterol to HDL cholesterol, and improve is defined as a decrease in the ratio of LDL cholesterol to HDL cholesterol; an LDL-cholesterol level of the patient decreases by at least 10% relative to an LDL-cholesterol level of the patient before ablation; or, a VLDL-cholesterol level of the patient decreases by at least 10% relative to a VLDL-cholesterol level of the patient before ablation.

Optionally, in both the first stage of treatment and second stage of treatment, the efficacy is determined by at least one of: a 10% decrease in either ALT or AST levels relative to ALT or AST levels before ablation; an absolute serum ferritin level of less than 1.5 ULN (upper limit normal) relative to a serum ferritin level before ablation; less than 5% hepatic steatosis (HS) relative to an HS level before ablation, as measured on liver biopsy; less than 5% hepatic steatosis (HS) relative to an HS level before ablation, as measured by magnetic resonance (MR) imaging, either by spectroscopy or proton density fat fraction; at least a 5% improvement in an NAFLD Fibrosis Score (NFS) relative to an NFS before ablation; at least a 5% improvement in an NAFLD Activity Score (NAS) relative to an NAS before ablation; at least a 5% improvement in a Steatosis Activity Fibrosis (SAF) score relative to an SAF score before ablation; at least a 5% decrease in a mean annual fibrosis progression rate relative to a mean annual fibrosis progression rate before ablation, as measured by histology, Fibrosis-4 (FIB-4) index, aspartate aminotransferase (AST) to platelet ratio index (APRI), serum biomarkers (Enhanced Liver Fibrosis (ELF) panel, Fibrometer, FibroTest, or Hepascore), or imaging (transient elastography (TE), MR elastography (MRE), acoustic radiation force impulse imaging, or supersonic shear wave elastography); at least a 5% decrease in circulating levels of cytokeratin-18 fragments relative to circulating levels of cytokeratin-18 fragments before ablation; at least a 5% decrease in liver stiffness relative to liver stiffness before ablation, as measured by vibration controlled transient elastography (VCTE/FibroScan); an improvement in NAS by at least 2 points, with at least 1-point improvement in hepatocellular ballooning and at least 1-point improvement in either lobular inflammation or steatosis score, and no increase in the fibrosis score, relative to NAS, hepatocellular ballooning, lobular inflammation, steatosis, and fibrosis scores before ablation; at least a 5% improvement in NFS scores relative to NFS scores before ablation; or, at least a 5% improvement in any of the above listed NAFLD parameters as compared to a sham intervention or a placebo.

The present specification also discloses a multi-stage method for treating cancerous or precancerous esophageal tissue by ablating the cancerous or precancerous esophageal tissue using a vapor ablation system, wherein the vapor ablation system comprises a controller having at least one processor in data communication with at least one pump and a catheter connection port in fluid communication with the at least pump, the multi-stage method comprising: connecting a proximal end of a first catheter to the catheter connection port to place the first catheter in fluid communication with the at least one pump, wherein the first catheter comprises at least two positioning elements separated along a length of the catheter and one or more ports positioned between the at least two positioning elements, wherein each of the at least two positioning elements has a first configuration and a second configuration, and wherein, in the first configuration, each of the at least two positioning elements is compressed within the catheter and in the second configuration, each of the at least two positioning elements is expanded to be at least partially outside the catheter; positioning the first catheter inside a patient such that, upon being expanded into the second configuration, a distal one of the at least two positioning elements is positioned adjacent the patient's esophagus and a proximal one of the at least two positioning elements is proximally positioned more than 1 cm from the distal one of the at least two positioning elements; expanding each of the at least two positioning elements into their second configurations; activating the controller, wherein, upon activation, the controller is configured to cause the at least one pump to deliver saline into at least one lumen in the first catheter and, wherein, upon activation, the controller is configured to cause an electrical current to be delivered to at least one electrode positioned within the at least one lumen of the first catheter; delivering vapor through ports positioned in the first catheter between the at least two positioning elements; using the controller, shutting off the delivery of saline and electrical current; removing the first catheter from the patient to complete a first stage of treating; waiting for at least six weeks; determining an efficacy of the first phase of treatment; depending upon the efficacy determination, connecting a proximal end of a second catheter to the catheter connection port to place the second catheter in fluid communication with the at least one pump, wherein the second catheter comprises a distal tip having at least one port and at least one positioning element attached to the distal tip such that, upon being in an operational configuration, the at least one positioning element encircles the at least one port and is configured to direct all vapor exiting from the at least one port; positioning the second catheter inside the patient such that a distal surface of the at least one positioning element is positioned adjacent the patient's esophagus; activating the controller, wherein, upon activation, the controller is configured to cause the at least one pump to deliver saline into at least one lumen in the second catheter and, wherein, upon activation, the controller is configured to cause an electrical current to be delivered to at least one electrode positioned within the at least one lumen of the second catheter; delivering vapor through the at least one port positioned at the distal end of the second catheter; using the controller, shutting off the delivery of saline and electrical current; and removing the second catheter from the patient to complete a second stage of treatment.

Optionally, in both the first stage of treatment and second stage of treatment, the delivery of saline and electrical current is automatically shut off after no more than 60 seconds.

Optionally, the method further comprises, in both the first stage of treatment and second stage of treatment, repeatedly activating the controller to deliver saline into the lumen and electrical current to the at least one electrode using at least one of a foot pedal in data communication with the controller, a switch on the catheter, or a switch on the controller.

Optionally, in both the first stage of treatment and second stage of treatment, vapor is delivered such that an amount of energy in a range of 5 calories per second to 2500 calories per second is delivered.

Optionally, in both the first stage of treatment and second stage of treatment, vapor is delivered such that an amount of energy in a range of 5 calories to 40 calories per gram of tissue to be ablated is delivered.

Optionally, in both the first stage of treatment and second stage of treatment, vapor is delivered such that at least fifty percent of a circumference of the small intestine is ablated.

Optionally, in the first stage of treatment, the at least two positioning elements, together with the esophageal tissue, define an enclosed volume wherein at least one of the at least two positioning elements is positioned relative the esophageal tissue to permit a flow of air out of the enclosed volume when the vapor is delivered.

Optionally, in the second stage of treatment, the at least one positioning element, together with the esophageal tissue, defines an enclosed volume and wherein the at least one positioning element is positioned relative the esophageal tissue to permit a flow of air out of the enclosed volume when the vapor is delivered.

The present specification also discloses a flexible heating chamber configured to be incorporated into a tip of a catheter, the flexible heating chamber comprising: an outer covering; an inner core coaxial to said outer covering; a first array of electrodes disposed between said outer covering and said inner core, wherein said first array of electrodes comprise a first metal ring having a plurality of first fins; and a second array of electrodes disposed between said outer covering and said inner core, wherein said second array of electrodes comprises a second metal ring having a plurality of second fins, and wherein said first and second fins interdigitate with each other such that a segmental space separates each of said first and second fins.

Optionally, said plurality of first and second fins extend radially into a space between said outer covering and said inner core, and wherein said plurality of first and second fins also extend along a longitudinal axis of the heating chamber.

Optionally, each of said plurality of first and second fins has a first dimension along a radius of the heating chamber and a second dimension along a longitudinal axis of the heating chamber.

Optionally, water or saline flows through said segmental spaces and electrical current is provided to said first and second array of electrodes causing said first and second fins to generate heat and vaporize said water or saline into steam.

Optionally, the heating chamber has a width ranging from 1 to 5 mm and a length ranging from 5 to 50 mm.

Optionally, the first array of electrodes has a range of 1 to 50 fins and the second array of electrodes has a range of 1 to 50 fins.

Optionally, said segmental space ranges from 0.01 to 2 mm.

The present specification also discloses a catheter for performing ablation of target tissue and having a body with a proximal end, a distal end, a first lumen and a second lumen, said catheter comprising: a proximal balloon and a distal balloon positioned proximate the distal end of the body; one or more ports located on the body between said proximal and distal balloons; and a first flexible heating chamber incorporated in the second lumen and placed proximate to the proximal balloon, said first flexible heating chamber comprising: an outer covering; an inner core coaxial to said outer covering; a first array of electrodes disposed between said outer covering and the inner core, wherein said first array of electrodes comprise a first metal ring having a plurality of first fins; and a second array of electrodes disposed between said outer covering and said inner core, wherein said second array of electrodes comprises a second metal ring having a plurality of second fins, and wherein said first and second fins interdigitate with each other such that a first segmental space separates each of said first and second fins.

Optionally, a first pump coupled to the proximal end of the body propels air through the first lumen to inflate the proximate and distal balloons, a second pump coupled to the proximal end of the body propels water or saline through the second lumen to supply said water or saline to a proximal end of the first heating chamber, and an RF generator coupled to the proximal end of the body supplies electrical current to said first and second array of electrodes causing said first and second fins to generate heat and vaporize said water or saline into steam for delivery to the target tissue through said ports.

Optionally, said plurality of first and second fins extend radially into a space between said outer covering and said inner core of the first heating chamber, and wherein said plurality of first and second fins also extend along a longitudinal axis of the first heating chamber.

Optionally, each of said plurality of first and second fins has a first dimension along a radius of the first heating chamber and a second dimension along a longitudinal axis of the first heating chamber.

Optionally, the catheter further comprises a second flexible heating chamber arranged in series with said flexible heating chamber, wherein the second flexible heating chamber comprises: an outer covering; an inner core coaxial to the outer covering; a third array of electrodes disposed between the outer covering and the inner core, wherein the third array of electrodes comprise a third metal ring having a plurality of third fins; and a fourth array of electrodes disposed between the outer covering and the inner core, wherein said fourth array of electrodes comprises a fourth metal ring having a plurality of fourth fins, and wherein the third and fourth fins interdigitate with each other such that a second segmental space separates each of said third and fourth fins.

Optionally, the plurality of third and fourth fins extend radially into a space between said outer covering and the inner core of the second heating chamber and said plurality of third and fourth fins also extend along a longitudinal axis of the second heating chamber.

Optionally, each of said plurality of third and fourth fins has a first dimension along a radius of the second heating chamber and a second dimension along a longitudinal axis of the second heating chamber.

Optionally, each of said first and second heating chambers has a width ranging from 1 to 5 mm and a length ranging from 5 to 50 mm.

Optionally, the first and third array of electrodes have a range of 1 to 50 fins and the second and fourth array of electrodes have a range of 1 to 50 fins.

Optionally, said first and second segmental spaces range from 0.01 to 2 mm.

The present specification also discloses a method of performing ablation of Barrett's esophagus tissue, comprising: inserting a catheter into an esophagus of a patient, said catheter having a body with a proximal end, a distal end, a first lumen and a second lumen, wherein the catheter comprises: a proximal balloon and a distal balloon positioned proximate the distal end of the body; one or more ports located on the body between said proximal and distal balloons; and at least one flexible heating chamber incorporated in the second lumen and placed proximate to the proximal balloon, said at least one flexible heating chamber comprising: an outer covering; an inner core coaxial to said outer covering; a first array of electrodes disposed between said outer covering and said inner core, wherein said first array of electrodes comprise a first metal ring having a plurality of first fins; and a second array of electrodes disposed between said outer covering and said inner core, wherein said second array of electrodes comprises a second metal ring having a plurality of second fins, and wherein said first and second fins interdigitate with each other such that a first segmental space separates each of said first and second fins; positioning the distal balloon distal to a portion of Barrett's esophagus and the proximal balloon proximal to a portion of Barrett's esophagus such that the ports are positioned in said portion of Barrett's esophagus; inflating the proximal and distal balloons to position the catheter in the esophagus; providing water or saline to the catheter; and providing electric current to said first and second array of electrodes causing said first and second fins to generate heat and vaporize said water or saline into steam, wherein said steam is delivered through said ports to ablate the Barrett's esophagus tissue.

Optionally, a first pump coupled to the proximal end of the body propels either water or air through the first lumen to inflate the proximate and distal balloons, a second pump coupled to the proximal end of the body propels water or saline through the second lumen to supply said water or saline to a proximal end of the heating chamber, and an RF generator coupled to the proximal end of the body supplies electrical current to said first and second array of electrodes.

Optionally, each of said plurality of first and second fins has a first dimension along a radius of the heating chamber and a second dimension along a longitudinal axis of the heating chamber.

The present specification also discloses a method of ablating a pancreatic tissue, comprising: providing an ablation device comprising: an echoendoscope; a catheter having a needle at a distal end and configured pass within a channel of said echoendoscope to deliver vapor to said pancreatic tissue; a controller programmed to determine an amount of thermal energy needed to ablate said pancreatic tissue, programmed to limit a maximum dose of said ablative agent based on a type of disorder being treated, and programmed to limit the amount of thermal energy delivered such that a pressure within the patient's pancreas does not exceed 5 atm; advancing said echoendoscope into a gastrointestinal tract of a patient and proximate said pancreatic tissue; localizing said pancreatic tissue using said echoendoscope; advancing said catheter through said channel of said echoendoscope such that said needle passes through a gastrointestinal wall at a puncture site and enters into said pancreatic tissue; and delivering vapor through said needle into said pancreatic tissue for ablation.

Optionally, the method further comprises the steps of: measuring at least one dimension of said pancreatic tissue using said echoendoscope; and said controller using said at least one measured dimension to calculate an amount of vapor to deliver.

Optionally, the method further comprises applying suction to said needle prior to delivering vapor to aspirate fluid and/or cells from said prostatic tissue.

Optionally, said needle comprises an outer sheath and said method further comprises circulating water through said outer sheath as vapor is delivered to cool said puncture site.

Optionally, the method further comprises using said echoendoscope to observe said pancreatic tissue as ablation is performed and stopping said ablation once adequate ablation has been achieved as per visual observation.

Optionally, ablation is terminated after a pressure measured in said pancreas remains in a range of 0.1 to 5 atm for a time period of at least 1 second. Optionally, the method further comprises delivering vapor again after ablation has been terminated for at least a time period of 1 second.

Optionally, ablation is stopped when a pressure measured in said ablation device exceeds 5 atm.

Optionally, a temperature of said pancreatic tissue is in a range of 100° C. to 110° C. for at least a portion of the ablation procedure.

Optionally, said ablation device further comprises a pressure sensor.

Optionally, said ablation device further comprises a temperature sensor.

The present specification also discloses a method of ablating pancreatic tissue comprising the steps of: providing an ablation device comprising: a catheter having a hollow shaft and a retractable needle through which an ablative agent can travel; at least one infusion port on said needle for the delivery of said ablative agent to said upper gastrointestinal tract tissue; at least one sensor for measuring at least one parameter of said catheter; and a controller comprising a microprocessor for controlling the delivery of said ablative agent; inserting an echoendoscope into an upper gastrointestinal tract of a patient; identifying the pancreatic tissue to be ablated using said echoendoscope; passing said catheter through said echoendoscope such that said at least one distal positioning element is positioned proximal to said pancreatic tissue to be ablated in the gastrointestinal tract; extending said needle through the catheter in the upper gastrointestinal tract lumen of said patient such that said infusion port is positioned within said pancreatic tissue of said patient; operating said at least one sensor to measure at least one parameter of said catheter; using said at least one parameter measurement to control the flow of ablative agent to deliver to said pancreatic tissue; and delivering said ablative agent through said at least one infusion port to ablate said pancreatic tissue.

The present specification also discloses a device for use with an endoscope for hot fluid ablation comprising: an elongate tubular member having a length and a lumen for conveying the hot fluid from a proximal end to a distal end, the distal end being open and adapted to spray vapor at a temperature and low pressure at a target tissue; and an insulating element covering at least a portion of the device; wherein an outer diameter of the device is configured to allow passage of the device through the endoscope.

The present specification also discloses a device for use with an endoscope for hot fluid ablation comprising: an elongate tubular member having a length and a lumen for conveying the hot fluid from a proximal end to a distal end, the distal end being open and adapted to spray vapor at a temperature and low pressure at a target tissue; and an insulating element covering at least a portion of the device; wherein an outer diameter of the device is configured to allow passage of the device through the endoscope.

Optionally, the hot fluid is steam or vapor. Optionally, the temperature ranges from 65° C. to 150° C. Optionally, the pressure is <5 atm. Optionally, the insulating element is heat resistant polymer.

The present specification also discloses a catheter for use in an ablation procedure comprising: a tubular member having an inner surface defining a channel for ablative fluid flow, a proximal end for receiving ablative fluid from a source, and a distal end being adapted to spray low pressure ablative agent at a target tissue; and an insulating element disposed longitudinally along at least a portion of the length of the tubular member.

The present specification also discloses a catheter for use with an endoscope in a thermal ablation procedure, the catheter comprising: a tubular member having a proximal end for receiving an ablative agent, an open distal end adapted to spray low pressure ablative agent at a target tissue, an inside surface comprising a heat resistant polymer defining a channel and configured to contact ablative agent flowing from the proximal end to the distal end; and a cooling element disposed longitudinally along at least a portion of an outer surface. Optionally, the cooling element is a liquid that passes longitudinally along at least a portion of an outer surface within a wall of the catheter.

The present specification also discloses a vapor ablation apparatus for vapor spray ablation, comprising: an endoscope; a catheter having a distal end, wherein the catheter is disposed within the endoscope; and a source of vapor attached to the catheter by a conduit, wherein the apparatus is configured such that, in use, high temperature, low pressure vapor exits the catheter distal end, and wherein the distal end of the catheter is adapted to spray vapor in a radial direction substantially perpendicular to the axis of the catheter.

The present specification also discloses a vapor spray apparatus for vapor spray ablation, comprising: an endoscope having a distal end provided with a lens, such that the endoscope is used to locate the target tissue; a catheter having a distal end, said catheter being connected to the endoscope and carried thereby; a source of vapor connected to the catheter by a conduit and disposed externally of the patient; wherein the apparatus is configured such that, in use, high temperature, low pressure vapors exits the catheter distal end.

The present specification also discloses a method of ablating a hollow tissue or a hollow organ comprising the steps of: replacing the natural contents of the hollow tissue or the organ with a conductive medium; and delivering an ablative agent to the conductive medium to ablate the tissue or organ.

The present specification also discloses a device for ablation comprising a port for delivering a conductive medium and a source of ablative agent.

Optionally, said ablation comprises one of cryoablation or thermal ablation.

Optionally, the device comprises ports to remove the content of the hollow organ or the conductive medium.

The present specification also discloses a method of ablating a blood vessel comprising the steps of: replacing a blood in a targeted vessel with a conductive medium; and delivering an ablative agent to the conductive medium to ablate the desired blood vessel.

Optionally, the method further comprises stopping a flow of blood into the target blood vessel. Optionally, the blood flow is occluded by application of a tourniquet. Optionally, the blood flow is occluded by application of an intraluminal occlusive element. Optionally, the intraluminal occlusive element comprises unidirectional valves.

Optionally, sensors are used to control a flow of the ablative agent.

Optionally, the conductive medium is one of water or saline.

The present specification also discloses a device for ablating a blood vessel comprising a catheter with a proximal end and a distal end, wherein the proximal end is operably connected to the distal end, a port at the distal end for infusion of a conductive medium for replacing a blood in a target vessel with a conductive medium, and a source at the distal end for delivering an ablative agent to said conductive medium.

Optionally, the device further comprises an occlusive element to restrict a flow of blood or the conductive medium. Optionally, the occlusive element comprises unidirectional valves. Optionally, the occlusive element is used to position the source of the ablative agent in the blood vessel.

Optionally, the device further comprises suction ports for removal of blood or the conductive medium.

Optionally, the device further comprises a sensor to measure a delivery of ablative agent, flow of blood or an ablation parameter.

The present specification also discloses a method of ablating a blood vessel wall comprising the steps of placing a catheter in a segment of the blood vessel, occluding a flow of blood to the segment of the blood vessel, replacing a portion of a blood in the segment with a conductive medium, adding an ablative agent into the conductive medium, and conducting ablative energy to the blood vessel wall through the conductive medium to cause ablation of said blood vessel wall.

The present specification also discloses a device for ablating a blood vessel comprising a coaxial catheter with a proximal end and a distal end, an outer sheath, an inner tubular member, at least one port for infusing a conductive medium, a source for delivery of an ablative agent, and at least one occlusive element configured to restrict a flow of blood and position the source of ablative agent in the blood vessel, wherein at least the outer sheath of the coaxial catheter is made of an insulating material.

The present specification also discloses a method of ablating a cyst comprising the steps of: providing an ablation device comprising a catheter having a handle at a proximal end and needle at a distal end; passing said catheter into a patient and advancing said catheter to said cyst; inserting said needle into said cyst; applying suction to said catheter to remove at least a portion of the contents of said cyst; injecting a conductive medium into said cyst through said needle; delivering an ablative agent through into said conductive medium through said needle; and applying suction to said catheter to remove said conductive medium and said ablative agent.

The present specification also discloses a method of ablating a cyst comprising the steps of placing a catheter in the cyst, replacing a portion of the contents in the cyst with a conductive medium, adding an ablative agent into the conductive medium, and conducting ablative energy to a cyst wall through the conductive medium to cause ablation of said cyst.

The present specification also discloses a device for ablating a cyst comprising a coaxial catheter with a proximal end and a distal end, an outer sheath, an inner tubular member, at least one port for infusing a conductive medium, a source for delivery of an ablative agent, and at least one port for removal of the contents of the cyst, wherein at least the outer sheath of the coaxial catheter is made of an insulating material.

The present specification also discloses a device for ablating a cyst comprising a single lumen catheter with a proximal end and a distal end, at least one port for infusing and delivering an ablative agent, a source for delivery of an ablative agent, wherein an electrode capable of passing electricity through the ablative agent to heat the ablative agent through a phase change from a liquid to a gas is provided within the single lumen of the catheter.

The present specification also discloses a method for ablating a cyst comprising the steps of accessing the cyst lumen/cavity with a needle, aspirating at least some of the contents within the cyst, inserting a microcatheter through the needle into the cyst, delivering a thermal ablative agent through the microcatheter into the cyst lumen, and removing the needle and microcatheter.

Optionally, the device further comprises a sensor to control the delivery of the ablative agent or for measurement of an ablation effect.

Optionally, the catheter comprises echogenic elements to assist with the placement of the catheter into the cyst under ultrasound guidance. Optionally, the method comprises visualizing deployment of the microcatheter using ultrasound imaging of 1-20 MHz.

Optionally, the catheter comprises radio-opaque elements to assist with the placement of the catheter into the cyst under radiological guidance.

Optionally, the cyst is fully or nearly collapsed through aspirating.

Optionally, after aspirating, a gas is used to inflate the cyst to allow for uniform distribution of the thermal ablative agent. Optionally, the gas is either air or carbon dioxide $(CO_2)$.

Optionally, the microcatheter extends beyond the needle to avoid heating of the needle. Optionally, the microcatheter extends beyond the needle by a distance of 1 mm to 20 mm.

Optionally, the microcatheter is shaped in a curve to be atraumatic to the tissue as it exits the needle.

Optionally, the needle is rotated while the thermal ablative agent exits the microcatheter to aid in the dispersion of the thermal ablative agent.

Optionally, a handle of the microcatheter is connected to a luer fitting on the needle. Optionally, an actuator on the handle of the microcatheter is slid to deploy the microcatheter to a fixed distance beyond a tip of the needle.

The present specification also discloses a method of ablating a solid tumor comprising the steps of placing a catheter in the tumor, instilling a conductive medium into the tumor, adding an ablative agent into the conductive medium, and conducting ablative energy to the tumor through the conductive medium to cause ablation of the tumor.

The present specification also discloses a device for ablating a tumor comprising an insulated catheter with a proximal end and a distal end, at least one port for infusing a conductive medium, and a source for delivery of an ablative agent.

Optionally, the device further comprises a sensor to control the delivery of the ablative agent or for measurement of an ablation effect.

Optionally, the catheter comprises echogenic elements to assist with the placement of the catheter into the cyst under ultrasound guidance.

Optionally, the catheter comprises radio-opaque elements to assist with the placement of the catheter into the cyst under radiological guidance.

The present specification also discloses a method of ablating tissue comprising the steps of: providing an ablation device comprising: a thermally insulating catheter having a hollow shaft and a retractable needle through which an ablative agent can travel; at least one infusion port on said needle for the delivery of said ablative agent to said tissue; and a controller comprising a microprocessor for controlling the delivery of said ablative agent; passing said catheter and extending the said needle with the said at least one infusion port so the needle and the infusion port are positioned within said tissue of said patient; and delivering said ablative agent through said at least one infusion port to ablate said tissue.

Optionally, said ablation device further comprises at least one sensor for measuring at least one parameter of said tissue and said method further comprises the steps of: operating said at least one sensor to measure at least one parameter of said tissue; and using said at least one parameter to determine the amount of ablative agent to deliver to said tissue.

Optionally, said ablation device further comprises at least one sensor for measuring at least one parameter of said catheter and said method further comprises the steps of: operating said at least one sensor to measure at least one parameter of said catheter; and using said at least one parameter to turn-off the delivery of ablative agent to said tissue.

Optionally, said at least one sensor comprises a temperature, pressure, infrared, electromagnetic, acoustic, or radiofrequency energy emitter and sensor.

Optionally, said catheter comprises at least one distal positioning element configured such that, once said positioning element is deployed, said catheter is positioned proximate said tissue for ablation. Optionally, said at least one positioning element is any one of an inflatable balloon, a wire mesh disc, a cone shaped attachment, a ring shaped attachment, or a freeform attachment. Optionally, said positioning element is covered by an insulated material to prevent the escape of thermal energy beyond said tissue to be ablated. Optionally, the positioning element is made of shape memory materials. Optionally, positioning can be deployed to change the maximum diameter.

Optionally, said at least one distal positioning element is separated from tissue to be ablated by a distance of greater than 0.1 mm.

Optionally, said delivery of said ablative agent is guided by predetermined programmatic instructions.

Optionally, said ablation device further comprises at least one sensor for measuring a parameter of said tissue and said method further comprises the steps of: operating said at least one sensor to measure a parameter of said tissue; and using said parameter measurement to control a flow of said ablative agent to said tissue.

Optionally, said sensor is any one of a temperature, pressure, photo, or chemical sensor.

Optionally, said ablation device further comprises a coaxial member configured to restrain said at least one positioning element and said step of deploying said at least one distal positioning element further comprises removing said coaxial member from said ablation device.

Optionally, said catheter further comprises at least one suction port and said method further comprises operating said at least one suction port to remove ablated tissue from the body.

Optionally, said ablation device further comprises an input device and said method further comprises the step of an operator using said input device to control the delivery of said ablative agent.

Optionally, said tissue is a cyst.

The present specification also discloses a method of ablating tissue comprising the steps of: providing an ablation device comprising: a catheter having a hollow shaft and a retractable needle through which an ablative agent can travel; at least one distal positioning element attached to a distal tip of said catheter; at least one infusion port on said needle for the delivery of said ablative agent to said tissue, said at least one infusion port configured to deliver said ablative agent into a space defined by said distal positioning element; and a controller comprising a microprocessor for controlling the delivery of said ablative agent; inserting said catheter such that said at least one positioning element is positioned proximate said tissue to be ablated; extending the needle through the catheter such that the infusion port is positioned proximate to the tissue; and delivering said ablative agent through said at least one infusion port to ablate said tissue.

Optionally, said ablation device further comprises at least one input port on said catheter for receiving said ablative agent.

Optionally, said tissue is a pancreatic cyst.

The present specification also discloses a method for providing ablation therapy to a patient's gastrointestinal tract comprising: inserting ablation catheter into the gastrointestinal tract, wherein the ablation catheter comprises at least one positioning element and a port for the delivery of vapor; creating a seal between an exterior surface of the at least one positioning element and a wall of the gastrointestinal tract, forming an enclosed volume in the gastrointestinal tract; delivering vapor through the ablation catheter into the enclosed volume; and condensing the vapor on a tissue within the gastrointestinal tract.

Optionally, the seal is temperature dependent. Optionally, the seal breaks when temperature inside the enclosed volume exceeds 90 degrees centigrade.

Optionally, the seal is pressure dependent. Optionally, the seal breaks when pressure inside the enclosed volume exceeds 5 atm.

The present specification also discloses a method for providing ablation therapy to a patient's gastrointestinal tract comprising: inserting an ablation catheter into the gastrointestinal tract; initiating a flow of saline through the ablation catheter, wherein the flow rate of saline is variable; heating the saline by delivering RF energy to the saline to generate vapor; delivering vapor through the ablation catheter into the gastrointestinal tract; and condensing the vapor on a tissue within the gastrointestinal tract.

Optionally, the flow rate of saline during heat therapy is different from flow rate of saline during the phase where no heat therapy is delivered.

Optionally, the flow rate of saline during heat therapy is higher from flow rate of saline during the phase where no heat therapy is delivered.

Optionally, the flow rate of saline during heat therapy is lower from flow rate of saline during the phase where no heat therapy is delivered.

The present specification also discloses a method for ablating a tissue, comprising: inserting a first ablation catheter into a patient's gastrointestinal (GI) tract, wherein the first ablation catheter comprises a distal positioning element, a proximal positioning element, and one or more vapor delivery ports between the distal and proximal positioning elements; expanding the distal positioning element; expanding the proximal positioning element to create a first seal between the peripheries of the distal and proximal positioning elements and the GI tract and form a first enclosed treatment volume between the distal and proximal positioning elements and a surface of the patient's GI tract; delivering vapor via the delivery ports; allowing the vapor to condense on tissue within the first enclosed treatment volume to circumferentially ablate the tissue; removing the first ablation catheter from the GI tract; examining an area of tissue ablated by the first ablation catheter to identify patches of tissue requiring focused ablation; inserting a second ablation catheter into the GI tract through an endoscope, wherein the second ablation catheter comprises a distal attachment or positioning element and at least one delivery port at a distal end of the catheter; expanding the distal attachment or positioning element to create a second seal between the periphery of the distal attachment or positioning element and the GI tract and form a second enclosed treatment volume between the distal attachment or positioning element and the surface of the patient's GI tract; delivering vapor via the at least one port; allowing the vapor to condense on the tissue within the second enclosed treatment volume to focally ablate the tissue; and removing the second ablation catheter from the GI tract.

The aforementioned and other embodiments of the present invention shall be described in greater depth in the drawings and detailed description provided below.

BRIEF DESCRIPTION OF THE DRAWINGS

These and other features and advantages of the present invention will be further appreciated, as they become better understood by reference to the detailed description when considered in connection with the accompanying drawings, wherein:

FIG. 1J is a flow chart of a plurality of steps of using the catheter of FIG. 1H or FIG. 1I to perform ablation of Barrett's esophagus tissue in an esophagus of a patient, in accordance with an embodiment of the present specification;

FIG. 1N is a flow chart illustrating a method for treating a gastrointestinal condition in a patient using a vapor ablation system, in accordance with embodiments of the present specification;

FIG. 6D illustrates a second plurality of configurations of the expandable tip of the catheter of FIG. 6A, in accordance with some embodiments of the present specification;

FIG. 7A illustrates the ablation device with a coaxial catheter design, in accordance with an embodiment of the present specification;

FIG. 7B illustrates a partially deployed positioning device, in accordance with an embodiment of the present specification;

FIG. 7C illustrates a completely deployed positioning device, in accordance with an embodiment of the present specification;

FIG. 7D illustrates the ablation device with a conical positioning element, in accordance with an embodiment of the present specification;

FIG. 7E illustrates the ablation device with a disc shaped positioning element, in accordance with an embodiment of the present specification;

FIG. 8E illustrates perspective views of the conical hood shaped positioning element attached to the catheter tip, in accordance with an embodiment of the present specification;

FIG. 8F shows a first configuration of the conical hood shaped positioning element, in accordance with an embodiment of the present specification;

FIG. 8G shows a second configuration of the conical hood shaped positioning element, in accordance with an embodiment of the present specification;

FIG. 8H shows a third configuration of the conical hood shaped positioning element, in accordance with an embodiment of the present specification;

FIG. 8K illustrates multiple views of another embodiment of a distal positioning element or attachment that is used with ablation catheters, for providing focused ablation, in accordance with the present specification;

FIG. 8L illustrates multiple views of another embodiment of a distal positioning element, similar to the distal positioning element of FIG. 8K, comprising an outlet port of a length of 18 mm and a width of 15 mm, in accordance with some embodiments of the present specification;

FIG. 8U illustrates additional photographs of a cap with an opening of the dimensions 14 mm and 7 mm, corresponding to cap of FIG. 8Q, cap of FIG. 8R, and the cap shown in FIG. 8S;

FIG. 8V illustrates additional photographs of a cap with an opening of the dimensions 14 mm and 7 mm, corresponding to cap of FIG. 8Q, cap of FIG. 8R, and the cap shown in FIG. 8S;

FIG. 9C is a flow chart illustrating a method of using a first ablation catheter to perform circumferential ablation and then a second ablation catheter to perform focal ablation, in accordance with some embodiments of the present specification;

FIG. 9E is a flow chart illustrating a multi-stage method of using a vapor ablation system for treating cancerous or precancerous esophageal tissue, in accordance with various embodiments of the present specification;

FIG. 9F is a flow chart illustrating a method of ablating a tissue inside a gastrointestinal (GI) tract of a patient with a pathophysiological metabolic condition, in accordance with other embodiments of the present specification;

FIG. 9G is a flow chart illustrating a method of using a vapor ablation system for ablating a target area within GI tract of a patient with a pathophysiological metabolic condition, in accordance with embodiments of the present specification;

FIG. 9H is a flow chart illustrating a method of using a vapor ablation system for ablating a target area in an intestine of a patient with non-alcoholic fatty liver disease (NAFLD) or non-alcoholic steatohepatitis (NASH), in accordance with embodiments of the present specification;

FIG. 9I is a flow chart illustrating a method of using a vapor ablation system for ablating a target area in an intestine of a patient with obesity, diabetes or a metabolic syndrome, in accordance with embodiments of the present specification FIG. 9J is a flow chart illustrating a method of using a vapor ablation system for ablating a target area in an intestine of a patient with obesity, diabetes or a metabolic syndrome, in combination with NASH and/or NAFLD, in accordance with embodiments of the present specification;

FIG. 9K is a flow chart illustrating a method of using a vapor ablation system for ablating a target area in an intestine of a patient with non-alcoholic fatty liver disease (NAFLD) or non-alcoholic steatohepatitis (NASH), in accordance with embodiments of the present specification;

FIG. 9L is a flow chart illustrating a method of using a vapor ablation system for ablating a target area in an intestine of a patient diagnosed with diabetes, prediabetes or obesity measured by an elevated level of BMI and/or a hemoglobin A1C and also diagnosed as having polycystic ovarian syndrome (PCOS), in accordance with embodiments of the present specification;

FIG. 9M is a flow chart illustrating a method of using a vapor ablation system for ablating a target area in an intestine of a patient with non-alcoholic fatty liver disease (NAFLD) or non-alcoholic steatohepatitis (NASH), with abnormal baseline levels of laboratory or radiology measurement indicative of inflammation of the liver, in accordance with embodiments of the present specification;

FIG. 11A illustrates a single lumen double balloon catheter comprising an in-line heating element, in accordance with an embodiment of the present specification;

FIG. 11B illustrates a coaxial lumen double balloon catheter comprising an in-line heating element, in accordance with an embodiment of the present specification;

FIG. 11C is a flow chart of a plurality of steps of using the catheter of FIG. 11A to perform ablation in a body lumen, such as Barrett's esophagus of a patient, in accordance with an embodiment of the present specification;

FIG. 12B is an exploded view of components upstream to an induction heating unit of the vapor generation system of FIG. 12A;

FIG. 12C is an exploded view of components downstream to the induction heating unit of the vapor generation system of FIG. 12A;

FIG. 16A shows a single multi-lumen shaft, in accordance with embodiments of the present specification;

FIG. 16B illustrates a pattern of vapor exit ports on a portion of the shaft of FIG. 16A, in accordance with embodiments of the present specification;

FIG. 16C is a first cross-sectional view of the shaft of FIG. 16A, in accordance with embodiments of the present specification;

FIG. 16D is a second cross-sectional view of the shaft of FIG. 16A, in accordance with embodiments of the present specification;

FIG. 16E is a perspective view of a non-telescoping catheter handle, in accordance with embodiments of the present specification;

FIG. 16F is a partial break-away view of the non-telescoping catheter handle, in accordance with embodiments of the present specification;

FIG. 17A shows a clamp in accordance with embodiments of the present specification;

FIG. 17B shows the clamp removably attached to a shaft of an endoscope, in accordance with embodiments of the present specification;

FIG. 17C shows an induction heating unit mounted on an endoscope separately from a catheter handle (also mounted on the endoscope), in accordance with embodiments of the present specification;

FIG. 17D illustrates an assembly of the induction heating unit being slidably mounted to the clamp of FIG. 17A, in accordance with an embodiment of the present specification.

FIG. 18 is an illustration of an embodiment of a disposable tubing set to be used with the ablation systems of the present specification;

FIG. 19 is an illustration of a telescoping catheter handle attached to an endoscope, in accordance with an embodiment of the present specification;

Figure 20A:
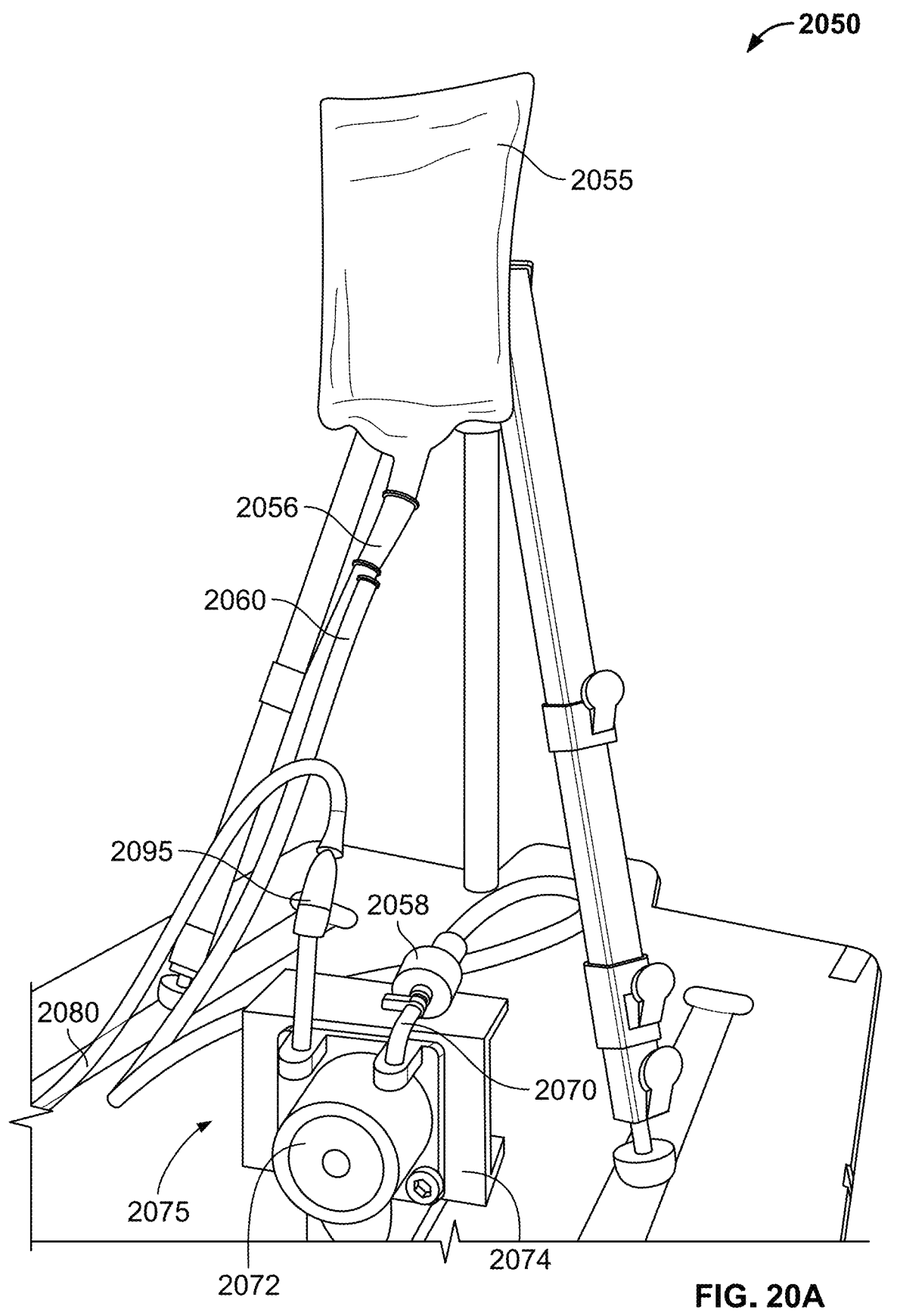
Figure 20B:
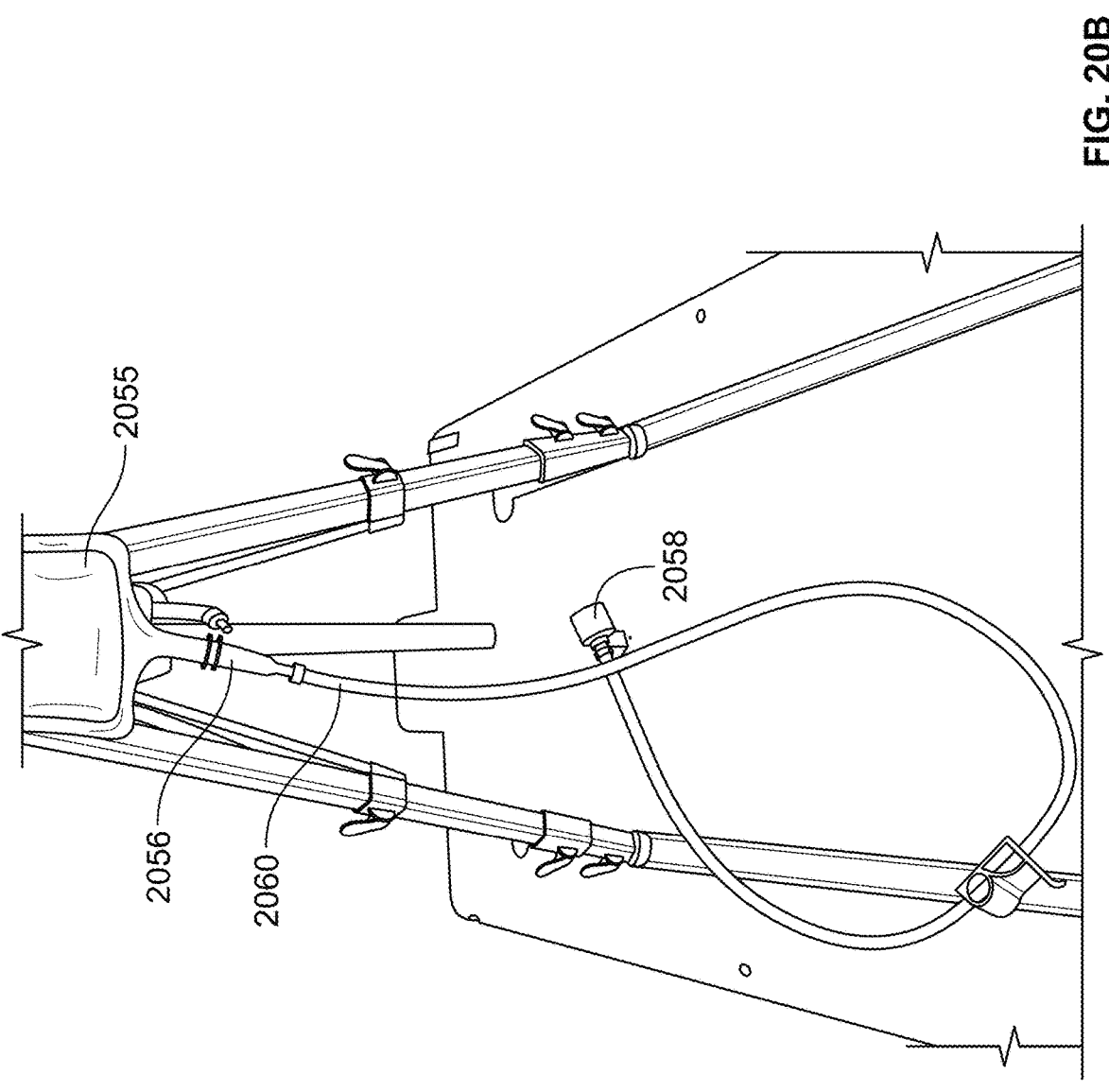
Figures 20C, 20D:
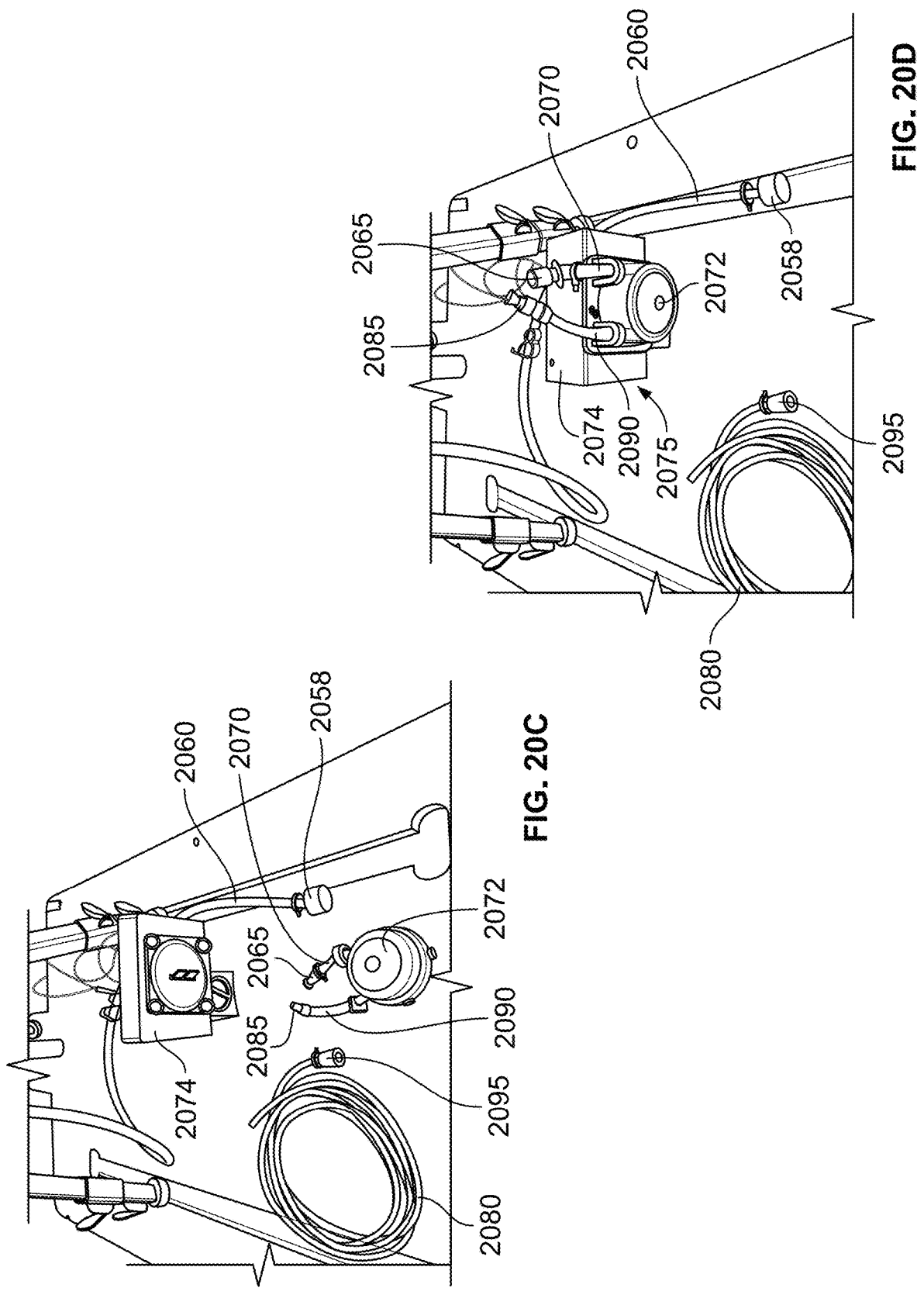
Figure 20E:
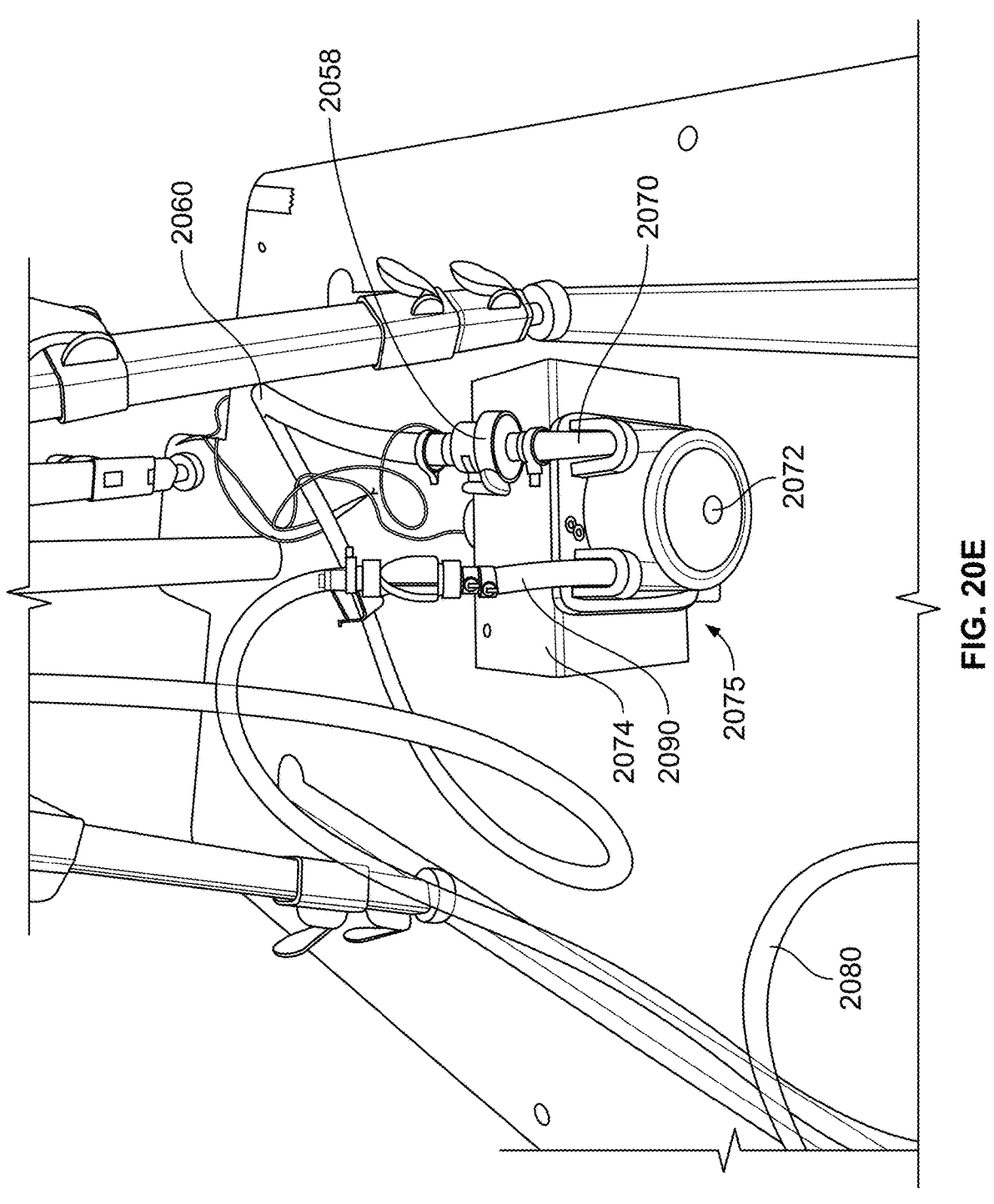
Figure 21:
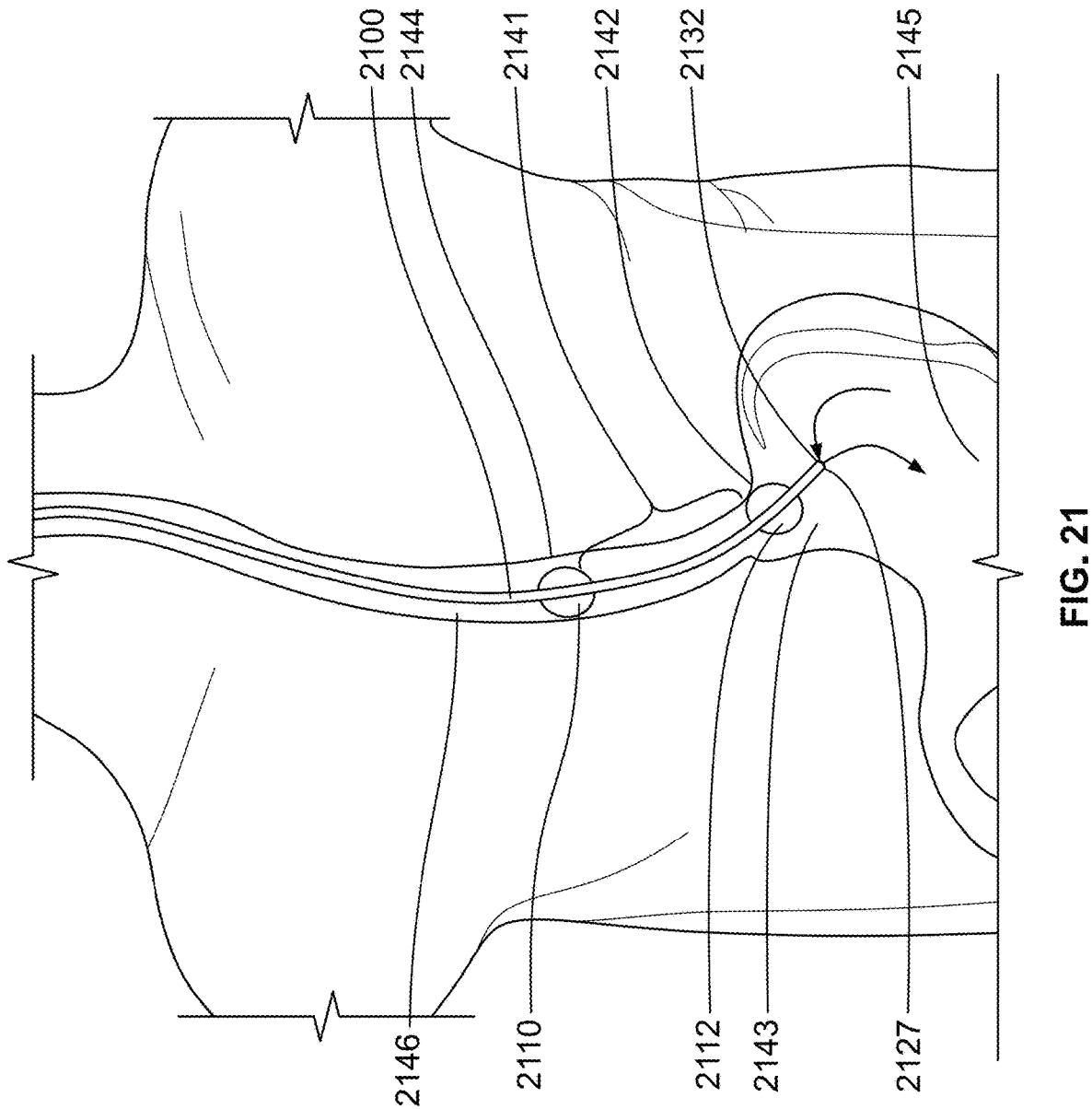
Figure 22:
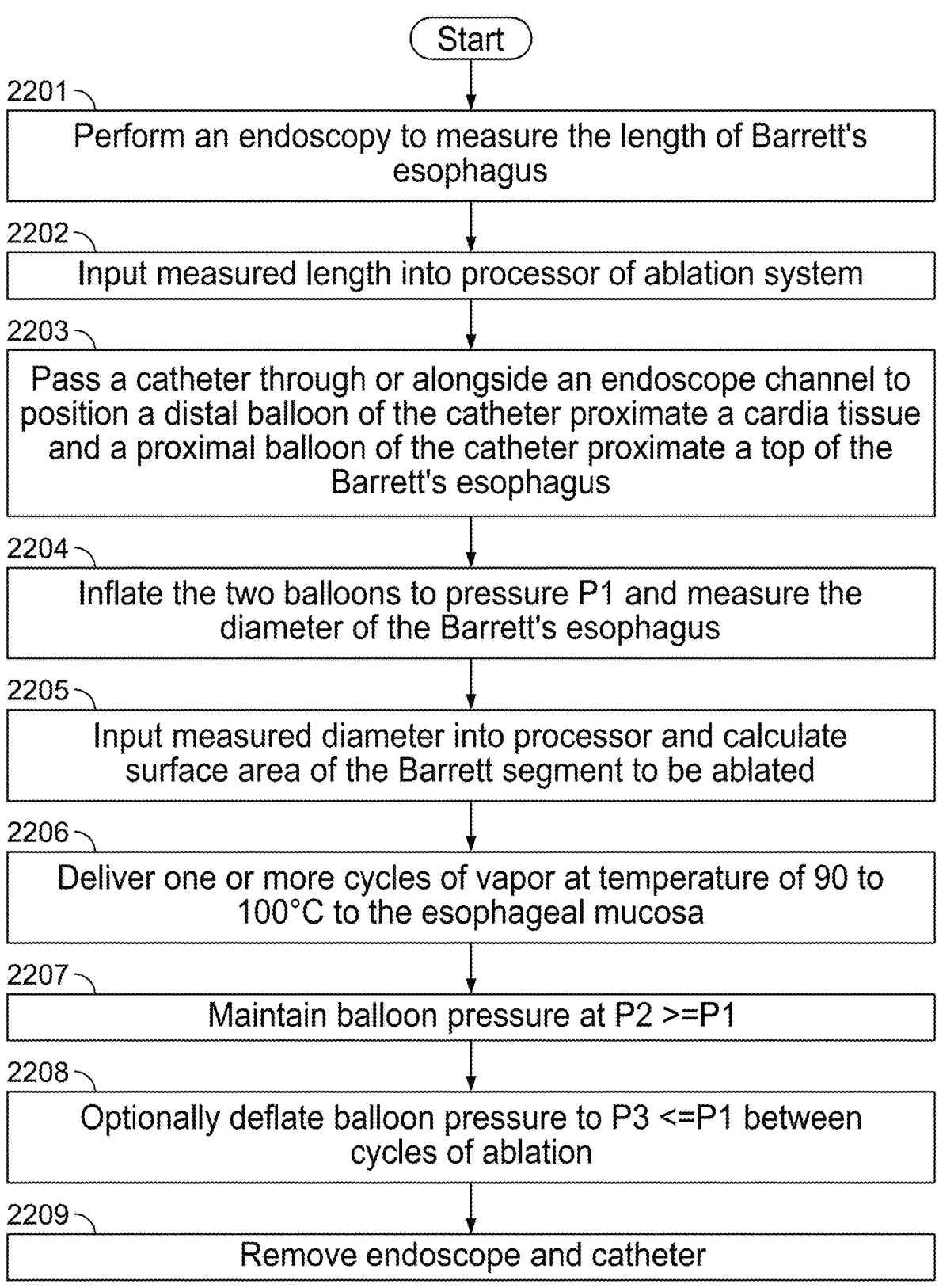
Figure 23A:
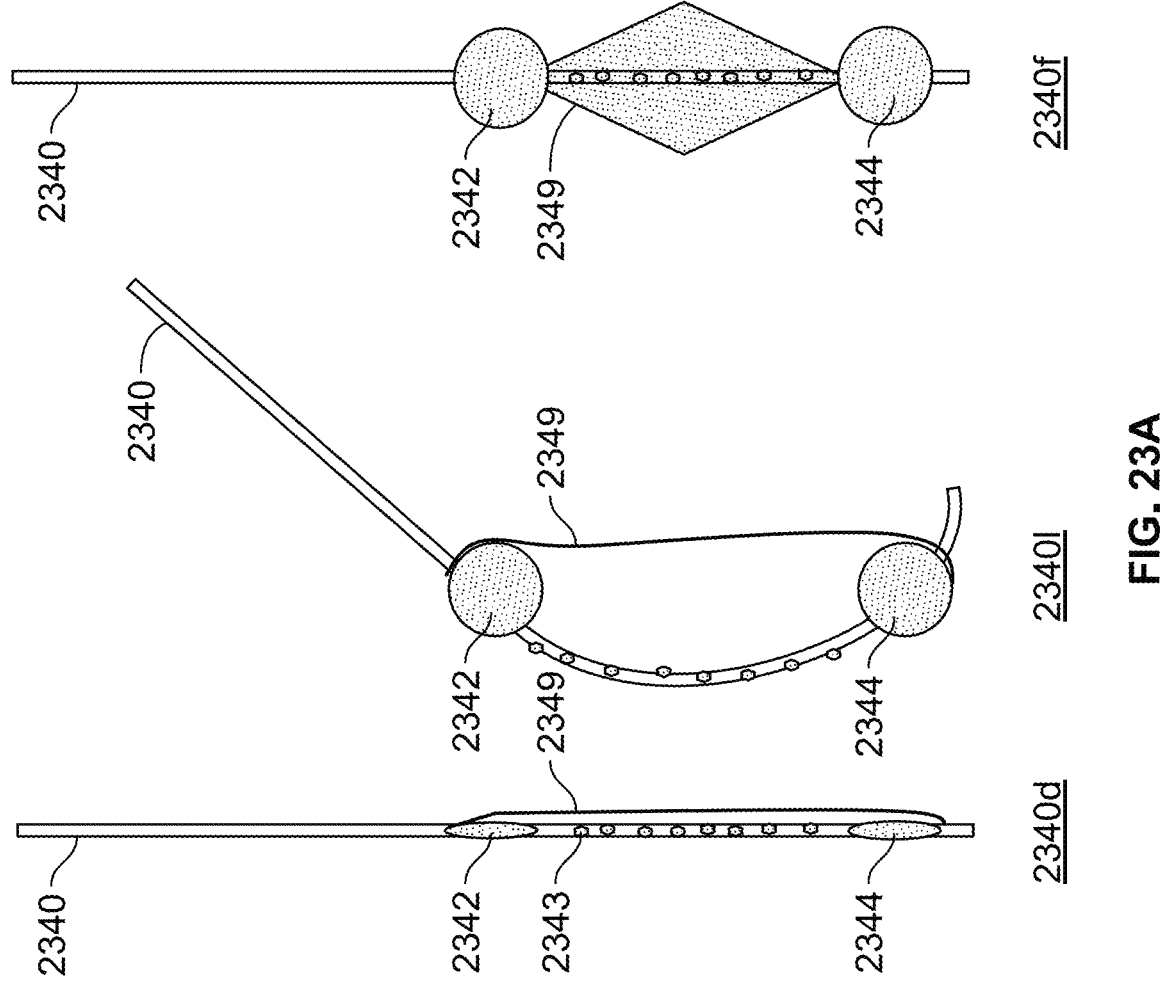
Figure 23B:
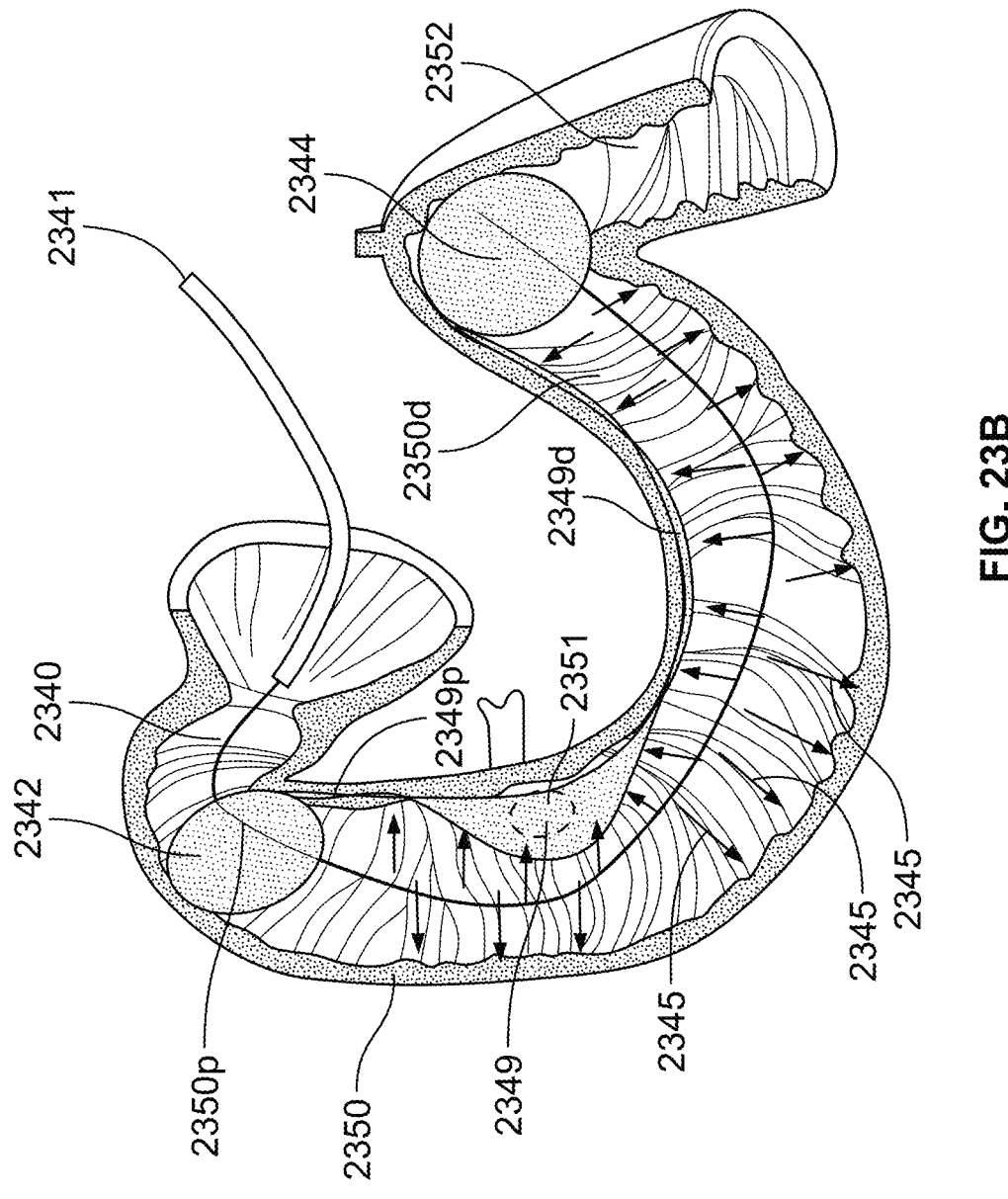
Figure 25:
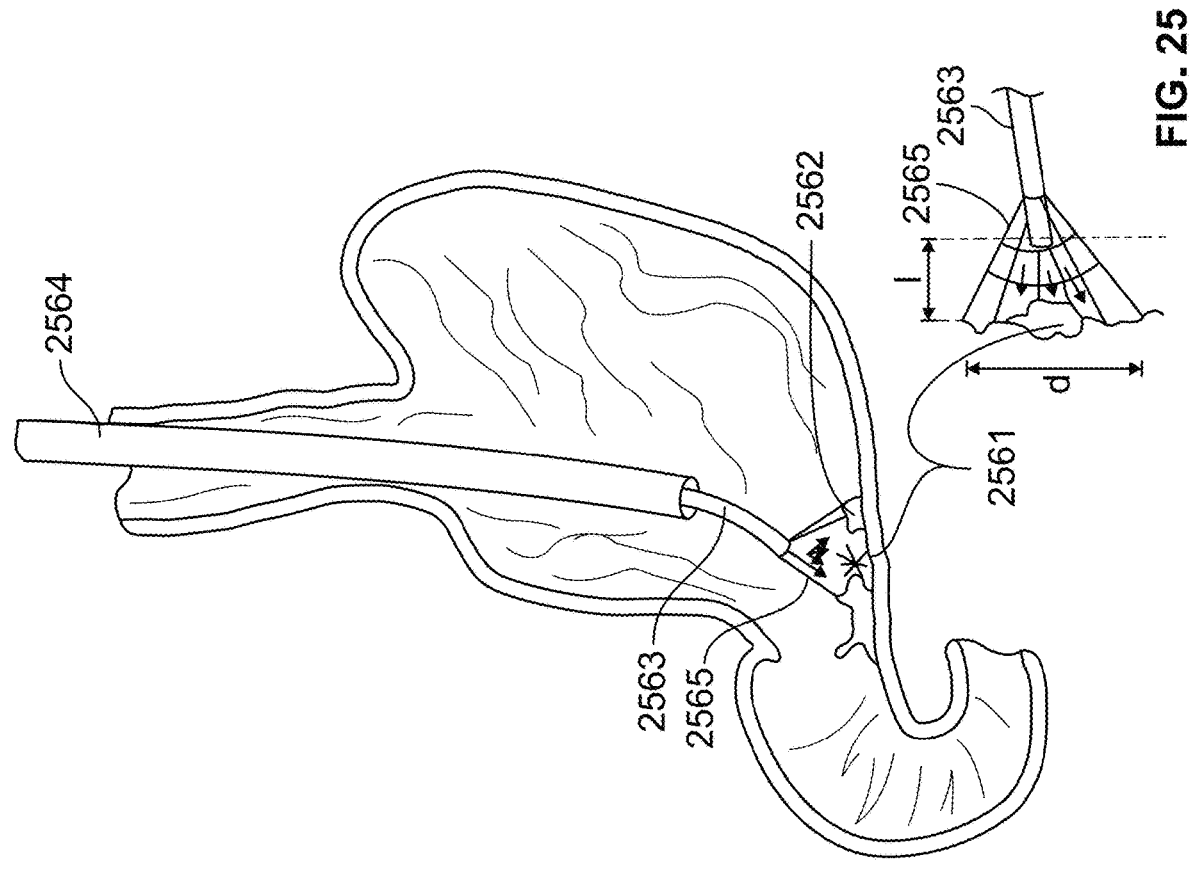
Figure 27A:
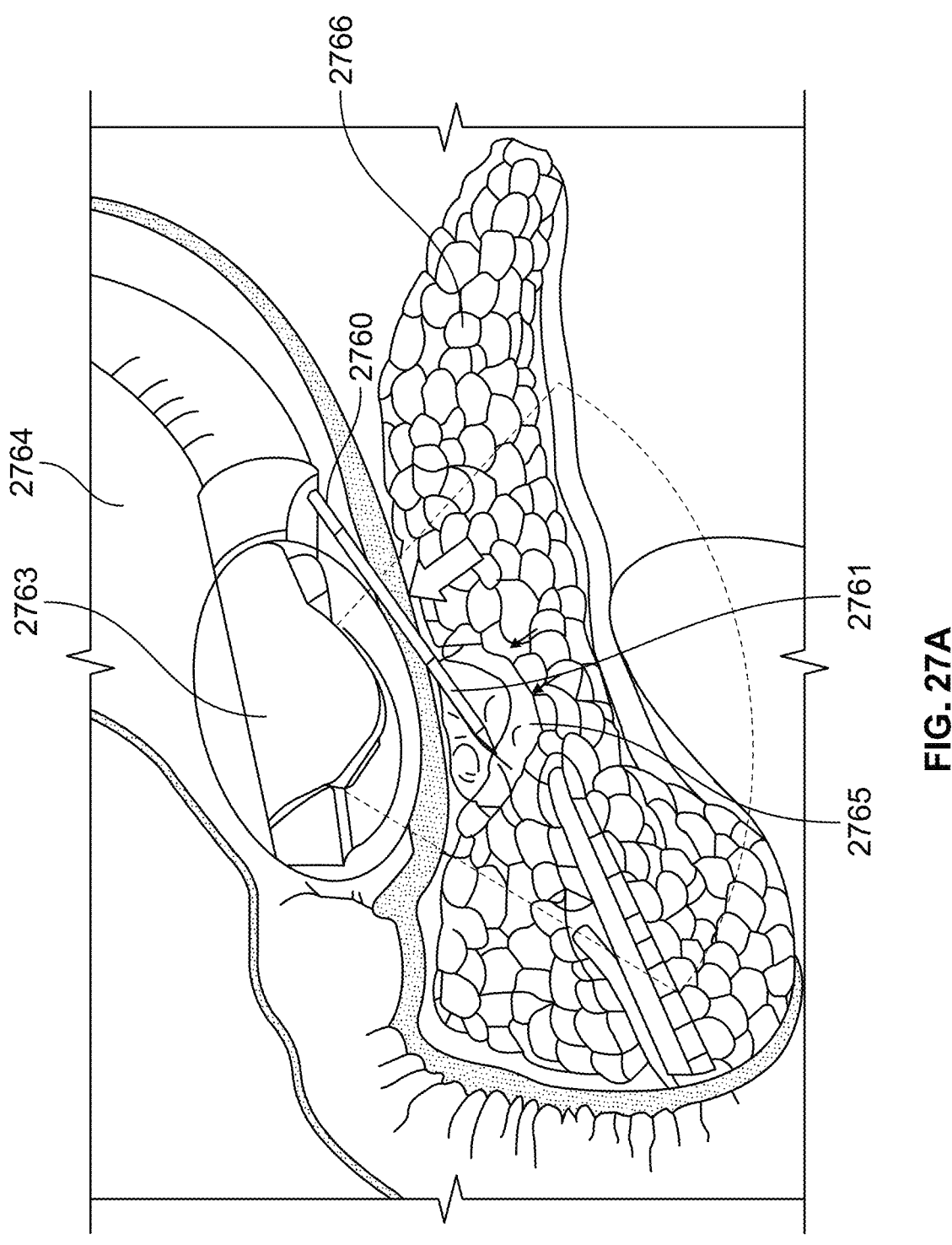
Figure 29A:
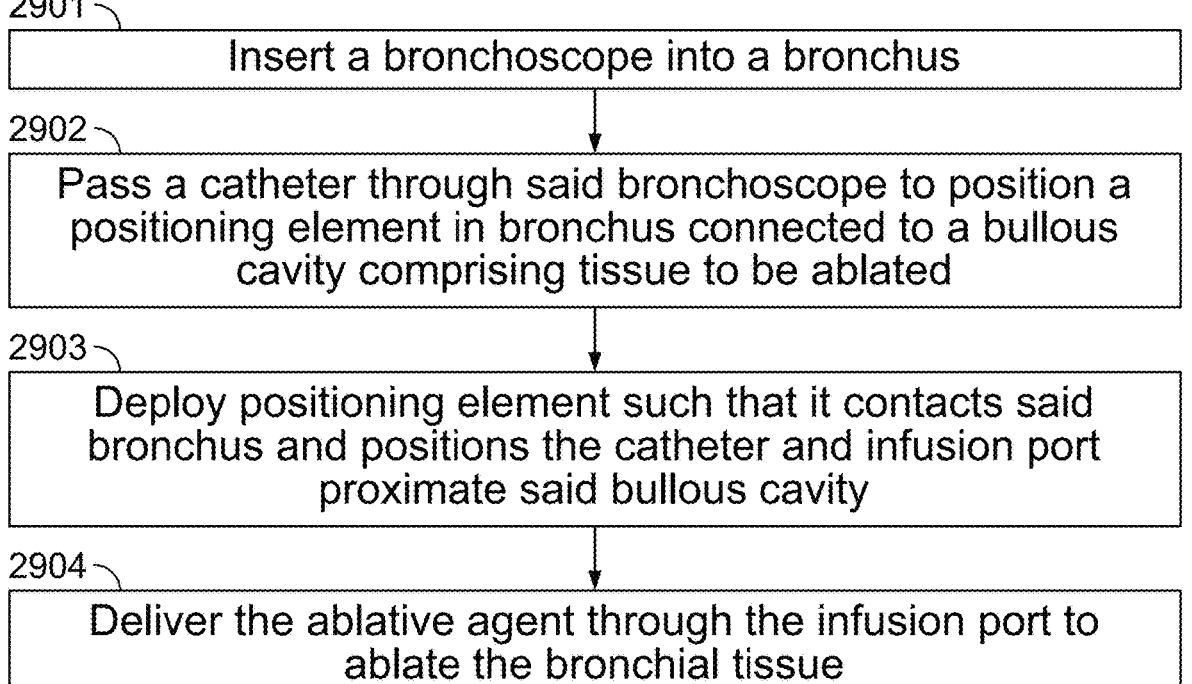
Figure 30A:
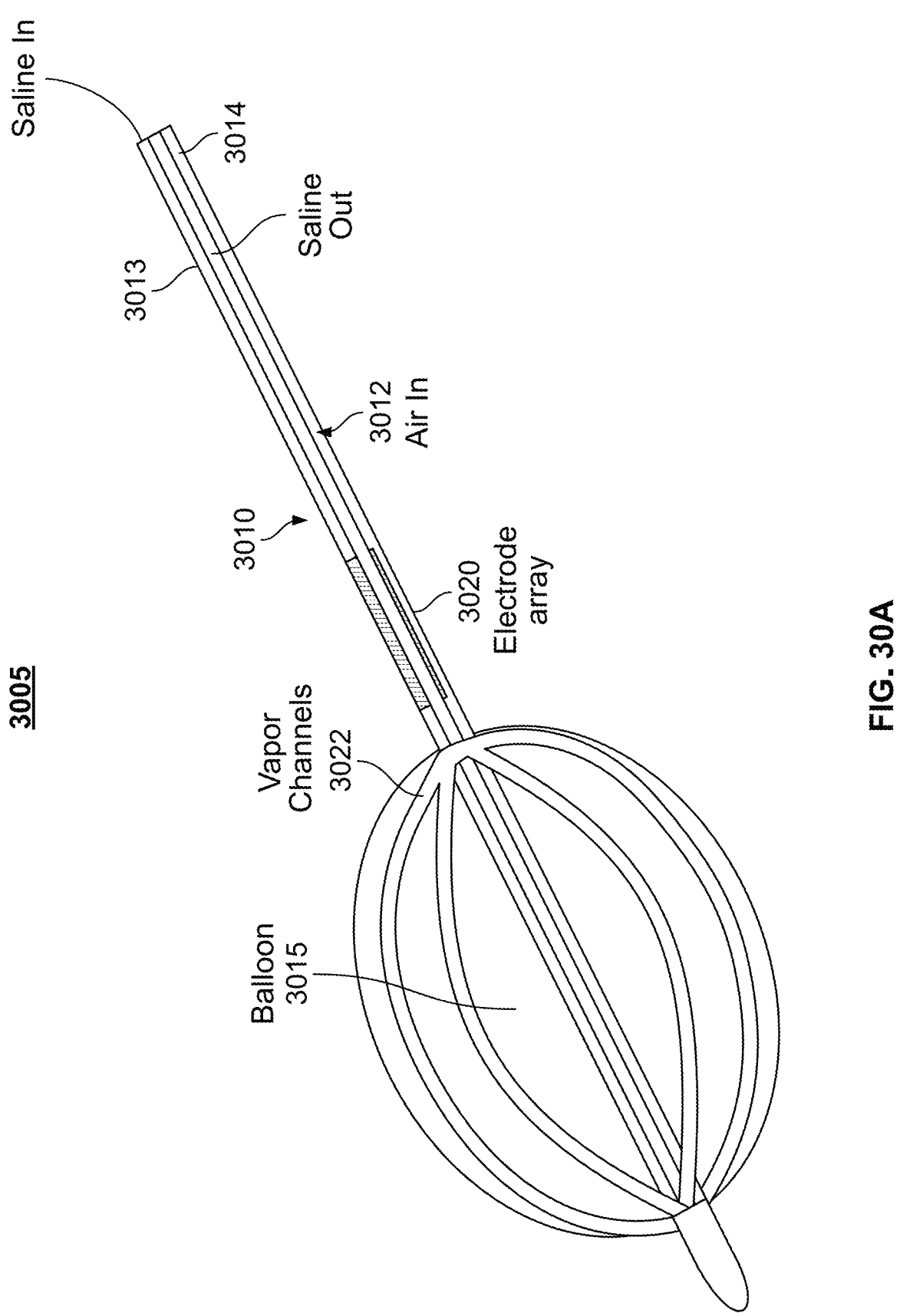
Figure 30C:
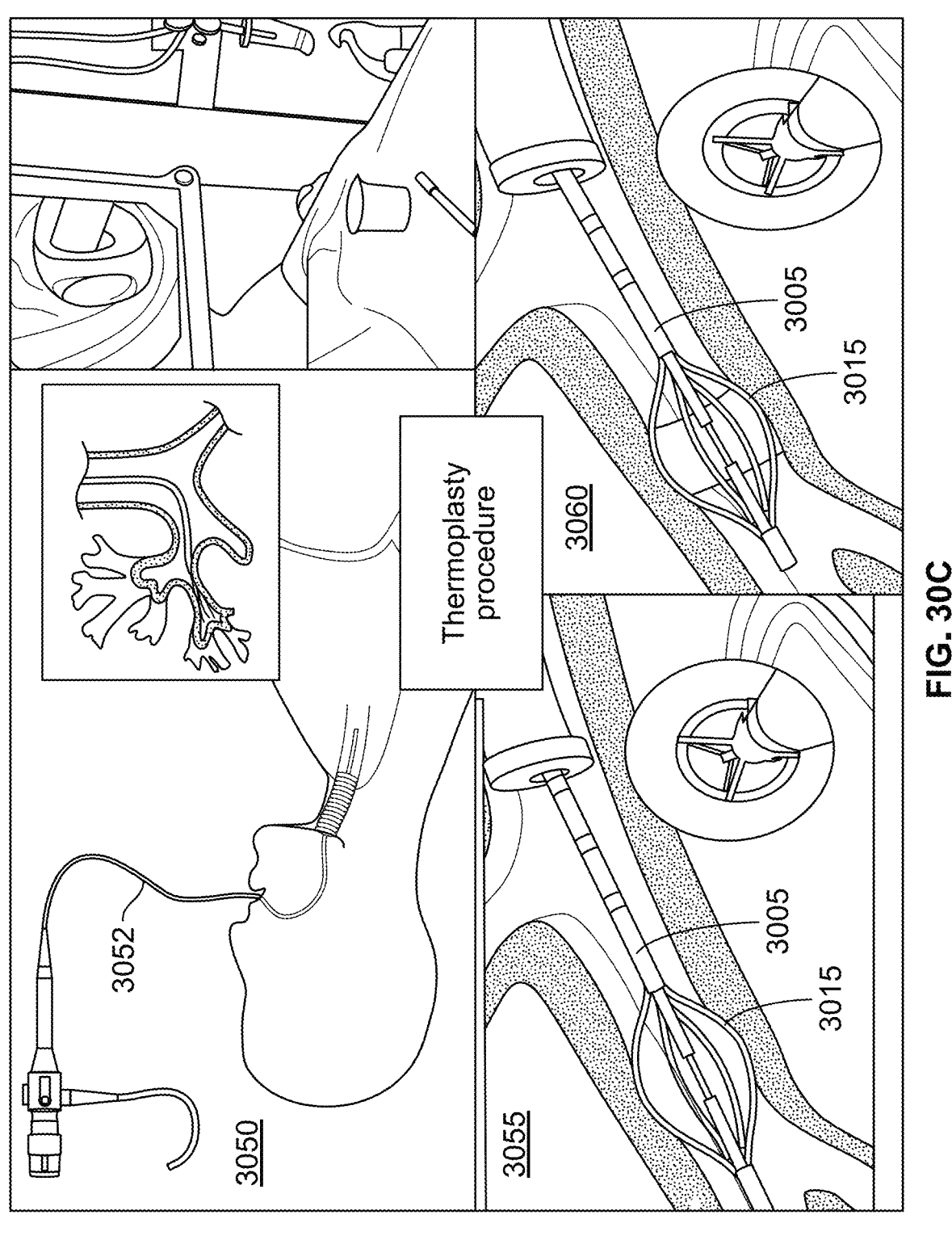
Figures 31A, 31B:
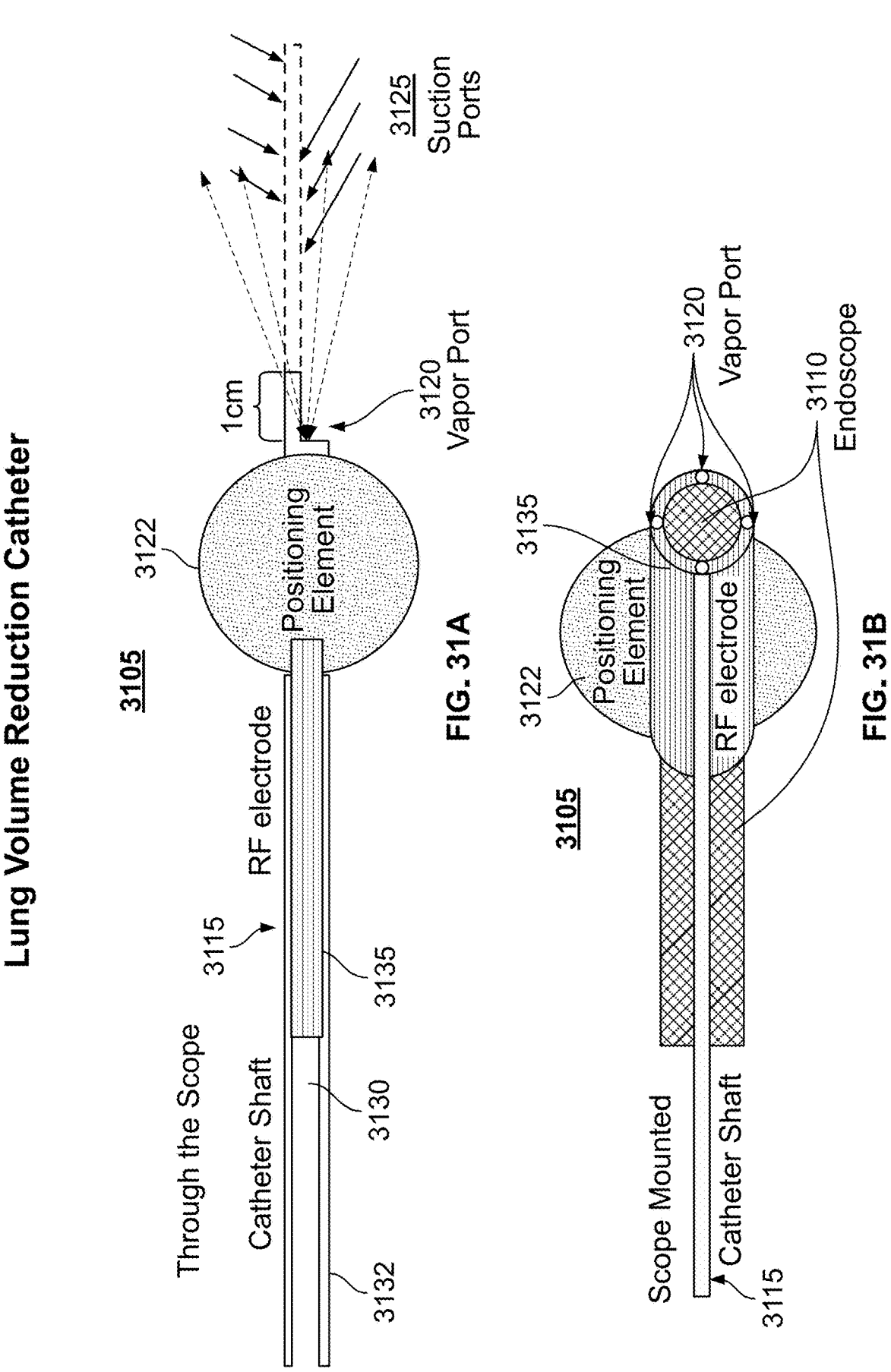
Figure 31C:
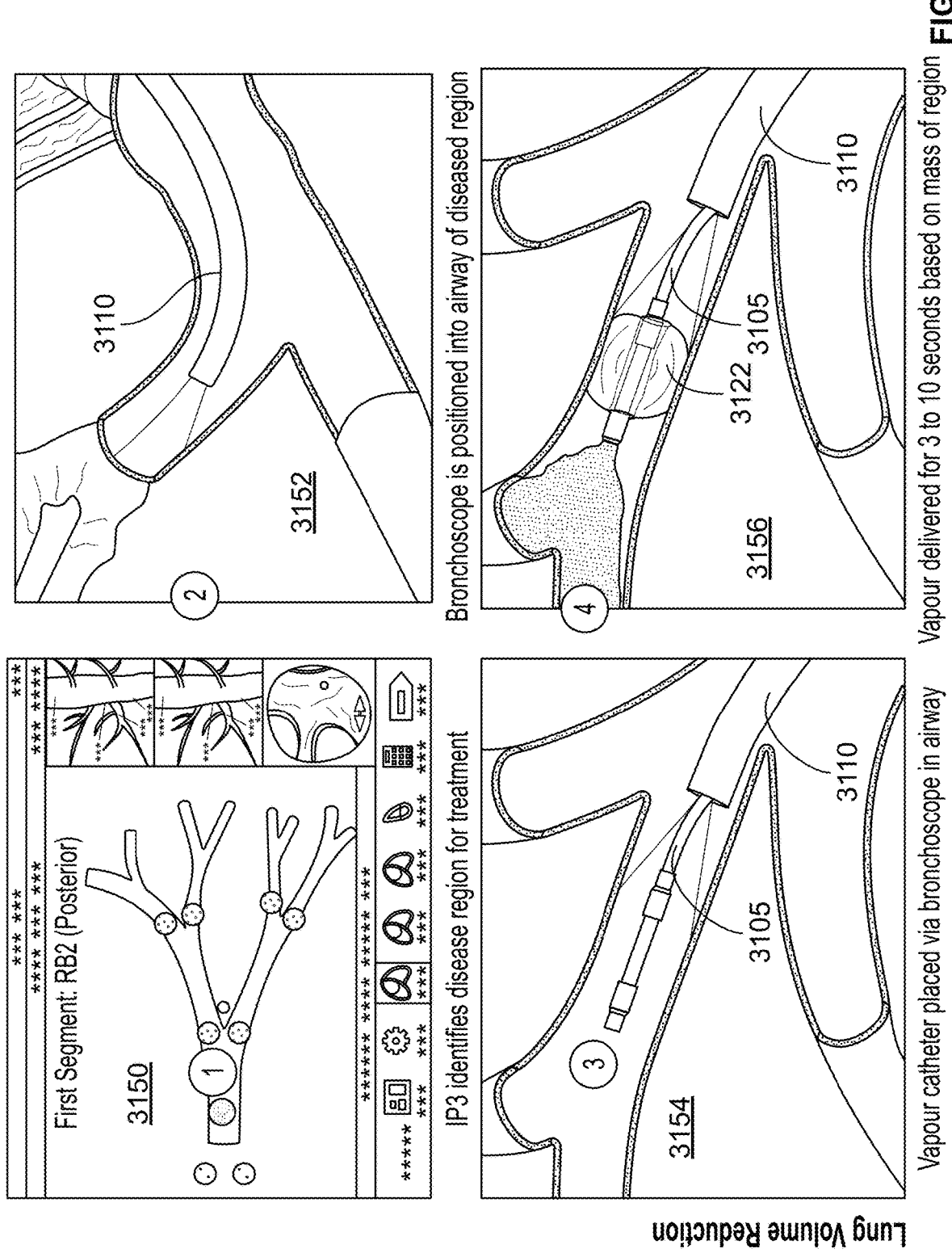
Figure 32A:
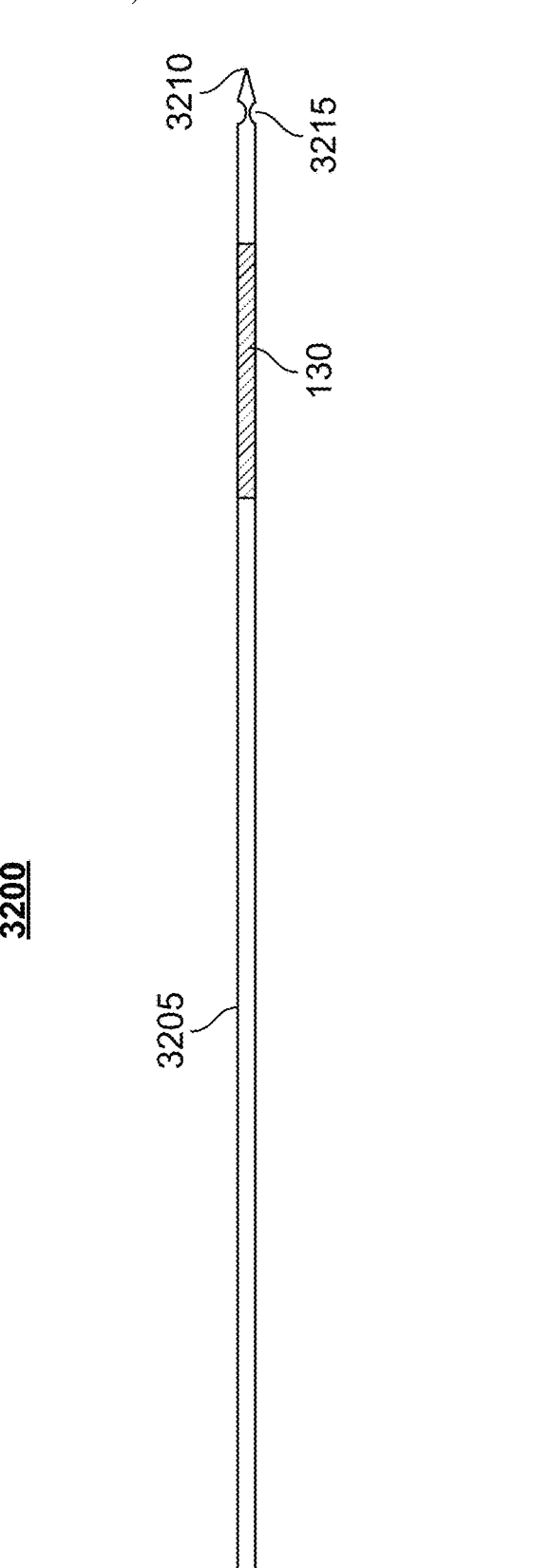
Figure 32B:
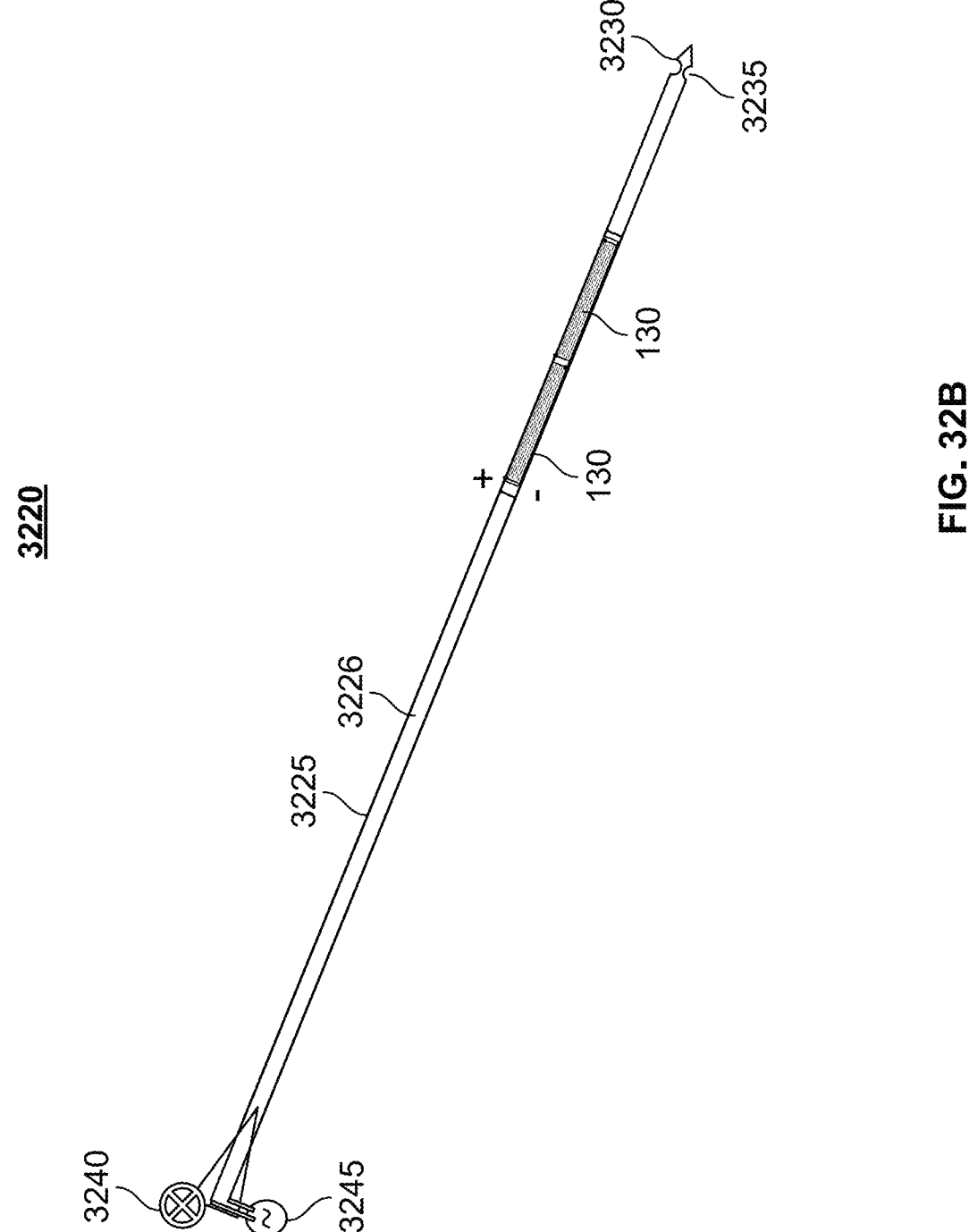
Figure 33:
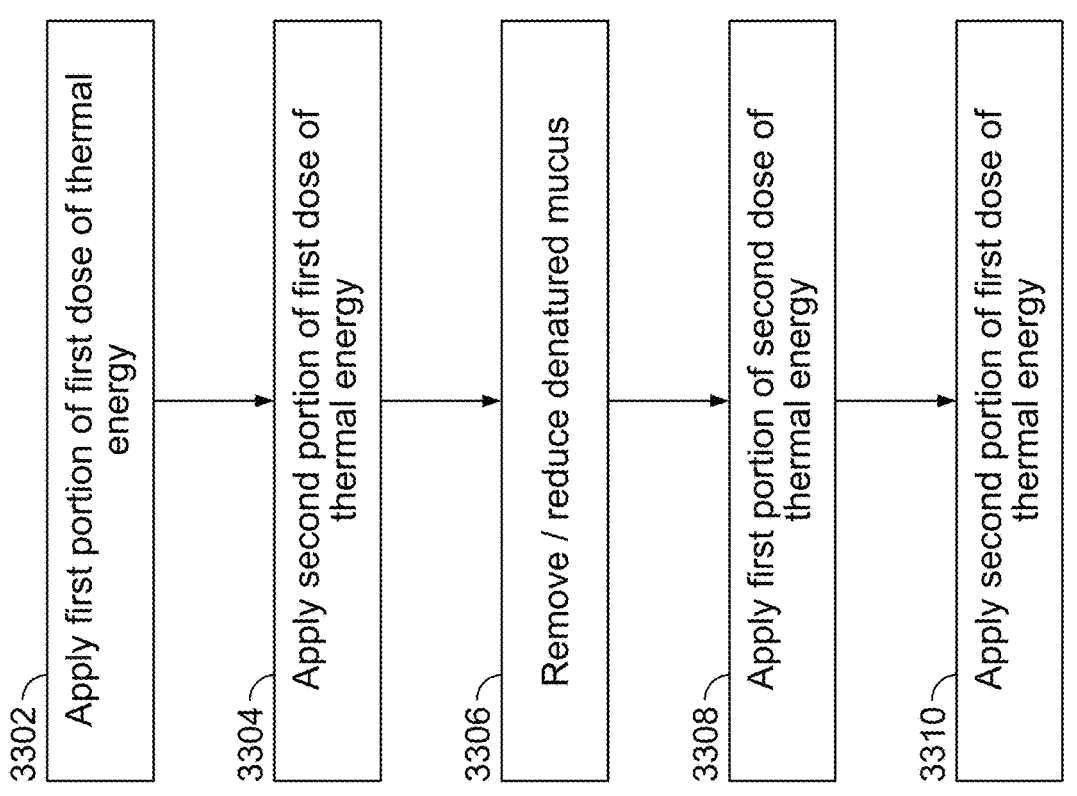
Figure 34:
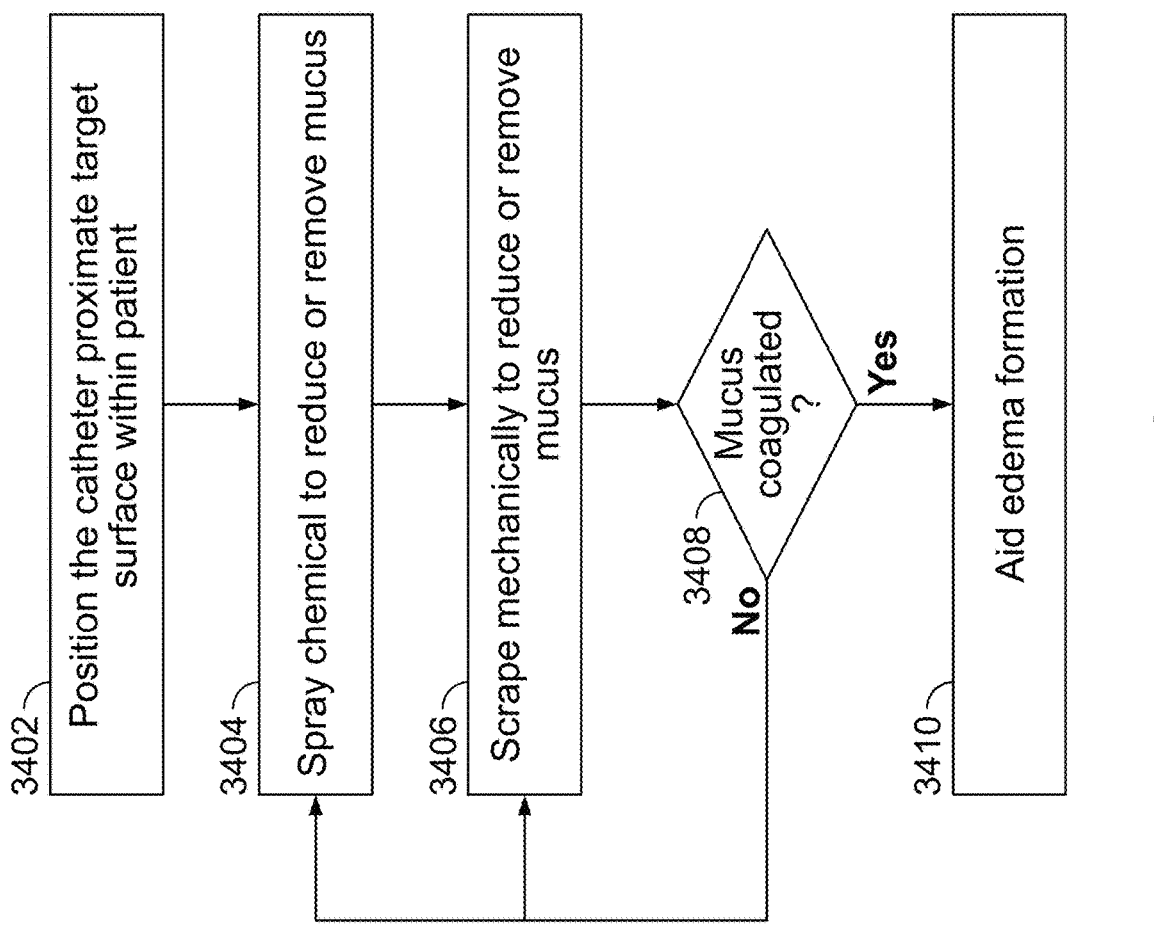
Figure 35:
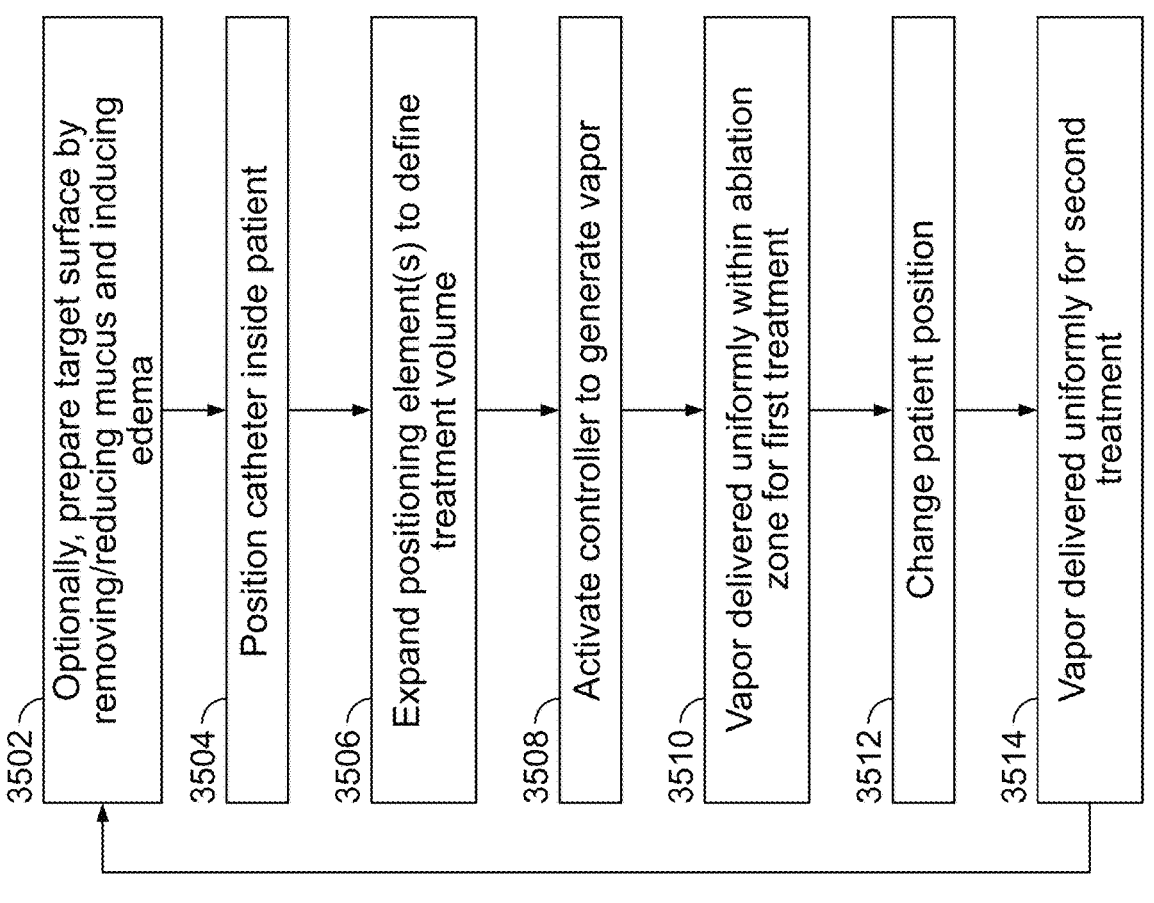
Figure 36A:
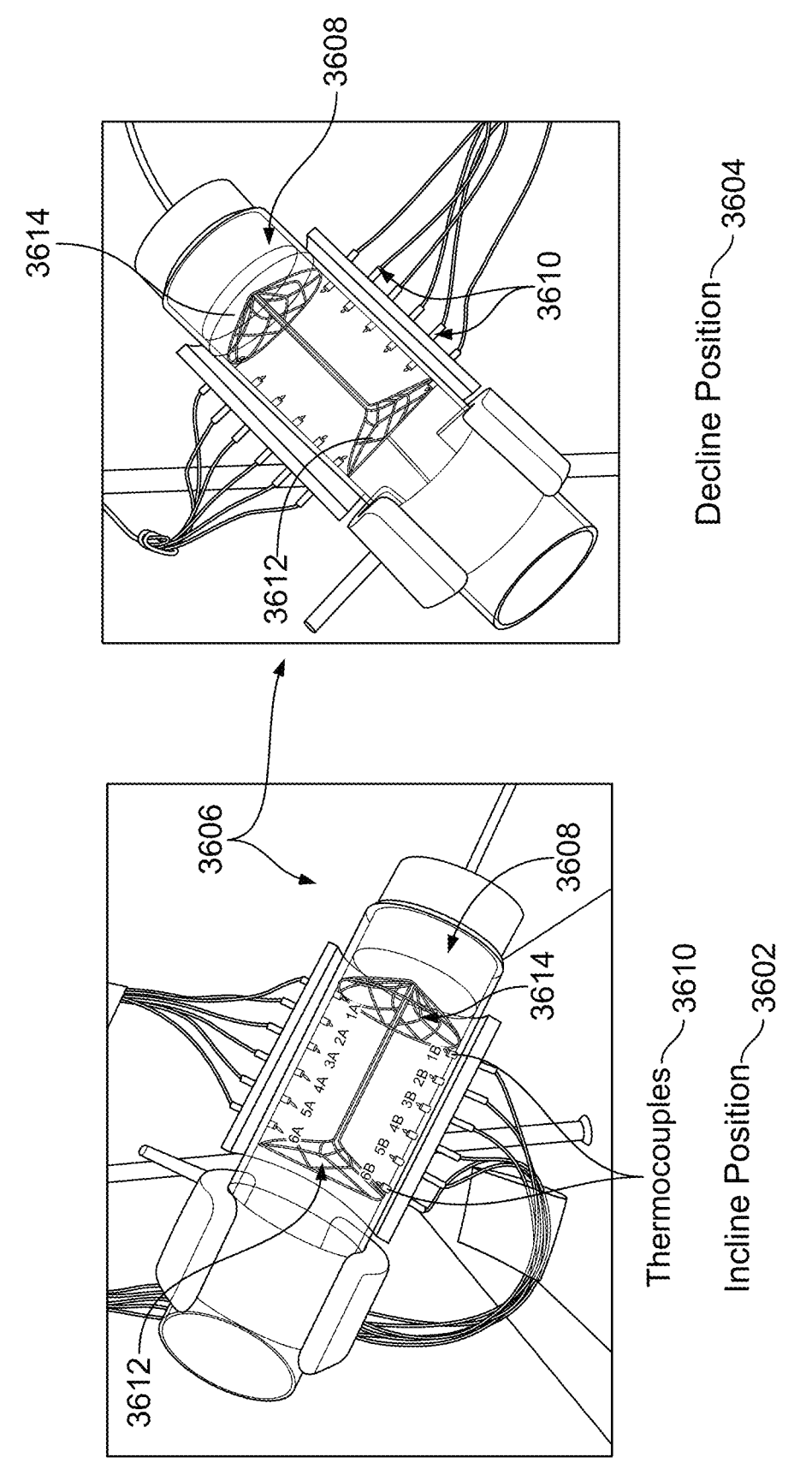
Figure 36B:
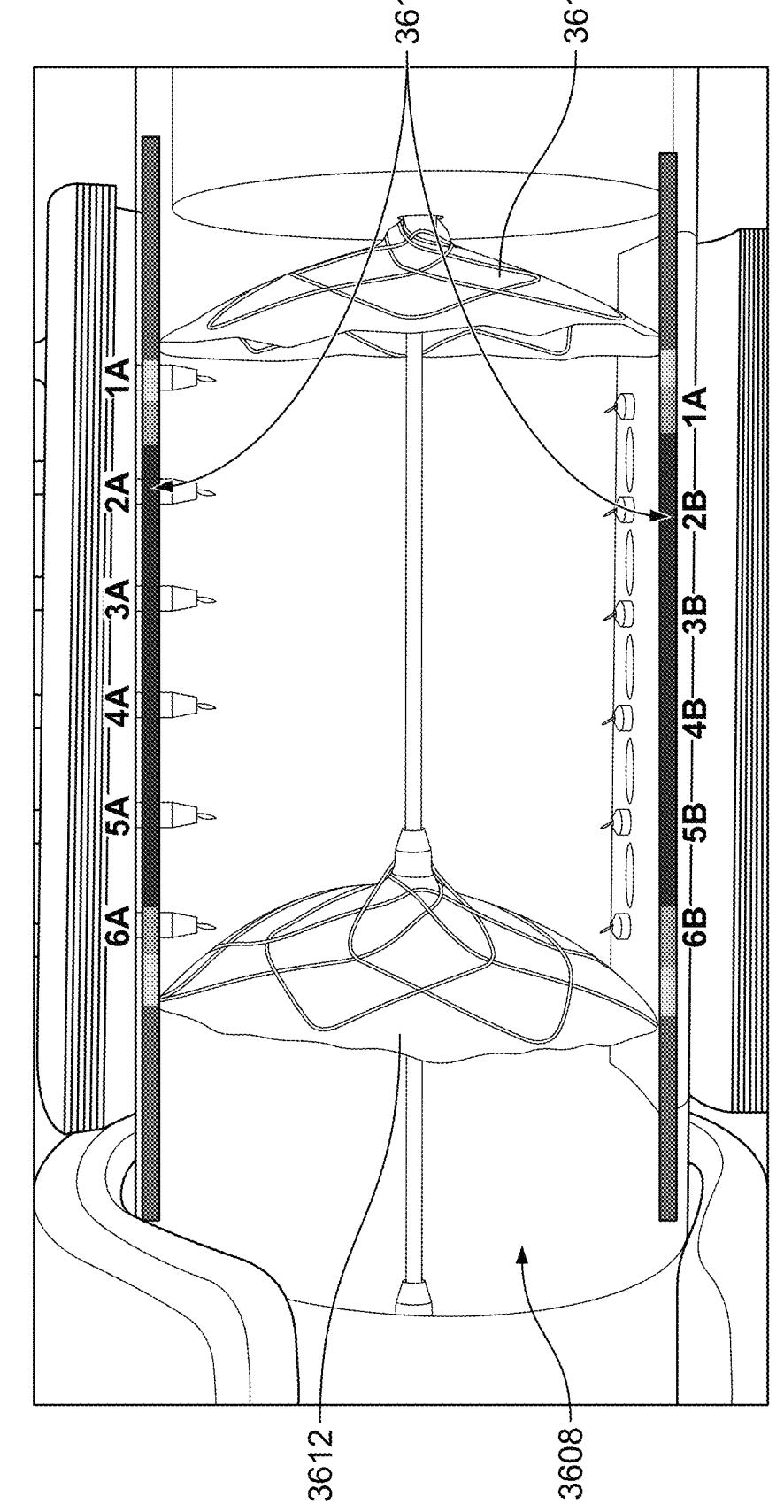
Figure 36C:
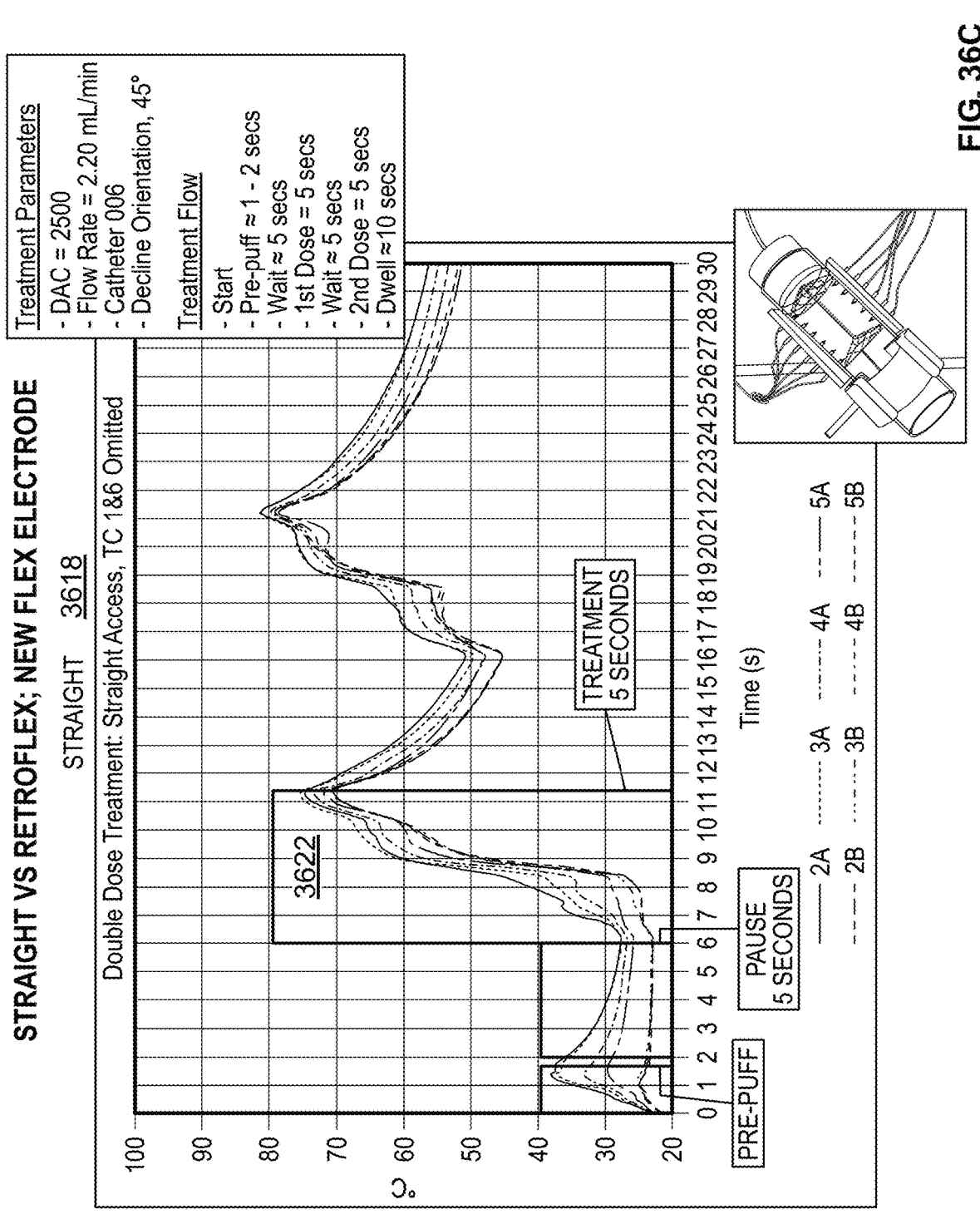
Figure 36C:
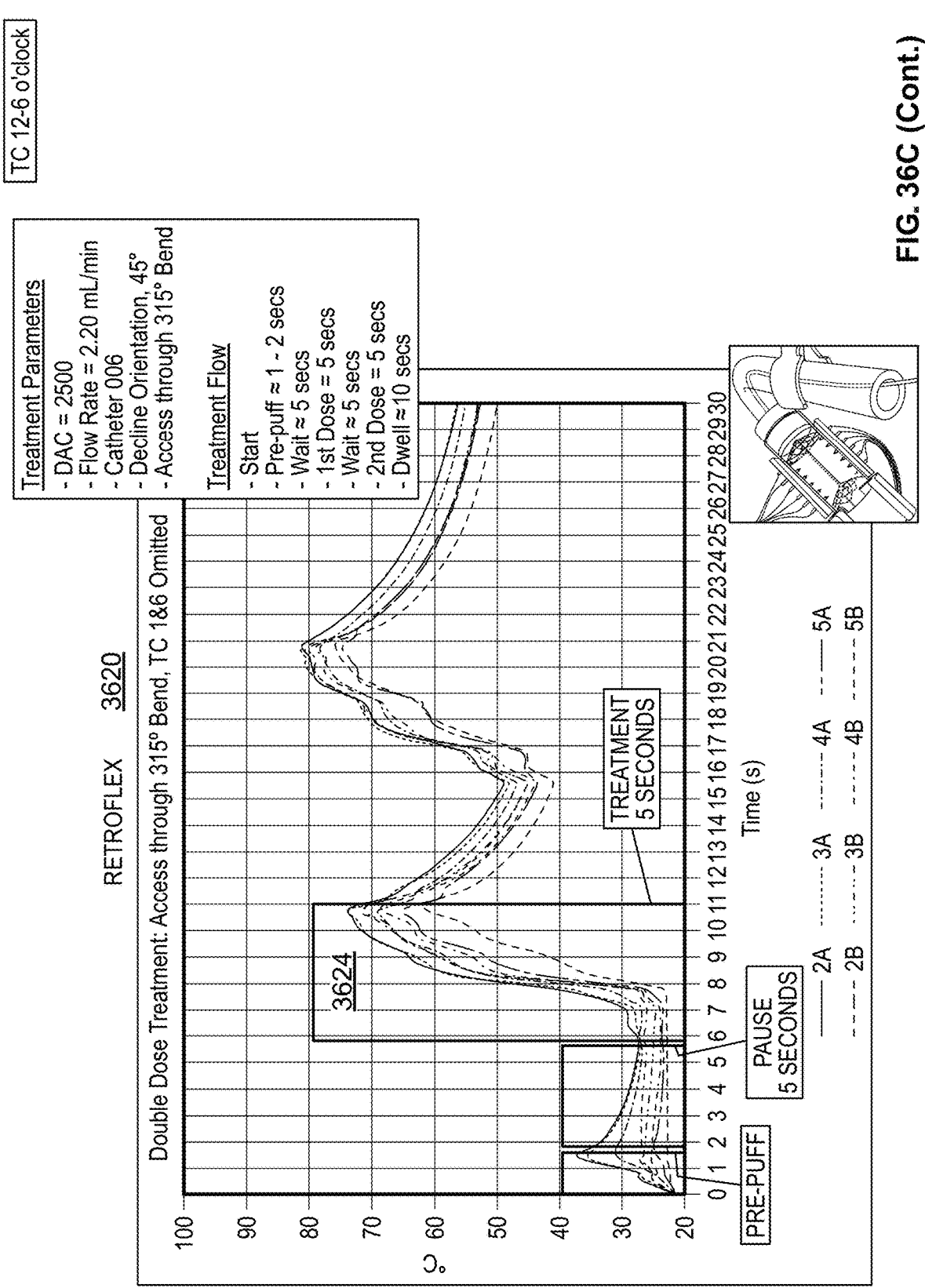
Figure 36D:
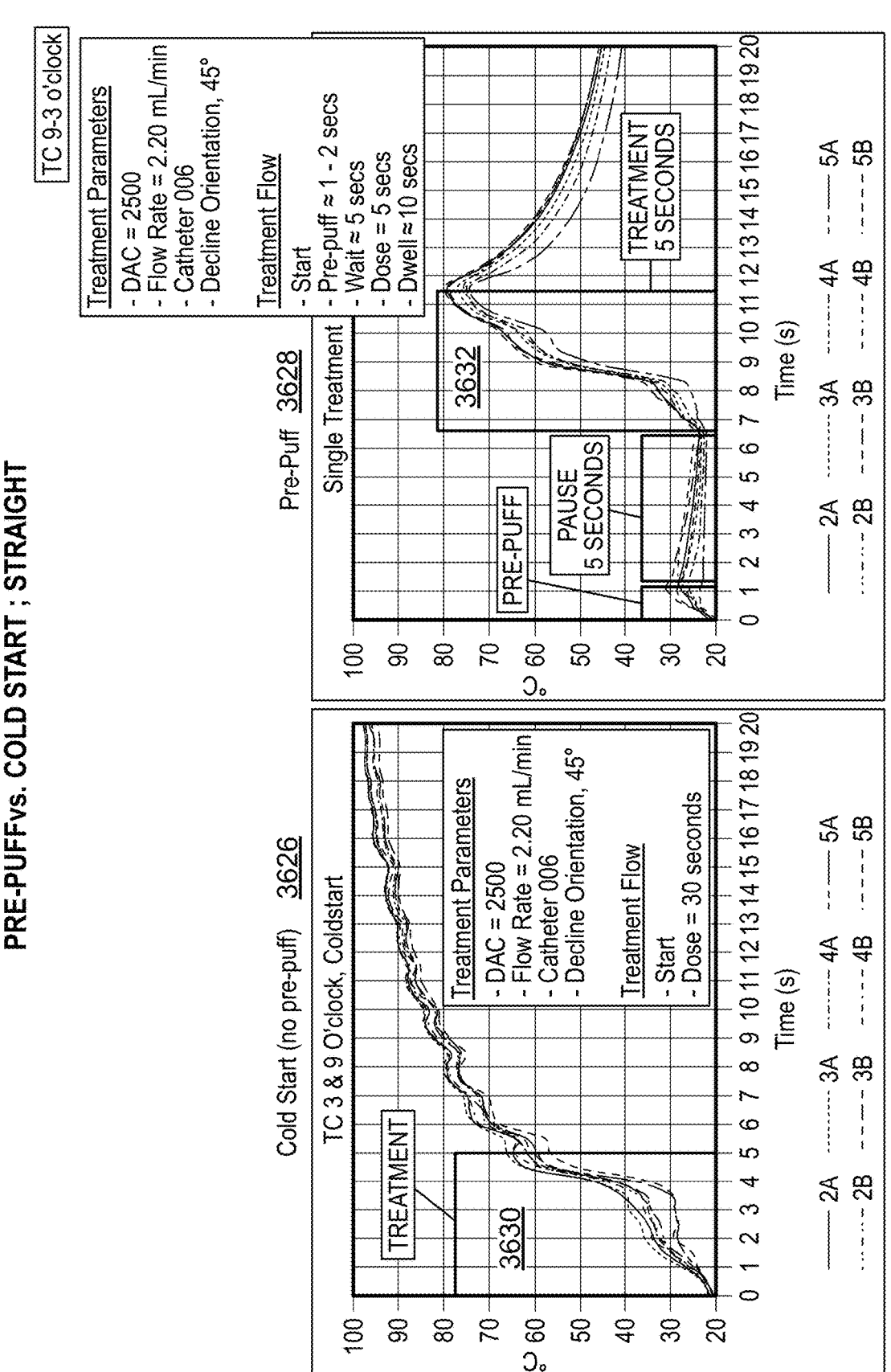
Figure 36E:
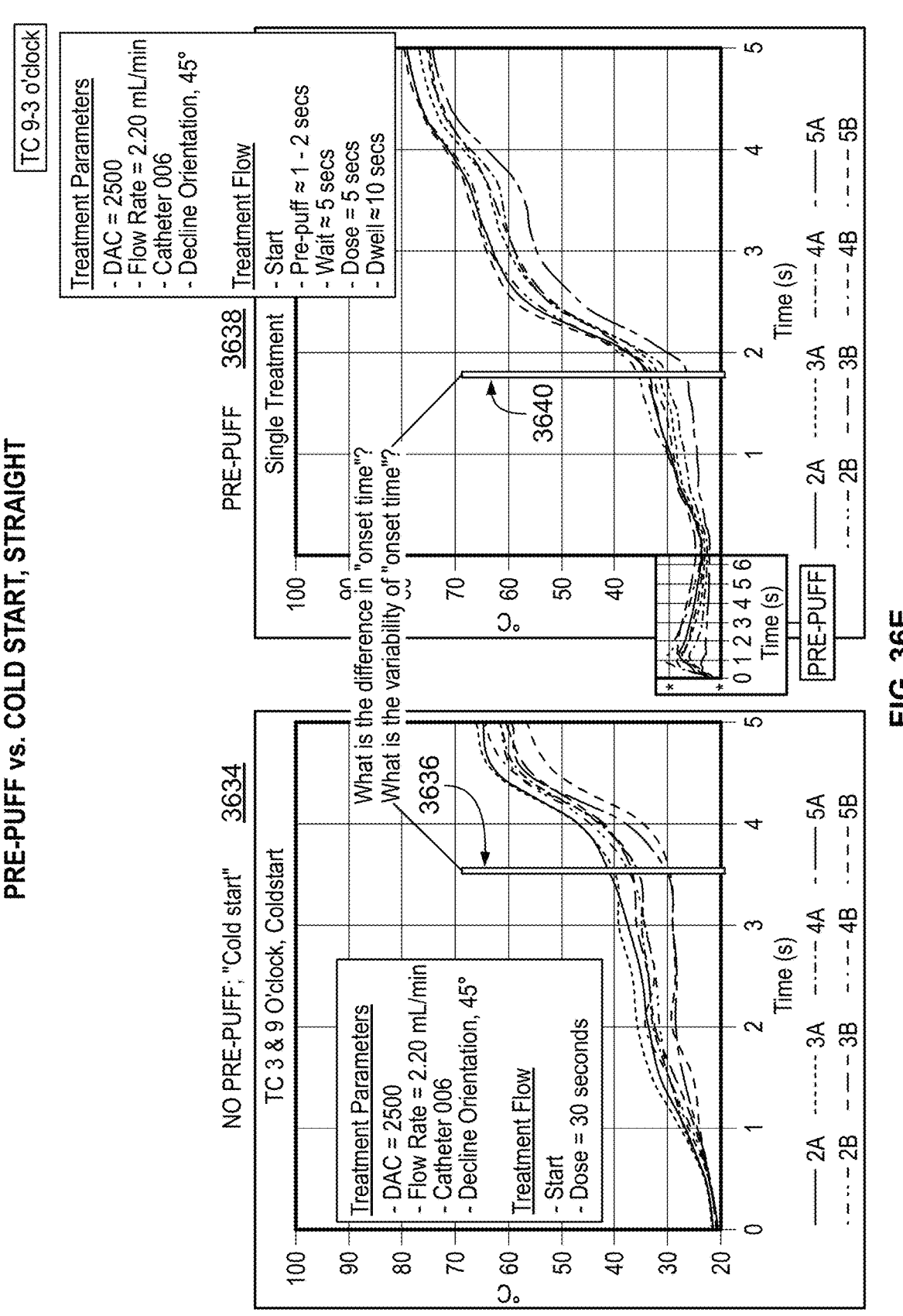
Figure 37A:
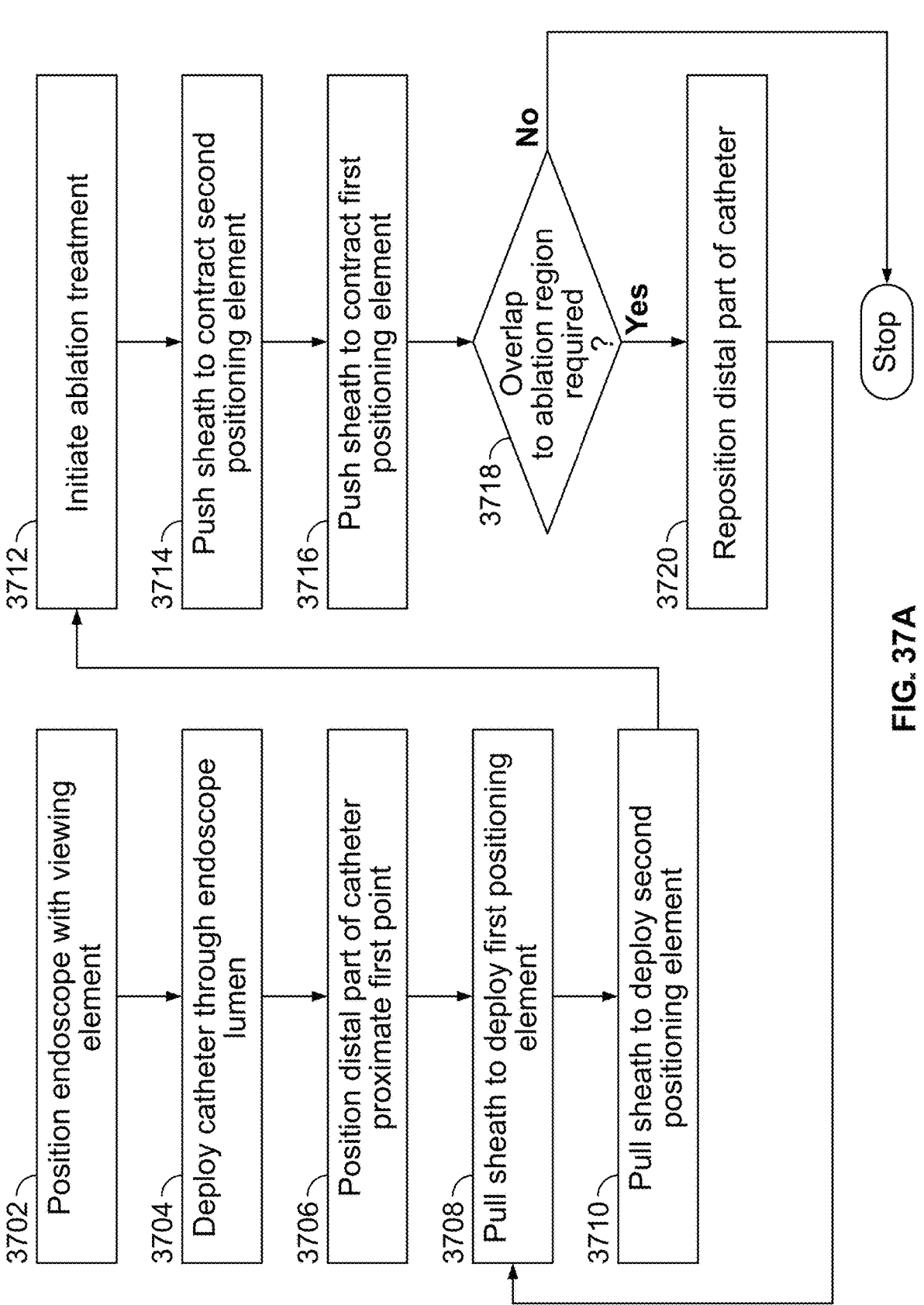
Figure 38A:
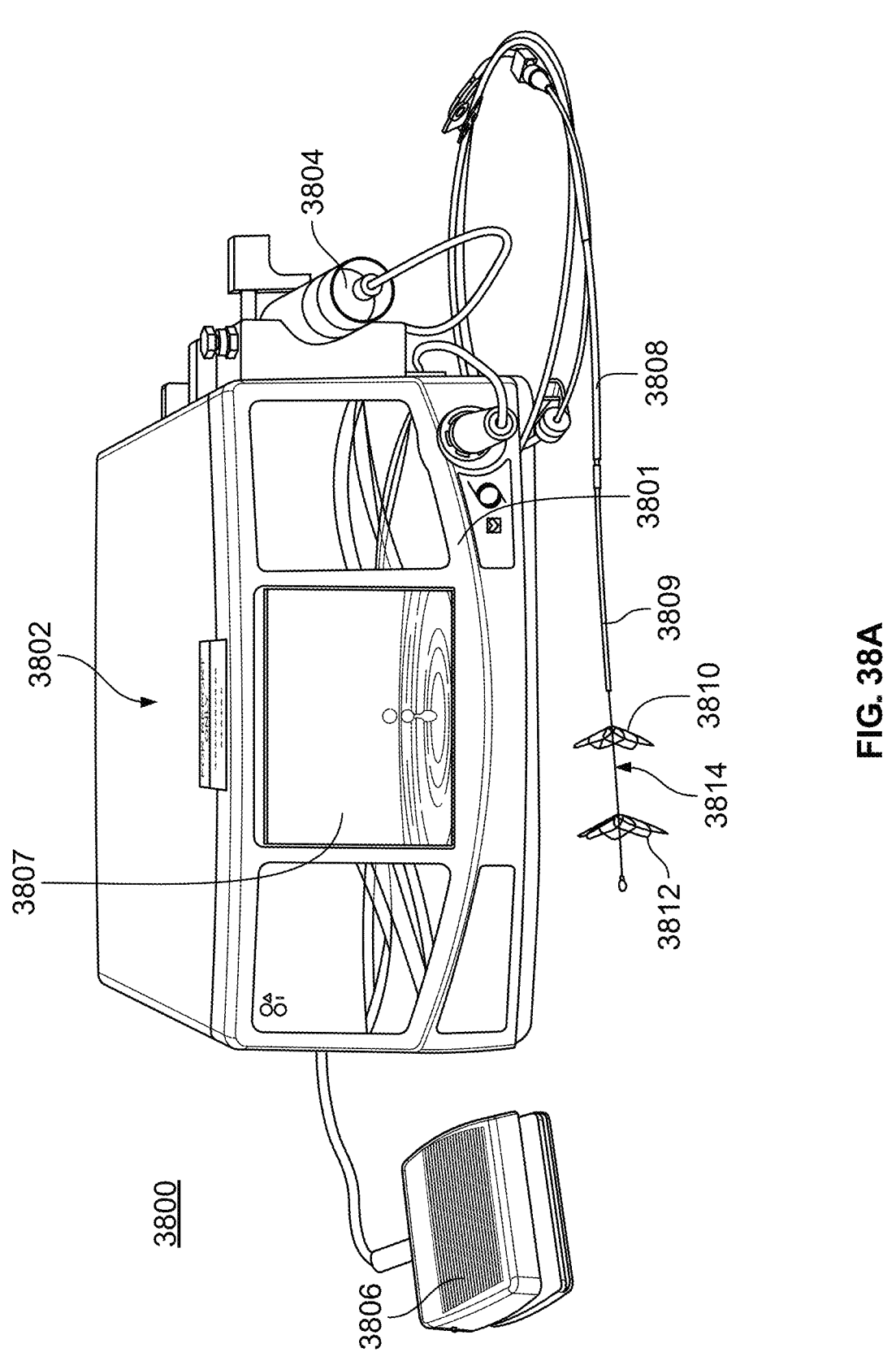
Figure 38B:
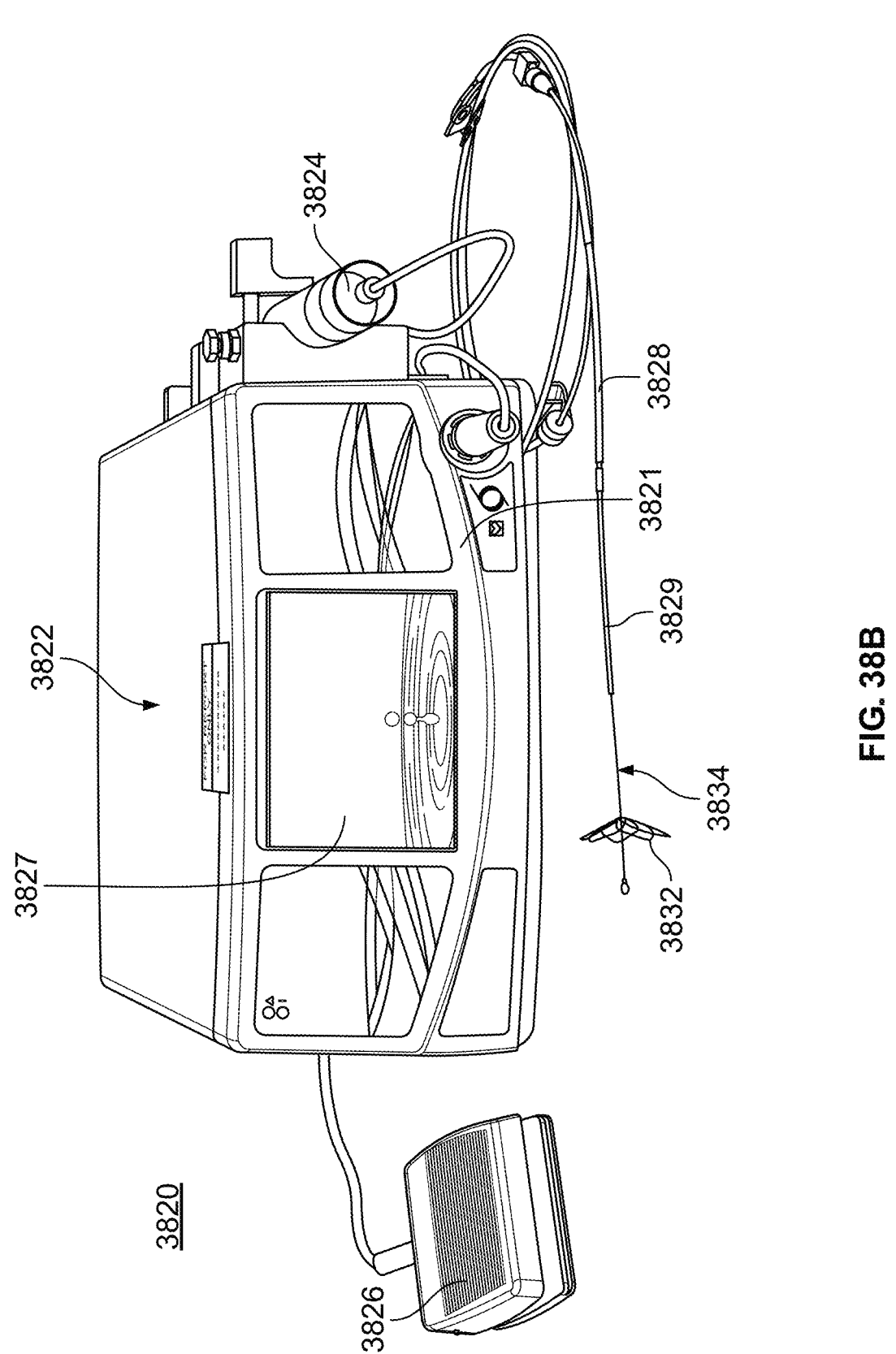
Figures 39A, 39B, 39C:
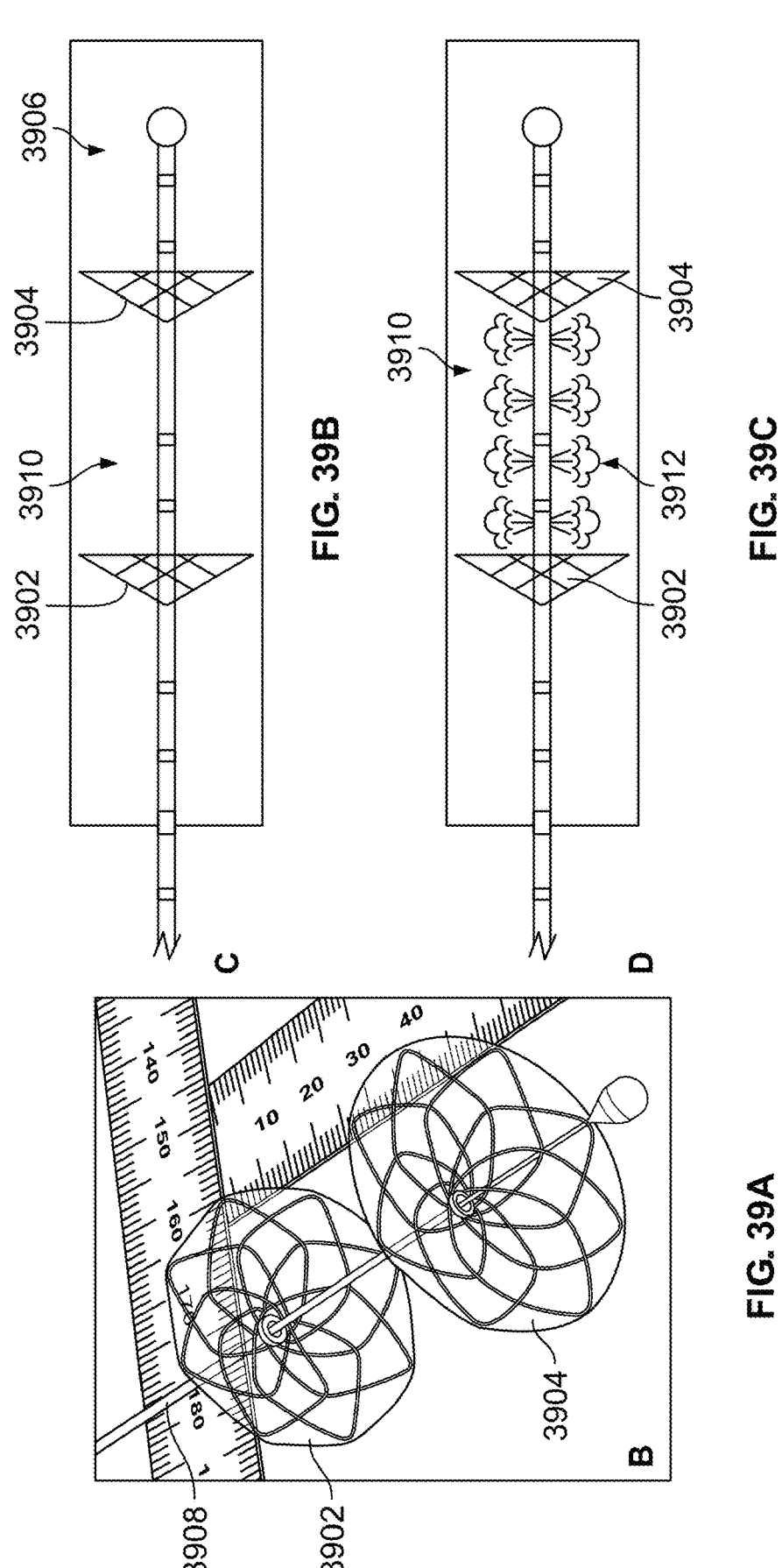
Figure 40:
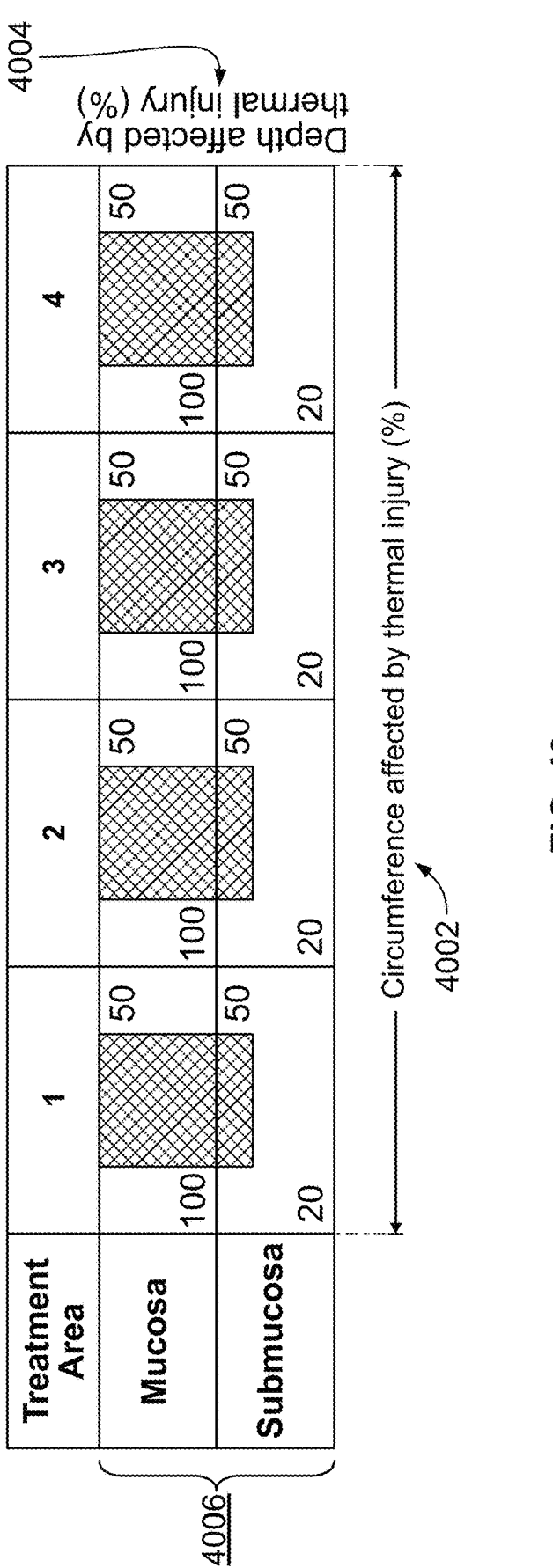
Figure 41:
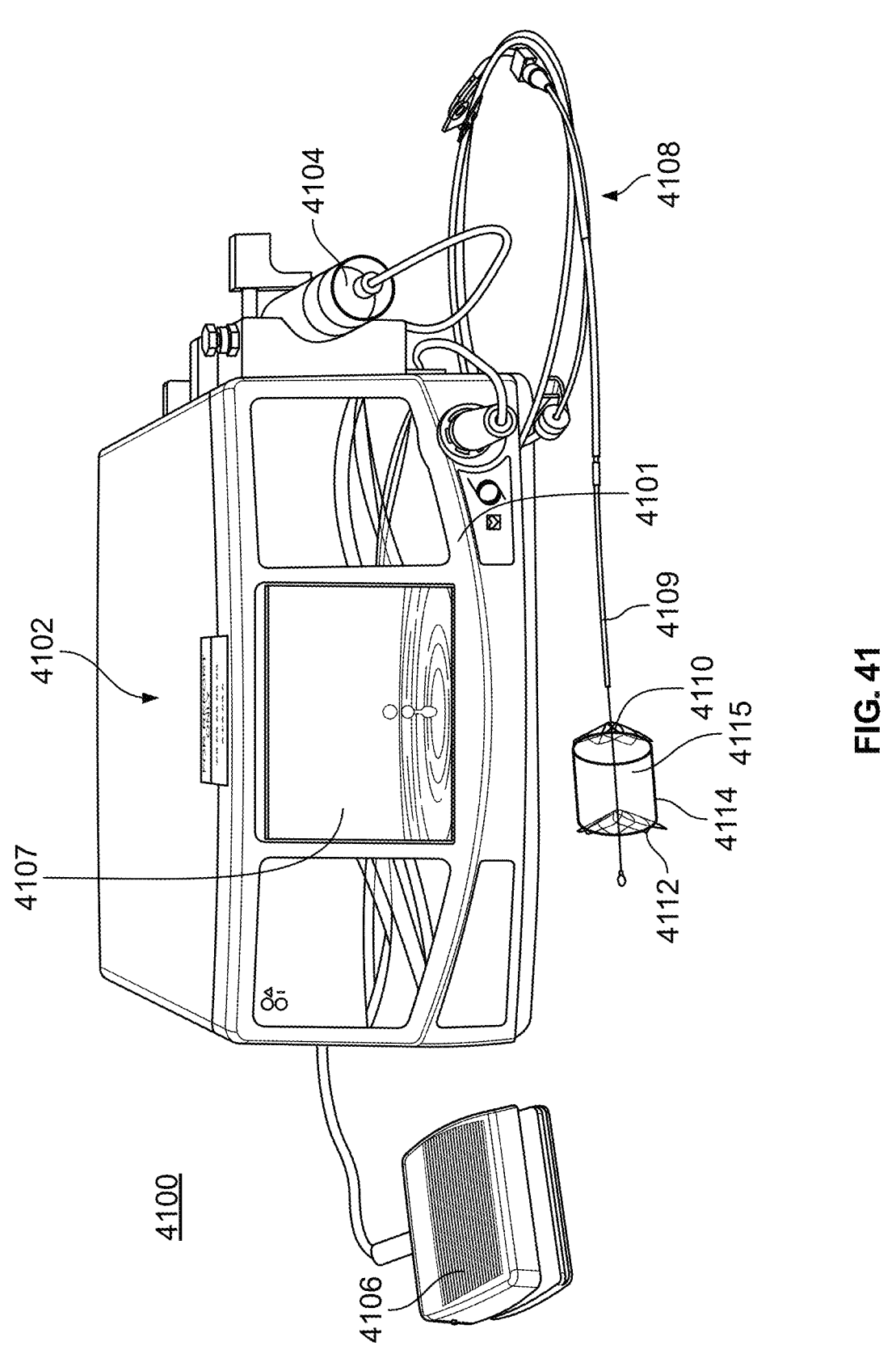
Figures 42, 43A, 43B:
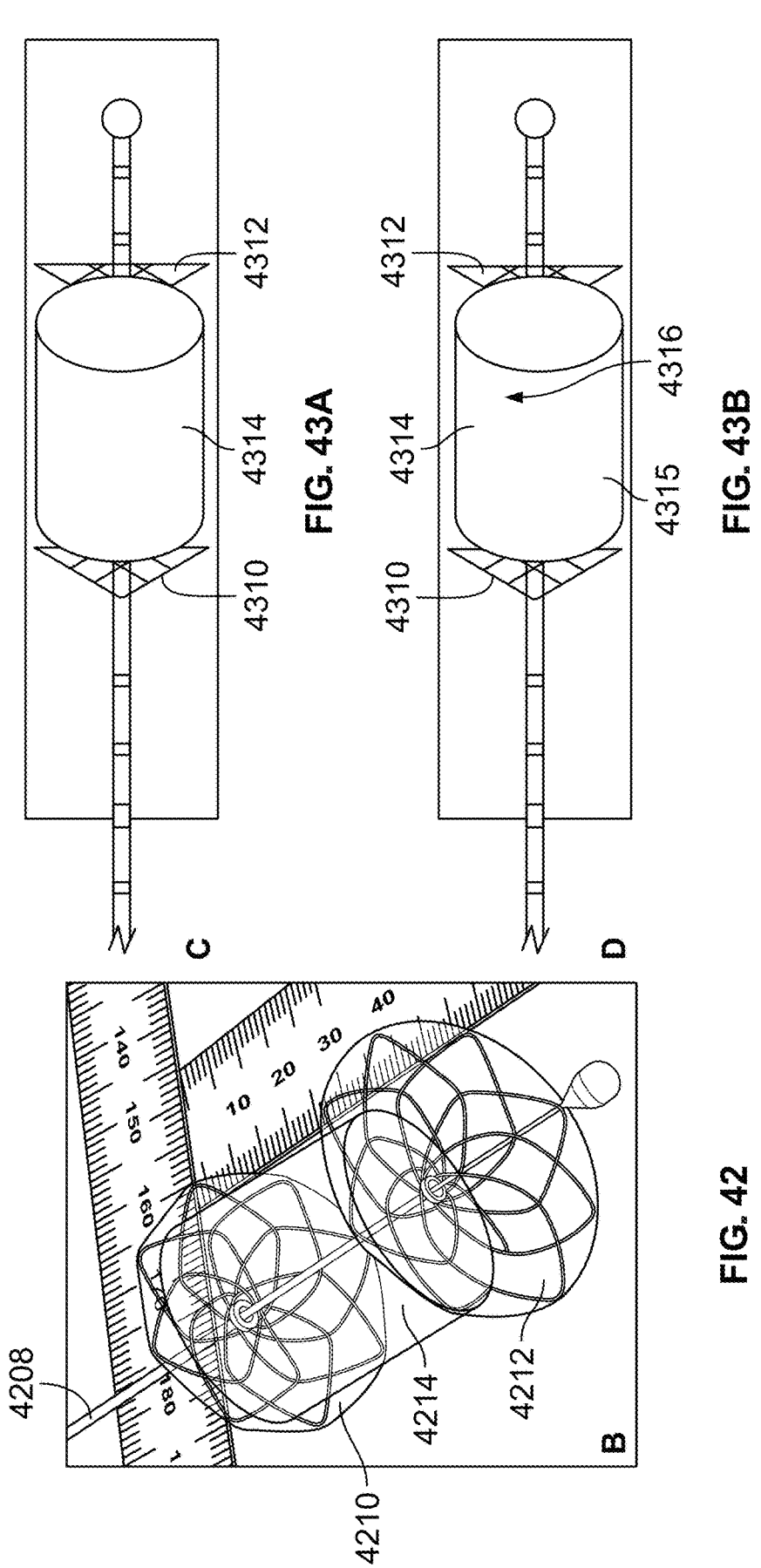
Figure 45B:
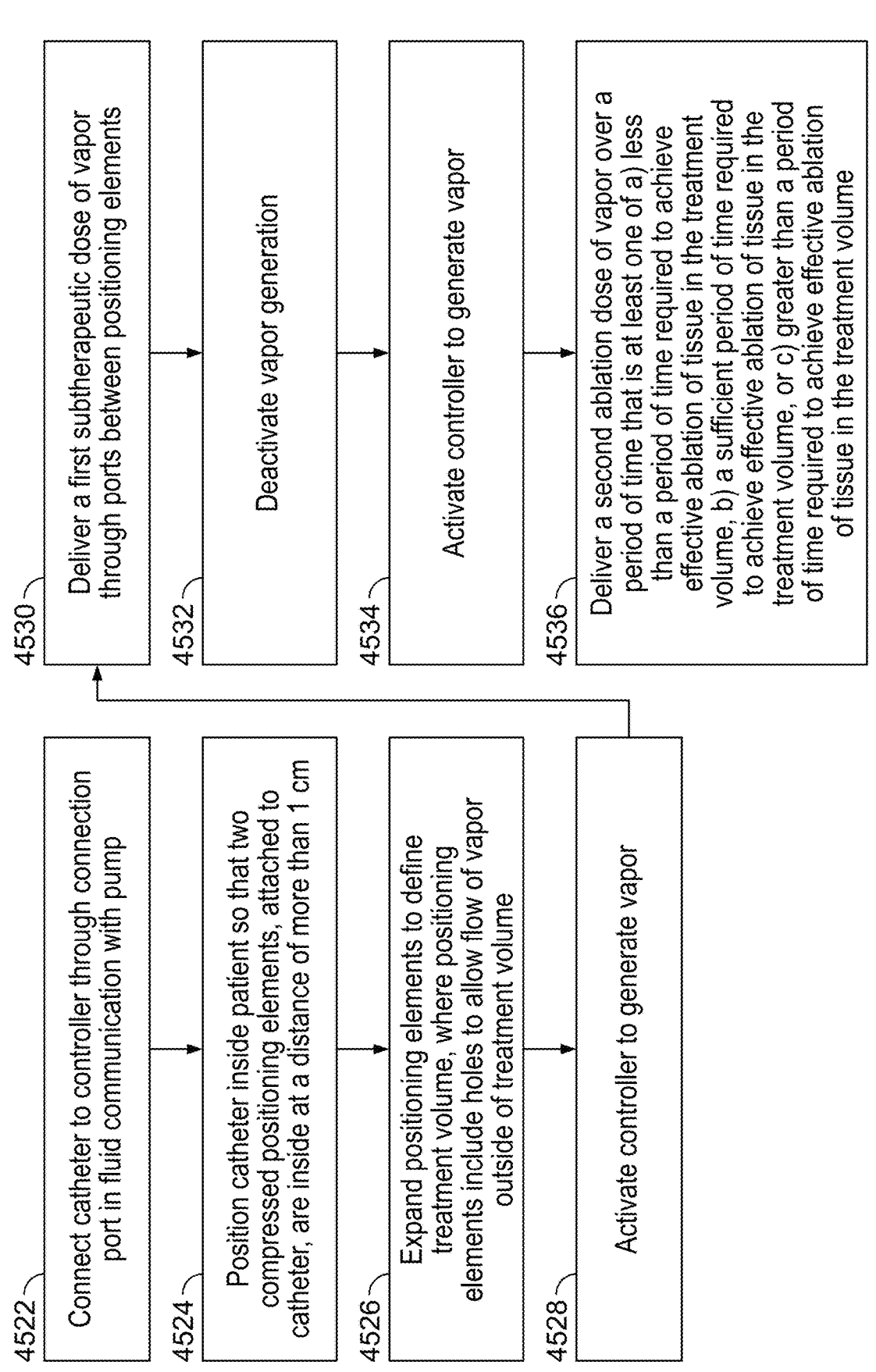
Figures 46B, 46C, 46D, 46E:
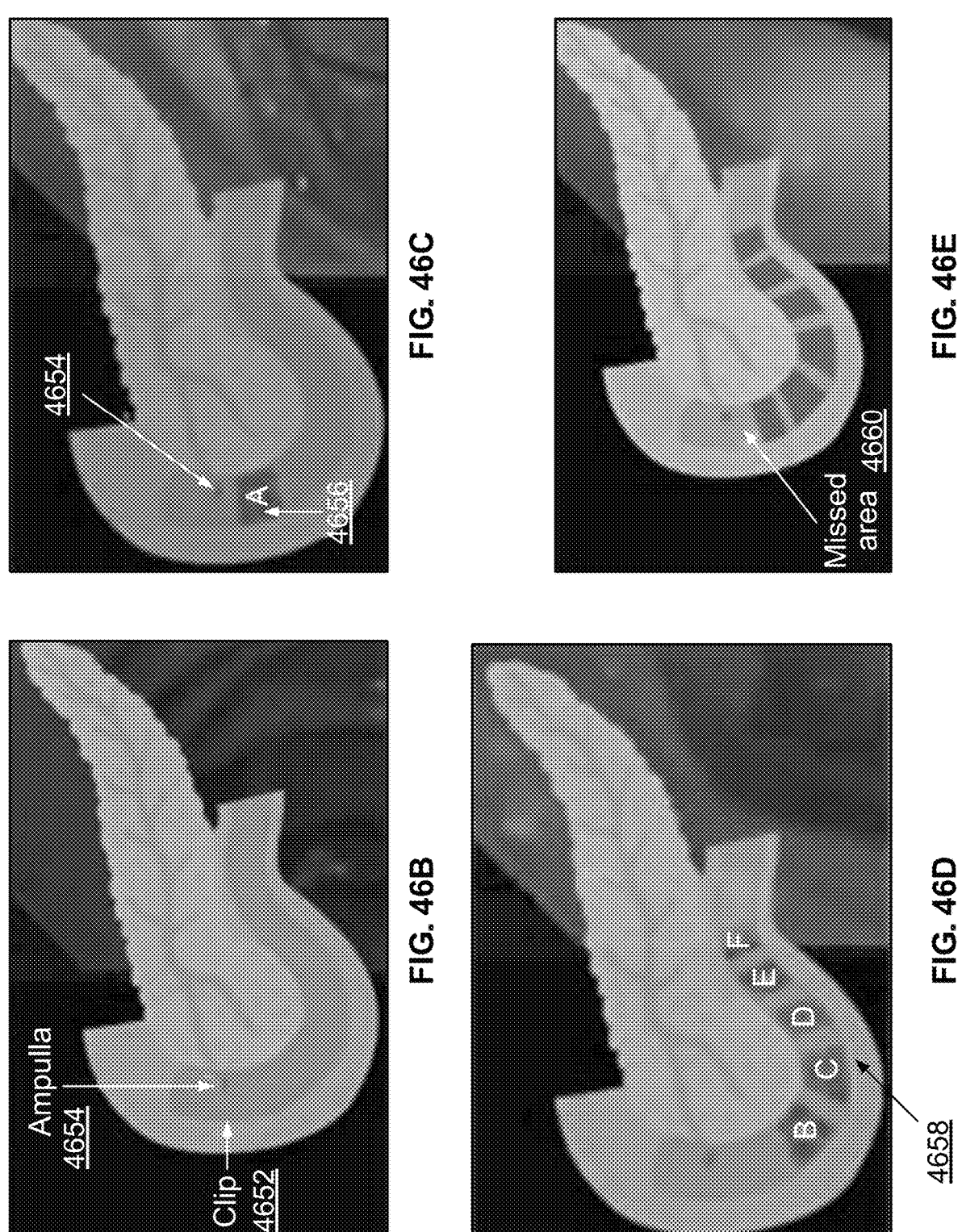
Figure 48:
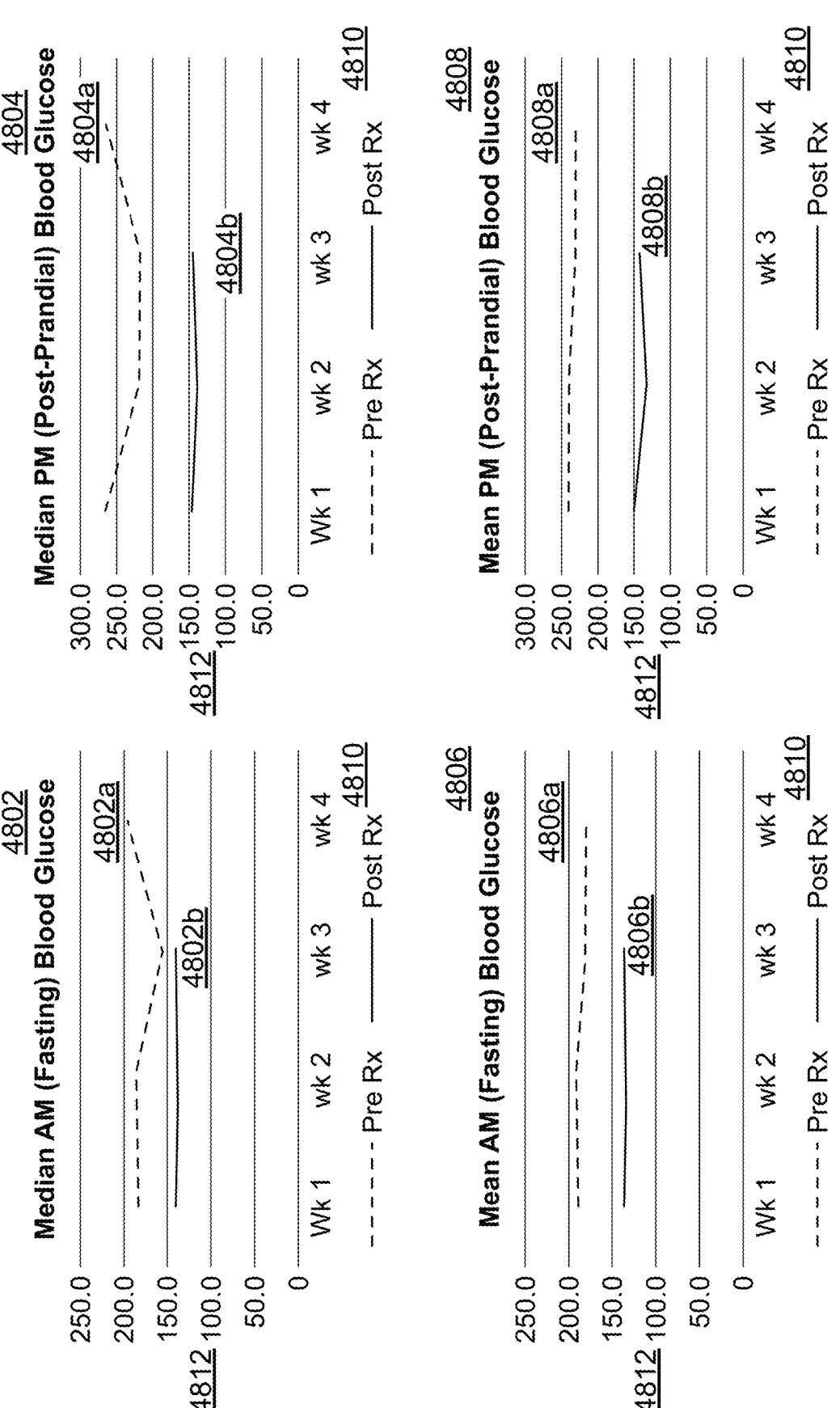
Figure 49B:
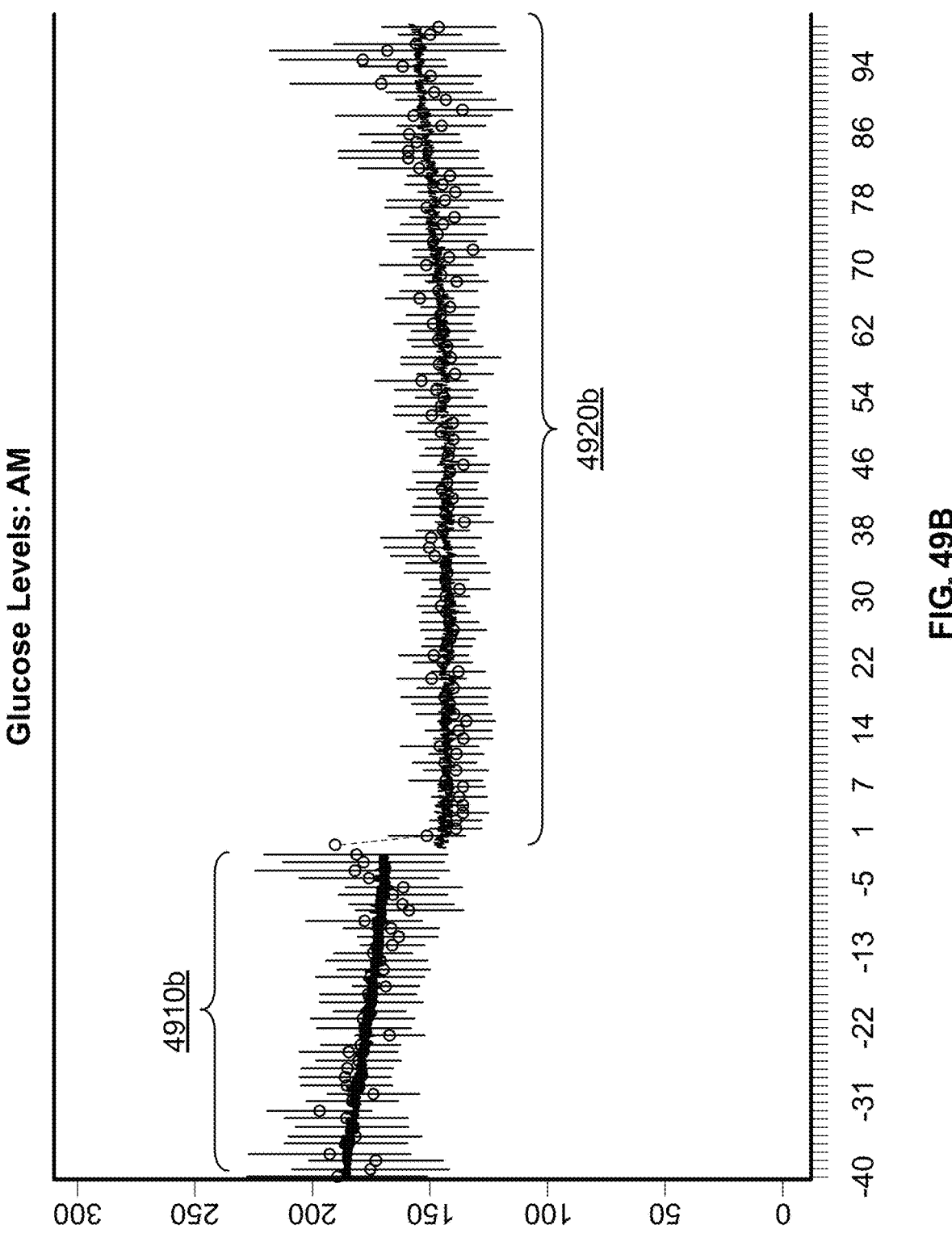
Figure 49D:
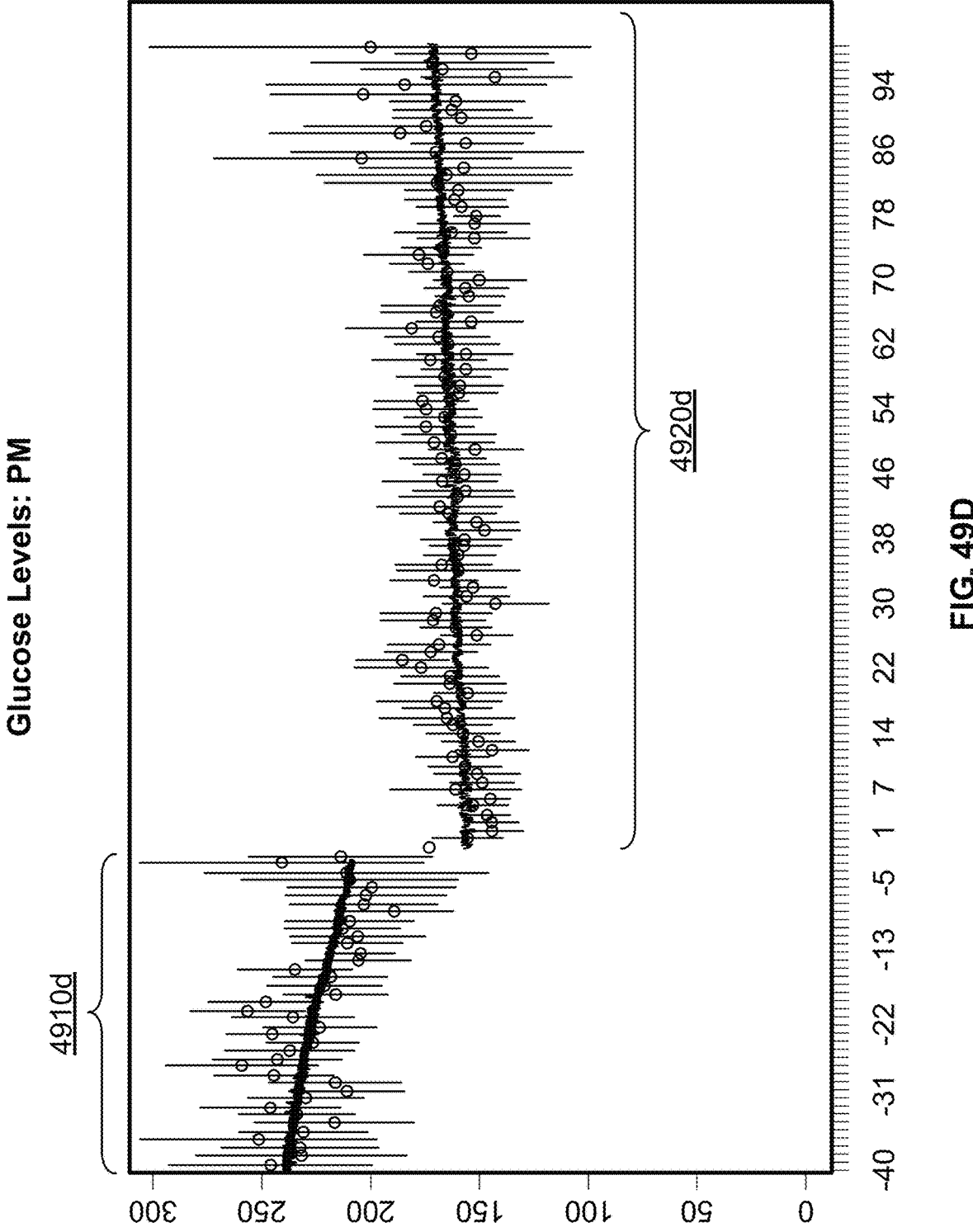
Figure 49E:
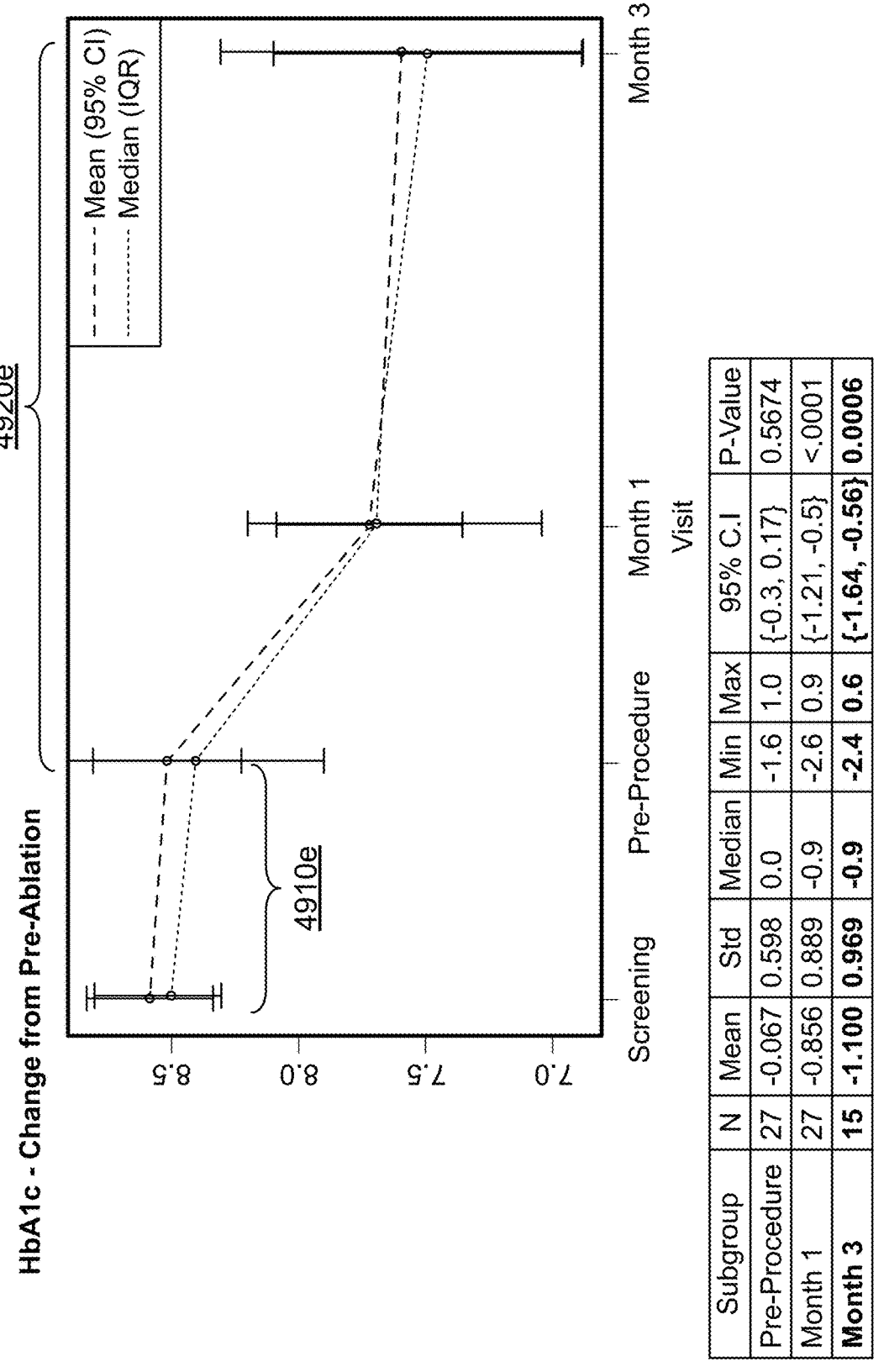
Figure 50:
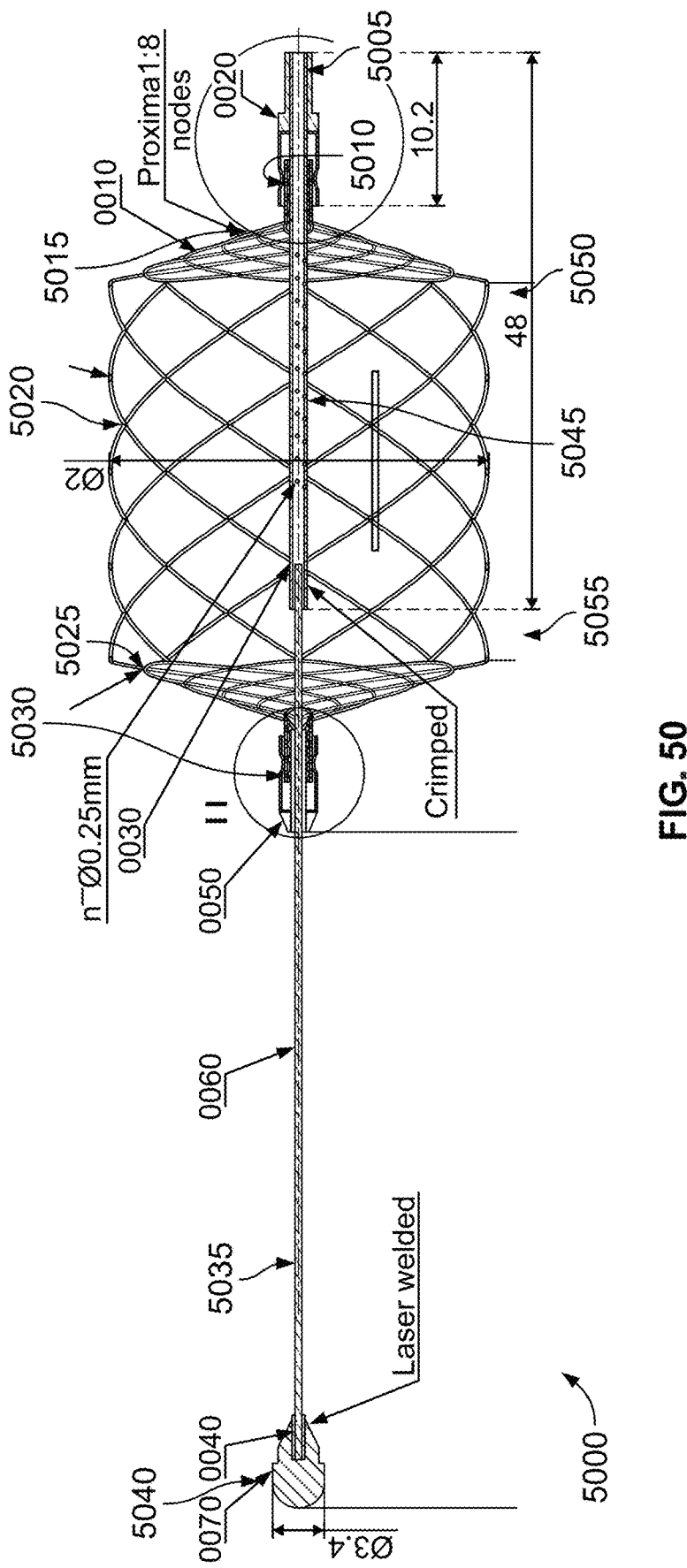

FIG. 20A is an assembled view of a vapor generator, in accordance with embodiments of the present specification;

FIG. 20B is a partial disassembled view of the vapor generator, in accordance with embodiments of the present specification;

FIG. 20C is a disassembled view of a disposable pump of the vapor generator, in accordance with embodiments of the present specification;

FIG. 20D is an assembled view of the disposable pump, in accordance with embodiments of the present specification;

FIG. 20E shows the disposable pump fluidically connected to other components of the vapor generator, in accordance with embodiments of the present specification;

FIG. 21 illustrates an ablation catheter placed in an upper gastrointestinal tract with Barrett's esophagus to selectively ablate the Barrett's tissue, in accordance with an embodiment of the present specification;

FIG. 22 is a flowchart illustrating a method of ablation of Barrett's esophagus in accordance with one embodiment of the present specification;

FIG. 23A illustrates deflated, lateral inflated, and frontal inflated views of an ablation catheter having an insulating membrane for duodenal ablation, in accordance with one embodiment of the present specification;

FIG. 23B illustrates the ablation catheter of FIG. 23A deployed in a duodenum of a patient, in accordance with one embodiment of the present specification;

FIG. 24 is a flowchart illustrating a method of ablation of a colon in accordance with one embodiment of the present specification;

FIG. 25 illustrates an upper gastrointestinal tract with a bleeding vascular lesion being treated by the ablation device, in accordance with an embodiment of the present specification;

FIG. 26 is a flowchart illustrating a method of ablation of an upper GI tract in accordance with one embodiment of the present specification;

FIG. 27A is an illustration of pancreatic ablation being performed on a pancreatic tumor in accordance with one embodiment of the present specification;

FIG. 27B is a flowchart listing the steps involved in one embodiment of a method of pancreatic ablation;

FIG. 27C is a flowchart listing the steps involved in one embodiment of a method of ablation of a pancreatic cyst;

FIG. 28 is a flowchart listing the steps involved in one embodiment of a method of tissue ablation in a bile duct;

FIG. 29A is a flowchart illustrating a method of ablation of bronchoalveolar tissue in accordance with an embodiment of the present specification;

FIG. 29B is a flowchart illustrating a method of ablation of bronchial tissue in accordance with another embodiment of the present specification;

FIG. 30A illustrates a cross-sectional view of a catheter for performing bronchial thermoplasty, in accordance with an embodiment of the present specification;

FIG. 30B illustrates a plurality of patterns of channels of a balloon of the catheter of FIG. 30A, in accordance with some embodiments of the present specification;

FIG. 30C illustrates a workflow for performing a bronchial thermoplasty procedure using the catheter of FIG. 30A, in accordance with an embodiment of the present specification;

FIG. 31A illustrates a lung volume reduction (LVR) catheter, in accordance with an embodiment of the present specification;

FIG. 31B illustrates the LVR catheter of FIG. 31A deployed through an endoscope/bronchoscope, in accordance with an embodiment of the present specification;

FIG. 31C is a workflow for performing lung volume reduction using the catheter of FIG. 31A, in accordance with an embodiment of the present specification;

FIG. 32A illustrates a needle catheter incorporating one flexible heating chamber of FIG. 1A through FIG. 1D, in accordance with an embodiment;

FIG. 32B illustrates the needle catheter of FIG. 32A incorporating two flexible heating chambers, in accordance with an embodiment;

FIG. 32C is a flowchart illustrating one embodiment of a method of ablation of a tissue using the needle catheter of FIG. 32A;

FIG. 33 is a flow chart of an exemplary process of preparing a target surface prior to an ablation treatment, in accordance with some embodiments of the present specification;

FIG. 34 is a flow chart illustrating a preparatory method used before application of vapor ablation for duodenal ablation, in accordance with some embodiments of the present specification; and FIG. 35 is another flow chart illustrating a method of using a vapor ablation system for duodenal ablation, in accordance with embodiments of the present specification;

FIG. 36A shows a temperature testing setup of a portion of a catheter with the positioning elements;

FIG. 36B shows an exemplary thermocouple map;

FIG. 36C shows exemplary temperature vs. time profiles for different electrode structures;

FIG. 36D shows a first set of exemplary temperature vs. time profiles for different protocols;

FIG. 36E shows a second set of exemplary temperature vs. time profiles for different protocols;

FIG. 37A describes an exemplary process of using an endoscope with a viewing element or a camera along with a catheter to perform ablation treatment in accordance with some embodiments of the present specification;

FIG. 37B illustrates a vapor contact zone relative to a treatment or therapeutic zone during an ablation treatment in accordance with some embodiments of the present specification;

FIG. 38A illustrates an exemplary embodiment of a vapor ablation system in accordance with some embodiments of the present specification;

FIG. 38B illustrates an exemplary embodiment of a vapor ablation system in accordance with other embodiments of the present specification;

FIG. 38C is a flow chart describing a method for using vapor ablation systems in accordance with some embodiments of the present specification;

FIG. 39A illustrates a perspective view of first positioning element and second positioning element of FIG. 38A;

FIG. 39B illustrates intraluminal positioning of distal end of catheter of FIG. 38A;

FIG. 39C illustrates generation of steam within the compartment formed between the two positioning elements of FIG. 38A;

FIG. 40 is a table illustrating histopathological evaluation of subacute ablation effect (t=48 hours) after circumferential radiofrequency ablation (C-RFA);

FIG. 41 illustrates an exemplary embodiment of a vapor ablation system in accordance with some embodiments of the present specification;

FIG. 42 illustrates a top side perspective view of a first positioning element and a second positioning element spaced along a catheter, in accordance with some embodiments of the present specification;

FIG. 43A illustrates side view of first positioning element and second positioning element in their deployed state, in accordance with some embodiments of the present specification;

FIG. 43B illustrates vapor generated during ablation, which is evenly distributed within a mesh, in accordance with embodiments of the present specification;

FIG. 44 is a flow chart illustrating an exemplary method of using vapor ablation devices of, in accordance with some embodiments of the present specification;

FIG. 45A is a flow chart illustrating an exemplary method of using vapor ablation devices, in accordance with some other embodiments of the present specification;

FIG. 45B is a flow chart illustrating an exemplary method of using vapor ablation devices, in accordance with another embodiment of the present specification;

FIG. 46A illustrates an exemplary process for duodenal ablation, in accordance with embodiments of the present specification;

FIG. 46B illustrates position of a clip positioned distal to the ampulla of Vater;

FIG. 46C illustrates a position of a first treatment volume or zone;

FIG. 46D illustrates a series of treatment zones created by repositioning the catheter and performing ablations;

FIG. 46E illustrates an area within the treatment area, which is identified to be non-ablated;

FIG. 47 is a flow chart illustrating an exemplary method of using vapor ablation devices of FIGS. 38A-39C and FIGS. 42-43B for duodenal ablation, in accordance with some embodiments of the present specification;

FIG. 48 is a set of graphs which illustrate an improvement in blood sugar levels after treatment in accordance with the embodiments of the present specification;

FIG. 49A is a graph to illustrate improvement in a patient's fasting blood glucose levels by performing ablation using any of the methods and systems described in the present specification;

FIG. 49B is another graph to illustrate improvement in a patient's fasting blood glucose levels by performing ablation using any of the methods and systems described in the present specification;

FIG. 49C is a graph to illustrate improvement in a patient's post-prandial blood glucose levels by performing ablation using any of the methods and systems described in the present specification;

FIG. 49D is another graph to illustrate improvement in a patient's post-prandial blood glucose levels by performing ablation using any of the methods and systems described in the present specification;

FIG. 49E is a graph to illustrate improvement in a patient's HbA1c levels by performing ablation using any of the methods and systems described in accordance with embodiments of the present specification; and FIG. 50 illustrated the treatment end of a catheter comprising an outer sheath that, when pulled proximally toward the clinician, unveils positioning elements and a wire mesh structure connecting the two positioning elements.

DETAILED DESCRIPTION

Embodiments of the present specification provide ablation systems and methods for treating various indications including, but not limited to, pre-cancerous or cancerous tissue in the esophagus, duodenum, bile duct, and pancreas. In various embodiments, steam, generated by heating saline, is used as an ablative agent. In various embodiments, the ablation systems include a generator for generating an ablative agent (steam generator), comprising a source for providing a fluid (saline) for conversion to a vapor (steam) and a catheter for converting and delivering said steam, wherein the catheter comprises at least one electrode embedded in a central lumen of the catheter and configured to function as a heating chamber to convert the saline to steam. The ablation systems further include an attachment at a distal end of the catheter, wherein the attachment comprises at least one of a needle, cap, hood, or disc. The attachment is configured to direct the delivery of ablative agent. The catheters may further include positioning elements to position the catheter for optimal steam delivery. The attachments and positioning elements are configured to create seals and form enclosed treatment volumes for the delivery of steam and ablation of target tissues. In embodiments, the ablation systems and methods of the present specification are configured to enclose an area or volume of tissue with at least one positioning attachment, fill that area or volume with vapor, allow the temperature in the area or volume to rise above 100° C., and then let the additional vapor escape, maintaining the temperature above 100° C. for a predetermined duration of time and the pressure in the area or volume less than 5 atm to allow the vapor to condense and ablate the tissue. The various embodiments described herein provide effective ablation methods and systems, which cause necrosis of tissue cells.

Configurations for the various catheters of the ablation systems of the embodiments of the present specification may be different based on the tissue or organ systems being treated. For example, in some embodiments, catheters for esophageal and duodenal ablation are similar, with the exception that the spacing between two positioning elements, positioned at distal and proximal ends of a distal portion of the catheter with at least one vapor delivery port between the two positioning elements, may be greater for esophageal applications (approximately 1-20 cm) than for duodenal applications (approximately 1-10 cm). Distribution and depth of ablation provided by the systems and methods of the present specification are dependent on the duration of exposure to steam, the ablation size, the temperature of the steam, the contact time with the steam, and the tissue type. In some embodiments, an outer wall of the catheter contains a cooling element, such as a cooling liquid, to limit the maximum temperature (cool) the outer surfaces of the catheter.

In some embodiments, a patient is treated in a two-step process to ensure complete or near complete ablation of a target tissue. In some embodiments, a patient is first treated with a catheter having two positioning elements-a distal positioning element that is initially deployed followed by a proximal positioning element deployed thereafter, and a tube length with at least one port positioned between the two positioning elements, thereby enabling wide area circumferential ablation. The positioning elements may be a balloon, a disc, or any other structure. A first seal is optionally created by contact of the periphery of the positioning elements with a patient's tissue at said distal and proximal positioning elements. The first seal may completely or partially seal and results in the formation of an enclosed first treatment volume, bounded by the distal positioning element at the distal end, the proximal positioning element at the proximal end, and the walls of the patient's tissue, such as the esophagus or duodenum, on the sides. Ablative energy, in the form of steam, is then delivered by the catheter via the ports into the first treatment volume, where it condenses and contacts the patient's tissue for circumferential ablation and cannot escape from the distal or proximal ends as it is blocked by the positioning elements or, alternatively, controllably escapes from the distal or proximal ends based on the configuration of the positioning elements, as further described below.

After ablation is performed using the catheter with two positioning elements, the ablation area is examined by the physician. Upon observing the patient, the physician may identify patches of tissue requiring focused ablation. A second step is then performed, wherein a second catheter with a needle or cap, hood, or disc attachment on the distal end is passed through an endoscope and used for focal ablation. The needle provides for directed, focal ablation and the cap, hood, or disc attachment encloses the focal ablation area, creating a second seal and an enclosed second treatment volume for ablation of the tissue. The seal is created by positioning at least a portion of a periphery of the cap, hood, or disc attachment in contact with a surface of a patient's tissue, such as the esophagus or duodenum, such that a portion of the patient's tissue is positioned within an area circumscribed by the attachment. In embodiments, the seal is a complete seal or a partial seal. A second treatment volume, configured to receive steam and bounded by the sides of the attachment and said circumscribed portion of patient tissue, is created when the seal is formed. Ablative energy, in the form of steam, is then delivered via the catheter by at least one port at the distal tip of the catheter into the second treatment volume, where it condenses and contacts the patient's tissue for focal ablation and cannot escape as it is bounded by the attachment or, alternatively, controllably escapes from the attachment based on the configuration of the attachment, as further described below. In one embodiment, the flow rate of vapor out of the enclosed, or partially enclosed, volume is a predefined percentage of the flow rate of vapor into the enclosed, or partially enclosed, volume from the catheter ports, where the predefined percentage is in a range of 1% to 80%, preferably less than 50%, and more preferably less than 30%. The at least one port is positioned at a distal end of the catheter such that it exits into the second treatment volume when the attachment is positioned.

During both the first and second steps, when creating the enclosed first and second treatment volumes, it is preferred to avoid creating a perfect (100%) seal. A perfect seal would trap air in the treatment volume. The trapped air would not be hot, relative to the steam used for ablation, and, therefore, would create 'cold air pockets' which act as a heat sink, sapping a portion of the thermal ablation energy of the steam and resulting in uneven distribution of the ablative energy of the steam. Creating less than a perfect seal allows for the air to be pushed out of the treatment volume, through a gap in the seal, as steam is delivered into the treatment volume.

Additionally, as the temperature in the treatment volume increases, no steam escapes until the temperature is greater than or equal to 100° C., at which point steam condensation stops and the steam is allowed to escape through the gap, preventing excessive pressurization of the treatment volume. In some embodiments, the generation of steam by heating saline is stopped by switching off the power to electrodes that generate heat until a time when a temperature of the ablation zone decreases to less than 45° C. or decreases by more than 25% from the peak temperature (such as for example, greater than or equal to 100° C.) during the ablation. In some embodiments, the catheter includes a filter with micro-pores which provides back pressure to the delivered steam, thereby pressurizing the steam as it enters the treatment volume from the catheter. The predetermined size of micro-pores in the filter determine the backpressure and hence the temperature of the steam being generated. During ablation with the attachment with two positioning elements, in various embodiments, a gap, or less than perfect seal, is positioned only at the distal positioning element, only at the proximal positioning element, or at both the distal and proximal positioning elements.

To create the gaps or less than perfect seals and allow air to leak or be pushed out of the treatment volumes, embodiments of the present specification provide positioning elements or attachments that have a range of 40% to 99% of their surface area in contact with the patient tissue. In embodiments, a surface area of a cross-sectional slice along a plane where a positioning element or attachment contacts the tissue is in a range of 20% to 99%. A low value, such as of 20%, represents an extremely porous seal, indicates that spacing exists between the positioning element or attachment and the tissue or that the positioning element or attachment includes voids therein, while a high value, such as 99%, represents a near perfect seal. Additionally, the first and second seals are considered low pressure seals, wherein pressure within the first and second treatment volumes formed by the seals is less than 5 atm and usually close to 1 atm. Therefore, as the pressure rises above a predetermined pressure level, the seal breaks and the heated air or vapor is allowed to escape, thereby obviating the need for a pressure sensor in the catheter itself.

In embodiments, one or more of the positioning elements or attachments are configured such that they permit a range of flow out of the treatment volumes enclosed by the two positioning elements or attachment. The permissible flow out is a function of steam flow into the enclosed volume, thereby acting as a relief valve and allowing for the maintenance of a desired pressure range (less than 5 atm) without regulation from the steam generator itself. In some embodiments, the positioning element or attachment comprises a plurality of spaces within the surface area of the positioning element or attachment and/or between the periphery of the positioning element or attachment and the tissue sufficient to permit a flow of fluid out of the enclosed volume in a range of 1 to 80% of the steam input flowrate to maintain the pressure level within the enclosed volume at less than 5 atm without regulation from the steam generator.

In some embodiments, the enclosed volume ranges from 3 cubic centimeters (cc) to 450 cc, when a surface area of mucosa to be ablated ranges from 5 square centimeter ($cm^2$) to 200 $cm^2$.

In embodiments, one or more of the positioning elements or attachment are deformable over the course of treatment. Positioning elements and attachments in accordance with the embodiments of the present specification are designed to physically modify or deform when a pressure in the treatment volume increases above 10% of a baseline pressure, therefore effectively acting as a pressure relief valve. As a result of the ability to deform, the flow out of the volume enclosed by the two positioning elements or attachment is variable. In an exemplary embodiment, only a small portion, if any, of flow out of the enclosed volume is blocked at the beginning of therapy. The percentage of flow that is blocked decreases over the course of the therapy, thereby increasing leakiness, due to pressure changes. In some embodiments, assuming a positioning element or attachment blocks flow out of an enclosed volume (or has the cross-sectional area covered) in a range of 100% (total flow blockage or total cross section covered) to 20% (only 20% of flow blocked or only 20% of cross sectional area covered) at the start of treatment, the percentage changes during treatment where the amount of blockage/cross sectional area is decreased by 1% to 25% relative to the starting percentage. In various embodiments, as previously stated, it is preferred that pressure sensors are not included in the catheter itself to reduce costs and possible sensor failure. Therefore, the deformable positioning elements naturally act as relief valves, without requiring active pressure sensing.

In various embodiments, the ablation devices and catheters described in the present specification are used in conjunction with any one or more of the heating systems described in U.S. patent application Ser. No. 14/594,444, entitled "Method and Apparatus for Tissue Ablation", filed on Jan. 12, 2015 and issued as U.S. Pat. No. 9,561,068 on Feb. 7, 2017, which is herein incorporated by reference in its entirety.

"Treat," "treatment," and variations thereof refer to any reduction in the extent, frequency, or severity of one or more symptoms or signs associated with a condition.

"Duration" and variations thereof refer to the time course of a prescribed treatment, from initiation to conclusion, whether the treatment is concluded because the condition is resolved or the treatment is suspended for any reason. Over the duration of treatment, a plurality of treatment periods may be prescribed during which one or more prescribed stimuli are administered to the subject.

"Period" refers to the time over which a "dose" of stimulation is administered to a subject as part of the prescribed treatment plan.

The term "effective ablation" is defined as the application of energy to tissue at a sufficient energy level so as to cause necrosis of tissue cells. A "sufficient energy level" may be achieved by modulating the temperature or thermal heat content of the vapor, by modulating the amount of time the tissue is subjected to vapor, and/or by appropriately configuring the vapor distribution and control components, such as the location of the fluid heating component within the catheter lumen, the location and relative distribution of ports along the catheter and the positioning elements.

The term "and/or" means one or all of the listed elements or a combination of any two or more of the listed elements.

In the description and claims of the application, each of the words "comprise" "include" and "have", and forms thereof, are not necessarily limited to members in a list with which the words may be associated. The terms "comprises" and variations thereof do not have a limiting meaning where these terms appear in the description and claims.

Unless otherwise specified, "a," "an," "the," "one or more," and "at least one" are used interchangeably and mean one or more than one.

The term "controller" refers to an integrated hardware and software system defined by a plurality of processing elements, such as integrated circuits, application specific integrated circuits, and/or field programmable gate arrays, in data communication with memory elements, such as random access memory or read only memory where one or more processing elements are configured to execute programmatic instructions stored in one or more memory elements.

The term "vapor generation system" refers to any or all of the heater or induction-based approaches to generating steam from water described in this application.

For any method disclosed herein that includes discrete steps, the steps may be conducted in any feasible order. And, as appropriate, any combination of two or more steps may be conducted simultaneously.

Also herein, the recitations of numerical ranges by endpoints include all numbers subsumed within that range (e.g., 1 to 5 includes 1, 1.5, 2, 2.75, 3, 3.80, 4, 5, etc.). Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present specification. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the specification are approximations, the numerical values set forth in the specific examples are reported as precisely as possible. All numerical values, however, inherently contain a range necessarily resulting from the standard deviation found in their respective testing measurements.

The devices and methods of the present specification can be used to cause controlled focal or circumferential ablation of targeted tissue to varying depth in a manner in which complete healing with re-epithelialization can occur. Additionally, the vapor could be used to treat/ablate benign and malignant tissue growths resulting in destruction, liquefaction and absorption of the ablated tissue. The dose and manner of treatment can be adjusted based on the type of tissue and the depth of ablation needed. The ablation device can be used not only for the treatment of cardiac arrhythmias, Barrett's esophagus and esophageal dysplasia, flat colon polyps, gastrointestinal bleeding lesions, endometrial ablation, pulmonary ablation, but also for the treatment of any mucosal, submucosal or circumferential lesion, such as inflammatory lesions, tumors, polyps and vascular lesions. The ablation device can also be used for the treatment of focal or circumferential mucosal or submucosal lesions of any hollow organ or hollow body passage in the body. The hollow organ can be one of gastrointestinal tract, pancreaticobiliary tract, genitourinary tract, respiratory tract or a vascular structure such as blood vessels. The ablation device can be placed endoscopically, radiologically, surgically or under direct visualization. In various embodiments, wireless endoscopes or single fiber endoscopes can be incorporated as a part of the device. In another embodiment, magnetic or stereotactic navigation can be used to navigate the catheter to the desired location. Radio-opaque or sonolucent material can be incorporated into the body of the catheter for radiological localization. Ferro- or ferromagnetic materials can be incorporated into the catheter to help with magnetic navigation.

Ablative agents such as steam, heated gas or cryogens, such as, but not limited to, liquid nitrogen are inexpensive and readily available and are directed via the infusion port onto the tissue, held at a fixed and consistent distance, targeted for ablation. This allows for uniform distribution of the ablative agent on the targeted tissue. The flow of the ablative agent is controlled by a microprocessor according to a predetermined method based on the characteristic of the tissue to be ablated, required depth of ablation, and distance of the port from the tissue. The microprocessor may use temperature, pressure or other sensing data to control the flow of the ablative agent. In addition, one or more suction ports are provided to suction the ablation agent from the vicinity of the targeted tissue. The targeted segment can be treated by a continuous infusion of the ablative agent or via cycles of infusion and removal of the ablative agent as determined and controlled by the microprocessor.

In the embodiments of the present specification, ablative fluid preferably means heated vapor but can include cryogenic fluid as well.

It should be appreciated that the devices and embodiments described herein are implemented in concert with a controller that comprises a microprocessor executing control instructions. The controller can be in the form of any computing device, including desktop, laptop, and mobile device, and can communicate control signals to the ablation devices in wired or wireless form.

The present invention is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

It should be noted herein that any feature or component described in association with a specific embodiment may be used and implemented with any other embodiment unless clearly indicated otherwise.

Figure 1A:
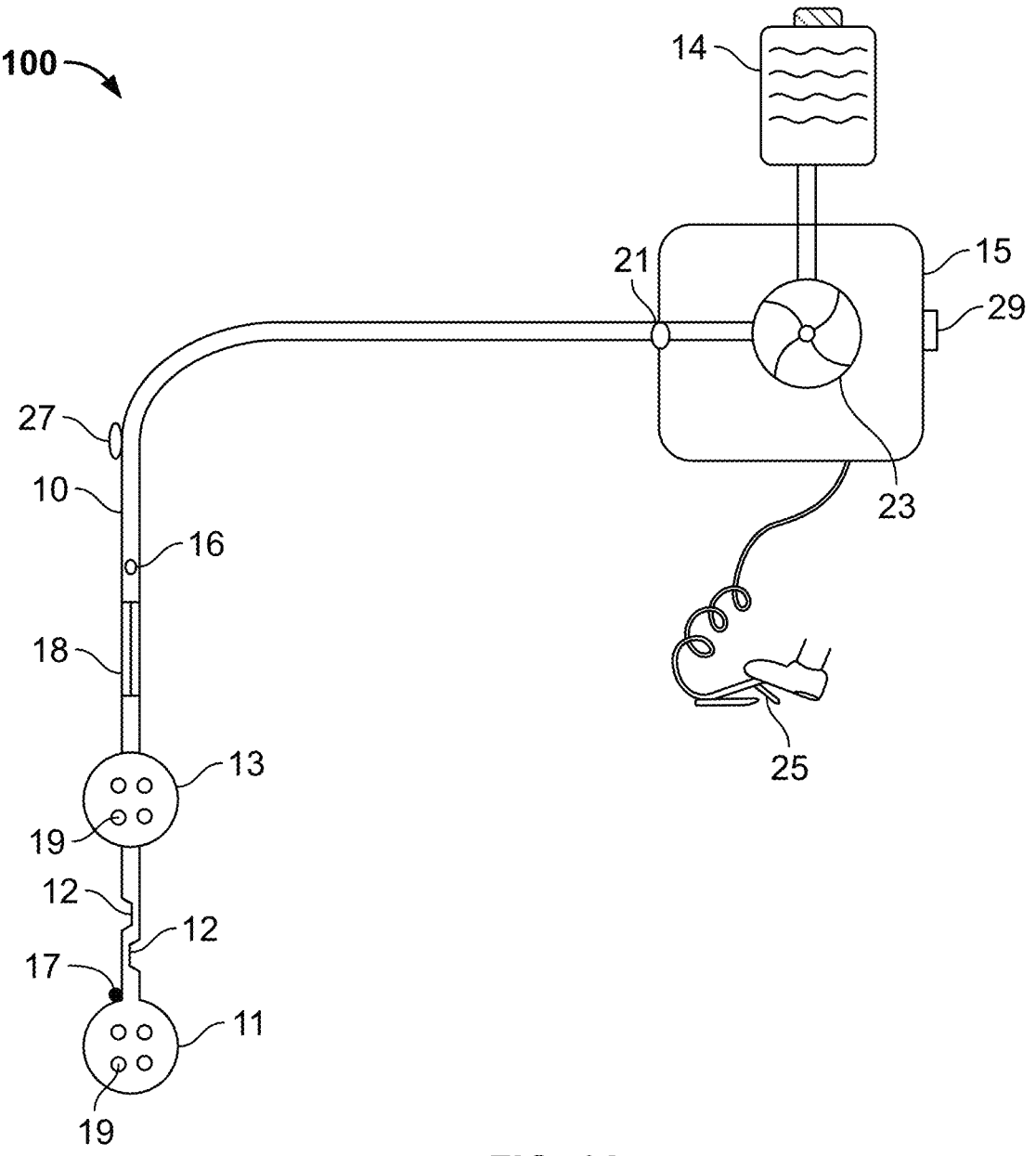
FIG. 1A illustrates an ablation system, in accordance with embodiments of the present specification.

FIG. 1A illustrates an ablation system 100, in accordance with embodiments of the present specification. The ablation system comprises a catheter 10 having at least one first distal attachment or positioning element 11 and an internal heating chamber 18, disposed within a lumen of the catheter 10 and configured to heat a fluid provided to the catheter 10 to change said fluid to a vapor for ablation therapy. In some embodiments, the catheter 10 is made of or covered with an insulated material to prevent the escape of ablative energy from the catheter body. The catheter 10 comprises one or more infusion ports 12 for the infusion of ablative agent, such as steam. In some embodiments, the one or more infusion ports 12 comprises a single infusion port at the distal end of a needle. In some embodiments, the catheter includes a second positioning element 13 proximal to the infusion ports 12. In various embodiments, the first distal attachment or positioning element 11 and second positioning element 13 may be any one of a disc, hood, cap, or inflatable balloon. In embodiments, catheter 10 shaft between first distal attachment or positioning element 11 and second positioning element 13 is flexible. Additionally, in embodiments, a section of a length ranging from 2 mm to 40 mm, proximal to second positioning element 13 (which is the proximal positioning element) is relatively more flexible than the catheter 10 shaft, to allow for positioning elements 11 and 13 to self-center within a hollow and/or tubular organ and be positioned within a tortuous anatomy. In some embodiments, the first distal attachment or positioning element 11 and second positioning element 13 include pores 19 for the escape of air or ablative agent. A fluid, such as saline, is stored in a reservoir, such as a saline pump 14, connected to the catheter 10. Delivery of the ablative agent is controlled by a controller 15 and treatment is controlled by a treating physician via the controller 15. The controller 15 includes at least one processor 23 in data communication with the saline pump 14 and a catheter connection port 21 in fluid communication with the saline pump 14. In some embodiments, at least one optional sensor 17 monitors changes in an ablation area to guide flow of ablative agent. In some embodiments, optional sensor 17 comprises at least one of a temperature sensor or pressure sensor. In some embodiments, the catheter 10 includes a filter 16 with micro-pores which provides back pressure to the delivered steam, thereby pressurizing the steam. The predetermined size of micro-pores in the filter determine the backpressure and hence the temperature of the steam being generated. In some embodiments, the system further comprises a foot pedal 25 in data communication with the controller 15, a switch 27 on the catheter 10, or a switch 29 on the controller 15, for controlling vapor flow. In some embodiments catheter 10 includes a wall longitudinally along at least a portion of its outer surface. The wall contains a cooling element, such as a cooling fluid, to limit the maximum temperature of the outer surfaces of catheter 10.

In one embodiment, a user interface included with the microprocessor 15 allows a physician to define device, organ, and condition which in turn creates default settings for temperature, cycling, volume (sounds), and standard RF settings. In one embodiment, these defaults can be further modified by the physician. The user interface also includes standard displays of all key variables, along with warnings if values exceed or go below certain levels.

The ablation device also includes safety mechanisms to prevent users from being burned while manipulating the catheter, including insulation, and optionally, cool air flush, cool water flush, and alarms/tones to indicate start and stop of treatment.

Figure 1B:
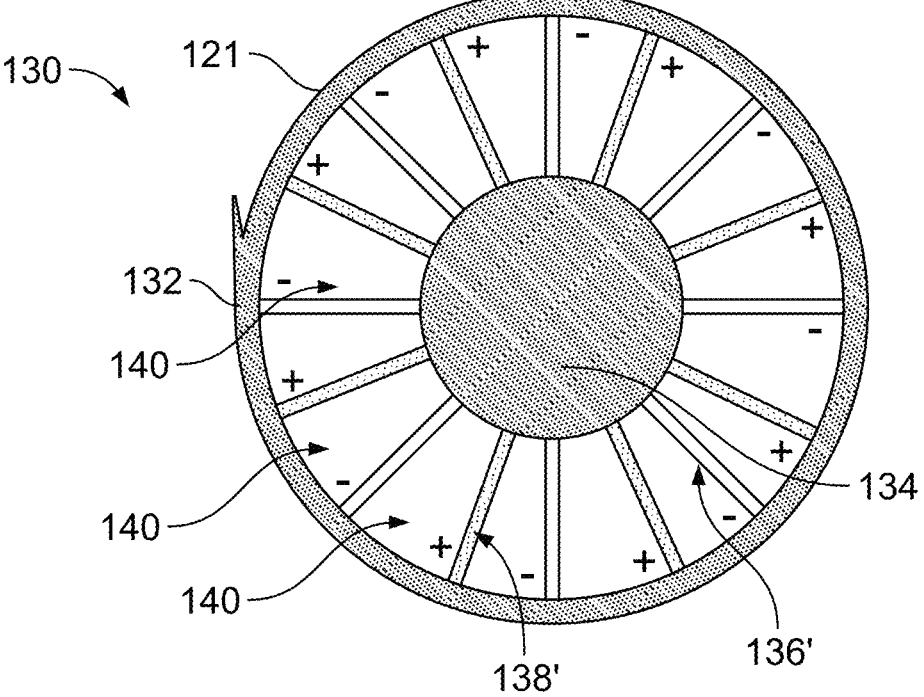
FIG. 1B is a transverse cross-section view of a flexible heating chamber, in accordance with an embodiment of the present specification.
Figure 1C:
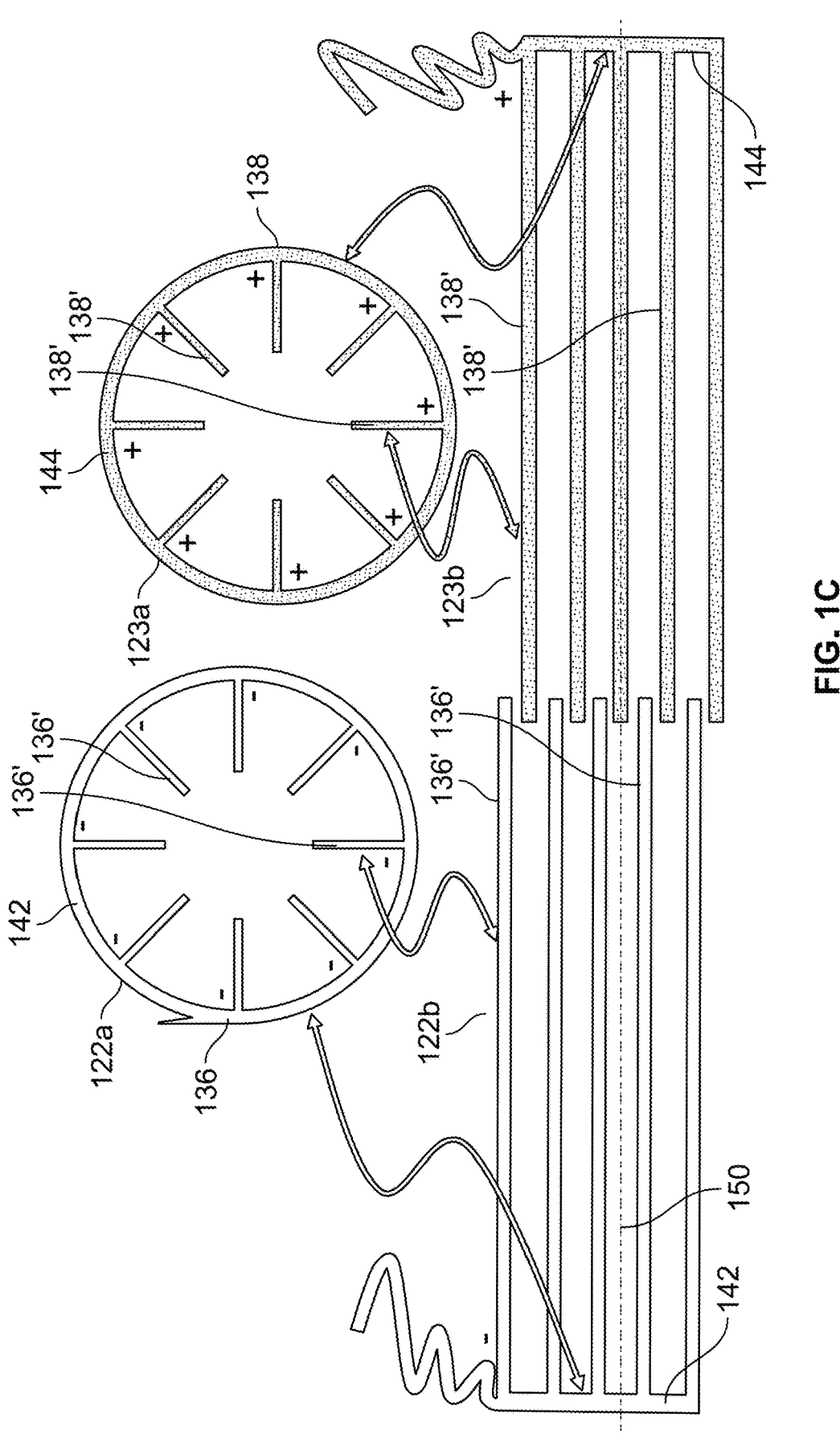
FIG. 1C illustrates transverse and longitudinal cross-section views of first and second arrays of electrodes of a flexible heating chamber, in accordance with an embodiment of the present specification.
Figure 1D:
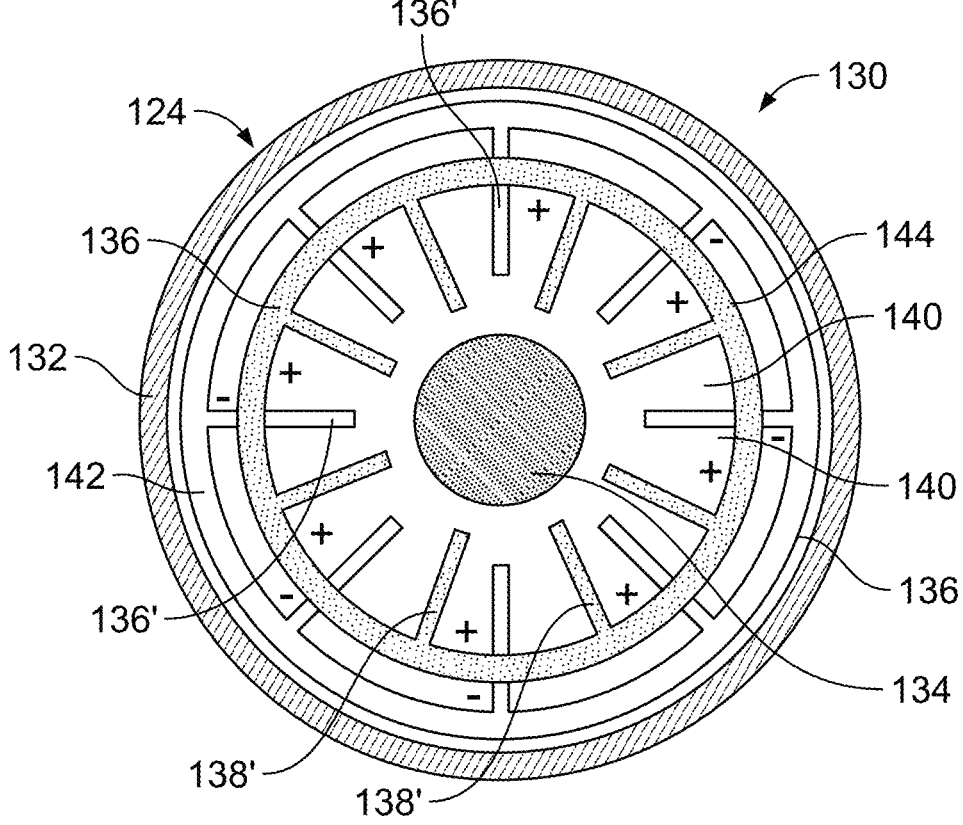
FIG. 1D is a transverse cross-section view of the heating chamber of FIG. 1B, including assembled first and second arrays of electrodes, in accordance with an embodiment of the present specification.
Figure 1E:
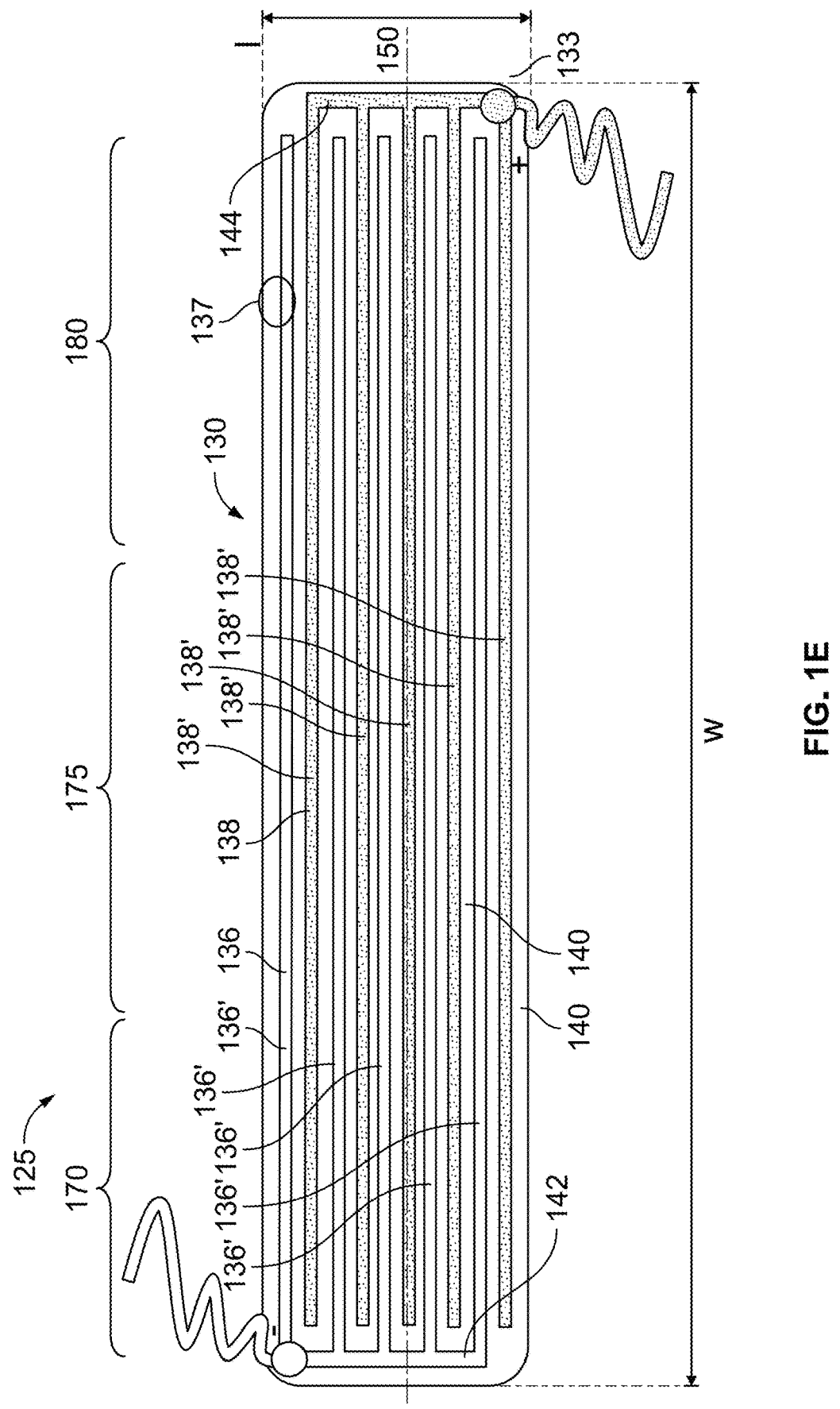
FIG. 1E is a longitudinal cross-section view of the heating chamber of FIG. 1B, including assembled first and second arrays of electrodes, in accordance with an embodiment of the present specification.
Figure 1F:
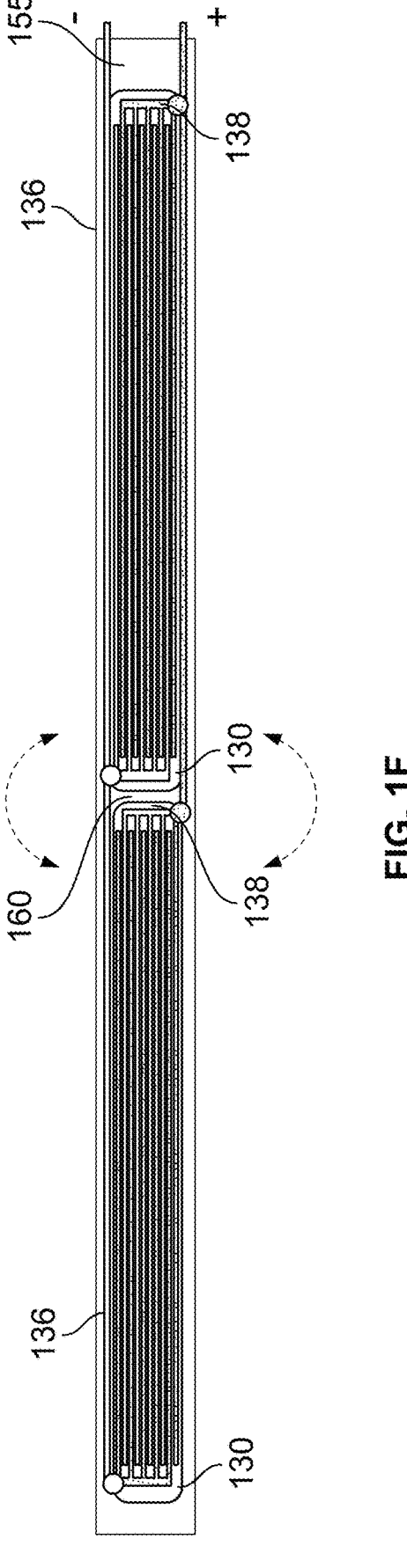
FIG. 1F is a first longitudinal view of two heating chambers of FIG. 1B arranged in series in a catheter tip, in accordance with an embodiment of the present specification.
Figure 1G:
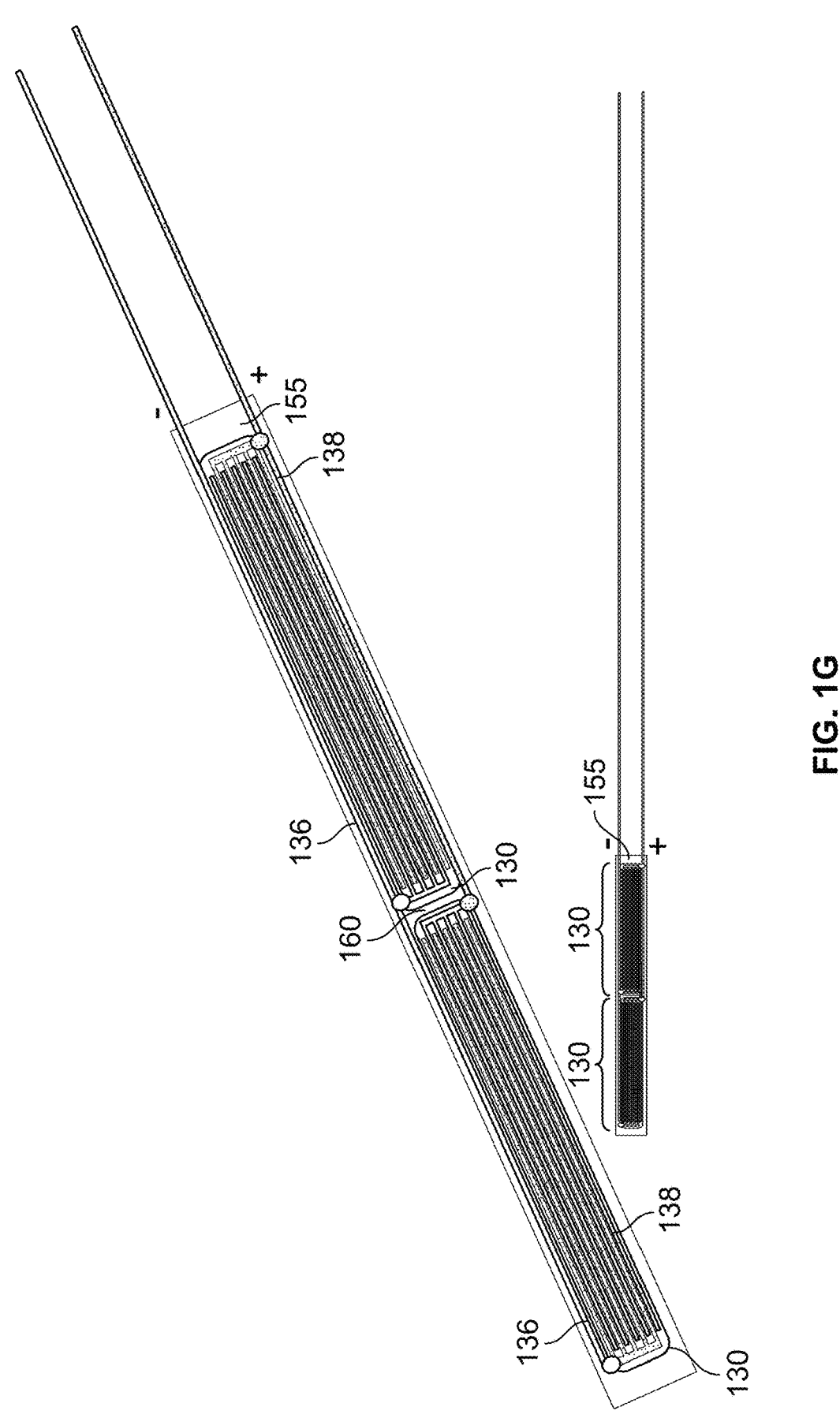
FIG. 1G is a second longitudinal view of two heating chambers of FIG. 1B arranged in series in a catheter tip, in accordance with an embodiment of the present specification.

FIG. 1B is a transverse cross-section view 121 of a flexible heating chamber 130 configured to be incorporated at or into a distal portion or tip of a catheter, in accordance with an embodiment of the present specification. FIG. 1C illustrates a transverse cross-section view 122a and a longitudinal cross-section view 122b of a first array of electrodes 136 along with a transverse cross-section view 123a and a longitudinal cross-section view 123b of a second array of electrodes 138 of a flexible heating chamber for a catheter, in accordance with an embodiment of the present specification. FIGS. 1D and 1E are, respectively, transverse and longitudinal cross-section views 124, 125 of the heating chamber 130 including assembled first and second electrodes 136, 138.

Referring now to FIGS. 1B, 1C, 1D, and 1E simultaneously, the heating chamber 130 comprises an outer covering 132 and a coaxial inner core, channel, or lumen 134. A plurality of electrodes, configured as first and second arrays of electrodes 136, 138, is disposed between the outer covering 132 and the inner lumen 134. In some embodiments, the first and second array of electrodes 136, 138 respectively comprise metal rings 142, 144 from which a plurality of electrode fins or elements 136', 138' extend radially into the space between the outer covering 132 and inner lumen 134 (see 122a, 123a). The electrode fins or elements 136', 138' also extend longitudinally along a longitudinal axis 150 of the heating chamber 130 (see 122b, 123b). In other words, each of the electrode fins 136', 138' have a first dimension along a radius of the heating chamber 130 and a second dimension along a longitudinal axis 150 of the heating chamber 130. The electrode fins or elements 136', 138' define a plurality of segmental spaces 140 there-between through which saline/water flows and is vaporized into steam. Electrical current is directed from the controller, into the catheter, through a lumen, and to the electrodes 136, 138 which causes the fins or elements 136', 138' to generate heat which is then transferred to the saline in order to convert the saline to steam. The first and second dimensions enable the electrodes 136, 138 to have increased surface area for heating the saline/water flowing in the spaces 140. In accordance with an embodiment, the first electrodes 136 have a first polarity and the second electrodes 138 have a second polarity opposite said first polarity. In an embodiment, the first polarity is negative (cathode) while the second polarity is positive (anode).

In embodiments, the outer covering 132 and the inner lumen 134 are comprised of silicone, Teflon, ceramic or any other suitable thermoplastic elastomer known to those of ordinary skill in the art. The inner lumen 134, outer covering 132, electrodes 136, 138 (including rings 142, 144 and fins or elements 136', 138') are all flexible to allow for bending of the distal portion or tip of the catheter to provide better positioning of the catheter during ablation procedures. In embodiments, the inner lumen 134 stabilizes the electrodes 136, 138 and maintains the separation or spacing 140 between the electrodes 136, 138 while the tip of the catheter flexes or bends during use.

As shown in FIGS. 1D and 1E, when the heating chamber 130 is assembled, the electrode fins or elements 136', 138' interdigitate or interlock with each other (similar to fingers of two clasped hands) such that a cathode element is followed by an anode element which in turn is followed by a cathode element that is again followed by an anode element and so on, with a space 140 separating each cathode and anode element. In various embodiments, each space 140 has a distance from a cathode element to an anode element ranging from 0.01 mm to 2 mm. In some embodiments, the first array of electrodes 136 has a range of 1 to 50 electrode fins 136', with a preferred number of 4 electrode fins 136', while the second array of electrodes 138 has a range of 1 to 50 electrode fins 138', with a preferred number of 4 electrode fins 138'. In various embodiments, the heating chamber 130 has a width w in a range of 1 to 5 mm and a length/in a range of 5 to 50 mm.

In accordance with an aspect of the present specification, multiple heating chambers 130 can be arranged in the catheter tip. Figures IF and IG are longitudinal cross-section views of a catheter tip 155 wherein two heating chambers 130 are arranged in series, in accordance with an embodiment of the present specification. Referring to Figures IF and IG, the two heating chambers 130 are arranged in series such that a space 160 between the two heating chambers 130 acts as a hinge to impart added flexibility to the catheter tip 155 to allow it to bend. The two heating chambers 130 respectively comprise interdigitated first and second arrays of electrodes 136, 138. Use of multiple, such as two, heating chambers 130 enables a further increase in the surface area of the electrodes 136, 138 while maintaining flexibility of the catheter tip 155.

Referring now to FIGS. 1B through 1G, for generating steam, fluid is delivered from a reservoir, such as a syringe, to the heating chamber 130 by a pump or any other pressurization means. In embodiments, the fluid is sterile saline or water that is delivered at a constant or variable fluid flow rate. An RF generator, connected to the heating chamber 130, provides power to the first and second arrays of electrodes 136, 138. As shown in FIG. 1E, during vapor generation, as the fluid flows through spaces 140 in the heating chamber 130 and power is applied to the electrodes 136, 138 causing the electrodes to heat, the fluid is warmed in a first proximal region 170 of the heating chamber 130. When the fluid is heated to a sufficient temperature, such as 100 degrees Centigrade at atmospheric pressure, the fluid begins to transform into a vapor or steam in a second middle region 175. All of the fluid is transformed into vapor by the time it reaches a third distal region 180, after which it can exit a distal end 133 of the heating chamber 130 and exit the catheter tip 155. If the pressure in the heating chamber is greater than atmospheric pressure, higher temperatures will be required and if it is lower than atmospheric pressure, lower temperatures will generate vapor.

In one embodiment, a sensor probe may be positioned at the distal end of the heating chambers within the catheter. During vapor generation, the sensor probe communicates a signal to the controller. The controller may use the signal to determine if the fluid has fully developed into vapor before exiting the distal end of the heating chamber. Sensing whether the saline has been fully converted into vapor may be particularly useful for many surgical applications, such as in the ablation of various tissues, where delivering high quality (low water content) steam results in more effective treatment. In some embodiments, the heating chamber includes at least one sensor 137. In various embodiments, said at least one sensor 137 comprises an impedance, temperature, pressure or flow sensor, with the pressure sensor being less preferred. In one embodiment, the electrical impedance of the electrode arrays 136, 138 can be sensed. In other embodiments, the temperature of the fluid, temperature of the electrode arrays, fluid flow rate, pressure, or similar parameters can be sensed. In embodiments, the sensor is also used to determine a change in temperature when the power supplied to the electrode or electrode arrays is switched off. The power may be switched off when the temperature of vapor for ablation has reached the required level and either immediately, or after a predefined period of time, the temperature needs to be reduced to a level of 45° C. or at least to a level below more than 25% from the maximum temperature level.

Figure 1H:
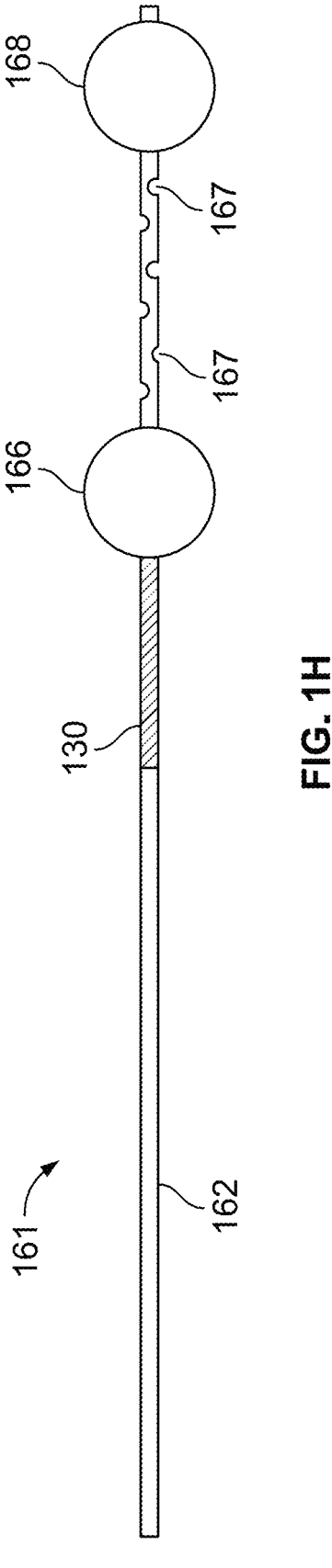
FIG. 1H illustrates a multiple lumen balloon catheter incorporating one heating chamber of FIG. 1B, in accordance with an embodiment of the present specification.
Figure 1I:
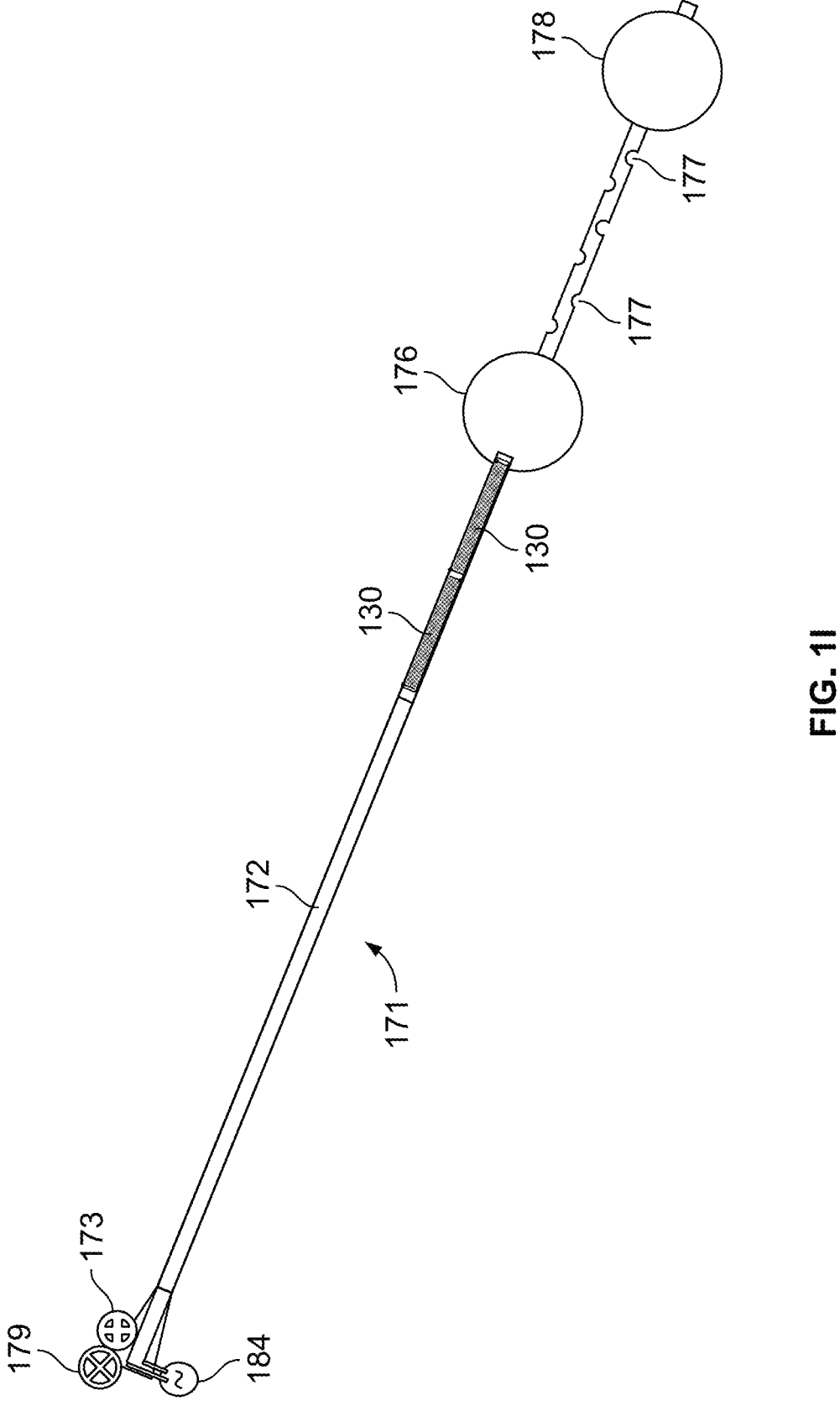
FIG. 1I illustrates a multiple lumen balloon catheter incorporating two heating chambers of FIG. 1B, in accordance with an embodiment of the present specification.

FIG. 1H and FIG. 1I illustrate multiple lumen balloon catheters 161 and 171 respectively, in accordance with embodiments of the present specification. The catheters 161, 171 each include an elongate body 162, 172 with a proximal end and a distal end. The catheters 161, 171 include at least one positioning element proximate their distal ends. In various embodiments, the positioning element is a balloon. In some embodiments, the catheters include more than one positioning element. In some embodiments, a section of the catheters 161, 171 that is proximal to the proximal positioning element is more flexible than the remainder of the catheter shaft. The flexible section may extend for 2 mm to 40 mm, in different embodiments. The flexible section allows for the positioning elements to self-center with the tubular organ and be positioned within tortuous anatomy.

In the embodiments depicted in FIGS. 1H and 1I, the catheters 161, 171 each include a proximal balloon 166, 176 and a distal balloon 168, 178 positioned proximate the distal end of the body 162, 172 with one or more infusion ports 167, 177 located on the body 162, 172 between the two balloons 166, 176, and 168, 178. In some embodiments, there may be a single infusion port 167, 177. In embodiments, the catheter shaft extending between the two balloons 166/176 and 168/178 is flexible. The body 162, 172 also includes at least one heating chamber 130 proximate and just proximal to the proximal balloon 166, 176. The embodiment of FIG. 1H illustrates one heating chamber 130 included in the body 165 proximate and just proximal to the proximal balloon 166. In some embodiments, multiple heating chambers are arranged in series in the body of the catheter.

In the embodiment of FIG. 1I, two heating chambers 130 are arranged in the body 172 proximate and just proximal to the proximal balloon 176. Referring to FIG. 1I, for inflating the balloons 176, 178 and providing electrical current and liquid to the catheter 171, a fluid pump 179, an air pump 173 and an RF generator 184 are coupled to the proximal end of the body 172. The air pump 173 pumps air via a first port through a first lumen (extending along a length of the body 172) to inflate the balloons 176, 178 so that the catheter 171 is held in position for an ablation treatment. In another embodiment, the catheter 171 includes an additional air port and an additional air lumen so that the balloons 176, 178 may be inflated individually. In some embodiments, balloon positioning elements 166/176, 168/178 are inflated with air or water. Water or any other fluid may be used to inflate the balloons. Volume of the fluid used for inflation determines the maximum diameter of the inflated balloon(s). The fluid pump 179 pumps the fluid through a second lumen (extending along the length of the body 172) to the heating chambers 130. The RF generator 184 supplies electrical current to the electrodes 136, 138 (FIGS. 1G, 1H), causing the electrodes 136, 138 to generate heat and thereby converting the fluid flowing through the heating chambers 130 into vapor. The generated vapor flows through the second lumen and exits the ports 177. The flexible heating chambers 130 impart improved flexibility and maneuverability to the catheters 161, 171, allowing a physician to better position the catheters 161, 171 when performing ablation procedures, such as ablating Barrett's esophagus tissue in an esophagus of a patient.

FIG. 1J is a flow chart of a plurality of steps of using the catheters 161, 171 of FIG. 1H or 1I to perform ablation of Barrett's esophagus tissue in an esophagus of a patient, in accordance with embodiments of the present specification. At step 185, insert the catheter 161, 171 into an esophagus of a patient. At step 186, position the distal balloon 168, 178 distal to a portion of Barrett's esophagus and the proximal balloon 166, 176 proximal to a portion of Barrett's esophagus such that infusion ports 167, 177 are positioned in said portion of Barrett's esophagus. At step 187, inflate the balloons 166, 176 and 168, 178 using an air or fluid pump to position the catheter 161, 171 in the esophagus. At step 188, provide fluid, such as water or saline, to the catheter 161, 171 via a fluid pump. Finally, at step 189, provide electrical current to electrodes 136, 138 using an RF generator to heat the electrodes and convert the fluid to vapor, wherein the generated vapor is delivered through the infusion ports 167, 177 to ablate the Barrett's esophagus tissue of the patient.

Figure 1K:
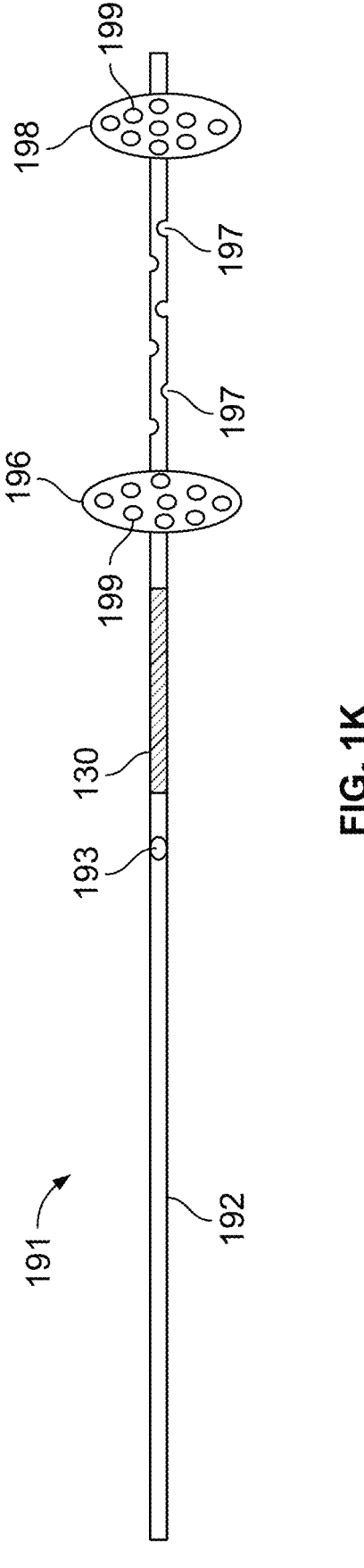
FIG. 1K illustrates a catheter with proximal and distal positioning elements and an electrode heating chamber, in accordance with embodiments of the present specification.

FIG. 1K illustrates a catheter 191 with proximal and distal positioning elements 196, 198 and an electrode heating chamber 130, in accordance with embodiments of the present specification. The catheter 191 includes an elongate body 192 with a proximal end and a distal end. The catheter 191 includes a proximal positioning element 196 and a distal positioning element 198 positioned proximate the distal end of the body 192 with one or more of infusion ports 197 located on the body 192 between the two positioning elements 196, 198. The body 192 also includes at least one heating chamber 130 within a central lumen. In some embodiments, the proximal positioning element 196 and distal positioning element 198 comprises compressible discs which expand on deployment. In some embodiments, the proximal positioning element 196 and distal positioning element 198 are comprised of a shape memory metal and are transformable from a first, compressed configuration for delivery through a lumen of an endoscope and a second, expanded configuration for treatment. In embodiments, the discs include a plurality of pores 199 to allow for the escape of air at the start of an ablation procedure and for the escape of steam once the pressure and/or temperature within an enclosed treatment volume created between the two positioning elements 196, 198 reaches a predefined limit, as described above. In some embodiments, the catheter 191 includes a filter 193 with micro-pores which provides back pressure to the delivered steam, thereby pressurizing the steam. The predetermined size of micro-pores in the filter determine the backpressure and hence the temperature of the steam being generated.

It should be appreciated that the filter 193 may be any structure that permits the flow of vapor out of a port and restricts the flow of vapor back into, or upstream within, the catheter. Preferably, the filter is a thin porous metal or plastic structure, positioned in the catheter lumen and proximate one or more ports. Alternatively, a one-way valve may be used which permits vapor to flow out of a port but not back into the catheter. In one embodiment, this structure 193, which may be a filter, valve or porous structure, is positioned within 5 cm of a port, preferably in a range of 0.1 cm to 5 cm from a port, and more preferably within less than 1 cm from the port, which is defined as the actual opening through which vapor may flow out of the catheter and into the patient.

Figures 1L, 1M:
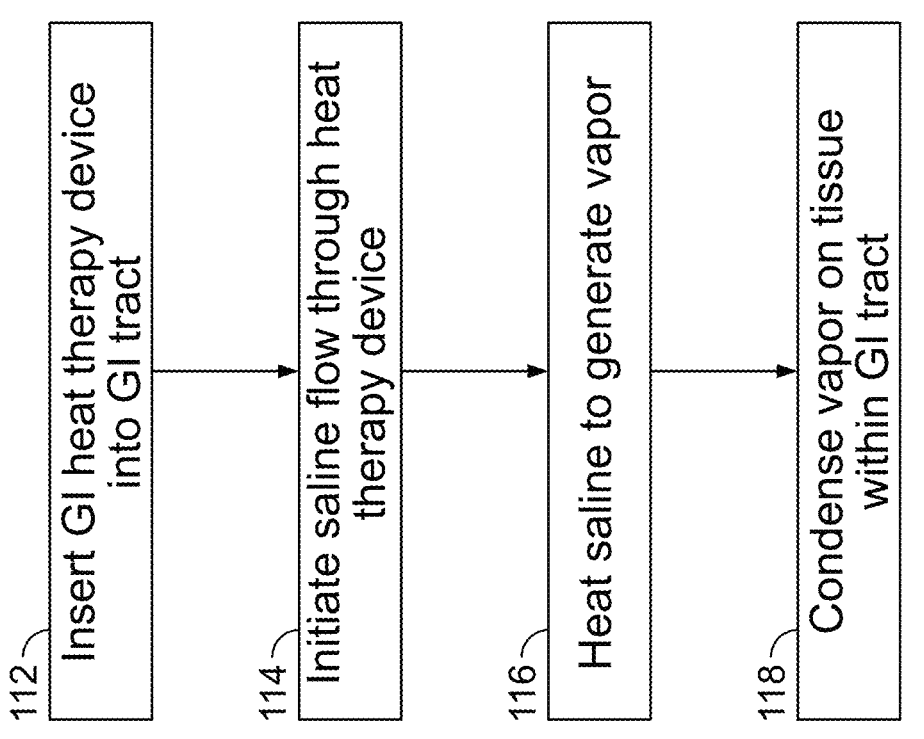
FIG. 1L is a flow chart illustrating a method of ablating a tissue inside a gastrointestinal tract of a patient, in accordance with some embodiments of the present specification.
FIG. 1M is a flow chart illustrating a method of ablating a tissue inside a gastrointestinal tract of a patient, in accordance with other embodiments of the present specification.

FIG. 1L is a flow chart illustrating a method of ablating a tissue inside a gastrointestinal tract of a patient, in accordance with some embodiments of the present specification. In embodiments, the method of FIG. 1L illustrates circumferential vapor ablation that is followed by a focused vapor ablation after observing the patient, to treat a pre-cancerous tissue, cancerous tissue, or otherwise unwanted tissue in the esophagus, duodenum, bile duct, or pancreas. In embodiments, ablation catheters disclosed in the present specification, such as ablation catheter 191 of FIG. 1K, are used to perform the ablation method of FIG. 1L.

At 102, an ablation catheter configured for the gastrointestinal (GI) tract is inserted into the GI tract of the patient. At 104, a seal is created between an exterior surface of the ablation catheter and an interior wall of the GI tract, forming a treatment volume. The seal is created by the expansion of one or more positioning elements of the ablation catheter, as explained in the embodiments of the present specification. In some embodiments, the seal is temperature dependent and it breaks or becomes porous when the temperature or pressure within the scaled portion or treatment volume exceeds a threshold value. In one embodiment, the specific temperature is 90° C. In some embodiments, the seal is pressure dependent and it begins to leak when the pressure within the sealed portion or treatment volume exceeds a specific pressure. In one embodiment, the specific pressure is 5 atm. At 106, vapor is delivered through the ablation catheter into the scaled portion within the GI tract, while the seal is still in place. At 108, the vapor condenses on the tissue under treatment, thereby ablating the tissue.

FIG. 1M is a flow chart illustrating a method of ablating a tissue inside a gastrointestinal tract of a patient, in accordance with other embodiments of the present specification. In embodiments, the method of FIG. 1M illustrates circumferential vapor ablation that is followed by focused vapor ablation after observing the patient, to treat a pre-cancerous tissue, cancerous tissue, or otherwise unwanted tissue in the esophagus, duodenum, bile duct, or pancreas. In embodiments, ablation catheters disclosed in the present specification, such as ablation catheter 191 of FIG. 1K, are used to perform the ablation method of FIG. 1M. At 112, an ablation catheter configured for the gastrointestinal (GI) tract is inserted into the GI tract of the patient. At 114, saline with a variable flow rate is introduced through the ablation catheter into the GI tract. At 116, the saline is heated using RF energy to generate vapor through the ablation catheter into the GI tract. In embodiments, the rate of flow of the saline during vapor delivery is different from flow of the saline during the phase where no therapy is delivered. In some embodiments, the rate of flow of saline during the therapy is lower than that during no therapy. In some embodiments, the rate of flow of saline during the therapy is lower than that during no therapy. At 118, the vapor condenses on the tissue under treatment, thereby ablating the tissue.

Exemplary Treatment-Gastrointestinal System

FIG. 1N is a flow chart illustrating a method for treating a gastrointestinal condition in a patient using a vapor ablation system, in accordance with embodiments of the present specification. In various embodiments, the condition may include, but is not limited to, obesity, excess weight, eating disorders, metabolic syndrome, and diabetes, fatty liver, non-alcoholic fatty liver disease (NAFLD), or non-alcoholic steatohepatitis (NASH). The vapor ablation system comprises a controller having at least one processor in data communication with at least one pump and a catheter connection port in fluid communication with the at least one pump. At step 101, a proximal end of a first catheter is connected to the catheter connection port to place the first catheter in fluid communication with the at least one pump. The first catheter comprises at least two positioning elements separated along a length of the catheter and at least one port positioned between the at least two positioning elements, wherein each of the at least two positioning elements has a first configuration and a second configuration, and wherein, in the first configuration, each of the at least two positioning elements is compressed within the catheter and in the second configuration, each of the at least two positioning elements is expanded to be at least partially outside the catheter. At step 103, the first catheter is positioned inside a patient such that, upon being expanded into the second configuration, a distal one of the at least two positioning elements is positioned within in the patient's small intestine and a proximal one of the at least two positioning elements is proximally positioned more than 1 cm from the distal one of the at least two positioning elements. Then, at step 105 each of the at least two positioning elements is expanded into their second configurations. At step 107, the controller is activated, wherein, upon activation, the controller is configured to cause the at least one pump to deliver saline into at least one lumen in the first catheter and, wherein, upon activation, the controller is configured to cause an electrical current to be delivered to at least one electrode positioned within the at least one lumen of the first catheter. The electrical current causes the electrode to heat and contact of the saline with the heating electrode converts the saline to steam which is delivered via the at least one port to ablate gastrointestinal tissue. In various embodiments, each treatment dose delivered to the gastrointestinal tract comprises the following parameters: 1-15 cm of contiguous or non-contiguous small intestine mucosa is treated; at least 50% of a circumference of a small intestine is treated; energy in a range of 5-25 J/cm$^2$; delivery period of 1-60 seconds; delivery rate of 5-2,500 cal/sec; total dose of 5-40 cal/gm of tissue to be ablated; target tissue temperature between 60° C. and 110° C.; vapor temperature between 99° C. and 110° C.; and pressure in the gastrointestinal tract less than 5 atm, and preferably less than 1 atm.

At step 109, the controller shuts off the delivery of saline and electrical current after a time period ranging from 1 to 60 seconds. In embodiments, the controller automatically shuts off the delivery of saline and electrical current. The controller is repeatedly activated at step 111 to deliver saline into the lumen and electrical current to the at least one electrode until the physician terminates the procedure. In some embodiments, the system further comprises a foot pedal in data communication with the controller, a switch on the catheter, or a switch on the controller, for controlling vapor flow and step 111 is achieved using the foot pedal in data communication with the controller, a switch on the catheter, or a switch on the controller. The first catheter is removed from the patient at step 113.

The physician then waits for at least at least six weeks at step 115 before evaluating the efficacy of treatment. In some embodiments, the physician waits a time frame ranging from six weeks to two years before evaluating efficacy of treatment. An efficacy of the treatment is determined at step 117 by measuring at least one physiological parameter relating to the gastrointestinal disorder, as disclosed in the present specification, and comparing the measured parameter to a desired therapeutic endpoint. If the therapeutic endpoint has been achieved, treatment is complete at step 129. If the therapeutic endpoint has not been achieved, ablation therapy is repeated at step 119.

It should be appreciated that, while the above discussion is directed to duodenal ablation, any ablation catheter or system of the present specification, used to ablate tissue in an organ, may be used with a controller, wherein the controller is configured to limit a pressure generated by ablation fluid, such as steam/vapor, within the organ to less than 5 atm or 100 psi. In various embodiments, the organ may be a pancreatic cyst, esophagus, duodenum/small bowel, uterine cavity, prostate, bronchus or alveolar space.

As the temperature in the treatment volume increases, no steam escapes until the temperature is greater than or equal to 100° C., at which point steam condensation stops and the steam is allowed to escape through a gap, preventing excessive pressurization of the treatment volume. In some embodiments, the catheter includes a filter with micro-pores which provides back pressure to the delivered steam, thereby pressurizing the steam as it enters the treatment volume from the catheter. The predetermined size of micro-pores in the filter determine the backpressure and hence the temperature of the steam being generated. During ablation with the attachment with two positioning elements, in various embodiments, a gap, or less than perfect seal, is positioned only at the distal positioning element, only at the proximal positioning element, or at both the distal and proximal positioning elements.

To create the gaps or less than perfect seals and allow air to leak or be pushed out of the treatment volumes, embodiments of the present specification provide positioning elements or attachments that have a range of 40% to 99% of their surface area in contact with the patient tissue. In embodiments, a surface area of a cross-sectional slice along a plane where a positioning element or attachment contacts the tissue is in a range of 20% to 99%. A low value, such as of 20%, represents an extremely porous seal, indicates that spacing exists between the positioning element or attachment and the tissue or that the positioning element or attachment includes voids therein, while a high value, such as 99%, represents a near perfect seal. Additionally, the first and second seals are considered low pressure seals, wherein pressure within the first and second treatment volumes formed by the seals is less than 5 atm and usually close to 1 atm. Therefore, as the pressure rises above a predetermined pressure level, the seal breaks and the heated air or vapor is allowed to escape, thereby obviating the need for a pressure sensor in the catheter itself.

In embodiments, one or more of the positioning elements or attachments are configured such that they permit a range of flow out of the treatment volumes enclosed by the two positioning elements or attachment. The permissible flow out is a function of steam flow into the enclosed volume, thereby acting as a relief valve and allowing for the maintenance of a desired pressure range (less than 5 atm) without regulation from the steam generator itself. In some embodiments, the positioning element or attachment comprises a plurality of spaces within the surface area of the positioning element or attachment and/or between the periphery of the positioning element or attachment and the tissue sufficient to permit a flow of fluid out of the enclosed volume in a range of 1 to 80% of the steam input flowrate to maintain the pressure level within the enclosed volume at less than 5 atm without regulation from the steam generator.

In some embodiments, the enclosed volume ranges from 3 cubic centimeters (cc) to 450 cc, when a surface area of mucosa to be ablated ranges from 5 square centimeter (cm²) to 200 cm².

Figure 1O:
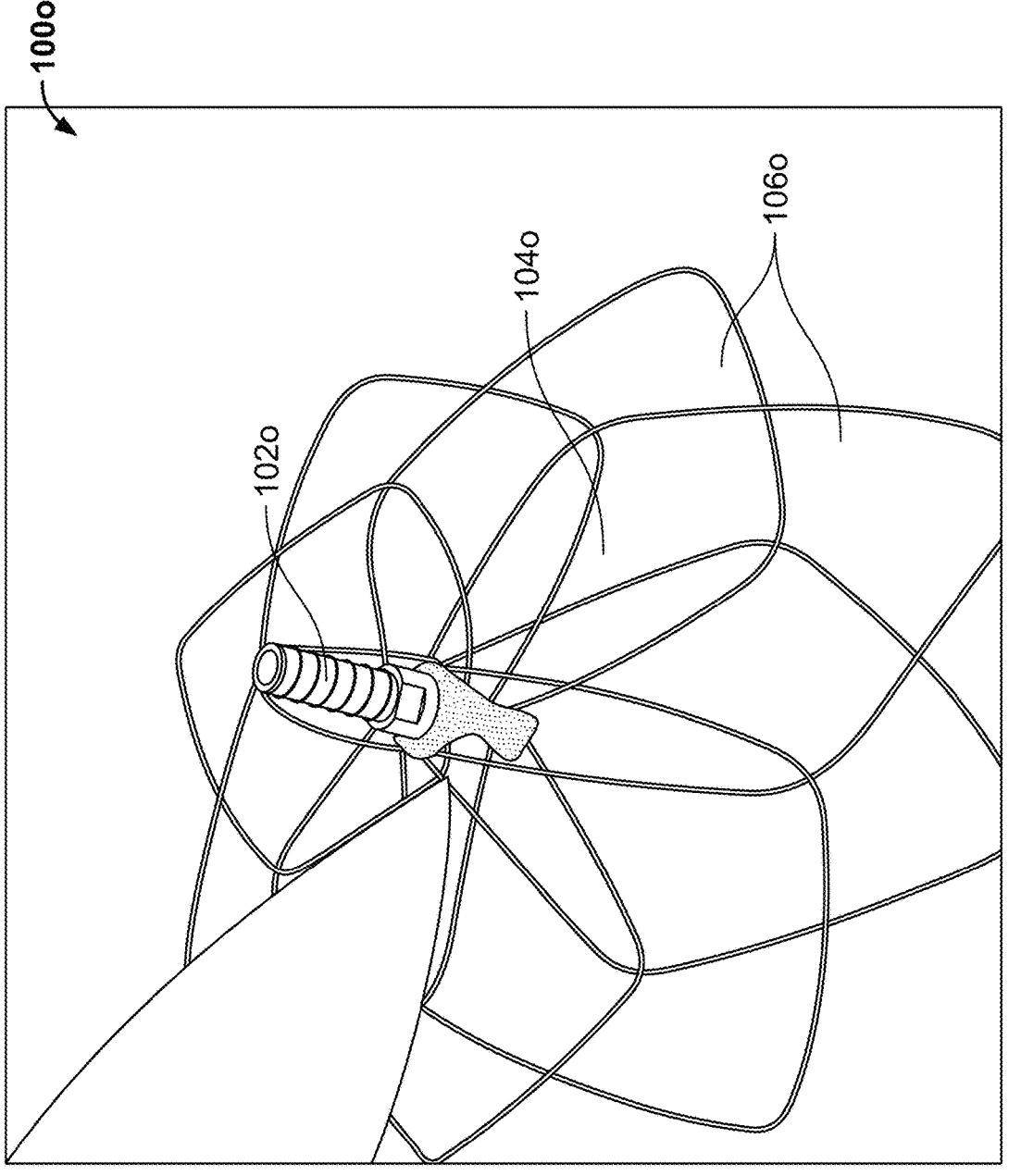
FIG. 1O illustrates an embodiment of a configuration of a positioning element that provides a partial seal, in accordance with an embodiment of the present specification.

FIG. 1O illustrates an embodiment of a configuration of a positioning element 1000 that provides a partial seal, in accordance with an embodiment of the present specification. The configuration comprises a substantially cylindrical proximal portion 1020, a substantially conical middle portion 1040 and a substantially conical base with a zig-zag edge in distal portion 1060. The substantially zig-zag shaped distal portion 1060 is attached as a base to the substantially conical middle portion 1040. In an alternate embodiment, the entire positioning element 1000 is in a substantially hollow conical shape, with the circular base of the cone configured with a zig-zag shaped edge.

In some embodiments, the substantially cylindrical proximal portion 1020 is attached, such as by using glue, to a distal tip of a catheter. In the configuration of positioning element 1000, the substantially cylindrical proximal portion 1020 has a diameter of 2 mm and a length of 7 mm, the substantially conical middle portion 1040 has a length of 20-35 mm (+/−2 mm) and a vertex or opening angle of 150 degrees, while the substantially zig-zag shaped distal portion 1060 has a circular base having a diameter of 30-40 mm (+/−2 mm). The total length of the middle and distal portions 1040, 1060 is 20-35 mm (+/−2 mm). Though FIG. 1O depicts a positioning element having conical or circular shapes, in other embodiments, the positioning element or attachments may have other three dimensional polygonal or curved shapes.

In various embodiments, the positioning element 1000 is mechanically compressed for passage into an endoscope channel or an outer catheter and expands when deployed or protruded.

In some embodiments, positioning element 1000 comprises a shape memory alloy, such as Nitinol, thereby allowing it to transform from a compressed configuration for delivery through an endoscope to an expanded configuration for treatment. In some embodiments, the compressed configuration approximates a cylindrical shape, to enable passing through the lumen of an endoscope, attached to the distal end of the catheter. On expansion, the conical base with zig-zag-shaped edge of positioning element 1000 has a surface area from which the steam exits. On expansion, the length shortens somewhat so the expanded configuration would have a shorter length than the compressed configuration. In an embodiment, use of an ablation catheter with positioning element 1000 creates a partial seal. The recesses of zig-zag shaped edge of the conical base distal portion 1060 provides a path for the steam to escape from a seal that is formed by the protrusions of the same edge.

In embodiments comprising more than one positioning element, each positioning element, similar to positioning element 1000, is partially porous and/or configured to not fully circumferentially contact the duodenum tissue to thereby allow vapor to escape. The positioning elements are configured to enable an amount of vapor escaping to be in a range of 0.1% to 50%, preferably 0.1% to 25%, and more preferably 1% to 20% or any increment in the aforementioned ranges, of the gas volume of the vapor emitted from the infusion ports in the treatment area. Further, the number of ports is in a range of 1 to 250 extending across a length of the catheter between the two positioning elements positioned over a length ranging from 1 to 20 cm. In some embodiments, a length between positioning elements is 3.6 cm. In some embodiments, a length between positioning elements is 2.5 cm. The number and axial distribution of the ports are important to enable the uniform distribution of vapor within the treatment area. In some embodiments, the ports comprise holes. In embodiments, the holes are drilled or laser drilled. In some embodiment, the ports comprise slots. In embodiments, the slots are cut in different directions, both axially and/or radially. In some embodiments, the ports comprise both holes and slots. In various embodiments, the size or diameter of the ports varies along the axis of the catheter to promote uniform distribution of steam. In some embodiments, the ports closest to the distal positioning element are larger than the holes closest to the proximal positioning element. The different sizing ensures steam is distributed toward the distal end uniformly.

Optionally, to further improve the uniformity of effective ablation, a wire mesh structure extends between the two positioning elements such that, upon expansion, the wire mesh structure forms a stent that substantially envelopes the catheter ports and keeps the tissue to be ablated at a predefined distance from each of the ports throughout the treatment area. In embodiments, the wire mesh expands to a predetermined diameter. In embodiments, the predetermined diameter ranges from 10 mm to 40 mm. Furthermore, the expanded wire mesh structure functions to center the ports, and therefore the vapor distribution, within the treatment area, equidistant from the circumferentially surrounding tissue.

Referring to FIG. 50, the treatment end 5000 of the catheter comprises an outer sheath that, when pulled proximally toward the clinician, unveils the positioning elements 5025, 5015 and wire mesh structure 5020 connecting the two positioning elements 5025, 5015. When positioned within the outer sheath, the positioning elements 5025, 5015 and connecting wire mesh structure 5020 are substantially pressed against the catheter body in a linear configuration. When expanded, the two positioning elements 5025, 5015 form wire discs or cones and the wire mesh structure 5020 is attached to the distal and proximal positioning element 5025, 5015 at various points along their respective outer peripheries.

A first wire or first member positioned within the catheter lumen 5005 is fixedly attached to a proximal end 5010 of the proximal positioning element 5015. Passing through or attached to the first wire or member 5005 is a second wire or member 5035 that is fixedly attached to a distal assembly 5030 of the distal positioning element 5025. The distal assembly 5030 is configured to slide relative to the second wire or member 5035 as it is moved proximally or distally. The relative movement of the distal assembly 5030 over the second wire 5035 helps move the distal positioning element 5025 relative to the proximal positioning element 5015 thereby expanding the wire mesh structure 5020 away from the central lumen where ports 5045 are located and toward a tissue surface. The ability of the distal positioning element 5025 to slide over the second wire 5035 allows the mesh to collapse and for the positioning elements to have a lower profile (smaller diameter). The mesh structure does not fold over the top of itself if the distal positioning element can slide along a rail wire. In other embodiments, the distal positioning element is fixed and does not slide and the wire mesh folds over itself, which increases the collapse diameter. The expanded diameter of wire mesh structure 5020 is in a range of 5 mm to 50 mm, and preferably within a range of 20-30 mm, and further preferably of approximately 25 mm. As shown in FIG. 50, the resulting expanded structure forms a substantially cylindrical or elliptical volume around the centrally positioned catheter body, serving to push tissue away from ports 5045 and center ports 5045 within the treatment volume. In some embodiments, a length of the cylindrical volume, extending between positioning elements 5015 and 5025 is in a range of 5 mm to 50 mm, and preferably within a range of 20-30 mm, and further preferably of approximately 25 mm. Preferably the circumference of the wire mesh structure measured at any point along its length is equal to 70 to 100% of the circumference of either positioning element. In certain embodiments, the shape of the wire mesh structure is conical, pyramidal or spherical.

FIG. 50 illustrates a deployed configuration of positioning elements 5025, 5015 and wire mesh structure 5020. To achieve a collapsed (initial) configuration, outer sheath of the catheter is pushed distally, away from the clinician, over first wire or member 5005, so that second wire or member 5035 that is fixedly attached to a distal assembly 5030 of the distal positioning element 5025 is approached by the outer sheath. Proximal end 5050 of wire mesh structure 5020 is attached to proximal positioning element 5015, while distal end 5055 of wire mesh structure 5020 is not fixed, such that pushing of the outer sheath results over first wire or member 5005 and positioning element 5015 results in a sliding movement of the distal end 5055 of wire mesh structure 5020 along a "rail". Allowing the distal end 5055 to slide along the rail enables wire mesh structure 5020 to collapse within the outer sheath of the catheter. If distal end 5055 was fixed, the wires of wire mesh structure 5020 would have to fold over themselves to collapse into first wire or member 5005, which would result in a larger profile and larger compression forces. In embodiments, the collapsed profile of wire mesh structure 5020 is as small as possible to fit within the internal diameter of the outer sheath that, in one embodiment, has an outer diameter of approximately 10.5 F. In embodiments, the outer diameter ranges from 5 F to 25 F.

Configurations of ports 5045 and positioning elements 5025, 5015 and, optionally, the wire mesh tissue control mechanism enabled by deployment of wire mesh structure 5020, a substantially uniform ablation is achieved in the treatment area for each ablation session. The treatment region may be defined by a plurality of sequentially positioned annular rings where each annular ring of the plurality of sequentially positioned annular rings comprises tissue. Each annular ring has an axial length, which may range from 0.05 to 2 mm, an average inner circumference and an average outer circumference where the difference between the average inner circumference and the average outer circumference defines an average thickness of the annular ring.

Uniformity of ablation within the treatment area is a function of an extent of effective ablation measured in three dimensions: first, in terms of contiguity of effective ablation across sequentially positioned annular rings defining the treatment region; second, in terms of contiguity over the internal surface area of each of the annular rings, where the internal surface area is defined by the average inner circumference and the axial length; and third, in terms of an amount of the thickness or variance of the thickness that is ablated.

In one embodiment, the positioning elements, ports, and vapor administration protocol, as collectively described above, are configured to achieve:

1. An effective ablation of at least 50%, preferably at least 60%, preferably at least 70%, and more preferably at least 80%, and up to 100% of the internal surface area of a given annular ring to yield an effectively ablated annular ring;

2. A consecutive sequence of effectively ablated annular rings where the internal surface areas of the consecutive sequence of effectively ablated annular rings comprise at least 50%, preferably at least 60%, preferably at least 70%, more preferably at least 80%, and up to 100% of the total surface area of the treatment region; and 3. For any given one of the consecutive sequence of effectively ablated annular rings, the variance in thickness of the effectively ablated region is no more than plus or minus 25% of the average or mean thickness of the effectively ablated region.

Figure 1P:
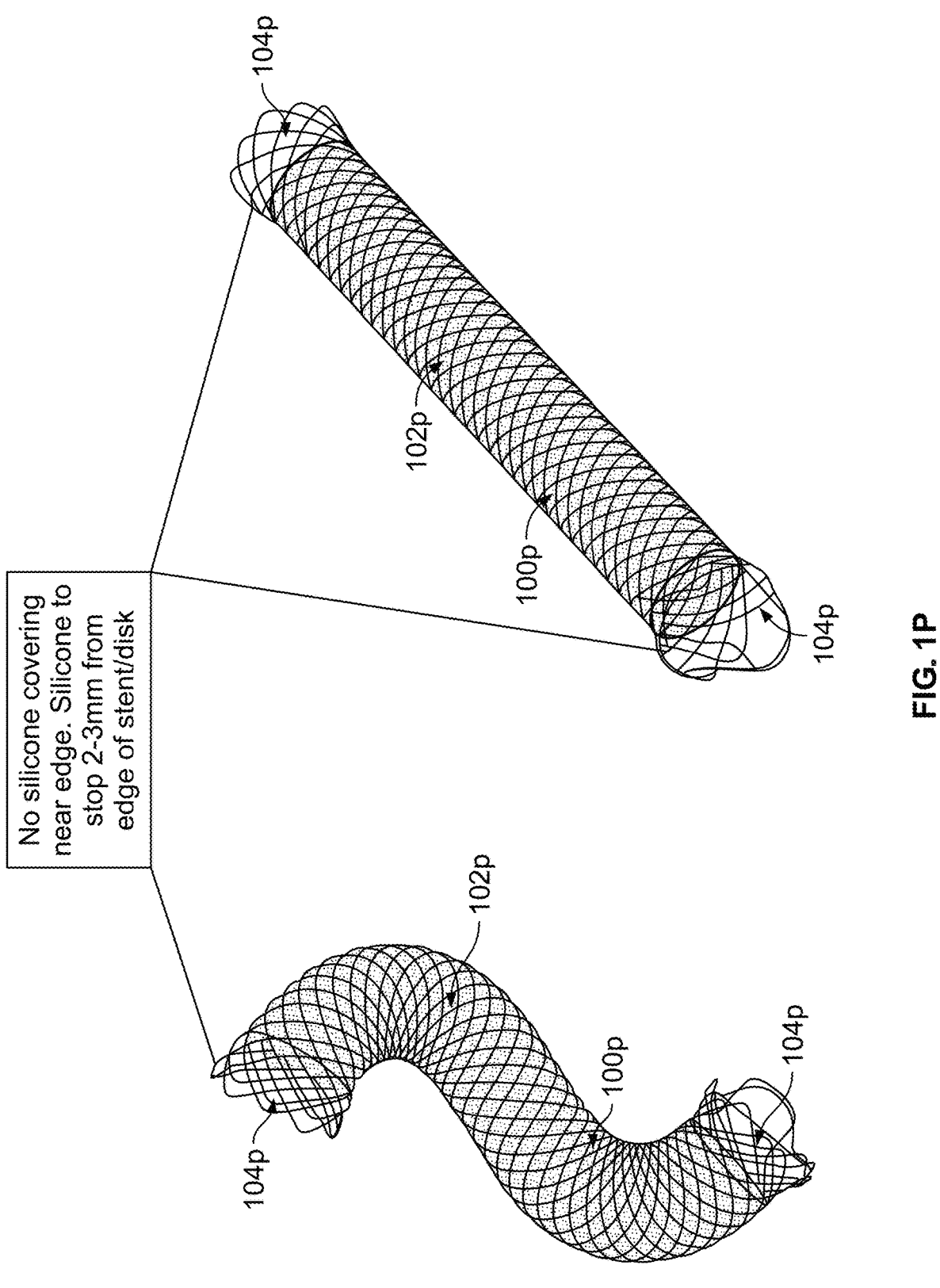
FIG. 1P illustrates two views of partial silicone coverings for various embodiments of positioning elements, in accordance with embodiments of the present specification.

FIG. 1P illustrates two views of partial silicone coverings for various embodiments of positioning elements, in accordance with the present specification. A representative positioning element 100p is shown in the form of a stent which is a NiTi tube, web or mesh coated with PTFE, ePTFE, polyester or silicone covering 102p. In some embodiments, the coating or covering 102p, such as of silicone, covers a portion of the positioning element 100p, leaving an uncovered portion 104p near the proximal and distal edges of the stent positioning element 100p. The uncovered portion may extend for 2 to 5 mm from the most distal edge of the covering 100p, which enables steam to escape, thereby acting as a pressure-relief.

Figure 1Q:
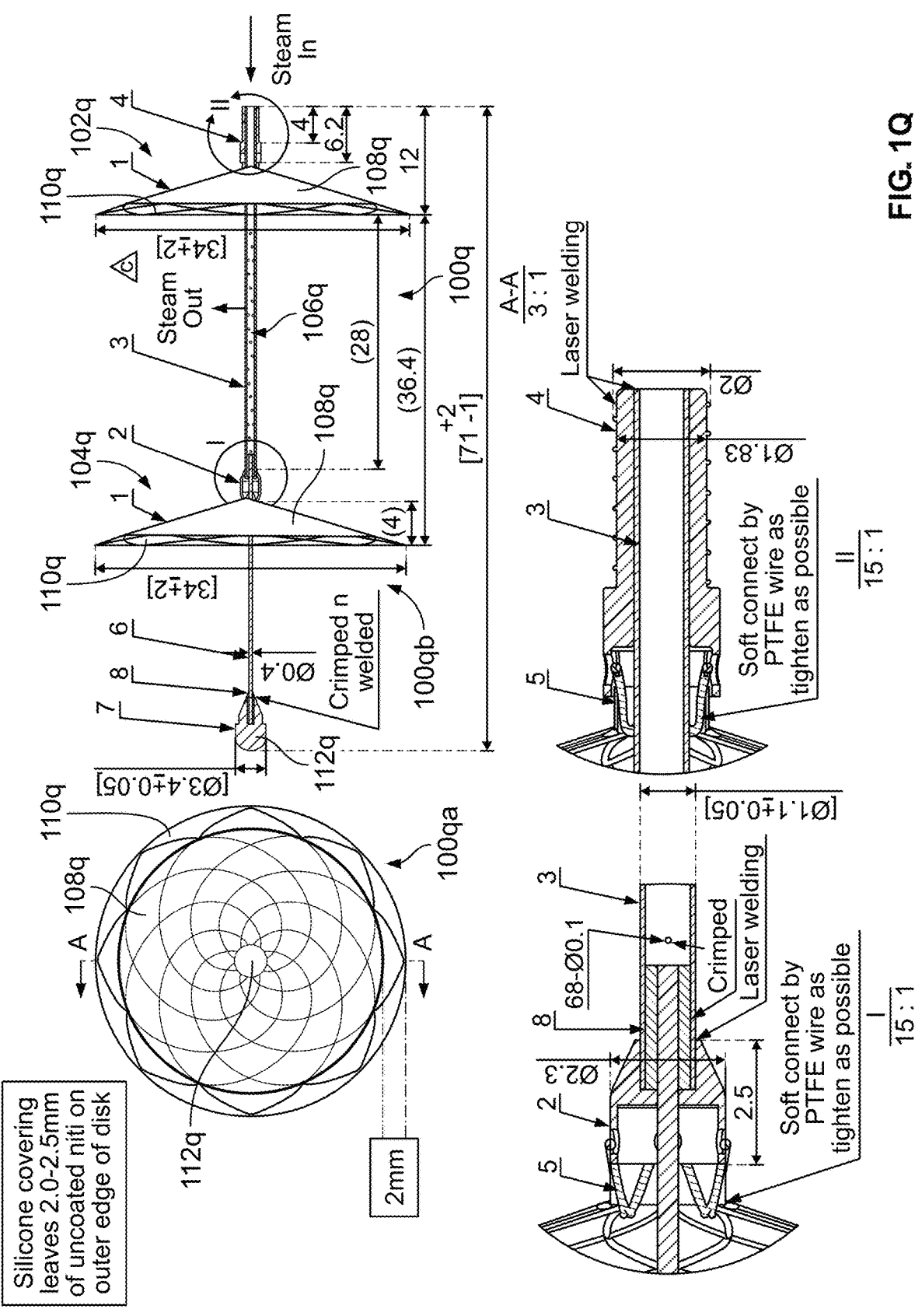
FIG. 1Q illustrates views of a catheter with proximal and distal positioning elements in accordance with embodiments of the present specification.

FIG. 1Q illustrates views of a catheter 100q with proximal and distal positioning elements 102q, 104q, in accordance with embodiments of the present specification. A view 100qa illustrates a front view from a distal end of the catheter 100q, and a view 100qb illustrates a side view of the catheter 100q. The catheter 100q includes an elongate body with a proximal end and a distal end. The catheter 100q includes a proximal positioning element 102p and a distal positioning element 104q positioned proximate the distal end of the catheter body with one or more infusion ports 106q located on the catheter body between the two positioning elements 102q, 104q. In some embodiments, the distance from and distal edge of the proximal catheter 102q to the proximal attachment portion of distal positioning element 104q is approximately 28 mm. The figure also illustrates a first set of exemplary dimensions for the positioning elements 102q, 104q, in accordance with an embodiment of the present specification. The substantially conical shaped hoods or positioning elements 102q, 104q have a distal diameter at a distal end of the cone in a range of 5 mm to 50 mm, a proximal diameter at a proximal end of the cone in a range of 1 mm to 4 mm, and a length of approximately 1 mm to 10 mm.

FIG. 1Q illustrates positioning elements 102q and 104q in an open or deployed configuration, such as when the positioning elements 102q and 104q are pushed out (unsheathed) of the outer catheter. In some embodiments, positioning elements 102q and 104q acquire a substantially conical shape, in the open or deployed configuration, having a distal end diameter in a range of 5 mm to 50 mm and a depth of approximately 1 mm to 10 mm. In some embodiments, each of positioning elements 102q and 104q is made using a NiTi tube, web, braid, or mesh coated with PTFE, ePTFE or silicone. In some embodiments, the coating, such as of silicone, covers a portion of or the entirety of positioning elements 102q and 104q. In some embodiments, each of the silicone-coated positioning elements 102q and 104q has one or more pores with diameter of each pore ranging from 10 microns to 1000 microns. The pores may allow for air or steam to vent out from the chamber formed between the two positioning elements 102q and 104q. In embodiments, the expandable positioning elements 102q, 104q have a specific size, that is equal. Size of positioning elements 102q, 104q may be based on the patient's anatomy. For a specific anatomy, the size of positioning elements 102q, 104q is fixed. In on example, the size of positioning elements 102q, 104q is the same for duodenum of all patients. During deployment, an outer sheath is pulled to unsheathe positioning elements 102q, 104q which then expand to the size of the lumen allowed within the organ that is being treated. Additionally, a length or distance from an outer point in the periphery of positioning element 102q to the same corresponding outer point in the periphery of positioning element 104q is always maintained to be the same regardless of the degree of expansion of positioning elements 102q, 104q, even when the volume of the ablation zone changes, provided that positioning elements 102q, 104q expand in the same direction. The ability to maintain the same distance between positioning elements 102q, 104q enables a user (physician) to consistently know the treatment zone length. In one example, the user knows the length or distance between positioning elements 102q, 104q is 3 cm, then it is also known that the ablation zone is of 3 cm, since the infusion ports 106q are located on the catheter body between the two positioning elements 102q, 104q.

The catheter body also includes at least one heating chamber (not shown) within a central lumen. In some embodiments, the proximal positioning element 103q and distal positioning element 104q comprises compressible discs which expand on deployment. In some embodiments, the proximal positioning element 102q and distal positioning element 104q are comprised of a shape memory metal and are transformable from a first, compressed configuration for delivery through a lumen of an endoscope and a second, expanded configuration for treatment. In embodiments, a partial silicone covering 108q coats the discs 102q and 104q, leaving an uncoated portion 110q of approximately 1 mm to 5 mm of the shape memory metal at the outer edges along the circumference of the discs 102q, 104q, to allow for the escape of air at the start of an ablation procedure and for the escape of steam once the pressure, temperature, ablation duration, and/or total energy within an enclosed treatment volume created between the two positioning elements 102q, 104q reaches a predefined limit, thereby acting as a pressure-relief or thermal-relief. In some embodiments, the catheter 100q includes a ball-tip or cap 112q at the most distal end of the catheter, distal to distal positioning element 104q. The ball-tip or cap 112q is crimped and welded to the distal tip of catheter 100q and configured with a smooth, curved exterior surface to provide an atraumatic passage for the catheter 100q. Additionally, the ball tip or cap is shaped or sized to approximate an outside diameter of the outer catheter.

Figure 1R:
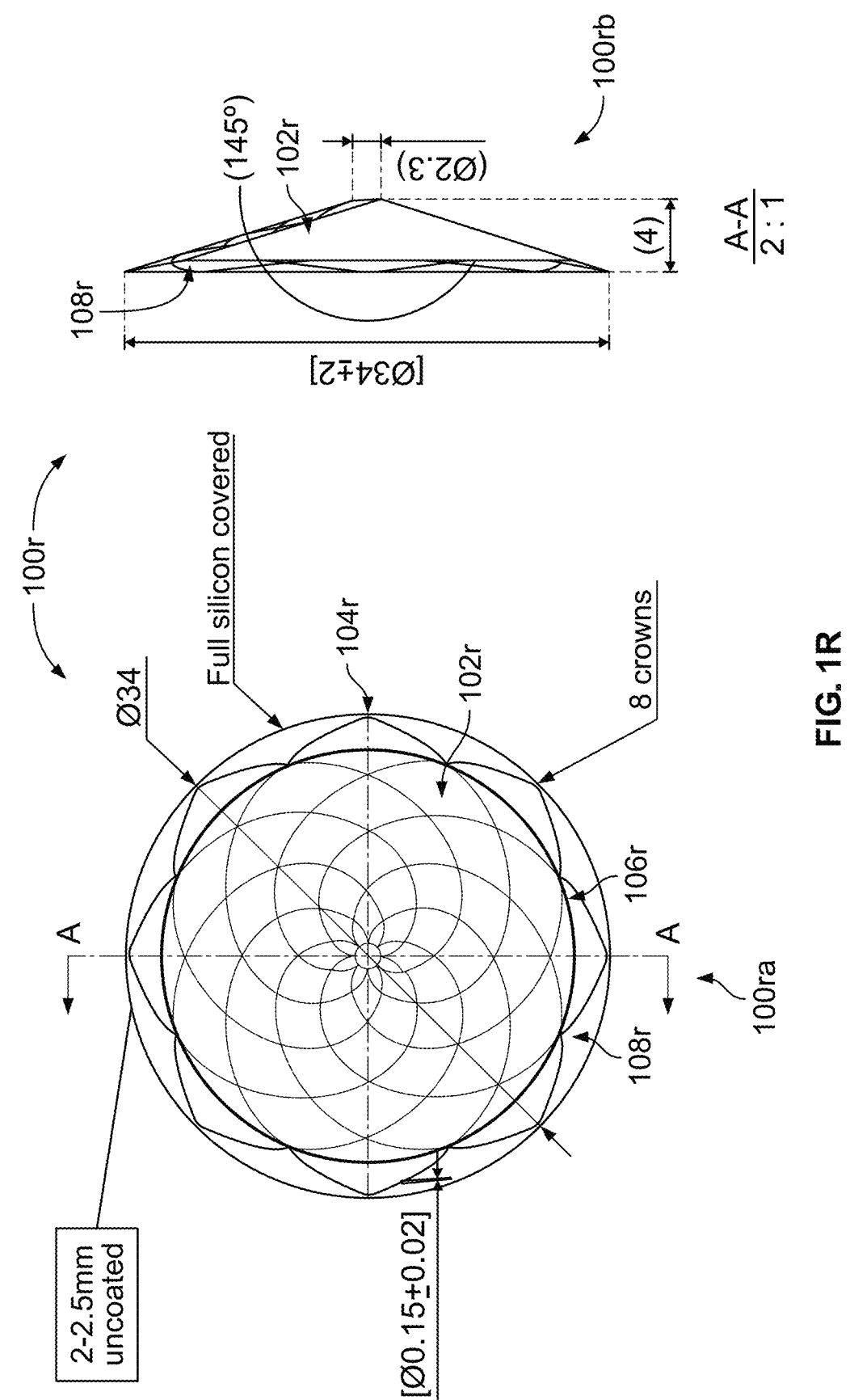
FIG. 1R illustrates a separate view of a conical positioning element comprising a partial silicone covering, in accordance with some embodiments of the present specification.

FIG. 1R illustrates a separate view of a conical positioning element 100r comprising a partial silicone covering, in accordance with some embodiments of the present specification. Positioning element 100r is comprised of a shape memory metal wire such as Nitinol, and is transformable from a first, compressed configuration for delivery through a lumen of an endoscope and a second, expanded configuration (as shown in the figure) for treatment. In some embodiments, the shape memory metal wire is weaved in the form of a flower or a mandala, as shown in a front view 100ra of the positioning element 100r. Another view 100rb shows the side view of the conical shape of the woven shape memory metal wire of positioning element 100r. In some embodiments, the diameter at the base of the cone, configured to be positioned towards a distal side of a catheter, has a diameter of approximately 34 mm. The proximal side of the positioning element 100r has a diameter of approximately 2.3 mm that attaches to a catheter lumen. A length from the proximal center of the cone to a center of the distal base of the cone, representing the height of the cone, is approximately 4 mm. The distal edge of the cone has a zig-zag shape comprising at least eight crowns 104r and an equal number of troughs 106r.

A silicone covering 102r partially coats the conical surface of the positioning element 100r, forming an angle of 145 degrees at the proximal tip of the cone. The coating covers most of the proximal surface of the positioning element 100r, leaving the distal circular edge near the base of the cone, uncoated. The uncoated portion 108r extends for a width of 1 mm to 5 mm of the distal edge of the positioning element 100r. In some embodiments, the uncoated portion extends from the circular edge of the positioning element 100r that is formed by troughs 106r to the edge formed by crowns 104r.

Figure 1S:
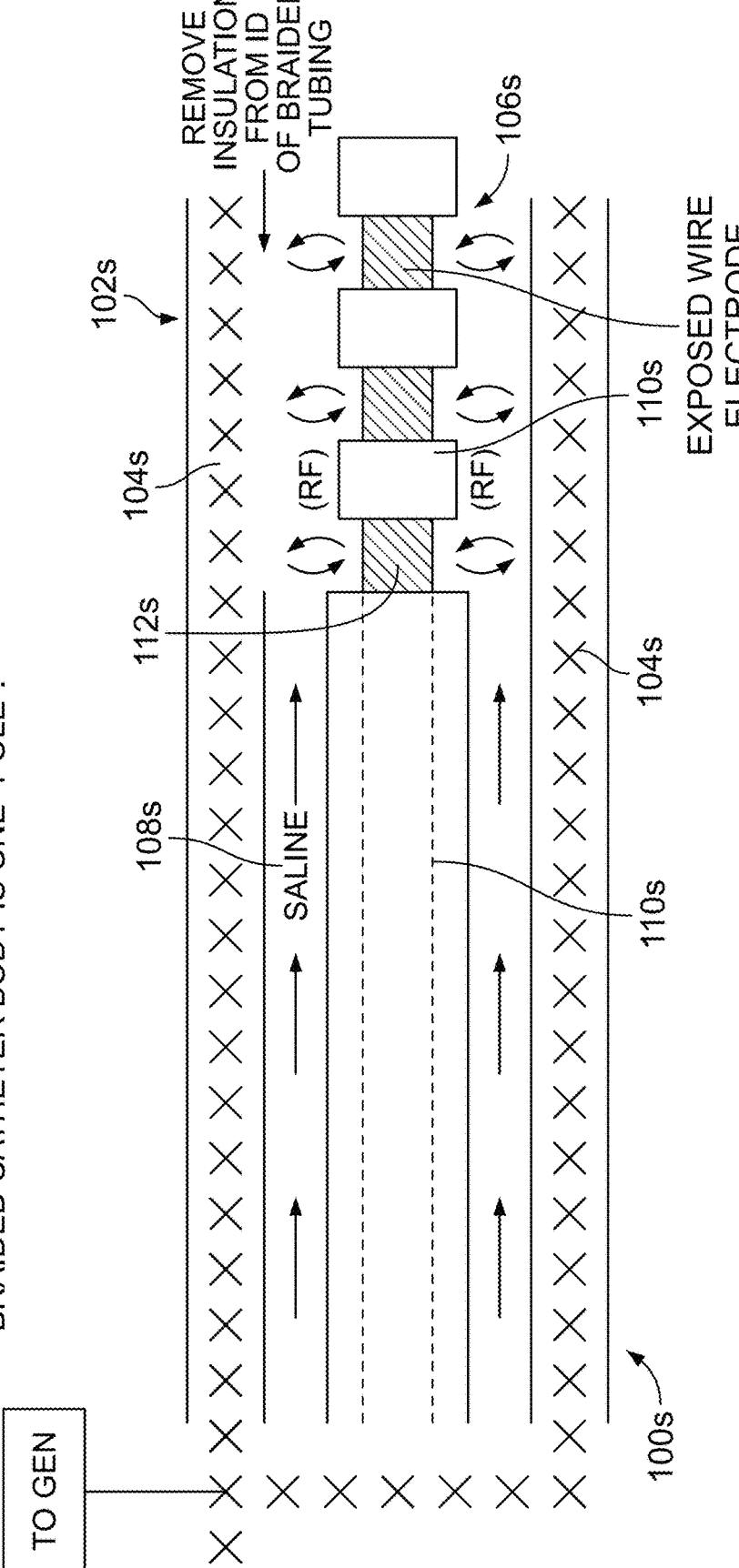
FIG. 1S illustrates an exemplary electrode structure within a flexible heating chamber configured to be incorporated at or into a distal portion or tip of a catheter, in accordance with an embodiment of the present specification.

FIG. 1S illustrates an exemplary electrode structure within a flexible heating chamber 102s configured to be incorporated at or into a distal portion or tip of a catheter 100s, in accordance with an embodiment of the present specification. The figure illustrates a longitudinal cross-section view of flexible heating chamber 100s for a catheter, in accordance with an embodiment of the present specification. The heating chamber 102s comprises a conductive braided outer covering 104s, a coaxial inner core 106s, and a channel, or lumen 108s. In embodiments, the entire length of the heating chamber 102s ranges from 5 mm to 75 mm. The length is established based on the surface area of the exposed conductors, power delivered to the saline and the saline flow rate. Each parameter can be adjusted to optimize the vapor output of the system. In some embodiments, flow rate of saline is constant while an applied RF voltage within the heating chamber is varied to optimize the vapor output. The coaxial inner core 106s is coaxial with and inside the braided outer covering 104. Lumen 108s is configured between outer covering 104s and coaxial inner core 106s, and enables the flow of saline that converts to steam when electrodes are operated. The coaxial inner core 106s is made from an outer insulated tubing 110s and can range in gauge size from 0.2 mm to 2.0 mm diameter. A conductive wire 112s is configured coaxially within tubing 110s. The wire 112s is intermittently exposed towards a distal side of the coaxial inner core 106s by removal sections of the insulation. The exposed length can range from 1 mm to 10 mm in length. The insulated sections can range from 0.5 mm to 10 mm in length. In embodiments, a diameter of the core 112s ranges from 0.2 mm to 2.5 mm. In embodiments, a thickness of the insulation ranges from 0.01 mm to 1 mm. The insulation provides better dielectric strength and also prevents outer covering 104s metal from contacting conductive wire 112s. The insulation prevents the inner conduction contacting the braided conductor under extreme bend conditions to avoid a short between the poles. The conductive braided outer covering 104s has a first polarity while the exposed wire 112s have a second polarity opposite the first polarity, thereby constituting a bipolar electrode configuration. In embodiments, the conductive core 112s and the conductive braid wire in the outer sheath are made from a highly electrically conductive metal, such as copper. In an embodiment, the first polarity is negative (cathode) while the second polarity is positive (anode). Operationally, electrical current is directed from the controller, into the catheter, through a lumen, and to the electrodes configured by the conductive braided covering 104s and the exposed wire 112s, which generates heat within lumen 108s, which is then transferred to the saline in order to convert the saline to steam.

In embodiments, the tubing 110s is comprised of silicone, Teflon, ceramic or any other suitable thermoplastic elastomer known to those of ordinary skill in the art. The conductive braided covering 104s, the coaxial inner core 106s, the tubing 110s and the wire 112s, are all flexible to allow for bending of the distal portion or tip of the catheter to provide better positioning of the catheter during ablation procedures.

Figure 1T:
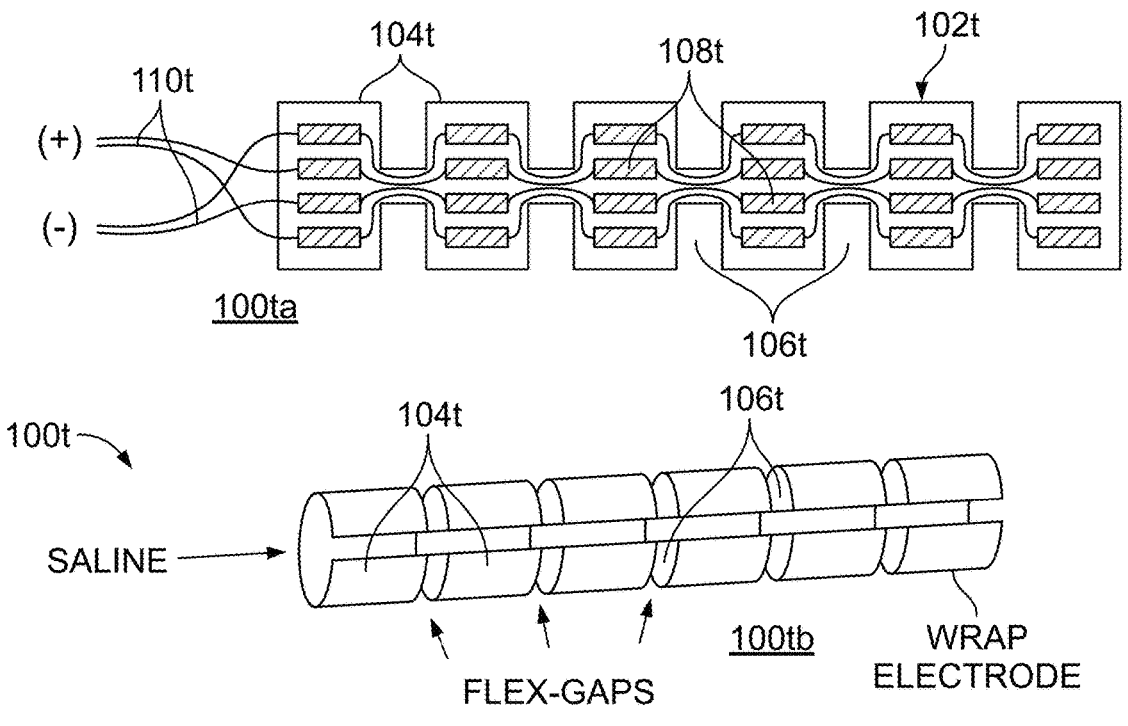
FIG. 1T illustrates another exemplary electrode configuration, in accordance with some embodiments of the present specification.

FIG. 1T illustrates another exemplary electrode configuration 100t, in accordance with some embodiments of the present specification. Electrode configuration 100t is configured to create a rolled flex circuit electrode or electrodes that is/are flexible. Referring to a view 100ta, an insulated sheet 102t is sectioned into a series of connected insulated strips 104t, allowing partial gaps 106t of equal widths between each strip 104t an exemplary length of 1 mm in length. In embodiments, each strip 104t has a length ranging from 2 mm to 10 mm. In embodiments, electrode configuration 100t comprises 1 to 100 strips 104t. Each gap is bridged with portions of contiguous insulated sheet 102t with an exemplary length of 5 mm. Further, a first surface of each strip 104t contains pairs of conductive surfaces 108t. In some embodiments, each strip 104t contains two or more pairs of conductive surfaces 108t. In embodiments, each strip 104t contains a range of two to 300 pairs of conductive surfaces 108t. Conductive wires 110t of opposite polarities are connected to an equal number of conductive surfaces 108t on a strip 104t. In embodiments, conductive wires 110t have a diameter ranging from 0.1 mm to 1 mm. Wires 108t continuously stretch through each strip, connecting conductive surfaces 108t of corresponding polarity. In embodiments, the insulated sheet 102t may be wrapped to form a cylindrical structure, with the first surface comprising the conductive surfaces inside the cylinder, therefore constituting a circumferential electrode as shown in a view 100tb. The gaps 106t enable additional flexibility of the electrode configuration 100t. In embodiments, electrode configuration 100t has a total length ranging from 5 mm to 150 mm. The electrode configuration 100t is placed in a heating chamber within a catheter lumen. Operationally, electrical current is directed from a controller, through the conductive wires that run through the lumen of the catheter and electrically connected to the electrode, and through exposed surfaces of the electrode and through the conductive saline flowing over the electrode assembly 100t, which heats the saline within the lumen in order to convert the saline to steam. Electrode configuration 100t comprises two poles to form a single bi-polar channel. In other embodiments, a multi-wire system comprises individually controlled bi-polar pairs. In embodiments, the individually controlled bi-polar pairs are controlled or activated at different times, or at different voltages/currents, to optimize the heating of saline as it passes through the electrode to optimize or improve the steam quality to produce as close as possible to pure steam exiting at 100° C. degrees.

Figure 1U:
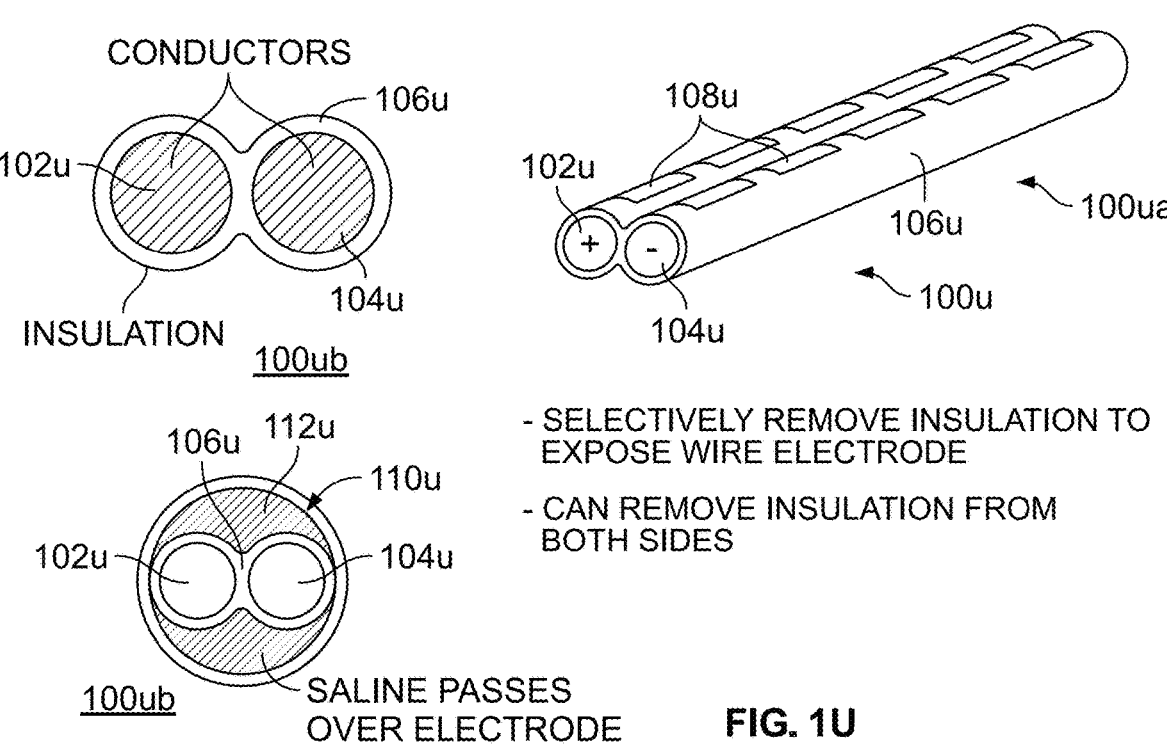
FIG. 1U illustrates another exemplary electrode configuration, in accordance with some embodiments of the present specification.

FIG. 1U illustrates another exemplary electrode configuration 100u, in accordance with some embodiments of the present specification. A first view 100ua illustrates a perspective view of electrode configuration 100u comprising a pair of wires 102u and 104u of opposite polarities, and encased parallel to each other within an insulated coating 106*u*. A second view 100*ub* illustrates cross-sectional view of the electrode configuration 100*u*. A third view illustrates a cross sectional view of the electrode configuration 100*u* within a catheter lumen 110*u*. Saline 112*u* is configured to pass through the lumen 110*u* over the electrode configuration 100*u*. Referring again to view 100*ua*, insulated coating 106*u* is selectively removed from the surfaces of wires 102*u* and 104 to provide exposed conductive surfaces 108*u*, where an exemplary length of exposed conductive surfaces is 10 mm. In embodiments, exposed conductive surfaces 108*u* are provided on a first surface, as shown in the figure. In some embodiments, exposed conductive surfaces 108*u* are provided additionally on a second surface opposite to the first surface of the insulated coating 106*u*. Operationally, electrical current is directed from a controller, into the catheter, through lumen 110*u*, and through the electrode configuration 100*t*. RF current flows between exposed surfaces 108*u* of wires 102*u* and 104*u* of opposite polarities, which send electrical energy through the conductive saline in order to convert the saline 112*u* to steam.

Needle Vapor Delivery Device

Figure 2A:
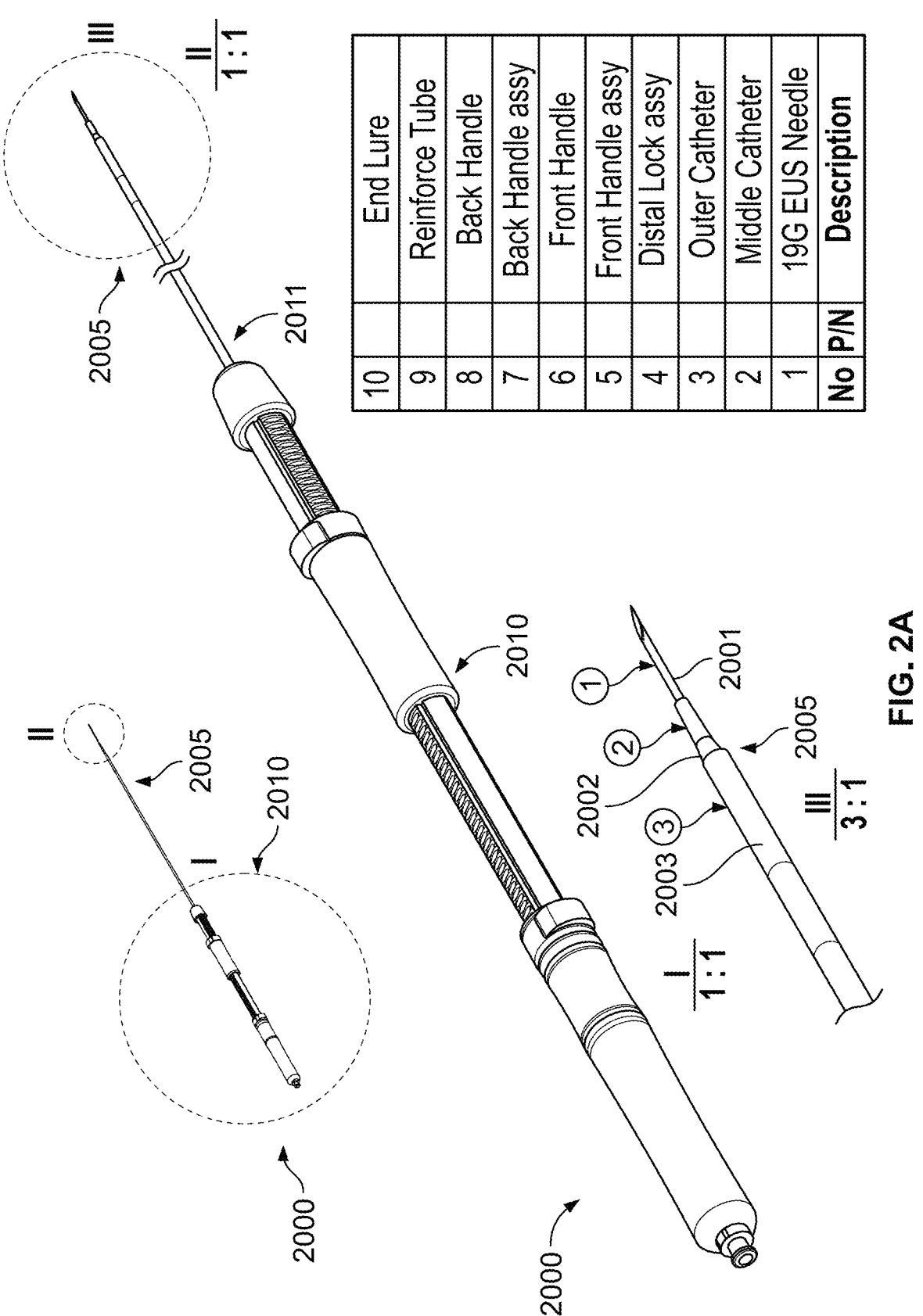
FIG. 2A shows perspective views of a needle ablation device, in accordance with an embodiment of the present specification.

FIG. 2A shows perspective views of a needle-based vapor delivery device 2000, in accordance with an embodiment of the present specification. The device 2000 comprises a needle 2005 protruding from a distal end 2011 of a composite handle 2010. The needle 2005 has a needle tip portion 2001 and is encompassed at its proximal end by an inner or middle catheter 2002 and an outer catheter 2003. In some embodiments, the composite handle 2010 and the needle 2005 are hollow. In some embodiments, the needle 2005 is retractable within the composite handle 2010. In some embodiments, the needle 2005 is of stainless steel, the middle catheter 2002 is of PTFE (Polytetrafluoroethylene) while the outer catheter 2003 is of braided Teflon.

Figure 2B:
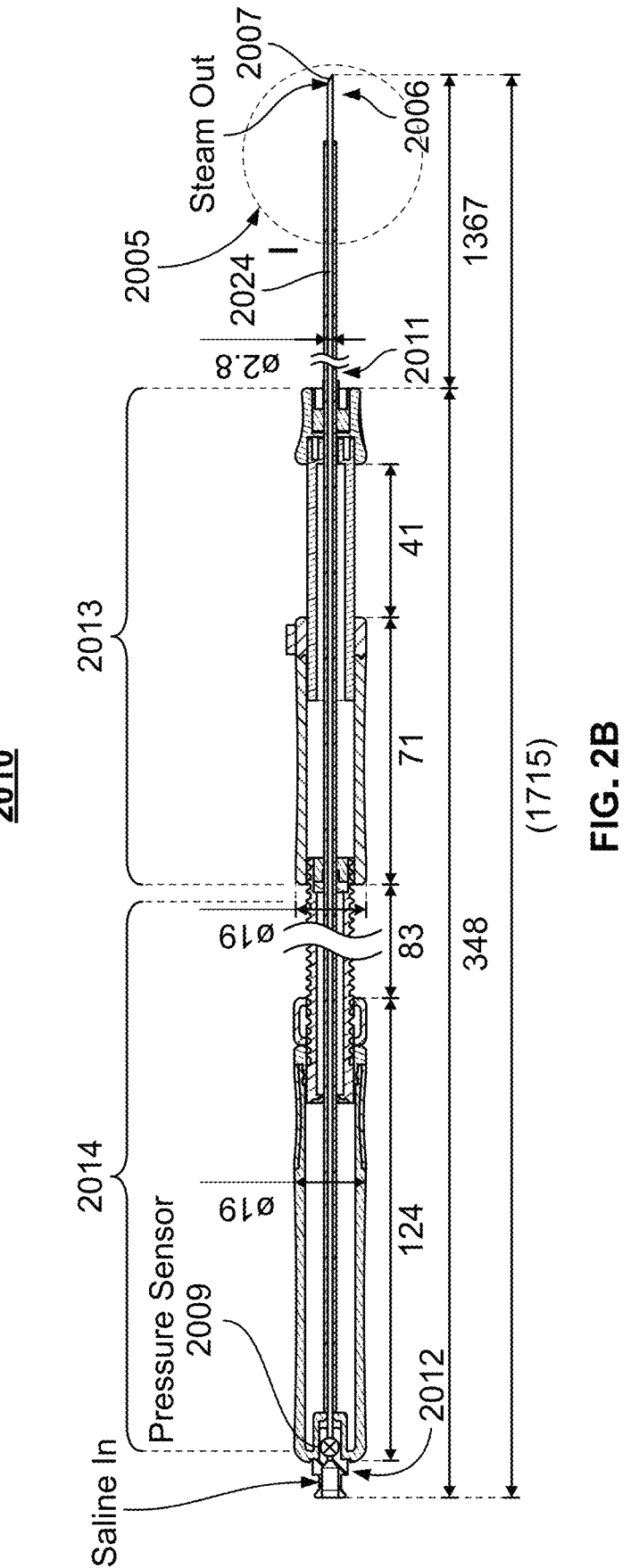
FIG. 2B shows a cross-sectional view of the needle ablation device of FIG. 2A, in accordance with an embodiment of the present specification.

FIG. 2B is a cross-sectional view of the composite handle 2010 illustrating the needle 2005 emanating from the distal end 2011, a front or distal handle portion 2013 and a back or proximal handle portion 2014. A lumen 2008 extends from a proximal end 2012 to the distal end 2011 of the composite handle 2010 and is in fluid communication with a lumen 2024 of the needle 2005. Saline enters the lumen 2008 from the proximal end 2012 and steam exits from at least one port 2007 located at a distal end 2006 of the needle 2005. A pressure sensor 2009 is located proximate the proximal end 2012 of the composite handle 2010.

Figure 2C:
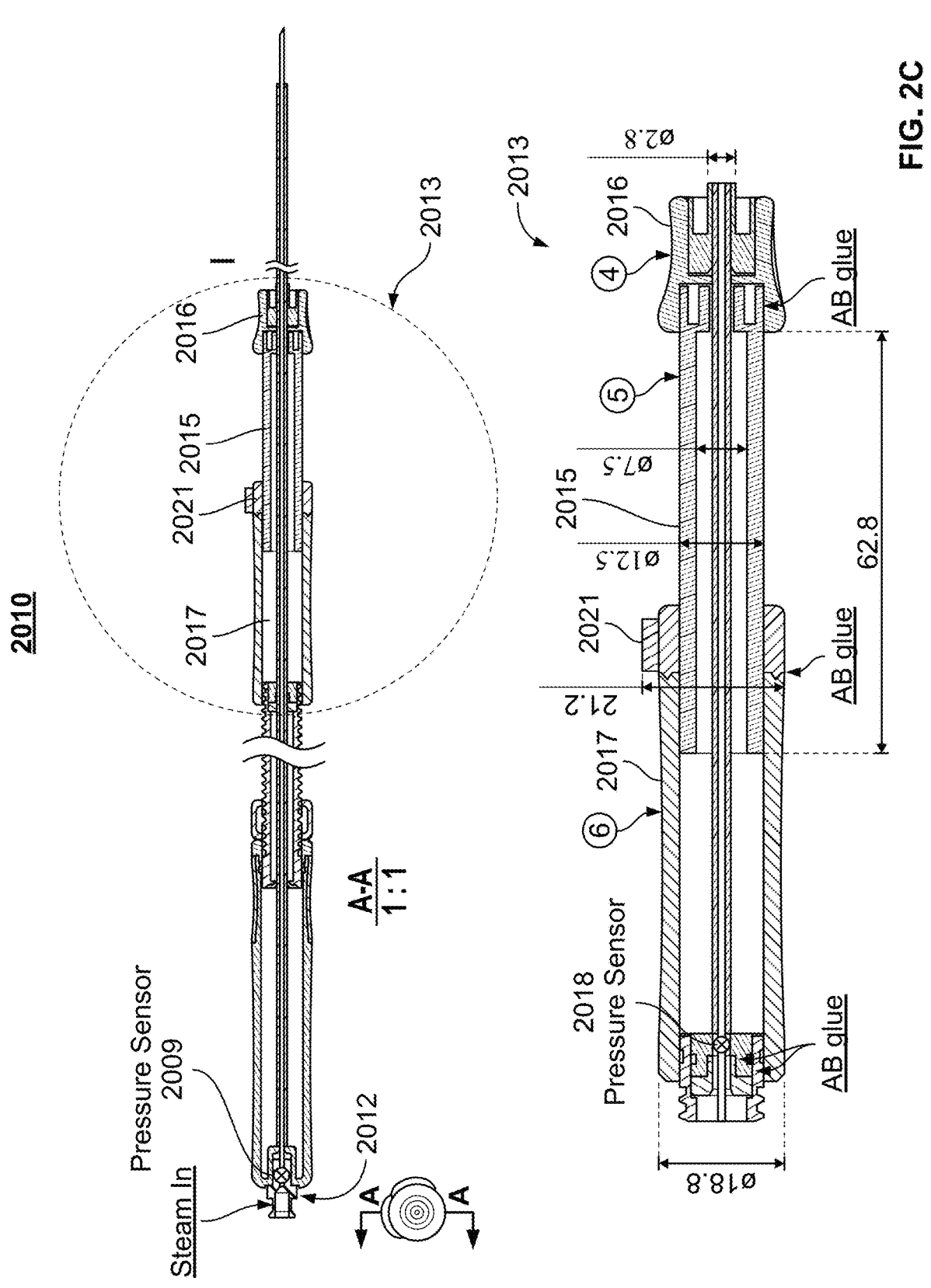
FIG. 2C shows a first enlarged cross-sectional view of the needle ablation device of FIG. 2A, in accordance with an embodiment of the present specification.

FIG. 2C shows an enlarged view of the front or distal handle portion 2013 of the composite handle 2010. Referring now to FIGS. 2B and 2C, the distal handle portion 2013 is an assembly comprising a front tube 2015 coupled, at its distal end, to a distal lock 2016 and, at its proximal end, to a front handle 2017. A lock 2021 secures the front tube 2015 to the front handle 2017. A pressure sensor 2018 is located proximate a proximal end of the front handle 2017 while pressure sensor 2009 is located proximate the proximal end 2012.

Figure 2D:
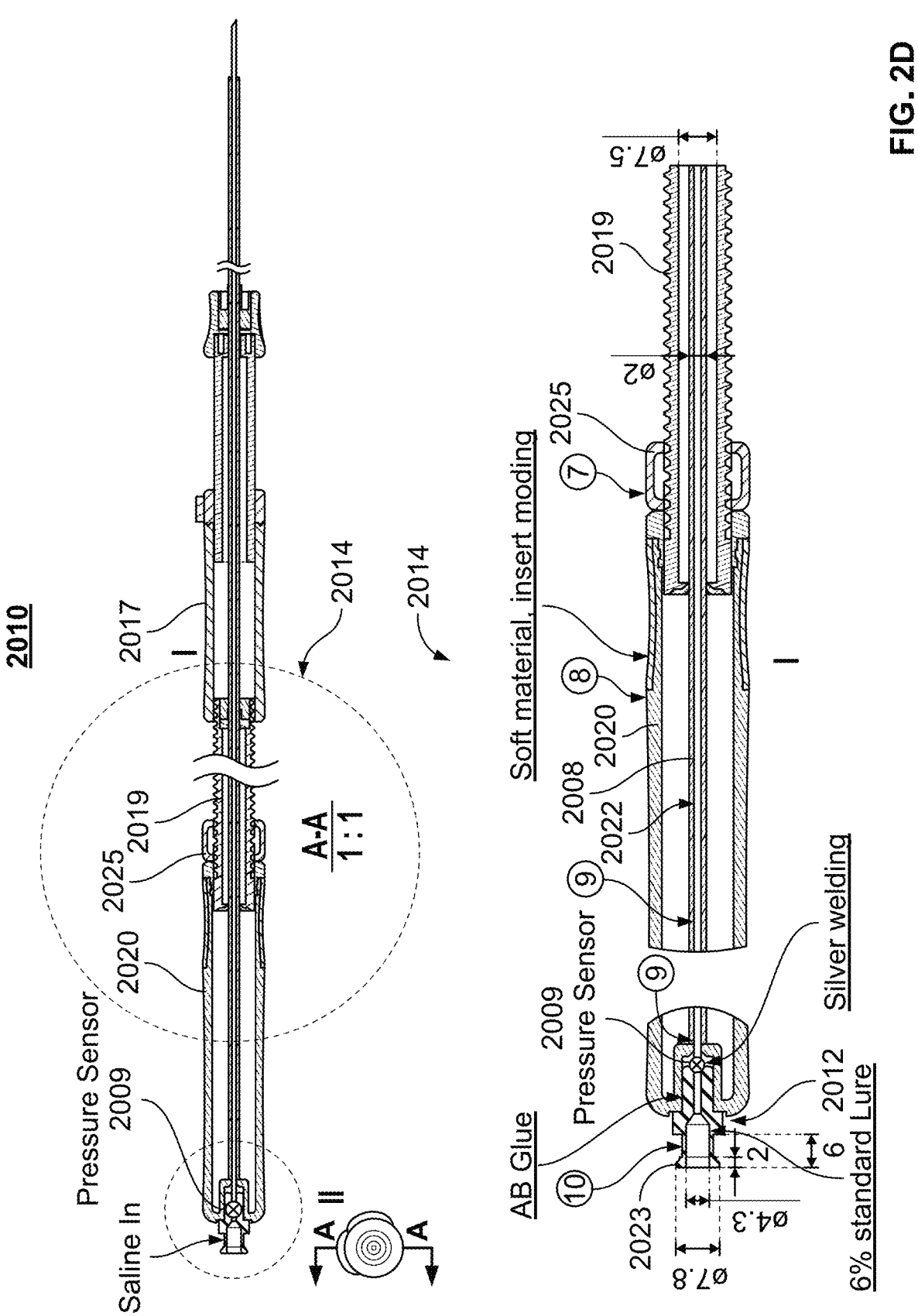
FIG. 2D shows a second enlarged cross-sectional view of the needle ablation device of FIG. 2A, in accordance with an embodiment of the present specification.

FIG. 2D shows an enlarged view of the back or proximal handle portion 2014 of the composite handle 2010. Referring now to FIGS. 2B, 2C and 2D, the proximal handle portion 2014 is an assembly comprising a back tube 2019 coupled, at its distal end, to the front handle 2017 and, at its proximal end, to a back handle 2020. A lock 2025 secures the back tube 2019 to the back handle 2020. The lumen 2008 is covered or encompassed within a reinforce tube or sheath 2022. The proximal end 2012 of the composite handle 2010 includes a lure connection 2023 defining an opening to enable saline to enter the lumen 2008. The pressure sensor

2009 is visible again in the enlarged view of the back or proximal handle portion 2014 of FIG. 2D.

Referring again to FIGS. 2A, 2B, 2C and 2D, in accordance with an exemplary embodiment, the device 2000 has the following dimensions: a length of 1715 mm from a proximal end of the lure connection 2023 to the distal end 2006 of the needle 2005, a length of 1367 mm from a distal end of the distal lock 2016 to the distal end 2006 of the needle 2005, a length of 41 mm from a proximal end of the distal lock 2016 to a distal end of the lock 2021, a length of 71 mm from the distal end of the lock 2021 to a proximal end of the front handle 2017, a length of 83 mm from the proximal end of the front handle 2017 to a distal end of the lock 2025, a length 124 mm from the distal end of the lock 2025 to the proximal end 2012, a length of 348 mm from the distal end of the distal lock 2016 to the proximal end of the lure connection 2023, a length of 62.8 mm from the proximal end of the distal lock 2016 to a proximal end of the front tube 2015, an outer diameter of 2.8 mm of the sheath 2022, an outer diameter of 19 mm of the front handle 2017 and the back handle 2020, an inner diameters of 7.5 mm of the front and back tubes 2015, 2019, and an outer diameters of 12.5 mm of the front and back tubes 2015, 2019.

Figure 3A:
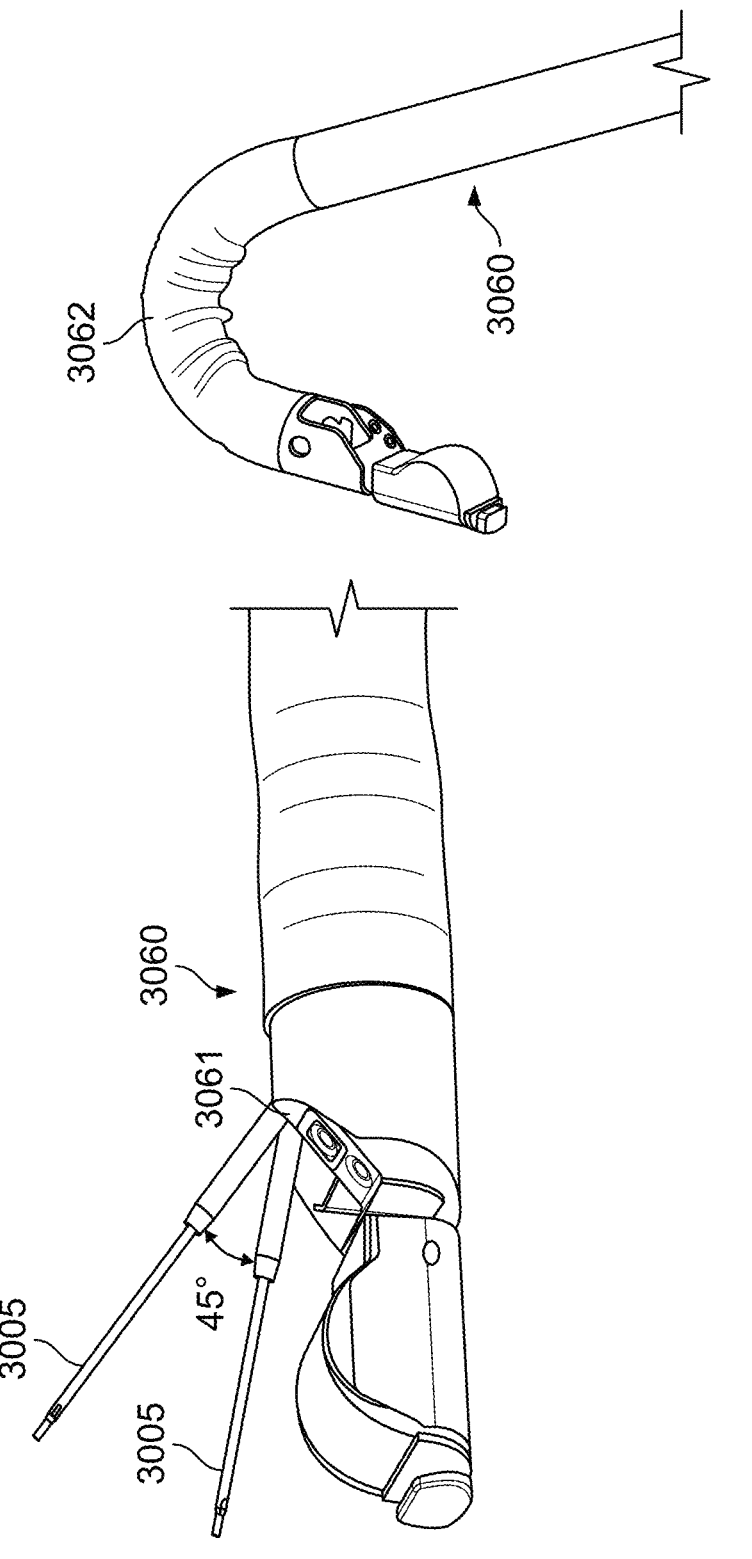
FIG. 3A shows perspective views of an endoscope and of the needle ablation device of FIG. 2A being deployed through the endoscope, in accordance with an embodiment of the present specification.
Figure 3B:
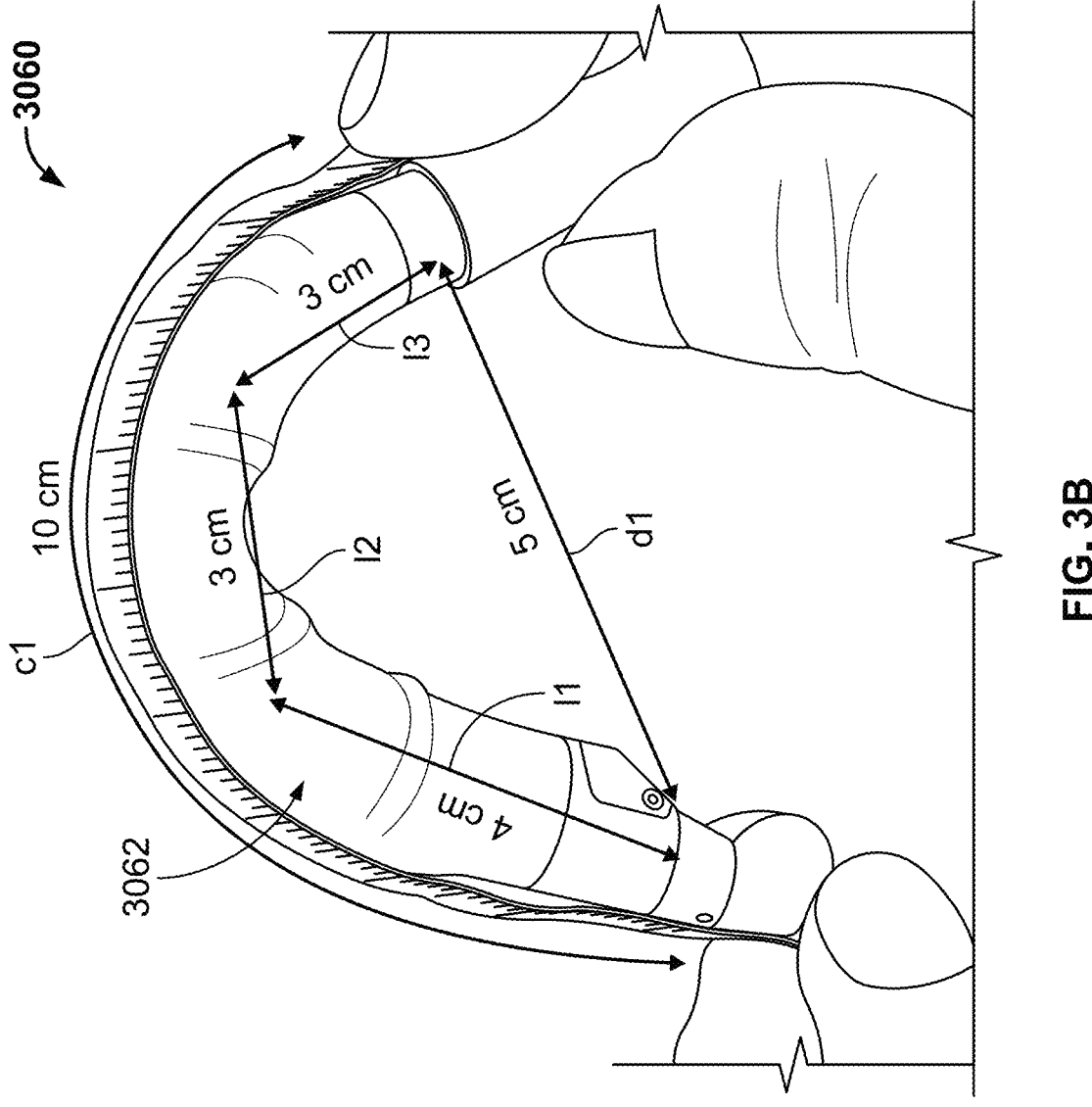
FIG. 3B shows a perspective view of a bending section of the endoscope, in accordance with an embodiment of the present specification.

In accordance with an aspect of the present specification, the needles of the needle ablation catheters and devices have a form factor that enables the needle to be functional with a conventional endoscope—that is, the form factor enables the needle to be slid through a working channel of the endoscope. FIGS. 3A and 3B illustrate a conventional endoscope 3060 with a bending section 3062 and a needle 3005 of a needle ablation catheter protruding from a working channel 3061 of the endoscope 3060. In embodiments, when bent, the bending section 3062 has a curve length $c_i$ of 10 cm comprising a first distal length $l_1$ of 4 cm, a second middle length $l_2$ of 3 cm and a third proximal length $l_3$ of 3 cm. When bent, a distance d1 between a distal end and a proximal end of the bending section 3062 is 5 cm. As shown in FIG. 3A, the needle 3005 is capable of bending or flexing by at least an angle of 45 degrees.

Figure 4A:
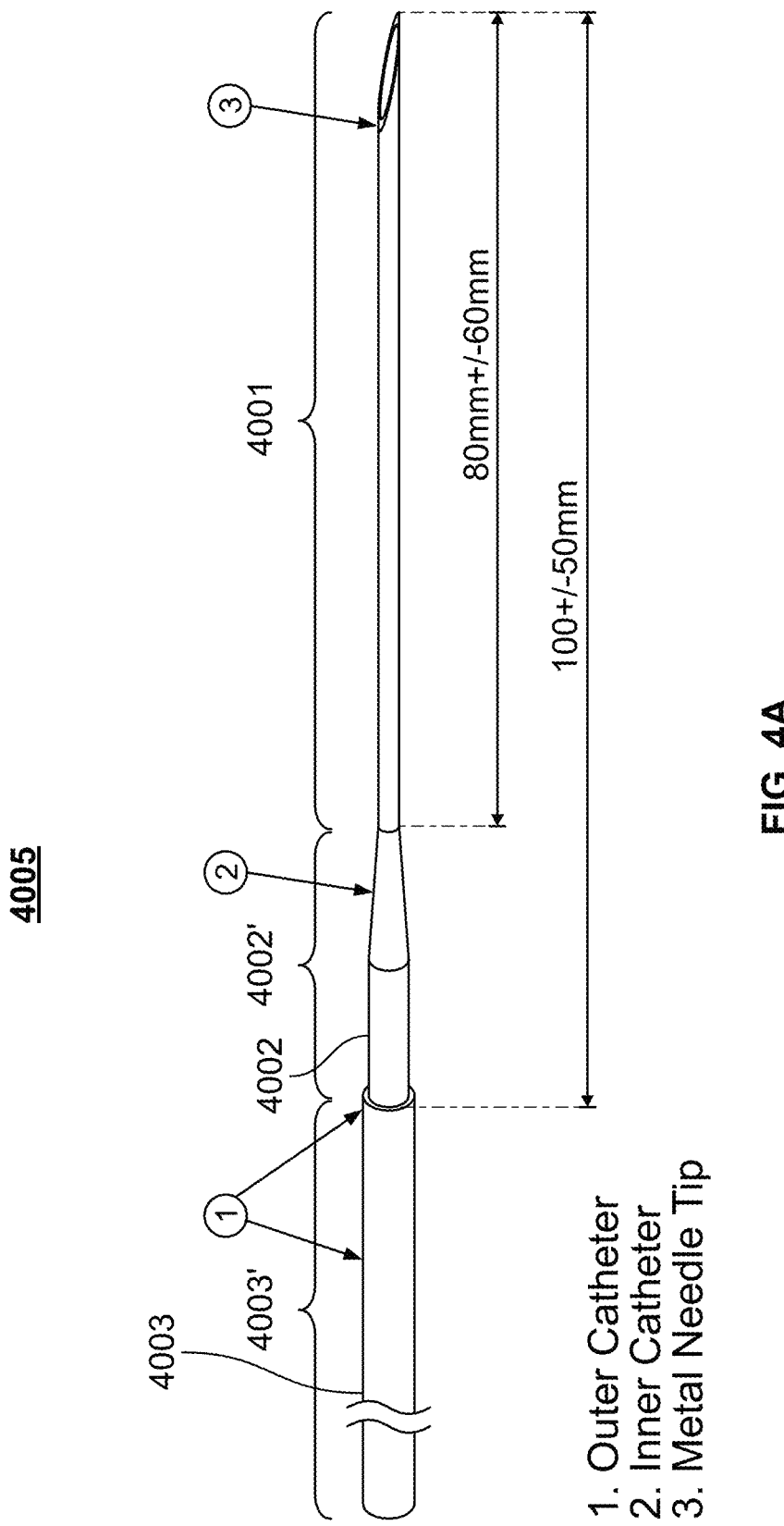
FIG. 4A shows a perspective view of a needle of a needle ablation device, in accordance with an embodiment of the present specification.
Figure 4B:
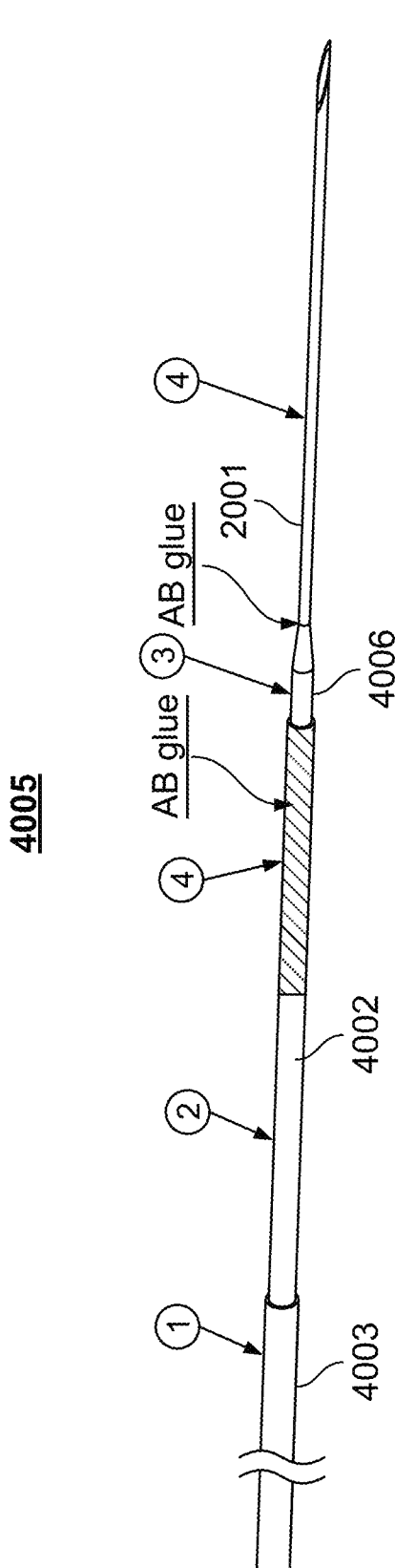
FIG. 4B shows another perspective view of the needle of the needle ablation device of FIG. 4A, in accordance with an embodiment of the present specification.
Figure 4C:
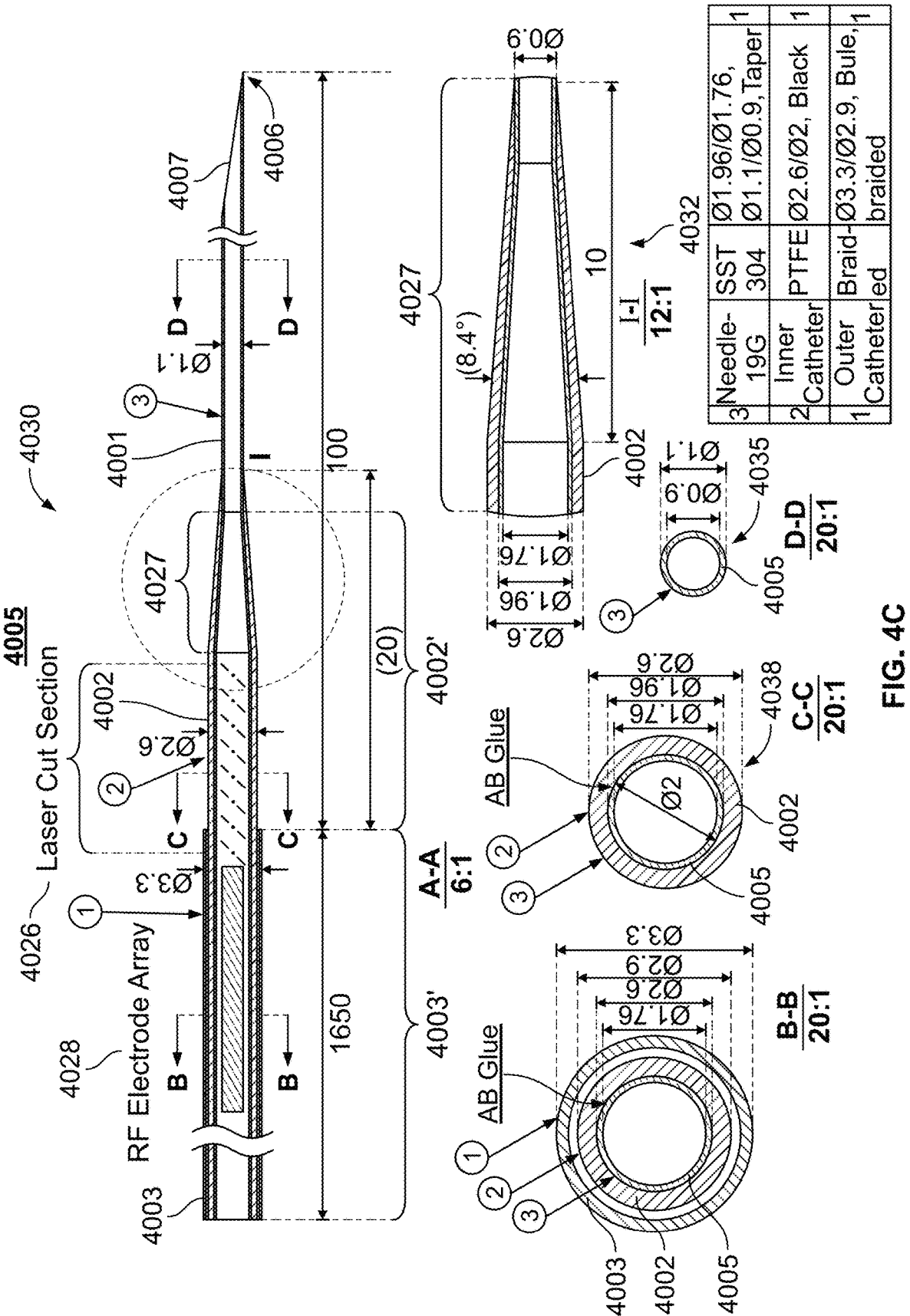
FIG. 4C shows cross-sectional views of the needle of the needle ablation device of FIG. 4A, in accordance with a first embodiment of the present specification.

FIGS. 4A, 4B show perspective views of a needle 4005 while FIG. 4C illustrates cross-sectional views of the needle 4005, in accordance with an embodiment of the present specification. In accordance with an embodiment, the needle 4005 can be distinguished into the distal needle tip portion 4001, a middle portion 4002' and a proximal portion 4003'. FIGS. 4A, 4B and a longitudinal cross-sectional view 4030 of FIG. 4C show the needle tip portion 4001, the inner or middle catheter 4002 and the outer catheter 4003. In accordance with an embodiment, the needle tip portion 4001 has a length of 80 mm (+/−60 mm) from a proximal end to a distal end of the needle tip portion 4001. The needle 4005 has a length of 100 mm (+/−50 mm) from a proximal end of the middle portion 4002' to the distal end of the needle tip portion 4001. The proximal portion 4003' has a length of 1650 mm.

Referring now to the longitudinal cross-sectional view 4030 of FIG. 4C, the middle portion 4002' comprises a proximal laser cut portion 4026 (also shown in FIG. 4B) and a distal tapered portion 4027. In accordance with an embodiment of the present specification, the proximal portion 4003' houses or accommodates at least one flexible heating chamber 4028 (comprising a plurality of RF electrodes) positioned proximate the proximal laser cut portion 4026 (the at least one flexible heating chamber 4028 is also shown in FIG. 4B). During operation, saline enters from the proximal end (2012 of FIG. 2B) to reach the heating chamber 4028 where the saline is converted to steam/vapor that exits through at least one port 4007 located at the distal end 4006 of the needle 4005.

As shown in an enlarged cross-sectional view 4032, in one embodiment, at a proximal end of the tapered portion 4027—the needle 4005 has an inner diameter of 1.76 mm and an outer diameter of 1.96 mm while the inner catheter 4002 has an outer diameter of 2.6 mm and an inner diameter of 2 mm. In another embodiment, the inner catheter 4002 has an outer diameter of 2.7 mm and an inner diameter of 2.4 mm. At a distal end of the tapered portion 4027, the needle 4005 has an inner diameter of 0.9 mm. From the proximal end to the distal end, the portion 4027 has a taper or slope of 8.4 degrees with respect to a horizontal axis. The length of the tapered portion 4027 is 10 mm.

As shown in an enlarged cross-sectional view 4035, at the tip portion 4001, the needle 4005 has an outer diameter of 1.1 mm and an inner diameter of 0.9 mm. As shown in an enlarged cross-sectional view 4038, at the middle portion 4002', the needle 4005 has an inner diameter of 1.76 mm and an outer diameter of 1.96 mm while the inner or middle catheter 4002 has an outer diameter of 2.6 mm. As shown in an enlarged cross-sectional view 4040, at the proximal portion 4003', the needle 4005 still has the inner diameter of 1.76 mm and the outer diameter of 1.96 mm, the inner or middle catheter 4002 still has the outer diameter of 2.6 mm while the outer catheter 4003 has an inner diameter of 2.9 mm and an outer diameter of 3.3 mm.

In some embodiments, the proximal portion 4003' of the needle 4005 has an inner diameter of greater than or equal to 1.5 mm (to accommodate the heating chamber 4028) while the needle tip portion 4001 has an outer diameter of less than or equal to 1.1 mm to minimize leaks and infection. In some embodiments, the needle 4005 is electrically insulated and does not have leaks along its length (see FIG. 4D). In various embodiments, the needle 4005 is sufficiently stiff at the tip and proximal portions 4001, 4003' and has a 10 to 20 cm flexible middle portion 4002' in order to make a bend in the endoscope.

Figure 4D:
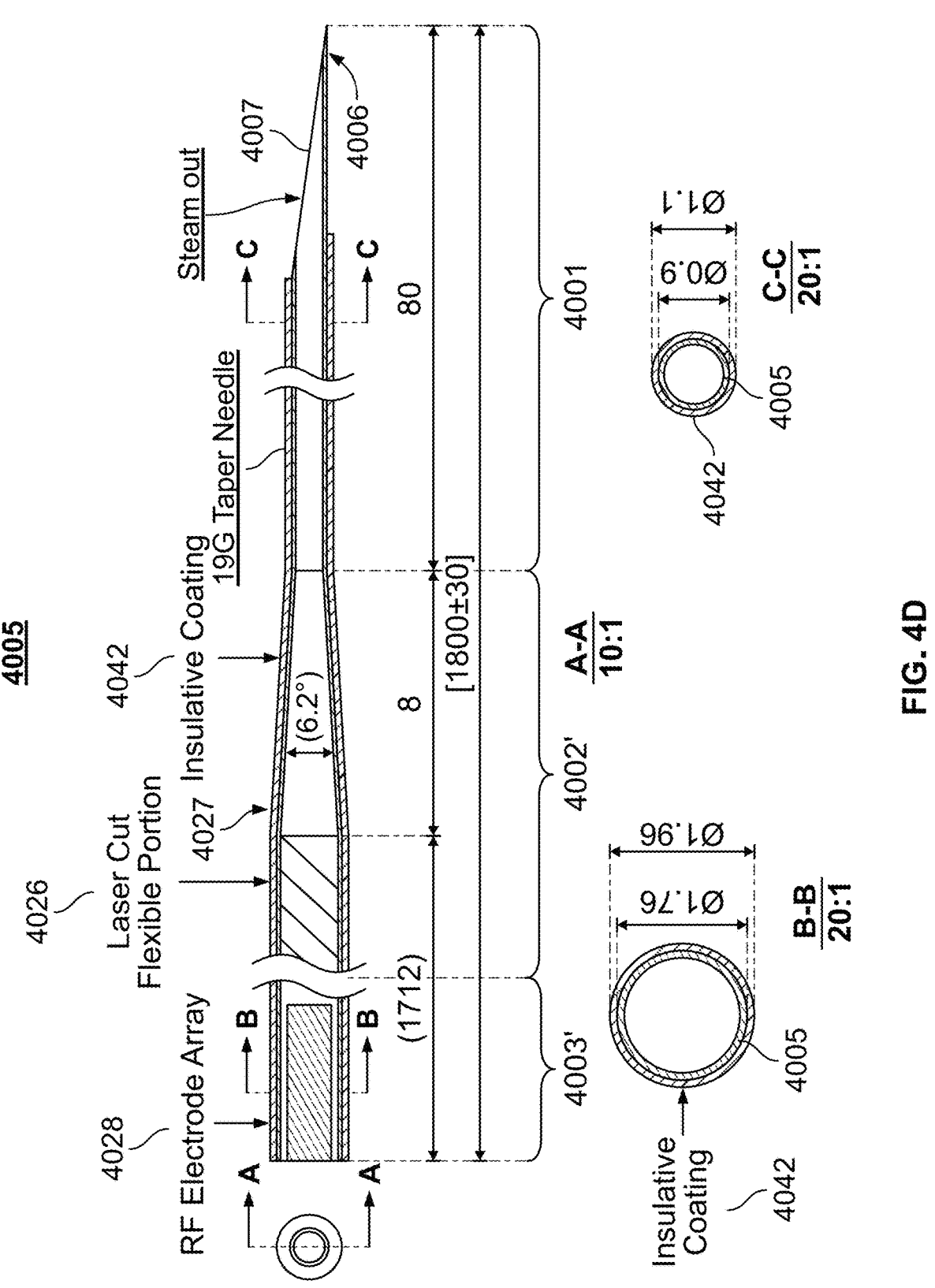
FIG. 4D shows cross-sectional views of the needle of the needle ablation device of FIG. 4A, in accordance with a second embodiment of the present specification.

FIG. 4D illustrates cross-sectional views of the needle 4005, in accordance with another embodiment of the present specification. In this embodiment, the needle 4005 is covered or sheathed in an insulating coating 4042 that covers the proximal portion 4003', the middle portion 4002' and the needle tip portion 4001 to a point proximate the at least one port 4007. In some embodiments, the insulating coating 4042 covers the entirety of the needle 4005, which, in some embodiments, comprises the distal 8 cm of the inner catheter. In some embodiments, needle 4005 diameter is within a range of 12 Birmingham Gauge (G) and 30G and needle 4005 length is in a range of 1 cm to 10 cm. In some embodiments, the slope of the needle taper is defined in a range of 12 G/1 cm to 30 G/10 cm. The proximal portion 4003' houses or accommodates at least one flexible heating chamber 4028 (comprising a plurality of electrodes) positioned proximate the proximal laser cut portion 4026.

Referring to FIG. 4D, in an embodiment, the needle 4005 has the following dimensions: a length of 80 mm from the distal end 4006 of the needle 4005 to the distal end of the middle portion 4002', a length of 8 mm from the distal end to the proximal end of the tapered portion 4027, a length of 1712 mm from the distal end of the laser cut portion 4026 to a proximal end of the proximal portion 4003', a total length of 1800 mm (+/−30 mm) from the proximal end of the proximal portion 4003' to the distal end 4006 of the needle 4005, and the tapered portion 4027 has a taper or slope in a range of 1 to 20 degrees (or any increment therein), preferably a range of 3 to 10 degrees (or any increment therein), and more preferably 6.2 degrees, with respect to a horizontal axis. At the tip portion 4001, the needle 4005 has an outer diameter of 1.1 mm and an inner diameter of 0.9 mm while at the proximal portion 4003', the needle 4005 has an inner diameter of 1.76 mm and an outer diameter of 1.96 mm.

Figure 4E:
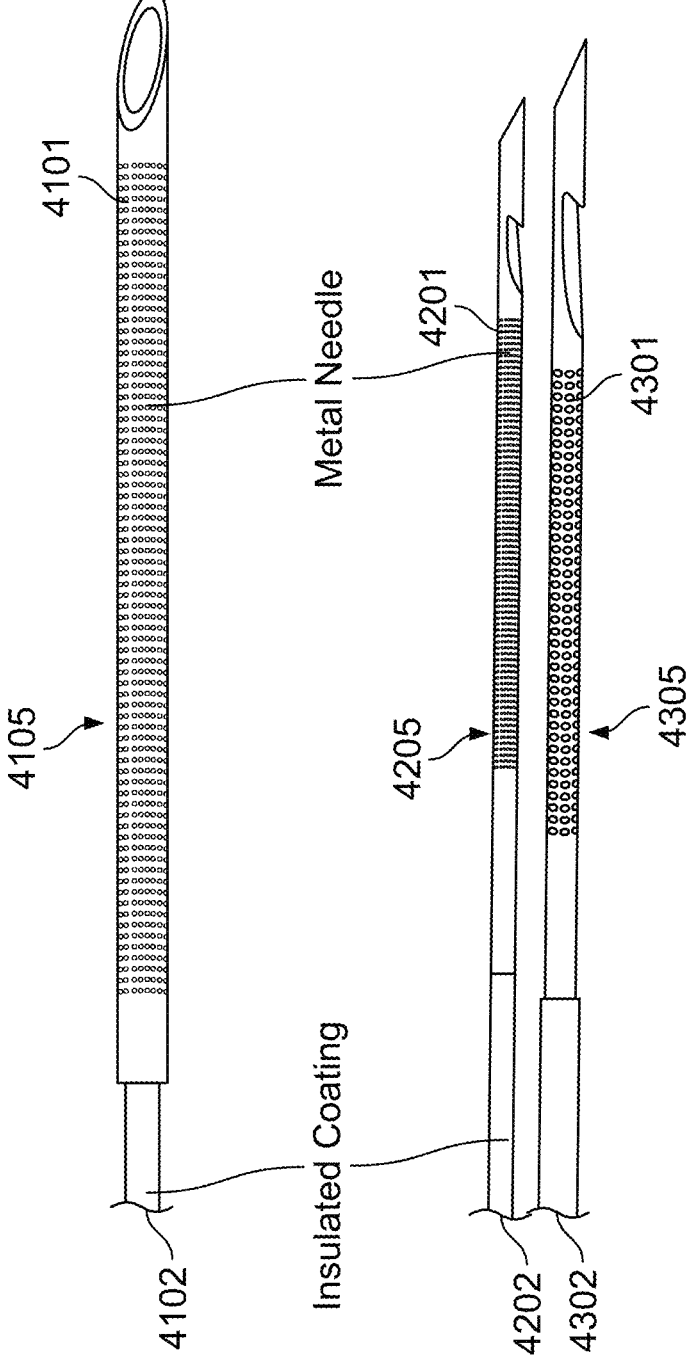
FIG. 4E shows perspective views of various needles illustrating the needle tip portions and insulating coatings, in accordance with embodiments of the present specification.

FIG. 4E shows perspective views of various needles 4105, 4205, 4305 illustrating the needle tip portions 4101, 4201, 4301 and insulating coatings 4102, 4202, 4302, in accordance with embodiments of the present specification. The needles 4105, 4205, 4305 are composed of metal such as, but not limited to, stainless steel while the insulating coatings 4102, 4202, 4302 comprise PTFE, ePTFE or silicone.

Figure 5A:
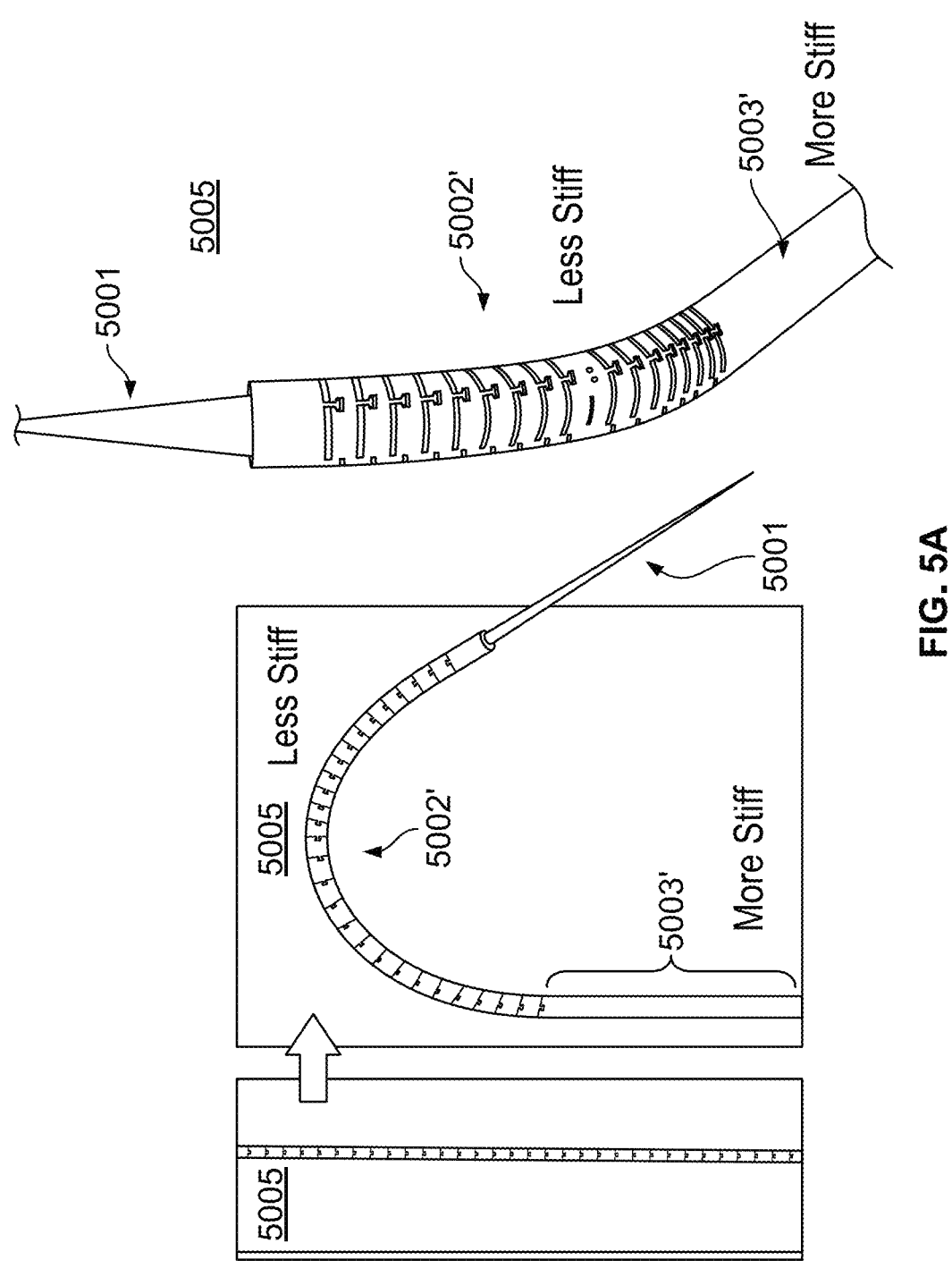
FIG. 5A shows perspective views of a needle of a needle ablation catheter having variable stiffness along its length, in accordance with an embodiment of the present specification.

In accordance with an aspect of the present specification, the needles of the needle ablation catheters are configured to have variable stiffness across their lengths. As shown in FIG. 5A, a proximal portion 5003' of a needle 5005 has a first stiffness, the middle portion 5002' has a second stiffness and a tip portion 5001 has a third stiffness. In some embodiments, the second stiffness is less than the first stiffness and the third stiffness. In some embodiments, the first and third stiffness are substantially same. In some embodiments, the first stiffness is greater than the third stiffness. In some embodiments, the first stiffness is less than the third stiffness.

Figure 5B:
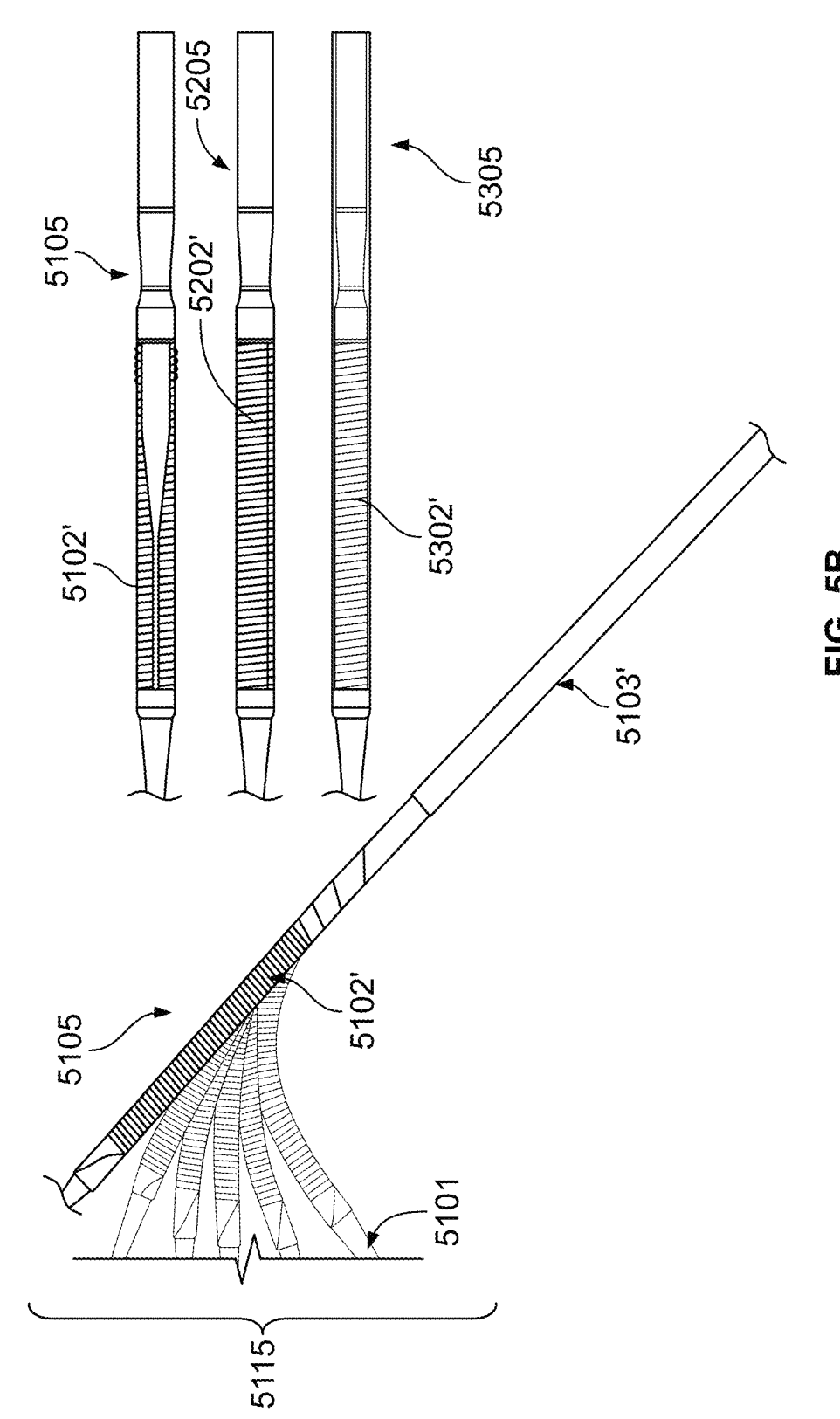
FIG. 5B shows perspective views of a plurality of needles of a needle ablation catheter having variable stiffness along their lengths, in accordance with some embodiments of the present specification.

Referring now to FIG. 4C in addition to FIGS. 5A and 5B, the middle portion 4002', 5002' includes the laser cut portion 4026 that imparts the middle portion 4002', 5002' with the second stiffness thereby enabling the needle 4005, 5005 to bend at the portion 4002', 5002' yet the comparatively higher first and third stiffness allows sufficient rigidity to the tip portion 4001, 5001 and the proximal portion 4003', 5003'. In some embodiments, the middle portion 4002', 5002' is configured to additionally include the tapered portion 4027. The tapered portion 4027 imparts further bendability and pliability to the middle portion 4002', 5002'.

FIG. 5B illustrates various needles 5105, 5205, 5305 of needle ablation catheters having variable stiffness, in accordance with some embodiments of the present specification. Each needle 5105, 5205, 5305 has a different laser cut pattern in the middle portion 5102', 5202', 5302', imparting each needle with a different stiffness in this portion and therefore a different degree of flexibility. For example, in an embodiment, needle 5105 has a middle portion 5102' laser cut such that the tip portion 5101 may be flexed in a range 5115 relative to the proximal portion 5103'. The variable stiffness allows for both bending at the middle portion and pushability along the catheter body.

Figure 5C:
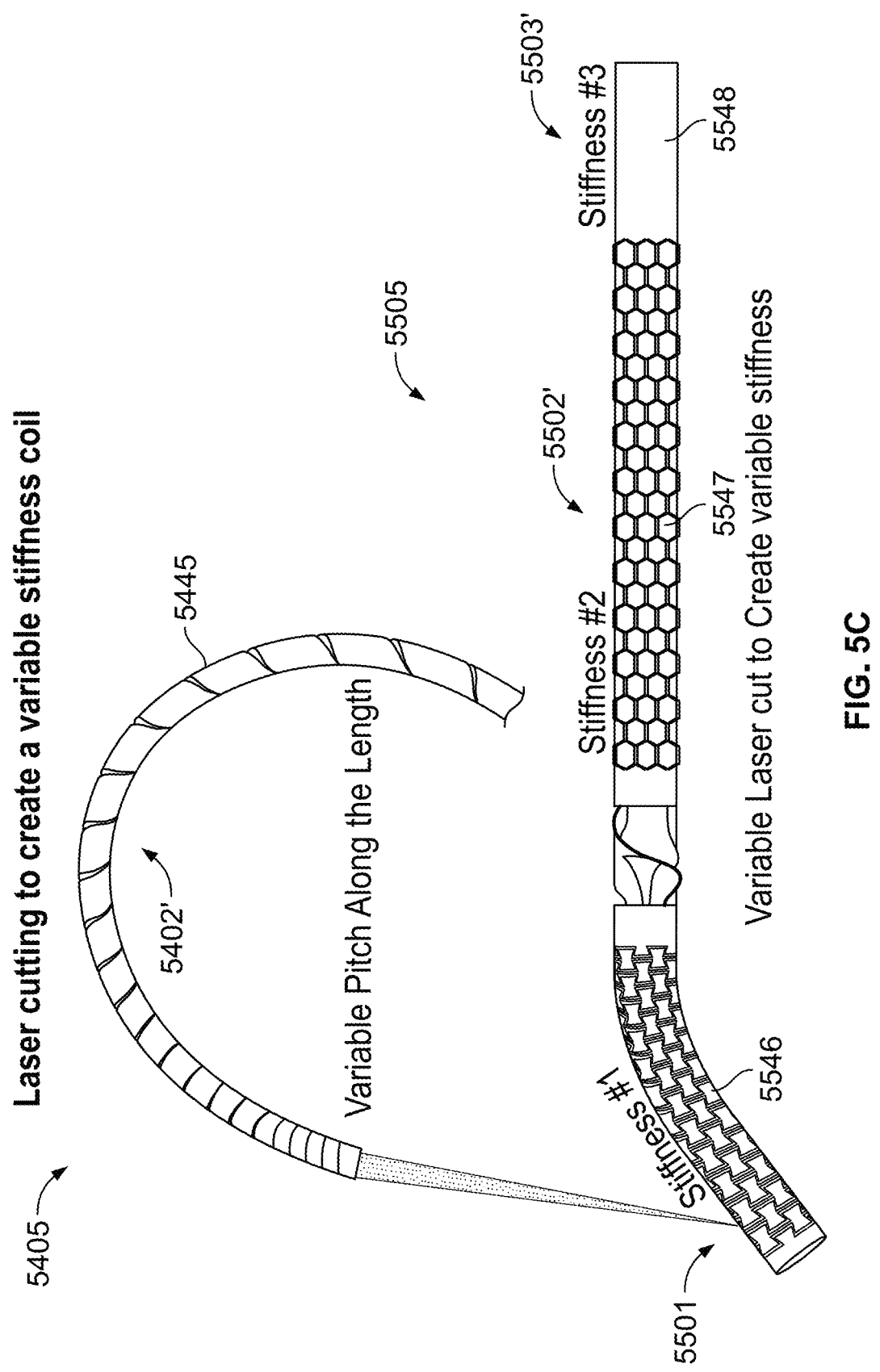
FIG. 5C shows first and second needles of needle ablation catheters having different laser cut portions, in accordance with some embodiments of the present specification.

FIG. 5C illustrates laser cutting patterns or designs to impart variable levels of stiffness to different portions of various needles 5405, 5505, in accordance with some embodiments of the present specification. As shown in FIG. 5C, in one embodiment, the middle portion 5402' of the needle 5405 is configured to have a substantially helical or spiral laser cutting 5445. A pitch of the cutting 2045 varies along the length of the middle portion 5402' to impart a predefined level of stiffness to enable the needle 5405 to bend along the middle portion 5402'. In another embodiment, a tip portion 5501 of a needle 5505 has a first laser cutting design 5546 imparting a first level of stiffness to the region, the middle portion 5502' has a second laser cutting design 5547 imparting a second level of stiffness to the region and the proximal portion 5503' has a third laser cutting design 5548 imparting a third level of stiffness to the region. In one embodiment, the first laser cutting design 5546 is such that less material of the needle 5505 in the tip portion 5501 is removed compared to the second laser cutting design 5547. As a result the second level of stiffness is comparatively less than the first level of stiffness. On the other hand, the third laser cutting design 5548 may involve removal of no or substantially no material in the proximal portion 5503'. Consequently, the third level of stiffness is greater than the first and second level of stiffness.

Figure 5D:
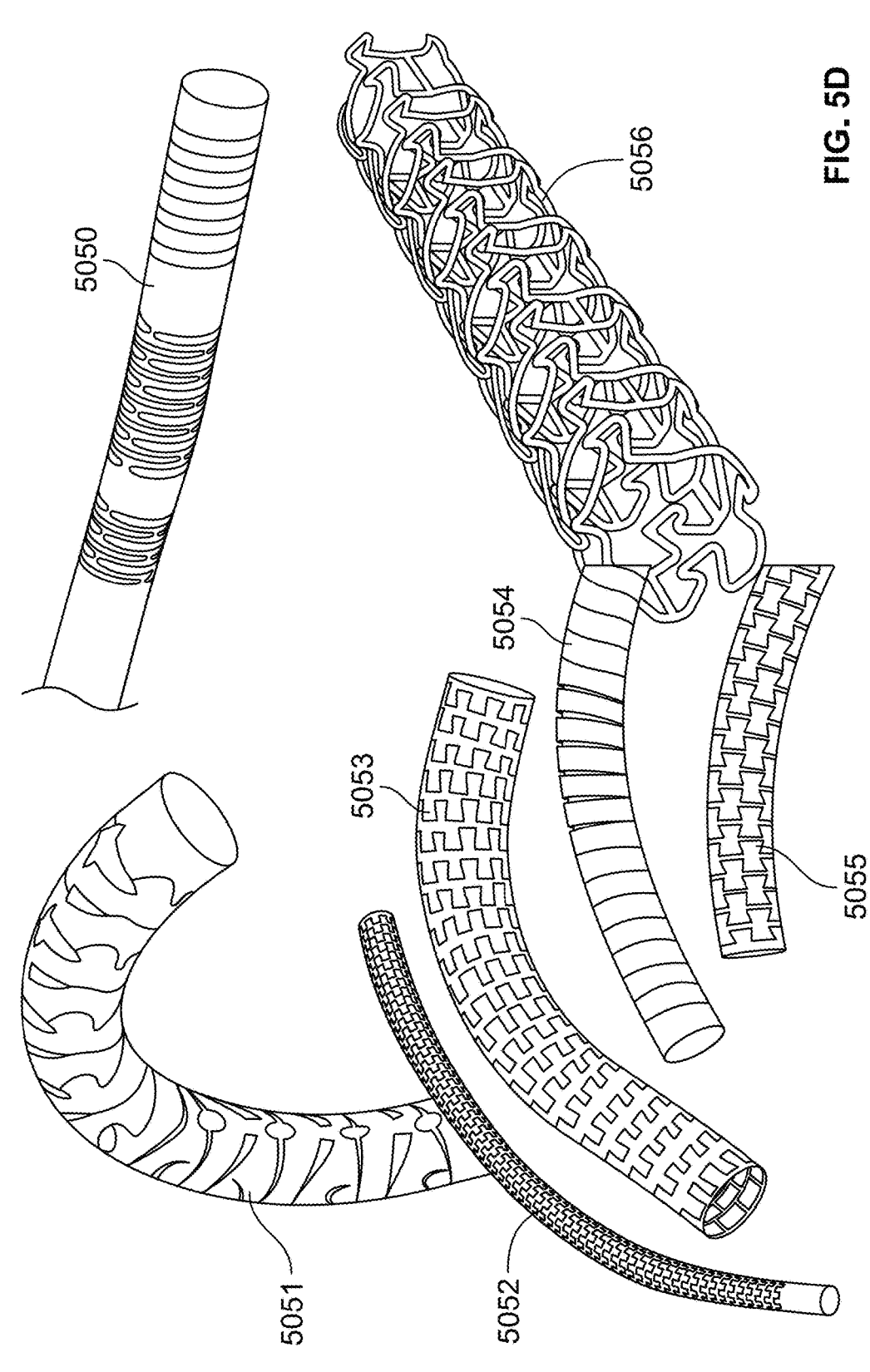
FIG. 5D shows a plurality of laser cutting patterns for a needle of a needle ablation catheter, in accordance with some embodiments of the present specification.

FIG. 5D illustrates additional laser cutting designs to impart variable levels of stiffness to different portions of various needles, in accordance with some embodiments of the present specification. The figure illustrates first, second, third, fourth, fifth, sixth and seventh laser cutting patterns 5050, 5051, 5052, 5053, 5054, 5055, 5056, respectively. For example, the pattern 5056 is sparsest and therefore imparts the least level of stiffness. Patterns 5052, 5054 and 5055 are comparatively dense, in that they involve less removal of the material of the needle, thereby corresponding to higher level of stiffness compared to the pattern 5056.

Figure 6A:
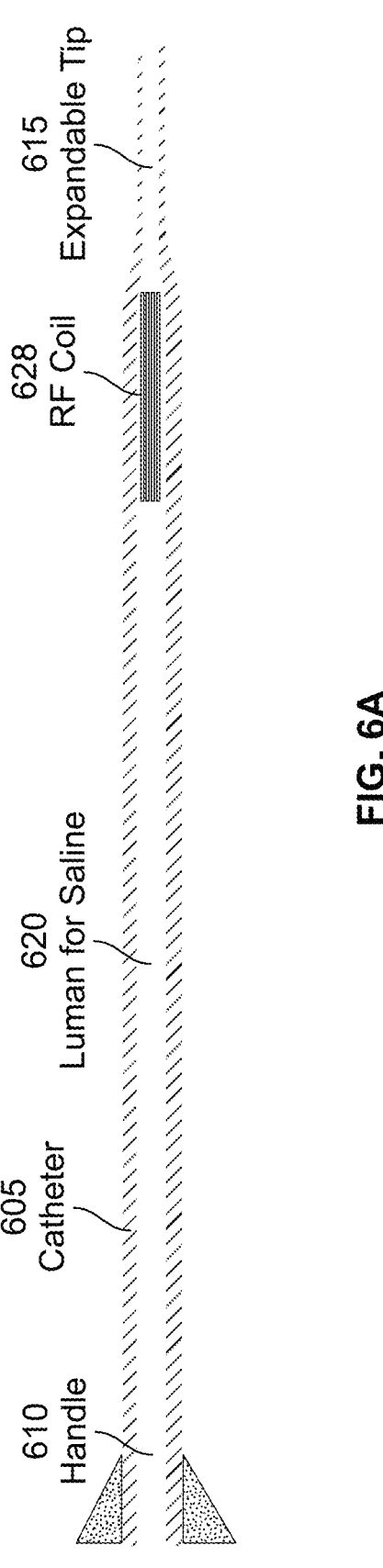
FIG. 6A is a first cross-sectional view of a catheter for insertion into a needle of the needle ablation device of FIG. 2A, in accordance with an embodiment of the present specification.
Figure 6B:
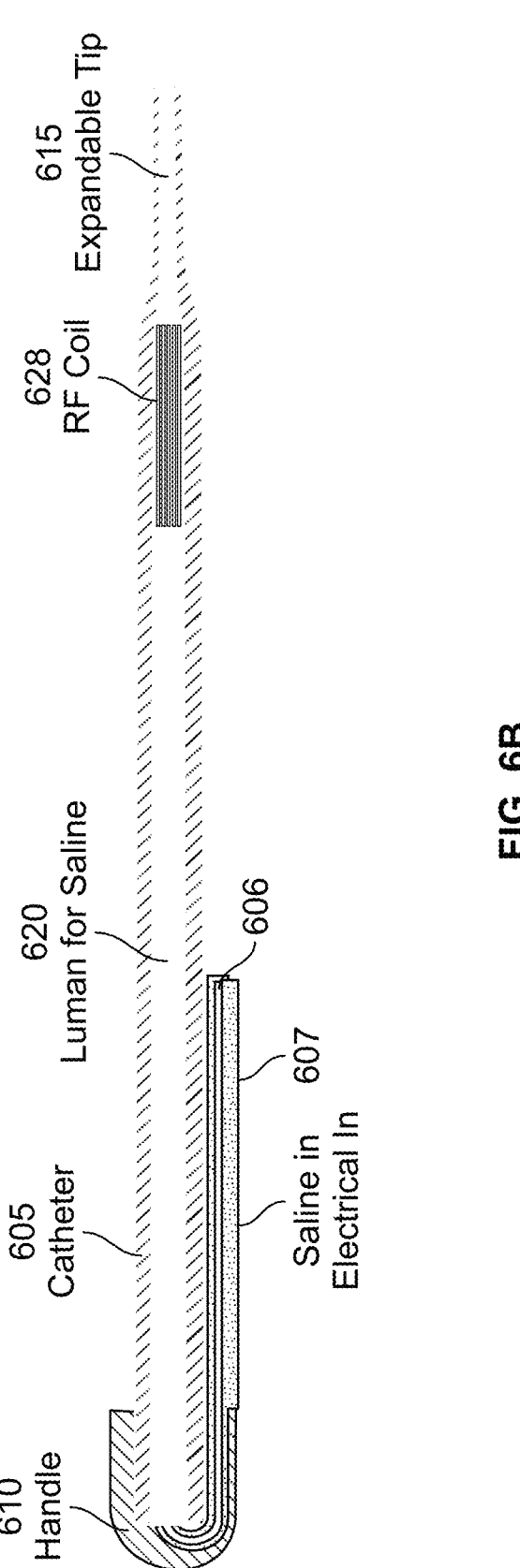
FIG. 6B is a second cross-sectional view of the catheter of FIG. 6A, in accordance with an embodiment of the present specification.

While in some embodiments, the needle 4005 houses the heating chamber 4028—as shown in FIGS. 4C and 4D, in some embodiments the heating chamber is housed in a separate vapor delivery catheter and not in the needle. FIGS. 6A and 6B illustrate longitudinal cross-sectional views of a vapor delivery catheter 605 having a handle 610 at a proximal end, an expandable tip 615 at a distal tip and a lumen 620 extending from the proximal end to the distal end of the catheter 605. As shown in FIG. 6B, in some embodiments, the handle 610 is configured to lock onto an endoscope handle without increasing a length of a resultant lever arm significantly. Saline and electrical connections (for the heating chamber 628) enter the handle 610 from the proximal end.

Referring now to FIGS. 6A and 6B, at least one flexible heating chamber 628 (comprising a plurality of electrodes) is positioned within the lumen 620 proximate a proximal end of the expandable tip 615. In accordance with an embodiment, an outer diameter of the expandable tip 615 is less than an inner diameter of a lumen of an ablation needle, such as the needle 4005 of FIGS. 4C and 4D, so that the tip 615 may slide easily into the lumen of the needle. In some embodiments, the vapor delivery catheter 605 is positioned within the needle, which in turn is positioned within an outer catheter. In some embodiments, the inner diameter of the outer catheter is 3.5 mm, an outer diameter of the needle 2005 is 3.1 mm and an outer diameter of the vapor delivery catheter 605 is 2.1 mm.

During operation saline enters the catheter 605 through the proximal end and is converted into steam/vapor that enters the lumen of the needle through the expandable tip 615. In embodiments, the catheter 605 includes a saline in port 606 for the delivery of saline and a connector 607 for an electrical connector for current delivery for the RF coil/heating chamber 628. The expandable tip 615 gets heated with the flowing vapor and expands radially such that the outer diameter of the tip 615 expands to approximate the inner diameter of the lumen of the needle. This causes blocking of the space between the expanded tip 615 and the needle to form a seal and prevent backflow of vapor between the catheter 605 and the needle.

Figure 6C:
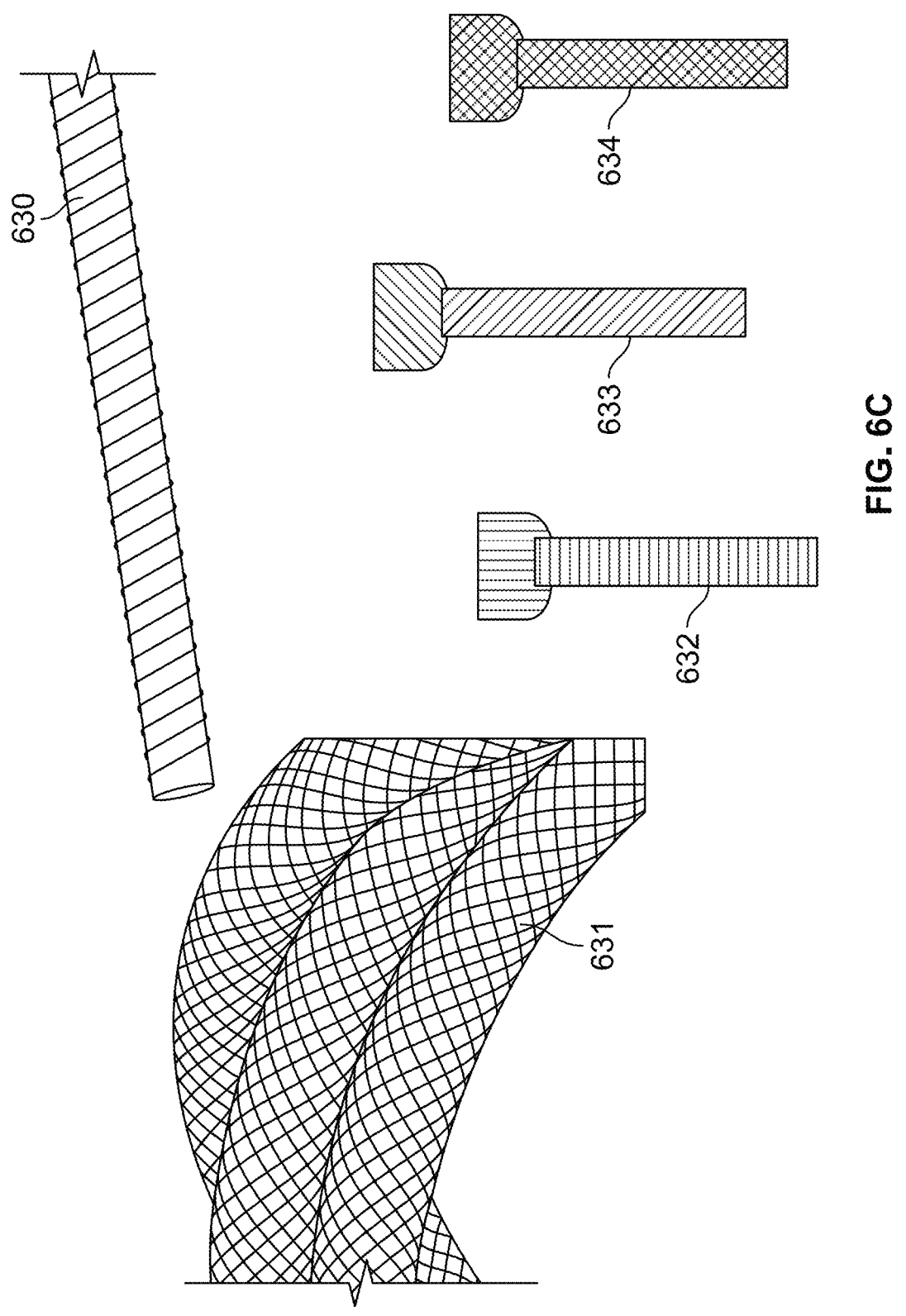
FIG. 6C illustrates a first plurality of configurations of an expandable tip of the catheter of FIG. 6A, in accordance with some embodiments of the present specification.

In some embodiments, the expandable tip 615 has an expandable metal coil covered by an insulating thermoplastic such as, but not limited to, PTFE, ePTFE, and silicone. In some embodiments, the metal of the expandable metal coil is a shape memory metal that exhibits radial expansion due to a transformation from a martensite state to an austenite state. In some embodiments, the metal of the expandable metal coil is steel that exhibits radial expansion due to thermal expansion of the steel. FIGS. 6C and 6D illustrate first and second plurality of expandable tip designs, in accordance with various embodiments of the present specification. FIG. 6C shows first, second, third, fourth and fifth web or mesh patters 630, 631, 632, 633, 634 respectively, for the expandable tip 615. FIG. 6D shows sixth, seventh, eighth and ninth web or mesh patterns 635, 636, 637, 638 respectively, for the expandable tip 615.

Positioning Elements

The positioning elements in FIGS. 7A to 7E have been disclosed in the aforementioned related applications. However, in this case, the positioning elements have been modified such that, upon the pressure within a volume enclosed by two or more positioning elements meeting or exceeding a predefined threshold value, such as 5 atm, the positioning element deforms by, for example, have one or more components, such as a plate, disc portion, flap, mesh weaving, bend inward or outward from the planes defining the original deployed shape to increase fluid flow from inside the enclosed volume to an area outside the enclosed volume. The deformation may be accomplished by adding a hinge, crease, groove, more flexible material, or other point of decreased material strength 51 between one or more of the components and the rest of the positioning element.

FIG. 7A illustrates an ablation device with a coaxial catheter design, in accordance with an embodiment of the present specification. The coaxial design has a handle 52a, an infusion port 53a, an inner sheath 54a and an outer sheath 55a. The outer sheath 55a is used to constrain the positioning device 56a in the closed position and encompasses ports 57a. FIG. 7B shows a partially deployed positioning device 56b, with the ports 57b still within the outer sheath 55b. The positioning device 56b is partially deployed by pushing the catheter 54b out of sheath 55b.

FIG. 7C shows a completely deployed positioning device 56c. The infusion ports 57c are out of the sheath 55c. The length 'l' of the catheter 54c that contains the infusion ports 57c and the diameter 'd' of the positioning element 56c are predetermined/known and are used to calculate the amount of thermal energy needed. FIG. 7D illustrates a conical design of the positioning element. The positioning element 56d is conical with a known length 'l' and diameter 'd' that is used to calculate the amount of thermal energy needed for ablation. FIG. 7E illustrates a disc shaped design of the positioning element 56e comprising circumferential rings 59c. In some embodiments, positioning element 56e has a diameter ranging from 5 mm to 55 mm. Positioning element 56e may be of any round shape, and may not necessarily be a perfect circle. The circumferential rings 59e are provided at a fixed predetermined distance from the catheter 54e and are used to estimate the diameter of a hollow organ or hollow passage in a patient's body.

Hood Vapor Delivery Device

Figure 8A:
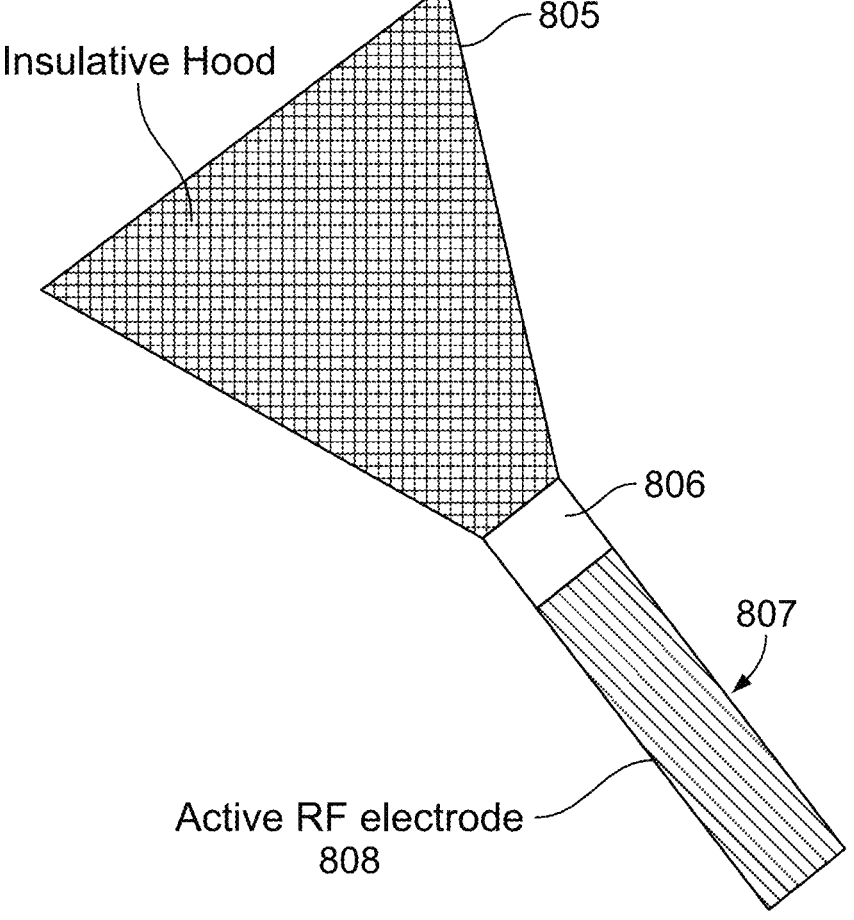
FIG. 8A illustrates a conical hood shaped positioning element, in accordance with an embodiment of the present specification.

FIG. 8A illustrates a positioning element or attachment 805, in accordance with an embodiment of the present specification. The positioning element 805 is configured as a substantially conical insulating hood that is attached proximate to a tip 806 of a catheter 807. In some embodiments, the positioning element has length and breadth of 0.5 cm and 5 cm, respectively. In alternative embodiments, the positioning element 805 is of a different structure, such as including and not limited to square, rectangular, and parallelogram. The catheter 807, in an embodiment, accommodates at least one flexible heating chamber 808 comprising a plurality of RF electrodes to convert saline, entering a proximal end of the catheter 807, into steam/vapor.

Figure 8B:
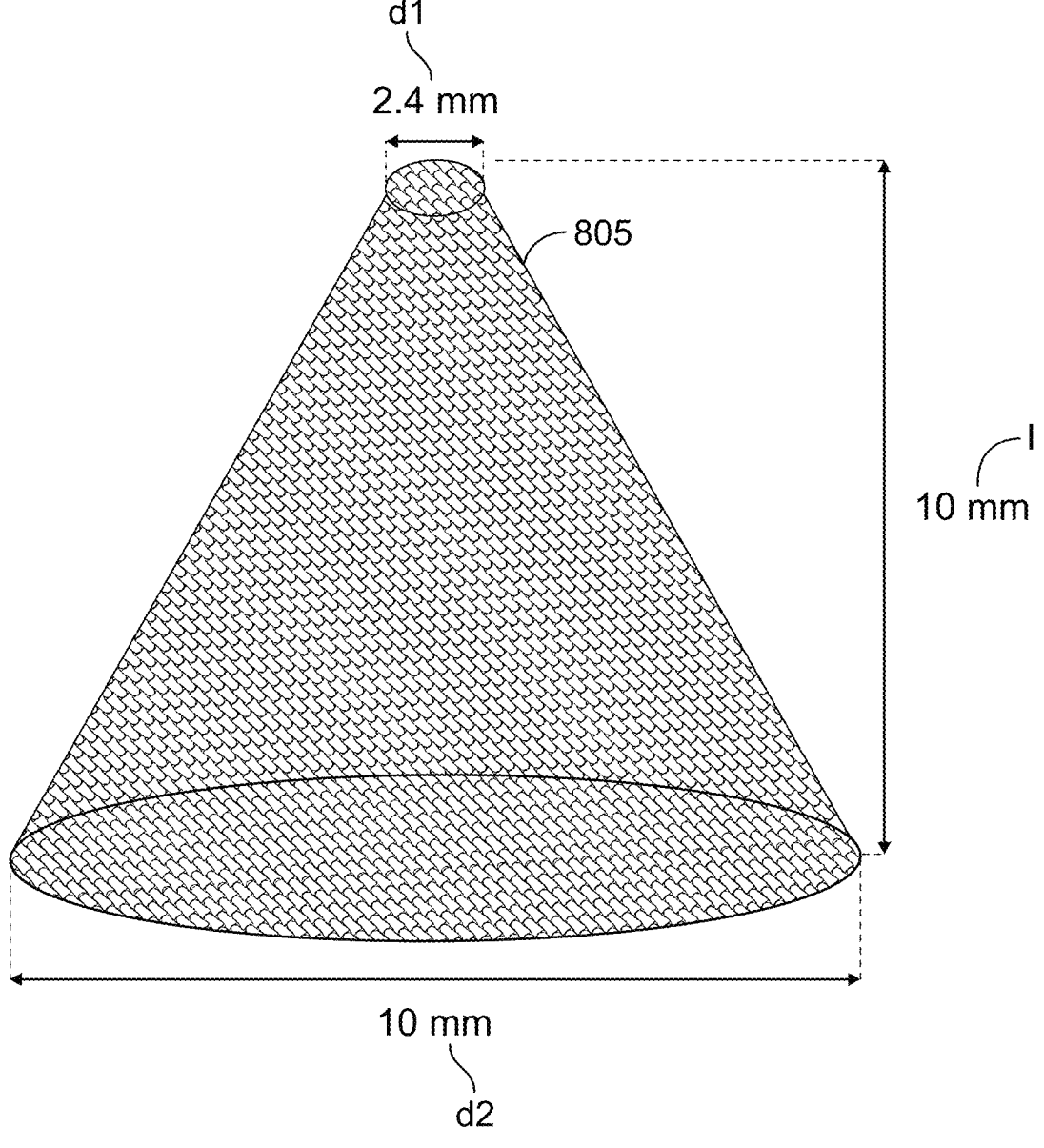
FIG. 8B illustrates a cross-sectional view of the conical hood shaped positioning element, in accordance with an embodiment of the present specification.

FIG. 8B illustrates a first set of exemplary dimensions for the positioning element 805, in accordance with an embodiment of the present specification. The substantially conical shaped hood or positioning element 805 has a proximal diameter $d_1$ of 2.4 mm, a distal diameter $d_2$ of 10 mm and a length 'l' of 10 mm. In various embodiments, length 'l' ranges from 0.1 mm to 10 cm and the distal diameter $d_2$ ranges from 0.1 mm to 10 cm. In preferred embodiments, the length 'l' and the distal diameter $d_2$ range from 5 mm to 5 cm.

Figure 8C:
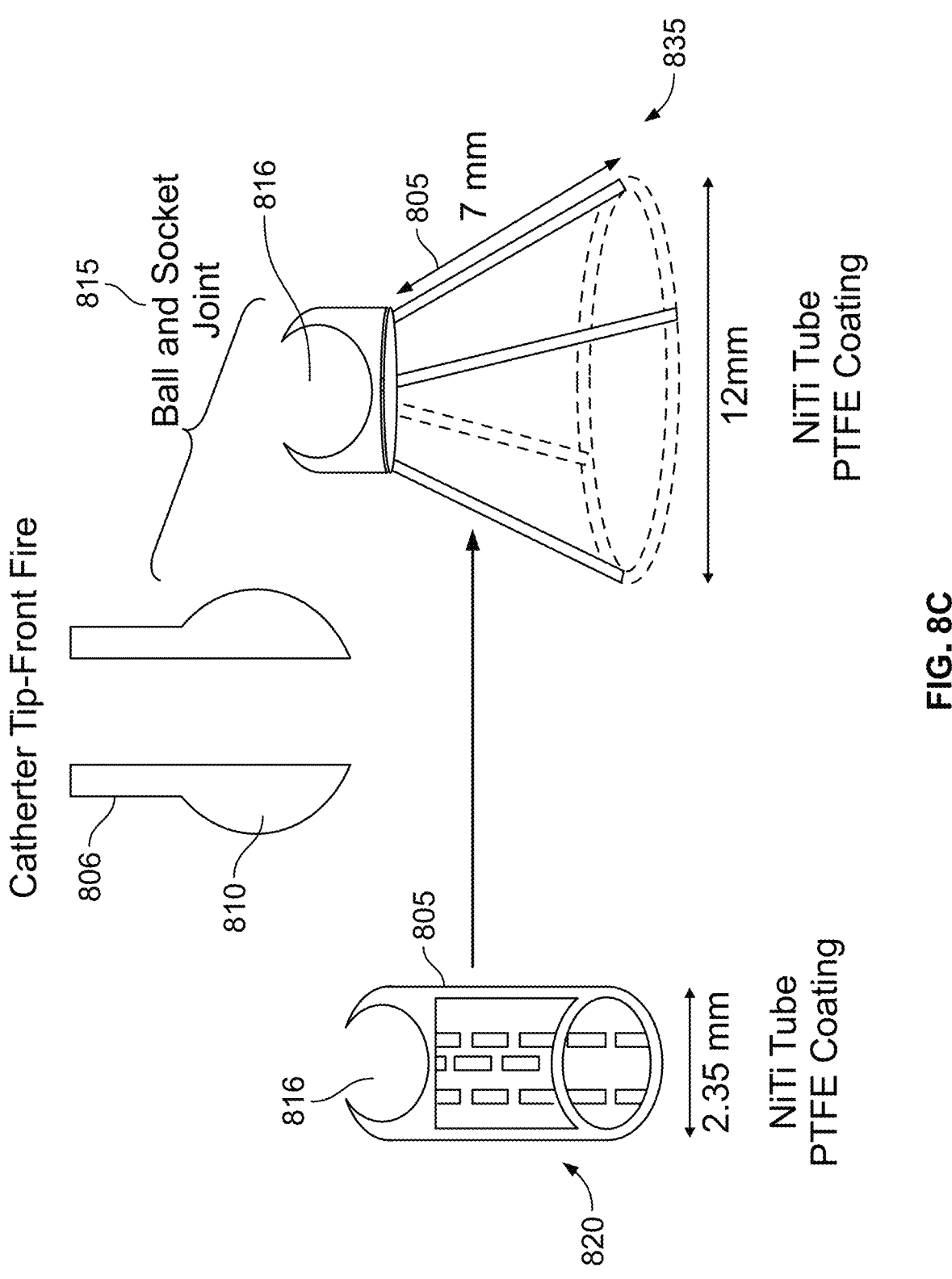
FIG. 8C illustrates a ball and socket attachment of the conical hood shaped positioning element to a catheter tip, in accordance with an embodiment of the present specification.
Figure 8D:
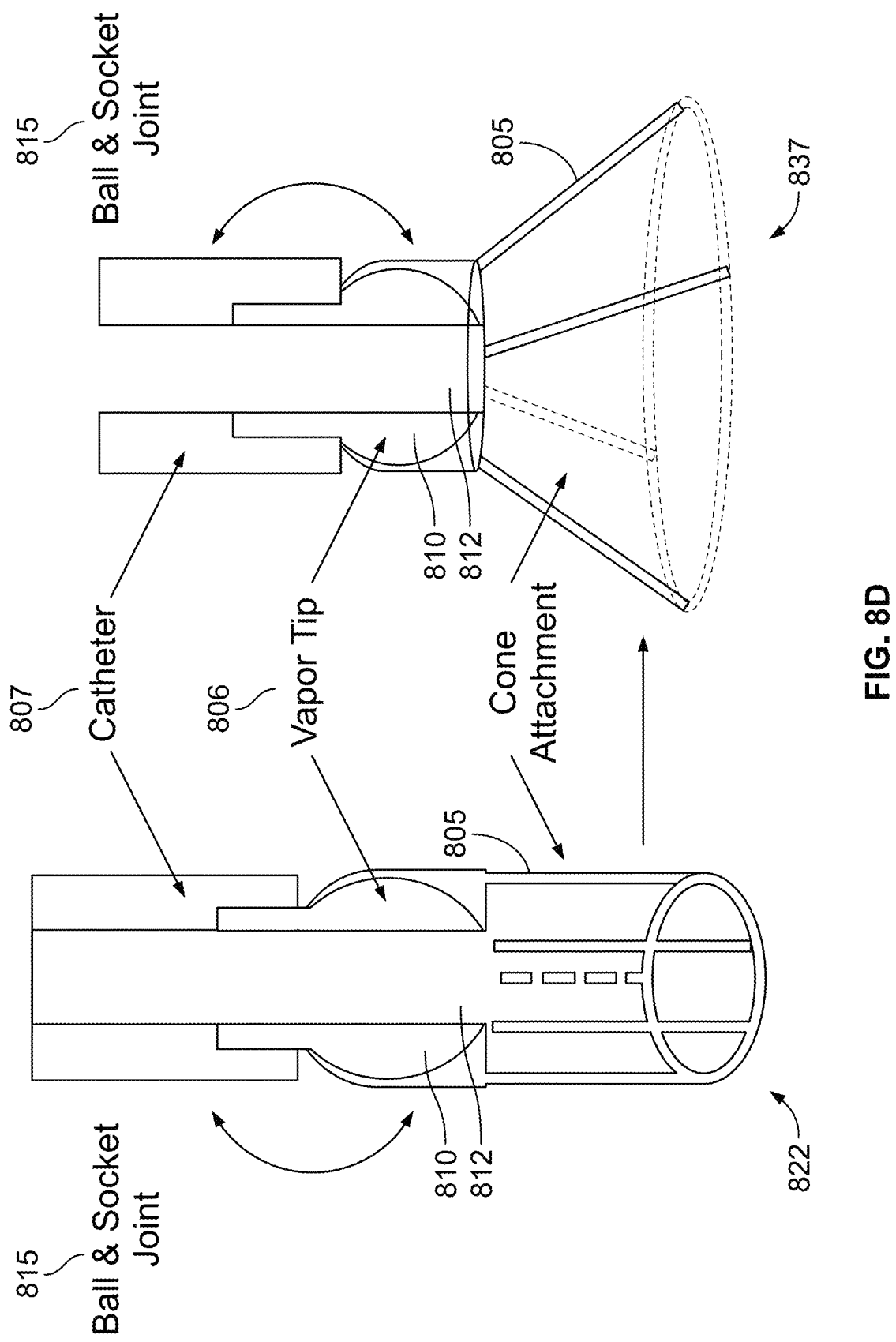
FIG. 8D illustrates cross-sectional views of the conical hood shaped positioning element attached to the catheter tip, in accordance with an embodiment of the present specification.

FIGS. 8C and 8D illustrate a ball and socket attachment 815 to couple the positioning element 805 to the tip 806 of the catheter 807, in accordance with an embodiment of the present specification. The tip 806, at its distal end, has a ball 810 and a front-fire or straight-fire port 812. The positioning element 805 has a socket 816 at its proximal end. As shown in FIG. 8D, when the positioning element 805 is attached to the tip 806, the ball 810 is accommodated within the socket 815 to form the ball and socket attachment 815.

Referring now to FIGS. 8C and 8D, the ball and socket attachment 815 enables ample movement of the positioning element 805 with respect to the tip 806. In some embodiments, a minimum range of movement, of the positioning element 805 with respect to the tip 806, is 90 degrees in any direction. The views 820, 822 illustrate the positioning element 805 in a closed configuration, such as when the positioning element 805 and the tip 806 are positioned within an outer catheter. In some embodiments, the positioning element 805 is in a substantially cylindrical shape of diameter 2.35 mm when in the closed configuration. The views 835, 837 illustrate the positioning element 805 in an open or deployed configuration, such as when the positioning element 805 and the tip 806 are pushed out of the outer catheter. The positioning element 805 acquires a substantially conical shape, in the open or deployed configuration, having a base diameter of 12 mm and a side of 7 mm, in some embodiments. In some embodiments, the positioning element 805 is a NiTi tube, web or mesh coated with PTFE, ePTFE or silicone. In some embodiments, the coating, such as of silicone, covers a portion of or the entirety of the positioning element 805. In some embodiments, the silicone-coated positioning element 805 has one or more pores with diameter of each pore ranging from 10 microns to 1000 microns. The pores may allow for air or steam to vent out from the chamber.

FIG. 8E shows a first perspective view 840, a second perspective view 842 and a longitudinal cross-sectional view 845 of the positioning element 805 attached to the tip 806 of the catheter 807, in accordance with an embodiment of the present specification. The catheter 807 is shown extending out from an outer catheter 847 such that the positioning element 805 is in the deployed configuration wherein the positioning element 805 acquires a substantially conical configuration. The tip 806 includes the front-fire or straight-fire port 812 at a distal end and/or two pairs of side ports 813 formed diametrically opposed on the sides of the tip 806 and positioned proximate the distal end of the tip 806. In some embodiments, the port 812 has a diameter of 0.9 mm, to allow a guide wire through, while the ports 813 have a diameter of 0.3 mm. In some embodiments, the catheter 807 has a length of 2500 mm from a proximal end of the catheter 807 to a distal end of the positioning element 805. In some embodiments, the outer catheter 847 has a length of 1800 mm (+/−50 mm) from a proximal end to a distal end of the outer catheter 847.

FIG. 8F illustrates perspective and cross-sectional views of a first configuration 850 of the positioning element 805, in accordance with an embodiment of the present specification. The first configuration 850 comprises a substantially cylindrical proximal portion 851*f* and a substantially conical distal portion 852*f*. In some embodiments, the substantially cylindrical proximal portion 851*f* is attached, such as by using glue, to the tip 806 as shown in FIG. 8E. In the first configuration 850, the substantially cylindrical proximal portion 851*f* has a diameter of 2.4 mm and a length of 3 mm, the substantially conical distal portion 852*f* has a base diameter of 10 mm (+/−1 mm), a length of 10 mm (+/−1 mm) and a vertex or opening angle of 41.6 degrees. The total length of the proximal and distal portions 851*f*, 852*f* is 13 mm.

FIG. 8G illustrates perspective and cross-sectional views of a second configuration 855 of the positioning element 805, in accordance with an embodiment of the present specification. The second configuration 855 comprises a substantially cylindrical proximal portion 851*g* and a substantially conical distal portion 852*g*. In some embodiments, the substantially cylindrical proximal portion 851*g* is attached, such as by using glue, to the tip 806 as shown in FIG. 8E. In the second configuration 855, the substantially cylindrical proximal portion 851*g* has a diameter of 2.4 mm and a length of 5 mm, the substantially conical distal portion 852*g* has a base diameter of 15 mm (+/−2 mm), a length of 15 mm (+/−1 mm) and a vertex or opening angle of 45.6 degrees. The total length of the proximal and distal portions 851*g*, 852*g* is 20 mm.

FIG. 8H illustrates perspective and cross-sectional views of a third configuration 860 of the positioning element 805, in accordance with an embodiment of the present specification. The third configuration 860 comprises a substantially cylindrical proximal portion 851*h* and a substantially conical distal portion 852*h*. In some embodiments, the substantially cylindrical proximal portion 851*h* is attached, such as by using glue, to the tip 806 as shown in FIG. 8E. In the third configuration 860, the substantially cylindrical proximal portion 851*h* has a diameter of 2.4 mm, the substantially conical distal portion 852*h* has a base diameter of 20 mm (+/−2 mm), a length of 20 mm (+/−2 mm) and a vertex or opening angle of 47.5 degrees. The total length of the proximal and distal portions 851*h*, 852*h* is 25 mm.

Figure 8I:
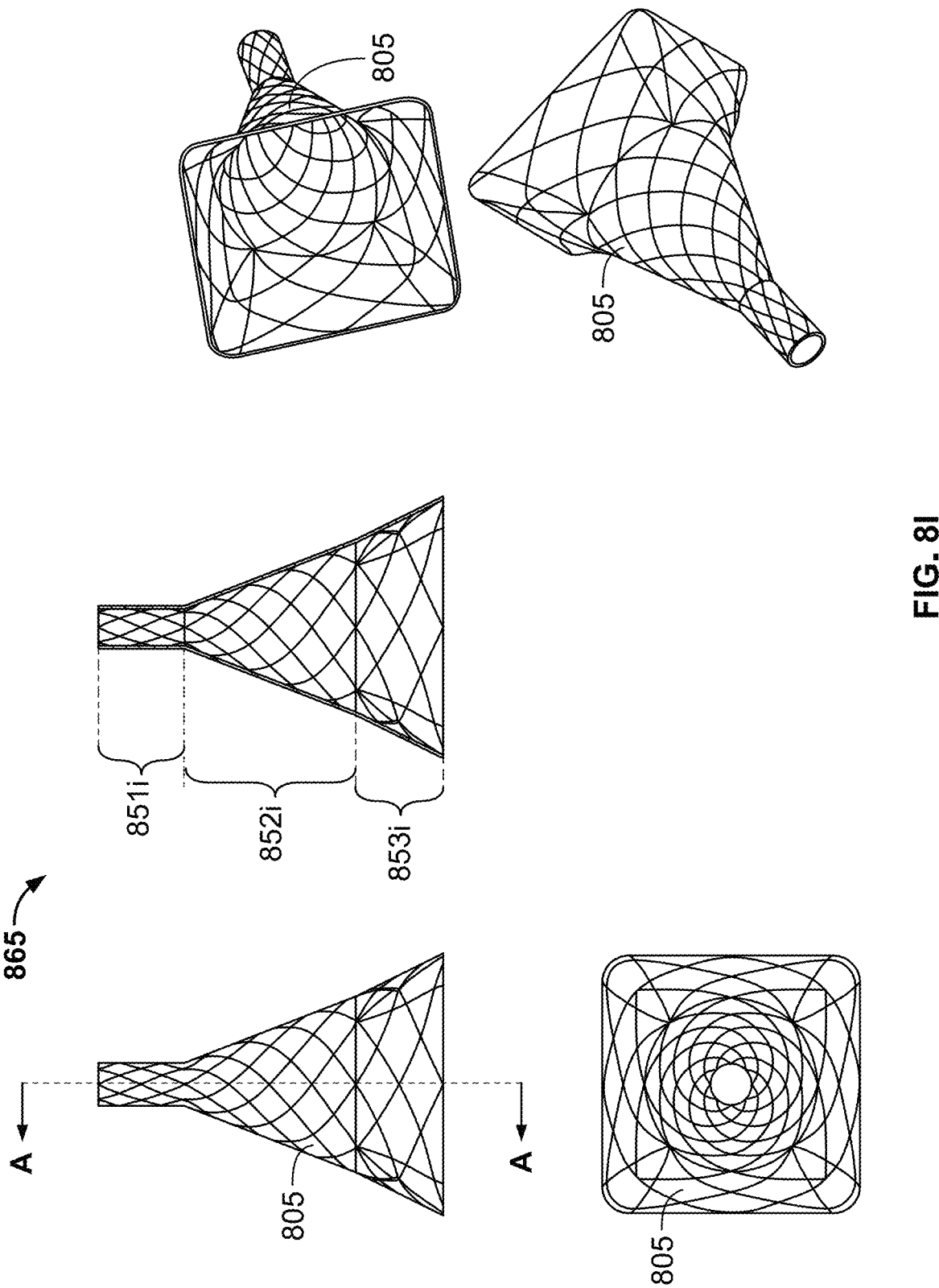
FIG. 8I shows a fourth configuration of the conical hood shaped positioning element having a pyramidal base, in accordance with an embodiment of the present specification.

FIG. 8I illustrates perspective and cross-sectional views of a fourth configuration 865 of the positioning element 805, in accordance with an embodiment of the present specification. The fourth configuration 865 comprises a substantially cylindrical proximal portion 851*i*, a substantially conical middle portion 852*i* and a substantially pyramidal distal portion 853*i*. The substantially pyramidal distal portion 853*i* is attached as a base to the substantially conical middle portion 852*i*. In an alternate embodiment, the entire positioning element 805 is substantially pyramidal shape.

In some embodiments, the substantially cylindrical proximal portion 851*i* is attached, such as by using glue, to the tip 806 as shown in FIG. 8E. In the fourth configuration 865, the substantially cylindrical proximal portion 851*i* has a diameter of 2.4 mm and a length of 5 mm, the substantially conical middle portion 852*i* has a length of 10 mm (+/−2 mm) and a vertex or opening angle of 41.6 degrees, while the substantially pyramidal distal portion 853*i* has a square base having each side of 15 mm (+/−2 mm). The total length of the middle and distal portions 852*i*, 853*i* is 15 mm (+/−2 mm). The total length of the proximal, middle and distal portions 8511, 852*i*, and 853*i* is 20 mm (+/−2 mm). Though FIGS. 8A through 8I depict positioning elements having conical and pyramidal or rectangular shapes, in other embodiments, the positioning element or attachments may have other three dimensional polygonal or curved shapes.

In various embodiments, the positioning element is mechanically compressed for passage into an endoscope channel or an outer catheter and expands when deployed or protruded.

In some embodiments, positioning element 805 comprises a shape memory alloy, such as Nitinol, thereby allowing it to transform from a compressed configuration for delivery through an endoscope to an expanded configuration for treatment. In some embodiments, the compressed configuration approximates a cylindrical shape, to enable passing through the lumen of an endoscope, attached to the distal end of the catheter, and has a 5 mm diameter and a length in a range of 0.5 cm to 5 cm. On expansion, the positioning element 805 has a surface area (from which the steam exits) in a range of 1 cm² to 6.25 cm². In a preferred embodiment, the surface area is square with dimensions of 1.5 cm by 1.5 cm. On expansion, the length shortens somewhat so the expanded configuration would have a shorter length than the compressed configuration. In an embodiment, use of an ablation catheter with positioning element 805 creates a seal forming an ablation area having a radius of 1 cm, a length of 1 cm, a surface area of 6.28 cm² and a treatment volume of 3.14 cm³.

In some embodiments, positioning element 56 (56a-56c of FIGS. 7A-7E) and 805 (FIGS. 8A-8I) comprises scalloped petals on a distal edge of its surface area. The scalloped petal-shaped positioning element structure enables the contact between the surface of the positioning element and the surrounding circumference of the GI tract, such as for example the duodenum, to provide a partial seal. Gaps between adjacent rounded portions of the scalloped petal-shaped positioning element provide for space for vapor or energy to escape outside of the targeted segment of the duodenum.

Referring to the various embodiments of the positioning elements described in context of FIGS. 7A to 7E, and 8A to 8I, in some embodiments, a range of vapor delivery times is between 1 second to 20 seconds for applications of the gastrointestinal (GI) areas. The duration where the mucosal temperature is >60° C. but <110° C. is between 1 second and 10 seconds. Multiple sessions could be repeated after an off time of >1 second and <30 minutes. Alternatively, the off time is defined by the temperature of the ablation zone, which is reduced to at least 45° C. or by more than 25% from the peak mucosal temperature during ablation, after which the power supply may be turned on again to increase the temperature. The duration of each session could be the same or different. In one embodiment, the duration of two or more sessions is the same, and in another embodiment the duration of a first session is less than a duration of a second session. In another embodiment, a duration of a first session is greater than a duration of a second session.

In various embodiments, multiple sessions with variable times/doses are applied. In some embodiments, each session is defined by a therapeutic time (T1) and dose (D1). In an embodiment, a first session is delivered for a time T2 that is less than T1 using dose D1 or for a time T2 that is less than, greater than or equal to T1 but at a dose D2 that is less than D1. The overall goal is to deliver less total energy in the first session than would be required to achieve an effective ablation of the mucosal layer. More specifically, the vapor dose applied in the first session is for a time such that the total energy delivered during the first session causes a structural change in the mucosa, but not an ablation of more than 25% of the mucosa in terms of surface area (preferably less than 25%, less than 20%, less than 15%, less than 10% and most preferably less than 5%) and not an ablation of more than 15% of the submucosa in terms of surface area (preferably less than 15%, less than 10%, and most preferably less than 5%).

After the first session, the physician waits for a time from 1 second to 30 minutes for a degree of said structural change to form. The structural change is at least one of edema, cellular injury, alternation of metabolic cellular processes, and/or inflammation but not an effective ablation that results in tissue necrosis. Certain structural changes, such as edema formation, help protect the muscularis propria layer from sustaining clinically significant thermal injury. After the structural change sets in, the physician delivers a second dose of vapor with a dose in a range of 1×T1 to 5×T1. Negative pressure, in the form of suction or vacuum, is applied to the ablated zone after the steam is turned off to increase blood flow to cool the tissue. This increase in blood flow could also increase the edema formation. Edema formation helps protect the muscularis propria layer from sustaining clinically significant thermal injury.

Figure 8J:
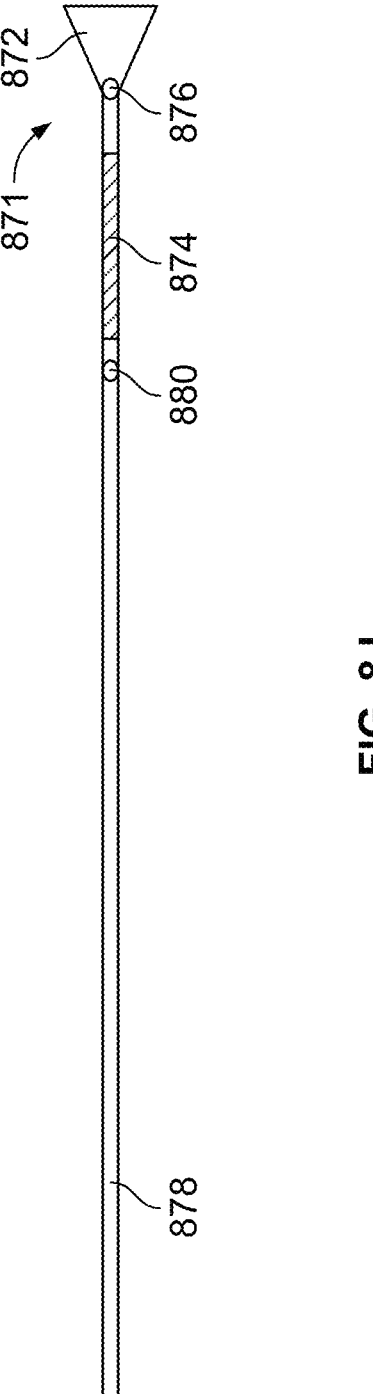
FIG. 8J illustrates an ablation catheter with a conical shaped attachment or positioning element and an electrode heating chamber, in accordance with some embodiments of the present specification.

FIG. 8J illustrates an ablation catheter 870 with at least one conical shaped attachment or positioning element 872 and an electrode heating chamber 874, in accordance with some embodiments of the present specification. In various embodiments, the attachment or positioning element 872 is similar to those described with reference to FIGS. 8A through 8I. The attachment or positioning element 872 is positioned at the distal end of the catheter 870, and at least one port 876 is positioned at the distal end of the catheter such that the port will deliver vapor or steam into a volume enclosed by the attachment or positioning element once the catheter 870 is deployed. In embodiments, distal tip 871 of the catheter 870 comprises the at least one port 876 and the at least one positioning element 872 attached to the distal tip 871 such that, upon being in an operational configuration, the at least one positioning element 872 encircles the at least one port 876 and is configured to direct all vapor exiting from the at least one port 876. In some embodiments, the attachment or positioning element 872 is comprised of a shape memory metal and is transformable from a first, compressed configuration for delivery through a lumen of an endoscope and a second, expanded configuration for treatment. Electrode heating chamber 874 is positioned within a lumen of the catheter body 878 and, in embodiments, is in a range of 1 mm to 50 cm from the delivery port 876. In some embodiments, the catheter 870 includes a filter 880 with micro-pores which provides back pressure to the delivered steam, thereby pressurizing the steam. The predetermined size of micro-pores in the filter determine the backpressure and hence the temperature of the steam being generated.

In various embodiments, the positioning elements may be any one of a disc, hood, cap, or inflatable balloon. In some embodiments, the positioning elements include pores for the escape of air or ablative agent. A fluid, such as saline, is stored in a reservoir, such as a saline pump, connected to the catheter 870. Delivery of the ablative agent is controlled by a controller and the treatment is controlled by a treating physician via the controller. The controller includes at least one processor in data communication with the saline pump and a catheter connection port in fluid communication with the saline pump. The controller is programmed to determine an amount of energy needed to ablate a tissue, such as for example a duodenal tissue. The controller is also programmed to limit a maximum dose of ablative agent based on a type of disorder being treated. The type of disorder may be a metabolic disorder, such as and not limited to Type-II Diabetes Mellitus, obesity, hyperlipidemia, NAFLD, or NASH. The controller is further programmed to limit the amount of energy delivered such that >50% of a contiguous circumference of the duodenal mucosa and <50% of contiguous circumference of a duodenal adventitia over a contiguous length of >2 cm is ablated. The treatment controlled by the controller and administered by the catheter 870 improves an abnormal measure of a metabolic syndrome prior to the ablation treatment is by 3 months and sustains the improvement through at least 6 months after treatment. In embodiments, metabolic disorder of Type-II Diabetes Mellitus where an abnormal measure prior to the ablation treatment is an elevated HbA1C is improved by at least 0.2 gm % by 3 months and stays improved by at least 0.2 gm % by 6 months. In embodiments, metabolic disorder of obesity where an abnormal measure prior to the ablation treatment is an elevated total body weight, is improved by at least 2% by 3 months and stays improved by at least 2% by 6 months. In embodiments, metabolic disorder of obesity where an abnormal measure prior to the ablation treatment is an elevated excess body weight, is improved by at least 5% by 3 months and stays improved by at least 5% by 6 months. In embodiments, metabolic disorder of hyperlipidemia where an abnormal measure prior to the ablation treatment is an elevated total cholesterol or LDL cholesterol, is improved by at least 5% by 3 months and stays improved by at least 5% by 6 months. In embodiments, metabolic disorder of NASH and/or NAFLD where an abnormal measure prior to the ablation treatment is an elevated HbA1C, is improved by at least 0.2 gm % by 3 months and stays improved by at least 0.2 gm % by 6 months. In some embodiments, at least one optional sensor monitors changes in an ablation area to guide flow of ablative agent. In some embodiments, the optional sensor comprises at least one of a temperature sensor or pressure sensor.

FIG. 8K illustrates multiple views of another embodiment of a distal positioning element or attachment 800k that is used with ablation catheters, for providing focused ablation, in accordance with the present specification. Distal attachment 800k is configured to be attached to a distal end of an endoscope. The ablation catheter is inserted through the working channel of the endoscope and positioned beyond the end of the working channel, within view of the endoscopic image. Distal attachment 800k is in the form of a cap that includes a polygonal shaped outlet port 802k for focused delivery of steam, and which defines the ablation zone or footprint that captures and concentrates the vapor. The footprint of outlet port 802k is shaped in the form of a polygonal to allow for easy adjacent positioning without overlap. The outlet port 802k creates an ablation zone that has a linear edge, allowing a user to position the catheter to border the previous ablation zone and align the straight edge of the polygon shape to a previously treated area. In the embodiments depicted in FIG. 8K, the outlet port 802k is rectangular shaped, and has length of ranging from 10 mm to 30 mm and a width ranging from 5 mm to 15 mm. FIG. 8L illustrates multiple views of another embodiment of a distal positioning element, similar to the distal positioning element 800k of FIG. 8K, comprising an outlet port 802l of a length of 18 mm and a width of 15 mm, in accordance with some embodiments of the present specification. The outlet 802k is at an angle to the distal end of the distal cap 800k in some embodiments the angle is 20 degrees. An outer edge or surface 804k of the distal cap 800k is rounded or curved to provide an atraumatic tip and prevent injury during intubation and advancement through the GI tract, avoiding edges that are too sharp and could cut the patient's anatomy, for example, the gastrointestinal (GI) tract. A proximal section 806k of the distal cap 800k is attached at an angle to the outlet port 802k. Section 806k has a tubular configuration forming a lumen 808k. In some embodiments, the angle of attachment of section 806k to a proximal surface of the distal cap 802k is approximately 20 degrees to allow for direct visualization of the target tissue through the endoscope. A proximal portion 810k of section 806k slides over and covers a distal portion of the endoscope to which the cap 800k is attached. Additionally, a distal portion 812k of section 806k is fixed at an angle to the proximal surface of outlet port 802k. In embodiments, a stiffening element is configured along the angle of attachment on outer surfaces of distal portion 812k and outlet port 802k.

Lumen 808k at its proximal side, is configured to be inserted into the outlet port of the catheter. Steam is directed from the lumen of the catheter, through its outlet and the lumen 808k of the cap 800k, and out the polygonal outlet port 802k for focused ablation when the outlet port of the cap is positioned against the target tissue. Position of at least one electrode proximate the distal end of the catheter ensures steam has a very short distance to travel to reach a target tissue after being generated.

Referring to FIG. 8K, the distal cap 800k is configured to be tilted or biased to one side, allowing for an even more focused ablation of a target tissue. In embodiments, the proximal end 810k of lumen 808k attaches to the distal end 812k of lumen 808k with a depression or a bellow shape 816k along the circumference of the tubular lumen 808k. At least one pivot point 818k on a side of the lumen 808k along the bellow shape 816k is configured to allow articulation of the lumen 808k in one direction, while limiting motion in a direction perpendicular to the one direction, in a lateral plane formed by the bellow shape 812k. In some embodiments, two pivot points 818k are provided at diametrically opposite sides of the bellow shape 816k. The bellow shape 816k allows flexing of the lumen 808k without distorting shape of the outlet port 802k. In some embodiments, the flexing enabled by the bellow shape 816k configuration varies in a range of up to 20 degrees in either direction. In some embodiments, the catheter includes a mechanism for tilting the distal cap 802k at a greater or lesser angle and for modifying the direction of the tilt. The tilted distal cap with polygonal outlet 802k provides for easier positioning of the catheter as the physician does not have to figure out how to bend or move the outlet surface to hit the desired target surface. The physician is only required to gently push the polygonal outlet port 802k against the GI tract for proper positioning. In some embodiments, the polygonal outlet port 802k has a surface area in a range of 0.5 cm² to 5 cm².

The different views of distal cap illustrated in FIG. 8K are configured to connect to the catheter distal end or tip. In embodiments, the distal is made from an optically clear material, such as silicone, so the user can see through the cap to visualize ablation zones. In some embodiments, the distal cap includes a groove and/or O-ring that attaches or snaps into the distal tip of the catheter. In some embodiments, the distal cap further comprises an additional channel that directs the vapor from the catheter lumen into the lumen 808k of cap 800k and toward the distal cap outlet port 802k. In some embodiments, the catheter lumen is positioned off-center of the catheter shaft, and the distal cap 800k further comprises a connecting member configured to insert into the catheter lumen and direct the vapor to the outlet port 802k of the distal cap 800k. In some embodiments, the distal cap lumen 808k has a length in a predefined range of 9 mm and a maximum thickness in a predefined range of 1 mm wall thickness to fit into, and stay within, the tubular organ lumen.

Figure 8M:
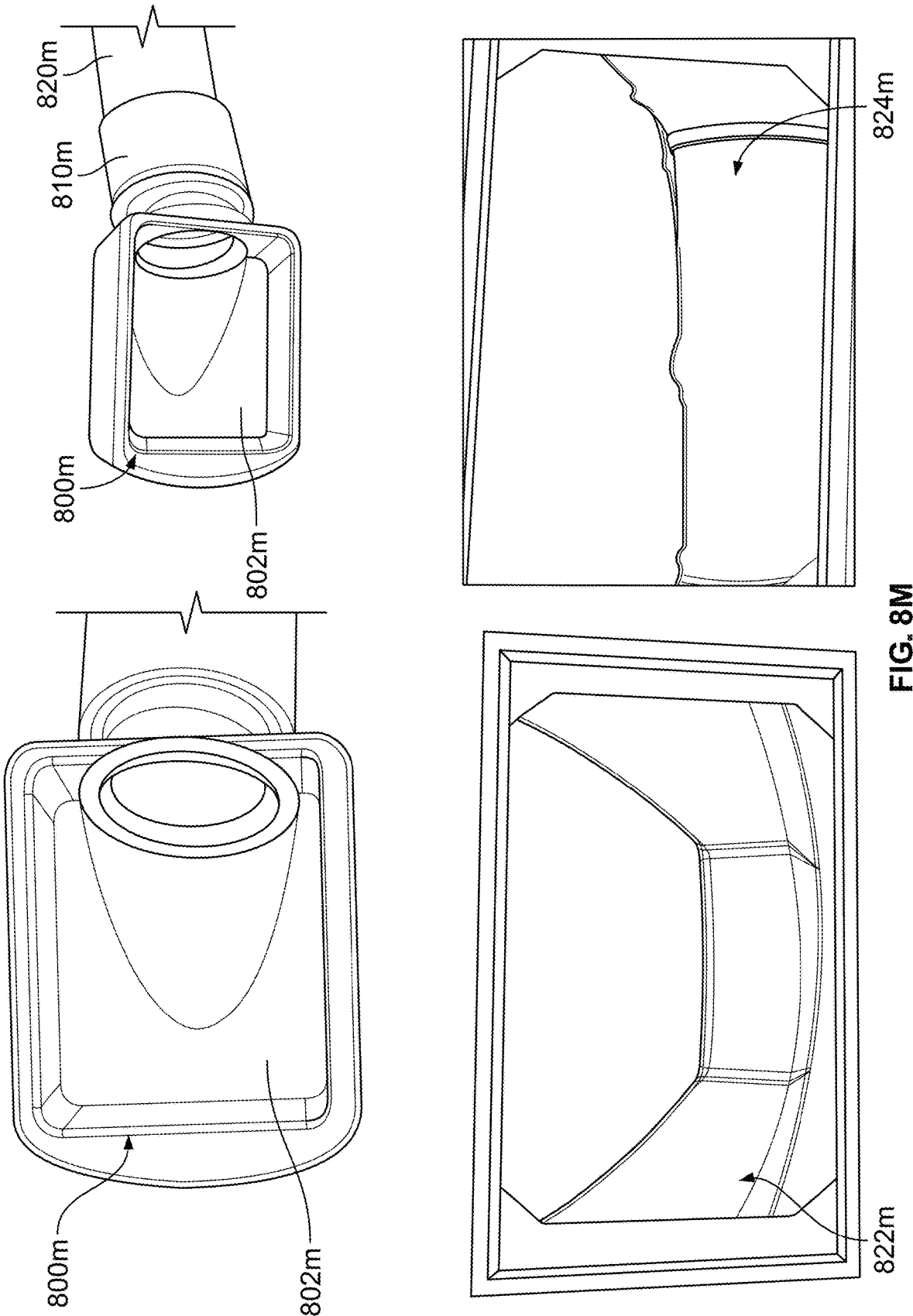
FIG. 8M illustrates photographs of an actual embodiment of a distal cap with an outlet port, connected to a distal tip of a catheter, in accordance with some embodiments of the present specification.

FIG. 8M illustrates photographs of an actual embodiment of a distal cap 800m with an outlet port 802m, connected to a distal tip of a catheter 820m, in accordance with some embodiments of the present specification. A proximal end 810m of the distal cap 800m, corresponding to proximal end 810k of distal cap 800k of FIG. 8K, is shown attached to and covering the distal tip of catheter 820m. In embodiments, the catheter 820m lumen is an endoscope that includes a camera, which is configured to capture views of the location of distal cap 800m as it moves through the internal organs of a patient. Views 822m and 824m illustrate some of the positions of the distal cap 800m, captured by the camera of catheter 820k, and visible on a display attached to the catheter 820k. FIG. 34A describes an exemplary process of using an endoscope with a viewing element or a camera along with a catheter to perform ablation treatment.

Figure 8N:
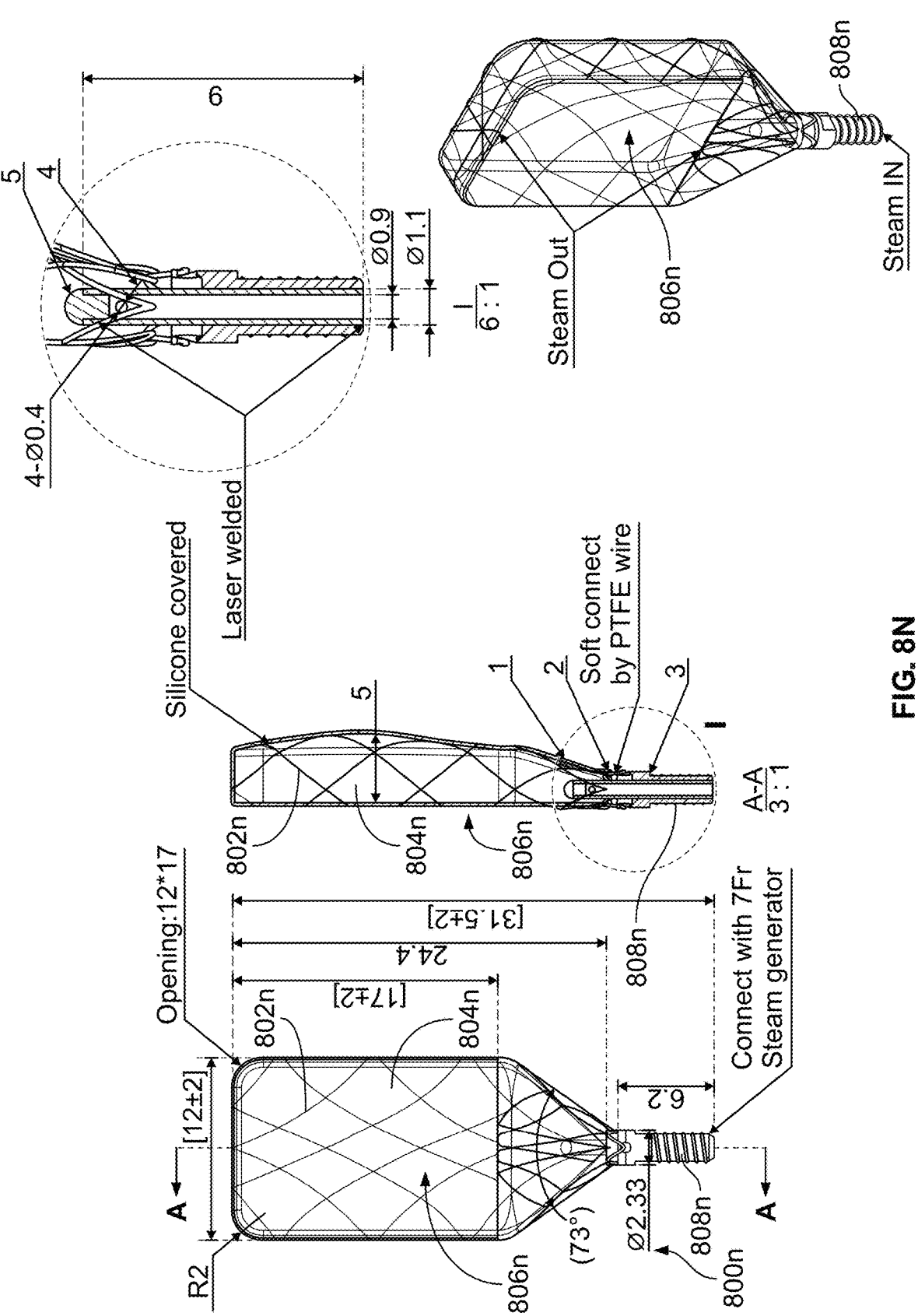
FIG. 8N illustrates different views of another embodiment of a distal cap that is used for focused ablation by attaching the cap to a distal end of a steam generator, in accordance with some embodiments of the present specification.

FIG. 8N illustrates different views of another embodiment of a distal cap 800n that is used for focused ablation by attaching the cap 800n to a distal end of a steam generator, in accordance with some embodiments of the present specification. The cap 800n is made from a wire 802n of a material composed of a shape memory alloy such as Nitinol. In some embodiments, the wire 802n has a diameter in a range of 0.1 to 0.14 mm. The wire 802n is woven to form a polygonal shape. The prism base forms the distal end of the cap 800n, while the converging sides opposite to the base form a proximal corner of the cap 800n. The polygonal prism has two parallel sides of length in a range of 15 to 19 mm. The side perpendicular to the two parallel sides, and the base of the prism, is located at a distal end of the cap 800n, and has a length in a range of 10 to 14 mm. FIG. 8T illustrates an embodiment of a cap 800t that has a base of length 12 mm. Referring again to FIG. 8N, a length from a center of the distal surface of the wired pentagonal block to its proximal side formed by the two converging sides of the prism, is approximately 24.4 mm. In FIG. 8T, the length from a center of the distal surface of the wired pentagonal block to its proximal side formed by the two converging sides of the prism, is shown to be 24.5 mm. An exemplary angle formed by the two converging sides of the pentagonal prism of FIGS. 8N and 8T is approximately 73 degrees. The shape formed by the woven wire 802n is covered with a Silicone sheet 804n, leaving an opening 806n on a first plane of the pentagonal prism. The first plane corresponds to the plane formed by front edges of the sides of the pentagonal prism shaped cap 800n. The open surface is provided on the first plane and corresponds to a rectangle shape formed by two parallel edges (of length in a range of 15 to 19 mm) in a single plane, of the two parallel sides. The surface formed by the converging edges in the first plane, is also covered with silicone sheet 804n. The opening 806n provides an exit for steam, that is configured to enter the area enclosed within the pentagonal block from a cylindrical connector 808n having a length of approximately 6.2 mm and a diameter of approximately 2.33 mm, attached to the proximal opening between the converging sides of the pentagonal prism. The connector 808n is further configured to connect to a steam generator at its proximal side. In some embodiments, the outer diameter of the catheter shaft that attaches connector 808n to steam generator is approximately 7 French (F) or 2.33 mm. Connector 808n connects to the steam generator through a flexible catheter shaft. Screw threads in connector 808n help secure connector 808n to the polymer braided catheter shaft. In some embodiments, the connector is bonded to the catheter shaft additionally with an adhesive to secure and seal the attachment. In alternate embodiments, the connection between opening 806n and the catheter shaft can be of any other nature. Each edge and corner created by the Silicone sheet 804n is rounded to enable an atraumatic advance of the cap 800n within an organ.

Figure 8O:
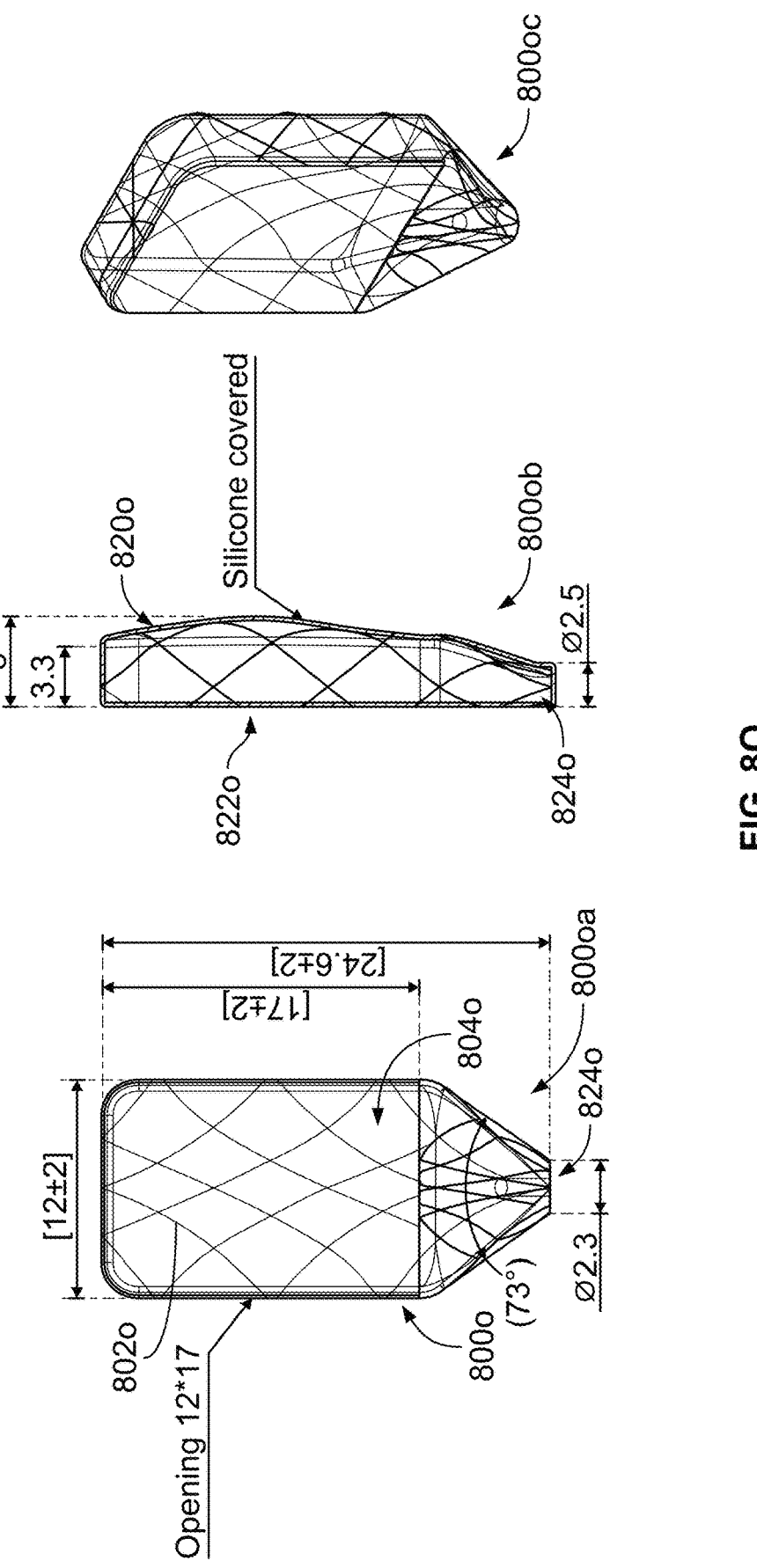
FIG. 8O illustrates additional view of a cap, which is the same as the cap illustrated without the connector portion, in accordance with some embodiments of the present specification.

FIG. 8O illustrates additional view of a hood 8000, which is the same as the cap 800k illustrated without the connector portion. A first view 800oa shows a front view of the hood 8000. A second view 800ob shows the side view of the hood 8000. A third view 800oc shows the front side perspective view of the hood 8000. Referring simultaneously to the three views, the figure shows a hollow pentagonal prism shape formed by a silicone laminate 8040 covering a woven wire structure 8020. A first convex surface 8200 is formed by the silicone sheet 8040 in the rectangular portion between the back edges of the two parallel sides. A second surface 8220, parallel to the first surface 8200 is formed by the rectangular portion between the front edges of the two parallel sides. The second surface 8220 is open and devoid of any Silicone sheet 8040. In embodiments, a distance between the corresponding rectangular edges of the front and back sides is approximately 3.3 mm, whereas a thickness of the hollow area formed at the center of the pentagonal prism, extending from second surface 8220 to the first convex surface 8200 is approximately 5 mm. The proximal portion of cap 8000, formed by the two converging sides of the pentagonal prism shape, leave an oval opening 824o to receive the connector from the steam generator. In some embodiments, the opening has a variable diameter ranging from 2.3 to 2.5 mm.

Figure 8P:
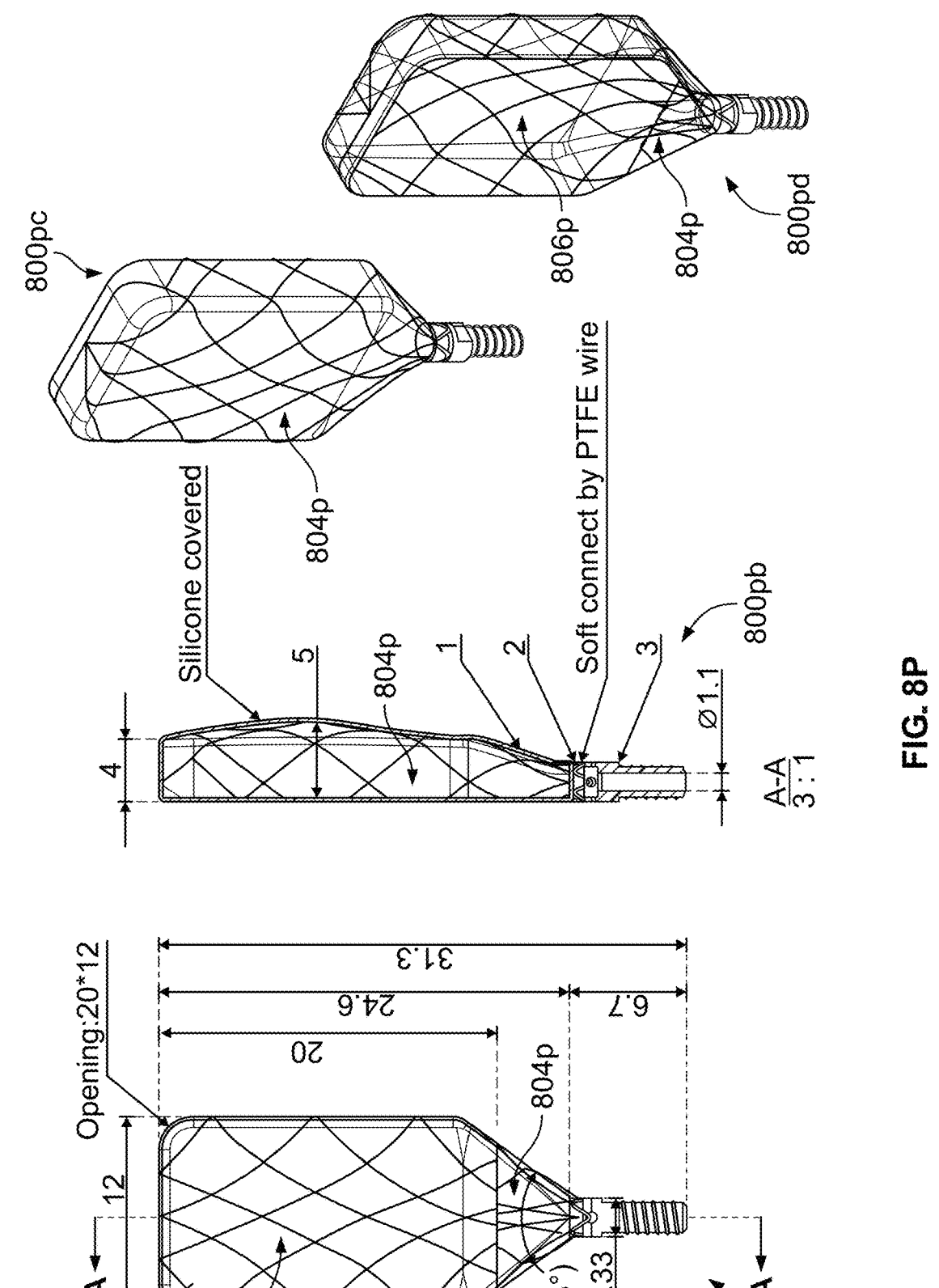
FIG. 8P illustrates different views of another embodiment of a distal cap in accordance with some embodiments of the present specification.

FIG. 8P illustrates different views of another embodiment of a distal hood 800p in accordance with some embodiments of the present specification. Cap 800p is similar in configuration to cap 800n of FIG. 8N. For brevity, features of cap 800p that are dissimilar to cap 800n only are described here. The remaining features should be considered similar to those described previously in context of FIG. 8N. A first view 800pa shows a front of the cap 800p. A second view 800pb shows a side of the cap 800p. A third view 800pc shows a back side perspective view of the cap 800p. A fourth view 800pd shows a front side perspective view of the cap 800p. In the embodiment of this figure, an opening 806p extends over a first surface of the pentagonal prism, where the first open surface corresponds to a rectangle formed by the front two parallel edges (of length in a range of 15 to 19 mm) in a single plane, of the two parallel sides; and continues over a part of the first surface between the two converging sides. A silicone sheet 804p covers the remaining portion of the first surface between the converging sides towards their proximal corner. The sheet 804p also covers all the other surfaces of the pentagonal prism. The prism base forms the distal end of the cap 800p, while the converging sides opposite to the base form a proximal corner of the cap 800p. In some embodiments, a length of the opening 806p from the prism's base to the proximal edge of the opening 806p between the converging sides, is approximately 20 mm. The additional size of the opening enables a greater amount of steam to exit the cap during an ablation procedure.

Figure 8Q:
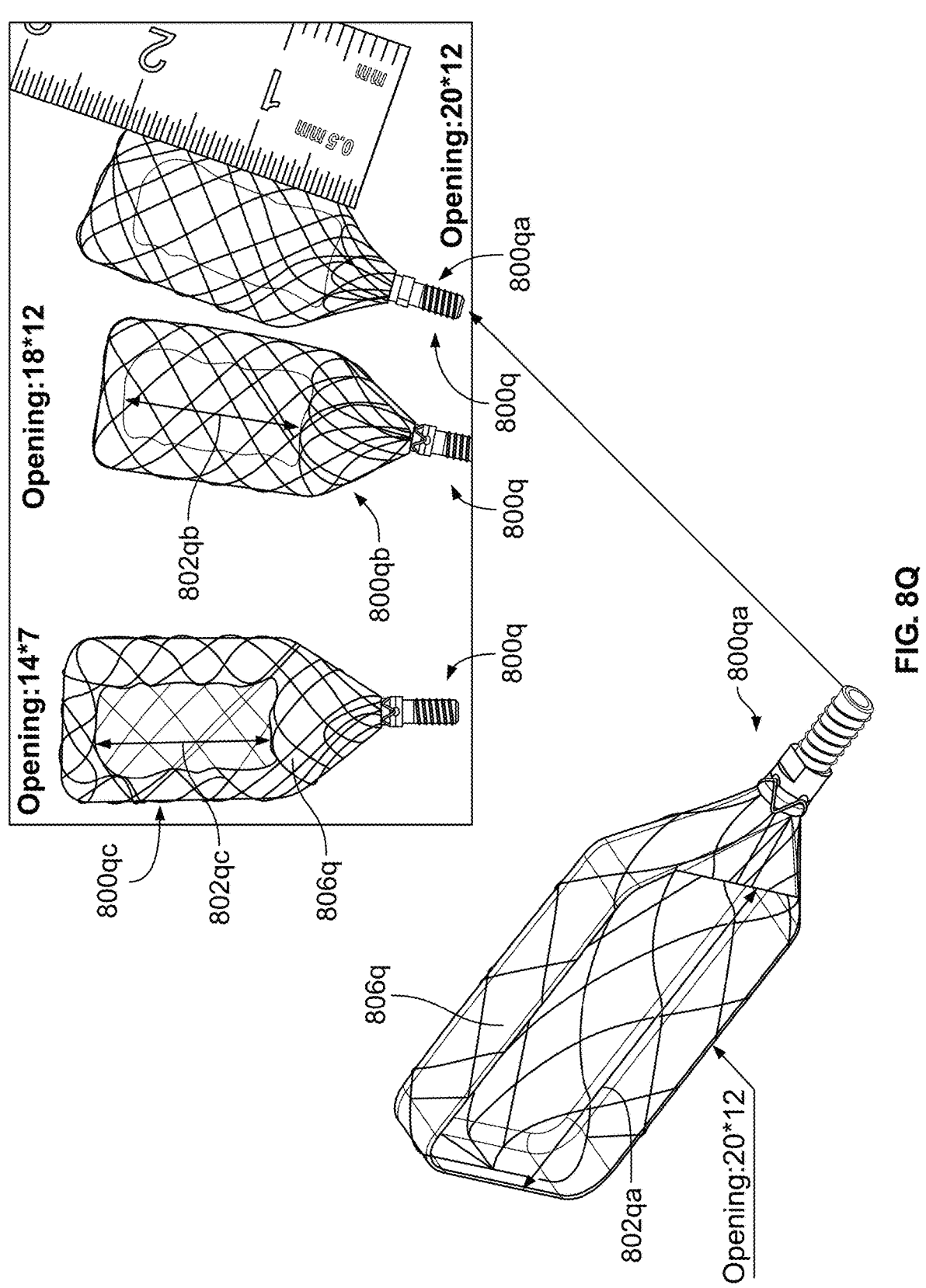
FIG. 8Q illustrates photographs of caps with openings of different sizes, in accordance with some embodiments of the present specification.

FIG. 8Q illustrates photographs of hood with openings of different sizes, in accordance with some embodiments of the present specification. A photo 800qa is of a cap with an opening 802qa of length and width of approximately 20 mm and 12 mm, respectively, as described in FIG. 8P. FIG. 8Q also shows an enlarged line drawing of the same cap 800qa with an opening 802qa of 20 mm by 12 mm. Another photo 800qb is of a cap with an opening 802qb with dimensions of 18 mm and 12 mm. Another photo 800qc is of a cap with an opening 802qc of dimensions 14 mm and 7 mm. As the size of the opening reduces, the surface area of a silicone sheet cover 804q increases, for a polygonal prism shaped cap 800q of the same size.

Figure 8R:
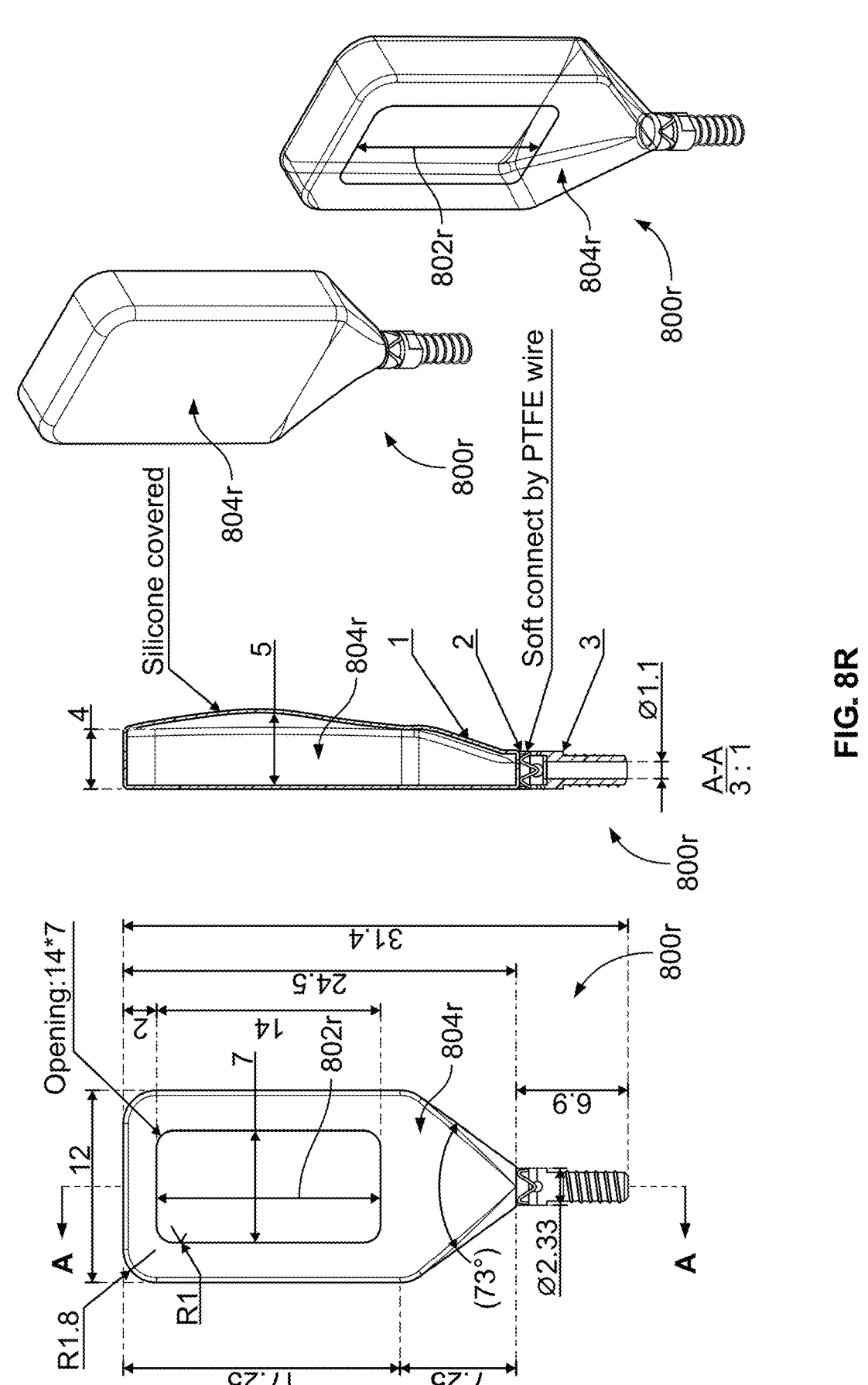
FIG. 8R illustrates multiple views of a cap with an opening of dimensions 14 mm and 7 mm, in accordance with some embodiments of the present specification.

FIG. 8R illustrates multiple views of a cap 800r with an opening 802r of dimensions 14 mm and 7 mm, in accordance with some embodiments of the present specification. The configuration of this cap 800r is similar to cap 800qc of FIG. 8Q. Opening 802r is provided on a first surface of the pentagonal prism shaped cap 800r. Shape of opening 802r is rectangular and corresponds to the rectangular shape formed in a first plane by the two parallel edges at the distal side of cap 800r. Opening 802r extends from after 2 mm from the distal edge adjacent to the two parallel sides forming the first plane of the pentagonal prism for 14 mm towards the proximal side, and from approximately 2.5 mm from either of the parallel sides, for about 7 mm centrally between the two parallel sides. The remaining portion of the first plane and the second plane opposite to the first plane, and all the remaining sides of the pentagonal prism shaped cap 800r is covered by a silicone sheet 804r.

Figure 8S:
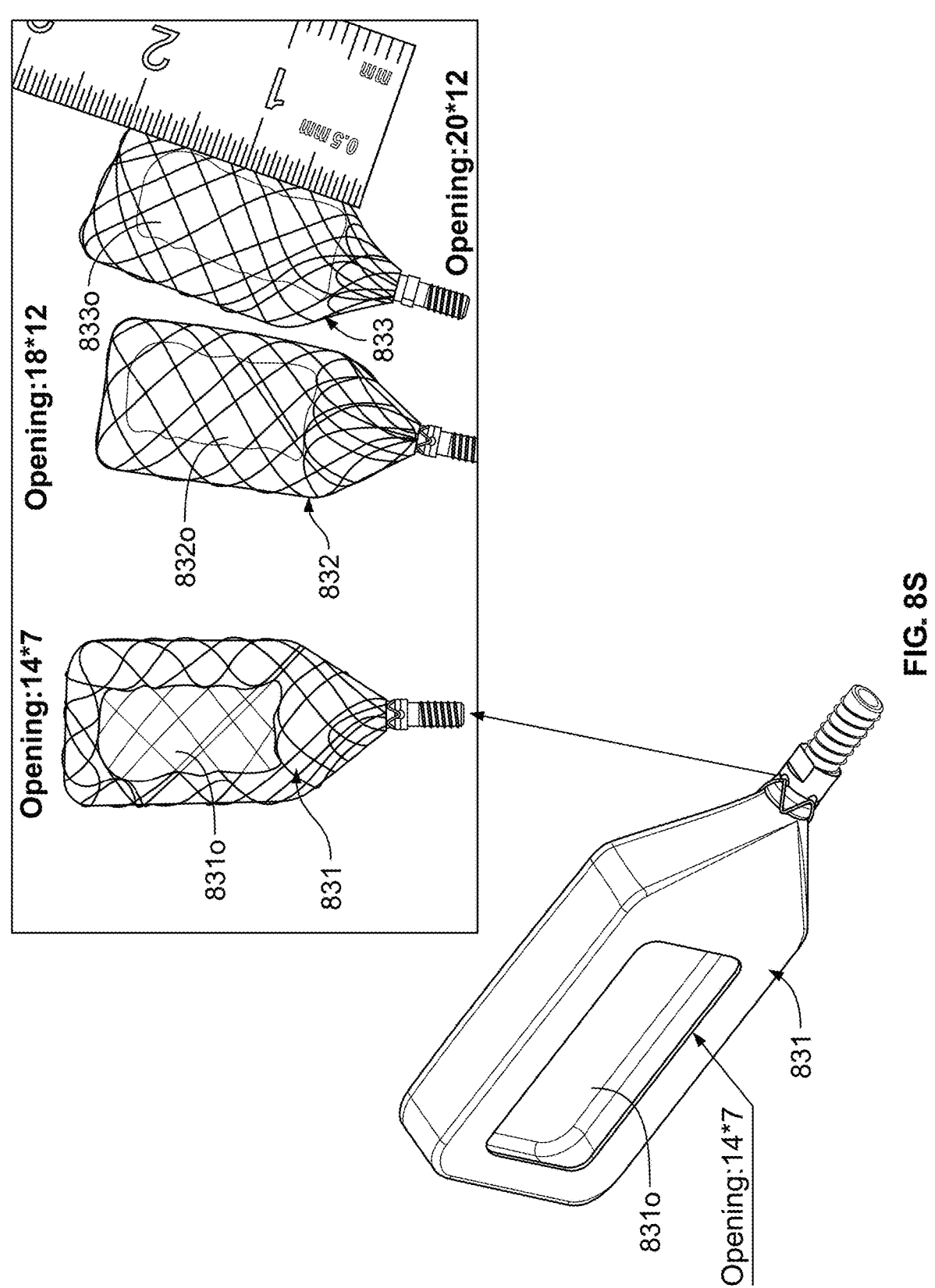
FIG. 8S illustrates caps with openings of different sizes, in accordance with some embodiments of the present specification.
Figure 8T:
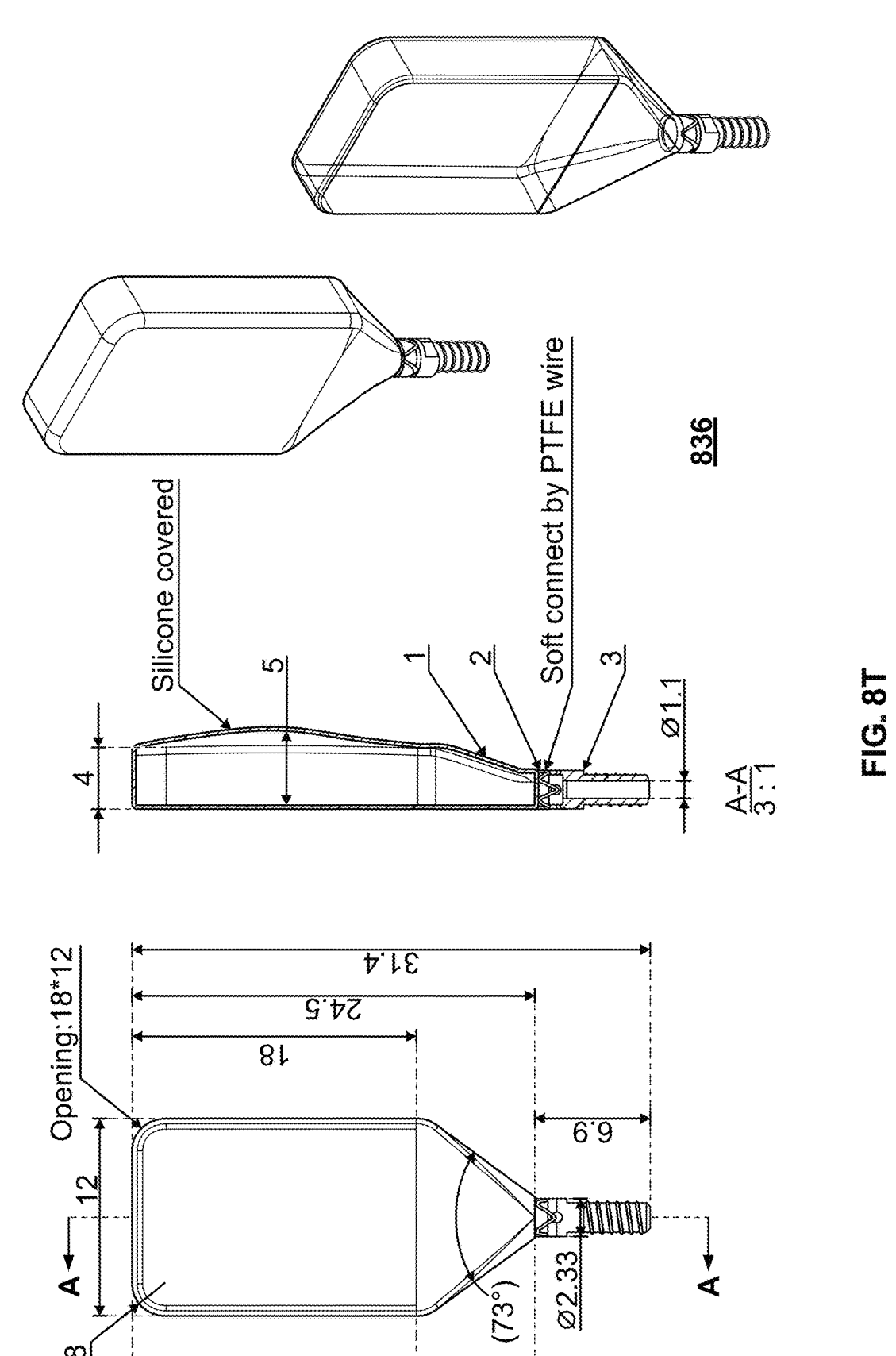
FIG. 8T illustrates an embodiment of a cap that has a base of length 12 mm, in accordance with some embodiments of the present specification.

FIG. 8S illustrates caps 831, 832, 833 with openings 831o, 832o, 833o of different sizes, in accordance with some embodiments of the present specification.

FIG. 8T illustrates an embodiment of a cap 836 that has a base of length 12 mm, in accordance with some embodiments of the present specification.

FIGS. 8U and 8V illustrate views of a hood 838 with an opening of the dimensions 14 mm and 7 mm, corresponding to cap 800qc of FIG. 8Q, hood 800r of FIG. 8R, and the hood shown in FIG. 8S.

Embodiments of caps and hoods illustrated and described in FIGS. 8K to 8W include an opening that is perpendicular to the axis of catheter shaft. In embodiments, the opening can be rotated to contact the tubular organ tissue all the way around the circumference. The embodiments of the present specification enable catheter shaft torque control. In some embodiments, a connector enables the connection between the opening and a lumen in the catheter shaft. Some illustrations show a threaded screw configuration of the connector that is screwed into the polymer braided catheter shaft and bonded with adhesive to secure and seal the junction.

Figure 8W:
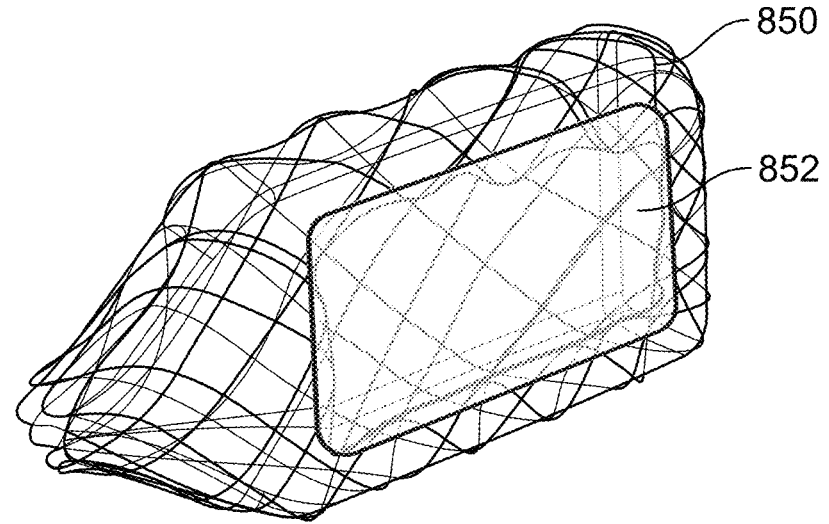
FIG. 8W illustrates another embodiment of the hood or cap illustrated and described in FIGS. 8K to 8V, including a mesh attached to the opening of cap, in accordance with the present specification.

FIG. 8W illustrates another embodiment of the hood or cap illustrated and described in FIGS. 8K to 8V, including a mesh 852 attached to the opening of cap 850, in accordance with the present specification. Mesh 852 covers the opening of cap 850 while providing a uniformly controlled outlet for the vapor that exit through the opening. In embodiments, the mesh material is nitinol, allowing the mesh to self-expand to its predetermined shape. In embodiments, the mesh is covered in silicone, a clear thin sheet polymer, or PTFE (woven, expanded, or deposited). In embodiments, the mesh comprises openings between the wires of the mesh for the exit of vapor. In embodiments, the openings in the mesh range from 1 mm×1 mm to 20 mm×20 mm, and preferably range from 10 mm to 15 mm in width and 20 mm to 25 mm in length.

Figures 9A, 9B:
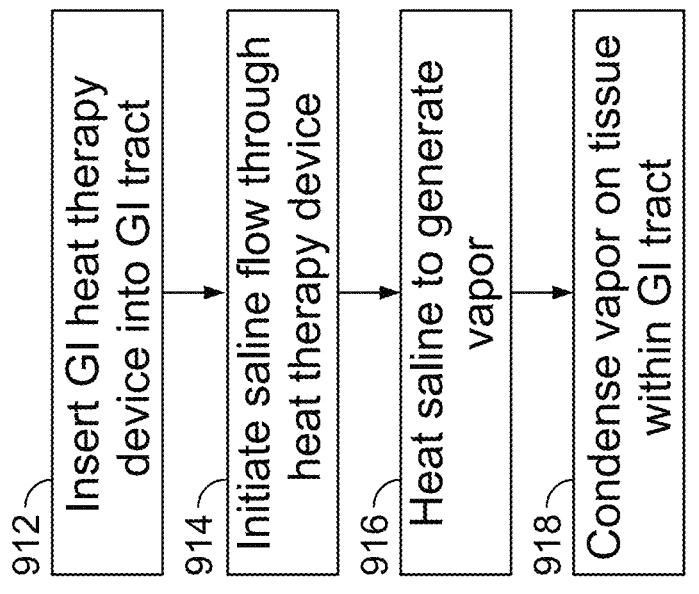
FIG. 9A is a flow chart illustrating a method of ablating a tissue inside a gastrointestinal tract of a patient, in accordance with some embodiments of the present specification.
FIG. 9B is a flow chart illustrating a method of ablating a tissue inside a gastrointestinal tract of a patient, in accordance with other embodiments of the present specification.

FIG. 9A is a flow chart illustrating a method of ablating a tissue inside a gastrointestinal tract of a patient, in accordance with other embodiments of the present specification. In embodiments, the method of FIG. 9A illustrates focal ablation that is performed after observing the patient following circumferential focused ablation, to treat any remaining pre-cancerous or cancerous tissue in the esophagus, duodenum, bile duct, and pancreas. In embodiments, ablation catheters disclosed in the present specification, such as ablation catheter 870 of FIG. 8J, are used to perform the ablation method of FIG. 9A. At 902, an ablation catheter configured for the gastrointestinal (GI) tract is inserted into the GI tract of the patient. At 904, a seal is created between an exterior surface of the ablation catheter and an interior wall of the GI tract, forming a treatment volume. The seal is created by the expansion of an attachment or positioning element of the ablation catheter, as explained in the embodiments of the present specification. In some embodiments, the seal is temperature dependent and it breaks when the temperature within the sealed portion or treatment volume exceeds a specific temperature. In one embodiment, the specific temperature is 90° C. In some embodiments, the seal is pressure dependent and it breaks when the pressure within the sealed portion or treatment volume exceeds a specific pressure. In one embodiment, the specific pressure is 5 atm. At 906, vapor is delivered through the ablation catheter into the sealed portion within the GI tract, while the seal is still in place. At 908, the vapor condenses on the tissue under treatment, thereby ablating the tissue.

FIG. 9B is a flow chart illustrating a method of ablating a tissue inside a gastrointestinal tract of a patient, in accordance with other embodiments of the present specification. In embodiments, the method of FIG. 9B illustrates focal ablation that is performed after observing the patient following circumferential focused ablation, to treat any remaining pre-cancerous or cancerous tissue in the esophagus, duodenum, bile duct, and pancreas. In embodiments, ablation catheters disclosed in the present specification, such as ablation catheter 870 of FIG. 8J, are used to perform the ablation method of FIG. 9B. At 912, an ablation catheter configured for the gastrointestinal (GI) tract is inserted into the GI tract of the patient. At 914, saline with a variable flow rate is introduced through the ablation catheter into the GI tract. At 916, the saline is heated using RF energy to generate vapor through the ablation catheter into the GI tract. In embodiments, the rate of flow of the saline during vapor delivery is different from flow of the saline during the phase where no therapy is delivered. In some embodiments, the rate of flow of saline during the therapy is lower than that during no therapy. In some embodiments, the rate of flow of saline during the therapy is lower than that during no therapy. At 918, the vapor condenses on the tissue under treatment, thereby ablating the tissue.

FIG. 9C is a flow chart illustrating a method of using a first ablation catheter to perform circumferential ablation and then a second ablation catheter to perform focal ablation, in accordance with some embodiments of the present specification. It should be noted that, optionally, in other embodiments, a first phase of circumferential ablation using a first ablation catheter is followed by a second phase of circumferential ablation using the same first ablation catheter, either immediately or at a later date, rather than using the second ablation catheter for focal ablation. The method of FIG. 9C includes a two-step, or phase, process to ensure complete or near complete ablation of a target tissue. In some embodiments, in a first phase, a patient is treated with a first ablation catheter having two positioning elements to perform circumferential ablation. In embodiments, the first ablation catheter having two positioning elements used for the first phase is similar to ablation catheter 1991 of FIG. 1K. At step 922, the first ablation catheter is inserted into a patient's GI tract. A distal positioning element is expanded at step 924. A proximal positioning element is then expanded at step 926, creating a first seal between the peripheries of the distal and proximal positioning elements and the GI tract and forming a first enclosed treatment volume between the two positioning elements and the surface of the patient's GI tract. Vapor is delivered via at least one port, positioned on the first ablation catheter between the positioning elements, into the first enclosed treatment volume at step 928. In some embodiments, the system comprises a foot pedal in data communication with a controller controlling the catheter, a switch on the catheter, or a switch on the controller, for controlling vapor flow and step 928 is achieved using the foot pedal in data communication with the controller, a switch on the catheter, or a switch on the controller. The vapor condenses on the tissue within the first enclosed treatment volume at step 930 to circumferentially ablate the tissue. The first ablation catheter having two positioning elements is then removed from the GI tract at step 932.

After ablation is performed using the first ablation catheter with two positioning elements, the ablation area is examined by the physician at step 934. Upon observing the patient, the physician may identify patches of tissue requiring focused ablation. A second phase is then performed, wherein a second ablation catheter with a needle or cap, hood, or disc attachment or positioning element on the distal end is used for focal ablation. The second phase may be performed immediately after the first phase or at a later date. In embodiments, the second ablation catheter with a needle or cap, hood, or disc attachment or positioning element on the distal end used for the second phase is similar to ablation catheter 870 of FIG. 8J. (Alternatively, in other embodiments, the physician may wait a period of time, ranging from six weeks to two years, measure the efficacy of the first phase, and then perform a second phase using the same first ablation catheter for another round of circumferential ablation.) At step 936, the second ablation catheter with a distal attachment or positioning element is inserted into the patient's GI tract through the lumen of an endoscope. The distal attachment or positioning element is expanded at step 938 to create a second seal between the periphery of the distal attachment or positioning element and the GI tract and form a second enclosed treatment volume between the distal attachment or positioning element and the surface of the patient's GI tract. Vapor is delivered via at least one port, positioned at the distal end of the catheter, into the second enclosed treatment volume at step 940. In some embodiments, the system comprises a foot pedal in data communication with a controller controlling the catheter, a switch on the catheter, or a switch on the controller, for controlling vapor flow and step 940 is achieved using the foot pedal in data communication with the controller, a switch on the catheter, or a switch on the controller. The vapor condenses on the tissue within the second enclosed treatment volume at step 942 to focally ablate the tissue. The second ablation catheter having a distal attachment or positioning element is then removed from the GI tract at step 944.

Figure 9D:
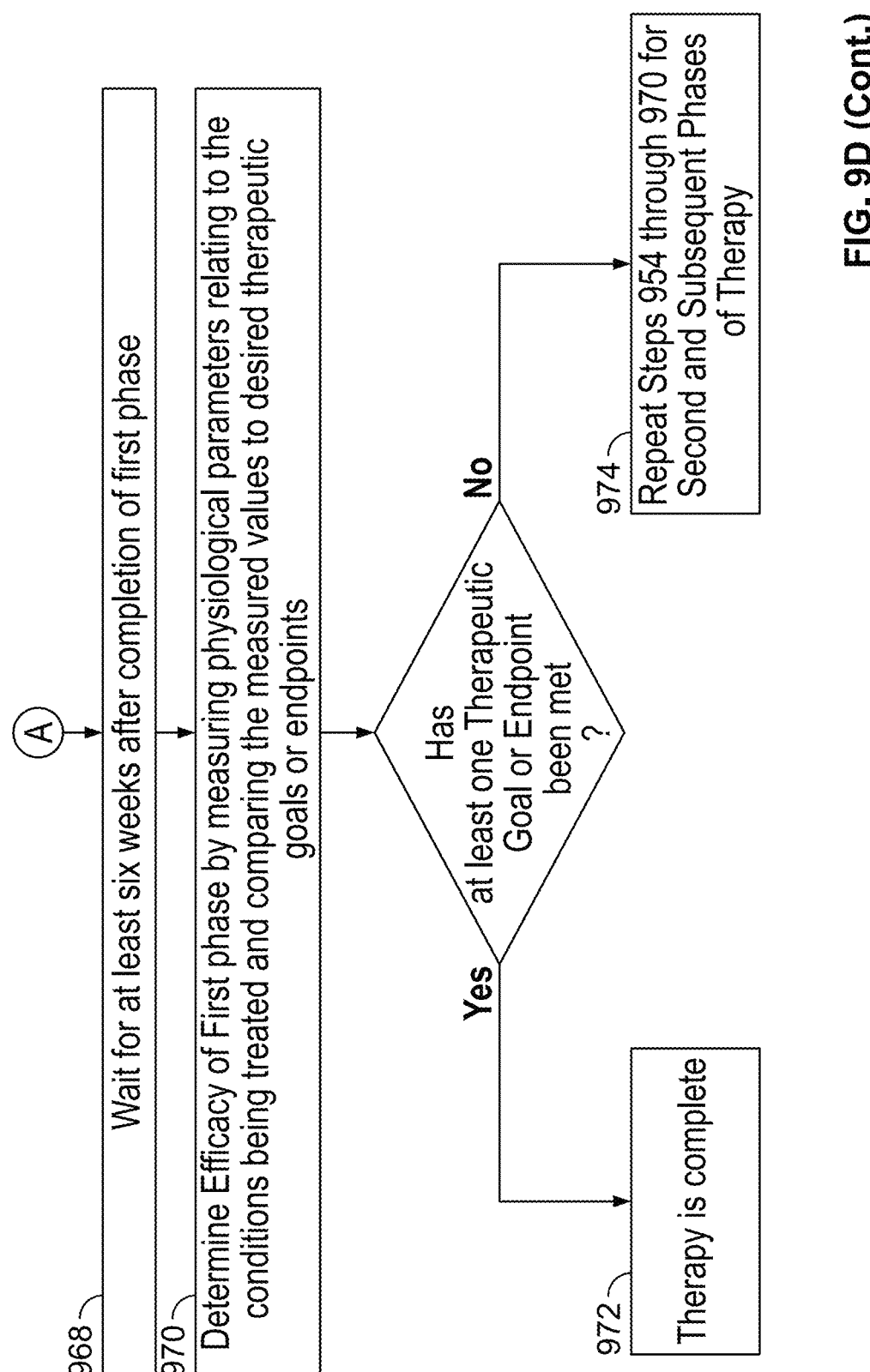
FIG. 9D is a flow chart illustrating a multi-phase method of using a vapor ablation system for duodenal ablation in order to treat obesity, excess weight, eating disorders, metabolic syndrome, diabetes, dyslipidemia, non-alcoholic steatohepatitis (NASH), non-alcoholic fatty liver disease (NAFLD), or a polycystic ovary disease, in accordance with embodiments of the present specification.

FIG. 9D is a flow chart illustrating a multi-phase method of using a vapor ablation system for duodenal ablation in order to treat obesity, excess weight, eating disorders, metabolic syndrome, diabetes, dyslipidemia, non-alcoholic steatohepatitis (NASH), non-alcoholic fatty liver disease (NAFLD), or a polycystic ovary disease, in accordance with embodiments of the present specification. At step 952, a patient is first screened to determine if the patient is a candidate for duodenal ablation using the ablation systems of the present specification. For diabetes, metabolic syndrome, obesity or excess weight, in various embodiments, the patient must have a BMI (Body Mass Index) of 25 or greater (overweight being 25-30, obese being 30 and above, and morbid obesity being above 35). In accordance with various aspects of the present specification, a patient with diabetes must have HbA1c levels of at least 6.5 gm %, fasting blood glucose levels of at least 126 mg/dL or a random plasma glucose level of at least 200 mg/dL, 2-hour plasma glucose levels of at least 200 mg/dL (11.1 mmol/L) during an oral glucose tolerance test (OGTT), or a fasting insulin concentration of at least 5.7 U/mL (109 pmol/L). For insulin resistance, in various embodiments, a patient must have a homeostatic model assessment of insulin resistance (HOMA-IR) of at least 1.6. In accordance with various aspects of the present specification, a patient with dyslipidemia must have a scrum triglyceride concentration of at least 130 mg/dL (1.47 mmol/L) or a ratio of triglyceride to high-density lipoprotein (HDL) cholesterol concentration of greater than 3.0 (1.8 SI units).

Additionally, the multi-phase method of using the vapor ablation system for duodenal ablation is used to treat obesity, excess weight, eating disorders, metabolic syndrome, diabetes, dyslipidemia, NASH, NAFLD, or a polycystic ovary disease, due to an increased peripheral resistance to insulin. For peripheral resistance to insulin, a patient must have HbgA1c levels of at least 5.7% (>60 pmol/L), fasting insulin greater than 10 µIU/mL (>60 pmol/L), fasting glucose greater than 100 mg/dL (>5.6 mmol/L), a homeostatic model assessment of insulin resistance (HOMA-IR) of at least 2.5, a triglyceride to HDL ratio of 3 or more, and skin folds at the hip that measure twice that at the triceps.

Continuous Glucose Monitoring (CGM) is a valuable tool for managing diabetes because it provides real-time information about blood glucose levels. The choice of the best metric for assessing diabetes control using CGM can vary depending on the specific goals and preferences of the individual with diabetes and their healthcare provider. Some commonly used metrics for evaluating diabetes control with CGM include Time in Range (TIR): TIR represents the percentage of time a person's blood glucose levels are within a target range, typically set between specific upper and lower glucose thresholds. The most common target range is 70-180 mg/dL (3.9-10 mmol/L), but it can be customized based on individual circumstances. A clinically meaningful improvement in TIR is an increase of at least 10% in TIR when adjusting treatment plans. Time Below Range (TBR): TBR indicates the percentage of time when blood glucose levels fall below the lower threshold of the target range. This helps identify instances of hypoglycemia, which is a critical aspect of diabetes management. Reducing TBR by 5% or more is often considered clinically meaningful, Time Above Range (TAR): TAR represents the percentage of time when blood glucose levels exceed the upper threshold of the target range. Elevated TAR may indicate hyperglycemia, which can lead to long-term complications. A decrease of at least 10% in TAR is considered clinically significant. Glycated Hemoglobin (HbA1c): While CGM provides real-time data, HbA1c is a standard blood test that offers an average of blood glucose levels over the previous 2-3 months. It provides a longer-term view of glucose control. A reduction of 0.5% in HbA1c as clinically meaningful. Glucose Management Indicator (GMI): GMI is a relatively new metric that provides an estimated HbA1c value based on CGM data. It offers a more immediate estimate of average glucose levels. A decrease of 0.5% or more in GMI is generally seen as a clinically meaningful improvement. Coefficient of Variation (CV): CV measures glucose variability. Lower CV values suggest more stable blood glucose levels, while higher values indicate greater fluctuations. A reduction of 10% or more in CV is often considered clinically meaningful. Time in Hypoglycemia and Hyperglycemia: In addition to TBR and TAR, you can specifically track the time spent in severe hypoglycemia (blood glucose levels <54 mg/dL or 3.0 mmol/L) or very high hyperglycemia (blood glucose levels>250 mg/dL or 13.9 mmol/L), depending on individual needs. Any reduction in severe hypoglycemic events should be considered a positive outcome. A clinically meaningful reduction in moderate hypoglycemia is a decrease of 10% or more in time spent in this range. A clinically significant improvement in moderate or severe hyperglycemia is a decrease of at least 10% in time spent in the respective range.

Patients screened at step 952 and determined to be candidates for duodenal ablation then proceed with an ablation procedure using a vapor ablation system in accordance with embodiments of the present specification. The vapor ablation system is configured to deliver circumferential ablation of a patient's duodenum or small intestine to treat any one or more of the conditions listed above. The vapor ablation system comprises a controller having at least one processor in data communication with at least one pump and a catheter connection port in fluid communication with the at least one pump. At step 954 of a first phase of treatment, a proximal end of a first catheter is connected to the catheter connection port to place the first catheter in fluid communication with the at least one pump. The first catheter comprises at least two positioning elements separated along a length of the catheter and at least two one or more ports positioned between the at least two positioning elements, wherein each of the at least two positioning elements has a first configuration and a second configuration, and wherein, in the first configuration, each of the at least two positioning elements is compressed within the catheter and in the second configuration, each of the at least two positioning elements is expanded to be at least partially outside the catheter. At step 956, the first catheter is positioned inside a patient such that, upon being expanded into the second configuration, a distal one of the at least two positioning elements is positioned within in the patient's small intestine and a proximal one of the at least two positioning elements is proximally positioned more than 1 cm from the distal one of the at least two positioning elements. Then, at step 958 each of the at least two positioning elements is expanded into their second configurations. At step 960, the controller is activated, wherein, upon activation, the controller is configured to cause the at least one pump to deliver saline into at least one lumen in the first catheter and, wherein, upon activation, the controller is configured to cause an electrical current to be delivered to at least one electrode positioned within the at least one lumen of the first catheter. The electrical current causes the electrode to heat and contact of the saline with the heating electrode converts the saline to vapor, or steam, which is delivered via the one or more ports to circumferentially ablate target tissue.

In various embodiments, the vapor is delivered to treat at least 1-15 cm of contiguous or non-contiguous small intestine mucosa. For insulin resistance, the vapor is delivered for ablating an area between 4 cm² and 100 cm² of small intestinal mucosa. In various embodiments, the vapor is delivered to treat at least 50% of a circumference of small intestine. In various embodiments, the vapor dose is characterized by at least one of: having an energy of 5-25 J/cm², delivered over 1-60 seconds, delivered at an energy rate of 5-2500 cal/sec, delivered such that the total dose is 5-40 calories/gram of tissue to be ablated, delivered to elevate a target tissue temperature above 60° C. but less than 110° C., has a vapor temperature between 99° C. and 110° C., or delivered such that a pressure in a small intestine is less than 5 atm, and preferably less than 1 atm.

At step 962, the controller shuts off the delivery of saline and electrical current after a time period ranging from 1 to 60 seconds. In embodiments, the controller automatically shuts off the delivery of saline and electrical current. The controller is repeatedly activated at step 964 to deliver saline into the lumen and electrical current to the at least one electrode until the physician terminates the procedure. In some embodiments, the system further comprises a foot pedal in data communication with the controller, a switch on the catheter, or a switch on the controller, for controlling vapor flow and step 964 is achieved using the foot pedal in data communication with the controller, a switch on the catheter, or a switch on the controller. The first catheter is removed from the patient at step 966 to complete a first phase of treatment.

At step 968, the physician then waits for at least six weeks after the completion of the first phase to allow the ablation therapy to take effect before evaluating the efficacy of the treatment. After at least six weeks, at step 970, a post-first phase evaluation is performed wherein the efficacy of the first phase of treatment is determined by measuring physiological parameters relating to the conditions being treated and comparing the measured values to desired therapeutic goals or endpoints.

In various embodiments, ablation therapy is provided to achieve the following therapeutic goals or endpoints for patients with obesity, excess weight, eating disorders, dyslipidemia, or diabetes and a first phase of treatment is considered successful for these patients if any one or more of the following therapeutic goals or endpoints is reached: a total body weight of the patient decreases by at least 1% relative to a total body weight of the patient before ablation; an excess body weight of the patient decreases by at least 1% relative to an excess body weight of the patient before ablation; a total body weight of the patient decreases by at least 1% relative to a total body weight of the patient before ablation and a well-being level of the patient does not decrease more than 5% relative to a well-being level of the patient before ablation; an excess body weight of the patient decreases by at least 1% relative to an excess body weight of the patient before ablation and a well-being level of the patient does not decrease more than 5% relative to a well-being level of the patient before ablation; a pre-prandial ghrelin level of the patient decreases by at least 1% relative to a pre-prandial ghrelin level of the patient before ablation; a post-prandial ghrelin level of the patient decreases by at least 1% relative to a post-prandial ghrelin level of the patient before ablation; an exercise output of the patient increases by at least 1% relative to an exercise output of the patient before ablation; a glucagon-like peptide-1 level of the patient increases by at least 1% relative to a glucagon-like peptide-1 level of the patient before ablation; a leptin level of the patient increases by at least 1% relative to a leptin level of the patient before ablation; the patient's appetite decreases, over a predefined period of time, relative to the patient's appetite before ablation; a peptide YY level of the patient increases by at least 1% relative to a peptide YY level of the patient before ablation; a lipopolysaccharide level of the patient decreases by at least 1% relative to a lipopolysaccharide level of the patient before ablation; a motilin-related peptide level of the patient decreases by at least 1% relative to a motilin-related peptide level of the patient before ablation; a cholecystokinin level of the patient increases by at least 1% relative to a cholecystokinin level of the patient before ablation; a resting metabolic rate of the patient increases by at least 1% relative to a resting metabolic rate of the patient before ablation; a plasma-beta endorphin level of the patient increases by at least 1% relative to a plasma-beta endorphin level of the patient before ablation; an HbA1c level of the patient decreases by at least 0.3% relative to an HbA1c level of the patient before ablation; a triglyceride level of the patient decreases by at least 1% relative to a triglyceride level of the patient before ablation; a total blood cholesterol level of the patient decreases by at least 1% relative to a total blood cholesterol level of the patient before ablation; a glycemia level of the patient decreases by at least 1% relative to a glycemia level of the patient before ablation; a composition of the person's gut microbiota modulates from a first state before ablation to a second state after ablation, wherein the first state has a first level of bacteroidetes and a first level of firmicutes, wherein the second state has a second level of bacteroidetes and a second level of firmicutes, wherein the second level of bacteroidetes is greater than the first level of bacteroidetes by at least 3%, and wherein the second level of firmicutes is less than the first level of firmicutes by at least 3%; or, a cumulative daily dose of the patient's antidiabetic medications decreases by at least 10% relative to a cumulative daily dose of the patient's antidiabetic medications before ablation.

In various embodiments, ablation therapy is provided to achieve the following therapeutic goals or endpoints for patients with dyslipidemia and a first phase of treatment is considered successful for these patients if any one or more of the following therapeutic goals or endpoints is reached: a lipid profile of the patient improves by at least 10% relative a lipid profile of the patient before ablation, wherein lipid profile is defined at least by a ratio of LDL cholesterol to HDL cholesterol, and improve is defined as a decrease in the ratio of LDL cholesterol to HDL cholesterol; an LDL-cholesterol level of the patient decreases by at least 10% relative to an LDL-cholesterol level of the patient before ablation; or, a VLDL-cholesterol level of the patient decreases by at least 10% relative to a VLDL-cholesterol level of the patient before ablation.

In various embodiments, ablation therapy is provided to achieve the following therapeutic goals or endpoints for patients with non-alcoholic steatohepatitis (NASH) or non-alcoholic fatty liver disease (NAFLD), and a first phase of treatment is considered successful for these patients if any one or more of the following therapeutic goals or endpoints is reached: at least a 10% decrease in either ALT or AST levels relative to ALT or AST levels before ablation; at least a 10% improvement in serum ferritin level or an absolute serum ferritin level of less than 1.5 ULN (upper limit normal) relative to serum ferritin levels before ablation; at least a 5% improvement in hepatic steatosis (HS) or less than 5% HS relative to HS levels before ablation, as measured on liver biopsy; at least a 5% improvement in HS or less than 5% HS relative to HS levels before ablation, as measured by magnetic resonance (MR) imaging, either by spectroscopy or proton density fat fraction; at least a 5% improvement in an NAFLD Fibrosis Score (NFS) relative to an NFS before ablation; at least a 5% improvement in an NAFLD Activity Score (NAS) relative to an NAS before ablation; at least a 5% improvement in a Steatosis Activity Fibrosis (SAF) score relative to an SAF score before ablation; at least a 5% decrease in a mean annual fibrosis progression rate relative to a mean annual fibrosis progression rate before ablation, as measured by histology, Fibrosis-4 (FIB-4) index, aspartate aminotransferase (AST) to platelet ratio index (APRI), serum biomarkers (Enhanced Liver Fibrosis (ELF) panel, Fibrometer, FibroTest, or Hepascore), or imaging (transient elastography (TE), MR elastography (MRE), acoustic radiation force impulse imaging, or supersonic shear wave elastography); at least a 5% decrease in circulating levels of cytokeratin-18 fragments relative to circulating levels of cytokeratin-18 fragments before ablation; at least a 5% improvement in FIB-4 index, aspartate aminotransferase (AST]) to platelet ratio index (APRI), serum biomarkers (Enhanced Liver Fibrosis (ELF) panel, Fibrometer, FibroTest, or Hepascore), or imaging (transient elastography (TE), MR elastography (MRE0, acoustic radiation force impulse imaging, or supersonic shear wave elastography) relative to FIB-4 index, aspartate aminotransferase (AST]) to platelet ratio index (APRI), serum biomarkers (Enhanced Liver Fibrosis (ELF) panel, Fibrometer, FibroTest, or Hepascore), or imaging (transient elastography (TE), MR elastography (MRE), acoustic radiation force impulse imaging, or supersonic shear wave elastography) before ablation; at least a 5% decrease in liver stiffness relative to liver stiffness before ablation, as measured by vibration controlled transient elastography (VCTE/FibroScan); an improvement in NAS by at least 2 points, with at least 1-point improvement in hepatocellular ballooning and at least 1-point improvement in either lobular inflammation or steatosis score, and no increase in the fibrosis score, relative to NAS, hepatocellular ballooning, lobular inflammation, steatosis, and fibrosis scores before ablation; at least a 5% improvement in NFS scores relative to NFS scores before ablation; or, at least a 5% improvement in any of the above listed NAFLD parameters as compared to a sham intervention or a placebo.

If any one of the above therapeutic goals or endpoints is met, therapy is completed at step 972 and no further ablation is performed. If none of the above therapeutic goals or endpoints are met, then the entire ablation procedure and evaluation, less the screening process, and comprising steps 954-970, is repeated for a second therapy phase, and subsequent therapy phases if therapeutic goals or endpoints are still not met, waiting at least six weeks each time between each ablation procedure and each evaluation.

FIG. 9E is a flow chart illustrating a multi-stage method of using a vapor ablation system for treating cancerous or precancerous esophageal tissue, in accordance with various embodiments of the present specification. The vapor ablation system comprises a controller having at least one processor in data communication with at least one pump and a catheter connection port in fluid communication with the at least one pump. At step 953, a proximal end of a first catheter is connected to the catheter connection port to place the first catheter in fluid communication with the at least one pump, wherein the first catheter comprises at least two positioning elements separated along a length of the catheter and one or more ports positioned between the at least two positioning elements, wherein each of the at least two positioning elements has a first configuration and a second configuration, and wherein, in the first configuration, each of the at least two positioning elements is compressed within the catheter and in the second configuration and each of the at least two positioning elements is expanded to be at least partially outside the catheter. At step 955, the first catheter is positioned inside a patient such that, upon being expanded into the second configuration, a distal one of the at least two positioning elements is positioned adjacent the patient's esophagus and a proximal one of the at least two positioning elements is proximally positioned more than 1 cm from the distal one of the at least two positioning elements. At step 957, each of the at least two positioning elements is expanded into their second configurations. At step 959, the controller is activated, wherein, upon activation, the controller is configured to cause the at least one pump to deliver saline into at least one lumen in the first catheter and, wherein, upon activation, the controller is configured to cause an electrical current to be delivered to at least one electrode positioned within the at least one lumen of the first catheter. The electrical current causes the electrode to heat and contact of the saline with the heating electrode converts the saline to vapor, or steam, which is delivered via the one or more ports to circumferentially ablate target tissue. In some embodiments, during the first stage of treatment, the at least two positioning elements, together with the esophageal tissue, define a first enclosed volume wherein at least one of the at least two positioning elements is positioned relative the esophageal tissue to permit a flow of air out of the second enclosed volume when the vapor is delivered.

In various embodiments, the vapor is delivered to treat at least 1-15 cm of contiguous or non-contiguous small intestine mucosa. In various embodiments, the vapor is delivered to treat at least 50% of a circumference of small intestine. In various embodiments, the vapor dose is characterized by at least one of: having an energy of 5-25 J/cm$^2$, delivered over 1-60 seconds, delivered at an energy rate of 5-2500 cal/see, delivered such that the total dose is 5-40 calories/gram of tissue to be ablated, delivered to elevate a target tissue temperature above 60° C. but less than 110° C., has a vapor temperature between 99° C. and 110° C., or delivered such that a pressure in a small intestine is less than 5 atm, and preferably less than 1 atm.

In various embodiments, the vapor is delivered to treat at least 1-15 cm of contiguous or non-contiguous small intestine mucosa. In various embodiments, the vapor is delivered to treat at least 50% of a circumference of small intestine. In various embodiments, the vapor dose is characterized at least one of: having an energy of 5-25 J/cm$^2$, delivered over 1-60 seconds, delivered at an energy rate of 5-2500 cal/sec, delivered such that the total dose is 5-40 calories/gram of tissue to be ablated, delivered to elevate a target tissue temperature above 60° C. but less than 110° C., has a vapor temperature between 99° C. and 110° C., or delivered such that a pressure in a small intestine is less than 5 atm, and preferably less than 1 atm.

At step 961, the controller shuts off the delivery of saline and electrical current. In embodiments, the controller automatically shuts off the delivery of saline and electrical current. Optionally, at step 963, the controller is reactivated to deliver saline into the lumen of the first catheter and electrical current to the electrode until the physician terminates the procedure. The catheter is removed from the patient at step 965 to complete treatment.

The physician waits for at least six weeks at step 967 before evaluating the efficacy of the first stage. After at least six weeks, at step 969, a post-first stage evaluation is performed wherein the efficacy of the first stage of treatment is determined by measuring physiological parameters relating to the conditions being treated and comparing the measured values to desired therapeutic goals or endpoints. (Alternatively, in other embodiments, a visible evaluation is performed immediately after completion of the first stage and, if deemed necessary based on the visual observation, a second stage of treatment using a second catheter is performed before waiting at least six weeks.)

In some embodiments, if the desired therapeutic goals or endpoints have not been achieved, a second stage of therapy may be performed. At step 971, a proximal end of a second catheter is connected to the catheter connection port to place the second catheter in fluid communication with the at least one pump, wherein the second catheter comprises a distal tip having at least one port and at least one positioning element attached to the distal tip such that, upon being in an operational configuration, the at least one positioning element encircles the at least one port and is configured to direct all vapor exiting from the at least one port. At step 973, the second catheter is positioned inside the patient such that a distal surface of the at least one positioning element is positioned adjacent the patient's esophagus. Optionally, the at least one positioning element is expandable from a first, collapsed configuration to an expanded, operational configuration and, at step 975, the at least one positioning element is expanded into the operation configuration. At step 977, the controller is activated, wherein, upon activation, the controller is configured to cause the at least one pump to deliver saline into at least one lumen in the second catheter and, wherein, upon activation, the controller is configured to cause an electrical current to be delivered to at least one electrode positioned within the at least one lumen of the second catheter. The electrical current causes the electrode to heat and contact of the saline with the heating electrode converts the saline to vapor, or steam, which is delivered via the at least one port to focally ablate target tissue. In some embodiments, during the second stage of treatment, the at least one positioning element, together with the esophageal tissue, defines a second enclosed volume wherein the at least one positioning element is positioned relative the esophageal tissue to permit a flow of air out of the second enclosed volume when the vapor is delivered.

In various embodiments, the vapor is delivered to treat at least 1-15 cm of contiguous or non-contiguous small intestine mucosa. In various embodiments, the vapor is delivered to treat at least 50% of a circumference of small intestine. In various embodiments, the vapor dose is characterized at least one of: having an energy of 5-25 J/cm$^2$, delivered over 1-60 seconds, delivered at an energy rate of 5-2500 cal/sec, delivered such that the total dose is 5-40 calories/gram of tissue to be ablated, delivered to elevate a target tissue temperature above 60° C. but less than 110° C., has a vapor temperature between 99° C. and 110° C., or delivered such that a pressure in a small intestine is less than 5 atm, and preferably less than 1 atm.

At step 979, the controller shuts off the delivery of saline and electrical current after a time period ranging from 1 to 60 seconds. In embodiments, the controller automatically shuts off the delivery of saline and electrical current. Optionally, in some embodiments, the controller is repeatedly activated at step 981 to deliver saline into the lumen and electrical current to the at least one electrode until the physician terminates the procedure. In some embodiments, the system further comprises a foot pedal in data communication with the controller, a switch on the catheter, or a switch on the controller, for controlling vapor flow and step 981 is achieved using the foot pedal in data communication with the controller, a switch on the catheter, or a switch on the controller. The second catheter is removed from the patient at step 983 to complete the second stage of treatment. In some embodiments, evaluations are performed at least six weeks to two years after completion of the second stage to determine efficacy of the second stage and, if desired therapeutic goals or endpoints are not achieved, further first and/or second stages, with further evaluations, may be performed as needed.

If any one of the therapeutic goals or endpoints described in the present specification is met, therapy is completed at step 972 and no further ablation is performed. If none of the above therapeutic goals or endpoints are met, then the entire ablation procedure and evaluation, less the screening process, and comprising steps 954-970, is repeated for a second therapy phase, and subsequent therapy phases if therapeutic goals or endpoints are still not met, waiting at least six weeks each time between each ablation procedure and each evaluation.

FIG. 9F is a flow chart illustrating a method of ablating a tissue inside a gastrointestinal (GI) tract of a patient with a pathophysiological metabolic condition, in accordance with other embodiments of the present specification. The metabolic condition is one of type-II DM/NASH/NAFLD/PCOS/Obesity or Prediabetes. In embodiments, ablation catheters disclosed in the present specification, such as ablation catheter 870 of FIG. 8J, are used to perform the ablation method of FIG. 9F. The ablation catheter is in fluid communication with a pump that is in turn in data communication with a controller that includes a programmable processor. At 902f, the ablation catheter configured for the gastrointestinal (GI) tract is inserted into the GI tract of the patient to deliver vapor from the catheter to the target area. The target area includes duodenal tissue in a portion of the duodenum of the patient. At 904f, the controller is used to control delivery of vapor to the duodenal tissue surface within the target area and into a depth of tissue within the target area to treat the pathophysiological metabolic condition. In embodiments, the controller delivers the vapor energy to perform a circumferential ablation of greater than or equal to 50% for ablating a mucosa, and perform a non-circumferential ablation of less than 50% for ablating a muscularis propria or an adventitia. In embodiments, the ablation is performed so that the ampulla or a periampullary region (5 mm around an ampulla) around the target area remain protected from ablation.

FIG. 9G is a flow chart illustrating a method of using a vapor ablation system for ablating a target area within GI tract of a patient with a pathophysiological metabolic condition, in accordance with embodiments of the present specification. In embodiments, ablation catheters disclosed in the present specification, such as ablation catheter 870 of FIG. 8J, are used to perform the ablation method of FIG. 9G. The ablation catheter is in fluid communication with a pump that is in turn in data communication with a controller that includes a programmable processor. At step 902g, a target area for ablation, required to treat the pathophysiological metabolic condition of the patient, is determined. The duration of ablation varies with the target anatomical location. Ablation is avoided all the way through the Muscularis Propria. In the duodenum, approximately less than or equal to 1 mm depth is ablated, which in one embodiment is achieved by ablation for 4 seconds. The depth of ablation achieved is based on the duration of ablation. In one example, the esophagus is treated for 5 seconds, and the duodenum is treated for 4 seconds to achieve a target depth of ablation. At step 904g, an ablation structure is selected to ablate the target area to a predetermined depth. The ablation structure includes one or more positioning elements and at least one vapor delivery port at a distal end of the catheter, which may be selected from the various embodiments described in the present specification. In embodiments, the vapor delivery ports are arranged around a circumference of the catheter. The target area is a portion of duodenum tissue in the GI tract. At step 906g, the selected ablation structure is advanced to reach a position that is adjacent to the target area. The target area is a portion of the gastrointestinal tract that includes at least a portion of the duodenum. At step 908g, the positioning elements of the ablation structure are moved into contact with a surface of the tissue within the target area. At step 910g, vapor is delivered from the vapor delivery ports to the tissue surface within the target area. In embodiments, the vapor is delivered for a predetermined duration such that the duration of vapor delivery enables the vapor to form a volume of ablated tissue within a portion of the target area at step 912g. The ablated tissue within the target area has the predetermined depth of ablation, controlled by the controller that enables the ablation for the predetermined duration.

FIG. 9H is a flow chart illustrating a method of using a vapor ablation system for ablating a target area in an intestine of a patient with non-alcoholic fatty liver disease (NAFLD) or non-alcoholic steatohepatitis (NASH), in accordance with embodiments of the present specification. In embodiments, ablation catheters disclosed in the present specification, such as ablation catheter 870 of FIG. 8J, are used to perform the ablation method of FIG. 9H. At step 902h, a patient diagnosed with NAFLD or NASH is selected. The diagnosis of the patient determines elevated baseline levels of liver enzymes indicative of inflammation of the liver. At step 904h, an ablation system is provided that includes a catheter for insertion into the intestine. The catheter further includes an elongate shaft comprising a distal portion, one or more positioning elements, and at least one vapor delivery port positioned around a circumference on the distal portion. At step 906h, the catheter is introduced into the patient diagnosed with either NAFLD or NASH. At step 908h, vapor is delivered to a mucosal tissue that is targeted for ablation within the patient's small intestine. The vapor is delivered by the catheter after positioning the catheter adjacent to the target tissue area using the positioning elements. The vapor is then delivered through the vapor delivery ports at the distal end of the catheter. The patient may be treated with vapor delivery multiple times to create an ablation area. The ablation area could be a contiguous area or an area having intervening length of unablated mucosal tissue. In some embodiments, the ablation area that is created with vapor delivery treatment performed multiple times, has a roughly circular shape with a diameter of at least 3 cm. In some embodiments, the ablation area that is created with vapor delivery treatment performed multiple times, has a circumferential area of greater than or equal to 50%. The vapor delivery treatment may be performed multiple times in a single session. Alternatively, the vapor delivery may be performed through multiple sessions spread over a period of different times in a day or over different days. An area ablated by vapor once is overlapped with ablation during the multiple vapor delivery treatments. The overlapping vapor delivery may be performed for the same duration or different duration as the initial duration of vapor delivery. The ablation treatment is configured to treat NAFLD or NASH that the patient is diagnosed for. The treatment is administered in accordance with the present specification such that the patient achieves a reduction in the elevated baseline levels of liver enzymes after treatment. In embodiments, the patient achieves the reduction in the levels of liver enzymes by 6 months after treatment and sustains the reduction through 12 months after treatment.

FIG. 9I is a flow chart illustrating a method of using a vapor ablation system for ablating a target area in an intestine of a patient with obesity, diabetes or a metabolic syndrome, in accordance with embodiments of the present specification. In embodiments, ablation catheters disclosed in the present specification, such as ablation catheter 870 of FIG. 8J, are used to perform the ablation method of FIG. 9I. At step 902i, a patient diagnosed with obesity, diabetes or a metabolic syndrome is selected. The diagnosis of the patient determines elevated baseline levels of liver enzymes indicative of inflammation of the liver. At step 904i, an ablation system is provided that includes a catheter for insertion into the intestine. The catheter further includes an elongate shaft comprising a distal portion, one or more positioning elements, and at least one vapor delivery port positioned around a circumference on the distal portion. At step 906*i*, the catheter is introduced into the patient diagnosed with obesity, diabetes or metabolic syndrome. At step 908*i*, vapor is delivered to a mucosal tissue that is targeted for ablation within the patient's small intestine. The vapor is delivered by the catheter after positioning the catheter adjacent to the target tissue area using the positioning elements. The vapor is then delivered through the vapor delivery ports at the distal end of the catheter. The patient may be treated with vapor delivery multiple times to create an ablation area. The ablation area could be a contiguous area or an area having intervening length of unablated mucosal tissue. In some embodiments, the ablation area that is created with vapor delivery treatment performed multiple times, has a roughly circular shape with a diameter of at least 3 cm. In some embodiments, the ablation area that is created with vapor delivery treatment performed multiple times, has a circumferential area of greater than or equal to 50%. The vapor delivery treatment may be performed multiple times in a single session. An area ablated by vapor once is overlapped with ablation during the multiple vapor delivery treatments. The overlapping vapor delivery may be performed for the same duration or different duration as the initial duration of vapor delivery. The ablation treatment is configured to treat obesity, diabetes or the metabolic syndrome that the patient is diagnosed for. The treatment is administered in accordance with the present specification such that the patient achieves a reduction in the elevated baseline levels of liver enzymes after treatment. In embodiments, the patient achieves the reduction in the levels of liver enzymes by 6 months after treatment and sustains the reduction through 12 months after treatment.

FIG. 9J is a flow chart illustrating a method of using a vapor ablation system for ablating a target area in an intestine of a patient with obesity, diabetes or a metabolic syndrome, in combination with NASH and/or NAFLD, in accordance with embodiments of the present specification. In embodiments, ablation catheters disclosed in the present specification, such as ablation catheter 870 of FIG. 8J, are used to perform the ablation method of FIG. 9J. At step 902*j*, a patient diagnosed with obesity, diabetes or a metabolic syndrome, in combination with NASH and/or NAFLD, is selected. The diagnosis of the patient determines elevated baseline levels of liver enzymes indicative of inflammation of the liver. At step 904*j*, an ablation system is provided that includes a catheter for insertion into the intestine. The catheter further includes an elongate shaft comprising a distal portion, one or more positioning elements, and at least one vapor delivery port positioned around a circumference on the distal portion. At step 906*j*, the catheter is introduced into the patient diagnosed with obesity, diabetes or metabolic syndrome, in combination with NASH and/or NAFLD. At step 908*j*, vapor is delivered to a mucosal tissue that is targeted for ablation within the patient's small intestine. The vapor is delivered by the catheter after positioning the catheter adjacent to the target tissue area using the positioning elements. The vapor is then delivered through the vapor delivery ports at the distal end of the catheter. The patient may be treated with vapor delivery multiple times to create an ablation area. The ablation area could be a contiguous area or an area having intervening length of unablated mucosal tissue. In some embodiments, the ablation area that is created with vapor delivery treatment performed multiple times, has a roughly circular shape with a diameter of at least 3 cm. In some embodiments, the ablation area that is created with vapor delivery treatment performed multiple times, has a circumferential area of greater than or equal to 50%. The vapor delivery treatment may be performed multiple times in a single session. An area ablated by vapor once is overlapped with ablation during the multiple vapor delivery treatments. The overlapping vapor delivery may be performed for the same duration or different duration as the initial duration of vapor delivery. The ablation treatment is configured to treat obesity, diabetes or the metabolic syndrome, in combination with NASH and/or NAFLD, which the patient is diagnosed for. The treatment is administered in accordance with the present specification such that the patient achieves a reduction in the elevated baseline levels of liver enzymes after treatment. In embodiments, the patient achieves the reduction in the levels of liver enzymes by 6 months after treatment and sustains the reduction through 12 months after treatment.

FIG. 9K is a flow chart illustrating a method of using a vapor ablation system for ablating a target area in an intestine of a patient with non-alcoholic fatty liver disease (NAFLD) or non-alcoholic steatohepatitis (NASH), in accordance with embodiments of the present specification. In embodiments, ablation catheters disclosed in the present specification, such as ablation catheter 870 of FIG. 8J, are used to perform the ablation method of FIG. 9K. At step 902K, a patient diagnosed with NAFLD or NASH is selected. The diagnosis of the patient determines elevated baseline levels of liver enzymes indicative of inflammation of the liver. At step 904*k*, an ablation system is provided that includes a catheter for insertion into the intestine. The catheter further includes an elongate shaft comprising a distal portion, one or more positioning elements, and at least one vapor delivery port positioned around a circumference on the distal portion. At step 906*k*, the catheter is introduced into the patient diagnosed with either NAFLD or NASH. At step 908*k*, vapor is delivered to a mucosal tissue that is targeted for ablation within the patient's small intestine. The vapor is delivered by the catheter after positioning the catheter adjacent to the target tissue area using the positioning elements. The vapor is then delivered through the vapor delivery ports at the distal end of the catheter. The patient may be treated with vapor delivery multiple times to create an ablation area. The ablation area could be a contiguous area or an area having intervening length of unablated mucosal tissue. In some embodiments, the ablation area that is created with vapor delivery treatment performed multiple times, has a roughly circular shape with a diameter of at least 3 cm. In some embodiments, the ablation area that is created with vapor delivery treatment performed multiple times, has a circumferential area of greater than or equal to 50%. The vapor delivery treatment may be performed multiple times in a single session. An area ablated by vapor once is overlapped with ablation during the multiple vapor delivery treatments. The overlapping vapor delivery may be performed for the same duration or different duration as the initial duration of vapor delivery. The ablation treatment is configured to treat NAFLD or NASH that the patient is diagnosed for. The treatment is administered in accordance with the present specification such that the patient achieves a reduction in the elevated baseline levels of liver enzymes after treatment. In embodiments, the patient achieves the reduction in the levels of liver enzymes by 6 months after treatment and sustains the reduction through 12 months after treatment.

FIG. 9L is a flow chart illustrating a method of using a vapor ablation system for ablating a target area in an intestine of a patient diagnosed with diabetes, prediabetes or obesity measured by an elevated level of BMI and/or a hemoglobin A1C and also diagnosed as having polycystic ovarian syndrome (PCOS), in accordance with embodiments of the present specification. In embodiments, ablation catheters disclosed in the present specification, such as ablation catheter 870 of FIG. 8J, are used to perform the ablation method of FIG. 9L. At step 902l, a patient diagnosed with diabetes, prediabetes or obesity measured by an elevated level of BMI and/or a hemoglobin A1C, and also diagnosed as having PCOS, is selected. At step 904l, an ablation system is provided that includes a catheter for insertion into the intestine. The catheter further includes an elongate shaft comprising a distal portion, one or more positioning elements, and at least one vapor delivery port positioned around a circumference on the distal portion. At step 906l, the catheter is introduced into the patient. At step 908l, vapor is delivered to a mucosal tissue that is targeted for ablation within the patient's small intestine. The vapor is delivered by the catheter after positioning the catheter adjacent to the target tissue area using the positioning elements. The vapor is then delivered through the vapor delivery ports at the distal end of the catheter. The patient may be treated with vapor delivery multiple times to create an ablation area. The ablation area could be a contiguous area or an area having intervening length of unablated mucosal tissue. In some embodiments, the ablation area that is created with vapor delivery treatment performed multiple times, has a roughly circular shape with a diameter of at least 3 cm. In some embodiments, the ablation area that is created with vapor delivery treatment performed multiple times, has a circumferential area of greater than or equal to 50%. The vapor delivery treatment may be performed multiple times in a single session. An area ablated by vapor once is overlapped with ablation during the multiple vapor delivery treatments. The overlapping vapor delivery may be performed for the same duration or different duration as the initial duration of vapor delivery. The ablation treatment is configured to treat PCOS that the patient is diagnosed for. The treatment is administered in accordance with the present specification such that the patient achieves a reduction in the elevated baseline levels of the BMI or hemoglobin A1C after treatment. In embodiments, the patient achieves the reduction in the levels of BMI or hemoglobin A1C by 3 months after treatment and sustains the reduction through 12 months after treatment.

FIG. 9M is a flow chart illustrating a method of using a vapor ablation system for ablating a target area in an intestine of a patient with non-alcoholic fatty liver disease (NAFLD) or non-alcoholic steatohepatitis (NASH), with abnormal baseline levels of laboratory or radiology measurement indicative of inflammation of the liver, in accordance with embodiments of the present specification. In embodiments, ablation catheters disclosed in the present specification, such as ablation catheter 870 of FIG. 8J, are used to perform the ablation method of FIG. 9M. At step 902m, a patient diagnosed with NAFLD or NASH, with abnormal baseline levels of laboratory or radiology measurement indicative of inflammation of the liver, is selected. The diagnosis of the patient determines elevated baseline levels of hemoglobin A1C indicative of diabetes or prediabetes. At step 904m, an ablation system is provided that includes a catheter for insertion into the intestine. The catheter further includes an elongate shaft comprising a distal portion, one or more positioning elements, and at least one vapor delivery port positioned around a circumference on the distal portion. At step 906m, the catheter is introduced into the patient diagnosed with either NAFLD or NASH. At step 908m, vapor is delivered to a mucosal tissue that is targeted for ablation within the patient's small intestine. The vapor is delivered by the catheter after positioning the catheter adjacent to the target tissue area using the positioning elements. The vapor is then delivered through the vapor delivery ports at the distal end of the catheter. The patient may be treated with vapor delivery multiple times to create an ablation area. The ablation area could be a contiguous area or an area having intervening length of unablated mucosal tissue. In some embodiments, the ablation area that is created with vapor delivery treatment performed multiple times, has a roughly circular shape with a diameter of at least 3 cm. In some embodiments, the ablation area that is created with vapor delivery treatment performed multiple times, has a circumferential area of greater than or equal to 50%. The vapor delivery treatment may be performed multiple times in a single session. An area ablated by vapor once is overlapped with ablation during the multiple vapor delivery treatments. The overlapping vapor delivery may be performed for the same duration or different duration as the initial duration of vapor delivery. The ablation treatment is configured to treat NAFLD or NASH that the patient is diagnosed for. The treatment is administered in accordance with the present specification such that the patient achieves an improvement in the abnormal baseline laboratory or radiology measurement after treatment. In embodiments, the patient achieves an improvement in the abnormal baseline laboratory or radiology measurement by 6 months after treatment and sustains the improvement through 12 months after treatment.

Figure 9N:
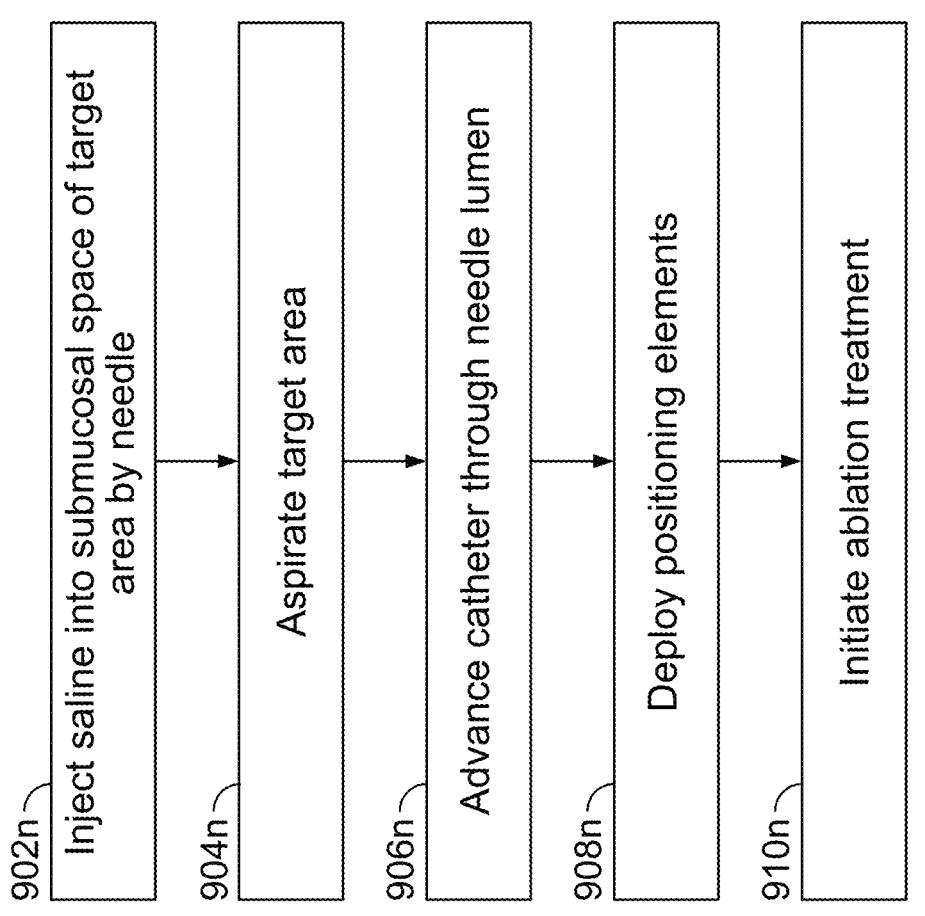
FIG. 9N is a flow chart illustrating a method of using a microcatheter for ablating tissue surface in a target area within a hollow or a tubular organ, in accordance with some embodiments of the present specification.

In some embodiments, the present specification provides methods and systems using catheter with needles, such as for example the needles of FIGS. 4A to 6D, for ablating tissue in any hollow and/or tubular organ. The organ can be one of gastrointestinal tract, pancreaticobiliary tract, genitourinary tract, respiratory tract or a vascular structure such as blood vessels. The catheter, also referred to herein as a microcatheter, passes through a needle. The catheter structure is largely similar to those described with reference to FIGS. 1A to 1K, except that the length of the electrode in the microcatheter is reduced. FIG. 9N illustrates an exemplary method of using a microcatheter for ablating tissue surface in a target area within a hollow or a tubular organ, in accordance with some embodiments of the present specification. At step 902n, the needle is used to inject saline into a sub-mucosal space of the tissue surface within the organ. In embodiments, multiple injections are made in the target ablation area. The submucosal injection limits ablation depth and protects the muscularis propria (muscular layers adjacent to submucosa) and adventitia layers. Additionally, the saline injection absorbs heat, slowing the penetration. At step 904n, all fluid is aspirated out of the target ablation zone prior to delivering ablative agent. Aspiration is performed to prevent formation of puddles of fluid in the ablation area. In some embodiments, prior to aspirating, mucus from the tissue surface of the target ablation area is also washed or removed. At step 906n, the microcatheter is passed through a lumen within the needle and out from the tip of the needle such that the electrode within the microcatheter is positioned outside the needle tip. As a result, the tip of needle is avoided from heating up. At step 908n, one or more positioning elements are deployed by expansion. At step 910n, the ablation procedure is initiated by generating vapor from saline and dispersing the vapor through one or more infusion ports configured along a circumference of the microcatheter. During the ablation procedure, a patient is positioned such that liquid does not pool in the ablative zone. In embodiments, the patient position is "prone" (stomach down) to minimize fluid pooling in the duodenum and GI tract. In some embodiments, the patient position is supine or left lateral. In embodiments, the patient is rotated during a procedure and between ablations as needed to move pooling liquid to a different location in the organ. The ablation procedure is controlled by a controller. The controller controls the delivery of vapor to the tissue surface within the target area and into a depth of tissue within the target area to treat the target area. After the ablation treatment, the controller shuts off the delivery of saline and electrical current. In embodiments, the controller automatically shuts off the delivery of saline and electrical current. Optionally, the controller is reactivated to deliver saline into the lumen of the microcatheter and electrical current to the electrode until the physician terminates the procedure. The microcatheter and the needle is removed from the patient to complete treatment.

In various embodiments, ablation therapy is provided to achieve the following therapeutic goals or endpoints for patients with obesity, excess weight, eating disorders, dyslipidemia, or diabetes and a first phase of treatment is considered successful for these patients if any one or more of the following therapeutic goals or endpoints is reached: a total body weight of the patient decreases by at least 1% relative to a total body weight of the patient before ablation; an excess body weight of the patient decreases by at least 1% relative to an excess body weight of the patient before ablation; a total body weight of the patient decreases by at least 1% relative to a total body weight of the patient before ablation and a well-being level of the patient does not decrease more than 5% relative to a well-being level of the patient before ablation; an excess body weight of the patient decreases by at least 1% relative to an excess body weight of the patient before ablation and a well-being level of the patient does not decrease more than 5% relative to a well-being level of the patient before ablation; a pre-prandial ghrelin level of the patient decreases by at least 1% relative to a pre-prandial ghrelin level of the patient before ablation; a post-prandial ghrelin level of the patient decreases by at least 1% relative to a post-prandial ghrelin level of the patient before ablation; an exercise output of the patient increases by at least 1% relative to an exercise output of the patient before ablation; a glucagon-like peptide-1 level of the patient increases by at least 1% relative to a glucagon-like peptide-1 level of the patient before ablation; a leptin level of the patient increases by at least 1% relative to a leptin level of the patient before ablation; the patient's appetite decreases, over a predefined period of time, relative to the patient's appetite before ablation; a peptide YY level of the patient increases by at least 1% relative to a peptide YY level of the patient before ablation; a lipopolysaccharide level of the patient decreases by at least 1% relative to a lipopolysaccharide level of the patient before ablation; a motilin-related peptide level of the patient decreases by at least 1% relative to a motilin-related peptide level of the patient before ablation; a cholecystokinin level of the patient increases by at least 1% relative to a cholecystokinin level of the patient before ablation; a resting metabolic rate of the patient increases by at least 1% relative to a resting metabolic rate of the patient before ablation; a plasma-beta endorphin level of the patient increases by at least 1% relative to a plasma-beta endorphin level of the patient before ablation; an HbA1c level of the patient decreases by at least 0.3% relative to an HbA1c level of the patient before ablation; a triglyceride level of the patient decreases by at least 1% relative to a triglyceride level of the patient before ablation; a total blood cholesterol level of the patient decreases by at least 1% relative to a total blood cholesterol level of the patient before ablation; a glycemia level of the patient decreases by at least 1% relative to a glycemia level of the patient before ablation; a composition of the person's gut microbiota modulates from a first state before ablation to a second state after ablation, wherein the first state has a first level of bacteroidetes and a first level of firmicutes, wherein the second state has a second level of bacteroidetes and a second level of firmicutes, wherein the second level of bacteroidetes is greater than the first level of bacteroidetes by at least 3%, and wherein the second level of firmicutes is less than the first level of firmicutes by at least 3%; or, a cumulative daily dose of the patient's antidiabetic medications decreases by at least 10% relative to a cumulative daily dose of the patient's antidiabetic medications before ablation.

In various embodiments, ablation therapy is provided to achieve the following therapeutic goals or endpoints for patients with dyslipidemia and a first phase of treatment is considered successful for these patients if any one or more of the following therapeutic goals or endpoints is reached: a lipid profile of the patient improves by at least 10% relative a lipid profile of the patient before ablation, wherein lipid profile is defined at least by a ratio of LDL cholesterol to HDL cholesterol, and improve is defined as a decrease in the ratio of LDL cholesterol to HDL cholesterol; an LDL-cholesterol level of the patient decreases by at least 10% relative to an LDL-cholesterol level of the patient before ablation; or, a VLDL-cholesterol level of the patient decreases by at least 10% relative to a VLDL-cholesterol level of the patient before ablation.

In various embodiments, ablation therapy is provided to achieve the following therapeutic goals or endpoints for patients with non-alcoholic steatohepatitis (NASH) or non-alcoholic fatty liver disease (NAFLD), and a first phase of treatment is considered successful for these patients if any one or more of the following therapeutic goals or endpoints is reached: at least a 10% decrease in either ALT or AST levels relative to ALT or AST levels before ablation; at least a 10% improvement in serum ferritin level or an absolute serum ferritin level of less than 1.5 ULN (upper limit normal) relative to serum ferritin levels before ablation; at least a 5% improvement in hepatic steatosis (HS) or less than 5% HS relative to HS levels before ablation, as measured on liver biopsy; at least a 5% improvement in HS or less than 5% HS relative to HS levels before ablation, as measured by magnetic resonance (MR) imaging, either by spectroscopy or proton density fat fraction; at least a 5% improvement in an NAFLD Fibrosis Score (NFS) relative to an NFS before ablation; at least a 5% improvement in an NAFLD Activity Score (NAS) relative to an NAS before ablation; at least a 5% improvement in a Steatosis Activity Fibrosis (SAF) score relative to an SAF score before ablation; at least a 5% decrease in a mean annual fibrosis progression rate relative to a mean annual fibrosis progression rate before ablation, as measured by histology, Fibrosis-4 (FIB-4) index, aspartate aminotransferase (AST) to platelet ratio index (APRI), serum biomarkers (Enhanced Liver Fibrosis (ELF) panel, Fibrometer, FibroTest, or Hepascore), or imaging (transient elastography (TE), MR elastography (MRE), acoustic radiation force impulse imaging, or supersonic shear wave elastography); at least a 5% decrease in circulating levels of cytokeratin-18 fragments relative to circulating levels of cytokeratin-18 fragments before ablation; at least a 5% improvement in FIB-4 index, aspartate aminotransferase (AST]) to platelet ratio index (APRI), scrum biomarkers (Enhanced Liver Fibrosis (ELF) panel, Fibrometer, FibroTest, or Hepascore), or imaging (transient elastography (TE), MR elastography (MRE0, acoustic radiation force impulse imaging, or supersonic shear wave elastography) relative to FIB-4 index, aminotransferase (AST]) to platelet ratio index (APRI), serum biomarkers (Enhanced Liver Fibrosis (ELF) panel, Fibrometer, FibroTest, or Hep-ascore), or imaging (transient elastography (TE), MR elas-tography (MRE), acoustic radiation force impulse imaging, or supersonic shear wave elastography) before ablation; at least a 5% decrease in liver stiffness relative to liver stiffness before ablation, as measured by vibration controlled tran-sient elastography (VCTE/FibroScan); an improvement in NAS by at least 2 points, with at least 1-point improvement in hepatocellular ballooning and at least 1-point improve-ment in either lobular inflammation or steatosis score, and no increase in the fibrosis score, relative to NAS, hepato-cellular ballooning, lobular inflammation, steatosis, and fibrosis scores before ablation; at least a 5% improvement in NFS scores relative to NFS scores before ablation; or, at least a 5% improvement in any of the above listed NAFLD parameters as compared to a sham intervention or a placebo.

Therapeutic Pressure Profiles for Ablation Therapy

In various embodiments, the catheters of the present specification measure and monitor pressure of the steam/vapor throughout an ablation therapy and maintain the pressure below a predefined limit, such as 5 atm or 5 psi, in order to limit the amount of thermal energy transferred to the tissues during the therapy.

Figure 10A:
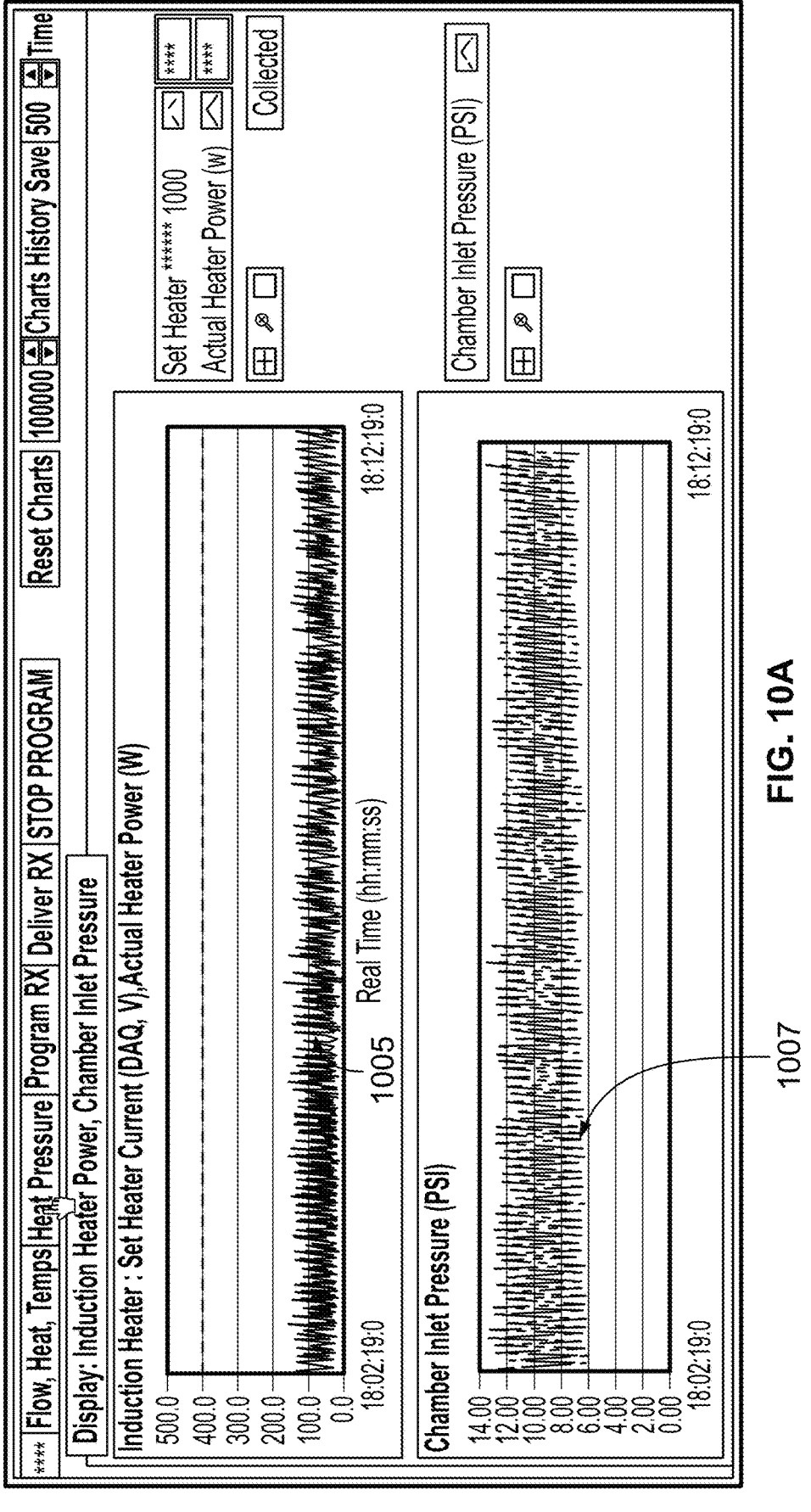
FIG. 10A shows first and second graphs illustrating energy consumption profile by a heating chamber (flexible heating chamber with RF electrodes or inductive coil based heating chamber) and pressure profile of vapor generated during an ablation therapy, in accordance with an embodiment of the present specification.
Figure 10B:
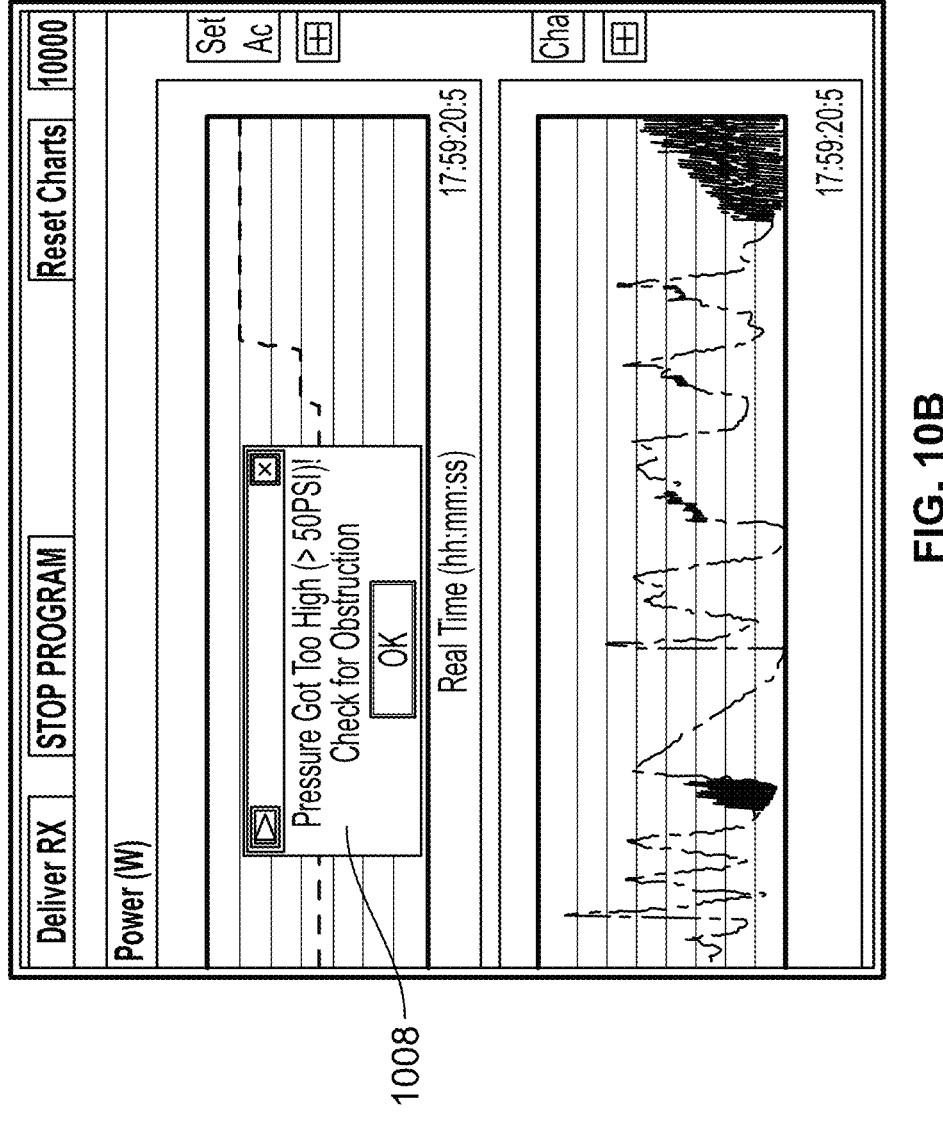
FIG. 10B illustrates an alert being generated when vapor pressure at the heating chamber reaches above a predefined limit, in accordance with an embodiment of the present specification.

In accordance with an aspect of the present specification, the energy consumed by the heating chamber is reflective of vapor pressure generated. FIG. 10A shows first and second graphs illustrating energy consumption profile by a heating chamber (flexible heating chamber with RF electrodes or inductive coil based heating chamber) and pressure profile of vapor generated during an ablation therapy, in accordance with an embodiment of the present specification. The first graph 1005 illustrates the power or energy consumption profile (in Watts) of the heating chamber with respect to time while the second graph 1007 illustrates the vapor pressure profile at an inlet of the heating chamber with respect to time. As shown in FIG. 10B the ablation therapy is stopped when the vapor pressure reaches above the predefined limit, such as 5 psi, and an alert 1008 is generated.

Figure 10C:
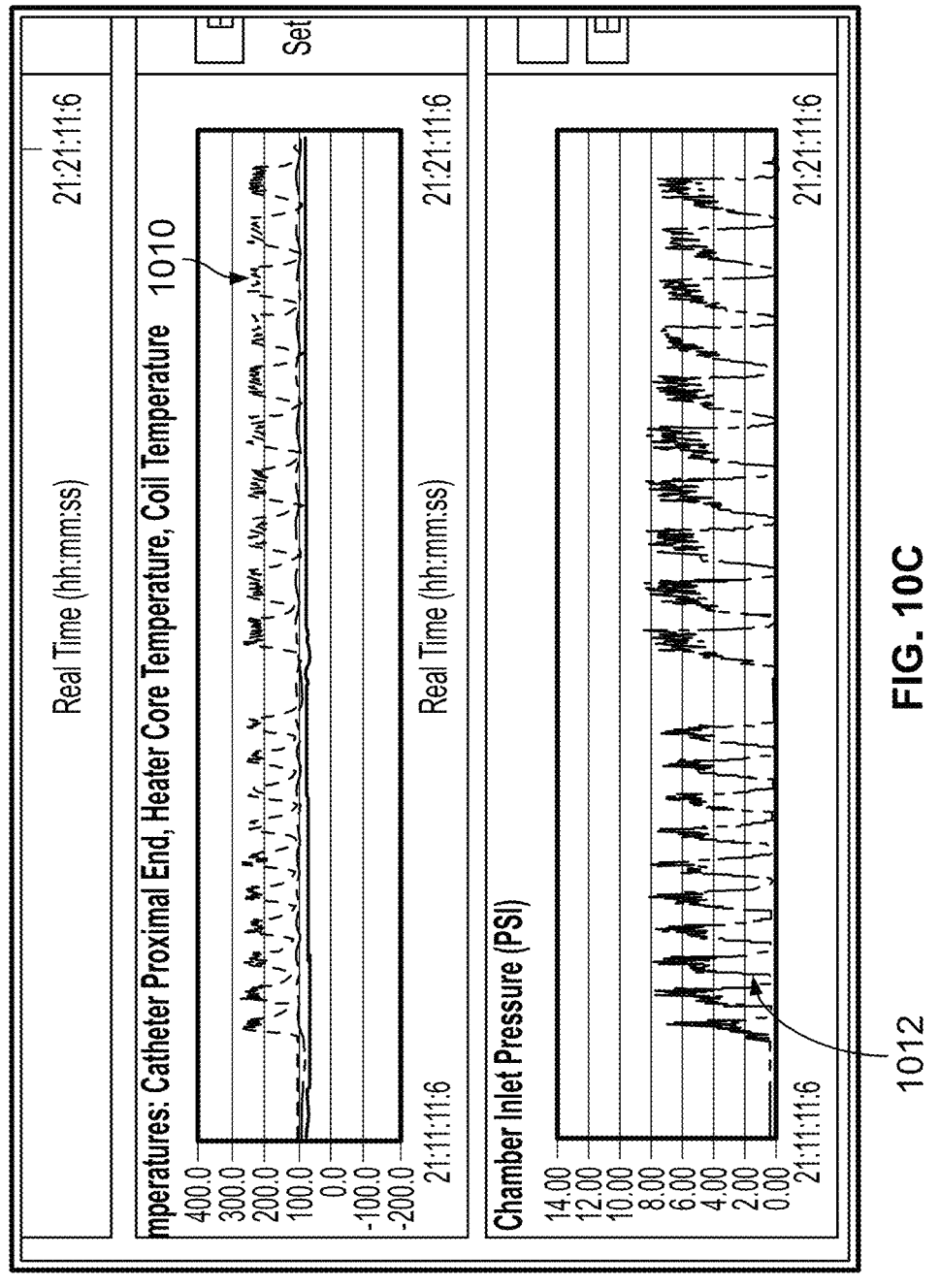
FIG. 10C shows third and fourth graphs illustrating a temperature profile of vapor and a pressure profile of vapor generated during an ablation therapy, in accordance with an embodiment of the present specification.

In accordance with another aspect of the present specifi-cation, the temperature of vapor correlates with the vapor pressure measured along the pathway of the vapor. FIG. 10C shows third and fourth graphs illustrating a temperature profile of vapor and a pressure profile of vapor generated during an ablation therapy, in accordance with an embodi-ment of the present specification. The third graph 1010 illustrates the temperature profile of vapor with respect to time while the fourth graph 1012 illustrates the vapor pressure profile along the vapor pathway with respect to time.

FIGS. 10D through 10P illustrate a plurality of exemplary vapor pressure based therapy profiles during ablation, in accordance with embodiments of the present specification. The pressure therapy profiles in each of the figures are shown as graphs having time (in seconds) on an X-axis and pressure (in atmospheres, atm) on a Y-axis.

Figure 10D:
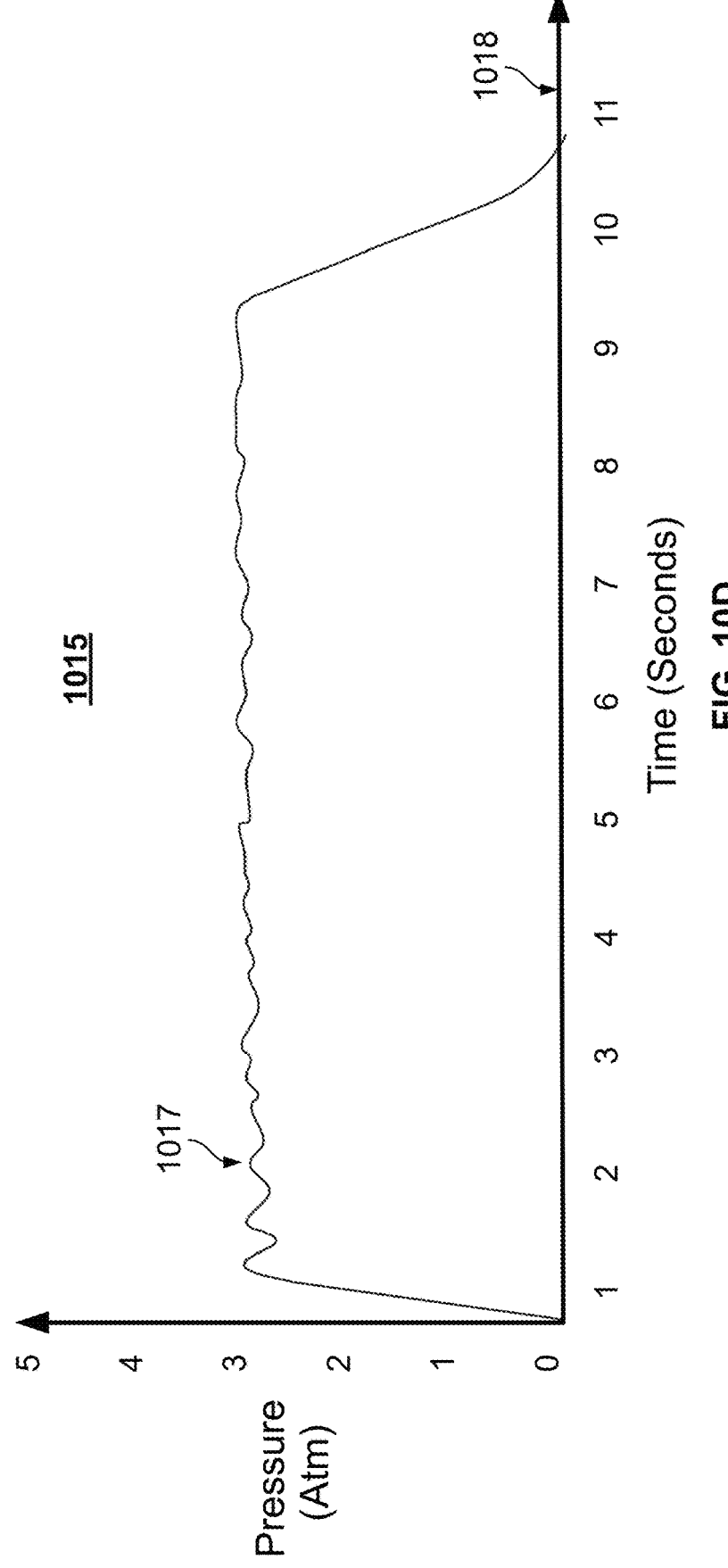
FIG. 10D illustrates a first pressure therapy profile, in accordance with an embodiment of the present specification.

FIG. 10D illustrates a pressure therapy profile 1015 wherein vapor delivery is initiated and pressure is raised to a desired maximum pressure 1017, such as 3 atm. The vapor pressure is maintained at the maximum pressure 1017 for a predefined time, such as 10 seconds, and thereafter the vapor delivery is stopped allowing the pressure to return to base-line 1018.

Figure 10E:
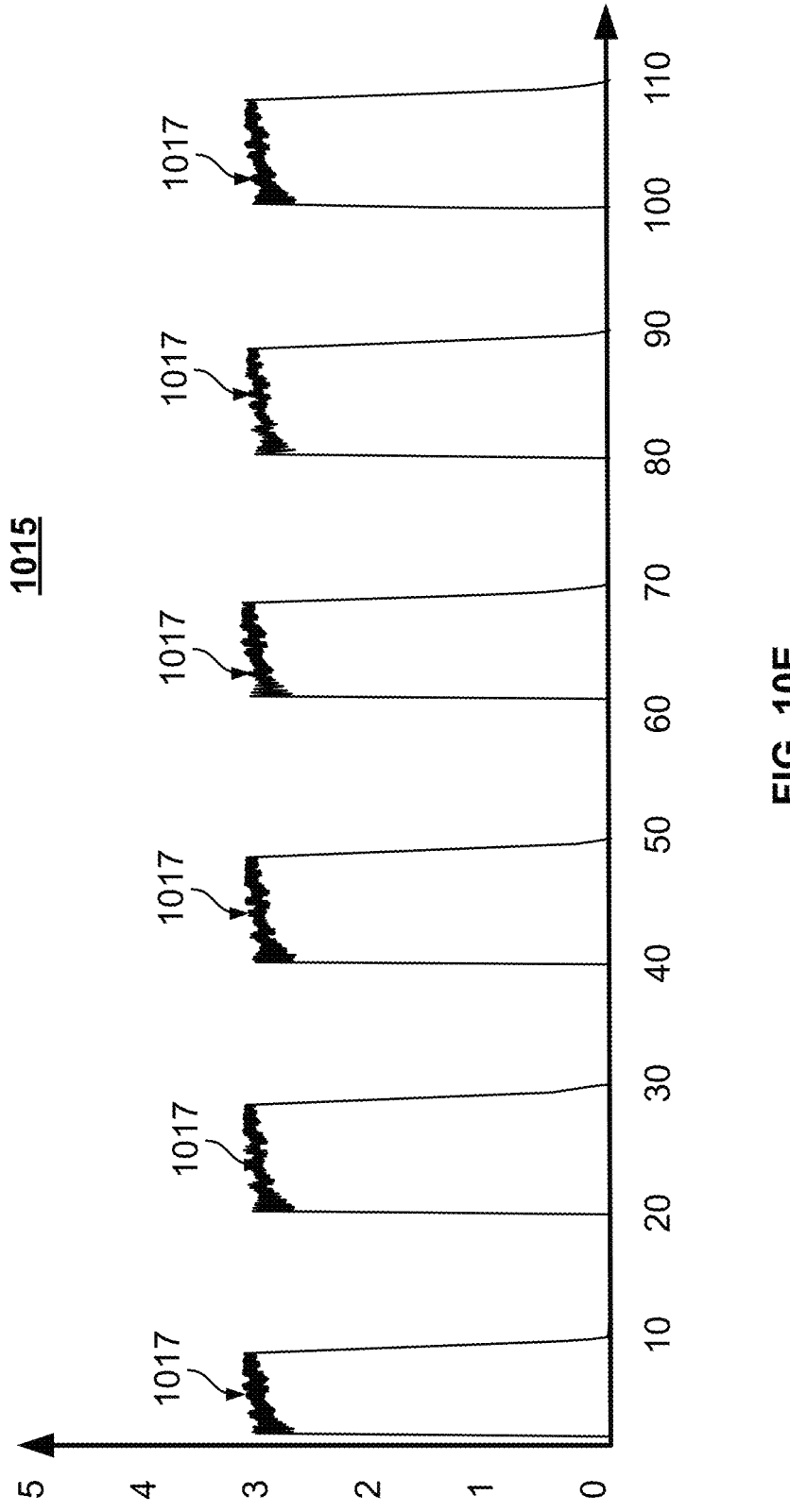
FIG. 10E illustrates a plurality of cycles of the first pressure therapy profile, in accordance with an embodiment of the present specification.
Figure 10F:
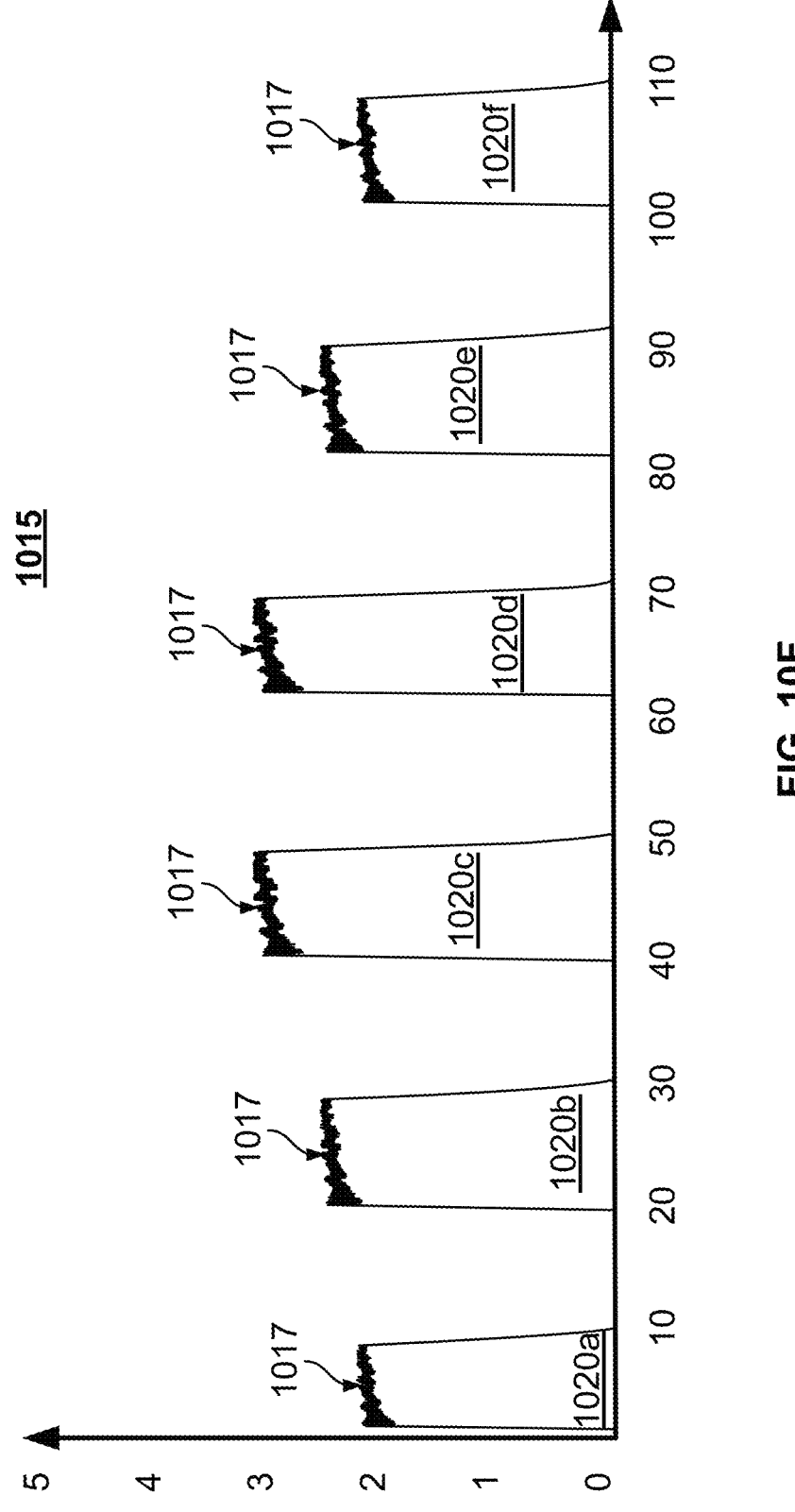
FIG. 10F illustrates a plurality of cycles of the first pressure therapy profile, in accordance with another embodiment of the present specification.

FIG. 10E illustrates the pressure therapy profile 1015 being repeated for a plurality of cycles, wherein the desired maximum pressure 1017 is same for each cycle. FIG. 10F illustrates the pressure therapy profile 1015 being repeated for a plurality of cycles wherein the desired maximum pressure 1017 is customized for each cycle. For example, the desired maximum pressure 1017 is: 2 atm for the first cycle 1020a, 2.5 atm for the second cycle 1020b and 3 atm for the third cycle 1020c. Thereafter, the desired maximum pressure 1017 is: maintained at 3 atm for the fourth cycle 1020d, 2.5 atm for the fifth cycle 1020e and 2 atm for the sixth cycle 1020f. In other words, the desired maximum pressure 1017 is increased and decreased for individual cycles 1020a through 1020f by increasing and decreasing the flow of vapor to create custom treatment profile.

Figure 10G:
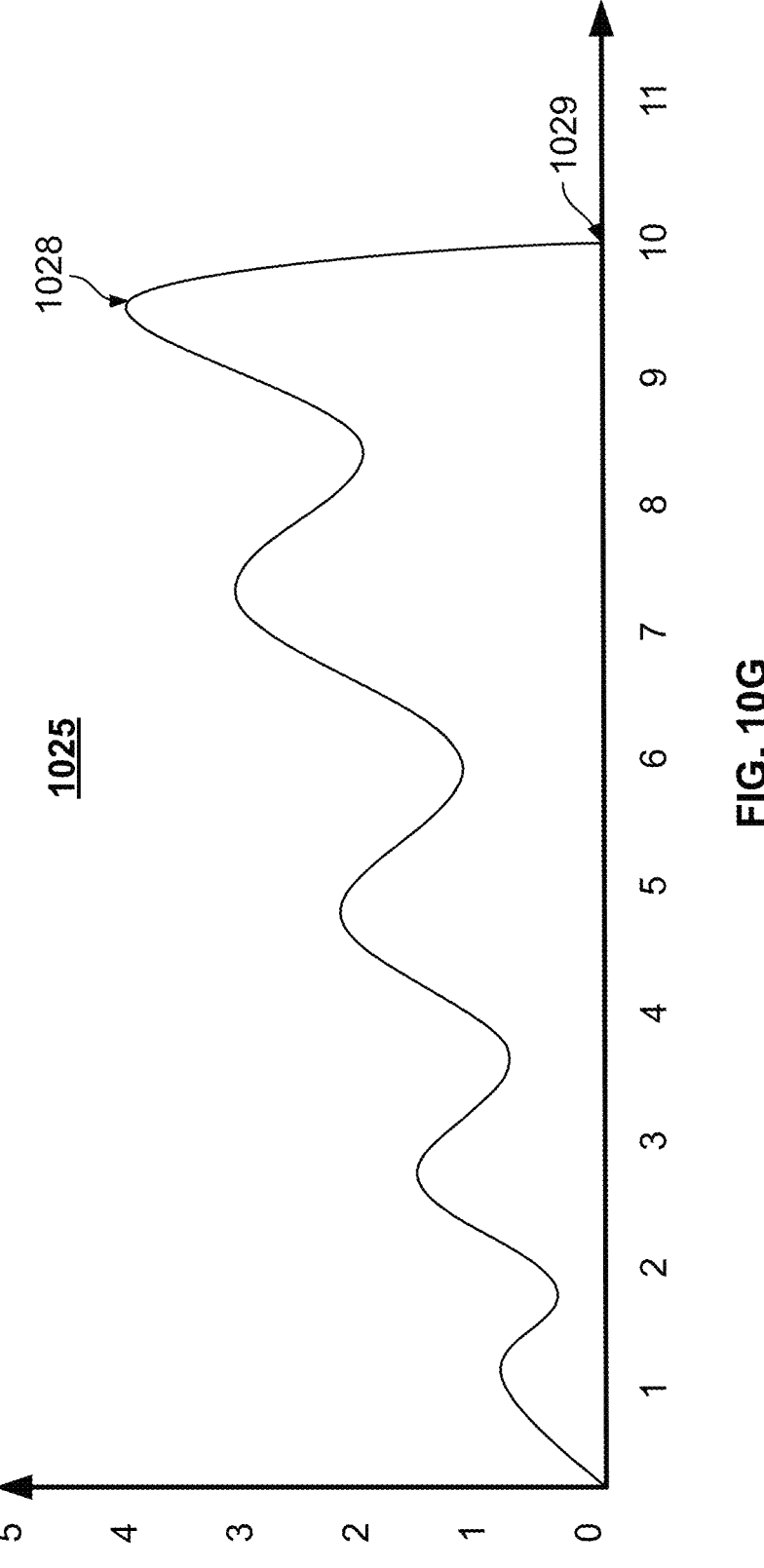
FIG. 10G illustrates a second pressure therapy profile, in accordance with an embodiment of the present specification.
Figure 10H:
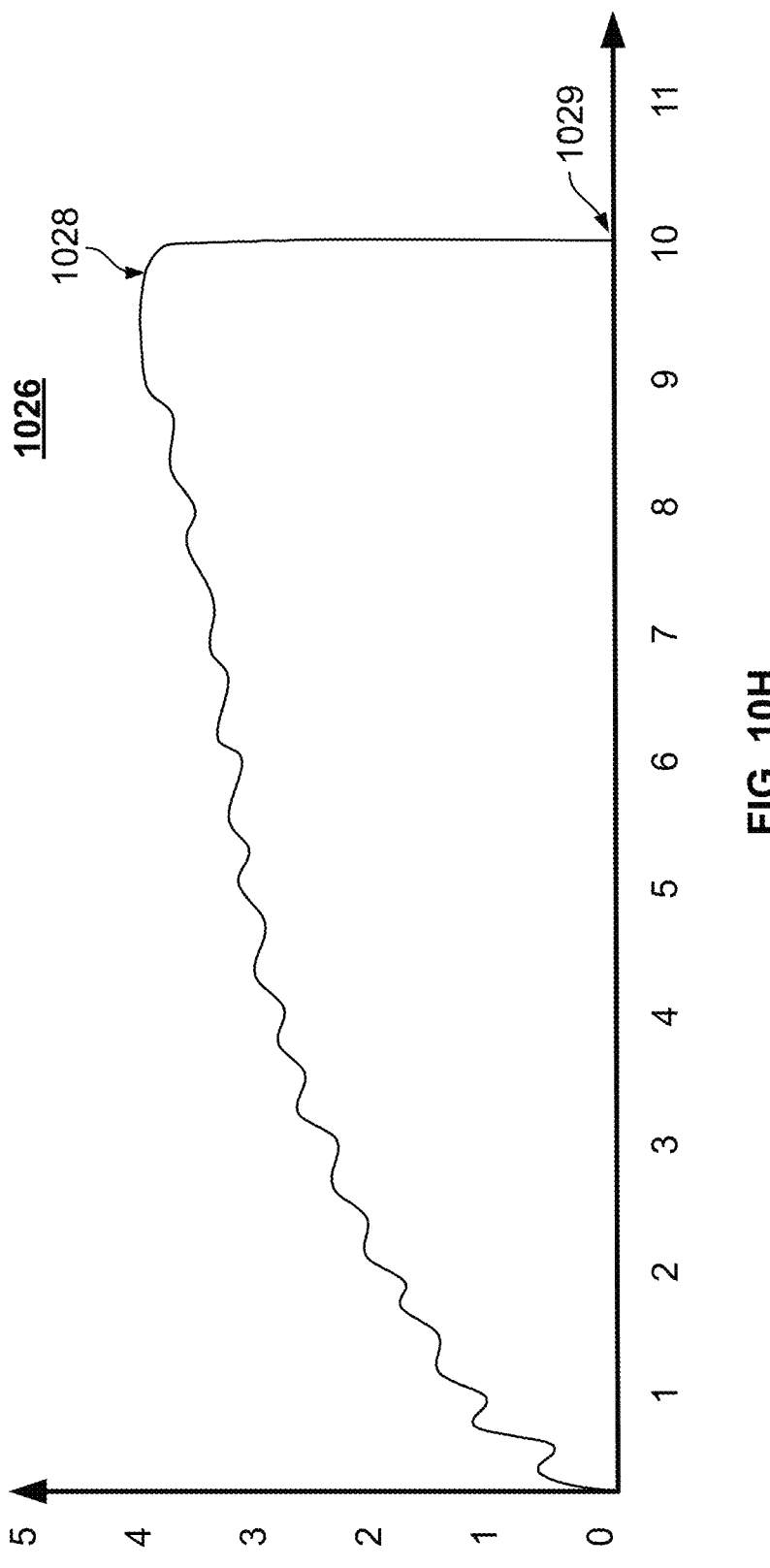
FIG. 10H illustrates the second pressure therapy profile, in accordance with another embodiment of the present specification.
Figure 10I:
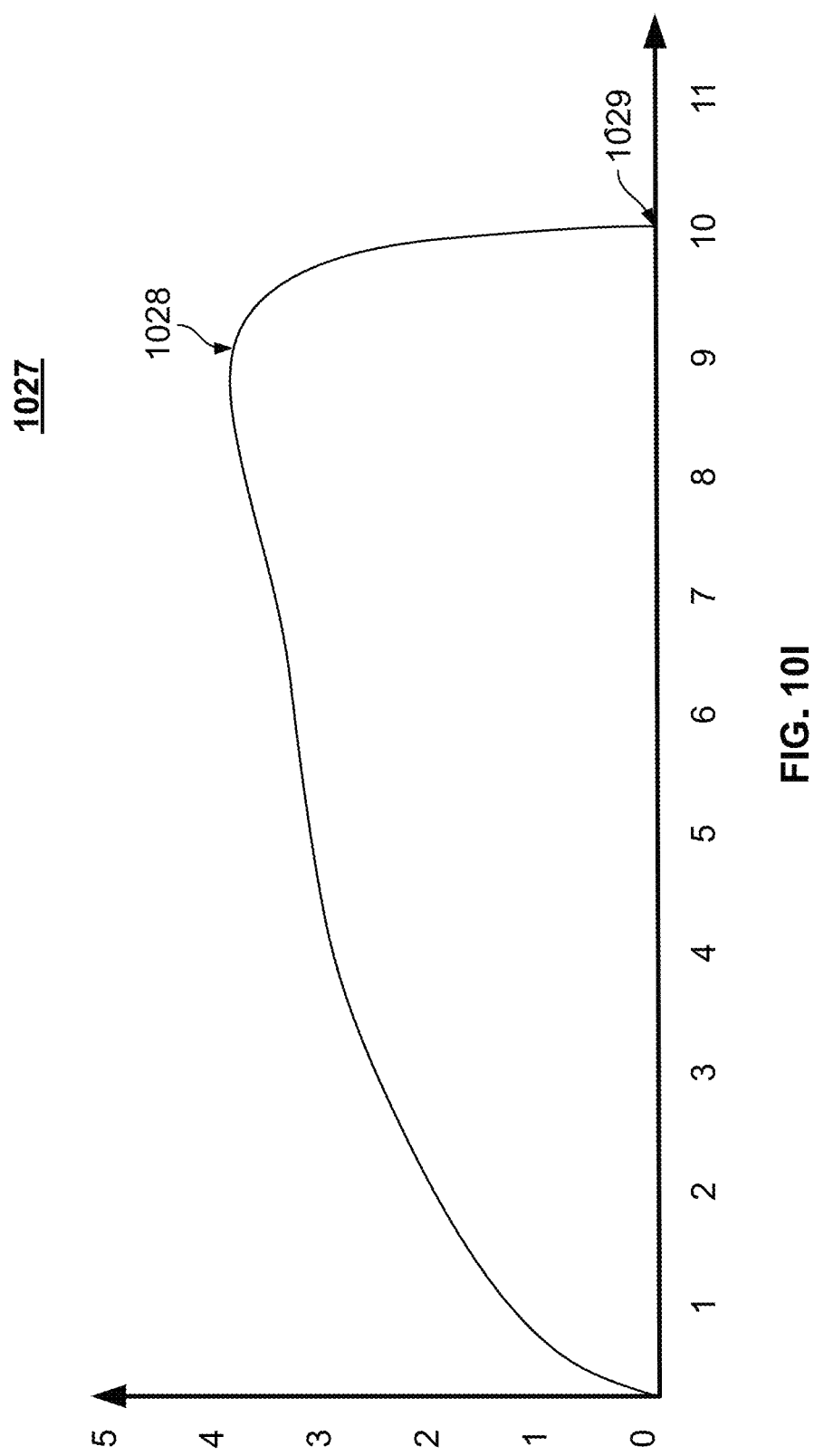
FIG. 10I illustrates the second pressure therapy profile, in accordance with another embodiment of the present specification.
Figure 10J:
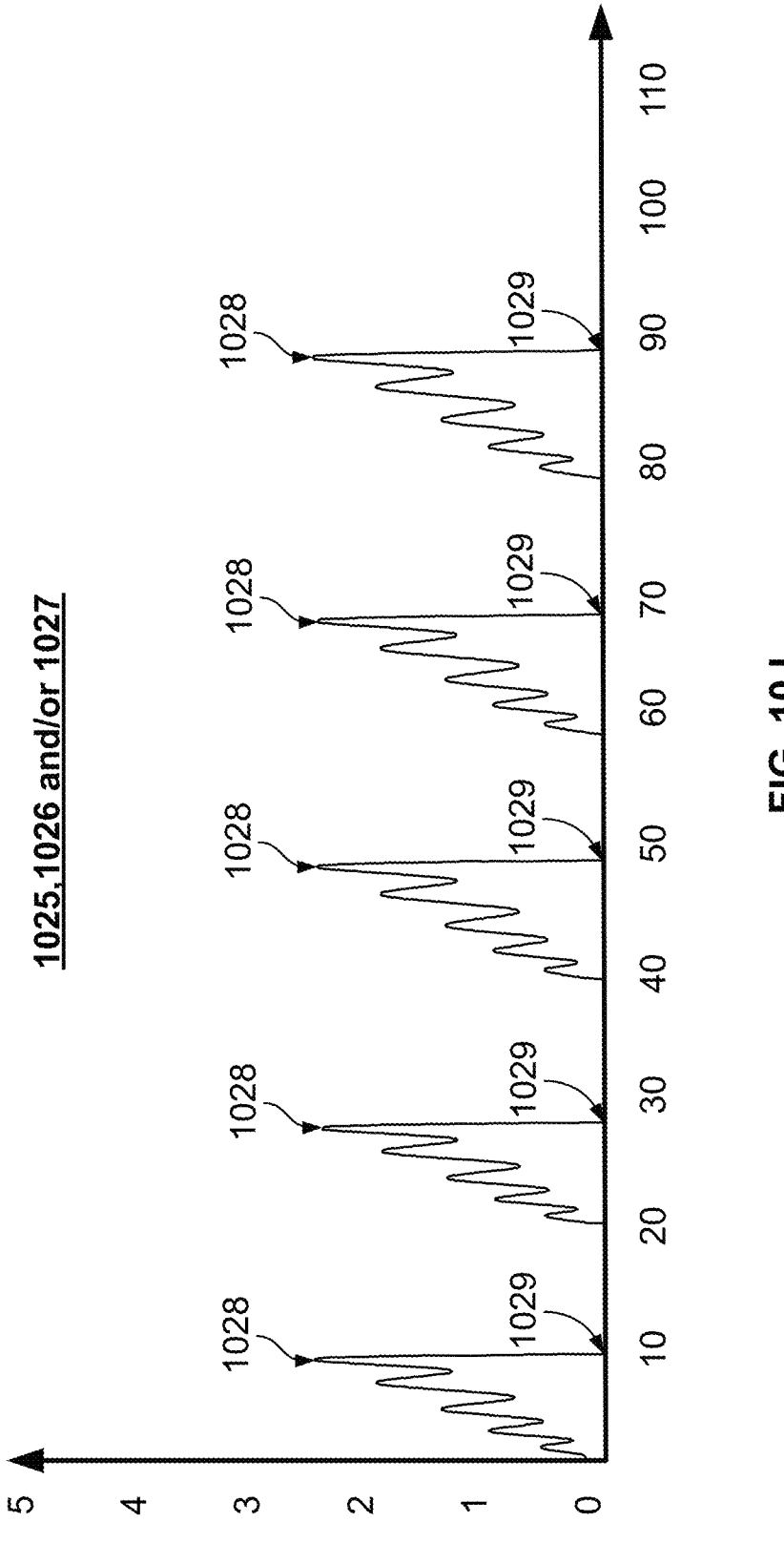
FIG. 10J illustrates a plurality of cycles of the second pressure therapy profile, in accordance with an embodiment of the present specification.

FIGS. 10G, 10H and 10I illustrate pressure therapy pro-files 1025, 1026 and 1027, wherein the pressure of vapor delivery is gradually increased to reach a target pressure 1028 at which time, the vapor delivery is aborted allowing the pressure to return to a baseline pressure 1029. FIG. 10J illustrates a plurality of cycles of at least one of the pressure therapy profiles 1025, 1026 and 1027, wherein for each cycle the therapy pressure builds up to the desired target pressure 1028 and then stops to return to the baseline pressure 1029 and recycles.

Figure 10K:
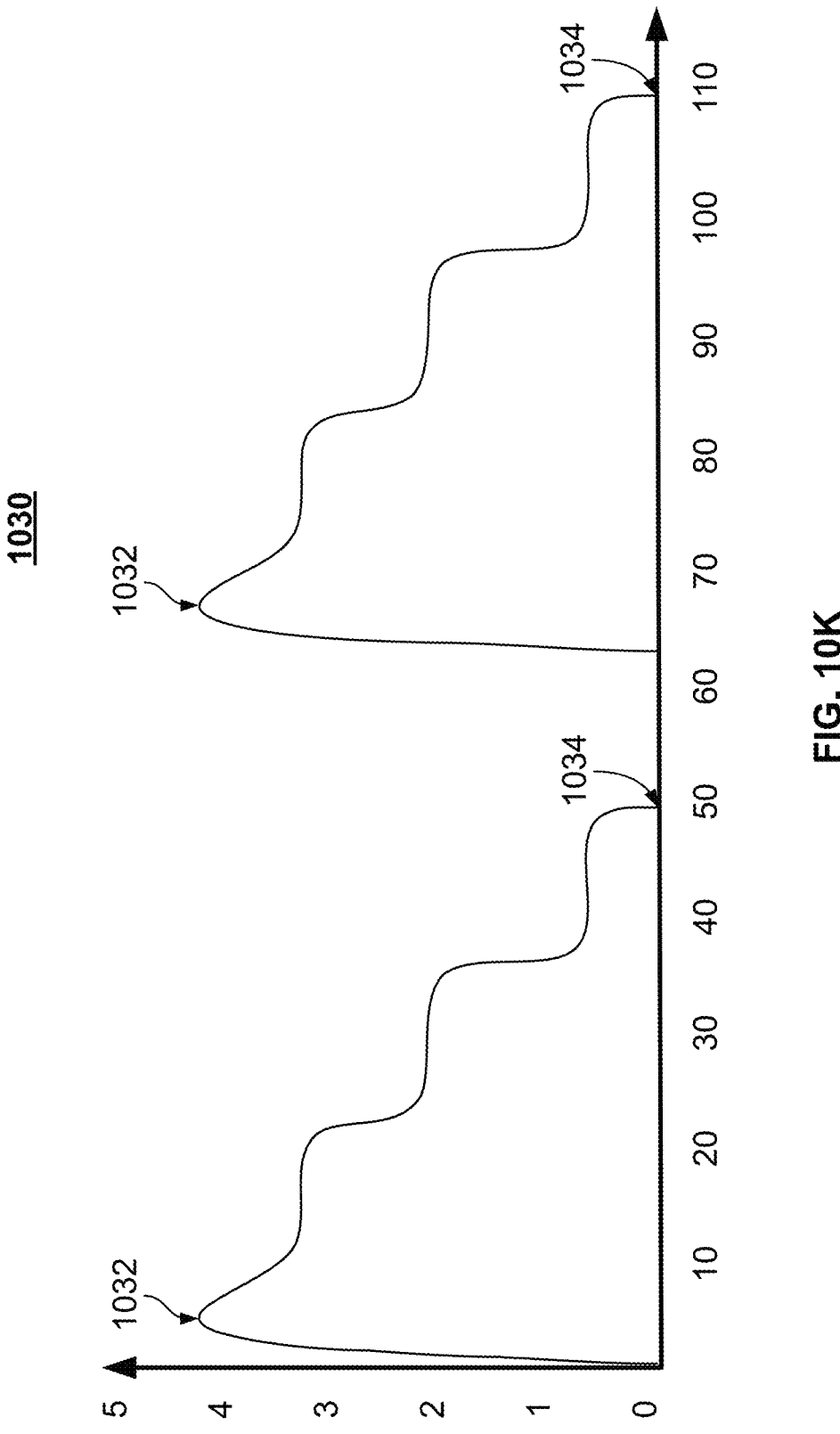
FIG. 10K illustrates a third pressure therapy profile, in accordance with an embodiment of the present specification.

FIG. 10K illustrates a pressure therapy profile 1030, wherein the pressure of vapor delivery is rapidly increased to reach a target pressure 1032 during a predefined period of time after which, the vapor delivery is gradually decreased allowing the pressure to slowly return to a baseline pressure 1034.

Figure 10L:
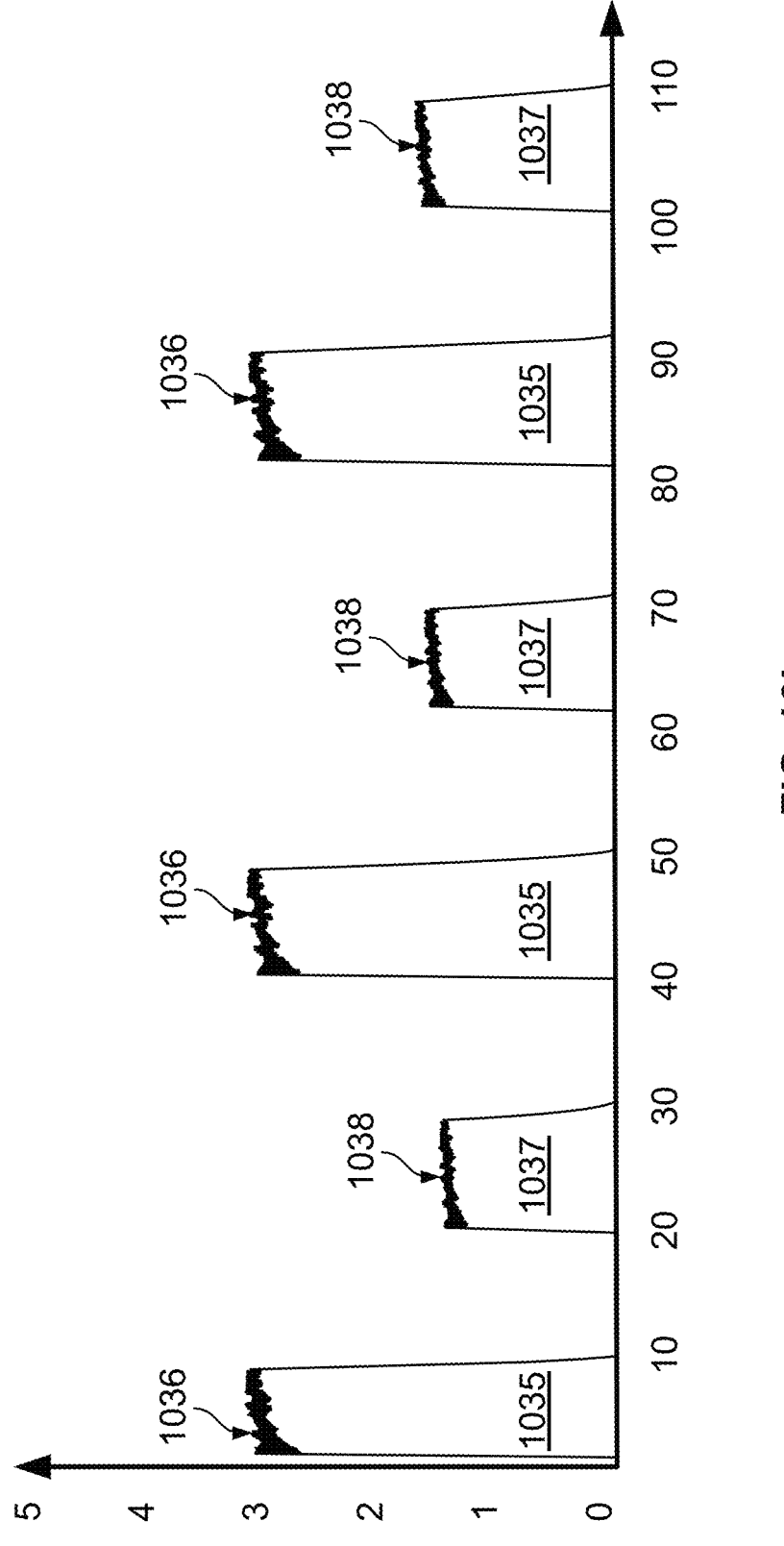
FIG. 10L illustrates a plurality of cycles of a pair of pressure profiles, in accordance with an embodiment of the present specification.

FIG. 10L illustrates a plurality of cycles of a pair of first and second pressure profiles 1035, 1037 wherein the first pressure profile 1035 has a first maximum pressure 1036 and the second pressure profile 1037 has a second maximum pressure 1038. In some embodiments, the first maximum pressure 1036 is higher than the second maximum pressure 1038. Thus, a higher pressure of vapor delivery is cycled with a lower pressure of vapor delivery.

Figure 10M:
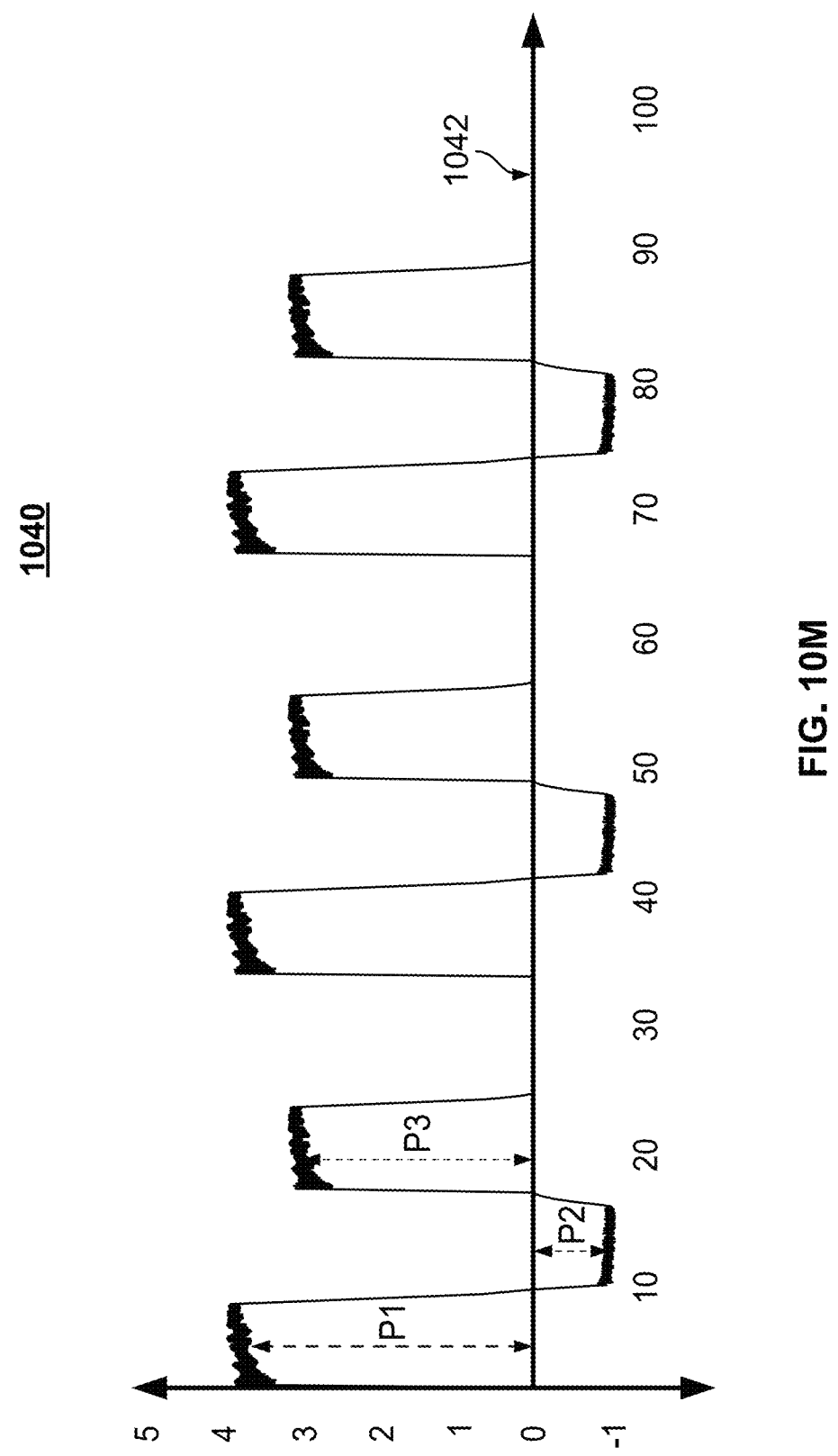
FIG. 10M illustrates a plurality of cycles of a fourth pressure profile, in accordance with an embodiment of the present specification.

FIG. 10M illustrates a plurality of cycles of a pressure profile 1040 wherein for each cycle the vapor is delivered to a pressure $P_1$ for a predetermined duration of time. Next, the vapor delivery is aborted and the pressure is allowed to decrease to a pressure $P_2$, below baseline 1042 for another predetermined duration of time. Thereafter, the vapor deliv-ery is reinitiated and delivered to a pressure $P_3$ for yet another predetermined duration of time. Finally, the vapor delivery is aborted allowing the pressure to return to base-line pressure 1042. In some embodiments, the pressure $P_1$ is comparable to or approximately equal to a sum of $P_2$ and $P_3$.

Figure 10N:
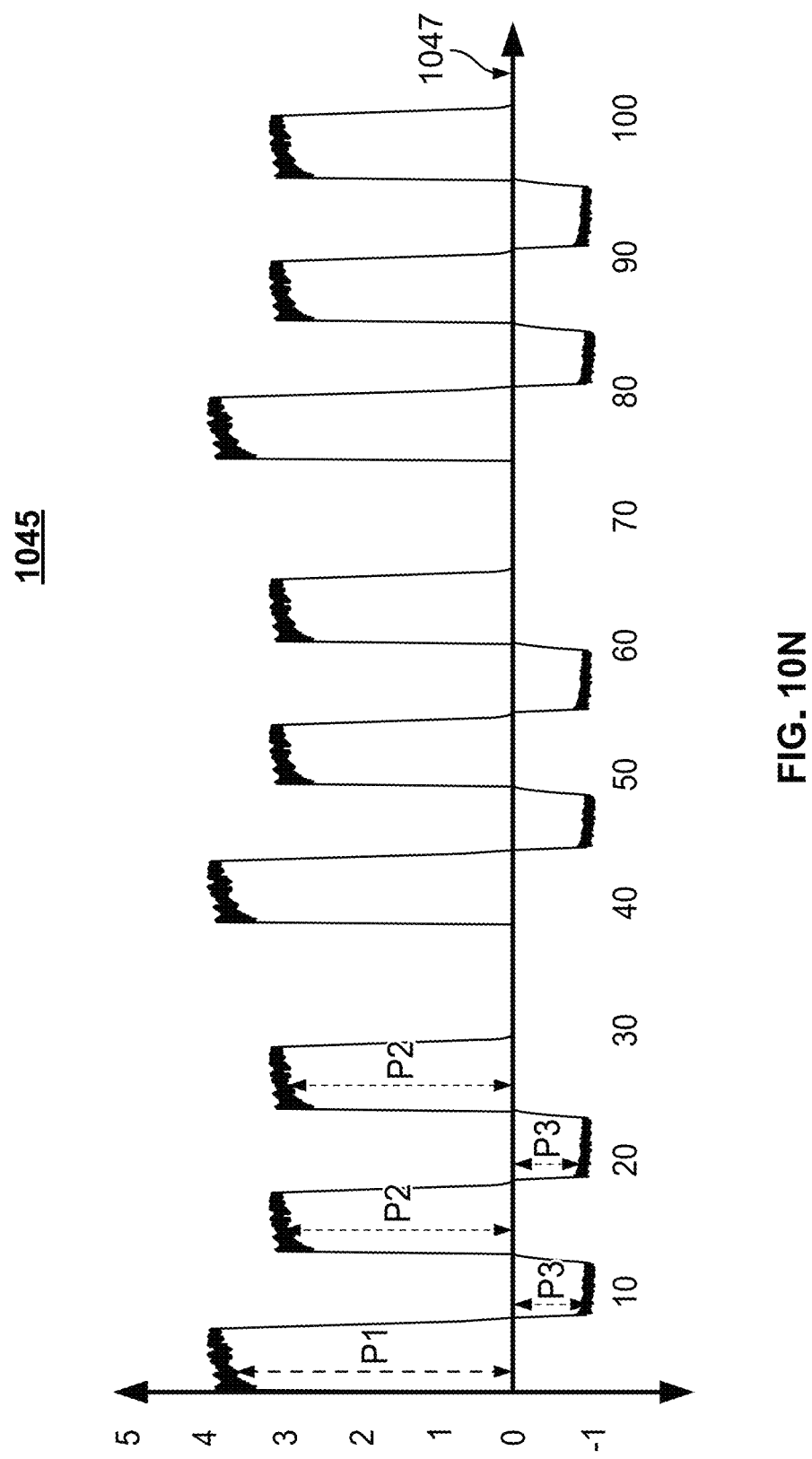
FIG. 10N illustrates a plurality of cycles of a fifth pressure profile, in accordance with an embodiment of the present specification.

FIG. 10N illustrates a plurality of cycles of a pressure profile 1045 wherein for each cycle the vapor is delivered to a pressure $P_1$ for a predetermined duration of time. Next, the vapor delivery is aborted and the pressure is allowed to decrease to a pressure $P_3$, below baseline 1047 for another predetermined duration of time. Now, the vapor delivery is reinitiated and delivered to a pressure $P_2$ for another prede-termined duration of time. Next, the vapor delivery is aborted and the pressure is allowed to decrease to the pressure $P_3$, below baseline 1047 for another predetermined duration of time. Thereafter, the vapor delivery is reinitiated and delivered to the pressure $P_2$ for another predetermined duration of time. Finally, the vapor delivery is aborted allowing the pressure to return to the baseline pressure 1047.

In some embodiments, the pressure $P_1$ is comparable to or approximately equal to a sum of $P_2$ and $P_3$.

Figure 10O:
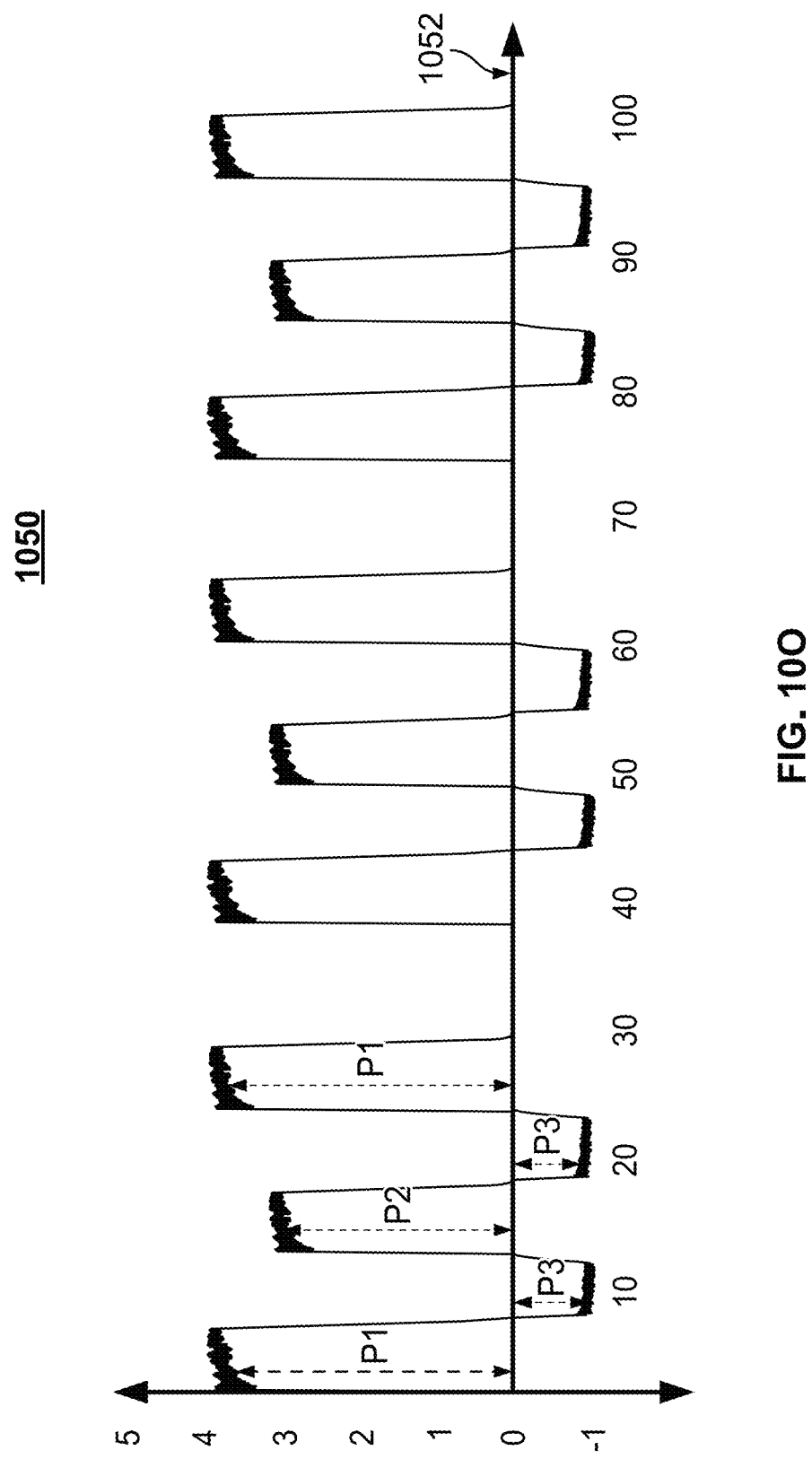
FIG. 10O illustrates a plurality of cycles of a sixth pressure profile, in accordance with an embodiment of the present specification.

FIG. 10O illustrates a plurality of cycles of a pressure profile 1050 wherein for each cycle the vapor is delivered to a pressure $P_1$ for a predetermined duration of time. Next, the vapor delivery is aborted and the pressure is allowed to decrease to a pressure $P_3$, below baseline 1052 for another predetermined duration of time. Now, the vapor delivery is reinitiated and delivered to a pressure $P_2$ for another predetermined duration of time. Next, the vapor delivery is aborted and the pressure is allowed to decrease to the pressure $P_3$, below baseline 1052 for another predetermined duration of time. Thereafter, the vapor delivery is reinitiated and delivered to the pressure $P_1$ for another predetermined duration of time. Finally, the vapor delivery is aborted allowing the pressure to return to the baseline pressure 1052. In some embodiments, the pressure $P_1$ is comparable to or approximately equal to a sum of $P_2$ and $P_3$.

Figure 10P:
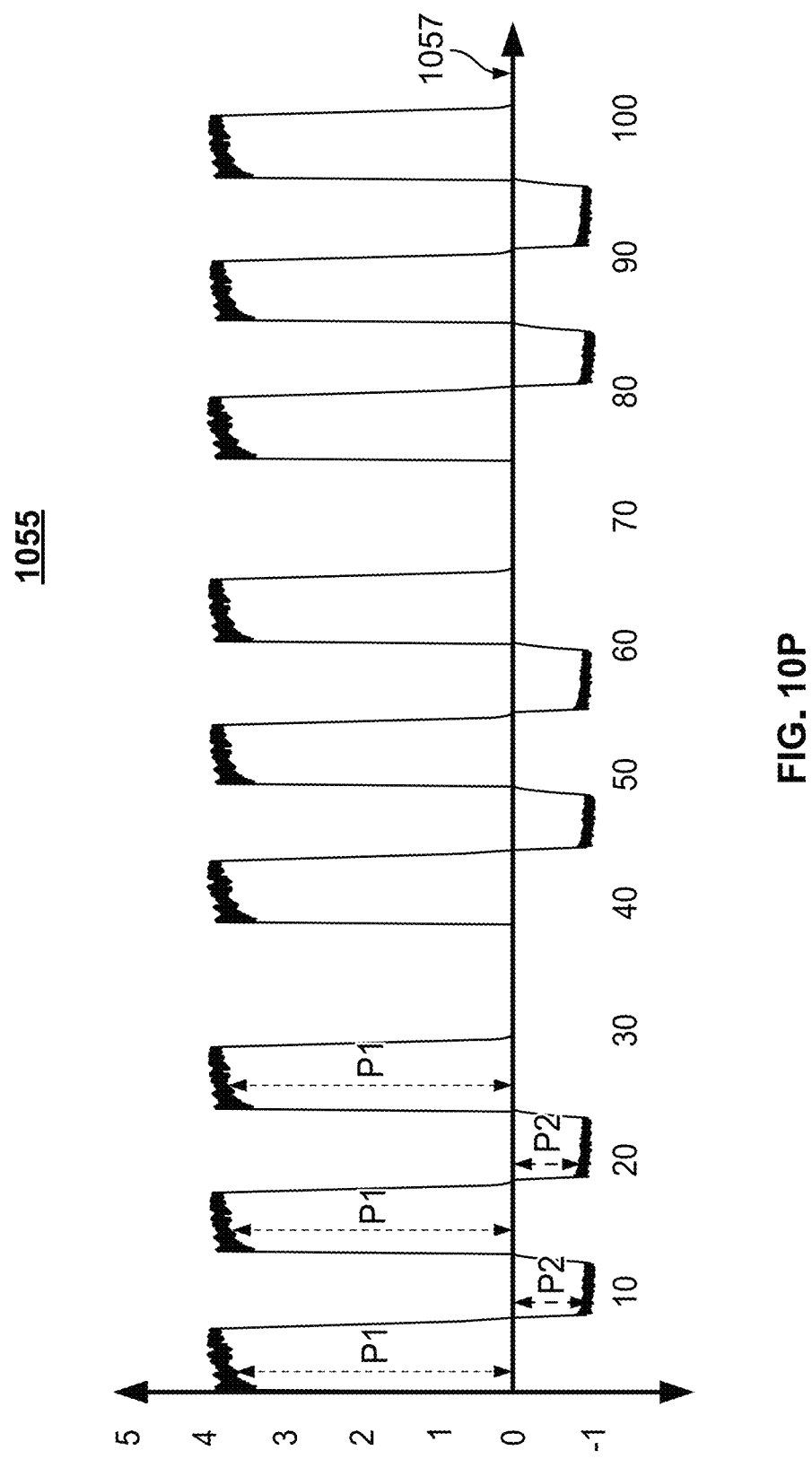
FIG. 10P illustrates a plurality of cycles of a seventh pressure profile, in accordance with an embodiment of the present specification.

FIG. 10P illustrates a plurality of cycles of a pressure profile 1055 wherein for each cycle the vapor is delivered to a pressure $P_1$ for a predetermined duration of time. Next, the vapor delivery is aborted and the pressure is allowed to decrease to a pressure $P_2$, below baseline 1057 for another predetermined duration of time. Now, the vapor delivery is reinitiated and delivered to the pressure $P_1$ for another predetermined duration of time. Next, the vapor delivery is aborted and the pressure is allowed to decrease to the pressure $P_2$, below baseline 1057 for another predetermined duration of time. Thereafter, the vapor delivery is reinitiated and delivered to the pressure $P_1$ for another predetermined duration of time. Finally, the vapor delivery is aborted allowing the pressure to return to the baseline pressure 1057. In some embodiments, the pressure $P_1$ is substantially greater than the pressure $P_2$.

Figure 11A:
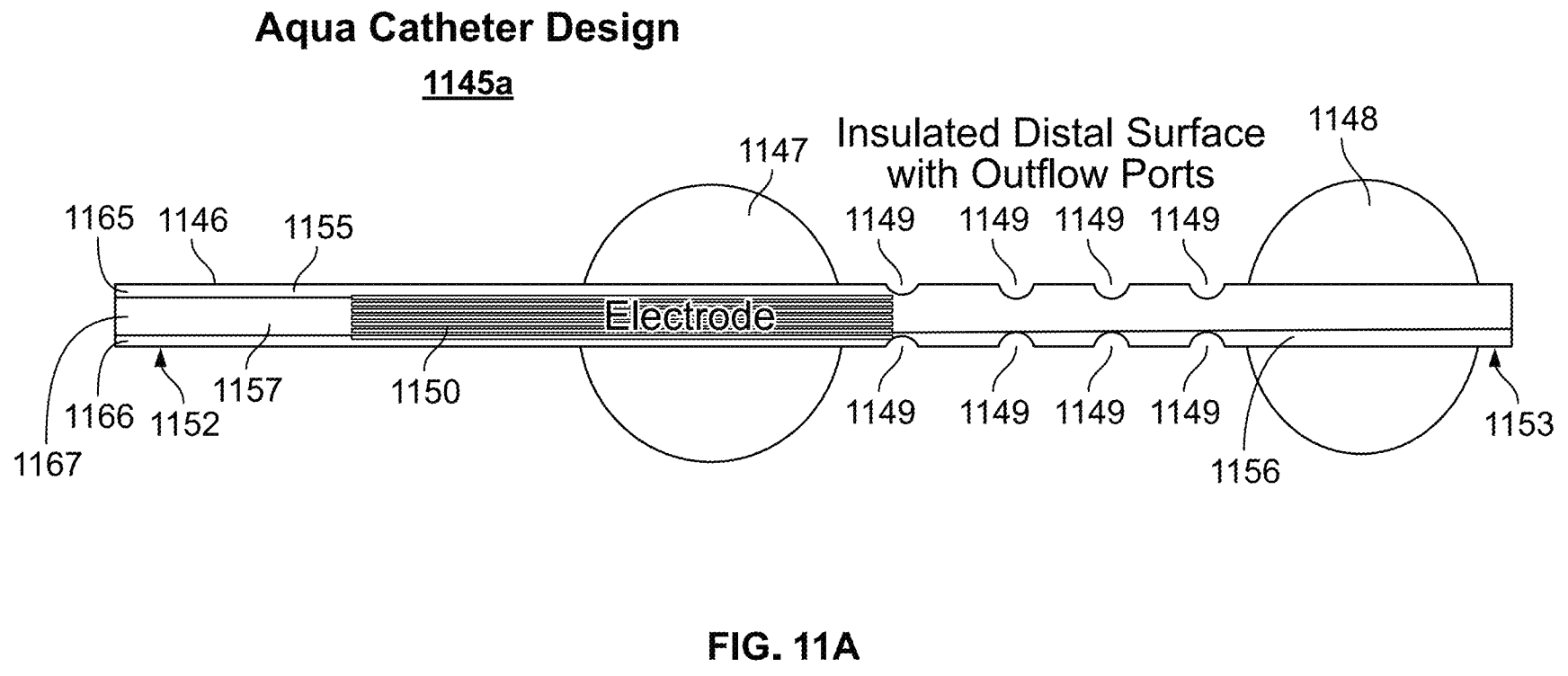
Figure 11B:
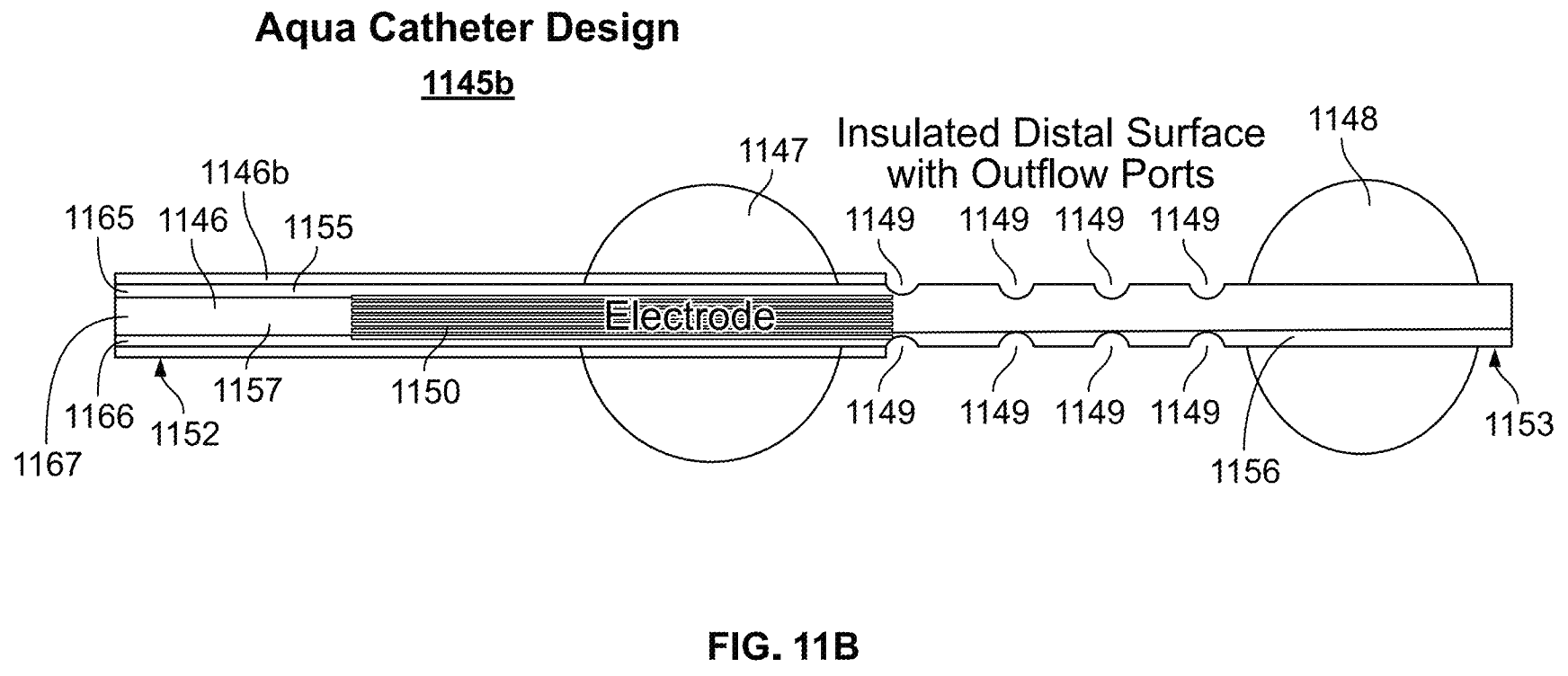

FIGS. 11A and 11B illustrate single and coaxial double balloon catheters 1145a, 1145b in accordance with embodiments of the present specification. The catheters 1145a, 1145b include an elongate body 1146 with a proximal end 11511 and a distal end 1153 and a first lumen 1155, a second lumen 1156, and a third lumen 1157 within. In an embodiment, the elongate body 1146 is insulated. The catheters 1145a, 1145b include at least one positioning element 1148 proximate their distal end 1153. In various embodiments, the positioning element is an inflatable balloon. In some embodiments, the catheters include more than one positioning element. As shown in FIG. 11B, the coaxial catheter 1145b includes an outer catheter 1146b that accommodates the elongate body 1146.

In the embodiments depicted in FIGS. 11A, 11B, the catheters 1145a, 1145b include a proximal first inflatable balloon 1147 and a distal second inflatable balloon 1148 positioned proximate the distal end of the body 1146 with a plurality of infusion ports 1149 located on the body 1146 between the two balloons 1147, 1148. It should be appreciated that, while balloons are preferred, other positioning elements, as previously described, may be used. It should also be appreciated that infusion ports 1149 may include one or more ports.

The body 1146 includes a first lumen 1155 (extending along a portion of the entire length of the body 1146) in fluid communication with a first input port 1165 at the proximal end 11511 of the catheter body 1146 and with said proximal first balloon 1147 to inflate or deflate the proximal first balloons 1147, 1148 by supplying or suctioning air or water through the first lumen 1155. In an embodiment, use of a two-balloon catheter as shown in FIGS. 11A and 11B results in the creation of a seal and formation of a treatment area having a radius of 3 cm, a length of 9 cm, a surface area of $169.56 \text{ cm}^2$ and a treatment volume of $254.34 \text{ cm}^3$. The body 1146 includes a second lumen 1156 (extending along the entire length of the body 1146) in fluid communication with a second input port 1166 at the proximal end 1152 of the catheter body 1146 and with said distal second balloon 1148 to inflate or deflate the distal second balloon 1148 by supplying or suctioning air through the second lumen 1156. In another embodiment, the body includes only a first lumen for in fluid communication with the proximal end of the catheters and the first and second balloons for inflating and deflating said balloons. The body 1146 also includes an in-line heating element 1150 placed within a second third lumen 1157 (extending along the length of the body 1146) in fluid communication with a third input port 1167 at the proximal end 1152 of the catheter body 1146 and with said infusion ports 1149. In one embodiment, the heating element 1150 is positioned within the third lumen 1157, proximate and just proximal to the infusion ports 1149. In an embodiment, the heating element 1150 comprises a plurality of electrodes. In one embodiment, the electrodes of the heating element 1150 are folded back and forth to increase a surface contact area of the electrodes with a liquid supplied to the third lumen 1157. The second third lumen 1157 serves to supply a liquid, such as water/saline, to the heating element 1150.

In various embodiments, a distance of the heating element 1150 from a nearest port 1149 ranges from 1 mm to 50 cm depending upon a type of therapy procedure to be performed.

A fluid pump, an air pump and an RF generator are coupled to the proximate end of the body 1146. The air pump propels air/fluid via said first and second inputs 1165, 1166 through the first and second lumens to inflate the balloons 1147, 1148 so that the catheters 1145a, 1145b are held in position for an ablation treatment. The fluid pump pumps a liquid, such as water/saline, via said third input 1167 through the second third lumen 1157 to the heating element 1150. The RF generator supplies power an electrical current to the electrodes of the heating element 1150, thereby causing the electrodes to heat and converting the liquid (flowing through around the heating element 1150) into vapor. The generated vapor exits the ports 1149 for ablative treatment of target tissue. In embodiments, the supply of liquid and electrical current, and therefore delivery of vapor, is controlled by a microprocessor.

FIG. 11C is a flow chart of a plurality of steps of using the catheters 1145a, 1145b to perform ablation in a body lumen, such as in Barrett's esophagus of a patient, in accordance with an embodiment of the present specification. At step 1171, insert the catheters 1145a, 1145b into a body lumen. In one embodiment, the body lumen is an esophagus of a patient. At step 1172, inflate the balloons 1147, 1148 to demarcate a target ablation area, such as Barrett's esophagus, and position the catheters 1145a, 1145b such that the infusion ports 1149 are positioned in the target ablation area, such as in a portion of Barrett's esophagus. At step 1173, provide liquid, such as water or saline, to a proximal end of the catheters 1145a, 1145b. Finally, at step 1174, provide electrical current to the electrodes of the heating element 1150 to heat the electrodes and convert the liquid to vapor wherein the generated vapor is delivered through the infusion ports 1149 to ablate the target tissue, such as Barrett's esophagus of the patient. In various embodiments, steps 1173 and 1174 are performed simultaneously or step 1174 is performed prior to step 1173.

Figure 12A:
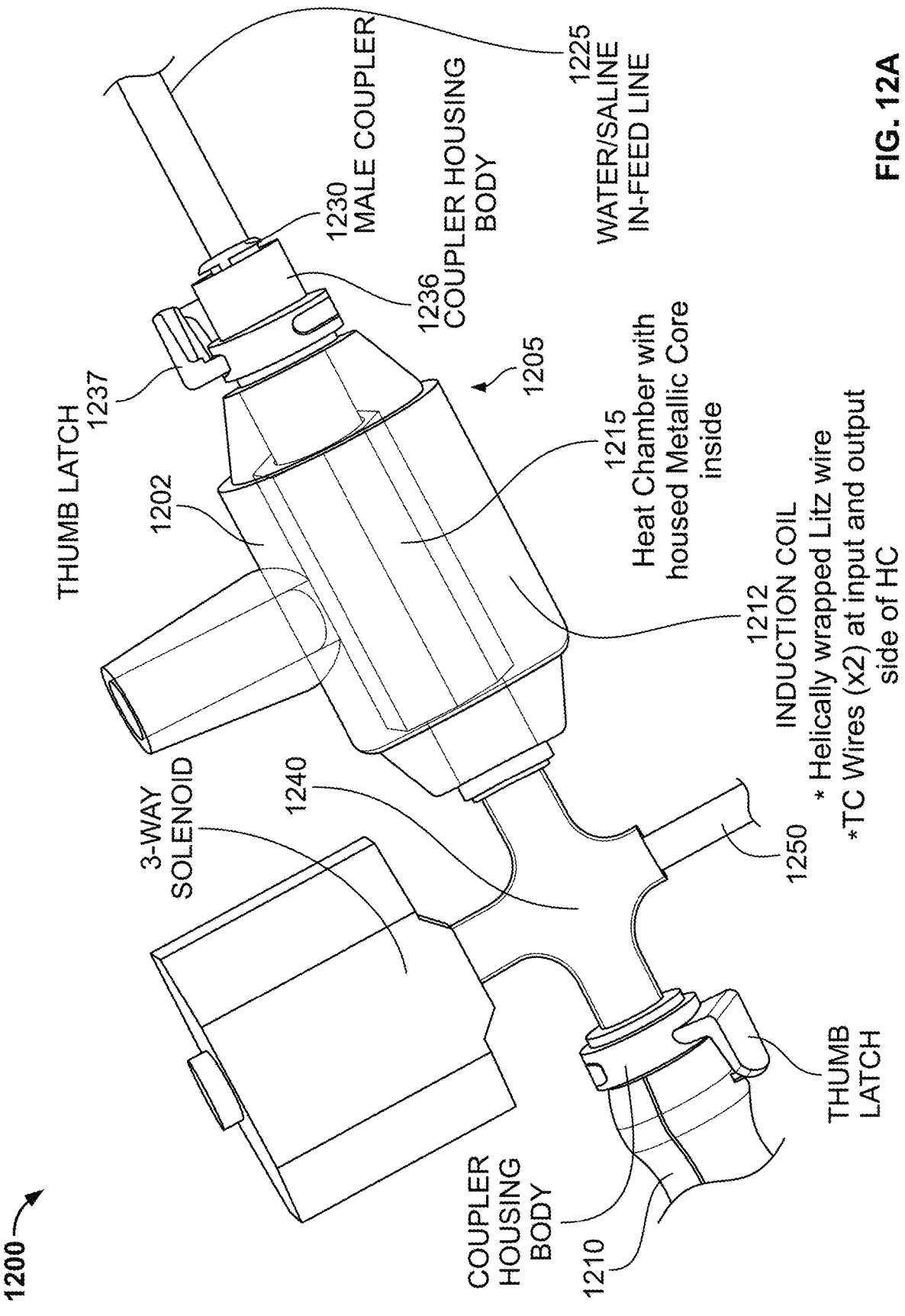
FIG. 12A is an assembled schematic view of a vapor generation system, in accordance with an embodiment of the present specification.

FIG. 12A is an assembled schematic view of a vapor generation system 1200 comprising an induction heating unit 1205 coupled or attached fluidically in-series (or in-line) with, and at a proximal end of, a catheter handle 1210, in accordance with an embodiment of the present specification, while FIGS. 12B and 12C are exploded views of components upstream and downstream to the induction heating unit 1205. Referring to FIGS. 12A, 12B and 12C simultaneously, the induction heating unit 1205 includes an induction coil 1212 surrounding a heating chamber 1215 that, in turn, houses a metallic or ferromagnetic core 1220 within. In embodiments, the induction coil 1212 comprises Litz electromagnetic conducing wire wound in a tight helical fashion. A power cable 1207 extends from the induction coil 1212 to a power generator. The induction coil 1212 is positioned in a thermally insulated external "soft skin" housing 1202. In embodiments, the housing 1202 is a thermally stable, over molded component consisting of low to medium durometer thermoplastic elastomer material such as Kraton®. Optionally, the induction heating unit 1205 further comprises at least one thermocouple 1214 to measure input and output temperature at the heating chamber 1215.

In embodiments, the heating chamber 1215 is manufactured from high temperature resistant materials such as, but not limited to, PEEK (polyetheretherketone) or polysulfone. The core 1220 may be fabricated from conductive metals or alloys such as, but not limited to, carbon steel, stainless steel or other ferro-magnetic materials such as Mu-metal (soft magnetic alloy with high Nickel/Iron content for high permeability and efficient electromagnetic conductance). Composition of an exemplary Mu metal may approximately be 77% nickel, 16% iron, 5% copper and 2% chromium or molybdenum.

The induction heating unit 1205 is reusable and securely locks onto the heating chamber 1215. In some embodiments, the induction heating unit 1205 snap fits over the heating chamber 1215. In some embodiments, the heating chamber 1215 incorporates male détentes on its outer surface which lock onto female détentes on an internal surface of the housing 1202. In this way, the induction heating unit 1205 positively locks over the heating chamber 1215, insulating the operator from the heat affected zone during ablation. In accordance with aspects of the present specification, once loaded over the heating chamber 1215, the induction heating unit 1205 can be rotated, about its longitudinal axis, based on operator preference, to ensure that the workspace around a catheter, associated with the catheter handle 1210, is clutter-free.

The core 1220 located inside the heating chamber 1215 serves as a heating element to convert saline/water, received through a saline/water in-feed tube 1225 at a proximal end of the induction heating unit 1205, to steam once electricity is passed through the induction coil 1212. The saline/water in-feed tube 1225 tracks from a disposable pump head and incorporates a first thumb latch 1237 operated first female coupler housing body 1236 at its distal end. The first female coupler housing body 1236 is configured to lock onto a first male coupler end cap 1230 extending from a proximal portion of the heating chamber 1215.

In embodiments, the core 1220 is solid or tubular. Optionally, the core 1220 may have fenestrations or a helical screw thread on its outer diameter to assist with water to steam conversion. The core 1220 is locked/held inside the heating chamber 1215 via the first male coupler end cap 1230. The first male coupler end cap 1230 connects the heating chamber 1215 to the first female coupler housing body 1236. Once the first male coupler 1230 has been inserted into the first female coupler housing body 1236, a water tight seal is created which prevents water/vapor leakage from the assembly. To de-couple the first male and female coupler parts, the first thumb latch 1237 is depressed and the parts are axially separated. The first male coupler end cap 1230 is water/steam contacting and is fabricated from a high temp resistant material such as PEEK or polysulfone, for example.

Figure 13A:
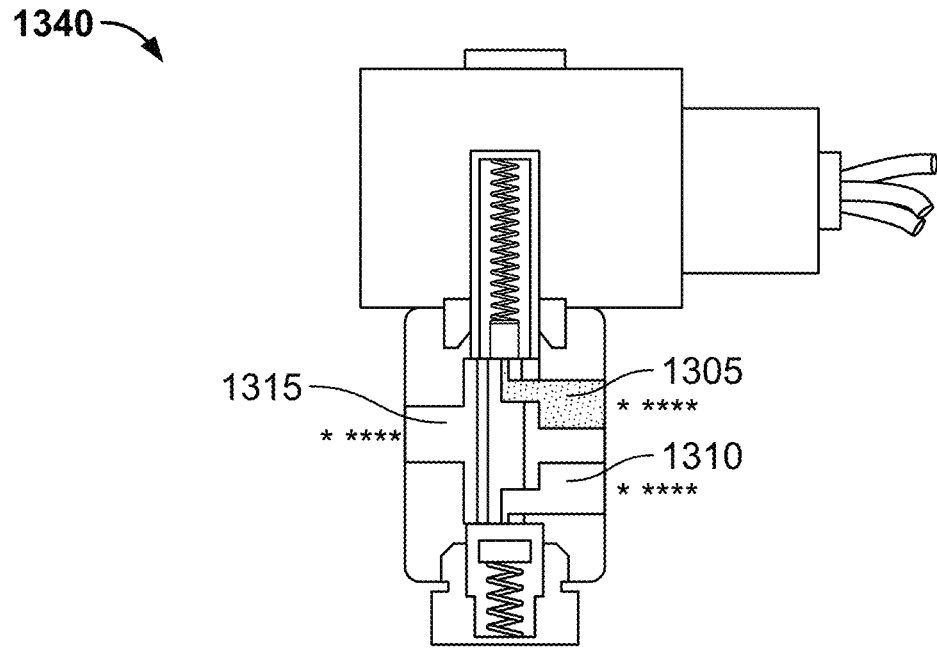
FIG. 13A illustrates a de-energized state of a 3-way flow control solenoid valve.
Figure 13B:
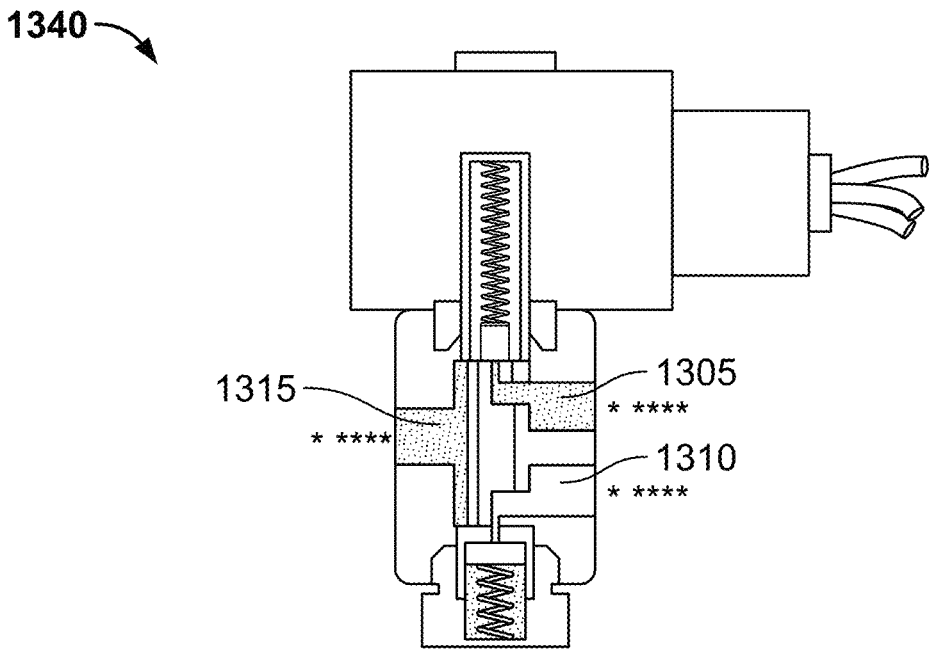
FIG. 13B illustrates an energized state of the 3-way flow control solenoid valve.

As shown in FIGS. 12A and 12C, a 3-way flow control valve 1240, such as a solenoid valve in an embodiment, is located downstream of the induction heating unit 1205 between the heating chamber 1215 and a second male coupler 1245 that connects the induction heating unit 1205 to the catheter handle 1210. FIGS. 13A and 13B respectively illustrate de-energized and energized states of a 3-way flow control solenoid valve 1340 (similar to the valve 740). The valve 1340 enables the following types of flow operations: a) normally closed flow operation—as shown in FIG. 13A, when the valve 1340 is de-energized, a pressure port 1305 is closed and an exhaust port 1310 is connected to a cylinder port 1315. When the valve 1340 is energized, the exhaust port 1310 is closed and the pressure port 1305 is connected to the cylinder port 1315; b) normally open flow operation—as shown in FIG. 13B, when the valve 1340 is de-energized, the pressure port 1305 is connected to the cylinder port 1315 and the exhaust port 1310 is closed. When the valve 1340 is energized, the pressure port 1305 is closed and the cylinder port 1315 is connected to the exhaust port 1310.

Referring back to FIGS. 12A through 12C, at the start of an ablation procedure, as the ablation system 1200 is being set up and "primed" there will be a residual reservoir of water already in the system 1200. This water (or condensate) must be drained from the system 1200 and an amount of high temperature vapor injected to a target ablation site, maximized. To prime the system 1200, the power generator is switched on and a duty cycle activated. Condensate flow is diverted to a condensate drainage line or tube 1250 until such time as only vapor exits this line. Once this occurs, a generator controller will energize the solenoid valve 1240 to an open position (FIG. 13B). In this way, the system 1200 is primed with vapor and drained of condensate, such that only vapor is delivered from the heating chamber 1215 to the catheter.

As shown in FIG. 12C, the second male coupler 1245 connects the valve 1240 to a second thumb latch 1255 operated second female coupler housing body 1260 positioned at a proximal end of the catheter handle 1210. In accordance with aspects of the present specification, the entire induction heating unit 1205 assembly is rotatable around a longitudinal axis of the catheter to ensure that associated power cables and tubing lines can be positioned as desired by the operator.

Figure 14A:
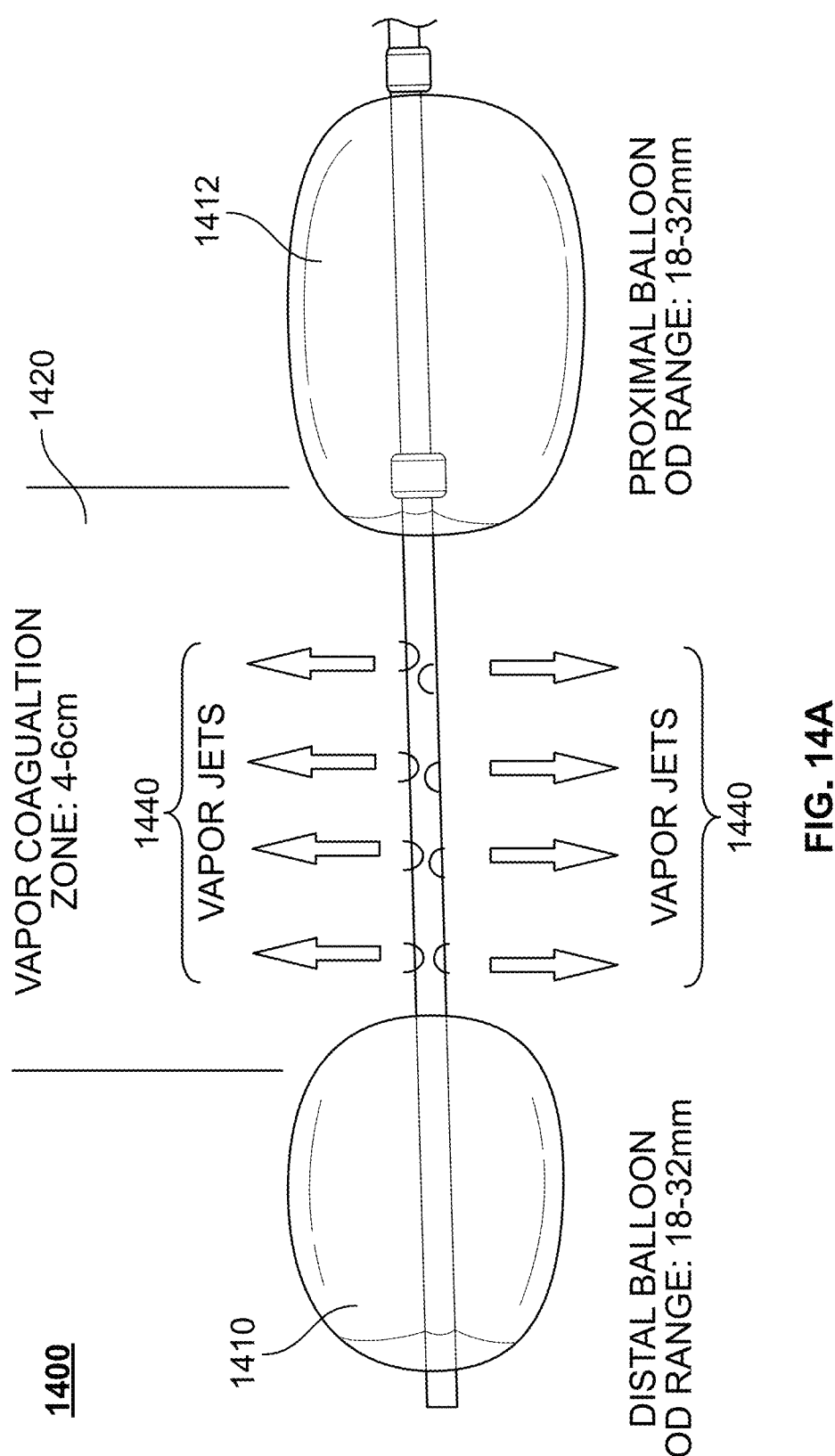
FIG. 14A shows a dual-balloon, multi-lumen catheter system, in accordance with embodiments of the present specification.
Figure 14B:
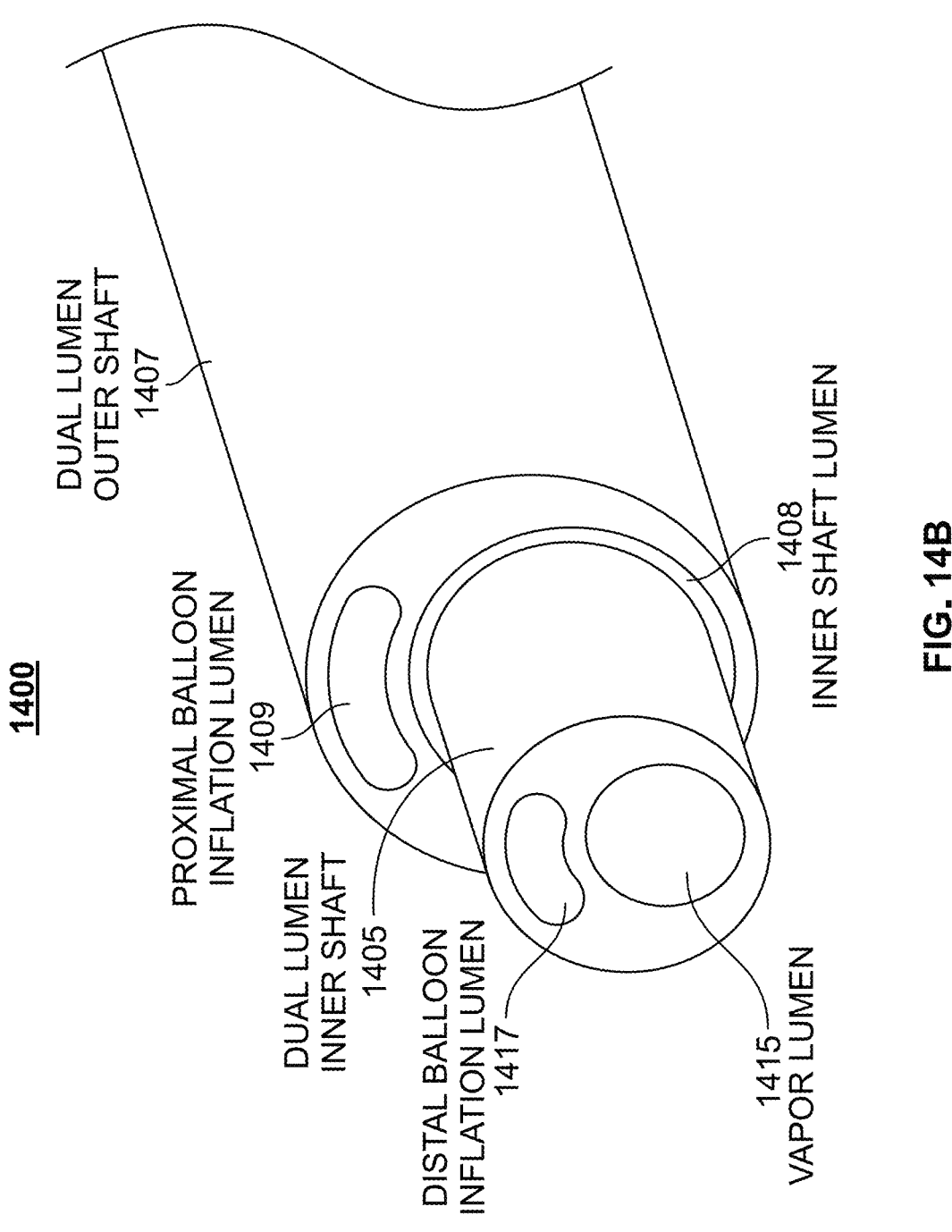
FIG. 14B shows two elongate catheter shafts, in accordance with embodiments of the present specification.

FIG. 14A shows a dual-balloon, dual shaft, multi-lumen catheter system 1400 while FIG. 14B shows two elongate catheter shafts 1405, 1407 for the catheter system 1400, in accordance with embodiments of the present specification. Referring to FIGS. 14A and 14B simultaneously, the catheter system 1400 comprises distal and proximal inflatable anchoring balloons 1410, 1412 that, in one embodiment, are respectively coupled with two different catheter shafts 1405, 1407. The catheter shafts 1405, 1407 are of a multi-lumen construction and are manufactured from polymer material which is capable of maintaining performance under continuous exposure to vapor/steam and temperatures ranging from 110° C. to 120° C., such as PEEK or polysulfone.

The outer shaft 1407 is connected to the proximal balloon 1412 while the inner shaft 1405 is connected to the distal balloon 1410. The outer shaft 1407 has a first lumen 1408 to accommodate the inner shaft 1405 and a second lumen 1409 to allow inflation fluid (such as air or water) to flow into the proximal balloon 1412 for inflation or be suctioned for deflation. The inner shaft 1405 telescopes axially within the first lumen 1408. The inner shaft 1405 has a first (vapor) lumen 1415 to enable ablation fluid, such as vapor, to flow through the catheter system 1400 and be released from one or more exit ports 1440 located between the distal and proximal balloons 1410, 1412 and a second lumen 1417 to allow inflation fluid (such as air) to flow into the distal balloon 1410 for inflation or be suctioned for deflation. Operationally, the first (vapor) lumen 1415 and the entire fluid pathway, is complete void of air and is constructed of non-expanding (pressure rated) materials. Presence of air in the lumen 1415 or a tendency for lumen 1415 to expand under pressure during delivery of steam, results in pooling as fluid continues to drip out of the catheter when the delivery of steam is stopped. Additionally, in embodiments, first lumen 1408, second lumen 1409 and second lumen 1417 are manufactured using non-expanding materials. Examples of the non-expanding materials may include thermo-set materials such as polyimide, such as braid rein-force polymer. The braid limits stretching or expansion under pressure. In some embodiments, the non-expanding material may include stainless steel, nitinol hypotubes, or laser cut hypotubes (laser cut for flexibility). Additionally, in some embodiments the material may include polymers such as PEEK.

Accordingly, both catheter shafts 1405, 1407 are capable of axial movement independently of each other. In this way, a distance between the distal and proximal balloons 1410, 1412 may be adjusted before or during an ablation proce-dure, thereby adjusting a length of a coagulation/ablation zone 1420. In some embodiments, the length of the zone 1420 ranges from 4 cm to 6 cm. In some embodiments, the lumens 1409 and 1417 have a "smiley" shaped cross-section. However, in alternate embodiments, the cross-section can be of other shapes such as, but not limited to, circular, square or rectangular.

Once positioned at an appropriate ablation treatment location, the distal and proximal balloons 1410, 1412 are inflated and anchored-such as, for example, against a wall of an esophagus-both distally and proximally. This ensures that a defined, controlled coagulation zone 1420 is achieved prior to the creation and delivery of vapor to the treatment site. In some embodiments, the diameters of both proximal and distal balloons 1410, 1412 are capable of being inflated to cover a range of desired esophageal diameters (ranging between 18 mm to 32 mm) to be treated. Once the balloons have been inflated in position, vapor is generated via the induction heating unit 1205 (FIG. 12A) at a proximal end of the catheter handle 1210 (FIG. 12A) outside a patient and injected through the vapor lumen 1415 of the inner shaft 1405.

Figure 14C:
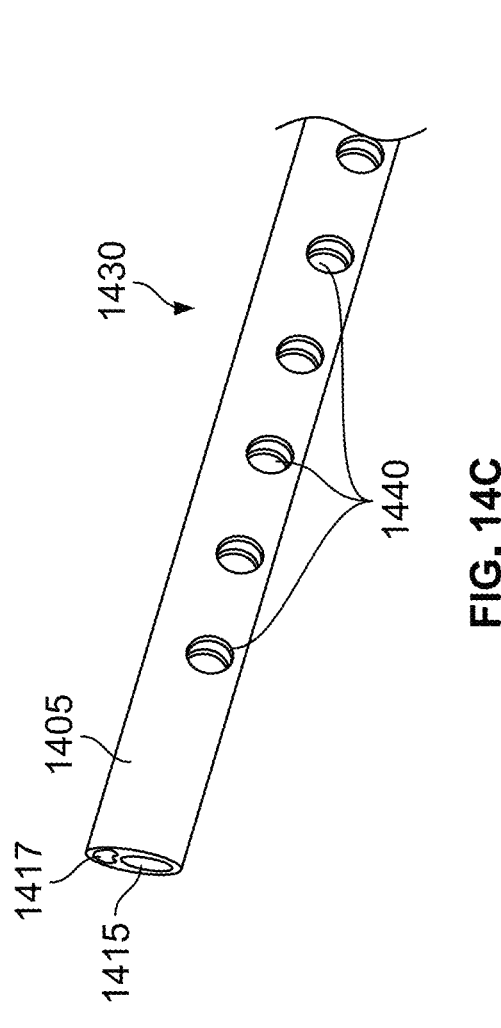
FIG. 14C illustrates a first eyehole pattern, in accordance with embodiments of the present specification.
Figure 14D:
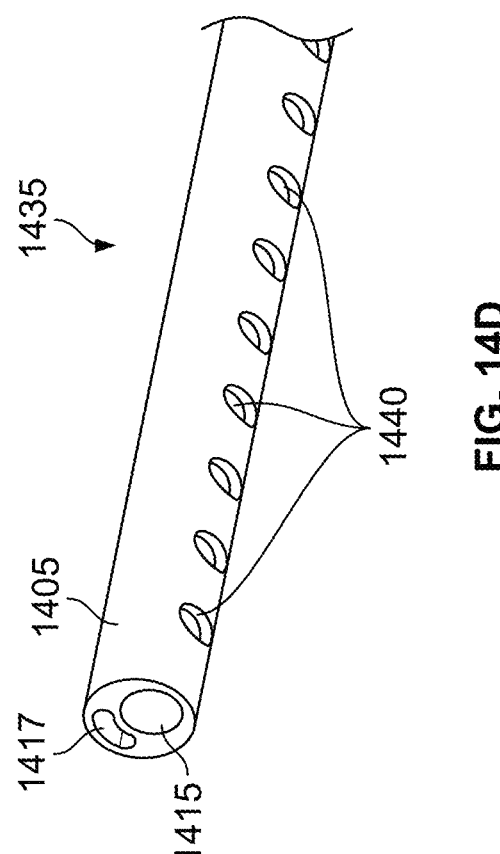
FIG. 14D illustrates a second eyehole pattern, in accordance with embodiments of the present specification.

A portion of the catheter shaft system 1400 between the balloons 1410, 1412 contains a number of eyeholes, con-figured around the circumference of the shafts 1405, 1407. These eyeholes serve as vapor exit ports 1440. FIGS. 14C and 14D respectively illustrate first and second eyehole patterns 1430, 1435, in accordance with embodiments of the present specification. The first eyeholes pattern 1430 has a plurality of exit ports 1440 formed on both sides of the inner shaft 1405 into the first (vapor) lumen 1415, positioned approximately 90 degrees about a circular axis on either side of the distal balloon inflation lumen 1417, while the second eyeholes pattern 1435 has a plurality of exit ports 1440 on a single side, opposite the distal balloon inflation lumen

1417, of the inner shaft 1405 into the first (vapor) lumen 1415. Vapor is delivered from these ports 1440, contacting and treating diseased tissue encapsulated in the coagulation/ablation zone 1420 demarcated by both balloons 1410, 1412.

Figure 14E:
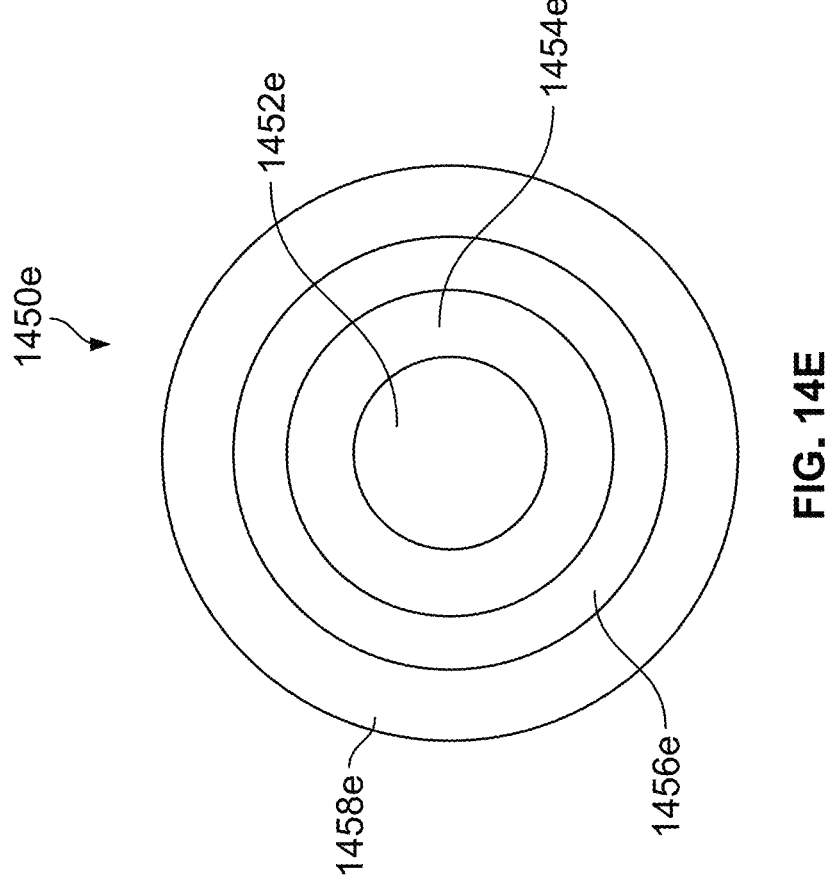
FIG. 14E illustrates a transverse cross-sectional view of a multi-lumen shaft of the catheter system of FIG. 14A, in accordance with an embodiment of the present specification.

FIG. 14E illustrates a transverse cross-sectional view of a multi-lumen shaft 1450c of the catheter system 1400 of FIG. 14A, in accordance with an embodiment of the present specification. The shaft 1450e comprises a first inner most lumen 1452e that allows water/saline to flow therein and also accommodates a heating element, such as the flexible heating chamber (comprising a plurality of electrodes) or an induction heating chamber (comprising an induction coil), a second lumen 1454e provides a pathway for inflation of the distal balloon 1410 or control of a distal positioning element, a third lumen 1456c that is configured as an inner sheath and a fourth lumen 1458e provides a pathway for inflation of the proximal balloon 1412 or control of a proximal positioning element. In embodiments the heating element is positioned substantially close to the plurality of vapor exit ports 1440. In various embodiments, the heating element is positioned not more than 6 inches back from a distal end of the proximal balloon 1412.

Further, in embodiments, the fourth lumen 1458e forming the catheter shaft is designed for high torque transmission or 1-to-1 torque transmission. In some embodiments, the fourth lumen 1458c forming the catheter shaft is formed using one of braid reinforced polymers, laser cut hypo-tubes, and multi-filar wound coils. Poor torque transmission of the catheter shaft could result in difficulty in rotating the shaft to accurately position the positioning elements, which is avoided by the configuration of the present specification.

Figure 15A:
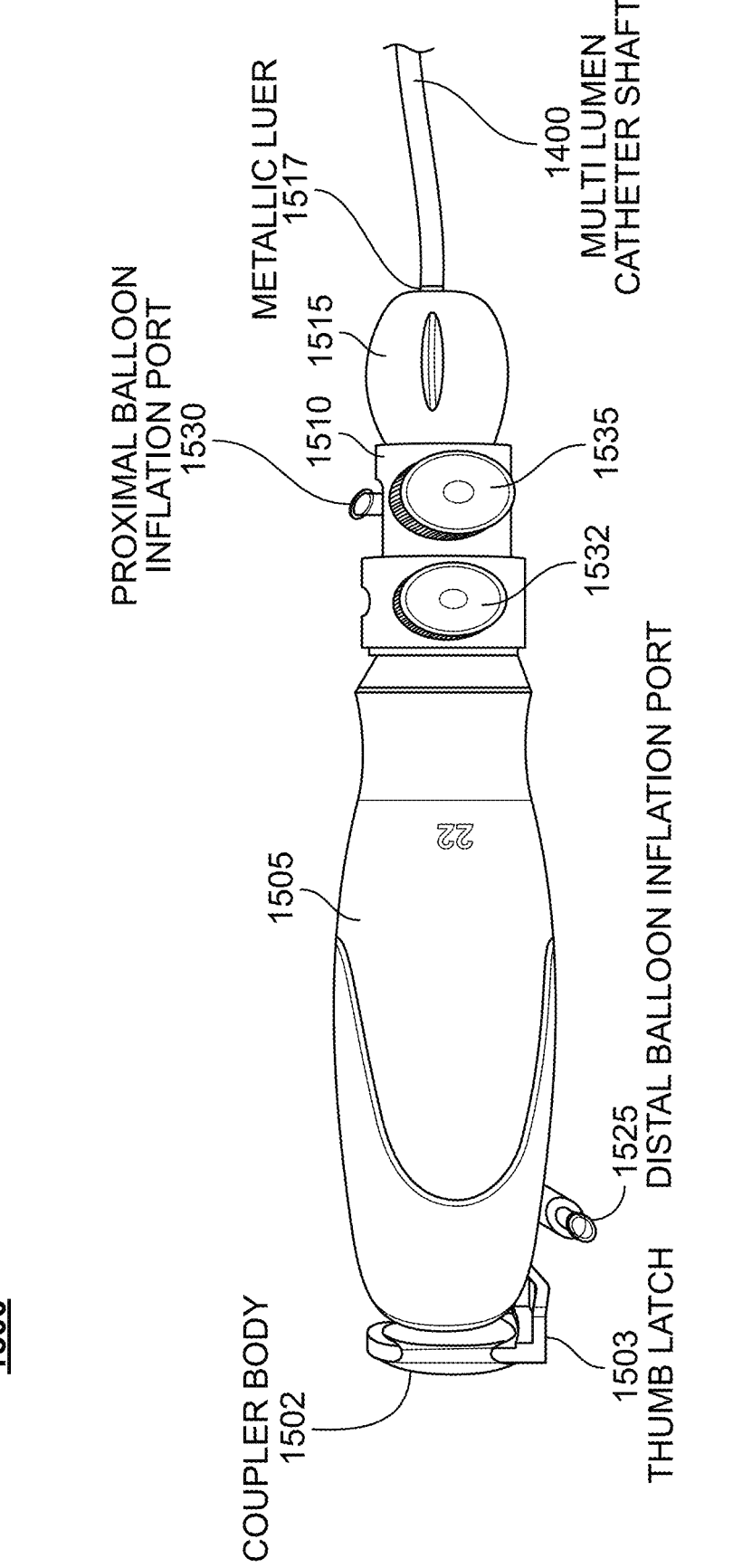
FIG. 15A shows a telescoping catheter handle with a first handle component in a first position relative to a second handle component, in accordance with embodiments of the present specification.
Figure 15B:
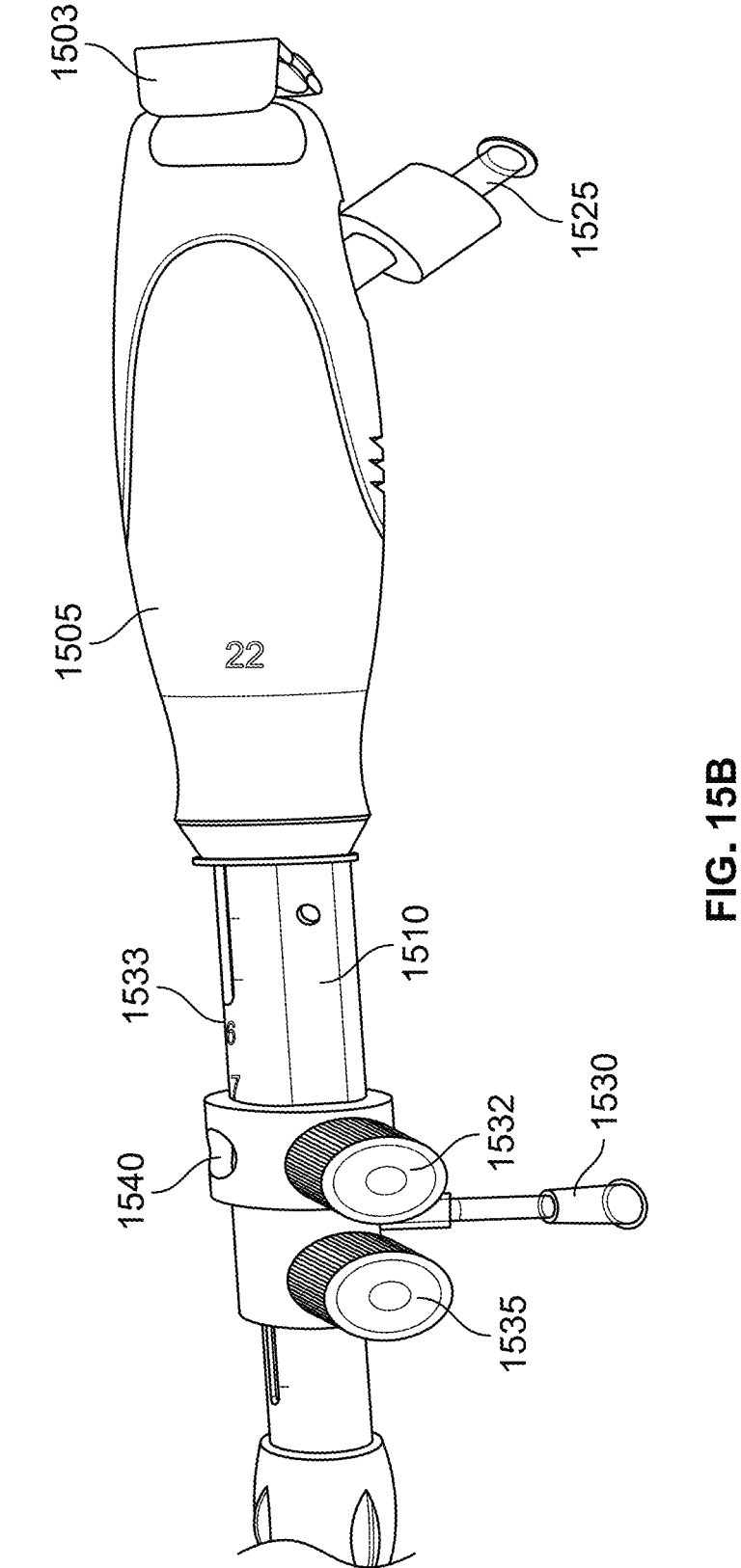
FIG. 15B shows the telescoping catheter handle with the first handle component in a second position relative to the second handle component, in accordance with embodiments of the present specification.

FIGS. 15A and 15B illustrate a telescoping catheter handle 1500 for use with the dual-balloon, dual shaft, multi-lumen catheter system 1400 of FIG. 14A, in accor-dance with embodiments of the present specification. Refer-ring now to FIGS. 14A, 14B, 15A and 15B simultaneously, the handle 1500 comprises a first handle component 1505 in a first position relative to a second handle component 1510, in accordance with one embodiment of the present specifi-cation. In one embodiment, the first handle component 1505 has an elongate body with a proximal end and distal end and comprises a thumb latch 1503 operated female coupler 1502 at the proximal end. In one embodiment, the second handle component 1510 has an elongate body with a proximal end and a distal end. The second handle component 1510 tele-scopes in and out of the distal end of the first handle component 1505 thereby adjusting the distance between the distal and proximal balloons 1410, 1412. A connector 1515 is included at the distal end of the second handle component 1510 and includes a luer component 1517 (at a distal end of the connector 1515) for attaching the catheter handle 1500 to a working channel port of an endoscope handle. The shaft of the dual-balloon, multi-lumen catheter system 1400 extends beyond the distal end of the second handle compo-nent 1510.

A first inlet port 1525 is located at the first handle component 1505 and attached to the inner shaft 1405 to inflate/deflate the distal balloon 1410. A second inlet port 1530 is located at the second handle component 1510 and attached to the outer shaft 1407 to inflate/deflate the proxi-mal balloon 1412. The first handle component 1505 includes a first thumbscrew 1532 to extend the catheter system 1400 beyond the endoscope and the second handle component 1510 includes a second thumbscrew 1535 to adjust a length of the coagulation/ablation zone 1420.

In the first position depicted in FIG. 15A, the first handle component 1505 is positioned most proximally relative to the second handle component 1510. Referring to FIG. 15B, the second handle component 1510 includes a plurality of markings 1533 along its body. In one embodiment, the markings 1533 are numbers. The first handle component 1505 includes a window 1540 proximate its distal end which aligns with one of said markings as the first handle component 1505 is moved longitudinally relative to the second handle component 1510. The marking 1533 in the window 1540 indicates the length of the catheter system 1400 extended beyond a distal end of the working channel of the endoscope and into a body lumen of a patient. FIG. 15B illustrates the catheter handle 1500 with the first handle component 1505 in a second position relative to the second handle component 1510. The marking 1533 in window 1540 indicates to an operator that the first handle component 1505 is in its most distal position relative to the second handle component 1510 and that the catheter system 900 is fully extended within the body lumen of the patient.

Figure 15C:
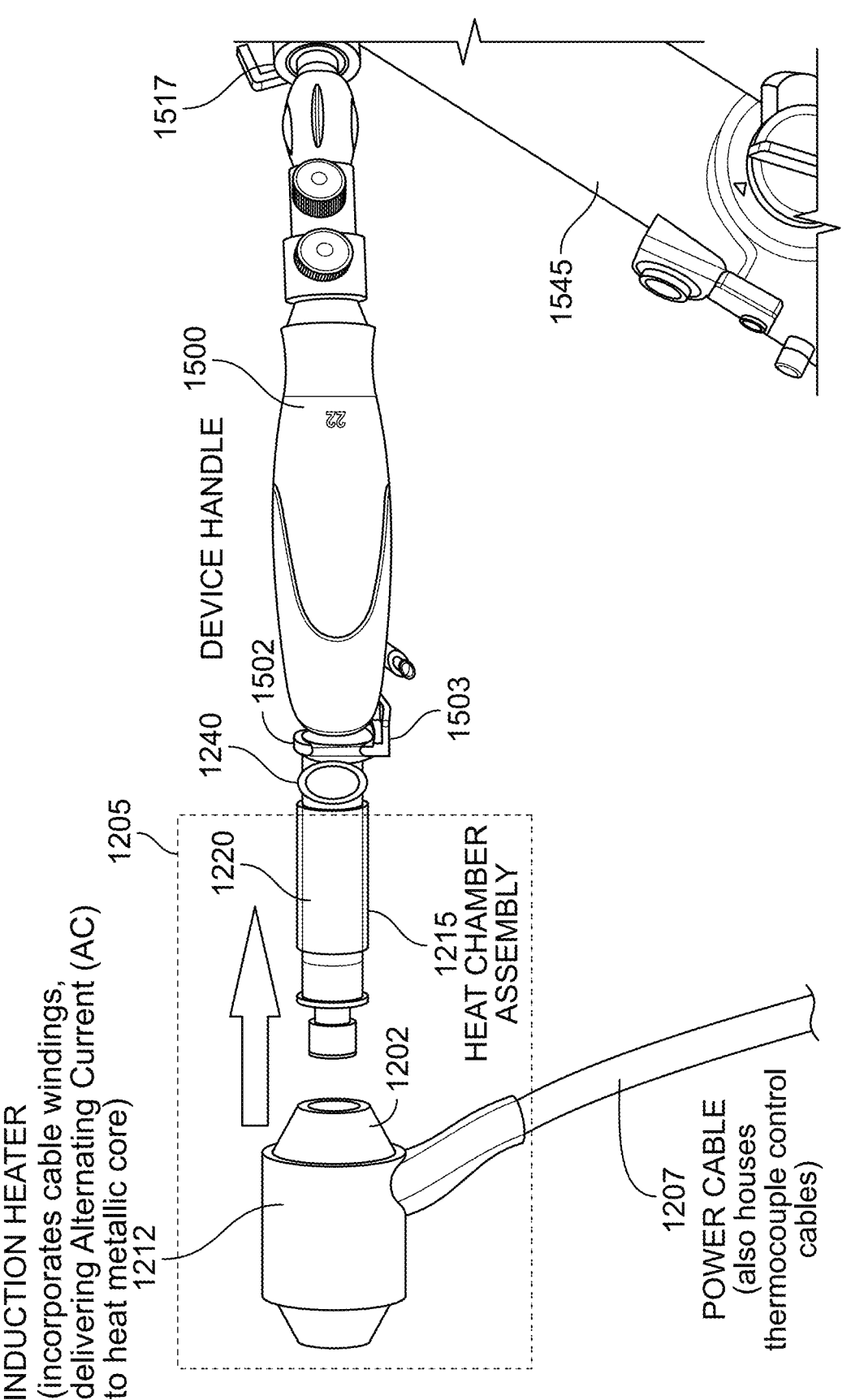
FIG. 15C illustrates an induction heating unit attached in-series with a proximal end of the catheter handle, in accordance with embodiments of the present specification.

Referring now to FIG. 15C along with FIGS. 12A, 12B, 12C, the catheter handle 1500 at its distal end is attached to a working channel port of the endoscope 1545 by means of the luer component 1517 or a latch-type locking mechanism in various embodiments. At its proximal end the catheter handle 1500 is connected to the induction heating unit 1205 through the thumb latch 1503 operated female coupler 1502. FIG. 15C shows a disassembled view of the inducting heating unit 1205 illustrating an assembly of the heating chamber 1215 and the core 1220 over which the housing 1202, comprising the induction coil 1212, is slidably attached. The power cable 1207 extends from the induction coil 1212 to a power generator. The 3-way flow control valve 1240 is also shown positioned between the catheter handle 1500 and the induction heating unit 1205. The thumb latch 1503 operated female coupler 1502 provides the operator with a mechanism to attach/detach the valve 1240 and the assembly of the heating chamber 1215 and the core 1220 from the catheter handle 1500.

Figures 15D, 15E, 15F:
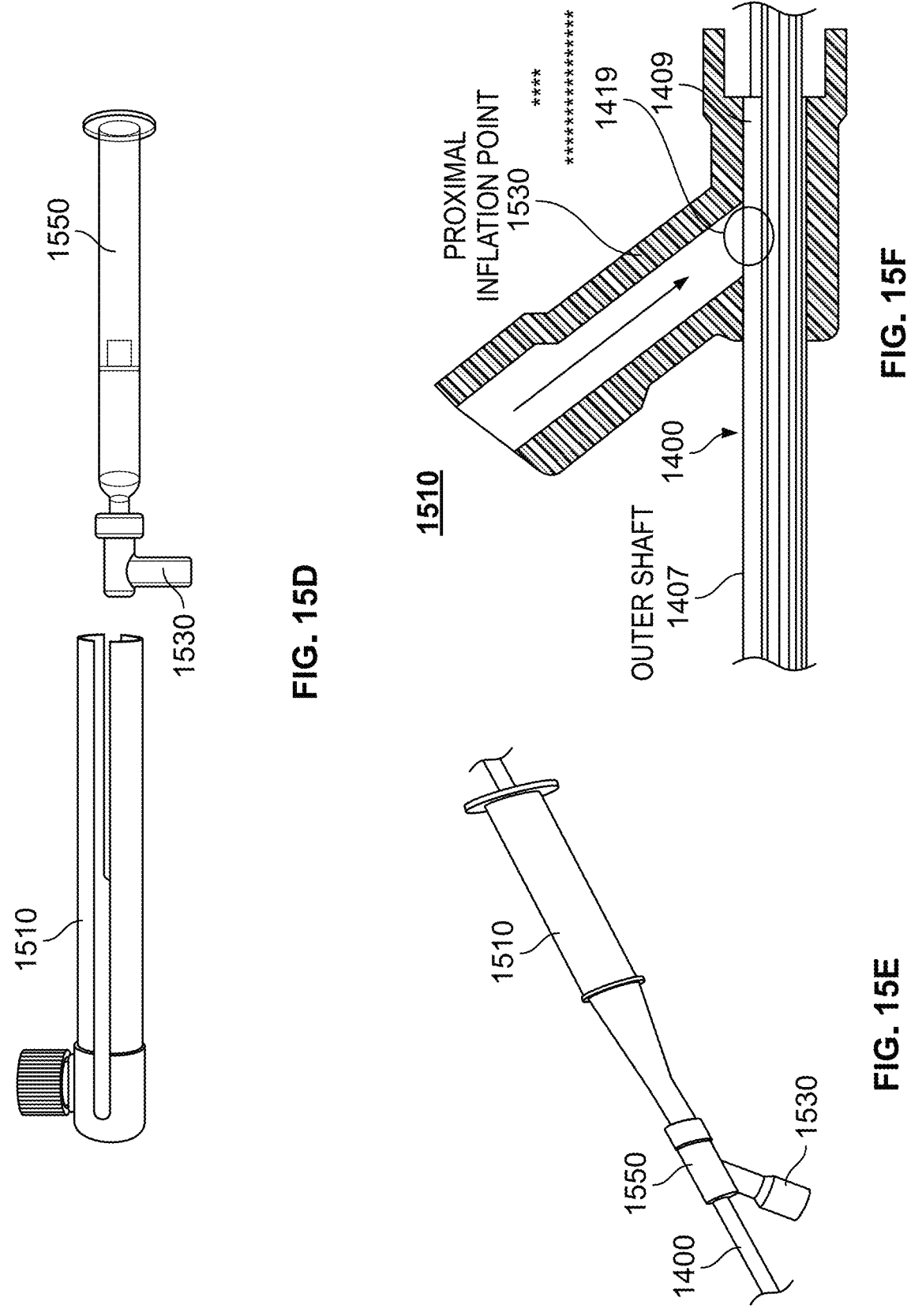
FIG. 15D shows a disassembled view of the second handle component of the catheter handle, in accordance with embodiments of the present specification.
FIG. 15E shows a perspective view of the second handle component separated out from the first handle component of the catheter handle, in accordance with embodiments of the present specification.
FIG. 15F shows a cross-sectional view of the second handle component of the catheter handle, in accordance with embodiments of the present specification.

FIG. 15D is a disassembled view of the second handle component 1510, FIG. 15E is a perspective view of the second handle component 1510 separated out from the first handle component 1505, while FIG. 15F is a cross-sectional view of the second handle component 1510. Referring now to FIGS. 15D, 15E, 15F along with FIGS. 14A and 14B, the second handle component 1510 houses a tube 1550 that, at its proximal end, is connected to the second inlet port 1530. The catheter system 1400 passes along the second handle component 1510 as shown in FIG. 15E, 15F. The second inlet port 1530 is in fluid communication via a skive 1419 into the second lumen 1409 of the outer shaft 1407 to enable inflation/deflation of the proximal balloon 1412.

Figures 15G, 15H:
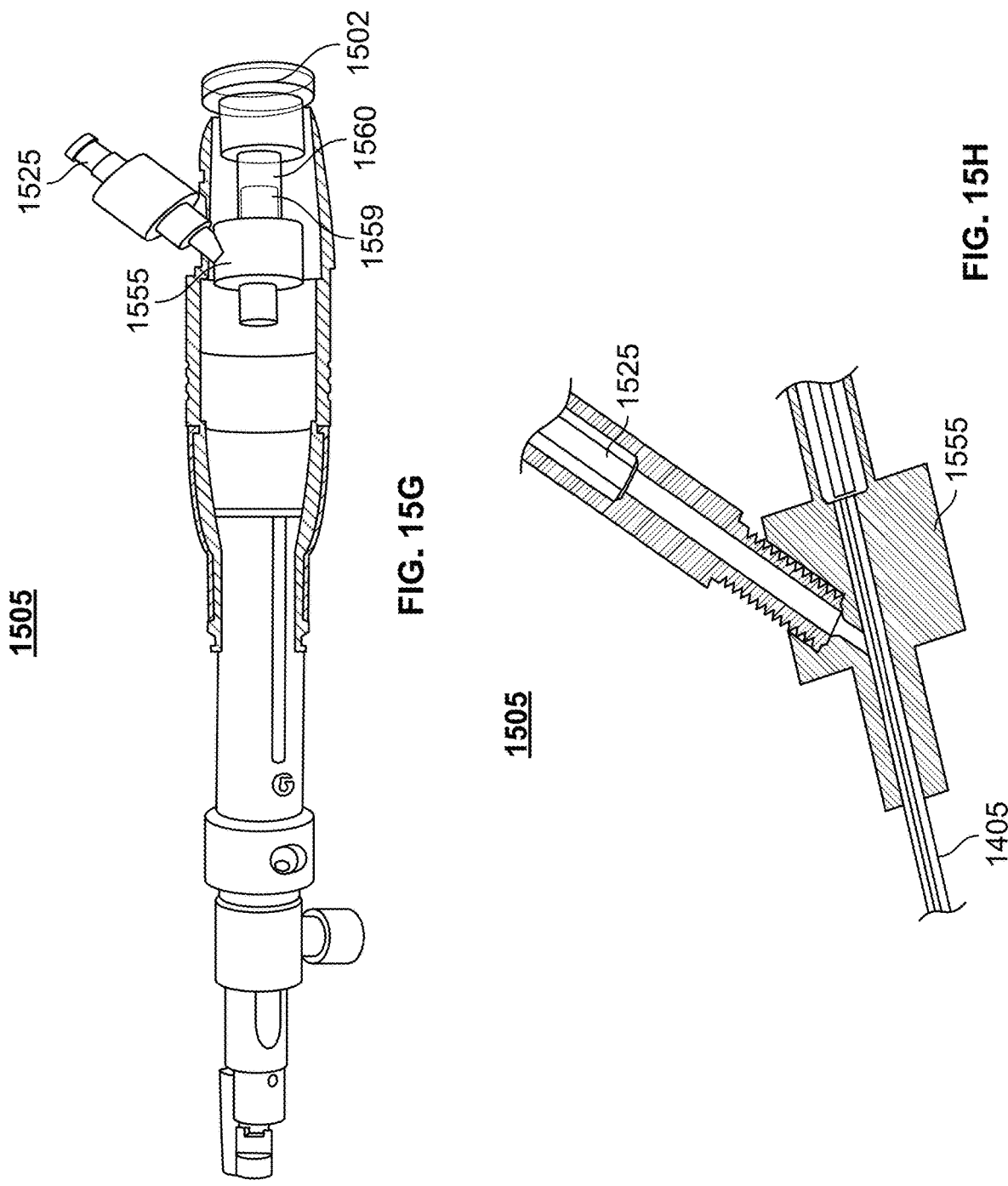
FIG. 15G shows a break-away view of the first handle component of the catheter handle, in accordance with embodiments of the present specification.
FIG. 15H is a cross-sectional view of the first handle component of the catheter handle, in accordance with embodiments of the present specification.

FIG. 15G is a break-away view of the first handle component 1505 while FIG. 15H is a cross-sectional view of the first handle component 1505. Referring now to FIGS. 15G, 15H along with FIGS. 14A, 14B, the first inlet port 1525 is attached (threaded, in an embodiment) into a manifold 1555 and is in fluid connection with the second lumen 1417 of the inner shaft 1405 to enable inflation/deflation of the distal balloon 1410. The housing 1560 of the female coupler 1502 attaches to a male luer 1559 of the manifold 1555.

Figure 16A:
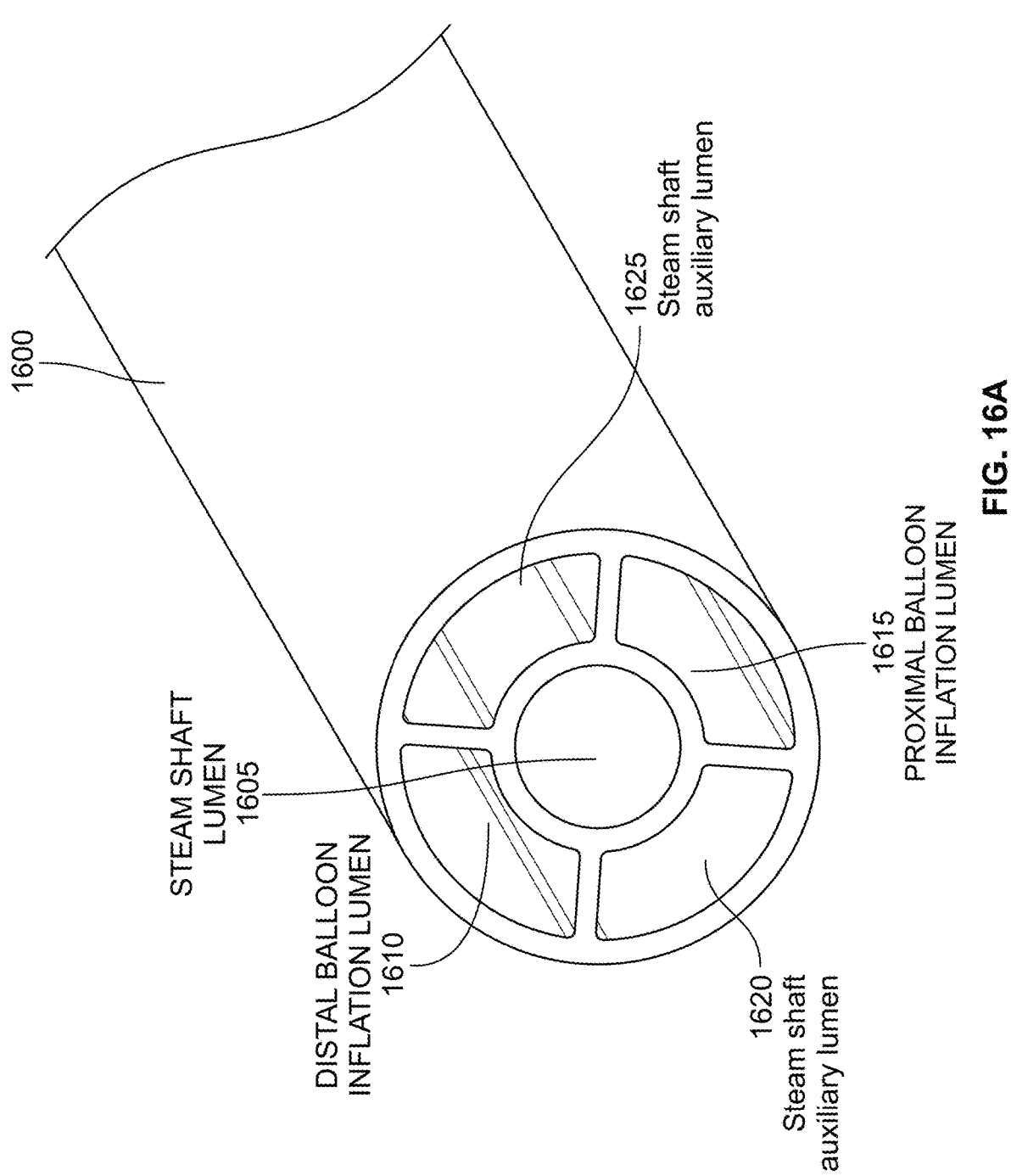

FIG. 16A shows a single multi-lumen shaft 1600 for the dual-balloon, multi-lumen catheter system 1400 of FIG. 14A, in accordance with embodiments of the present specification. Referring now to FIGS. 16A and 14A simultaneously, the distal and proximal balloons 1410, 1412 are coupled with the single multi-lumen shaft 1600. As a result, a distance between the balloons 1410, 1412 is fixed and thus, a length of the coagulation/ablation zone 1420 is also fixed.

A distal portion of the shaft 1600 between the balloons 1410, 1412 contains a number of eyeholes that serve as vapor exit ports 1440.

In accordance with an embodiment, the shaft 1600 includes five lumens and is manufactured from polymer material which is capable of maintaining performance under continuous exposure to vapor/steam and temperatures ranging from 110° C. to 120° C., such as PEEK or polysulfone. A first lumen 1605 allows ablation fluid, such as steam/vapor, to flow therethrough and exit from the vapor exit ports 1440. A second lumen 1610 is in fluid communication with the distal balloon 1410 to enable an inflation fluid, such as air, to flow or be suctioned therethrough for inflation/deflation of the balloon 1410. A third lumen 1615 is in fluid communication with the proximal balloon 1412 to enable the inflation fluid, such as air or water, to flow or be suctioned therethrough for inflation/deflation of the balloon 1412. Fourth and fifth lumens 1620, 1625 serve as auxiliary lumens for the first (steam) lumen 1605. The fourth and fifth lumens 1620, 1625 are in fluid communication with the first lumen 1605 at a distal portion of the shaft 1600 to allow flow of vapor from the first lumen 1605 through fourth and fifth lumens 1620, 1625 and out exit ports 1440 to ablate target tissue.

Figures 16B, 16C, 16D:
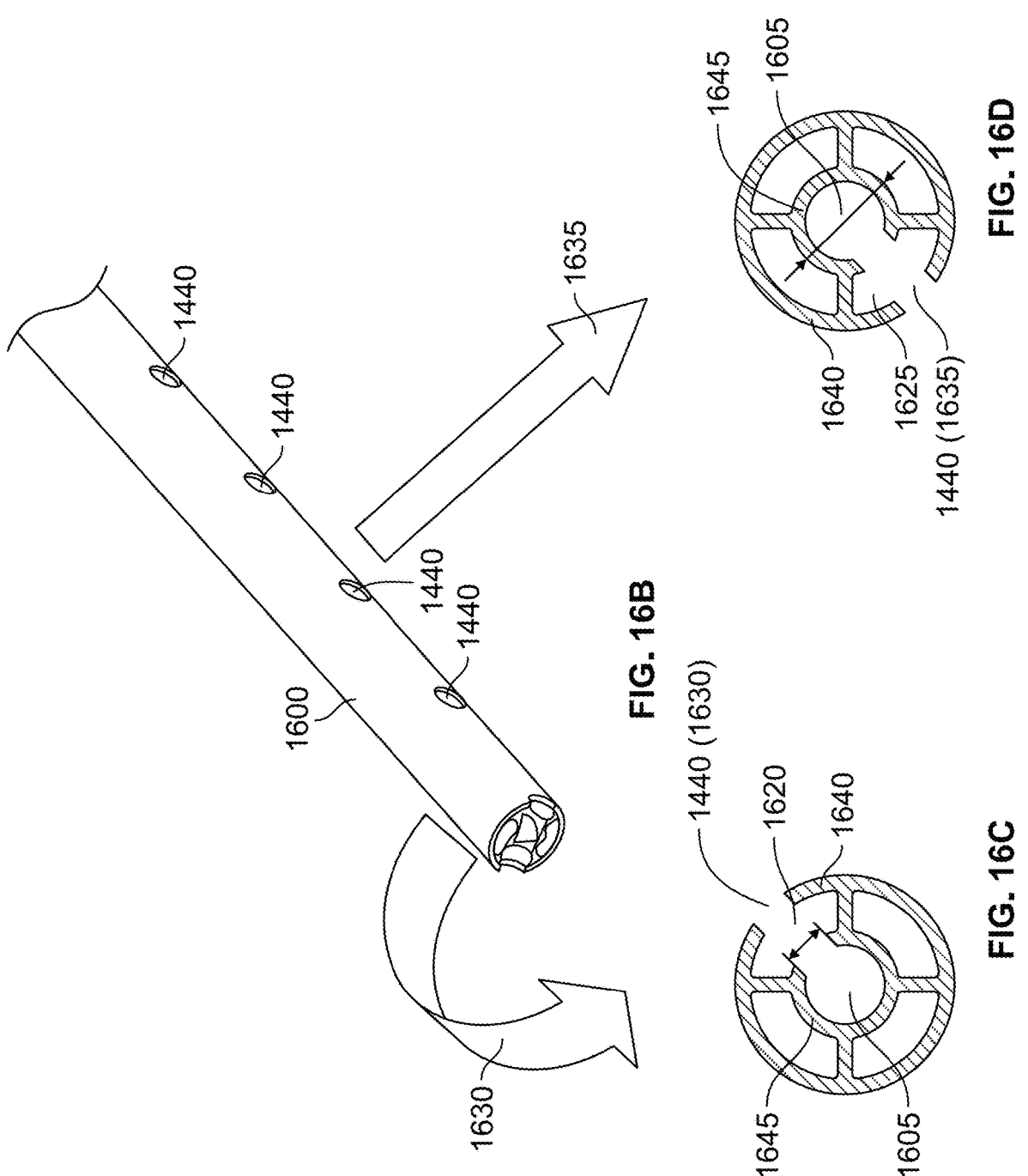

FIG. 16B illustrates a pattern of vapor exit ports 1440 at the distal portion of the shaft 1600 in accordance with an embodiment of the present specification. As shown, the vapor exit ports 1440 are arranged on first and second sides 1630, 1635 along a longitudinal axis of the shaft 1600 such that the two sides 1630, 1635 are 180° opposed. As shown in FIGS. 16C, 16D, the steam or vapor lumen 1605 is located in the center of the shaft 1600. To inject vapor from the central steam lumen 1605, the ports 1440 are drilled/laser cut through the outer wall 1640 of the shaft 1600, through the auxiliary lumens 1620, 1625 and through the inner wall 1645 of the steam lumen 1605.

Figure 16E:
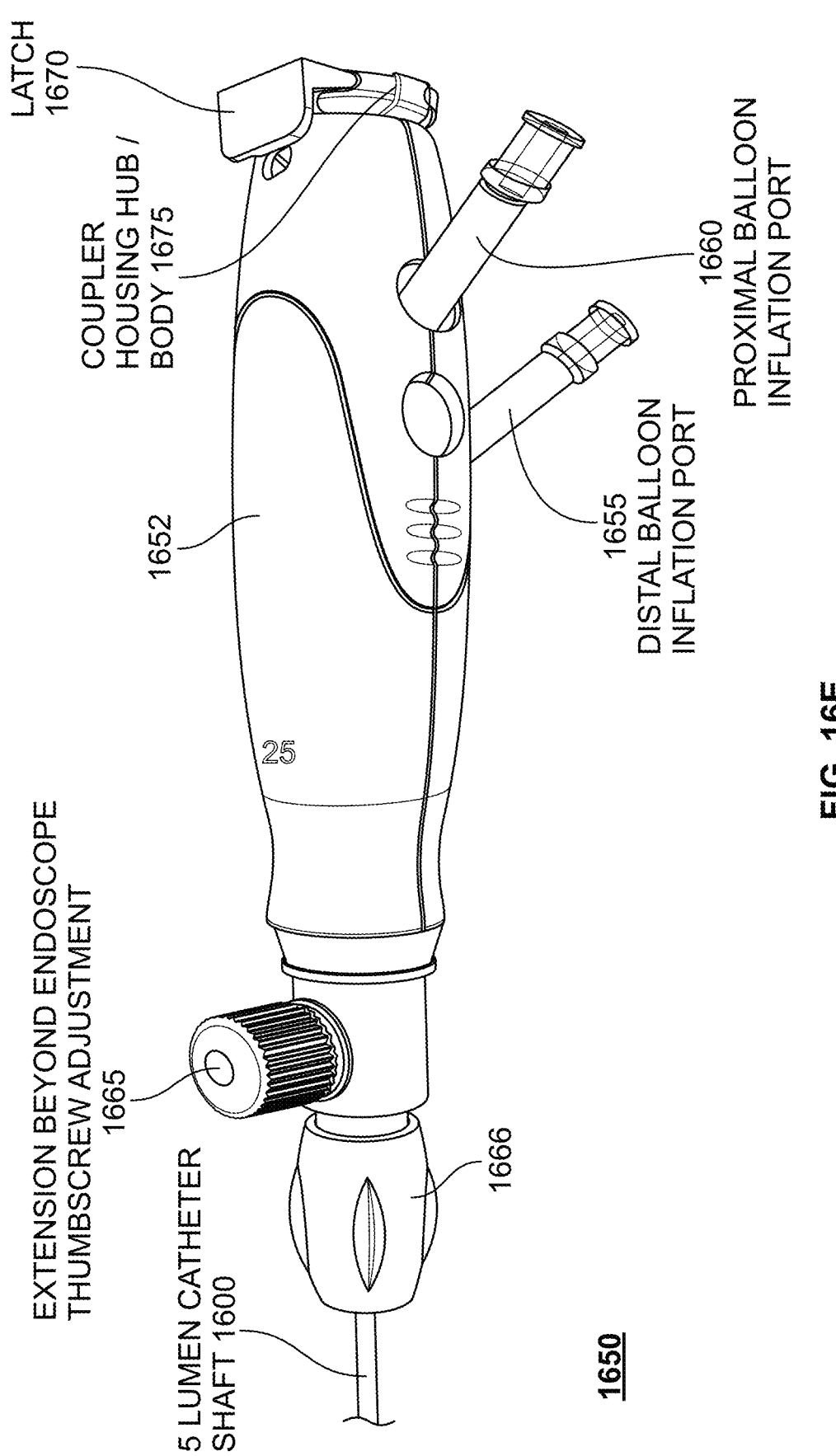
Figure 16F:
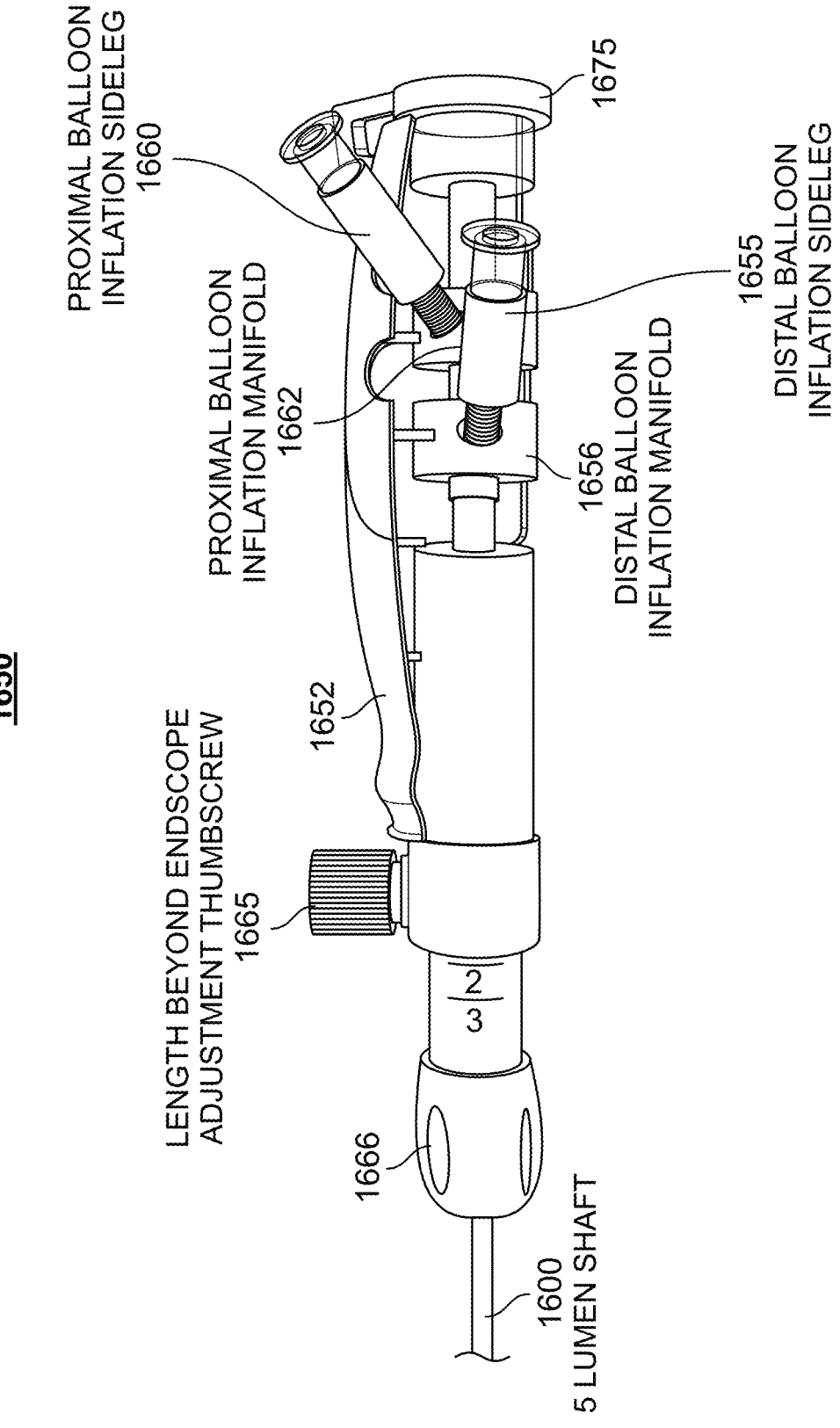

FIGS. 16E and 16F illustrate, respectively, perspective and break-away views of a non-telescopic catheter handle 1650 for use with the single multi-lumen shaft 1600, in accordance with embodiments of the present specification. Referring to FIGS. 16E and 16F along with FIG. 14A, the catheter handle 1650 has an elongate body 1652 comprising: a first inlet port 1655 attached to a first manifold 1656 that holds the port 1655 in fluid communication with the second lumen 1610 to enable inflation/deflation of the distal balloon 1410; and a second inlet port 1660 attached to a second manifold 1662 that holds the port 1660 in fluid communication with the third lumen 1615 to enable inflation/deflation of the proximal balloon 1412. In some embodiments, the first and second manifolds 1656, 1662 are configured to be coupled to the shaft 1600 and fabricated from PEEK/polysulfone. First and second tubing lines (not shown) are respectively connected to the first and second ports 1655, 1660. Proximal ends of both tubing lines are connected to two independent inflation pumps which are housed in a generator. Inflation and deflation (if desired) of both balloons 1410, 1412 is controlled via both lines. In embodiments, both tubing lines are flexible polymer extrusions and are disposable.

A connector 1666 is positioned at a distal end of the body 1652 and a luer component is attached at a distal end of the connector 1666 to enable the handle 1650 to be attached to a working channel port of an endoscope. The catheter shaft 1600 extends beyond the distal end of the connector.

A thumbscrew 1665 is positioned proximate a distal end of the handle 1650 to enable adjustment of the shaft 1600 beyond the endoscope when the handle 1600 is attached to a working channel of the endoscope. A thumb latch 1670 operated female coupler 1675 is positioned at a proximal end of the handle 1650 to enable an induction heating unit (such as the unit 1205) to be attached in-series or in-line to the handle 1650 (similar to as illustrated in FIG. 15C). The second manifold 1662 is fluidically connected to the housing body of the female coupler 1675.

In accordance with aspects of the present specification, it is preferred that the thumbscrew 1665 and the thumb latch 1670 be facing in the same direction so that orientation is towards the operator when the handle 1650 is locked onto the endoscope. It is also preferred that both ports 1655, 1660 are positioned or oriented approximately 90 degrees opposed to the thumb latch 1670 so that they provide favorable ergonomics for the operator and do not interfere with handle 1650 manipulation during an ablation procedure.

Figures 17A, 17B, 17C:
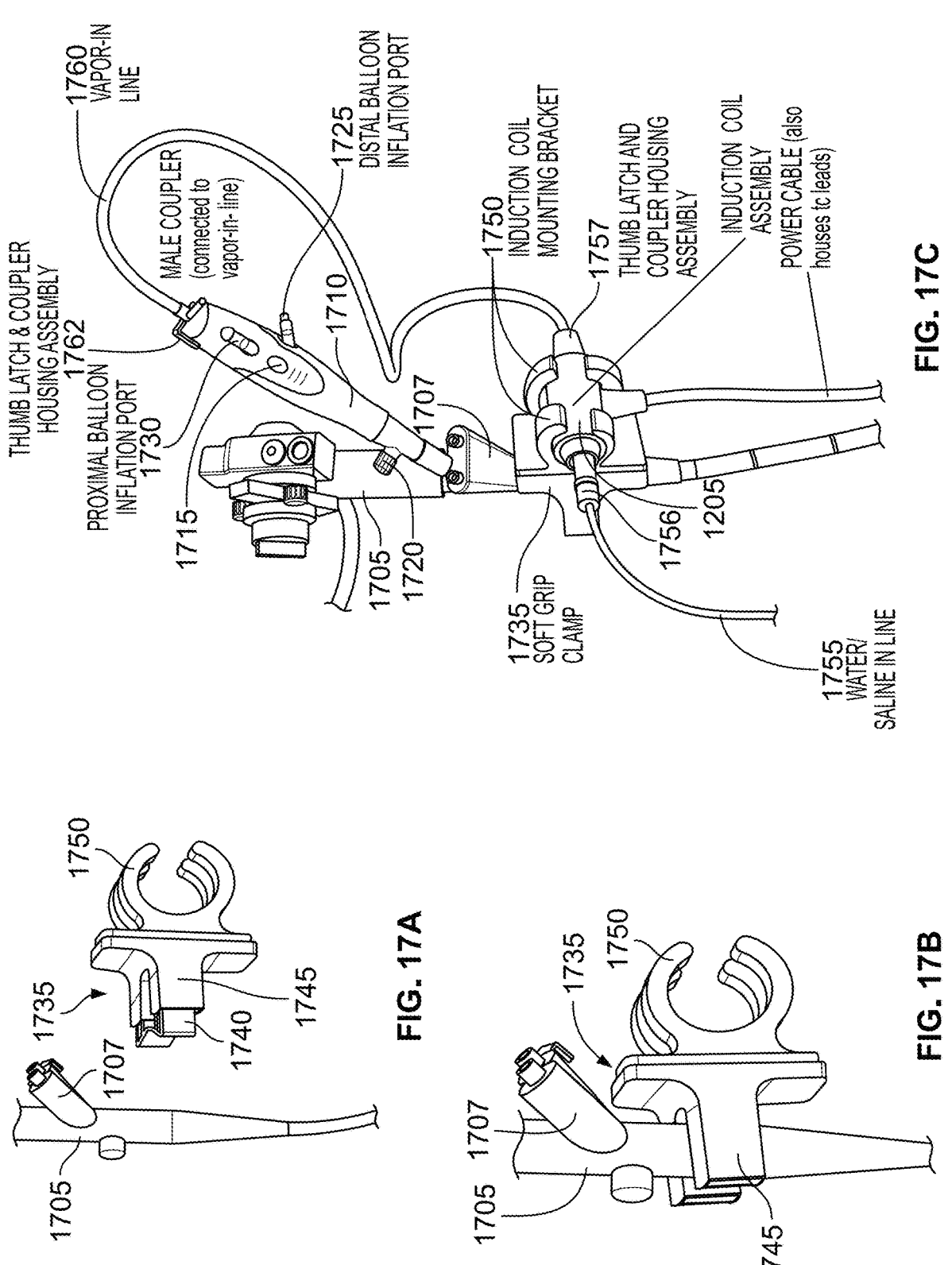

In accordance with an aspect of the present specification, FIG. 17C shows an induction heating unit being removably mounted onto an endoscope, while FIGS. 17A and 17B illustrate perspective views of a clamp in accordance with embodiments of the present specification. Referring now to FIGS. 17A, 17B and 17C along with FIG. 12A, the induction heating unit 1205, comprising an assembly of the heating chamber 1215 (with the core 1220) and the induction coil 1212, is mounted on a body of an endoscope 1705, below a biopsy port bifurcation 1707 on the endoscope 1705. Mounting the induction heating unit 1205 to this location reduces the moment arm and weight on a catheter handle 1710 and moves a number of components away from the immediate handle working space around the thumbscrews 1715, 1720 as well as distal and proximal balloon inflation ports 1725, 1730 for inflation/deflation of distal and proximal balloons of a dual-balloon multi-lumen catheter (such as catheter system 1400 of FIG. 14A). In some embodiments, the catheter handle 1710 is a telescopic handle (such as the handle 1500 of FIG. 15A) while in other embodiments the catheter handle 1710 is a non-telescopic handle (such as the handle 1650 of FIG. 16E).

Figure 17D:
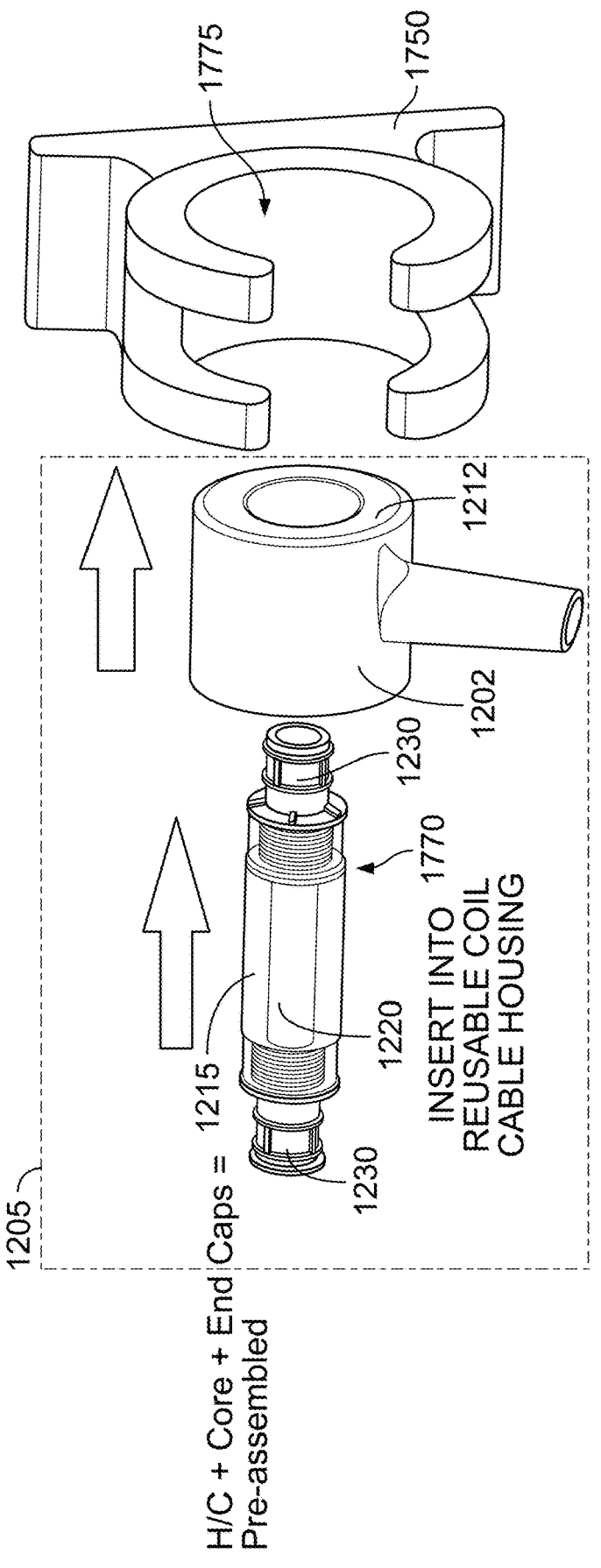

The induction heating unit 1205 is removably attached to a main shaft of the endoscope 1705 using a soft grip clamp 1735. In an embodiment, the clamp 1735 consists of a soft, deformable, rubber grip 1740 attached to a rigid polymeric frame 1745 which incorporates a bracket 1750 to mount the induction heating unit 1205. In an embodiment, the bracket 1750 is configured as a C-clamp. As shown in FIG. 17D, the heating chamber 1215, the core 1220 and the two male coupler end caps 1230 are pre-assembled as a module 1770, in accordance with an embodiment. Next, the module 1770 is slidably inserted into the housing 1202, comprising the induction coil 1212, thereby forming the induction heating unit 1205. Subsequently, the induction heating unit 1205 is slid into an approximately C-shaped space 1775 of the bracket 1750.

Referring back to FIGS. 17A, 17B and 17C, once the induction heating unit 1205 is slidably mounted into the C-clamp the assembly is loaded on to the shaft of the endoscope 1705, below the biopsy port. The deformable nature of the rubber grip 1740 provides a secure attachment to the endoscope 1705. This orientation of the clamp 1735 can be easily adjusted to suit preferred orientation of the induction heating unit 1205 during an ablation procedure. The clamp 1735 may be removed by simply pulling outward on the bracket assembly.

A disposable water/saline tube line 1755 connects to a thumb latch operated female coupler 1756 at a proximal end of the induction heating unit 1205 while a disposable vapor delivery tube line 1760 is connected to the unit 1205 via a thumb latch operate female coupler 1757 at a distal end of the unit 1205 and to the handle 1710 via another thumb latch operated female coupler 1762 at a proximal end of the handle 1710. In various embodiments, the vapor delivery tube line 1760 is made of PEEK, polysulfone, high temperature Nylon, polycarbonate or polyimide material. In some embodiments, this tube may also be braided reinforced to make the tubing more resistant to kinking during the procedure. It should be appreciated that, although not shown in FIG. 17C, a 3-way flow control valve, such as valve 1240, is positioned between the unit 1205 and the handle 1710.

Figure 18:
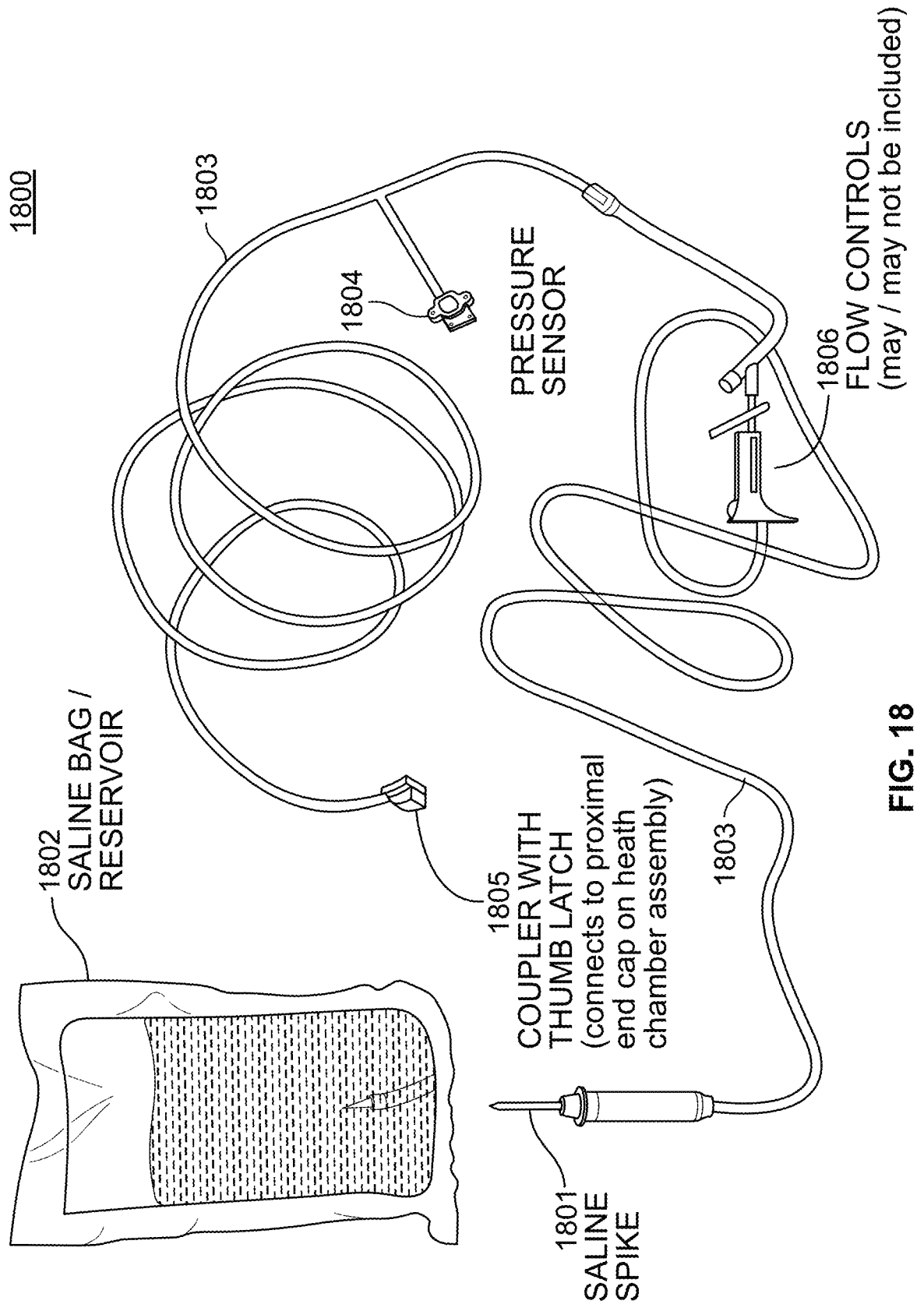

FIG. 18 is an illustration of an embodiment of a disposable tubing set 1800 to be used with the ablation systems of the present specification. In an embodiment, the tubing set 1800 includes a rigid plastic spike 1801 to puncture a saline bag or reservoir 1802, flexible polymeric tubing 1803, a pressure sensor 1804, and a coupler with thumb latch 1805. The pressure sensor 1804 connects to a microcontroller on the vapor generator and is used to monitor and control pressure in the system once vapor generation and delivery has been initiated. The coupler with thumb latch 1805 is configured to securely lock the tubing 1803 to the proximal end of the induction heating unit. Alternatively, in an embodiment, the coupler with thumb latch 1805 is replaced with a male coupler to connect with the female coupler 1756 at the proximal end of the inducting heating unit 1205 depicted in FIG. 17C. In an embodiment, the tubing set 1800 also includes a flow control component with thumb dial 1806 for controlling a rate flow from the saline bag or reservoir 1802.

The tubing set 1800 also includes first and second disposable inflation line tubes that are flexible polymer extrusions. Distal ends of the first and second inflation line tubes respectively connect to distal and proximal balloon inflation ports of a catheter handle. Proximal ends of the first and second inflation line tubes are connected to two independent inflation pumps. Inflation and deflation (if desired) of both distal and proximal balloons is controlled via the first and second inflation line tubes.

Figure 19:
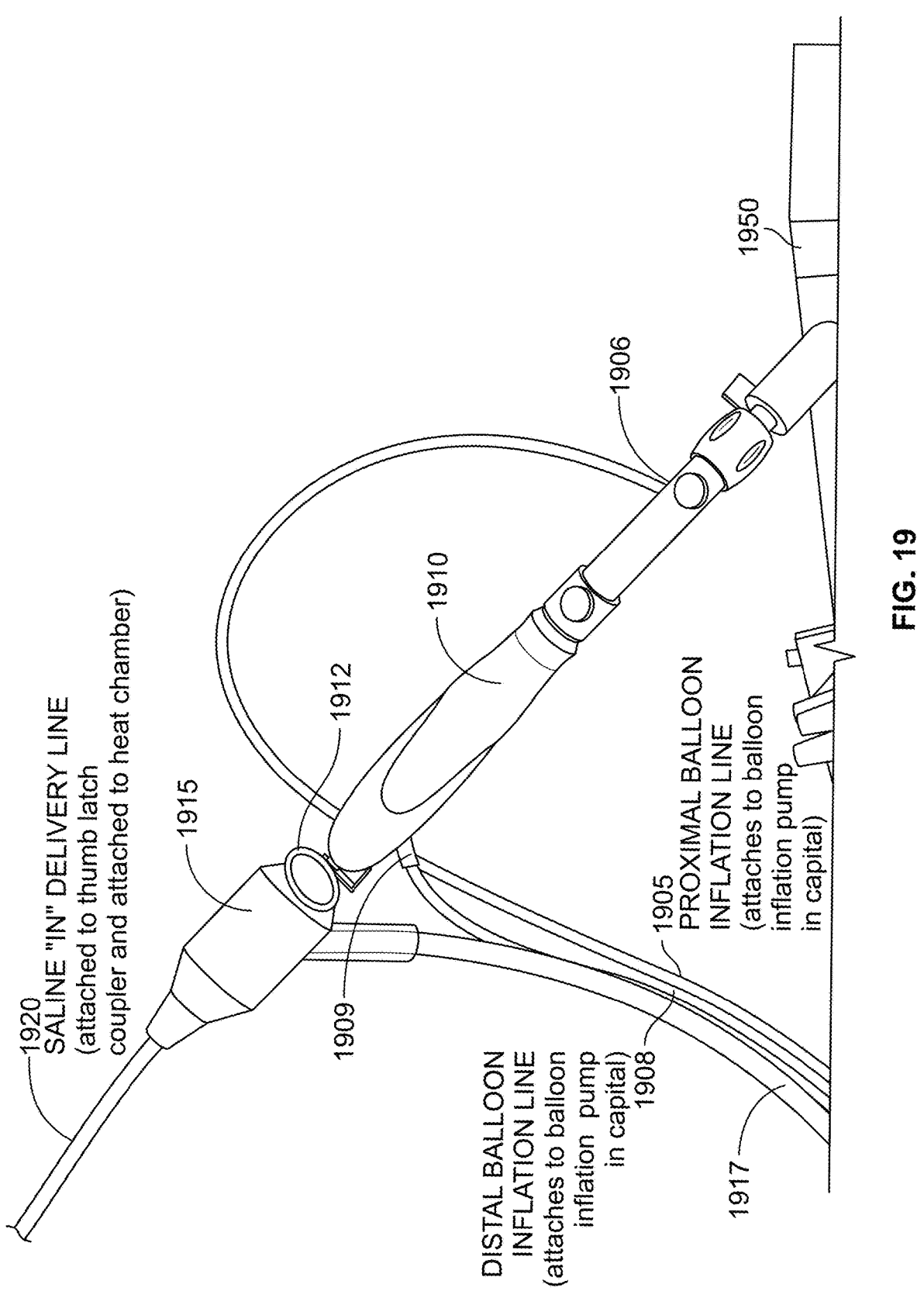

FIG. 19 is an illustration of a telescoping catheter handle 1910 attached to an endoscope 1950, in accordance with an embodiment of the present specification. A proximal balloon inflation line 1905 is connected to a proximal balloon inflation port 1906 for inflation of a proximal balloon and a distal balloon inflation line 1908 is attached to a distal balloon inflation port 1909 for inflation of a distal balloon. An induction heating unit 1915 is attached to the proximal end of the catheter handle 1910 and includes a power line 1917 for providing electrical current to the wire of the induction coil. A saline delivery line 1920 is connected to the proximal end of the induction heating unit 1915. A three-way valve 1912 is included between the catheter 1910 and induction heating unit 1915 for priming the system to remove residual water before vapor generation.

FIG. 20A is an assembled view of a vapor generator 2050, FIG. 20B is a partial disassembled view of the vapor generator 2050, FIG. 20C is a disassembled view of a disposable pump of the vapor generator 2050, FIG. 20D is an assembled view of the disposable pump and FIG. 20E shows the disposable pump fluidically connected to other components of the vapor generator 2050, in accordance with an embodiment of the present specification. Referring to FIGS. 20A through 20E, simultaneously, the vapor generator 2050 comprises a water/saline bag or reservoir 2055 fluidically attached to a first tube 2060. At one end, the first tube 2060 has a rigid plastic spike 2056 to puncture the reservoir 2055 while at another end the first tube 2050 has a first latch operated female connector 2058 for quick connection to a first male coupler end cap 2065 of an in-feed tube portion 2070 of a disposable pump 2075.

The disposable pump 2025 comprises a pump head 2072 that attaches to a pump motor housing 2074. The first tube 2060 feeds water/saline from the reservoir 2055 to the pump 2075. Pressurized water/saline, output by the pump 2075, is carried forward by a second tube 2080 that attaches to a second male coupler end cap 2085, of a tube portion 2090 of the pump 2075, by means of a second female coupler 2095. The second tube 2080 supplies pressurized water/saline to a heating chamber of an induction heating unit.

Gastrointestinal Ablation

FIG. 21 illustrates an ablation catheter placed in an upper gastrointestinal tract with Barrett's esophagus to selectively ablate the Barrett's tissue, in accordance with an embodiment of the present specification. Referring to FIG. 21, the upper gastrointestinal tract comprises Barrett's esophagus 2141, gastric cardia 2142, gastroesophageal junction 2143 and displaced squamo-columnar junction 2144. The area between the gastroesophageal junction 2143 and the displaced squamo-columnar junction 2144 is Barrett's esophagus 2141, which is targeted for ablation. Distal to the cardia 2142 is the stomach 2145 and proximal to the cardia 2142 is the esophagus 2146. The ablation device is passed into the esophagus 2146 and the balloons 2110, 2112 are positioned such that the balloon 2112 is placed in the gastric cardia 2142 abutting the gastroesophageal junction 2143. This affixes the ablation catheter and its infusion ports (shown in FIG. 4A) in the center of the esophagus 2146 and allows for uniform delivery of the ablative agent to the Barrett's esophagus 2141. It should be appreciated that the fluid delivery port 2127 and the suction port 2132 are positioned at a site away from the tissue being ablated so that a) the delivery of fluid does not significantly interfere with delivery of the ablative agent and b) the suction process does not result in suction of the ablative agent.

FIG. 22 is a flowchart illustrating a method of ablation of Barrett's esophagus in accordance with one embodiment of the present specification. Referring to FIG. 22, in the first step 2201, an endoscopy is performed on the patient to measure the length of Barrett's esophagus in the patient. Thereafter in step 2202, the measured length is input into a processor of an ablation system used to calculate the amount of ablative energy needed to ablate the Barrett's esophagus. In another embodiment, the measured length is used as a reference to select a catheter of appropriate ablation segment length to approximate the length of Barrett's esophagus. Next, in step 2203, a catheter having a first positioning balloon at its distal end and a second positioning balloon at its proximal end is passed through the endoscope channel or alongside the endoscope channel such that the distal balloon is positioned proximate a cardia tissue of a patient and the proximal balloon is positioned proximate the top of the Barrett's esophagus.

In the next step 2204, the two balloons are inflated to a set pressure (P$_1$) and the diameter of the Barrett's esophagus is measured using the proximal balloon. This diameter is manually or automatically input into the processor and a surface area of the Barrett's segment to be ablated is calculated, as shown in step 2205.

Next, in step 2206, one or more cycles of vapor is delivered to the esophageal mucosa through one or more vapor delivery ports on the catheter at a temperature in a range of 90 to 100° C. to ablate the Barrett's esophagus. In step 2207, the balloon pressures during the delivery of ablative agent are maintained at a pressure P$_2$ which is greater than or equal to pressure P$_1$. Optionally, in step 2208, the balloons are deflated to a pressure P$_3$ which is less than or equal to pressure P$_1$ between the cycles of ablation. Finally, the endoscope and the catheter are removed after the ablation is complete in step 2209.

It should be appreciated that any ablation catheter or system of the present specification, used to ablate tissue in an organ, may be used with a controller, wherein the controller is configured to limit a pressure generated by ablation fluid, such as steam/vapor, within the organ to less than 5 atm or 100 psi.

FIG. 23A illustrates deflated 2340d, lateral inflated 23401, and frontal inflated 2340f views of an ablation catheter 2340 having an insulating membrane 2349 for duodenal ablation, in accordance with one embodiment of the present specification. In some embodiments, the catheter 2340 comprises a water-cooled catheter having a proximal inflatable balloon 2342 and a distal inflatable balloon 2344 with an insulating membrane 2349 which extends from a proximal end of the proximal balloon 2342 to a distal end of the distal balloon 2344. One or more vapor delivery ports 2343 are positioned on the catheter 2340 between the proximal balloon 2342 and distal balloon 2344. Once the balloons 2342, 2344 are inflated, as depicted in lateral view 23401, the stretching of the insulating membrane 2349 between the balloons 2342, 2344 causes the catheter 2340 to bow, helping to position the insulating membrane over the ampulla of Vater, thereby providing a protective shield over the ampulla during vapor ablation therapy.

FIG. 23B illustrates the ablation catheter 2340 of FIG. 23A deployed in a duodenum 2350 of a patient, in accordance with one embodiment of the present specification. The catheter 2340 has been deployed through a working channel of an endoscope 2341 such that the distal inflatable balloon 2344 is positioned in the distal duodenum 2350d, proximal to the jejunum 2352, and the proximal inflatable balloon 2342 is positioned in the proximal duodenum 2350p. The insulating membrane 2349 is positioned over the ampulla of Vater 2351 to prevent ablative agent 2345 delivered to the duodenum 2350 from damaging said ampulla 2351. Proximal portions 2349p and distal portions 2349d of the insulating membrane 2349 are attached to the proximal inflatable balloon 2342 and distal inflatable balloon 2344 respectively, such that the insulating membrane 2349 becomes stretched to conform to the shape of the duodenum 2350 once the catheter 2340 is deployed.

In various embodiments, ablation therapy provided by the vapor ablation systems of the present specification is delivered to treat a variety of conditions and efficacy of treatment is determined by measuring certain physiological parameters, as further described below, in a range of time from at least six weeks to two years after treatment. If the therapeutic endpoints are not achieved after a period of at least six weeks, ablation therapy is repeated. Physiological parameters are then measured after at least another six weeks, and ablation therapy may be repeated and evaluated in a similar six week cycle, until the desired therapeutic endpoint is achieved.

In various embodiments, ablation therapy, particularly duodenal ablation, provided by the vapor ablation systems of the present specification is delivered to treat at least one of fatty liver, non-alcoholic fatty liver disease (NAFLD), non-alcoholic steatohepatitis, type II diabetes, metabolic syndrome, overweight patients, and obesity. In various embodiments, ablation therapy, particularly duodenal ablation, provided by the vapor ablation systems of the present specification is delivered to achieve the following therapeutic endpoints: treat type II diabetes by achieving at least a 10% reduction in HbA1c or fasting blood glucose level when measured at least six weeks after treatment; treat metabolic syndrome; or treat hyperlipidemia by achieving at least a 5% reduction in either total cholesterol or LDL or triglyceride or at least a 5% improvement in the HDK cholesterol, as measured at least six weeks after treatment.

In case of the treatment for fatty liver or Non-Alcoholic Fatty Liver Disease (NAFLD)/Non-Alcoholic Steatohepatitis, ablation therapy, particularly duodenal ablation, provided by embodiments of the vapor ablation systems of the present specification is delivered to achieve the following therapeutic endpoints, as measured at least six weeks after treatment: at least a 10% decrease in either ALT or AST levels; a relative improvement of 10% in serum Ferritin level or an absolute level of no more than 1.5 ULN (upper limit normal); at least a 5% relative improvement in hepatic steatosis (HS), or no more than 5% HS as measured on liver biopsy; at least a 5% relative improvement in HS as measured by magnetic resonance (MR) imaging, cither by spectroscopy or proton density fat fraction; at least a 5% relative improvement in NAFLD Fibrosis Score (NFS); at least a 5% relative improvement in NAFLD Activity Score (NAS); at least a 5% relative improvement in Steatosis Activity Fibrosis (SAF) score; at least 10% of patients showing a decrease in the mean annual fibrosis progression rate as measured by histology, Fibrosis-4 (FIB-4) index, aspartate aminotransferase (AST) to platelet ratio index (APRI)), scrum biomarkers (Enhanced Liver Fibrosis (ELF) panel, Fibrometer, FibroTest, and Hepascore), or imaging (Transient Elastography (TE), MR Elastography (MRE), acoustic radiation force impulse imaging, and supersonic shear wave elastography); at least a 5% relative improvement in circulating levels of cytokeratin-18 fragments; at least a 5% relative improvement in FIB-4 index, aspartate aminotransferase (AST) to platelet ratio index (APRI), serum biomarkers (Enhanced Liver Fibrosis (ELF) panel, Fibrometer, FibroTest, and Hepascore), or imaging (TE, MRE, acoustic radiation force impulse imaging, and supersonic shear wave elastography); at least a 5% relative improvement in liver stiffness measured by vibration controlled transient elastography (VCTE (FibroScan)); at least 10% of patients showing an improvement in NAS by 2 points with at least 1-point improvement in hepatocellular ballooning and 1-point improvement in either the lobular inflammation or steatosis score, and no increase in the fibrosis score; at least 10% of patients showing an improvement in the NFS scores; and at least 5% of patients showing an improvement in any of the above listed NAFLD parameter as compared to a sham intervention or a placebo. In various embodiments, the relative therapeutic goals and endpoints are provided relative to one or more pre-treatment levels of the correspondingly stated physiological indicators.

In various embodiments, ablation therapy, particularly duodenal ablation, provided by the vapor ablation systems of the present specification is delivered to treat obesity in a person by achieving one of the following therapeutic endpoints, as measured at least six weeks after treatment: a total body weight of the person reduces by at least 1% relative to a total body weight of the person before ablation; an excess body weight of the person reduces by at least 1% relative to an excess body weight of the person before ablation; a total body weight of the person reduces by at least 1% relative to a total body weight of the person before ablation and a well-being level of the person does not reduce more than 5% relative to a well-being level of the person before ablation;

an excess body weight of the person reduces by at least 1% relative to an excess body weight of the person before ablation and a well-being level of the person does not reduce more than 5% relative to a well-being level of the person before ablation; after at least one ablation, a pre-prandial ghrelin level of the person reduces by at least 1% relative to a pre-prandial ghrelin level of the person before ablation; after at least one ablation, a post-prandial ghrelin level of the person reduces by at least 1% relative to a post-prandial ghrelin level of the person before ablation; after at least one ablation session, exercise output of the patient increases by at least 1% relative to the exercise output of the patient before ablation; after at least one ablation, a glucagon-like peptide-1 level of the person increases by at least 1% relative to a glucagon-like peptide-1 level of the person before ablation; after at least one ablation, a leptin level of the person increases by at least 1% relative to a leptin level of the person before ablation; after at least one ablation, the patient's appetite decreases, over a predefined period of time, relative to the patient's appetite before ablation; after at least one ablation, a peptide YY level of the person increases by at least 1% relative to a peptide YY level of the person before ablation; after at least one ablation, a lipopolysaccharide level of the person reduces by at least 1% relative to a lipopolysaccharide level of the person before ablation; after at least one ablation, a motilin-related peptide level of the person reduces by at least 1% relative to a motilin-related peptide level of the person before ablation; after at least one ablation, a cholecystokinin level of the person increases by at least 1% relative to a cholecystokinin level of the person before ablation; after at least one ablation, a resting metabolic rate of the person increases by at least 1% relative to a resting metabolic rate of the person before ablation; after at least one ablation, a plasma-beta endorphin level of the person increases by at least 1% relative to a plasma-beta endorphin level of the person before ablation; after at least one ablation, the person's level of hemoglobin A1c decreases by an amount equal to at least 0.3%; after at least one ablation, a triglyceride level of the person decreases by at least 1% relative to a triglyceride level of the person before ablation; after at least one ablation, a total blood cholesterol level of the person decreases by at least 1% relative to a total blood cholesterol level of the person before ablation; after at least one ablation, a glycemia level of the person decreases by at least 1% relative to a glycemia level of the person before ablation; after at least one ablation, a composition of the person's gut microbiota modulates from a first state to a second state, wherein the first state has a first level of bacteroidetes and a first level of firmicutes, wherein the second state has a second level of bacteroidetes and a second level of firmicutes, wherein the second level of bacteroidetes is greater than the first level of bacteroidetes by at least 3%, and wherein the second level of firmicutes is less than the first level of firmicutes by at least 3%; after at least one ablation, the cumulative daily dose of a patient's antidiabetic medications decrease by at least 10%; after at least one ablation, a patient's lipid profile improves by at least 10%; after at least one ablation, a patient's LDL-cholesterol decreases by at least 10%; and, after at least one ablation, a patient's VLDL-cholesterol decreases by at least 10%. In various embodiments, the relative therapeutic goals and endpoints are provided relative to one or more pre-treatment levels of the correspondingly stated physiological indicators.

In trials using the vapor ablation systems and methods of the present specification, patients having poorly controlled Type 2 Diabetes Mellitus using oral hypoglycemic agents experienced an improvement of HbA1C levels and a reduction in the dosing of oral hypoglycemic agents. Treatment was provided for approximately six months and extended up to two years.

Specifically, embodiments of the present invention lead to a substantial improvement in a patient's fasting glucose levels, post-prandial glucose levels within 24 hours of treatment. Referring to FIGS. 49A and 49B, by performing ablation using any of the methods and systems described herein to the patient's duodenum, the patient's fasting (or morning/AM) blood glucose levels improve by at least 10% or 20 mg/dl 4920a, 4920b from the pretreatment level 4910a, 4920a within 24 hours of treatment. Further, those levels are maintained at the same or a greater level of improvement for at least 30 days post treatment.

Referring to FIGS. 49C and 49D, by performing ablation using any of the methods and systems described herein to the patient's duodenum, the patient's post-prandial (or evening/PM) blood glucose levels improve by at least 10% or 30 mg/dl 4920c, 4920d from the pretreatment level 4910c, 4910d within 24 hours of treatment. Further, those levels are maintained at the same or a greater level of improvement for at least 30 days post treatment.

Referring to FIG. 49E, by performing ablation using any of the methods and systems described herein to the patient's duodenum, the patient's HbA1c levels improve 4920e by at least 0.6% from the pretreatment levels 4910e within 4 weeks of treatment and are maintained at the same or greater level of improvement for at least 6 months post treatment.

Further, by performing ablation using any of the methods and systems described herein to the patient's duodenum, patients experienced a weight loss of $3.4\pm2.5$ kg over 4 weeks, and $3.0\pm5.6$ kg over 12 weeks, with a BMI change of $1.3\pm0.96$ over 4 weeks, and $1.12\pm2.2$ over 12 weeks, relative to pre-treatment weight and BMI values. By performing ablation using any of the methods and systems described herein to the patient's duodenum, patients experienced a decrease in liver enzyme values of aspartate aminotransferase (ALT) of $9.1\pm11.4$ and alanine aminotransferase (AST) of $4.2\pm6.8$ over 12 weeks, relative to pre-treatment ALT and AST levels. By performing ablation using any of the methods and systems described herein to the patient's duodenum, patients experienced a decrease in urine albumin-creatinine ratio (uACR) of $0.28\pm0.57$ over 12 weeks relative to pretreatment uACR values. Patients experienced a decrease in Homeostatic Model Assessment for Insulin Resistance (HOMA-IR) values of $0.98\pm2.4$ over 12 weeks relative to pre-treatment HOMA-IR values.

The ablation systems and methods of the present specification, particularly duodenal ablation, may be used to treat a condition including any one of obesity, excess weight, eating disorders, metabolic syndrome and diabetes, NASH/NAFLD or a polycystic ovary disease. In accordance with various aspects of the present specification, the ablation systems and methods, particularly duodenal ablation, enable treating people with a BMI (Body Mass Index) of 25 or greater (overweight being 25-30, obese being 30 and above, and morbid obesity being above 35). In accordance with various aspects of the present specification, the ablation systems and methods, particularly duodenal ablation, also enable treating people with HbA1c levels of at least 6.5 gm %, fasting blood glucose levels of at least 126 mg/dL or a random plasma glucose level of at least 200 mg/dL, a 2-hour plasma glucose level of at least 200 mg/dL (11.1 mmol/L) during an oral glucose tolerance test (OGTT). The ablation systems and methods, particularly duodenal ablation, can also be used to treat nondiabetic, normotensive overweight individuals, with a serum triglyceride concentration of at least 130 mg/dL (1.47 mmol/L), a ratio of triglyceride to high-density lipoprotein (HDL) cholesterol concentration of at least 3.0 (1.8 SI units), and fasting insulin concentration of at least 5.7 μU/mL (109 pmol/L). The ablation systems and methods, particularly duodenal ablation, can also be used to treat patients with insulin resistance defined as homeostatic model assessment of insulin resistance (HOMA-IR) of at least 1.6, or associated disorders. The ablation systems and methods, particularly duodenal ablation, can also be used to treat patients with dyslipidemia.

FIG. 24 is a flowchart illustrating a method of ablation of a colon in accordance with one embodiment of the present specification. Referring to FIG. 24, the first step 2401 includes inserting an endoscope into the lower gastrointestinal tract of a patient. Next, in step 2402, a catheter of an ablation device is passed through the endoscope, wherein the catheter includes a hollow shaft through which an ablative agent can travel, at least one positioning element, at least one input port for receiving an ablative agent, and at least one infusion port for delivering the ablative agent. The catheter is passed through the endoscope such that the positioning element is positioned proximate to the colonic tissue to be ablated. In an embodiment, the ablation device includes a controller comprising a microprocessor for controlling the delivery of the ablative agent. The positioning element is deployed in the colonic lumen of the patient such that the positioning element contacts a portion of the colon of the patient and the catheter and infusion port are positioned within the colonic lumen in step 2403. In one embodiment, the positioning element is positioned over and encompasses the colonic tissue. Finally, in step 2406, an ablative agent is delivered through the infusion port to ablate the colonic tissue.

Optionally, a sensor is used to measure at least one dimension of the colon in step 2404 and the measurement is used to determine the amount of ablative agent to be delivered in step 2405.

In various embodiments, ablation therapy provided by the vapor ablation systems of the present specification is delivered to achieve the following therapeutic endpoints for duodenal ablation: maintain a tissue temperature at 100° C. or less; ablate at least 50% of a surface area of a duodenal mucosa; ablate a duodenal mucosa without significant ablation of an ampullary mucosa; reduce fasting blood glucose by at least 5% relative to pre-treatment fasting blood glucose; reduce HbA1c by at least 5% relative to pre-treatment HbA1c; reduce total body weight by at least 1% relative to pre-treatment body weight; reduce excess body weight by at least 3% relative to pre-treatment excess body weight; reduce mean blood pressure by at least 3% relative to pre-treatment mean blood pressure; and reduce total cholesterol by at least 3% relative to pre-treatment total cholesterol.

FIG. 25 illustrates an upper gastrointestinal tract with a bleeding vascular lesion being treated by an ablation device, in accordance with an embodiment of the present specification. The vascular lesion is a visible vessel 2561 in the base of an ulcer 2562. The ablation catheter 2563 is passed through the channel of an endoscope 2564. The conical positioning element 2565 is placed over the visible vessel 2561. The conical positioning element 2565 has a known length 'l' and diameter 'd', which are used to calculate the amount of thermal energy needed for coagulation of the visible vessel to achieve hemostasis. The conical positioning element has an optional insulated membrane that prevents escape of thermal energy or vapor away from the disease site.

In one embodiment, the positioning attachment must be separated from the ablation region by a distance of greater than 0.1 mm, preferably 1 mm and more preferably 1 cm. In one embodiment, the length 'l' is greater than 0.1 mm, preferably between 5 and 10 mm. In one embodiment, diameter 'd' depends on the size of the lesion and can be between 1 mm and 10 cm, preferably 1 to 5 cm.

FIG. 26 is a flowchart illustrating a method of ablation of an upper GI tract in accordance with one embodiment of the present specification. Referring to FIG. 26, the first step 2601 includes inserting an endoscope into the upper gastro-intestinal tract of a patient. Next, in step 2602, a catheter of an ablation device is passed through the endoscope, wherein the catheter includes a hollow shaft through which an ablative agent can travel, at least one positioning element, at least one input port for receiving an ablative agent, and at least one infusion port for delivering the ablative agent. The catheter is passed through the endoscope such that the positioning element is positioned proximate to the upper GI tract tissue to be ablated. In an embodiment, the ablation device includes a controller comprising a microprocessor for controlling the delivery of the ablative agent. The position-ing element is deployed in the upper GI tract lumen of the patient such that the positioning element contacts a portion of the upper GI tract of the patient and the catheter and infusion port are positioned within the upper GI tract lumen in step 2603. In one embodiment, the positioning element is positioned over and encompasses the upper GI tract tissue. Finally, in step 2606, an ablative agent is delivered through the infusion port to ablate the upper GI tract tissue.

Optionally, a sensor is used to measure at least one dimension of the upper GI tract in step 2604 and the measurement is used to determine the amount of ablative agent to be delivered in step 2605.

FIG. 27A is an illustration of pancreatic ablation being performed on a pancreatic tumor 2765 in accordance with one embodiment of the present specification. The ablation device 2760 includes a needle 2761 configured to be inserted into a lesion to deliver vapor for ablation. The ablation device 2760 is passed through a channel of an echoendo-scope 2763 which has been inserted into a gastrointestinal tract 2764 of a patient to view the patient's pancreas 2766. Vapor is delivered through the needle 2761 of the ablation device 2760 to ablate the pancreatic tumor 2765.

FIG. 27B is a flowchart listing the steps involved in one embodiment of a method of pancreatic ablation. At step 2770, an echoendoscope is advanced proximate a pancreatic tissue. A pancreatic lesion to be ablated is localized using the echoendoscope at step 2771. At step 2772, dimensions of the lesion are measured using the echoendoscope. One of the measured dimensions is used to calculate an amount of vapor to deliver at step 2773. The ablation needle is passed through a channel in the echoendoscope and through a puncture in the gastrointestinal wall into the pancreatic lesion at step 2774. At step 2775, suction is optionally applied on the needle to aspirate fluid/cells from the lesion. Vapor is passed through the needle into the pancreatic lesion to heat the lesion while water is simultaneously circulated through an outer sheath of the needle to cool the puncture site at step 2776. The area of ablation is observed with the echoendoscope at step 2777. The passage of vapor is stopped once adequate ablation is achieved at step 2778. At step 2779, the ablation needle is removed from the echoe-ndoscope and the echoendoscope is removed from the patient.

FIG. 27C is a flowchart listing the steps involved in one embodiment of a method of ablation of a pancreatic cyst. In step 2780, an endoscopic ultrasound (EUS) is performed to define the size of the cyst. The size of the cyst is input into a microprocessor of a controller of an ablation system in step 2781 to calculate the amount of ablative therapy to be provided. An echotip vapor delivery needle is placed into the cyst under EUS guidance in step 2782. In step 2783, some fluid is aspirated from the cyst to decrease fluid volume of the cyst. One or more cycles of vapor delivery are delivered to the cyst in step 2784 to heat fluid in the cyst to a temperature in a range of 45 to 100° C., ablating the lining of the cyst wall without significantly damaging the sur-rounding pancreatic tissue. Optionally, post-ablation fluid is aspirated from the cyst in step 2785. The needle is removed from the cyst in step 2786.

In embodiments, a device is provided for ablating the cyst within a hollow or a tubular organ such as: gastrointestinal tract, pancreaticobiliary tract, genitourinary tract, respira-tory tract or a vascular structure such as blood vessels. The device includes a single lumen catheter (microcatheter) with a proximal end and a distal end. At least one port is located near the distal end for infusing and delivering an ablative agent. A source for the delivery of the ablative agent is connected to the catheter lumen. Additionally, an electrode in the lumen is configured that is capable of passing elec-tricity through the ablative agent to heat the ablative agent through a phase change from a liquid to a gas. During operation, the cyst lumen/cavity is accessed with a needle. The needle aspirates at least some of the contents within the cyst. The cyst is fully or nearly collapsed through aspiration. After aspiration, a gas (CO2, air) is used to inflate the cyst to allow for uniform distribution of the ablative agent. The microcatheter is inserted through the needle into the cyst to deliver the thermal ablative agent into the cyst lumen. In some embodiments, the microcatheter extends beyond the tip of the needle by a length ranging from 1 mm-20 mm, so that the electrode within the microcatheter is positioned outside the needle tip, to avoid heating of the needle. The microcatheter includes a handle that is connected to the needle with a luer fitting, such that an actuator can be slid on the handle to deploy the microcatheter beyond the tip of the needle by a fixed distance. In embodiments, the distal tip of the microcatheter is atraumatic to the tissue, such as by curving as it exits the tip of the needle. In some embodi-ments, the microcatheter and/or the needle are rotated during ablation to ensure uniform dispersion of the ablative agent. Subsequently, after ablation, the needle and the microcath-eter are removed. The microcatheter is retracted by the actuator on its handle. In embodiments, the microcatheter is observed during deployment using ultrasound imaging of 1-20 MHz.

In various embodiments, ablation therapy provided by the vapor ablation systems of the present specification is deliv-ered to achieve the following therapeutic endpoints for a tumor in or proximate the bile duct: maintain a tissue temperature of 100° C. or less; ablate at least 50% of the surface area of a targeted cancer mucosa to a sufficient depth such that after ablation a cross-sectional area improves by at least 10% relative to a pre-treatment cross-sectional area; biliary flow improves by at least 10% relative to pre-treatment biliary flow; tumor volume decreases by at least 10% relative to a pre-treatment tumor volume.

FIG. 28 is a flowchart listing the steps involved in one embodiment of a method of tissue ablation in a bile duct. At step 2801, an endoscopic retrograde cholangiopancreatography (ERCP) is performed. Next in step 2802, the bile duct is intubated with a cannula and a guide wire is placed therein. In step 2803, the length of the bile duct segment to be ablated is measured. The length is then input into a controller of an ablation system to determine an amount of ablative therapy to provide in step 2804. In another embodiment, the length is used to select a catheter of appropriate ablation segment length. A catheter of the ablation system is then passed through the ERCP channel over the guide-wire. The catheter includes a first positioning element, a second positioning element distal to the first positioning element, and one or more delivery ports positioned on the catheter between the first and second positioning elements. The catheter is passed through the ERCP channel such that the second first positioning element (balloon) is placed distal to the bile duct to be ablated and the first positioning element (balloon) is placed proximal to the bile duct to be ablated in step 2805. In step 2806, the two balloons are inflated to a set pressure P1 and the diameter of the bile duct is measured using a diameter of either of the two balloons or an average of the diameters of the two balloons. The measured bile duct diameter is entered into the controller, either manually or automatically, and used to calculate the surface area of the bile duct to be ablated in 2807. Thereafter, one or more cycles of vapor is delivered to the bile duct through one or more of the vapor delivery ports at a temperature in a range of 90 to 100° C. to ablate the bile duct tissue in 2808. In one embodiment, the balloon pressure is maintained during the delivery of ablative agent at a pressure P2 which is greater than or equal to pressure P1 in 2809. Optionally, the balloons are deflated to a pressure P3 which is less than or equal to P1 between the cycles of ablation in 2810. The endoscope and the catheter are removed after the ablation is complete in step 2811.

Bronchial Ablation

Regarding pulmonary function, there are four lung volumes and four lung capacities. A lung capacity consists of two or more lung volumes. The lung volumes are tidal volume (VT), inspiratory reserve volume (IRV), expiratory reserve volume (ERV), and residual volume (RV). The four lung capacities are total lung capacity (TLC), inspiratory capacity (IC), functional residual capacity (FRC), and vital capacity (VC). Measurement of the single-breath diffusing capacity for carbon monoxide (DLCO) is a fast and safe tool in the evaluation of both restrictive and obstructive lung disease. Arterial blood gases (ABGs) are a helpful measurement in pulmonary function testing in selected patients. The primary role of measuring ABGs in individuals that are healthy and stable is to confirm hypoventilation when it is suspected on the basis of medical history, such as respiratory muscle weakness or advanced COPD. Spirometry includes tests of pulmonary mechanics such as measurements of forced vital capacity (FVC), forced expiratory volume at the end of the first second of forced expiration (FEV$_1$), forced expiratory flow (FEF) values, forced inspiratory flow rates (FIFs), and maximum voluntary ventilation (MVV). Measuring pulmonary mechanics assesses the ability of the lungs to move large volumes of air quickly through the airways to identify airway obstruction.

In various embodiments, ablation therapy provided by the vapor ablation systems of the present specification is delivered to achieve the following therapeutic endpoints for pulmonary ablation: maintain a tissue temperature at 100° C. or less; reduce TLC, defined as the volume in the lungs at maximal inflation, by at least 5% relative to pre-treatment TLC; increase VT, defined as the volume of air moved into or out of the lungs during quiet breathing, by at least 5% relative to pre-treatment VT; decrease RV, defined as the volume of air remaining in the lungs after a maximal exhalation, by 5% relative to pre-treatment RV; increase ERV, defined as the maximal volume of air that can be exhaled from the end-expiratory position, by 5% relative to pre-treatment ERV; increase IRV, defined as the maximal volume that can be inhaled from the end-inspiratory level, by at least 5% relative to pre-treatment IRV; increase IC by at least 5% relative to pre-treatment IC; increase inspiratory vital capacity (IVC), defined as the maximum volume of air inhaled from the point of maximum expiration, by at least 5% relative to pre-treatment IVC; increase VC, defined as the volume of air breathed out after the deepest inhalation, by at least 5% relative to pre-treatment VC; decrease FRC, defined as the volume in the lungs at the end expiratory position, by at least 5% relative to pre-treatment FRC; decrease RV by at least 5% relative to pre-treatment RV; decrease alveolar gas volume ($V^A$) by at least 5% relative to pre-treatment $V^A$; no change in actual lung volume including the volume of the conducting airway ($V^L$) relative to pre-treatment $V^L$; increase DLCO by at least 5% relative to pre-treatment DLCO; increase partial pressure of oxygen dissolved in plasma (PaO$_2$) by at least 2% and/or decrease partial pressure of carbon dioxide dissolved in plasma (PaCO$_2$) by at least 1% relative to pre-treatment PaO$_2$ and PaCO$_2$ levels; increase any spirometry results by at least 5% relative to pre-treatment spirometry results; increase FVC, defined as the vital capacity from a maximally forced expiratory effort, by at least 5% relative to pre-treatment FVC; increase forced expiratory volume over time (FEV$^t$), defined as the volume of air exhaled under forced conditions in the first t seconds, by at least 5% relative to pre-treatment FEV$^t$; increase FEV$_1$ by at least 5% relative to pre-treatment FEV$_1$; increase FEF by at least 5% relative to pre-treatment FEF; increase FEF$^{max}$, defined as the maximum instantaneous flow achieved during a FVC maneuver, by at least 5% relative to pre-treatment FEF$^{max}$; increase FIF by at least 5% relative to pre-treatment FIF; increase peak expiratory flow (PEF), defined as the highest forced expiratory flow measured with a peak flow meter, by at least 5% relative to pre-treatment PEF; increase MVV, defined as the volume of air expired in a specified period during repetitive maximal effort, by at least 5% relative to pre-treatment MVV.

FIG. 29A is a flowchart illustrating a method of ablation of bronchoalveolar tissue in accordance with an embodiment of the present specification. Referring to FIG. 29A, the first step 2901 includes inserting a bronchoscope into the bronchus of a patient. Next, in step 2902, a catheter of an ablation device is passed through the bronchoscope, wherein the catheter includes a hollow shaft through which an ablative agent can travel, at least one positioning element, and at least one infusion port for delivering the ablative agent. In an embodiment, the ablation device includes a controller comprising a microprocessor for controlling the delivery of the ablative agent. The catheter is inserted into the bronchoscope such that the positioning element is positioned in a bronchus connected to a bullous cavity comprising bronchial tissue to be ablated. The positioning element is deployed such that it contacts a portion of the bronchus and the catheter and infusion port are positioned proximate the bullous cavity in step 2903. In one embodiment, the bronchoscope is used as a fixation point to assist in positioning the catheter and the infusion port within the bullous cavity.

Finally, in step 2904, an ablative agent is delivered through the infusion port to ablate the bronchial tissue.

FIG. 29B is a flowchart illustrating a method of ablation of bronchial tissue in accordance with another embodiment of the present specification. Referring to FIG. 29B, the first step 2911 includes inserting a bronchoscope into the bronchus of a patient. Next, in step 2912, a catheter of an ablation device is passed through the bronchoscope, wherein the catheter includes a hollow shaft through which an ablative agent can travel, at least one first positioning element, at least one second positioning element positioned distal to said at least one first positioning element, and at least one infusion port for delivering the ablative agent. In an embodiment, the ablation device includes a controller comprising a microprocessor for controlling the delivery of the ablative agent. The catheter is inserted into the bronchoscope such that the first positioning element is positioned in a bronchus proximal to a bronchial tissue to be ablated and said second positioning element is positioned distal to said bronchial tissue to be ablated. The positioning elements are deployed to contact the bronchus proximal and distal to the tissue to be ablated and the catheter and infusion port are positioned proximate the tissue to be ablated in step 2913. Finally, in step 2914, an ablative agent is delivered through the infusion port to ablate the bronchial tissue.

Bronchial Thermoplasty

FIG. 30A illustrates a cross-sectional view of a catheter 3005 for performing bronchial thermoplasty, in accordance with an embodiment of the present specification. The catheter 3005 includes an elongate body 3010 having a proximal end and a distal end, and an inflatable multilayer balloon 3015 at the distal end. In some embodiments, the elongate body 3010 has first, second and third lumens 3012, 3013, 3014.

The first lumen 3012 allows air to be pumped, from the proximal end, into the balloon 3015 for inflation. The second lumen 3013 accommodates a heating element 3020 that may be a flexible heating chamber with a plurality of RF electrodes. Saline/water is allowed to be pumped, from the proximal end, into the second lumen 3013 to enter the heating element 3020 for conversion into steam/vapor. The third lumen 3014 allows saline/water to flow out from the proximal end.

The multilayer balloon 3015 comprises of outer and inner balloon layers fused together. A plurality of fluid channels or paths 3022 are defined and sandwiched between the outer and inner layers. The channels 3022 are in fluid communication with the second and third lumens 3013, 3014 such that steam/vapor generated in the second lumen 3013 circulates through the channels 3022 and flows out of the catheter through the third lumen 3014. During operation, the balloon 3015 is inflated to contact target tissue and steam/vapor is allowed to circulate through the channels 3022 to create a deep burn in the target tissue without scarring. This results in steam non-contiguously spreading over the tissue area in a manner that is controlled and can be circulated.

In various embodiments, the channels 3022 are configured into a plurality of patterns (such as, but not limited to, a wave, series of lines, sine wave, square wave) such that the circulating steam/vapor creates ablation proximate the area of the channels 3022 without any ablation in the remaining area (that is, area devoid of the channels 3022) of the balloon 3015. In embodiments, the balloon 3022 is actively air-cooled to control a volume of tissue ablated. In various embodiments, the catheter 3005 has a plurality of applications in nerve or muscle ablation in hollow organs where circumferential ablation is not needed-such as, for example, in PV (Pulmonary Vein) ablation (heart), Renal Denervation (Hypertension) and Hepatic Vein Ablation (Diabetes). In an exemplary application of PV ablation, the channels 3022 create a pattern of ablation in a PV sufficient to block conduction of electrical activity from a PV to a Left Atrium (LA) without causing a significant stricture in the PV, wherein a length of the circumferential pattern of ablation is greater than the circumference of the PV proximate the ablation. In some embodiments, a distance between two adjacent circumferential ablation patterns is greater than two times the thickness of the PV.

FIG. 30B illustrates a plurality of patterns of the channels 3022, in accordance with various embodiments of the present specification. The figure shows first, second, third, fourth, fifth, sixth and seventh exemplary patterns 3031, 3032, 3033, 3034, 3035, 3036, 3037. For each of the patterns, a first path 3040 shows a direction of flow of steam/vapor while a second path 3045 shows a direction of flow of water/saline out. The patterns of the channels 3022 determine the ablation pattern.

FIG. 30C illustrates a workflow for performing a bronchial thermoplasty procedure using the catheter 3005, in accordance with an embodiment of the present specification. At step 3050 an endoscope tube 3052 is inserted into a patient's lung to position proximate a target tissue area for ablation. At step 3055, the catheter 3005 is inserted through a working channel of the endoscope 3052 such that the balloon 3015 is positioned at the target tissue area. Thereafter, at step 3060, the balloon 3015 is inflated with air/fluid such that the balloon 3015 contacts the target tissue area. Steam/vapor is now circulated through the patterned channels 3022 of the balloon to ablate the target tissue area.

Lung Volume Reduction

FIG. 31A illustrates a lung volume reduction (LVR) catheter 3105 while FIG. 31B illustrates the LVR catheter 3105 deployed through an endoscope/bronchoscope 3110, in accordance with embodiments of the present specification. Referring now to FIGS. 31A, 31B, the catheter 3105 includes an elongate shaft 3115 having a proximal end and a distal end. The distal end has at least one vapor delivery port 3120 and a plurality of suction ports 3125. A positioning element 3122 is located proximate the at least one vapor delivery port 3120. In some embodiments, the positioning element 3122 is an inflatable balloon.

In some embodiments, the elongate shaft 3115 has first and second lumens 3130, 3132 extending from the proximal end to the distal end. The first lumen 3130 accommodates a heating element 3135 such as a flexible heating chamber comprising a plurality of RF electrodes of the present specification. Saline/water enters the proximal end to reach the heating element 3135 where it is converted to steam/vapor for delivery through the at least one vapor delivery port 3120. The second lumen 3132 is in fluid communication with the plurality of suction ports 3125. During operation, vapor is delivered through the at least one vapor delivery port 3120 and air is suctioned in through the plurality of suction ports 3125 thereby producing circulation of thermal energy between the vapor delivery port 3120 and the suction ports 3125. In an embodiment, a third lumen (not shown) allows air to be pumped into the balloon 3122 for inflation. FIG. 31B shows the catheter 3105 deployed through a working channel of the endoscope 3110.

In some embodiments, the at least one vapor delivery port 3120 is at least 1 cm apart from a closest of the plurality of suction ports 3125.

FIG. 31C is a workflow for performing lung volume reduction using the catheter 3105, in accordance with an embodiment of the present specification. At step 3150, diseased region is identified for ablation therapy. At step 3152, the bronchoscope 3110 is positioned into the airway of the diseased region. At step 3154, the catheter 3105 is deployed through a working channel of the bronchoscope 3110 such that the catheter 3105 is positioned proximate the diseased region. At step 3156, the balloon 3122 is inflated, steam/vapor is delivered to the diseased region (through the vapor delivery port 3120) for a predefined period of time, such as 3 to 10 seconds (depending upon the mass of the diseased region), while air is suctioned in through the suction ports 3125.

FIG. 32A illustrates a needle catheter 3200 incorporating one flexible heating chamber 130 of FIGS. 1A through 1D, in accordance with an embodiment. FIG. 32B illustrates a needle catheter 3220 incorporating two flexible heating chambers 130, in accordance with an embodiment. Referring now to FIGS. 32A and 32B, the catheters 3200, 3220 each comprise an elongate body 3205, 3225 having a proximal end and a distal end. The bodies 3205, 3225 each have a lumen along their length and at least one needle 3210, 3230 at their distal ends. In some embodiments, the needle is retractable. In an embodiment, at least one infusion port 3215, 3235 is positioned proximate a proximal end of the needle 3210, 3230, or on the needle 3210, 3230, which may be hollow. In various embodiments, the at least one infusion port 3215, 3235 is positioned in a range of 1 mm to 50 cm from the heating chamber(s) 130. In various embodiments, the needle catheters 3200, 3220 comprise any of the needle embodiments discussed in the present specification. At least one heating chamber 130 is incorporated in the catheters 3200, 3220 proximate the distal end of the bodies 3205, 3225. The embodiment of FIG. 32A illustrates one heating chamber 130 while the embodiment of FIG. 32B illustrates two heating chambers 130 arranged in series. Referring to FIG. 32B, a water pump 3240, coupled to the proximal end of the body 3225, supplies water/saline to a proximal end of the heating chambers 130 through a lumen 3226 in the catheter body 3225. An RF generator 3245 provides electrical current to a plurality of electrodes (such as, electrodes 136, 138) included in the heating chambers 130, which causes said electrodes to generate heat, wherein said heat is transferred to said water/saline to convert the water/saline to vapor, which is then delivered via infusion port 3235 to ablate a target tissue.

In some embodiments, the catheters 3200, 3220 may optionally include at least one positioning element, such as an inflatable balloon, at the distal end of the bodies 3205, 3225.

During use, the pump 3240 delivers water/saline to the proximal end of the heating chambers 130 while the RF generator 3245 causes the electrodes to heat up and vaporize the water/saline flowing through the heating chambers 130. The generated vapor exits through the at least one port 3235. The flexible heating chambers 130 impart improved flexibility and maneuverability to the catheters 3200, 3220, allowing a physician to better position the catheters 3200, 3220 when performing needle ablation procedures.

FIG. 32C is a flowchart illustrating one embodiment of a method of ablation of a tissue using the needle catheters 3200, 3220 of FIGS. 32A and 32B. In the first step 3232, the catheter is inserted such that the at least one positioning element is positioned proximate to the tissue to be ablated. The next step 3234 involves extending the needle through the catheter such that the at least one infusion port is positioned proximate to the tissue. At step 3236, water/saline is provided to the heating chamber (to more than one heating chambers, in some embodiments) by operating the water pump. At step 3238, electric current is provided to electrodes of the heating chamber, using the RF generator, to convert water/saline to vapor that exits the infusion ports to ablate the tissue. In another embodiment, the device does not include a positioning element and the method does not include a step of positioning the positioning element proximate the tissue to be ablated.

Surface Preparation Prior to Therapeutic Treatment

In some embodiments, a target surface area for ablation is prepared by removing mucus or any other type of contamination from the surface, prior to initiating an ablation treatment. In one embodiment, a chemical is sprayed at the target surface to reduce or remove mucus. The chemical may include, for example, N acetyl cysteine, hypertonic saline, or any other mucolytic agent. In embodiments, the dose of N acetyl cysteine ranges from 0.1% to 10% by volume of a 10 ml to 500 ml solution. A tube is inserted through the catheter lumen, wherein the tube comprises a spraying nozzle at its distal end. In some embodiments, a tube for applying a chemical is integrated into the catheter. In other embodiments, a chemical is injected through a channel of an endoscope. The controller is activated to operate at least one pump connected to a container comprising the chemical and to a proximal end of the tube positioned within the catheter lumen. In another embodiment, the mucus is removed by scraping the surface of the target area and suctioning the coagulated mucus that is collected as a result of the scraping. In some embodiments, both the chemical spraying and the mechanical scraping are performed sequentially to effectively reduce or remove mucus. In some embodiments, at least one or both—the chemical spraying and the mechanical scraping—are performed repeatedly to effectively reduce or remove mucus. Preparing the target surface area before an ablation treatment bares the target surface to yield an increasingly uniform ablation that can be applied to a greater surface area.

In some embodiments, a surface preparation process precedes the actual ablation treatment of a target surface area. The surface preparation process comprises coagulating mucus from the surface by using methods such as, for example, those described above in the form of chemical spraying and scraping. The coagulation is then followed by a superficial ablation of the mucosa. The superficial ablation may comprise an ablation session that is delivered to the target surface for a time<T1 at dose D1. Optionally, the physician may wait for a time from 1 second to 30 minutes for a certain degree of edema to set in and then delivers a second ablation session with a dose in a range of 1×D1 to 5×D1. Negative pressure, in the form of suction or vacuum, is applied to the ablated zone after the steam is turned off to increase blood flow to cool the tissue. The surface preparation process bares the target surface to yield an increasingly uniform ablation during a subsequent treatment that can be applied to a greater surface area than without the surface preparation process.

In some embodiments, the superficial ablation process is repeatedly performed to effectively reduce and remove mucus and other contaminants from the target surface. FIG. 33 is a flowchart illustrating an exemplary process of preparing a target surface prior to an ablation treatment, in accordance with some embodiments of the present specification. At steps 3302 and 3304, a first dose of a thermal energy is applied using the vapor ablation system in accordance with the various embodiments of the present specification. The first dose is delivered in two portions. At step 3302, a first portion of the first dose of the thermal energy is delivered to the target surface to denature the mucus covering the surface of the duodenum. In some embodiments, the first portion is delivered for a time<T1 at a dose D1. At step 3304, a second portion of the first dose of the thermal energy is delivered to the duodenal mucosal tissue. In some embodiments, the second portion is delivered after a time period ranging from 1 second to 30 minutes, with a dose in a range of 1×D1 to 5×D1. At step 3306, at least the denatured mucus on the target surface of the duodenum is removed or reduced by at least one of a chemical spray such as N acetyl cysteine, and mechanical scraping and suctioning. At steps 3308 and 3310, a second dose of thermal energy is applied using the vapor ablation system. At step 3308, a first portion of the second dose of thermal energy is utilized to denature the mucus covering the duodenum. In embodiments, the first portion of the second dose is the same as the first portion of the first does. In some embodiments, the first portion of the second does is different than the first portion of the first does. At step 3310, a second portion of the second dose of the thermal energy is delivered to the duodenal mucosal tissue. The second portion of the second dose of the thermal energy is greater than the second portion of the first dose of the thermal energy.

FIG. 34 is a flow chart illustrating a preparatory method used before application of vapor ablation for duodenal ablation, in accordance with some embodiments of the present specification. At step 3402, the vapor ablation device is positioned within a patient. Components of a vapor ablation system in accordance with the above-described methods and systems are used for preparation of the target surface area. The vapor ablation system comprises a controller having at least one processor in data communication with at least one pump and a catheter connection port in fluid communication with the at least one pump. A proximal end of a catheter is connected to the catheter connection port to place the catheter in fluid communication with the at least one pump. The catheter comprises one or more positioning elements. In an embodiment, the catheter comprises two positioning elements that are separated along a length of the catheter and at least two ports are positioned between the two positioning elements. Each positioning element has a first configuration and a second configuration. In the first configuration, the positioning elements are compressed within the catheter and in the second configuration, the positioning elements are expanded to be at least partially outside the catheter. At step 3402, the catheter is positioned inside a patient such that, upon being expanded into the second configuration, a distal one of at least two positioning elements is positioned within in the patient's small intestine and a proximal one of the two positioning elements is proximally positioned more than 1 cm from the distal one of the at least two positioning elements. The two positioning elements are expanded into their second configurations. The same configuration is used per ablation. The discs or positioning elements may be used to mechanically scrape the mucosa.

At step 3404, the controller is activated to cause the at least one pump to deliver a chemical into at least one lumen of the catheter. An example of the chemical includes N acetyl cysteine. Ports near the distal end of the catheter spray the chemical on the target surface to reduce or remove mucus that may be present on the target surface. At step 3406, optionally, the target surface is scraped with a mechanical tool for scraping. In embodiments, the tool comprises a distal attachment cap on the catheter. In other embodiments, the tool comprises a brush or a separate catheter. In some embodiments, a tip of an endoscope or the distal positioning element of the catheter is used to scrape the mucus. The tool comprises a mucus trap at a proximal end of the catheter lumen. The tool scrapes the mucus-covered target surface. The controller is activated to suction through the catheter lumen and pull the scraped mucus through an opening in the distal end of the lumen. The suctioned mucus is then collected in the trap, wherein the trap may include a container connected to the proximal side of the catheter lumen. In some embodiments, the process of step 3406 is repeated after ablation. Additionally, the process of step 3406 is performed each time before and after ablation. In methods that comprise at least two phases of ablation, such as for examples a first phase of circumferential ablation and a second phase of focused ablation, as described in the previous embodiments, step 3406 is performed before the commencement of the second phase of ablation as well.

At step 3408, optionally, the physician may determine whether the mucus has been coagulated sufficiently. If not, the processes of steps 3404 and 3406 are repeated. In some embodiments, only step 3406 is repeated. In different cases, the steps are repeated for 2-3 times, to coagulate mucus before delivering therapeutic treatments to the target surface.

At 3410, once the mucus is coagulated, first ablation session is delivered to the target surface for a time<T1 at dose D1. Then, the physician waits for a time period for an inflammatory response, or a certain degree of edema induced by thermal injury, to set in and then delivers a second ablation session with a dose in a range of 1×D1 to 5×D1. In embodiments, the time period ranges from immediately after the cessation of the first ablation session to 300 minutes after the cessation of the first ablation session. In some embodiments, there is no change in the positioning or configuration of the positioning elements between the first ablation session and the second ablation session. Optionally, in some embodiments, scraping is performed between the first ablation session and the second ablation session. Scraping serves to further prepare the surface for ablation coverage by removing mucus and also promoting edema, which adds thickness to the mucosa to provide protection against deep ablations in the muscularis layer. Negative pressure, in the form of suction or vacuum, is applied to the ablated zone after the steam is turned off to increase blood flow to cool the tissue. This process increases blood flow in the target surface and could also increase the edema formation. Negative pressure causes the exudation of fluid out of the capillaries and lymphatics in the duodenal wall. Edema formation helps protect muscularis propria layer from sustaining clinically significant thermal injury. In some embodiments, negative pressure is applied to the tissue surface before treatment.

In various embodiments, ablation therapy is provided to induce an acute inflammatory response with predominant neutrophils; and increase elastin production and/or increase healthy collagen.

FIG. 35 is another flow chart illustrating a method of using a vapor ablation system for duodenal ablation. The method may be used to treat at least one of excess weight, obesity, eating disorders, metabolic syndrome, dyslipidemia, diabetes, polycystic ovarian disease, fatty liver disease, non-alcoholic fatty liver disease, or non-alcoholic steatohepatitis disease. The vapor ablation system comprises a controller having at least one processor in data communication with at least one pump and a catheter connection port in fluid communication with the at least one pump. At step 3502, optionally a target surface area within the duodenum is prepared for ablation by reducing or removing mucus and inducing edema, such as for example by using one or more of the methods described above in context of FIGS. 33 and 34. The target surface is prepared using the catheter of the vapor ablation system. The same or a different catheter may be used for subsequent ablation treatment, wherein the catheter used for the treatment is connected at its proximal end to the catheter connection port to place the catheter in fluid communication with the at least one pump. The catheter comprises one or more positioning elements. Multiple positioning elements are separated along a length of the catheter and at least two ports are positioned between adjacent positioning elements. Each positioning element has a first configuration and a second configuration, and wherein, in the first configuration, each positioning element is compressed within the catheter and in the second configuration, each positioning element is expanded to be at least partially outside the catheter. In some embodiments, at least one positioning element comprises scalloped petals on a distal edge of its surface area. The scalloped petal-shaped positioning element structure enables the contact between the surface of the positioning element and the surrounding circumference of the duodenum to provide a partial seal. Gaps between adjacent rounded portions of the scalloped petal-shaped positioning element provide for space for vapor to escape outside of the targeted segment of the duodenum, thereby enabling a temperature within an ablation zone to be maintained for a period of time.

At step 3504, the catheter is positioned inside a patient such that, upon being expanded into the second configuration, a distal one of at least two positioning elements is positioned within in the patient's small intestine and a proximal one of the at least two positioning elements is proximally positioned more than 1 cm from the distal one of the at least two positioning elements. In some embodiments, the distance between the at least two positioning elements ranges from 2 cm to 5 cm to enable ablation along a length of 2 cm to 5 cm within the duodenum. At step 3506, each of the at least two positioning elements are expanded into their second configurations to define a treatment volume. Surface areas of each of the at least two positioning elements comprise a plurality of spaces to permit a flow of vapor out of the treatment volume in a range of 1 to 80% of a vapor input flow rate. At step 3508, the controller is activated, wherein, upon activation, the controller is configured to cause the at least one pump to deliver saline into at least one lumen in the catheter. Additionally, upon activation, the controller is configured to cause an electrical current to be delivered to at least one electrode positioned within the at least one lumen of the catheter to thereby generate vapor from the saline. At step 3510, the generated vapor is delivered through ports positioned in the catheter between the at least two positioning elements and into the treatment volume to ablate a first ablative zone. In embodiments, the vapor is able to concurrently deliver substantially similar amount of energy to an ablative zone, or section of the intestinal mucosa, in a length of 2 cm to 25 cm. In embodiments, the energy delivered is in a range of 100-500 J per ablation with a cumulative dose of 1000-10,000 J per treatment. Additionally, in embodiments, at the end of treatment, cumulatively 25% to 90% of the targeted duodenal mucosa and a cumulative length of 4 cm to 15 cm is ablated. Concurrently, contiguous submucosa ablation is limited to less than 50% and contiguous muscularis propria ablation of less than 5% (optionally, without lifting the mucosa). Furthermore, in embodiments, thermal energy is delivered at a faster rate relative to conventional methods of vapor ablation, wherein the present specification delivers thermal energy continuously for a duration of 1 second to 10 seconds. Faster heating in accordance with the present embodiments overcome the need to protect the submucosa and muscularis propria by injection as is required in relatively gradual heating methods.

At step 3512, the controller is deactivated and a position of the patient is changed from a first position to a second position. In embodiments, changing the position of the patient from the first position to the second position comprises rotating the patient in a range of 45 degrees to 180 degrees. In embodiments, possible positions for the first position and second position include left lateral side, right lateral side, supine, and prone. At step 3514, the controller is activated and a second treatment is performed similar to those described in steps 3508 and 3510. The treatment is delivered to the same ablation zone defined between the at least two positioning elements. Changing the position of the patient to the second position and then delivering the ablation treatment creates a more uniform thermal vapor distribution throughout the ablation volume.

In embodiments, steps 3502 to 3514 are repeated as the catheter is moved axially through a patient's gastrointestinal (GI) tract, or duodenum, to reposition the catheter and further ablate the GI tract or duodenum. In embodiments, the energy delivered each time the catheter is moved and ablation is performed is substantially equal. In other embodiments, energy delivered each time the catheter is moved and ablation is performed is different. In some embodiments, the positioning elements are closed as the catheter is moved to allow for better visualization and positioning. In other embodiments, the positioning elements remain open to scrape the tissue and allow for a faster procedure without the need to close and re-open the positioning elements. This also prevents debris from getting trapped between the inner and outer elements of the catheter. In embodiments, visualization of the catheter during repositioning is provided by a camera on an endoscope or by radiological visualization.

FIG. 36A illustrates an inclined position 3602 and a declined position 3604 of a model 3606 of a catheter shaft 3608 with thermocouples 3610 positioned along a length of the shaft 3608 between a distal positioning element 3612 and a proximal positioning element 3614, in accordance with some embodiments of the present specification. Positioning multiple thermocouples 3610 along the length of the shaft 3608 where the vapor is generated for ablation, enables the system illustrated in FIG. 36 to measure the temperature variation at different positions along the length of the shaft 3608. There are not significant differences in the temperature profile in the inclined position 3602 and the declined position 3604. However, during either inclination or declination, there is a slight effect of gravity, so that the temperatures along the top of shaft 3608 increase in temperature faster than the measurements on the bottom of shaft 3608.

FIG. 36B illustrates a thermocouple map 3616 that shows the temperature variation within the catheter shaft 3608 along its length, between the positioning elements 3612 and 3614. The different colors on the map 3616 indicate different temperatures measurements at those locations within the length of shaft 3608 between the positioning elements 3612 and 3614. FIG. 36B illustrates that the temperatures in the far corners of shaft 3608 (including thermocouples or sensors 1 and 6) between positioning elements 3612 and 3614, are slightly cooler than in the center (including sensors 2 to 5). The vapor travels a little farther to reach the temperature sensors (thermocouples) in the corners, and also these sensors are close to the cooler tissue and to air outside of the positioning elements 3612 and 3614. Some of the vapor may escape beyond the positioning elements 3612 and 3614. Some embodiments of the catheter tip assembly are configured to force more vapor into those cooler areas. The colors indicated by the map 3616 is used in the subsequent graphs described in FIGS. 36C, 36D, and 36E, to indicate the change in temperatures measured at each colored location over a course of time.

FIG. 36C illustrates a graph 3618 for a straight catheter shaft and a graph 3620 for a flexible catheter shaft that may be bent, showing the temperature variations at different positions within the length of shaft 3608 between the positioning elements 3612 and 3614. All the measurements are recorded for a power supply DAC of 2500, for heating fluid that has a flow rate of 2.2. ml/min, in a catheter shaft at a declined position 3604 at 45 degrees angle. Referring to graph 3618, the change in temperatures measured over the map 3616 is shown for a pre-puff duration of 2 seconds from the start, followed by a waiting period of 5 seconds, after which a first ablation dose is delivered for a period of 5 seconds. The graph 3618 further shows the temperatures fall over the next 5 seconds during which the ablation is paused again, and then a second dose of 5 seconds is delivered during which the temperatures rise further. The goal of this is to try to get better surface area ablation coverage without increasing the maximum temperature and depth of ablations. Referring to the first window 3622 of time during which the first dose is delivered, a steep and almost instantaneous rise is temperature is seen. Referring to graph 3620, the change in temperatures measured over the map 3616 is shown for a pre-puff duration of 2 seconds from the start, followed by a waiting period of 5 seconds, after which a first ablation dose is delivered for a period of 5 seconds. The graph 3620 further shows the temperatures fall over the next 5 seconds during which the ablation is paused again, and then a second dose of 5 seconds is delivered during which the temperatures rise further. The graph 3620 illustrates the temperature changes for a catheter 3608 that is bent at an angle of about 315 degrees along a path of the vapor. Referring to the first window 3624 of time during which the first dose is delivered, a delay of about 2 seconds is seen before the temperatures start rising along a steep slope. Variation in temperatures attained at different positions in the shaft 3608, indicated by the lines of different colors corresponding to map 3616, is high at the end of the duration of the first dose, when compared to the end of first dose in window 3622 of a straight catheter.

FIG. 36D illustrates a graph 3626 for ablation treatment starting from cold and a graph 3628 for ablation treatment starting after a pre-puff operation, showing the temperature variations at different positions within the length of a straight shaft 3608 between the positioning elements 3612 and 3614. A cold start implies that fluid (saline) is present in the catheter and the vapor is delivered while the fluid is present, with a press of a switch. As the system starts to generate vapors, the fluid is pushed out because not all the fluid is turned to vapor when it starts up. On the other hand, during a pre-puff, a non-therapeutic cold-start is performed for 1-2 seconds to clear out the fluid and start generating vapors. The pre-puff function heats up the fluid in the catheter, followed by a pause for a fixed amount of time (5 seconds in this example), then the therapeutic vapor delivery is initiated. During pre-puff, the temperatures in the catheter shaft rise more rapidly and the temperatures are more consistent (resulting in less intra-chamber temperature variability). Referring to graph 3626, a window 3630 shows a 5 second duration of administering a first dose from a cold start. Graph 3628 shows a window 3632 of the same duration (5 seconds) of administering a first dose of ablation after a pre-puff operation of about 2 seconds, and a pause of about 5 seconds. Comparing windows 3630 and 3632 shows that the temperatures attained at the end of the dose in window 3630 is lower than that in window 3632. Therefore, a pre-puff operation before administering a first ablation dose enables the vapor to heat to higher temperatures more quickly relative to ablation performed from a cold start. In embodiments, a complete pre-puff operation may include powering the electrodes for heating for about 2 seconds, followed by discontinuing the power and providing a pause for about 5 seconds.

FIG. 36E illustrates a graph 3634 showing an onset time 3636 for an ablation treatment from cold start and a graph 3638 showing an onset time 3640 for an ablation treatment preceded by a pre-puff operation. In embodiments, the onset time may be described as the time during a treatment window at which the temperatures within the shaft 3608 between the positioning elements 3612 and 3614, begin to continuously rise along a steep slope. Comparing graphs 3634 and 3638 shows that onset time 3636 is greater than onset time 3640. Therefore, a pre-puff operation can reduce the onset time.

The thermocouple graphs provide a bench test to characterize temperature between the positioning elements during a treatment. The models illustrated herein are used to evaluate different configurations of catheters and positioning elements to optimize the vapor delivery. Objective of the catheter configurations is to have less temperature variability within the chamber, as well as less variability between the thermocouples. The graphs are observed while different configurations are assembled, to achieve slope of temperature rise that is consistent and as fast as possible. Various aspects of the catheter influence the temperature variability observed from the graphs, including design of the positioning elements, size of the catheter shaft between the positioning elements (larger chamber means less vapor energy per surface area and larger chambers may need more time to get the same ablation depth).

FIG. 37A is a flow chart illustrating an exemplary process of using an endoscope to deploy an ablation system for treatment in accordance with embodiments of the present specification. At step 3702, an endoscope device is positioned within an organ of a patient such that the distal end of the endoscope device approaches a target area for ablation treatment. The process of FIG. 37A is described herein with reference to duodenum but may be used within any other organ as well. FIG. 8M illustrates an embodiment of an endoscope with a viewing element at its distal tip, which is used to communicate imaging data captured by the viewing element to a display connected to the endoscope. The viewing element enables a user (physician) to visualize the treatment zone using a conventional endoscope easily and directly, and then deploy the positioning elements using a single pull operation.

At step 3704, a lumen in the endoscope, parallel to the lumen including the viewing element at its distal end, is used to deploy a catheter. The catheter is an ablation device from among the embodiments of the present specification. The catheter includes two positioning elements-a first distal positioning element and a second proximal positioning element. An example embodiments of a catheter with two positioning elements is illustrates in FIG. 1Q. Infusion ports are configured along the catheter shaft between the two positioning elements, which disperse vapor for ablation, in accordance with the operation of the ablation device as described in the various embodiments of the present specification.

At step 3706, a distal end of the catheter is positioned within the body of the patient proximate a first point. The first point is preferably the point where the first distal positioning element needs to be deployed. At step 3708, an outer sheath of the catheter is pulled back using a knob, button, or any other type of a trigger, as may be provided in a handle portion of the endoscope and/or the catheter. The outer sheath is pulled to deploy the first distal positioning element near the first point within the duodenum. The positioning elements are deployed when they emerge from the catheter and expand from a compressed or contracted configuration to their expanded shape, such as discs of FIG. 1Q. At step 3710, the catheter sheath is continually pulled to also deploy second proximal positioning element. In embodiments, the distance with the two positioning elements is constant, such that length from an outer point on the periphery on first element to the same outer point on the periphery of second element is the same irrespective of the degree of expansion of the positioning elements. As a result, the user/physician always knows the length of an ablation treatment zone, which corresponds to the length of the chamber formed between the two positioning elements. In some embodiments, catheter sheath is pulled to deploy the two positioning elements. In alternative embodiments, the positioning element are deployed in the endoscope (by moving the outer sheath of the catheter), and then using the endoscope as a sheath. The positioning elements emerge out and expand when they exit the endoscope and compress and contract when the catheter is pulled back into the endoscope. In some embodiments, the sheath is replaced with a suture that restrains (and then is pulled to remove suture and remove the restrain). During the entire process of FIG. 37A, the viewing element of the endoscope is able to generate images on the display connected to the endoscope, which aids visualization of the placement of the ablation device in real time. In case of duodenal ablation, the physician is able to visually confirm that the second proximal positioning element is sufficiently distal to the Ampulla of Vater. Image recognition methods, such as for example artificial intelligence (AI), may be combined with the imaging data to detect structures like the Ampulla of Vater, degree of ablation, boundaries of ablation, among other parameters, to aid the user/physician.

At step 3712, the ablation treatment is initiated. Heating element within the catheter is activated to heat saline/fluid and convert it to vapor for ablation. The vapor is dispersed through infusion ports that are configured around circumference of the catheter shaft between the two positioning elements. Dimensions of the expanded positioning elements in their deployed configuration is substantially unaffected by the vapor. FIG. 37B illustrates a vapor contact zone 3724 relative to a treatment or therapeutic zone 3726. Catheter shaft 3728 with a first distal positioning element 3730 and a second proximal positioning element 3732 is positioned within a duodenum for ablation treatment. Shaft 3728 portion between elements 3730 and 3732 is configured with infusion ports that disperse vapor for ablation. Positioning elements 3730 and 3732 are either partially or completely covered by a membrane. Shape of the positioning elements 3730 and 3732 and the extent of membrane that covers them define the vapor contact zone 3724 and the therapeutic ablation zone 3726. Zone 3726 is specifically within the chamber formed between the two positioning elements 3730 and 3732. FIGS. 36A to 36E describe the significance of optimizing heat distribution in the chamber formed by the two positioning elements 3730 and 3732. Vapor escapes therapeutic zone (TZ) 3726 and also contacts some portions of the duodenum outside the distal side of distal positioning element 3730 and proximal side of the proximal positioning element 3732. Outside of ablation zone or TZ 3726, the temperature may rise but the level of ablation is non-therapeutic. The area contacted by the vapor is the vapor contact zone (VZ) 3724 and includes non-therapy areas. In embodiments, TZ is greater than 75% of the VZ, but is less than 100% of the VZ. In embodiments, more than 90% of the heat is contained within TZ 3726. The ratio of TZ to VZ is controlled by the vapor delivery controller in accordance with the embodiments of the present specification. Distance between the two positioning elements 3730 and 3732 also affects the duration of ablation, and therefore the depth of ablation. Greater separation between elements 3730 and 3732 results in a greater possibility that the vapor loses heat and results in uneven ablation in TZ 3726. On the other hand, if separation between elements 3730 and 3732 is too small, TZ 3726 would be too small and the therapy would take too long, if the target treatment area in the body is longer. In one example, ablation treatment is required over a length of at least 6 cm within the duodenum, whereas the distance between the two positioning elements 3730 and 3732 is only 2 cm. In this example, the ablation device has to be repeatedly repositioned to cover the entire target area, resulting in a longer duration of treatment. A longer duration may result in vapor temperature changes that are too large over the distance of the target area. In embodiments, the treatment is performed over a duration of 1 to 10 seconds. Positioning elements 3730 and 3732 allow for a controlled amount of diffusion of vapor over a period of time. The diffusion increases over the treatment period. Rate of diffusion is greater than 0% and less than 50%. Design of positioning elements 3730 and 3732 enable some of the energy to escape. In embodiments, the amount of energy that escapes is greater than 0% and less than 25%.

In embodiments, more than 50% of the target tissue's surface area is ablated by the embodiments of the present specification. Additionally, the depth of ablation is 50% or less (of a circumference of a muscularis propria) to prevent stricture formation.

The treatment is initiated by a trigger such as a pedal (see FIG. 1A) that is pressed by the user/physician. In embodiments, the time taken from initiating the treatment to the achieving a temperature of the target tissue that is sufficient for ablation is less than 5 seconds. In most cases, a tissue temperature rise to at least 60° C. is sufficient for ablation. During operation using a pre-puff step followed by a pause of about 5 seconds, the subsequent heating raises tissue temperature from baseline to about 80° C. in less than 5 seconds. In embodiments, less than 10 cubic centimetres (cc) of saline is used to achieve the target temperature.

At step 3714, the outer sheath of the catheter is pushed forward to cover, contract, and compress the second proximal positioning element. At step 3726, the sheath is continually pushed forward to additionally cover, contract, and compress first distal positioning element 3730. At step 3718, the user/physician may determine whether the entire target area has been treated. If not, the distal part of the catheter is repositioned at step 3720, followed by repeating of steps 3708 to 3718 at the new position. The catheter is repositioned such that a portion of the previous therapeutic zone is overlapped by the next therapeutic zone, ensuring that no part of the target area is left untreated. In some embodiments, the length of overlap is in a range of 1 mm to 10 mm.

In embodiments, each duodenal ablation procedure includes at least two treatments, where each treatment ablates 2-3 cm of tissue. The full range of ablated tissue is in a range of 4-15 cm. The temperature for ablation is in a range of 60° C. to 90° C. The treatment time for each position may vary from 1-10 seconds, and the total procedure may vary from 2-80 seconds. Once the entire distance of the target area is treated, the process is stopped, and the catheter is withdrawn.

In some cases, the process of treatment through ablation is easier when the submucosa is separated from the mucosa during ablation. In some embodiments, the separation is achieved by inducing an edema response by delivering a non-ablative level of vapor, which generates a thicker mucosa after a waiting time in a range of 5 to 10 minutes. In various embodiments, multiple sessions with variable times/doses are applied. In some embodiments, each session is defined by a therapeutic time (T1) and dose (D1). In an embodiment, a first session is delivered for a time T2 that is less than T1 using dose D1 or for a time T2 that is less than, greater than or equal to T1 but at a dose D2 that is less than D1. The overall goal is to deliver less total energy in the first session than would be required to achieve an effective ablation of the mucosal layer. More specifically, the vapor dose applied in the first session is for a time such that the total energy delivered during the first session causes a structural change in the mucosa, but not an ablation of more than 25% of the mucosa in terms of surface area (preferably less than 25%, less than 20%, less than 15%, less than 10% and most preferably less than 5%) and not an ablation of more than 15% of the submucosa in terms of surface area (preferably less than 15%, less than 10%, and most preferably less than 5%).

After the first session, the physician waits for a time from 1 second to 30 minutes for a degree of said structural change to form. The structural change is at least one of edema, cellular injury, alternation of metabolic cellular processes, and/or inflammation but not an effective ablation that results in tissue necrosis. Certain structural changes, such as edema formation, help protect the muscularis propria layer from sustaining clinically significant thermal injury. After the structural change sets in, the physician delivers a second dose of vapor with a dose in a range of 1×T1 to 5×T1. Negative pressure, in the form of suction or vacuum, is applied to the ablated zone after the steam is turned off to increase blood flow to cool the tissue. This increase blood flow could also increase edema formation.

In some embodiments, alternatively, fluid is injected between the submucosa and the mucosa to generate edema. Once the edema is generated, the therapeutic vapor is delivered to the target area.

The RFVA system in accordance with embodiments of the present specification, consists of a bipolar radiofrequency generator and through-the-scope catheters delivering heated vapor to the esophageal tissue. Further, a circumferential RFVA (C-RFVA) catheter is also discussed within embodiments of the present specification, which enables ablation of larger surface area. Tip of a C-RFVA catheter contains two positioning elements, which include in an embodiment two compliant disks, which can be unfolded or expanded through retraction of a sheath. Deployment of the positioning element creates a closed compartment of approximately 3 cm in length which enables circumferential tissue ablation by containment of the generated vapor. Further in embodiments, the ablation system of the present specification is firstly tested by activating its controller to generate vapor ex vivo. Subsequently, the catheter is inserted into the working channel of the endoscope followed by deployment of the positioning elements with subsequent vapor ablation.

A single C-RFVA application starts with preheating of 3 sec to ensure adequate vapor ejection. After a pause of 3 sec, a single ablation of either 4 sec or 5 sec is performed. A double C-RFVA application consists of a similar preheating phase (3 sec preheating with subsequent 3 sec pause) immediately followed by two ablations of either 4 sec or 5 sec each with a pause of 5 sec in between these consecutive ablations.

FIG. 38A illustrates an exemplary embodiment of a vapor ablation system 3800 in accordance with some embodiments of the present specification. System 3800 consists of a controller 3802 having a processor and comprising a bipolar RF generator 3801 with an integrated syringe pump 3804, a foot pedal 3806 and a catheter 3808. The processor of controller 3822 is in electrical communication with catheter 3828. In some embodiments, catheter 3808 a 10.5 Fr disposable catheter which can be inserted through a 3.7 mm working channel of an endoscope. Catheter 3808 has a proximal end and a distal end, wherein the proximal end is attached to pump 3804 and the distal end is configured for insertion in a body cavity. The distal end of circumferential catheter 3808 contains two positioning elements-a first positioning element 3810 and a second positioning element 3812 separated from each other by a distance. In some embodiments, the first and the second positioning elements 3810 and 3812 are configured as discs. Ports or spray holes 3814 are positioned between positioning elements 3810 and 3812, which provide an outlet for vapor. Once catheter 3808 is connected to controller 3802 and syringe 3804 with saline, bipolar radiofrequency energy (50-60 W) is delivered to an electrode 3809 in the catheter. As a fluid, preferably saline, flows over the electrode, heated vapor is generated at a temperature of 100° C. and delivered to the target tissue through ports 3814 at the distal end of catheter 3808. The distal end of catheter 3808 contains two positioning elements 3810 and 3812 which can each be changed between a compressed, pre-delivery configuration and an expanded, deployment configuration. In embodiments, the two positioning elements 3810 and 3812 can be unfolded through retraction of a sheath. In some embodiments, deployment of positioning elements 3810 and 3812, creates a closed compartment of approximately 3 cm in length, which enables circumferential tissue ablation by containment of the generated vapor. Dosages of the RFVA system are defined as the duration of vapor delivered in seconds (sec). In embodiments, a user controls the delivery of vapor with foot pedal 3806, which is in electrical communication with the controller 3802. In some embodiments, system 3800 includes an interface (GUI) 3807 on the controller 3802 or an actuator on the catheter 3808 for controlling the delivery of vapor.

FIG. 38B illustrates an exemplary embodiment of a vapor ablation system 3820 in accordance with other embodiments of the present specification. System 3820 consists of a controller 3822 having a processor and comprising a bipolar RF generator 3821 with an integrated syringe pump 3824, a foot pedal 3826 and a catheter 3828. The processor of controller 3822 is in electrical communication with catheter 3828. In some embodiments, catheter 3828 is a 10.5 Fr disposable catheter which can be inserted through a 3.7 mm working channel of an endoscope. Catheter 3828 has a proximal end and a distal end, wherein the proximal end is attached to pump 3824 and the distal end is configured for insertion in a body cavity. The distal end of circumferential catheter 3808 contains at least one positioning element 3832 proximate said distal end. In some embodiments, the at least one positioning element is configured as a disc. Ports or spray holes 3834 are positioned on the catheter 3828 proximal to, distal to, or both proximal and distal to the at least one positioning element 3832, which provide an outlet for vapor. Once catheter 3828 is connected to generator 3822 and syringe 3824 with saline, bipolar radiofrequency energy (50-60 W) is delivered to an electrode 3829 in the catheter. As saline slowly flows over the electrode, heated vapor is generated at a temperature of 100° C. and delivered to the target tissue through ports 3834 at the distal end of catheter 3828. The distal end of catheter 3828 contains the at least one positioning element 3832 which can be changed between a compressed, pre-delivery configuration and an expanded, deployment configuration. In embodiments, the at least one positioning element 3832 can be unfolded through retraction of a sheath. Deployment of at least one positioning element 3832, creates a closed compartment of approximately 3 cm in length, which enables circumferential tissue ablation by containment of the generated vapor. Dosages of the RFVA system are defined as the duration of vapor delivered in seconds (sec). In embodiments, a user controls the delivery of vapor with foot pedal 3826, which is in electrical communication with the controller 3822. In some embodiments, system 3820 includes an interface (GUI) 3827 on the controller 3822 or an actuator on the catheter 3828 for controlling the delivery of vapor.

FIG. 38C is a flow chart describing a method for treating at least one of excess weight, obesity, eating disorders, metabolic syndrome, dyslipidemia, diabetes, polycystic ovarian disease, fatty liver disease, non-alcoholic fatty liver disease, or non-alcoholic steatohepatitis disease by ablating duodenal tissue using vapor ablation systems of the present specification, for example, the vapor ablation system described with reference to FIG. 38B or FIG. 38A. The vapor ablation system comprises a catheter having at least one positioning element configured to expand outward from the catheter, wherein, upon expansion, the at least one positioning element defines a portion of a first treatment zone. Ports are positioned on the catheter and are configured to direct ablative fluid from within the catheter out toward the first treatment zone. The vapor ablation system further comprises a controller having at least one processor in electrical communication with the catheter.

At step 3842, the catheter is positioned in a patient's duodenum. At step 3844, the at least one positioning element is expanded to define the portion of the first treatment zone. At step 3846, the controller is activated. Upon activation, the controller delivers a first fluid to the catheter and causes the catheter to heat the first fluid to form a first ablative fluid such that the first ablative fluid leaves the catheter through the ports over a first period of time. Delivery of the first ablative fluid over the first period of time constitutes a first dose, wherein the first dose comprises less energy than required to achieve effective ablation of tissue in the first treatment zone. In some embodiments, the first dose is a subtherapeutic dose. After the first period of time, at step 3848, the user waits for a second period of time to permit a structural change in a mucosa layer or submucosa layer of the duodenum. In embodiments, the structural change is at least one of an edema, inflammation, cellular injury, or alternation of metabolic cellular processes. After the second period of time, at step 3850, the controller is activated again. Upon activation, the controller is configured to deliver a second fluid to the catheter and cause the catheter to heat the second fluid to a second ablative fluid such that the second ablative fluid leaves the catheter through the ports over a third period of time. Delivery of the second ablative fluid over the third period of time constitutes a second dose, wherein the second dose comprises at least one of a) less energy than required to achieve effective ablation of tissue in the first treatment zone, b) sufficient energy required to achieve effective ablation of tissue in the first treatment zone, or c) more energy than required to achieve effective ablation of tissue in the first treatment zone. In various embodiments, the second dose is a subtherapeutic dose, a therapeutic dose, or a supratherapeutic dose.

In various embodiments, a volume of the first ablative fluid delivered over the first period of time and a volume of the second ablative fluid delivered over the third period of time are substantially equal or are different. In various embodiments, a volume of the first ablative fluid delivered over the first period of time is less than a volume of the second ablative fluid delivered over the third period of time. In some embodiments, the first period of time is at least 20% less than the third period of time. In some embodiments, the second period of time is in a range of 1 second to 50 minutes. In some embodiments, each of the first dose and the second dose has an energy in a range of 50 Joules to 200 Joules.

Optionally, after the third period of time, at step 3852, the catheter is moved proximally or distally within the patient's duodenum. After moving the catheter, at step 3854, a portion of a second treatment zone is defined. In embodiments, defining the portion of the second treatment zone comprises expanding the at least one positioning element and expanding a second positioning element, wherein the second treatment zone is defined by the at least one positioning element being one on end of the second treatment zone and the second positioning element being on the other end of the second treatment zone. In embodiments, the second treatment zone at least partially overlaps with the first treatment zone. In some embodiments, the second treatment zone and the first treatment zone have between 5% and 95% of their respective tissue in common. In some embodiments, the second treatment zone and the first treatment zone have between 15% and 85% of their respective tissue in common. After defining the portion of the second treatment zone, at step 3856, the controller is activated again. Upon activation, the controller delivers a third fluid to the catheter and causes the catheter to heat the third fluid to form a third ablative fluid such that the third ablative fluid leaves the catheter through the ports over a fourth period of time. Delivery of the third ablative fluid over the fourth period constitutes a third dose, wherein the third dose comprises less energy than required to achieve effective ablation of tissue in the second treatment zone.

After the fourth period of time, at step 3858, the user waits for a fifth period of time to permit a structural change in a mucosa layer or submucosa layer of the duodenum. After the fifth period of time, at step 3860, the controller is activated again. Upon activation, the controller is configured to deliver a fourth fluid to the catheter and cause the catheter to heat the fourth fluid to a fourth ablative fluid such that the fourth ablative fluid leaves the catheter through the ports over a sixth period of time. Delivery of the fourth ablative fluid delivered over the sixth period of time constitutes a fourth dose, wherein the fourth dose comprises at least one of a) less energy than required to achieve effective ablation of tissue in the second treatment zone, b) sufficient energy required to achieve effective ablation of tissue in the second treatment zone, or c) more energy than required to achieve effective ablation of tissue in the second treatment zone. In embodiments, the at least one positioning element and the second positioning element are configured to permit no more than 25% of the third ablative fluid and no more than 25% of the fourth ablative fluid to escape the second treatment zone. In embodiments, the at least one positioning element and the second positioning element are configured to permit no more than 50% of the third ablative fluid and no more than 50% of the fourth ablative fluid to escape the second treatment zone.

Optionally, at step 3862, the catheter is moved throughout an entire length the duodenum to form a plurality of treatment zones in addition to the first treatment zone and the second treatment zone. In some embodiments, each of the plurality of treatment zones overlaps with a neighboring treatment zone such that they share between 5% and 95% of their respective tissue in common. In some embodiments, each of the plurality of treatment zones overlaps with a neighboring treatment zone such that they share between 25% and 75% of their respective tissue in common.

In various embodiments, each of the first treatment zone, second treatment zone, and the plurality of treatment zones does not encompass the patient's ampulla. In various embodiments, a treatment zone of the first treatment zone, second treatment zone, and the plurality of treatment zones that is nearest to the patient's ampulla begins less than 1 cm away from the patient's ampulla.

In embodiments, the catheter is positioned in the patient's duodenum using an endoscope, wherein, when the endoscope and catheter are positioned in the patient's duodenum, no other device is positioned in the patient's duodenum outside said endoscope.

In some embodiments, wherein the catheter further comprises a second positioning element, the second positioning element together with the at least one positioning element define the first treatment zone and both the at least one positioning element and the second positioning element are configured to permit at least a portion of the first ablative fluid to escape from the first treatment zone. In some embodiments, the at least one positioning element and the second positioning element are configured to permit no more than 25% of the first ablative fluid and no more than 25% of the second ablative fluid to escape the first treatment zone. In some embodiments, the at least one positioning element and the second positioning element are configured to permit no more than 50% of the first ablative fluid and no more than 50% of the second ablative fluid to escape the first treatment zone. In some embodiments, after delivering the first dose and the second dose to the first treatment zone, the at least one positioning element and the second positioning element are at least partially closed, and the catheter is moved proximally or distally from the first treatment zone, the at least one positioning element and the second positioning element are re-expanded to define a second treatment zone that overlaps with, but is not the same as, the first treatment zone. In some embodiments, two doses of ablative fluid are delivered to the second treatment zone and then the steps of collapsing, moving, and re-expanding are repeated to form a plurality of treatment zones such that the first treatment zone, second treatment zone and plurality of treatment zones extend an entire length of the patient's duodenum.

In some embodiments, at least two doses of ablative fluid are applied to each of the plurality of treatment zones, wherein each of the plurality of treatment zones overlaps with a neighboring one of the plurality of treatment zones such that they share in a range of 5% to 95% of their tissue in common. In some embodiments, a first of the at least two doses is a subtherapeutic dose and a second of the at least two doses is at least one of a subtherapeutic dose, a therapeutic dose, or a supratherapeutic dose.

In some embodiments, two doses of ablative fluid are delivered to the second treatment zone and then the steps of collapsing, moving, and re-expanding are repeated to form a plurality of treatment zones such that the first treatment zone, second treatment zone and plurality of treatment zones extend a length of the patient's duodenum in a range of 9 cm to 23 cm. In some embodiments, at least two doses of ablative fluid are applied to each of the plurality of treatment zones, wherein each of the plurality of treatment zones overlaps with a neighboring one of the plurality of treatment zones such that they share in a range of 5% to 95% of their tissue in common. In some embodiments, a first of the at least two doses is a subtherapeutic dose and a second of the at least two doses is at least one of a subtherapeutic dose, a therapeutic dose, or a supratherapeutic dose.

In some embodiments, the patient's fasting glucose is measured before performing an ablation procedure and within 24 hours after performing the ablation procedure and the patient's fasting glucose within 24 hours after performing the ablation procedure is at least 10% or 20 mg/dl less than the patient's fasting glucose before performing the ablation procedure.

In some embodiments, the patient's fasting glucose is measured before performing an ablation procedure and approximately 30 days after performing the ablation procedure and the patient's fasting glucose approximately 30 days after performing the ablation procedure is at least 10% or 20 mg/dl less than the patient's fasting glucose before performing the ablation procedure.

In some embodiments, the patient's post-prandial glucose is measured before performing the ablation procedure and within 24 hours after performing the ablation procedure and the patient's post-prandial glucose within 24 hours after performing the ablation procedure is at least 10% or 30 mg/dl less than the patient's post-prandial glucose before performing the ablation procedure.

In some embodiments, the patient's post-prandial glucose is measured before performing the ablation procedure and approximately 30 days after performing the ablation procedure and the patient's post-prandial glucose approximately 30 days after performing the ablation procedure is at least 10% or 30 mg/dl less than the patient's post-prandial glucose before performing the ablation procedure.

In some embodiments, the patient's HbA1c level is measured before performing the ablation procedure and approximately four weeks after performing the ablation procedure and the patient's HbA1c level approximately four weeks after performing the ablation procedure is at least 0.6% less than the patient's HbA1c level before performing the ablation procedure.

In some embodiments, the patient's HbA1c level is measured before performing the ablation procedure and approximately six months after performing the ablation procedure and the patient's HbA1c level approximately six months after performing the ablation procedure is at least 0.6% less than the patient's HbA1c level before performing the ablation procedure.

In some embodiments, each of the first treatment zone, second treatment zone and the plurality of treatment zones is defined by a plurality of consecutively positioned annular rings, wherein each of the plurality of consecutively positioned annual rings has an internal surface area, and wherein, after the ablation procedure is performed, at least 60% of the internal surface area of each of the plurality of consecutively positioned annual rings is effectively ablated.

In some embodiments, each of the first treatment zone, second treatment zone and the plurality of treatment zones is defined by a plurality of consecutively positioned annular rings, wherein, after the ablation procedure is performed, each of the plurality of consecutively positioned annular rings has an effectively ablated region, wherein the effectively ablated region's thickness along a length of each of the plurality of consecutively positioned annular rings varies no more than 50% from an average thickness of the effectively ablated region.

FIG. 39A illustrates a perspective view of first positioning element 3902 (element 3810 of FIG. 38A) and second positioning element 3904 (element 3812 of FIG. 38A). FIG. 39B illustrates intraluminal 3906 positioning of distal end of catheter 3908 (catheter 3808 of FIG. 38A) where positioning elements 3902 and 3904 are deployed resulting in formation of a compartment 3910 of a length corresponding to the distance between the first and the second positioning elements 3902 and 3904. In some embodiments, the compartment has a length of approximately 3 cm. FIG. 39C illustrates generation of steam 3912 within compartment 3910. Generated steam 3912 is contained within compartment 3910 to induce circumferential ablation.

Radiofrequency vapor ablation (RFVA) is a newly developed ablation technique which may serve as an alternative for radiofrequency ablation (RFA) in the treatment of Barrett's esophagus. Treatment process and outcomes using data on circumferential RFVA (C-RFVA) in a porcine model, are now described. Tests were conducted to assess temperature distribution of device of FIGS. 38 and 39A-39C. After introduction of the endoscope inside the patient, the esophagus was inspected and rinsed with water if necessary. In most cases, for each patient, four or five treatment areas were appointed with electrocoagulation markings, starting at least 8 cm below the upper esophageal sphincter and with approximately 5 cm in between treatment zones. The depth of the ablation effect was scored as a percentage from the total thickness for each of the different esophageal wall layers, the circumferential extent as a percentage from the total surface area, and the homogeneity as continuous (uniform damage without interruptions) or patchy (damage alternated with unaffected areas). Dosages comprising single and double applications of 4 sec and 5 sec were evaluated. A single C-RFVA application started with preheating of 3 sec to ensure adequate vapor ejection. After a pause of 3 sec, a single ablation of either 4 sec or 5 sec was performed. The double C-RFVA applications consisted of a similar preheating phase (3 sec preheating with subsequent 3 sec pause) immediately followed by two ablations of either 4 sec or 5 sec with a pause of 5 sec in between these consecutive ablations. In the experiment, C-RFVA was performed using a catheter containing two compliant positioning elements that, upon deployment, created a chamber of 3 cm in length. A total of 35 and 24 treatment areas were ablated in 7 and 6 pigs with a designated survival period of 48 hours and 28 days, respectively.

FIG. 40 is a table illustrating histopathological evaluation of subacute ablation effect (t=48 hours) after circumferential radiofrequency ablation (C-RFA) of duodenal tissue. The table illustrates data pertaining to percentage of a circumference affected by thermal injury of duodenal tissue, shown along x-axis 4062; and percentage of depth affected by thermal injury shown along y-axis 4064, for different treatment areas 4066. Different treatment areas 4066 include the mucosa and the submucosa. According to treatment area 4066, both the circumference (x-axis 4062) and the depth (y-axis 4064) affected by thermal injury are scored as a percentage for each of the different duodenal wall layers. Further, the table illustrates data recorded at 48 hours after the ablation. In addition, a pattern generated by the thermal injury in the different forms of ablation was scored as continuous indicating homogeneous damage. The table further shows up to 100% depth affected by thermal injury, and up to 50% of the circumference affected by thermal injury in the mucosa. The table also shows up to 20% depth affected by thermal injury, and up to 50% of the circumference affected by thermal injury in the submucosa.

The ablation device, in accordance with some embodiments of the present specification, additionally uses a mesh that connects a first positioning element with a second positioning element. In embodiments, the positioning elements are discs. In embodiments, the mesh is made from Nitinol and self-expands to a predetermined shape. In embodiments, the wires of the mesh are coated with silicone, a polymer, or PTFE. The mesh connects the two positioning elements to push away intraluminal tissue, so as to ensure that the tissue does not touch the vapor emitting that catheter from a location between the two positioning elements. Presence of the mesh avoids uneven heating on the intraluminal cavity. As a result, the compartment created between the two positioning elements look more like a stent. One end of the "stent" will float so that it collapses easily. FIG. 41 illustrates an exemplary embodiment of a vapor ablation system 4100 in accordance with some embodiments of the present specification. System 4100 consists of a controller 4102 having a processor and comprising a bipolar RF generator 4101 with an integrated syringe pump 4104, a foot pedal 4106 and a catheter 4108. The processor of the controller 4102 is in electrical communication with the catheter 4108. Catheter 4108 has a proximal end and a distal end, wherein the proximal end is attached to pump 4104 and the distal end is configured for insertion in a body cavity. The distal end of circumferential catheter 4108 contains two positioning elements-a first positioning element 4110 and a second positioning element 4112 separated from each other by a distance. In some embodiments, the first and the second positioning elements 4110 and 4112 are configured as discs. A mesh 4114 is attached to proximal positioning element 4110 and extends for the length between elements 4110 and 4112, such that when elements 4110 and 4112 are deployed, mesh 4114 expands into a stent like structure. Ports or spray holes 4115 are positioned between positioning elements 4110 and 4112, which provide an outlet for vapor, which then passes through mesh 4114 to the target tissue. Once catheter 4108 is connected to controller 4102 and syringe 4104 with saline, bipolar radiofrequency energy (50-60 W) is delivered to an electrode 4109 in the catheter. As a fluid, preferably saline, flows over the electrode, heated vapor is generated at a temperature of 100° C. and delivered to the target tissue through ports 4115 and the mesh 4114 at the distal end of catheter 4108. Mesh 4114 pushes away any tissue that could otherwise touch the vapor emitting portion of catheter 4108, and avoids uneven ablation. The two positioning elements 4110 and 4112 can each be changed between a compressed, pre-delivery configuration and an expanded, deployment configuration and the mesh 4114 also compresses to a collapsed configuration. In embodiments, the two positioning elements 4110 and 4112 and mesh 4114 can be unfolded through retraction of a sheath. Dosages of the RFVA system are defined as the duration of vapor delivered in seconds (sec). In embodiments, a user controls the delivery of vapor with foot pedal 4106, which is in electrical communication with the controller 4102. In some embodiments, system 4100 includes an interface (GUI) 4107 on the controller 4102 or an actuator on the catheter 4108 for controlling the delivery of vapor.

FIG. 42 illustrates a top side perspective view of a first positioning element 4210 and a second positioning element 4212 spaced along a catheter 4208. A mesh 4214 is attached to first positioning element 4210 and extends up to second positioning element 4212. FIG. 43A illustrates a side view of first positioning element 4310 and second positioning element 4312 in their deployed state. FIG. 43B illustrates vapor 4316 generated during ablation, which is evenly distributed within a volume 4315 defined by the space within the mesh 4314 and between the first positioning element 4310 and the second positioning element 4312.

FIG. 44 is a flow chart illustrating an exemplary method of using vapor ablation devices, in accordance with some embodiments of the present specification. The method described herein is used for treating at least one of excess weight, obesity, eating disorders, metabolic syndrome, dyslipidemia, diabetes, polycystic ovarian disease, fatty liver disease, non-alcoholic fatty liver disease, or non-alcoholic steatohepatitis disease by ablating the a body tissue using a vapor ablation system. Referring simultaneously to FIGS. 38A-39C and FIGS. 42-43B, at step 4402, a proximal end of a catheter 3808/4208 is connected to a catheter connection port to place catheter 3808/4208 in fluid communication with pump 3804. As described previously, a controller 3802/4202 having at least one processor is in data communication with at least one pump 3804/4204, which in some embodiments is a syringe pump, and the catheter connection port that is in fluid communication with pump 3804/4204. Catheter 3808/4208 includes two positioning elements 3810/4210 and 3812/4212 at its distal end. One or more ports are positioned in the length between the two elements 3810/4210 and 3812/4212. At step 4404, catheter 3808/4208 is positioned inside a patient. Positioning elements 3810/4210 and 3812/4212 are originally in their first configuration where they are compressed within the catheter. At step 4406, upon positioning catheter 3808/4208 inside the patient, elements 3810/4210 and 3812/4212 are deployed to an expanded (second) configuration. Elements 3810/4210 and 3812/4212 are separated by a length of at least 1 cm. In some embodiments, a length of catheter between the two elements 3810/4210 and 3812/4212 is approximately 3 cm. The expanded configurations of elements 3810/4210 and 3812/4212 and the space between them, defines a treatment volume within the patient. A surface area of the proximal one of the two positioning elements (element 3810/4210) and the surface area of the distal one of the two positioning elements (3812/4210) comprise a plurality of spaces sufficient to permit a flow of vapor outside of the treatment volume in a range of 1 to 80% of a vapor input flow rate such that vapor flows proximal to positioning element 3810/4210 and/or flows distal to positioning element 3812/4212. At step 4408, controller 3802/4202 is activated. Activation causes pump 3804/4204 to deliver saline into a lumen in catheter 3808/4208. Additionally, upon activation, controller 3202/4202 causes an electrical current to be delivered to an electrode positioned within the lumen of first catheter 3808/4208. The electrode is located at a place different from the first and second positioning elements 3810/4210 and 3812/4212. Consequently, vapor is generated from the saline at the vapor flow rate. At step 4410, the generated vapor of a subtherapeutic dose is delivered through the ports between the two positioning elements 3810/4210 and 3812/4212 and into the treatment volume.

In some embodiments, the subtherapeutic dose has a duration of 0.5 seconds from the start. In embodiments, the subtherapeutic dose has a duration in a range of 0.1 seconds to 5 seconds. For the duodenum, with a diameter between 20-30 mm, the preferred subtherapeutic dose is approximately 2 seconds from the steam initiation.

In some embodiments, therapeutic and sub-therapeutic doses, are defined and controlled based on a total energy of the dose. As time can vary with power output, in embodiments, a total energy endpoint can provide more consistent amounts of steam and therefore more consistent temperatures. In some embodiments, a subtherapeutic dose ranges between 50 Joules and 250 Joules. In some embodiments, a therapeutic dose for a duodenum (20-30 mm) ranges from 150 J to 1,000 Joules. In some embodiments, a therapeutic dose for a duodenum (20-30 mm) ranges from 150 J to 500 Joules.

The objective of the subtherapeutic dose is to cause edema or prime the surface for ablation. At step 4412, controller 3802/4202 is deactivated briefly to introduce a waiting period. In some embodiments, the waiting period is in a range of 1 second to 50 minutes. At step 4414, controller 3802/4202 is reactivated.

At step 4416, a first therapeutic ablation dose is delivered. In some embodiments, the therapeutic dose is delivered for a period in a range of 1 second to 10 seconds or at an energy in a range of 150 Joules to 500 Joules.

FIG. 45A is a flow chart illustrating an exemplary method of using vapor ablation devices, in accordance with some other embodiments of the present specification. The method described herein is used for treating at least one of excess weight, obesity, eating disorders, metabolic syndrome, dyslipidemia, diabetes, polycystic ovarian disease, fatty liver disease, non-alcoholic fatty liver disease, or non-alcoholic steatohepatitis disease by ablating the a body tissue using a vapor ablation system. Referring simultaneously to FIGS. 38A-39C and FIGS. 42-43B, at step 4502, a proximal end of a catheter 3808/4208 is connected to a catheter connection port to place catheter 3808/4208 in fluid communication with pump 3804. As described previously, a controller 3802/4202 having at least one processor is in data communication with at least one pump 3804/4204, which in some embodiments is a syringe pump, and the catheter connection port that is in fluid communication with pump 3804/4204. Catheter 3808/4208 includes two positioning elements 3810/4210 and 3812/4212 at its distal end. One or more ports are positioned in the length between the two elements 3810/4210 and 3812/4212. At step 4504, catheter 3808/4208 is positioned inside a patient. Positioning elements 3810/4210 and 3812/4212 are originally in their first configuration where they are compressed within the catheter. At step 4506, upon positioning catheter 3808/4208 inside the patient, elements 3810/4210 and 3812/4212 are deployed to an expanded (second) configuration. Elements 3810/4210 and 3812/4212 are separated by a length of at least 1 cm. In some embodiments, a length of catheter between the two elements 3810/4210 and 3812/4212 is approximately 3 cm. The expanded configurations of elements 3810/4210 and 3812/4212 and the space between them, defines a treatment volume within the patient. A surface area of the proximal one of the two positioning elements (element 3810/4210) and the surface area of the distal one of the two positioning elements (3812/4210) comprise a plurality of spaces sufficient to permit a flow of vapor outside of the treatment volume in a range of 1 to 80% of a vapor input flow rate such that vapor flows proximal to positioning element 3810/4210 and/or flows distal to positioning element 3812/4212. At step 4508, controller 3802/4202 is activated. Activation causes pump 3804/4204 to deliver saline into a lumen in catheter 3808/4208. Additionally, upon activation, controller 3202/4202 causes an electrical current to be delivered to an electrode positioned within the lumen of catheter 3808/4208. The electrode is located at a place different from the first and second positioning elements 3810/4210 and 3812/4212. Consequently, vapor is generated from the saline at the vapor flow rate. At step 4510, the generated vapor of a first subtherapeutic dose is delivered through the ports between the two positioning elements 3810/4210 and 3812/4212 and into the treatment volume. In some embodiments, the first subtherapeutic dose has a duration of 0.1 seconds to 5 seconds from the start of activating controller 3802/4202. In some embodiments, the first subtherapeutic dose has a duration of 2 seconds from the start of activating controller 3802/4202. In some embodiments, the first subtherapeutic dose has an energy of 150 Joules. The objective of the first subtherapeutic dose is to cause edema or prime the surface for ablation. At step 4512, controller 3802/4202 is deactivated briefly to introduce a waiting period. In some embodiments, the waiting period is in a range of 1 second to 50 minutes. In some embodiments, the waiting period is 5 seconds. At step 4514, controller 3802/4202 is reactivated. At step 4516, a second subtherapeutic ablation dose is delivered. In some embodiments, the second subtherapeutic dose is delivered for a period of 2 to 10 seconds. In some embodiments, the second subtherapeutic dose has an energy ranging from 150 Joules to 500 Joules. The second subtherapeutic dose is delivered to result in ablation of a mucosal or submucosal surface.

FIG. 45B is a flow chart illustrating an exemplary method of using vapor ablation devices, in accordance with another embodiment of the present specification. Referring to FIG. 45B, the method includes providing a supra-dose to achieve effective ablation. The method described herein is used for treating at least one of excess weight, obesity, eating disorders, metabolic syndrome, dyslipidemia, diabetes, polycystic ovarian disease, fatty liver disease, non-alcoholic fatty liver disease, or non-alcoholic steatohepatitis disease by ablating the a body tissue using a vapor ablation system. Referring simultaneously to FIGS. 38A-39C and FIGS. 42-43B, at step 4522, a proximal end of a catheter 3808/4208 is connected to a catheter connection port to place catheter 3808/4208 in fluid communication with pump 3804. As described previously, a controller 3802/4202 having at least one processor is in data communication with at least one pump 3804/4204, which in some embodiments is a syringe pump, and the catheter connection port that is in fluid communication with pump 3804/4204. Catheter 3808/4208 includes two positioning elements 3810/4210 and 3812/4212 at its distal end. One or more ports are positioned in the length between the two elements 3810/4210 and 3812/4212. At step 4524, catheter 3808/4208 is positioned inside a patient. Positioning elements 3810/4210 and 3812/4212 are originally in their first configuration where they are compressed within the catheter. At step 4526, upon positioning catheter 3808/4208 inside the patient, elements 3810/4210 and 3812/4212 are deployed to an expanded (second) configuration. Elements 3810/4210 and 3812/4212 are separated by a length of at least 1 cm. In some embodiments, a length of catheter between the two elements 3810/4210 and 3812/4212 is approximately 3 cm. The expanded configurations of elements 3810/4210 and 3812/4212 and the space between them, defines a treatment volume within the patient. A surface area of the proximal one of the two positioning elements (element 3810/4210) and the surface area of the distal one of the two positioning elements (3812/4210) comprise a plurality of spaces sufficient to permit a flow of vapor outside of the treatment volume in a range of 1 to 80% of a vapor input flow rate such that vapor flows proximal to positioning element 3810/4210 and/or flows distal to positioning element 3812/4212. At step 4528, controller 3802/4202 is activated. Activation causes pump 3804/4204 to deliver saline into a lumen in catheter 3808/4208. Additionally, upon activation, controller 3202/4202 causes an electrical current to be delivered to an electrode positioned within the lumen of catheter 3808/4208. The electrode is located at a place different from the first and second positioning elements 3810/4210 and 3812/4212. Consequently, vapor is generated from the saline at the vapor flow rate. At step 4530, the generated vapor of a first subtherapeutic dose is delivered through the ports between the two positioning elements 3810/4210 and 3812/4212 and into the treatment volume. In some embodiments, the first subtherapeutic dose has a duration of 0.1 seconds to 5 seconds from the start of activating controller 3802/4202. In some embodiments, the first subtherapeutic dose has a duration of 2 seconds from the start of activating controller 3802/4202. In some embodiments, the first subtherapeutic dose has an energy of 150 Joules. The objective of the first subtherapeutic dose is to cause edema or prime the surface for ablation. At step 4532, controller 3802/4202 is deactivated briefly to introduce a waiting period. In some embodiments, the waiting period is in a range of 1 second to 50 minutes. In some embodiments, the waiting period is 5 seconds. At step 4534, controller 3802/4202 is reactivated. At step 4536, a second ablation dose is delivered. In embodiments, the second ablation dose is delivered over a period of time that is at least one of a) less than a period of time required to achieve effective ablation of tissue in the treatment volume, b) a sufficient period of time required to achieve effective ablation of tissue in the treatment volume, or c) greater than a period of time required to achieve effective ablation of tissue in the treatment volume. In embodiments, the second ablation dose is delivered for a period ranging from 1 to 120 seconds. In some embodiments, the second ablation dose has an energy ranging from 150 Joules to 1500 Joules. IN some embodiments, the second ablation dose is delivered to result in ablation of a mucosal or submucosal surface.

Duodenal Ablation

Referring now to FIG. 46A, an exemplary process for duodenal ablation is illustrated. The process is initiated after inserting an endoscope that includes channels for delivery of a catheter in accordance with the various embodiments of the present specification. At step 4602, the duodenal tissue is prepared by washing the duodenal mucosa with 2% N-Acetyl-Cysteine solution and then suctioning the fluid. At step 4604, the Ampulla of Vater is identified and used as a landmark to demarcate the proximal end of a treatment area. At step 4606, a clip is applied to the contralateral wall to mark the proximal end of the treatment area. FIG. 46B illustrates position of a clip 4652 just distal to the ampulla of Vater 4654. At step 4608, a distal end of the catheter is positioned at a distal side of the clip. A sheath is partially withdrawn to enable expansion of a first distal positioning element at a distal side of the clip, and further withdrawn to enable expansion of a second proximal positioning element on a proximal side to the first distal positioning element still on a distal side of the clip. The first and second positioning elements are at a distance from each other along a length of the catheter, such that in their expanded (deployed) configurations they form a first treatment volume enclosed by the first and the second positioning elements and the duodenal mucosal surface. A proximal end of the treatment volume is proximate the ampulla of Vater, however there is no need to maintain a distance of 1 cm from the ampulla of Vater. In some embodiments, the first and second positioning elements are disc shaped or umbrella shaped. The positioning elements do not create a perfect seal, therefore allowing partial vapor to escape during ablation. FIG. 46C illustrates a position of a first treatment volume or zone 4656.

In some embodiments, treatment is performed in a series of treatments in a proximal to distal direction, starting just distal to the ampulla of Vater and moving distally toward the jejunum. In other embodiments, treatment is performed in a series of treatments in a distal to proximal direction, starting 15-30 cm distal to the ampulla of Vater, near the jejunum, and moving proximally toward the ampulla of Vater. In other embodiments, any combination of treatment sequence, i.e. applying a first ablation near the ampulla of Vater, then treating a very distal 10-30 cm beyond the first treatment, then treating in a distal direction back to the first treatment near the ampulla of Vater. Optionally, in some embodiments, treatment is also applied to the duodenum tissue proximal to the ampulla of Vater. In some embodiment, treatment is applied between the ampulla of Vater and the pylorus. In some embodiments, one of the proximal positioning element or the distal positioning element is positioned to cover the ampulla of Vater, with ablation performed anywhere adjacent and even touching the ampulla. There is no minimum or maximum distance of ablation that must be maintained to or from the ampulla. In embodiments, ablation is performed up to 30 cm to 40 cm distally beyond the ampulla. In various embodiments, each of the treatments areas or ablation zones has a length of approximately 2 cm. For example, in some embodiments, if ablation is applied to a single layer of adjacent treatments, 8 treatments will cover approximately 16 cm in length. In various embodiments, ablation is applied to overlap treatments or ablation zones. Additionally, in embodiments, treatment is applied to come back and treat at a same location already treated. There is no limit to the number of treatments that can be applied. In embodiments, a location is not treated and then immediately treated again. Treatment is first moved to a new location, and then back to a previous location. When treatment is a applied to a same location for a second time, it is desirable for the temperature at the same location to have returned to body temperature so that the second treatment is not stacking heat.

At step 4610, a first ablation is delivered within the first treatment zone defined between the first and second positioning elements at a location on a distal side of the clip. At step 4612, the catheter is repositioned to define a second treatment zone on a proximal side to the first treatment zone to perform a second ablation. The process of repositioning the catheter is continued to perform a series of ablations within a series of treatment zones. A check is performed at step 4614 to ensure whether the length of the treatment area is covered. If not, the process of repositioning the catheter to perform ablation is continued to generate a series of treatment zones. FIG. 46D illustrates a series of treatment zones 4658 created by repositioning the catheter and performing ablations. The catheter is repositioned to perform the sequence of ablations so that the treatment zones have a minimum overlap. At step 4616, the duodenal mucosa is assessed following the first sequence of ablation performed up to step 4614. The assessment is performed with an imaging element. At step 4618, a second series of ablations are performed over the treatment zones of the first series of ablations. At step 4620, the entire ablated segment is reviewed to identify possibility of complications and/or non-ablated areas. FIG. 46E illustrates an area 4660 within the treatment area, which is identified to be non-ablated. At step 4621, optionally if non-ablated regions are identified (such as region 4660) within the series of treatment zones, those regions are targeted and ablation is selectively performed on them, which can be termed as touch-up ablations. At step 4624, once the ablations are completed, the positioning elements are retracted and the catheter is removed.

FIG. 47 is a flow chart illustrating an exemplary method of using vapor ablation devices of FIGS. 38-39 and FIGS. 42-43 for duodenal ablation, in accordance with some embodiments of the present specification. The duodenal ablation is achieved in embodiments of the present specification, by delivering a series of "subtherapeutic" doses to a target tissue of the duodenum. When a series of subtherapeutic doses are applied to the same target tissue, the effect of the "subtherapeutic" doses aggregate to ablate just enough of a surface area of the mucosa layer without damaging too much of the muscularis layer. The method described herein is used for treating at least one of excess weight, obesity, eating disorders, metabolic syndrome, dyslipidemia, diabetes, polycystic ovarian disease, fatty liver disease, non-alcoholic fatty liver disease, or non-alcoholic steatohepatitis disease by ablating the duodenal tissue using a vapor ablation system. At step 4702, a proximal end of a catheter is connected to a catheter connection port to place catheter in fluid communication with a pump. As described previously, a controller having at least one processor is in data communication with at least one pump, which in some embodiments is a syringe pump, and the catheter connection port that is in fluid communication with the pump. The catheter includes two positioning elements at its distal end. One or more ports are positioned in the length between the two elements. At step 4704, the catheter is positioned inside the duodenum of a patient, proximate to the target tissue. The positioning elements are originally in their first configuration where they are compressed within the catheter. At step 4706, upon positioning the catheter, the positioning elements are deployed to an expanded (second) configuration. In some embodiments, the positioning elements are separated by a length of at least 1 cm. In some embodiments, length of the catheter between the two positioning elements is approximately 3 cm. The expanded configurations of positioning elements and the space between them, defines a treatment volume (or zone) within the duodenum. A surface area of the proximal one of the two positioning elements and the surface area of the distal one of the two positioning elements comprise a plurality of spaces sufficient to permit a flow of vapor outside of the treatment volume in a range of 1 to 80% of a vapor input flow rate such that vapor flows proximal to positioning element and/or flows distal to positioning element. At step 4708, the controller is activated. Activation causes pump to deliver saline into a lumen in the catheter. Additionally, upon activation, the controller causes an electrical current to be delivered to an electrode positioned within the lumen of the catheter. The electrode is located at a place different from the first and second positioning elements. Consequently, vapor is generated from the saline at the vapor flow rate. At step 4710, the generated vapor of a first subtherapeutic dose is delivered through the ports between the two positioning elements and into treatment volume. In some embodiments, the first subtherapeutic dose has a duration in a range of 0.5 second to 5 seconds from the start of activating the controller. In some embodiments, the first subtherapeutic dose has an energy of 50 Joules to 200 Joules. The first subtherapeutic dose ablates less than 50% of the circumference of the duodenal target tissue and no more than 5% of the muscularis. More preferably, less than 30% of the circumference of the duodenal target tissue is ablated using a range of energy from 150 J-200 J. In some embodiments an energy of approximately 180 J is delivered. The objective of the first subtherapeutic dose is to cause edema or prime the tissue surface for ablation. At step 4712, the ablation is paused for a duration greater than thermal relaxation time to allow the target tissue surface to cool. In some cases, the waiting period is in a range of 1 to 120 seconds. At step 4714, ablation is restarted to deliver a second subtherapeutic dose of vapor to the same target tissue that was ablated by the first subtherapeutic dose. The second subtherapeutic dose results in the cumulative ablation of more than 50% of the circumference of the duodenal target tissue yet still no more than 5% of the muscularis is affected. In some embodiments, the second subtherapeutic dose is delivered for a period of 1 to 10 seconds.

FIG. 48 is a set of graphs 4802, 4804, 4806 and 4808 which illustrate an improvement in blood sugar levels after treatment in accordance with the embodiments of the present specification. All graphs 4802, 4804, 4806 and 4808 show the time line along an x-axis 4810 from week 1 to week 4, and sugar (glucose) levels along a y-axis 4812. Graph 4802 illustrates blood sugar levels of a first patient during fasting. Line 4802a illustrates progression of glucose levels across four weeks before receiving the treatment in accordance with the embodiments of the present specification. Line 4802b illustrates progression of glucose levels across four weeks after receiving the treatment in accordance with the embodiments of the present specification. Graph 4804 illustrates blood sugar levels of the first patient postprandial. Line 4804a illustrates progression of glucose levels across four weeks before receiving the treatment in accordance with the embodiments of the present specification. Line 4804b illustrates progression of glucose levels across four weeks after receiving the treatment in accordance with the embodiments of the present specification. Graph 4806 illustrates blood sugar levels of a second patient during fasting. Line 4806a illustrates progression of glucose levels across four weeks before receiving the treatment in accordance with the embodiments of the present specification. Line 4806b illustrates progression of glucose levels across four weeks after receiving the treatment in accordance with the embodiments of the present specification. Graph 4808 illustrates blood sugar levels of the second patient postprandial. Line 4808a illustrates progression of glucose levels across four weeks before receiving the treatment in accordance with the embodiments of the present specification. Line 4808b illustrates progression of glucose levels across four weeks after receiving the treatment in accordance with the embodiments of the present specification. All the graphs demonstrate the effectiveness of the treatment in accordance with embodiments of the present specification, in lowering or reducing the glucose levels.

All the embodiments of the present specification provide systems, devices, and methods that enable management of diseases such as diabetes, including type 2 diabetes. The treatment systems and methods of the present specification enable diabetes management, which may have been treated previously by the patient with daily insulin and having a first HbA1c level of more than 0.1% and no more than 5%. Embodiments of the present specification provide an alternative to existing treatment methods and devices that result in a therapeutic benefit to selected patient diagnosed with type 2 diabetes that is being treated with daily insulin at a first dosage level and having a first HbA1c level of at least 7.5%, and where the benefit comprises a reduced risk of hypoglycemia wherein the risk of hypoglycemia is reduced to a level of no more than 0.1% occurrence rate of serious hypoglycemic events per year; and the results in reduction of daily insulin daily insulin to a second dosage level less than the first dosage level and maintains a second HbA1c level that is no greater than the first HbA1c level.

Unlike prior art devices, the present invention can be passed through a conventional endoscope, thereby eliminating the need to manipulate more than one large devices side-by-side. Accordingly, in a preferred use, only the endoscope with the catheter is positioned in the patient's duodenum and no other medical device is required to be used in the duodenum outside the endoscope. Furthermore, because of the small and malleable form factor, the disclosed catheters can be advanced from just adjacent the ampulla of Vater through entire duodenum. The ability to extend through the entire duodenum enables increased ease of coverage, from a minimum of 6 cm to upwards of 15 cm and every increment therein. This effective ablation is achieved by performing 5-6 ablation sessions sequentially, each partially overlapping the previous treatment region.

The above examples are merely illustrative of the many applications of the system of the present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A method for treating at least one of excess weight, obesity, eating disorders, metabolic syndrome, dyslipidemia, diabetes, polycystic ovarian disease, fatty liver disease, non-alcoholic fatty liver disease, or non-alcoholic steatohepatitis disease by ablating duodenal tissue using a vapor ablation system, wherein the vapor ablation system comprises a catheter having at least one positioning element configured to expand outward from the catheter, wherein, upon expansion, the at least one positioning element defines a portion of a first treatment zone, wherein ports are positioned on the catheter and are configured to direct ablative fluid from within the catheter out toward said first treatment zone, and wherein the vapor ablation system further comprises a controller having at least one processor in electrical communication with the catheter, the method comprising:

positioning the catheter in a patient's duodenum;

causing the at least one positioning element to expand and define the portion of the first treatment zone;

activating the controller, wherein, upon activation, the controller delivers a first fluid to the catheter and causes the catheter to heat the first fluid to form a first ablative fluid such that the first ablative fluid leaves the catheter through the ports over a first period of time, wherein the first ablative fluid delivered over the first period constitutes a first dose and wherein the first dose comprises less energy than required to achieve effective ablation of tissue in the first treatment zone;

after the first period of time, waiting a second period of time to permit a structural change in a mucosa layer or submucosa layer of the duodenum; and after said second period of time, activating the controller, wherein, upon activation, the controller is configured to deliver a second fluid to the catheter and cause the catheter to heat the second fluid to a second ablative fluid such that the second ablative fluid leaves the catheter through the ports over a third period of time, wherein the second ablative fluid delivered over the third period constitutes a second dose and wherein the second dose comprises at least one of a) less energy than required to achieve effective ablation of tissue in the first treatment zone, b) sufficient energy required to achieve effective ablation of tissue in the first treatment zone, or c) more energy than required to achieve effective ablation of tissue in the first treatment zone.

2. The method of claim 1, wherein the first dose is a subtherapeutic dose.

3. The method of claim 2, wherein the second dose is a subtherapeutic dose.

4. The method of claim 2, wherein the second dose is a therapeutic dose.

5. The method of claim 2, wherein the second dose is a supratherapeutic dose.

6. The method of claim 1, wherein a volume of the first ablative fluid delivered over the first period of time and a volume of the second ablative fluid delivered over the third period of time are substantially equal.

7. The method of claim 1, wherein a volume of the first ablative fluid delivered over the first period of time and a volume of the second ablative fluid delivered over the third period of time are different.

8. The method of claim 1, wherein a volume of the first ablative fluid delivered over the first period of time is less than a volume of the second ablative fluid delivered over the third period of time.

9. The method of claim 1, further comprising, after said third period of time, moving the catheter proximally or distally within the patient's duodenum.

10. The method of claim 9, further comprising, after moving said catheter, defining a portion of a second treatment zone.

11. The method of claim 10, wherein defining the portion of the second treatment zone comprises expanding the at least one positioning element and expanding a second positioning element and wherein the second treatment zone is defined by the at least one positioning element being one on end of the second treatment zone and the second positioning element being on the other end of the second treatment zone.

12. The method of claim 10, wherein the second treatment zone at least partially overlaps with the first treatment zone.

13. The method of claim 10, wherein the second treatment zone and the first treatment zone have between 5% and 95% of their respective tissue in common.

14. The method of claim 10, wherein the second treatment zone and the first treatment zone have between 15% and 85% of their respective tissue in common.

15. The method of claim 10, further comprising:

after defining the portion of the second treatment zone, activating the controller, wherein, upon activation, the controller delivers a third fluid to the catheter and causes the catheter to heat the third fluid to form a third ablative fluid such that the third ablative fluid leaves the catheter through the ports over a fourth period of time, wherein the third ablative fluid delivered over the fourth period constitutes a third dose and wherein the third dose comprises less energy than required to achieve effective ablation of tissue in the second treatment zone;

after the fourth period of time, waiting a fifth period of time to permit a structural change in a mucosa layer or submucosa layer of the duodenum; and after said fifth period of time, activating the controller, wherein, upon activation, the controller is configured to deliver a fourth fluid to the catheter and cause the catheter to heat the fourth fluid to a fourth ablative fluid such that the fourth ablative fluid leaves the catheter through the ports over a sixth period of time, wherein the fourth ablative fluid delivered over the sixth period of time constitutes a fourth dose and wherein the fourth dose comprises at least one of a) less energy than required to achieve effective ablation of tissue in the second treatment zone, b) sufficient energy required to achieve effective ablation of tissue in the second treatment zone, or c) more energy than required to achieve effective ablation of tissue in the second treatment zone.

16. The method of claim 15, further comprising moving the catheter throughout an entire length the duodenum to form a plurality of treatment zones in addition to the first treatment zone and the second treatment zone.

17. The method of claim 16, wherein each of the plurality of treatment zones overlaps with a neighboring treatment zone such that they share between 5% and 95% of their respective tissue in common.

18. The method of claim 16, wherein each of the plurality of treatment zones overlaps with a neighboring treatment zone such that they share between 25% and 75% of their respective tissue in common.

19. The method of claim 16, wherein each of the first treatment zone, second treatment zone, and the plurality of treatment zones does not encompass the patient's ampulla.

20. The method of claim 16, wherein a treatment zone of the first treatment zone, second treatment zone, and the plurality of treatment zones that is nearest to the patient's ampulla begins less than 1 cm away from the patient's ampulla.

\* \* \* \* \*